(12) United States Patent
Siddiqui-Jain et al.

(10) Patent No.: US 11,013,741 B1
(45) Date of Patent: May 25, 2021

(54) AXL KINASE INHIBITORS AND USE OF THE SAME

(71) Applicant: Sumitomo Dainippon Pharma Oncology, Inc, Cambridge, MA (US)

(72) Inventors: Adam Siddiqui-Jain, South Jordan, UT (US); Paul Flynn, Citrus Heights, CA (US); Akihito Nonoyama, Hyogo (JP); Akihito Kiguchiya, Nara (JP)

(73) Assignee: Sumitomo Dainippon Pharma Oncology, Inc., Cambridge, MA (US)

( * ) Notice: Subject to any disclaimer, the term of this patent is extended or adjusted under 35 U.S.C. 154(b) by 0 days.

(21) Appl. No.: 16/376,452

(22) Filed: Apr. 5, 2019

Related U.S. Application Data

(60) Provisional application No. 62/813,705, filed on Mar. 4, 2019, provisional application No. 62/778,856, filed on Dec. 12, 2018, provisional application No. 62/767,475, filed on Nov. 14, 2018, provisional application No. 62/760,882, filed on Nov. 13, 2018, provisional application No. 62/698,638, filed on Jul. 16, 2018, provisional application No. 62/695,609, filed on Jul. 9, 2018, provisional application No. 62/688,161, filed on Jun. 21, 2018, provisional application No. 62/678,980, filed on May 31, 2018, provisional application No. 62/663,146, filed on Apr. 26, 2018, provisional application No. 62/653,394, filed on Apr. 5, 2018.

(51) Int. Cl.
*A61K 31/506* (2006.01)
*C07D 403/12* (2006.01)
*A61P 35/02* (2006.01)
*A61K 31/519* (2006.01)

(52) U.S. Cl.
CPC .......... *A61K 31/506* (2013.01); *A61K 31/519* (2013.01); *A61P 35/02* (2018.01); *C07D 403/12* (2013.01); *C07B 2200/13* (2013.01)

(58) Field of Classification Search
CPC ............................ C07D 403/12; A61K 31/506
See application file for complete search history.

(56) References Cited

U.S. PATENT DOCUMENTS

| | | | |
|---|---|---|---|
| 5,310,763 A | 5/1994 | Campion et al. |
| 5,861,510 A | 1/1999 | Piscopio et al. |
| 5,863,949 A | 1/1999 | Robinson et al. |
| 5,932,595 A | 8/1999 | Bender et al. |
| 5,958,935 A | 9/1999 | Davis et al. |
| 6,077,864 A | 6/2000 | Burgess et al. |
| 6,087,392 A | 7/2000 | Reiter |
| 6,090,852 A | 7/2000 | Dack et al. |
| 6,110,964 A | 8/2000 | Robinson |
| 6,114,361 A | 9/2000 | Robinson et al. |
| 6,147,061 A | 11/2000 | Reiter |
| 6,153,609 A | 11/2000 | Robinson et al. |
| 6,169,088 B1 | 1/2001 | Matsuno et al. |
| 6,214,872 B1 | 4/2001 | Robinson |
| 6,303,636 B1 | 10/2001 | Robinson, Jr. et al. |
| 6,495,568 B1 | 12/2002 | Dack et al. |
| 6,511,993 B1 | 1/2003 | Dack et al. |
| 6,587,123 B2 | 7/2003 | Ando et al. |
| 6,599,890 B1 | 7/2003 | McClure et al. |
| 6,939,874 B2 | 9/2005 | Harmange et al. |
| 7,030,242 B2 | 4/2006 | Noe et al. |
| 7,282,504 B2 | 10/2007 | Armistead et al. |
| 7,411,001 B2 | 8/2008 | Barrett et al. |
| 7,514,446 B2 | 4/2009 | Davis-Ward et al. |
| 7,528,143 B2 | 5/2009 | Noronha et al. |
| 7,625,903 B2 | 12/2009 | Johnson et al. |
| 7,655,649 B2 | 2/2010 | Bilodeau et al. |
| 7,741,330 B1 | 6/2010 | Chen et al. |
| 7,834,024 B2 | 11/2010 | Li et al. |
| 7,893,074 B2 | 2/2011 | Garcia-Echeverria et al. |
| 7,943,627 B2 | 5/2011 | Baenteli et al. |
| 7,964,592 B2 | 6/2011 | Garcia-Echeverria et al. |
| 7,998,966 B2 | 8/2011 | Bearss et al. |
| 8,039,479 B2 | 10/2011 | Michellys et al. |
| 8,067,395 B2 | 11/2011 | Jankowski et al. |
| 8,133,900 B2 | 3/2012 | Hood et al. |
| 8,138,199 B2 | 3/2012 | Noronha et al. |
| 8,263,590 B2 | 9/2012 | Garcia-Echeverria et al. |
| 8,268,850 B2 | 9/2012 | Li et al. |
| 8,329,742 B2 | 12/2012 | Boivin et al. |
| 8,338,439 B2 | 12/2012 | Singh et al. |

(Continued)

FOREIGN PATENT DOCUMENTS

| | | |
|---|---|---|
| CN | 101657431 | 2/2010 |
| EP | 0 606 046 | 7/1994 |

(Continued)

OTHER PUBLICATIONS

PCT/US19/26094, Jun. 7, 2019, Invitation to Pay Additional Fees.

(Continued)

*Primary Examiner* — Golam M Shameem
(74) *Attorney, Agent, or Firm* — Hamilton, Brook, Smith & Reynolds, P.C.

(57) ABSTRACT

Tartrate salts of the compound of structure (I),

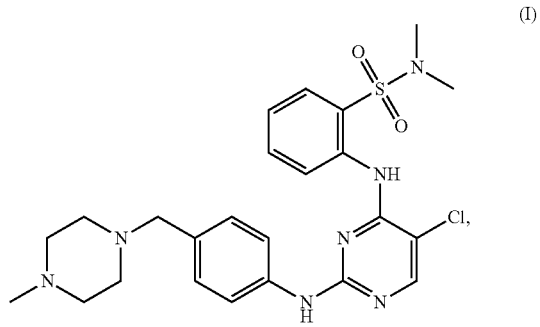

crystalline forms thereof, and therapeutic applications thereof for treating solid tumors (e.g., advanced solid tumor) or hematopoietic cancers. Also provided herein are methods for synthesizing the tartrate salts and the crystalline forms thereof.

11 Claims, 109 Drawing Sheets

(56) References Cited

U.S. PATENT DOCUMENTS

| | | | |
|---|---|---|---|
| 8,354,407 B2 | 1/2013 | Djung et al. |
| 8,377,921 B2 | 2/2013 | Michellys et al. |
| 8,431,694 B1 | 4/2013 | Babu et al. |
| 8,513,293 B2 | 8/2013 | Wallace et al. |
| 8,563,549 B2 | 10/2013 | Burger et al. |
| 8,604,014 B2 | 12/2013 | Belvin et al. |
| 8,604,042 B2 | 12/2013 | Noronha et al. |
| 8,642,624 B2 | 2/2014 | Chen et al. |
| 8,722,663 B2 | 5/2014 | Takasu et al. |
| 8,853,369 B2 | 10/2014 | Pei et al. |
| 8,901,120 B2 * | 12/2014 | Bearss ............... C07D 239/48 514/235.8 |
| 8,987,233 B2 | 3/2015 | Pan et al. |
| 9,040,549 B2 | 5/2015 | Bourke et al. |
| 9,133,134 B2 | 9/2015 | Chen et al. |
| 9,199,944 B2 | 12/2015 | Lee et al. |
| 9,206,176 B2 | 12/2015 | Bearss et al. |
| 9,409,911 B2 | 8/2016 | Honigberg et al. |
| 9,469,642 B2 | 10/2016 | Chen et al. |
| 9,481,654 B2 | 11/2016 | Li et al. |
| 9,540,385 B2 | 1/2017 | Chen et al. |
| 9,597,329 B2 | 3/2017 | Sebti et al. |
| 9,624,224 B2 | 4/2017 | Chen et al. |
| 9,637,487 B2 | 5/2017 | Chen et al. |
| 9,708,326 B2 | 7/2017 | Chen et al. |
| 9,714,247 B2 | 7/2017 | Zeng et al. |
| 9,745,319 B2 | 8/2017 | Ren et al. |
| 9,758,539 B2 | 9/2017 | Siddiqui-Jain et al. |
| 9,795,605 B2 | 10/2017 | Buggy et al. |
| 9,862,722 B2 | 1/2018 | Chen et al. |
| 9,913,842 B2 | 3/2018 | Singh et al. |
| 9,980,964 B2 | 5/2018 | Haq et al. |
| 9,987,276 B2 | 6/2018 | Singh et al. |
| 10,016,435 B2 | 7/2018 | Buggy et al. |
| 10,125,140 B1 | 11/2018 | Purro et al. |
| 10,202,356 B2 | 2/2019 | Mollard et al. |
| 2003/0166620 A1 | 9/2003 | Lee et al. |
| 2005/0012070 A1 | 1/2005 | Inoue et al. |
| 2005/0171134 A1 | 8/2005 | Davis et al. |
| 2005/0227992 A1 | 10/2005 | Hurley et al. |
| 2006/0270694 A1 | 11/2006 | Wong |
| 2007/0032514 A1 | 2/2007 | Zahn et al. |
| 2007/0105839 A1 | 5/2007 | Imbach et al. |
| 2007/0191405 A1 | 8/2007 | Noronha et al. |
| 2008/0182852 A1 | 7/2008 | Johnson et al. |
| 2008/0214558 A1 | 9/2008 | Vankayalapati et al. |
| 2009/0054428 A1 | 2/2009 | Barlaam et al. |
| 2009/0298830 A1 | 12/2009 | Mann et al. |
| 2010/0029675 A1 | 2/2010 | Hwang |
| 2010/0190770 A1 | 7/2010 | Li et al. |
| 2010/0204221 A1 | 8/2010 | Vankayalapati et al. |
| 2010/0331350 A1 | 12/2010 | Honigberg et al. |
| 2011/0028405 A1 | 2/2011 | Harrison et al. |
| 2011/0098280 A1 | 4/2011 | Garcia-Echeverria et al. |
| 2011/0230476 A1 | 9/2011 | Niu et al. |
| 2011/0269721 A1 | 11/2011 | Hood |
| 2012/0040955 A1 | 2/2012 | Harrison et al. |
| 2012/0238540 A1 | 9/2012 | Holcomb et al. |
| 2012/0252821 A1 | 10/2012 | Honigberg et al. |
| 2012/0277254 A1 | 11/2012 | Honigberg et al. |
| 2012/0283276 A1 | 11/2012 | Honigberg et al. |
| 2012/0283277 A1 | 11/2012 | Honigberg et al. |
| 2013/0012525 A1 | 1/2013 | Honigberg et al. |
| 2013/0035334 A1 | 2/2013 | Honigberg et al. |
| 2013/0197014 A1 | 8/2013 | Chen et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0039168 A1 | 2/2014 | Birau et al. |
| 2014/0057907 A1 | 2/2014 | Honigberg et al. |
| 2014/0079690 A1 | 3/2014 | Buggy et al. |
| 2014/0080844 A1 | 3/2014 | Chen et al. |
| 2014/0128413 A1 | 5/2014 | Honigberg et al. |
| 2014/0128414 A1 | 5/2014 | Honigberg et al. |
| 2014/0135347 A1 | 5/2014 | Honigberg et al. |
| 2014/0142123 A1 | 5/2014 | Honigberg et al. |
| 2014/0142126 A1 | 5/2014 | Chen et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0187564 A1 | 7/2014 | Honigberg et al. |
| 2014/0187565 A1 | 7/2014 | Honigberg et al. |
| 2014/0194446 A1 | 7/2014 | Buggy et al. |
| 2014/0212485 A1 | 7/2014 | Honigberg et al. |
| 2014/0243355 A1 | 8/2014 | Honigberg et al. |
| 2014/0336206 A1 | 11/2014 | Honigberg et al. |
| 2015/0018336 A1 | 1/2015 | Chen et al. |
| 2015/0184249 A1 | 7/2015 | Chang et al. |
| 2015/0273033 A1 | 10/2015 | Bosch et al. |
| 2015/0374694 A1 | 12/2015 | Boden et al. |
| 2016/0022683 A1 | 1/2016 | Fardis et al. |
| 2016/0287592 A1 | 10/2016 | Chang et al. |
| 2017/0246167 A1 | 8/2017 | Singh et al. |
| 2017/0266186 A1 | 9/2017 | Buggy et al. |
| 2017/0369451 A1 | 12/2017 | Allwein et al. |
| 2019/0119221 A1 | 4/2019 | Mollard et al. |

FOREIGN PATENT DOCUMENTS

| | | |
|---|---|---|
| EP | 0 818 442 | 1/1998 |
| JP | 4607879 B2 | 1/2011 |
| JP | 4796487 B2 | 10/2011 |
| RU | 2 343 148 | 1/2009 |
| WO | WO 1996/33980 A1 | 10/1996 |
| WO | WO 1998/034915 | 8/1998 |
| WO | WO 2000/035436 | 6/2000 |
| WO | WO 2001/060816 A1 | 8/2001 |
| WO | WO 2002/016351 A1 | 2/2002 |
| WO | WO 2003/095448 | 11/2003 |
| WO | WO 2004/058772 A1 | 7/2004 |
| WO | WO 2005/016894 A1 | 2/2005 |
| WO | WO 2005/037825 A2 | 4/2005 |
| WO | WO 2005/082892 | 9/2005 |
| WO | WO 2006/054652 A1 | 5/2006 |
| WO | WO 2006/116733 A2 | 11/2006 |
| WO | WO 2006/124874 | 11/2006 |
| WO | WO 2007/014011 | 2/2007 |
| WO | WO 2007/020888 A1 | 2/2007 |
| WO | WO 2007/053452 A1 | 5/2007 |
| WO | WO 2008/055233 A1 | 5/2008 |
| WO | WO 2008/092049 A1 | 7/2008 |
| WO | WO 2008/106635 A1 | 9/2008 |
| WO | WO 2008/121742 | 10/2008 |
| WO | WO 2008/124085 | 10/2008 |
| WO | WO 2008/128072 A3 | 12/2008 |
| WO | WO 2012/135800 A1 | 10/2012 |
| WO | WO 2012/135801 A1 | 10/2012 |
| WO | WO 2013/064068 | 5/2013 |
| WO | WO 2014/025486 | 2/2014 |
| WO | WO 2014/152588 | 9/2014 |
| WO | WO 2014/151871 A9 | 12/2014 |
| WO | WO 2015/054572 | 4/2015 |
| WO | WO 2017/091546 A1 | 6/2017 |
| WO | WO 2019/195753 A1 | 10/2019 |

OTHER PUBLICATIONS

Invitation to Pay Additional Fees for International Application No. PCT/US19/26094 dated Jun. 7, 2019.

Ahn et al., Synthesis and Antiproliferative Activity of Pyridinylcarbonylpyrimidines Against Melanoma Cell Line, *Bull. Korean Chem. Soc.* 32(4):1209-1214, 2011.

Alessi et al., Mechanism of Activation of Protein Kinase B by Insulin and IGF-1, *The EMBO Journal* 15(23):6541-6551, 1996.

Anderton et al., Induction of Heart Valve Lesions by Small-Molecule ALK5 Inhibitors, *Toxicologic Pathology* 39(6):916-924, 2011.

Angelillo-Scherrer et al., Role of Gas6 in Erythropoiesis and Anemia in Mice, *J. Clin. Invest.* 118(2):583-596, 2008.

Barlaam et al., Inhibitors of the tyrosine kinase EphB4. Part 4: Discovery and optimization of a benzylic alcohol series, *Bioorganic & Medicinal Chemistry Letters* 21:2207-2211, 2011.

(56) References Cited

OTHER PUBLICATIONS

Baxter et al., Acquired mutation of the tyrosine kinase JAK2 in human myeloproliferative disorders, *Lancet* 365(9464):1054-1061, 2005.
Bellido-Martin et al., Vitamin K-dependent actions of Gas6, *Vitam. Horm.* 78:185-209, 2008.
Bellosta et al., Signaling Through the ARK Tyrosine Kinase Receptor Protects From Apoptosis in the Absence of Growth Stimulation, *Oncogene* 15:2387-2397, 1997.
Bellosta et al., The Receptor Tyrosine Kinase ARK mediates Cell Aggregation by Homophilic Binding, *Molecular and Cellular Biology* 15(2):614-625, 1995.
Benekli et al., Signal transducer and activator of transcription proteins in leukemias, *Blood* 101(8):2940-2954, 2003.
Blume-Jensen et al., Oncogene Kinase Signaling, *Nature* 411:355-365, 2001.
Braunger et al., Intracellular Signaling of the Ufo/Axl Receptor Tyrosine Kinase is Mediated Mainly by a Multi-Substrate Docking Site, *Oncogene* 14(22):2619-2631, 1997.
Breslin et al., Design, Synthesis, and Anaplastic Lymphoma Kinase (ALK) Inhibitory Activity for a Novel Serial of 2,4,8,22-Tetraazatetracyclo[14.3.1.1.3,7.19,13]-docosa-1(20),3(22),4,6,9(21),10,12, 16,18-nonaene Macrocycles, *Journal of Medicinal Chemistry* 55:449-464, 2012.
Brunetto et al., First-in-human, Pharmacokinetic and Pharmacodynamic Phase I Study of Resminostat, an Oral Histone Deacetylase Inhibitor, in Patients with Advanced Solid Tumors, *Clin. Cancer Res.* 19(19):5494-5504, 2013. (20 pages).
Buchanan et al., Discovery of 2,4-bis-arylamino-1,3-pyrimidines as insulin-like growth factor-1 receptor (IFG-1R) inhibitors, *Bioorganic & Medicinal Chemistry Letters* 21:2394-2399, 2011.
Buggy et al., CRA-024781: a novel synthetic inhibitor of histone deacetylase enzymes with antitumor activity in vitro and in vivo, *Mol. Cancer Ther.* 5(5):1309-1317, 2006. (9 pages).
CAS Registry No. 1192474-26-2, Benzeneethanol, 3-bromo-5-[[5-chloro-4-[(3-hydroxyphenyl)amino]-2-pyrimidinyl]amino]-, Feb. 7, 2010, 67 pages.
CAS Registry No. 1251954-86-5, Benzamide, 3-[[4-[2-amino-3-flurophenyl)amino]-5-chloro-2-pyrimidinyl]amino]-N-ethyl-4-fluoro-, Nov. 9, 2010, 11 pages.
CAS Registry No. 698998-35-5, 2,4-Pyrimidinediamine, 5-bromo-N2-(3,4-dimethoxyphenyl)-N4-[4-(1H-pyrazol-3-yl)phenyl]-, Jun. 25, 2004, 1 page.
CAS Registry No. 794466-29-8, 2,4-Pyrimidinediamine, 5-bromo-N4[2-(4-morpholinyl)phenyl]-N2-(3,4,5-trimethoxyphenyl)-, Dec. 8, 2004, 1 page.
Choi et al., Design and synthesis of 7H-pyrrolo[2,3-d]pyrimidines as focal adhesion kinase inhibitors. Part 1, *Bioorganic & Medicinal Chemistry Letters* 16:2173-2176, 2006.
Compound Summary for CID 49702158, Pub Chem, Dec. 23, 2015, 10 pages.
Compound Summary for CID 69861127, PubChem, Dec. 23, 2015, 11 pages.
Compound Summary for CID 69898605, PubChem, Dec. 23, 2015, 11 pages.
Ember et al., Acetyl-lysine Binding Site of Bromodomain-Containing Protein 4 (BRD4) Interacts with Diverse Kinase Inhibitors, *ACS Chem. Biol.* 9(5):1160-1171, 2014.
Filippakopoulos et al., Selective inhibition of BET bromodomains, *Nature* 468(7327):1067-1073, 2010.
Fish et al., Identification of a Chemical Probe for Bromo and Extra C-Terminal Bromodomain Inhibition through Optimization of a Fragment-Derived Hit, *J. Med. Chem.* 55(22):9831-9837, 2012.
Fridell et al., GAS6 induces AXL-Mediated Chemotaxis of Vascular Smooth Muscle Cells, *The Journal of Biological Chemistry* 273:7123-7126, 1998.
Fruman et al., Xid-like phenotypes: a B Cell Signalosome Takes Shape, *Immunity* 13(1):1-3, 2000.
Fry, Phosphoinositide 3-kinase signalling in breast cancer: how big a role might it play? *Breast Cancer Res* 3:304-312, 2001.

Giles et al., A Phase I Study of Intravenous LBH589, a Novel Cinnamic Hydroxamic Acid Analogue Histone Deacetylase Inhibitor, in Patients with Refractory Hematologic Malignancies, *Clin. Cancer Res.* 12(15):4628-4635, 2006.
Goldberg et al., Rapid generation of a high quality lead for transforming growth factor-beta (TGF-beta) type I receptor (ALK5), *J. Med. Chem* 52:7901-7905, 2009.
Göttlicher et al., Valproic acid defines a novel class of HDAC inhibitors inducing differentiation of transformed cells, *EMBO J.* 20(24):6969-6978, 2001.
Gould et al., Gas6 receptors Axl, Sky and Mer enhance platelet activation and regulate thrombotic responses, *Journal of Thrombosis and Haemostasis* 3(4):733-741, 2005.
Graham et al., Cloning and mRNA expression analysis of a novel human protooncogene, c-mer, *Cell Growth and Differentiation* 5:647-657, 1994.
Green et al., Overexpression of the Axl tyrosine kinase receptor in cutaneous SCC-derived cell lines and tumours, *Journal of Cancer* 94:1446-1451, 2006.
Gura et al., Systems for identifying new drugs are often faulty, *Science* 278:1041-1042, 1997.
Hafizi et al., Gas6 and protein S. Vitamin K-dependent ligands for the Axl receptor tyrosine kinase subfamily, *FEBS Journal* 273(23):5231-5244, 2006.
Hafizi et al., Interaction of Axl receptor tyrosine kinase with C1-TEN, a novel C1 domain-containing protein with homology to tensin, *Biochemical and Biophysical Research Communications* 299:793-800, 2002.
Hafizi et al., Signaling and functional diversity within the Axl subfamily of receptor tyrosine kinases, *Cytokine & Growth Factor Reviews* 17:295-304, 2006.
Hallek et al., iwCLL guidelines for diagnosis, indications for treatment, response assessment, and supportive management of CLL, *Blood* 131(25):2745-2760, 2018.
Hanada et al., Structure, regulation and function of PKB/AKT—a major therapeutic target, *Biochimica et Biophysica Acta* 1697:3-16, 2004.
Hendriks, Drug discovery: New Btk inhibitor holds promise, *Nat. Chem. Biol* 7(1):4-5, 2011.
Hubbard et al., Protein Tyrosine Kinase Structure and Function, *Annual Review of Biochemistry* 69:373-398, 2000.
Hughes et al., 4-Aryl-5-cyano-2-aminopyrimidines as VEGF-R2 inhibitors: Synthesis and biological evaluation, *Bioorganic & Medicinal Chemistry Letters* 17:3266-3270, 2007.
James et al., A unique clonal JAK2 mutation leading to constitutive signalling causes polycythaemia vera, *Nature* 434:1144-1148, 2005.
Johnson et al., Relationships between drug activity in NCI preclinical in vitro and in vivo models and early clinical trials, *British Journal of Cancer* 84(10):1424-1431, 2001.
Keating et al., Lymphoblastic leukemia/lymphoma in mice overexpressing the Mer (MerTK) receptor tyrosine kinase, *Oncogene* 25:6092-6100, 2006.
Knutson et al., Synergistic Anti-Tumor Activity of EZH2 Inhibitors and Glucocorticoid Receptor Agonists in Models of Germinal Center Non-Hodgkin Lymphomas, *PLoS One* 9(12):e111840, 2014. (22 pages).
Korshunov et al., Axl mediates vascular remodeling induced by deoxycorticosterone acetate-salt hypertension, *Hypertension* 50:1057-1062, 2007.
Korshunov et al., Axl, a receptor tyrosine kinase, mediates flow-induced vascular remodeling, *Circulation Research* 98:1446-1452, 2006.
Kurosaki, Functional dissection of BCR signaling pathways, *Curr. Opin. Immunol.* 12:276-281, 2000.
Lemke et al., Immunobiology of the TAM receptors, *Nature Reviews Immunology* 8:327-336, 2008.
Levine et al., Activating mutation in the tyrosine kinase JAK2 in polycythemia vera, essential thrombocythemia and myeloid metaplasia with myelofibrosis, *Cancer Cell* 7:387-397, 2005.
Li et al., Axl as a potential therapeutic target in cancer: role of Axl in tumor growth, metastasis and angiogenesis, *Oncogene* 28:3442-3455, 2009.

(56) References Cited

OTHER PUBLICATIONS

Linger et al., TAM receptor tyrosine kinases: biologic functions, signaling, and potential therapeutic targeting in human cancer, *Advanced Cancer Research* 100:35-83, 2008.

Malani et al., Synthesis, characterization and in vitro screening on bacterial, fungal and malarial strain of piprazinyl cyano biphenyl based compounds, *Bioorg Chemistry* 51:16-23, 2013.

Manfioletti et al., The protein encoded by a growth arrest-specific gene (gas6) is a new member of the vitamin K-dependent proteins related to protein S, a negative coregulator in the blood coagulation cascade, *Molecular and Cellular Biology* 13(8):4976-4985, 1993.

Manning et al., Evolution of protein kinase signaling from yeast to man, *TRENDS in Biochemical Sciences* 27(10):514-520, 2002.

Mark et al., rse, a novel receptor-type tyrosine kinase with homology to Axl/Ufo, is expressed at high levels in the brain, *Journal of Biological Chemistry* 269:10720-10728, 1994.

Mazzacurati et al., The PIM inhibitor AZD1208 synergizes with ruxolitinib to induce apoptosis of ruxolitinib sensitive and resistant JAK2-V617F-driven cells and inhibit colony formation of primary MPN cells, *Oncotarget* 6(37):40141-40157, 2015.

Mollard et al., Design, Synthesis and Biological Evaluation of a Series of Novel Axl Kinase Inhibitors, *ACS Medicinal Chemistry Letters* 2:907-912, 2011.

Myers et al., AXL Inhibitors in Cancer: A Medicinal Chemistry Perspective, *J. Med. Chem.* 59(8):3593-3608, 2016.

Noel et al., Abstract C244: Development of the BET bromodomain inhibitor OTX015, *Mol. Cancer Ther.* 12(11), 2013. (4 pages).

Paquin et al., Design and synthesis of 4-[(s-triazin-2-ylamino)methyl]-N-(2-aminophenyl)-benzamides and their analogues as a novel class of histone deacetylase inhibitors, *Bioorg. Med. Chem. Lett.* 18(3):1067-1071, 2008.

Parry et al., Dinaciclib (SCH 727965), a Novel and Potent Cyclin-Dependent Kinase Inhibitor, *Mol. Cancer Ther.* 9(8):2344-2353, 2010.

Paruch et al., Discovery of Dinaciclib (SCH 727965): A Potent and Selective Inhibitor of Cyclin-Dependent Kinases, *ACS Med. Chem. Lett.* 1(5):204-208, 2010.

Pearce et al., 18. Failure modes in anticancer drug discovery and development, in Neidle (ed.), *Cancer Drug Design and Discovery*, Elsevier, 2008, pp. 424-435.

Peeters et al., Fusion of TEL, the ETS-Variant Gene 6 (ETV6), to the Receptor-Associated Kinase JAK2 as a Result of t(9; 12) in a Lymphoid and t(9; 15; 12) in a Myeloid Leukemia, *Blood* 90(7):2535-2540, 1997.

Picaud et al., PFI-1—a highly Selective Protein Interaction Inhibitor, Targeting BET Bromodomains, *Cancer Res.* 73(11):3336-3346, 2013. (20 pages).

Piekarz et al., Inhibitor of histone deacetylation, depsipeptide (FR901228), in the treatment of peripheral and cutaneous T-cell lymphoma: a case report, *Blood* 98(9):2865-2868, 2001.

Plumb et al., Pharmacodynamic Response and Inhibition of Growth of Human Tumor Xenografts by the Novel Histone Deacetylase Inhibitor PXD101, *Mol. Cancer Ther.* 2(8):721-728, 2003.

Reiter et al., The t(8;9)(p22;p24) Is a Recurrent Abnormality in Chronic and Acute Leukemia that Fuses PCM1 to JAK2, *Cancer Res* 65(7):2662-2667, 2005.

Rescigno et al., A putative receptor tyrosine kinase with unique structural topology, *Oncogene* 6(10):1909-1913, 1991.

Richon et al., A class of hybrid polar inducers of transformed cell differentiation inhibits histone deacetylases, *Proc. Natl. Acad. Sci. USA* 95(6):3003-3007, 1998.

Robinson et al., The protein tyrosine kinase family of the human genome, *Oncogene* 19(49):5548-5557, 2000.

Rothlin et al., TAM receptors are pleiotropic inhibitors of the innate immune response, *Cell* 131:1124-1136, 2007.

Sainaghi et la., Gas6 induces proliferation in prostate carcinoma cell lines expressing the Axl receptor, *Journal of Cell Physiology* 204(1):36-44, 2005.

Saito et al., A synthetic inhibitor of histone deacetylase, MS-27-275, with marked in vivo antitumor activity against human tumors, *Proc. Natl. Acad. Sci. USA* 96(8):4592-4597, 1999.

Sawabu et al., Growth arrest-specific gene 6 and Axl signaling enhances gastric cancer cell survival via Akt pathway, *Mol. Carcinog.* 46(2):155-164, 2007.

Schaeffer et al., Tec family kinases in lymphocyte signaling and function, *Curr. Opin. Immunol.* 12(3):282-288, 2000.

Seal et al., Identification of a novel series of BET family bromodomain inhibitors: binding mode and profile of I-BET151 (GSK1210151A), *Bioorg. Med. Chem. Lett.* 22(8):2968-2972, 2012.

Shankar et al., Gas6/Axl signaling activates the phosphatidylinositol 3-kinase/Akt1 survival pathway to protect oligodendrocytes from tumor necrosis factor alpha-induced apoptosis, *The Journal of Neuroscience* 26(21):5638-5648, 2006.

Shannon et al., JAKing up hematopoietic proliferation, *Cancer Cell* 7(4):291-293, 2005.

Sharif et al., Twist mediates suppression of inflammation by type I IFNs and Axl, *The Journal of Experimental Medicine* 203(8):1891-1901, 2006.

Shieh et al., Expression of axl in lung adenocarcinoma and correlation with tumor progression, *Neoplasia* 7(12):1058-1064, 2005.

Simone, *Oncology: Introduction*, Cecil Textbook of Medicine, 20th Edition, vol. 1, pp. 1004-1010, 1996.

Sinha et al., Axl Inhibition Primes Chronic Lymphocytic Leukemia B Cells to Apoptosis and Shows Synergistic/Additive Effects in Combination with BTK Inhibitors, *Clin. Cancer Res.* 21(9):2115-2126, 2015.

Sun et al., Clinical implications of coexpression of growth arrest-specific gene 6 and receptor tyrosine kinases Axl and Sky in human uterine leiomyoma, *Molecular Human Reproduction* 9(11):701-707, 2003.

Takemoto et al., Proliferation of adult T cell leukemia/lymphoma cells is associated with the constitutive activation of JAK/STAT proteins, *Proc. Natl Acad. Sci. USA* 94:13897-13902, 1997.

Thompson et al., Minimal Residual Disease in Chronic Lymphocytic Leukemia in the Era of Novel Agents, *JAMA Oncol.* 4(3):394-400, 2018.

Toogood et al., Discovery of a Potent and Selective Inhibitor of Cyclin-Dependent Kinase 4/6, *J. Med. Chem.* 48(7):2388-2406, 2005.

Traxler, Protein Tyrosine Kinase Inhibitors in Cancer Treatment, *Exp. Opin. Ther. Patents* 7(6):571-588, 1997.

Ulrich, Crystallization, *Kirk-Othmer Encyclopedia of Chemical Technology*:3-26, 2002.

Vajkoczy et al., Dominant-negative inhibition of the Axl receptor tyrosine kinase suppresses brain tumor cell growth and invasion and prolongs survival, *PNAS* 103(15):5799-5804, 2006.

Venugopal et al., A Phase I Study of Quisinostat (JNJ-26481585), an Oral Hydroxamate Histone Deacetylase Inhibitor with Evidence of Target Modulation and Antitumor Activity, in Patients with Advanced Solid Tumors, *Clin. Cancer Res.* 19(15):4262-4272, 2013.

Vippagunta et al., Crystalline solids, *Advanced Drug Delivery Reviews* 48:3-26, 2001.

Walz et al., Activated JAK2 with the V617F Point Mutation Promotes G1/S Phase Transition, *J. Biol Chem* 281:18177-18183, 2006.

Wang et al., TIG1 Promotes the Development and Progression of Inflammatory Breast Cancer through Activation of Axl Kinase, *Cancer Res.* 73(21):6516-6525, 2013. (22 pages).

Wyatt et al., Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design, *J. Med. Chem.* 51(16):4986-4999, 2008.

Zenkl et al., Sugar-responsive fluorescent nanospheres, *Macromol. Biosci.* 8:146-152, 2008.

Zhao et al., The Making of I-BET762, a BET Bromodomain Inhibitor Now in Clinical Development, *J. Med. Chem.* 56(19):7498-7500, 2013.

International Search Report and Written Opinion, dated Oct. 20, 2014, in connect with International Application No. PCT/US2014/026595.

(56) References Cited

OTHER PUBLICATIONS

International Search Report and Written Opinion, dated Aug. 6, 2019, in connect with International Application No. PCT/US2019/026094.

International Preliminary Report on Patentability (Chapter II Demand), dated Apr. 24, 2020 in connect with International Application No. PCT/US2019/026094.

Corrected International Preliminary Report on Patentability (Chapter II Demand), dated Aug. 12, 2020 in connect with International Application No. PCT/US2019/026094.

[No Author Listed] Pubchem CID 132131624, 2-[[2-[[4-(Aminomethyl)phenyl]amino]-5-chloro-4-pyrimidinyl]amino]-N-methylbenzenesulfonamide, created Jan. 28, 2017, 6 pages.

[No Author Listed] Pubchem CID 20615641, 4-[[4-(4-Sulfoanilino)pyrimidin-2-yl]amino]benzoic acid, created Dec. 5, 2007—5 pages.

[No Author Listed] Pubchem CID 56839178, TP-0903, Created Mar. 19, 2012, 13 pages.

Guo et al., Axl Inhibition Induces the Antitumor Immune Response Which Can Be Further Potentiated by PD-1 Blockade in the Mouse Cancer Models. Oncotarget, 8(52):89761-8977 (2017).

Matsuno et al., Potent and Selective Inhibitors of Platelet-Derived Growth Factor Receptor Phosphorylation. 1. Synthesis, Structure-Activity Relationship, and Biological Effects of a New Class of Quinazoline Derivatives. Journal of Medicinal Chemistry, 45(14):3057-3066 (2002).

Robertson et al, A Comparison of the Requirements for Antitumour Activity and Antibacteriophage Lambda Activity for a Series of Non-Intercalative DNA-Binding Agents. European Journal of Cancer and Clinical Oncology 18(3):271-279 (1982).

Singh et al, Chemotherapy of Filariasis—On the Search of New Agents Effective on the Reproductive System of Female Adult Worms. Zeitschrift Feur Naturforschung, Section C, Biosciences, 45(11/12):1210-1214 (1990).

Warner et al., Identification of a Lead Small-Molecule Inhibitor of the Aurora Kinases Using a Structure-Assisted, Fragment-Based Approach. Molecular Cancer Therapeutics, 5(7):1764-1773 (2006).

* cited by examiner

Table 1: Selected gene list of RA and Compound of Structure (I) responding genes

|         | Untreated | RA    | RA + Cmpd of Str (I) | Cmpd of Str (I) |
|---------|-----------|-------|----------------------|-----------------|
| ADH1A   | 1.0       | 1.7   | 3.5                  | 0.2             |
| APOA2   | 1.0       | 1.1   | 3.2                  | 2.3             |
| ALDH1A2 | 1.0       | 3.1   | 5.7                  | 1.4             |
| CD38    | 1.0       | 138.0 | 6.6                  | 0.6             |
| CYP26A1 | 1.0       | 166.2 | 18.1                 | 1.1             |
| CYP26B1 | 1.0       | 13.5  | 2.4                  | 0.4             |
| DHRS3   | 1.0       | 702.7 | 11.2                 |                 |
| DLX5    | 1.0       | 18.4  | 4.2                  | 1.8             |
| EGR1    | 1.0       | 0.4   | 6.0                  | 1.6             |
| FOXA1   | 1.0       | 1.9   | 5.0                  | 2.3             |
| HNP1B   | 1.0       | 0.5   | 2.8                  | 0.1             |
| HSD17B2 | 1.0       | 1.3   | 5.6                  | 0.4             |
| ISL1    | 1.0       | 1.2   | 4.0                  | 0.0             |
| LHX1    | 1.0       | 0.6   | 3.1                  | 0.6             |
| PPARG   | 1.0       | 1.3   | 2.2                  | 0.2             |
| RARA    | 1.0       | 1.0   | 0.8                  | 1.2             |
| RBP4    | 1.0       | 3.0   | 8.1                  | 0.8             |
| RXRG    | 1.0       | 1.3   | 7.8                  | 0.3             |
| SHH     | 1.0       | 1.2   | 3.9                  | 0.4             |
| STRA6   | 1.0       | 2.4   | 2.8                  | 0.4             |
| TGM2    | 1.0       | 341.8 | 9.7                  | 1.5             |
| UCP1    | 1.0       | 1.6   | 4.5                  | 2.2             |

Fig. 29

➤ Proliferation assay

A2780cis, 3days after treatment

\*\*P<0.01. \*\*\*P<0.001 vs Vehicle
Dunnett's test

| D Value | Relative Intensity | D Value | Relative Intensity |
|---|---|---|---|
| 6.850 | 11.30% | 22.447 | 9.50% |
| 7.031 | 50.00% | 22.690 | 26.30% |
| 7.492 | 57.40% | 22.775 | 28.10% |
| 8.163 | 10.30% | 23.217 | 12.50% |
| 8.677 | 19.20% | 23.584 | 15.90% |
| 9.500 | 10.30% | 24.227 | 4.60% |
| 9.884 | 32.80% | 25.058 | 4.50% |
| 10.300 | 29.40% | 25.617 | 41.00% |
| 10.744 | 20.6 % | 26.089 | 9.8 % |
| 11.289 | 100.00% | 26.626 | 3.9 % |
| 12.440 | 2.50% | 26.984 | 16.1 % |
| 12.814 | 11.80% | 27.498 | 19.3 % |
| 13.299 | 14.10% | 27.528 | 20.8 % |
| 13.731 | 17.60% | 28.258 | 17.6 % |
| 14.027 | 3.70% | 28.653 | 9.1 % |
| 14.483 | 26.90% | 29.036 | 3.2 % |
| 14.638 | 14.00% | 29.517 | 3.6 % |
| 15.000 | 15.80% | 30.041 | 4.4 % |
| 15.421 | 64.00% | 30.136 | 6.1 % |
| 15.744 | 6.80% | 30.560 | 6.0 % |
| 16.060 | 8.00% | 31.052 | 13.2 % |
| 16.341 | 41.70% | 31.473 | 4.3 % |
| 17.093 | 29.80% | 32.064 | 2.9 % |
| 17.404 | 37.30% | 32.438 | 6.5 % |
| 17.589 | 24.60% | 33.380 | 5.3 % |
| 18.323 | 23.80% | 34.574 | 3.2 % |
| 18.909 | 25.10% | 37.489 | 3.2 % |
| 18.986 | 25.30% | | |
| 19.328 | 23.0 % | | |
| 19.930 | 59.00% | | |
| 20.194 | 17.00% | | |
| 20.520 | 24.80% | | |
| 20.743 | 22.00% | | |
| 21.241 | 9.60% | | |
| 21.669 | 26.20% | | |

Fig. 94

| D Value | Relative Intensity |
|---|---|
| 6.823 | 3.6 % |
| 7.012 | 19.8 % |
| 7.601 | 100.0 % |
| 8.243 | 32.1 % |
| 8.478 | 7.8 % |
| 8.674 | 6.1 % |
| 9.827 | 45.3 % |
| 10.544 | 5.8 % |
| 10.812 | 6.2 % |
| 11.320 | 33.2 % |
| 12.007 | 7.6 % |
| 12.809 | 68.7 % |
| 13.726 | 4.4 % |
| 13.959 | 11.6 % |
| 14.466 | 9.2 % |
| 14.987 | 30.6 % |
| 15.315 | 16.1 % |
| 15.377 | 22.1 % |
| 15.762 | 3.7 % |
| 16.313 | 12.4 % |
| 17.051 | 15.3 % |
| 17.378 | 76.1 % |
| 17.667 | 37.2 % |
| 18.896 | 65.4 % |
| 19.428 | 21.5 % |
| 19.777 | 9.2 % |
| 19.895 | 14.3 % |
| 20.511 | 6.9 % |
| 20.769 | 5.3 % |
| 21.660 | 28.0 % |
| 22.747 | 17.9 % |

Fig. 96

| Form | DSC Peak (°C) | DSC Onset (°C) | DSC ΔHf (J/g) | TGA Weight Change (%) |
|---|---|---|---|---|
| Form A' | 182.31 | 170.52 | 78.40 | 5.166 |

| Form | DSC Peak (°C) | DSC Onset (°C) | DSC ΔHf (J/g) | TGA Weight Change (%) |
|---|---|---|---|---|
| Form A | 189.72 | 187.06 | 128.0 | 2.917 |

| Form | DSC Peak (°C) | DSC Onset (°C) | DSC ΔHf (J/g) | TGA Weight Change (%) |
|---|---|---|---|---|
| Form B | 142.03 | 131.62 | 35.30 | 4.398 |

| Form | DSC Peak (°C) | DSC Onset (°C) | DSC ΔHf (J/g) | TGA Weight Change (%) |
|---|---|---|---|---|
| Form D | 146.41 | 127.43 | 35.44 | 3.142 |

| Form | DSC Peak (°C) | DSC Onset (°C) | DSC ΔHf (J/g) | TGA Weight Change (%) |
|---|---|---|---|---|
| Form E | 122.63 | 102.33 | 71.64 | 4.108 |

| Form | DSC Peak (°C) | DSC Onset (°C) | DSC ΔHf (J/g) | TGA Weight Change (%) |
|---|---|---|---|---|
| Form F | 107.70 | 61.06 | 114.6 | 4.561 |

| Form | DSC Peak (°C) | DSC Onset (°C) | DSC ΔHf (J/g) | TGA Weight Change (%) |
|---|---|---|---|---|
| Form G | 137.83 | 128.61 | 39.83 | 2.538 |

| Form | DSC Peak (°C) | DSC Onset (°C) | DSC ΔHf (J/g) | TGA Weight Change (%) |
|---|---|---|---|---|
| Form H | 147.24 | 139.36 | 34.84 | 3.718 |

| Form | DSC Peak (°C) | DSC Onset (°C) | DSC ΔHf (J/g) | TGA Weight Change (%) |
|---|---|---|---|---|
| Form I | 124.34 | 118.60 | 29.58 | 3.628 |

| Cell Line | KRAS Status | IC50 |
|---|---|---|
| HCT-15 | WT | 109 nM |
| HT-29 | WT | 84 nM |
| SW-480 | G12V | 108 nM |
| COLO-205 | WT | 123 nM |
| HCT-116 | G13D | 4.5 nM |

Form A

Form D

AXL KINASE INHIBITORS AND USE OF THE SAME

CROSS-REFERENCE

This application claims priority under 35 U.S.C. § 119(e) to U.S. Provisional Application, U.S. Ser. No. 62/813,705, filed Mar. 4, 2019, U.S. Provisional Application, U.S. Ser. No. 62/778,856, filed Dec. 12, 2018, U.S. Provisional Application, U.S. Ser. No. 62/767,475, filed Nov. 14, 2018, U.S. Provisional Application, U.S. Ser. No. 62/760,882, filed Nov. 13, 2018, U.S. Provisional Application, U.S. Ser. No. 62/698,638, filed Jul. 16, 2018, U.S. Provisional Application, U.S. Ser. No. 62/695,609, filed Jul. 9, 2018, U.S. Provisional Application, U.S. Ser. No. 62/688,161, filed Jun. 21, 2018, U.S. Provisional Application, U.S. Ser. No. 62/678,980, filed May 31, 2018, U.S. Provisional Application, U.S. Ser. No. 62/663,146, filed Apr. 26, 2018, and U.S. Provisional Application, U.S. Ser. No. 62/653,394, filed Apr. 5, 2018, the entire contents of each of which are incorporated by reference herein.

BACKGROUND OF THE INVENTION

AXL is a cell surface receptor tyrosine kinase of the TAM family. The AXL receptor binds growth factors like vitamin K-dependent protein growth-arrest-specific gene 6 (GAS6) and transduces signals from the extracellular matrix into the cytoplasm. It is reported that AXL is an inhibitor of the innate immune response and may play a role in multiple cellular processes relating to cell growth and development.

AXL is found to be involved in various aspects of tumor growth, including cancer cell proliferation, invasiveness and migration, as well as sternness, angiogenesis, and immune modulation. As such, AXL becomes a promising cancer treatment target.

SUMMARY OF THE INVENTION

In one aspect, the present disclosure provides a tartrate salt of the compound of structure (I):

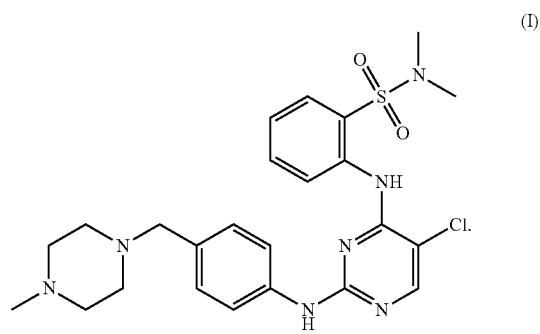

(I)

In some embodiments, the tartrate salt disclosed herein may have a molar ratio of tartaric acid to the compound of structure (I) of about 1:1 to about 2:1. For example, the tartrate salt may have a molar ratio of tartaric acid to the compound of structure (I) of about 2:1. Any of the tartrate salts disclosed herein may be a salt of L-(+)-tartaric acid.

In another aspected, the present disclosure provides a crystalline form of any of the tartrate salts disclosed herein. In some embodiments, the crystalline form is crystalline Form A, having a molar ratio of tartaric acid to the compound of structure (I) of about 2:1. In some examples, Form A can be in substantially pure form. In some embodiments, the crystalline form comprises Form A. In some embodiments, the crystalline form consists essentially of Form A.

Any of the crystalline forms disclosed herein may be characterized by an x-ray powder diffraction (XRPD) pattern comprising peaks, in units 2-theta, at 11.2±0.2, 17.1±0.2, and 19.9±0.2. Optionally, the crystalline form may further comprise a peak, in units 2-theta, at 15.4±0.2. Alternatively or in addition, the crystalline form may further comprise a peak, in units 2-theta, at 7.0±0.2. In some examples, the crystalline form as disclosed herein can be characterized by an XRPD pattern comprising three or more peaks, in units of 2-theta, selected from 7.0±0.2, 11.2±0.2, 15.4±0.2, 16.3±0.2, 17.1±0.2, 19.9±0.2, 21.6±0.2, and 25.5±0.2. In on the examples, the XRPD pattern may comprise 4, 5, 6, 7, or 8 peaks, in units of 2-theta, selected from 7.0±0.2, 11.2±0.2, 15.4±0.2, 16.3±0.2, 17.1±0.2, 19.9±0.2, 21.6±0.2, and 25.5±0.2. In one specific example, the XRPD pattern is substantially identical to the XRPD pattern shown in FIG. 61.

Alternatively or in addition, any of the crystalline forms disclosed herein may be characterized by a differential scanning calorimetry (DSC) thermogram comprising an endotherm peak in units ° C. of about 185.0-194.0. In some embodiments, the endotherm peak has an onset temperature of about 186.3° C. In some embodiments, the crystalline form as disclosed herein may be characterized by a DSC thermogram comprising endotherm peaks in units ° C. at about 107.8, about 152.1, and about 189.1. In one particular example, the crystalline form may have a DSC thermogram that is substantially identical to the thermogram shown in FIG. 64.

Further, any of the crystalline forms disclosed herein may be characterized by a thermogravimetric analysis (TGA) thermogram showing weight loss of about 1.8% at 160° C. For example, the TGA thermogram is substantially identical to the thermogram shown in FIG. 64.

Any of the crystalline forms disclosed herein may have an initial purity of at least 99% and a subsequent purity of at least 99% after being stored for up to about 15 days at about 25° C.±2° C. at a relative humidity of 60±5%. In some embodiments, the crystalline form may an initial purity of at least 99% and a subsequent purity of at least 99% after being stored for up to about 15 days at about 40° C.±2° C. at a relative humidity of 75±5%.

Also within the scope of the present disclosure is a composition comprising any of the tartrate salts disclosed herein or any of the crystalline forms also disclosed herein. In some embodiments, the composition comprises Form A in substantially pure form. In some embodiments, the composition comprises at least 90% Form A by weight. In some embodiments, the composition consists essentially of crystalline Form A.

Any of the compositions disclosed herein may be a pharmaceutical composition and further comprises a pharmaceutically acceptable carrier or diluent. In some embodiments, the pharmaceutical composition may further comprises one or more additional therapeutic agents, for example, hormone therapeutic agents, chemotherapeutic agents, immunotherapeutic agents, cell growth factors, or agents to inhibit cell growth factor receptor action. Any of the pharmaceutical compositions disclosed herein may be formulated for oral administration. For example, the pharmaceutical composition may be formulated as a capsule or tablet.

Further, the present disclosure provides a unit dose comprising any of the pharmaceutical compositions disclosed herein. The unit dose may comprise about 1-100 mg of the tartrate salt. In some embodiments, the unit dose disclosed herein may comprise about 1 mg, 4 mg, 16 mg, 25 mg, 50 mg, 75 mg, or 100 mg of the tartrate salt. In some embodiments, the unit dose can be formulated in a gelatin hard capsule for oral administration.

In another aspect, the present disclosure provides a method of treating a cancer, the method comprising administering to a subject (e.g., a human) in need thereof a therapeutically effective amount of any of the tartrate salts disclosed herein, any of the crystalline forms disclosed herein, any of the pharmaceutical compositions comprising such, or any of the unit doses also disclosed herein.

In some embodiments, the method disclosed herein comprises administering to the subject a therapeutically effective amount of a tartrate salt having a molar ratio of tartaric acid to the compound of structure (I) of about 2:1. In some examples, the method comprises administering to the subject a therapeutically effective amount of the crystalline Form A, which may be in substantially pure form.

In a further aspect, provided herein is a method of treating cancer in a subject comprising administering to the subject a compound of structure (I):

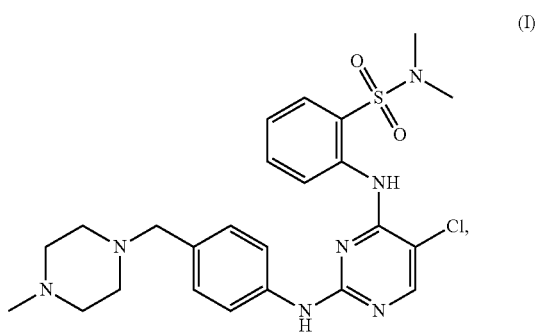

or a pharmaceutically acceptable salt or crystalline form thereof. The compound, or pharmaceutically acceptable salt, or crystalline form thereof, can be administered to the subject orally once daily at a dose from about 1.5 mg/m$^2$ to about 65 mg/m$^2$, or at a dose of about 20 mg to about 100 mg. The subject may have any of the tumor (e.g., advanced solid tumor) or hematopoietic cancer as disclosed herein. In some embodiments, the subject may have undergone one or more prior cancer therapy, e.g., those disclosed herein.

In some embodiments, the compound of structure (I), or pharmaceutically acceptable salt, or crystalline form thereof, can be administered orally at a dose of about 1.0, about 1.5, about 3.0, about 6.0, about 9.0, about 12.0, about 16.0, about 21.0, about 28.0, about 37.0, about 49.0, or about 65.0 mg/m$^2$. For example, the compound of structure (I), or pharmaceutically acceptable salt, or crystalline form thereof, can be administered to the subject as a single anti-cancer agent at a daily dose of about 25 mg, about 33 mg, about 45 mg, about 50 mg, about 58 mg, about 75 mg, or about 100 mg. In specific examples, the compound of structure (I), or pharmaceutically acceptable salt, or crystalline form thereof, is administered orally to the subject concurrently with a second anti-cancer agent and the daily dose of the compound of structure (I), or pharmaceutically acceptable salt, or crystalline form thereof is about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In any of the methods disclosed herein, the cancer can be a solid tumor or a hematological cancer. Exemplary solid tumors include, but are not limited to, a tumor of the bones, digestive organs, reproductive organs, head, neck, lung, heart, skin, nervous system, endocrine system, neuroendocrine system, urinary system, soft tissue, or brain. Exemplary hematopoietic cancers include, but are not limited to, multiple myeloma, myelodysplastic syndrome (MDS), acute myelogenous leukemia (AML), acute lymphoblastic leukemia (ALL), acute lymphocytic leukemia, chronic lymphogenous leukemia, chronic lymphocytic leukemia (CLL), small lymphocytic lymphoma (SLL), mantle cell lymphoma, diffuse large B-cell lymphoma, follicular lymphoma, or non-Hodgkin's lymphoma.

In some embodiments, the cancer is an advanced solid tumor and/or has shown disease progress after receiving one or more prior cancer therapy. For example, the solid tumor can be a resistant, recurrent, refractory, or relapsed solid tumor. In some examples, the one or more prior cancer therapy comprises a hormone therapeutic agent, a chemotherapeutic agent (e.g., an alkylating agent, a platinum-based agent, an antimetabolite, an anti-cancer antibiotic, or a plant-derived anti-cancer agent), an immunotherapeutic agent, or a cell surface receptor inhibitor. Exemplary chemotherapeutic agents include, but are not limited to, carboplatin, cisplatin, miboplatin, nedaplatin, and oxaliplatin.

In some embodiments, the subject has undergone one or more prior cancer therapy, which may comprise immunotherapy, chemotherapy, or a combination thereof.

In some embodiments, the subject has a solid tumor, which may be non-small cell lung cancer (NSCLC), colorectal carcinoma (CRC), ovarian cancer, melanoma, breast carcinoma, neurodocrine carcinoma, prostate adenocarcinoma, cholangiocarcinoma, uterine carcinoma, and pancreatic cancer.

In some embodiments, the subject may have at least stable disease after receiving an immunotherapy. For example, the subject may have received up to two cycles of the immunotherapy.

In some embodiments, the subject may have EGFR$^+$ NSCLC. In some examples, the subject may have demonstrated disease progression after receiving one or more chemotherapies comprising one or more tyrosine kinase inhibitors (TKIs), which may comprise an EGFR TKI. In some examples, the subject may have at least stable disease after taking up to two lines of the TKIs.

In some embodiments, the subject may have BRAF-, KRAS-, or NRAS-mutated colorectal carcinoma (CRC).

In some embodiments, the subject may have persistent or recurrent ovarian cancer. For example, the subject may have refractory or resistant to a platinum-based agent, has undergone prior therapy, or both. In some examples, the platinum-based agent is carboplatin, cisplatin, miboplatin, nedaplatin, or oxaliplatin.

In some embodiments, the subject may have BRAF-mutated melanoma. In some examples, the subject may have progressed disease after an immunotherapy, a chemotherapy comprising one or more BRAF/MEK inhibitors, or a combination thereof.

In some embodiments, the subject may be resistant to an immunotherapy and wherein the method further comprising subjecting the subject to the same immunotherapy. In some examples, the immunotherapy comprises an anti-PD-1 or an anti-PD-L1 agent.

In any of the methods disclosed herein (e.g., a method for treating EGFR+ NSCLC), the subject may be resistant to a chemotherapy comprising a TKI. Such a method may further comprise subjecting the subject to the same chemotherapy.

In any of the methods disclosed herein, the subject is not taking steroids at an amount equivalent to 15 mg/day of prednisone. Alternatively or in addition, the method may further comprises administering to the subject concomitant steroids. In some embodiments, the subject may be free of an anticancer therapy at least within the month prior to the first dosing of the tartrate salt, free of CYP2C19 metabolizers, and/or H2-receptor antagonists at least within 7 days prior to the first dosing of the tartrate salt.

In any of the methods disclosed herein, the subject can be administered orally the tartrate salt, the crystalline form thereof, or the pharmaceutical composition comprising such at a daily dose of about 1.0, 1.5, 3.0, 6.0, 9.0, 12.0, 16.0, 21.0, 28.0, 37.0, 49.0, or 65.0 mg/m$^2$ of the tartrate salt. In some examples, the subject can be administered orally the tartrate salt, the crystalline form thereof, or the pharmaceutical composition at a daily dose of the tartrate salt of about 20-100 mg, optionally about 25-75 mg, for example, about 50 mg.

Any of the methods disclosed herein may comprise one or more a treatment cycles, each consisting of about 28 days, and wherein in each treatment cycle, the tartrate salt, the crystalline form thereof, or the pharmaceutical composition is administered to the subject daily for 21 days, followed by a drug holiday period of seven days.

In other embodiments, the subject to be treated by any of the methods disclosed herein may have a hematological cancer, which can be chronic lymphocytic leukemia (CLL) or small lymphocytic lymphoma (SLL). In some embodiments, the subject has undergone one or more prior therapies for CLL or SLL. In some embodiments, the subject can be intolerant to the prior therapies or has progressive disease after the prior therapies. In some examples, the prior therapies may comprise a B-cell receptor antagonist, a BCL-2 antagonist, or a combination thereof. In other embodiments, the subject may not be concurrently treated by another cancer therapy. In some examples, the subject may be administered orally the tartrate salt, the crystalline form thereof, or the pharmaceutical composition at a daily dose of about 20-100 mg, optionally about 25 mg-100 mg of the tartrate salt, for example, about 25 mg, about 33 mg, about 45 mg, about 50 mg, about 58 mg, about 75 mg, or about 100 mg.

In some examples, the method for treating the hematopoietic cancer may further comprise administering to the subject a BTK inhibitor, which may be ibrutinib, acalabrutinib, zanubrutinib, and LOXO-305. In one particular example, the BTK inhibitor can be ibrutinib. In some examples, the subject was subject to a prior treatment of the BTK inhibitor and has progressed on the BTK inhibitor treatment. In some examples, the subject can be administered the tartrate salt, the crystalline form thereof, or the pharmaceutical composition comprising such at a daily dose of about 20 mg-100 mg (e.g., about 25-75 mg) of the tartrate salt, for example, about 20 mg, about 25 mg, about 33 mg, about 45 mg, about 50 mg, about 58 mg, about 75 mg, or about 100 mg.

In some embodiments, any of the methods disclosed herein may comprise one or more treatment cycles, each consisting of about 28 days, and wherein in each cycle, the subject is administered the tartrate salt, the crystalline form thereof, or the pharmaceutical composition comprising such orally once daily for 28 days.

Any of the methods disclosed herein may further comprise (a) monitoring the subject for tumor lysis syndrome (TLS); (b) administering to the subject an antibiotic, an anti-viral agent, an anti-fungal agent, or a combination thereof, or a combination thereof.

In some embodiments, the subject may have an elevated level of soluble AXL, AXL expression and/or phosphorylation, growth arrest specific 6 (GAS6), a mesenchymal transcription factor, or a combination thereof, as relative to a reference level of soluble AXL, GAS6, or the mesenchymal transcription factor. In some examples, the method may further comprise, prior to the administering step, identifying a subject having an elevated level of soluble AXL, AXL expression and/or phosphorylation, growth arrest specific 6 (GAS6), a mesenchymal transcription factor, or a combination thereof, as relative to a reference level of soluble AXL, GAS6, or the mesenchymal transcription factor. In some examples, the identifying step can be performed by obtaining a peripheral blood sample or a bone marrow sample of a candidate subject, and measuring the level of soluble AXL, the level of GAS6, the level of the mesenchymal transcription factor, or a combination thereof in the peripheral blood sample or the bone marrow sample.

Any of the methods disclosed herein may further comprise, after the administering step, examining the subject for one or more symptoms of diarrhea, nausea, vomiting, dysgeusia, anemia, and thrombocytopenia. In addition, the method may further comprise lowering the daily dose of the tartrate salt or terminating the treatment if the one or more symptoms are detected.

In some embodiments, the method disclosed herein may further comprise administering an effective amount of one or more therapeutic agents to the subject. The one or more therapeutic agents may comprise one or more tyrosine kinase inhibitors. In some examples, the one or more tyrosine kinase inhibitors may comprise an EGFR inhibitor. In other examples, the one or more therapeutic agents may comprises an immune checkpoint inhibitor, for example, a PD-1 or PD-L1 inhibitor. Examples of PD-1 inhibitors include, but are not limited to, pembrolizumab, nivolumab, or a combination thereof. Examples of PD-L1 inhibitors include, but are not limited to, atezolizumab, avelumab, durvalumab, or a combination thereof. Alternatively or in addition, the one or more therapeutic agents may comprise a CDK inhibitor, for example, a CDK9 inhibitor, which, in some instances, may be alvocidib, or a pharmaceutically acceptable salt or prodrug thereof. In some examples, the CDK9 inhibitor is a prodrug of alvocidib, which may have the following structure (II'):

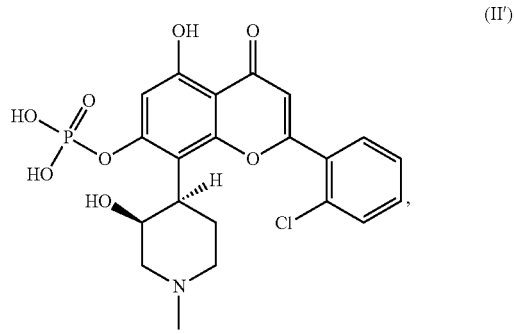 [SMILES: CN1CC[C@H](c2c(OP(=O)(O)O)cc(O)c3c(=O)cc(-c4ccccc4Cl)oc23)[C@H](O)C1]

or a pharmaceutically acceptable salt or zwitterionic form thereof.

In some examples, the one or more therapeutic agents comprise a platinum-based chemotherapeutic agents.

Exemplary additional therapeutic agents to be used in combination with the compound of structure (I), or a pharmaceutically acceptable salt thereof (e.g., any of the tartarate salts disclosed herein) may comprise carboplatin, gemcitabine, bevacizumab, topotecan, rucaparib, olaparib, niraparib, nivolumab, pembrolizumab, atezolizumab, avelumab, durvalumab, ipilimumab, or a combination thereof.

In yet another aspect, the present disclosure provides a method comprising administering an effective amount of a compound of structure (I):

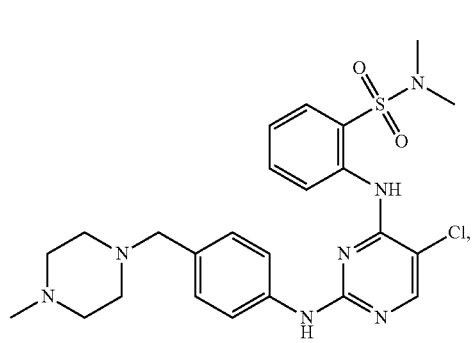 [SMILES: CN1CCN(Cc2ccc(Nc3ncc(Cl)c(Nc4ccccc4S(=O)(=O)N(C)C)n3)cc2)CC1]

(I)

or a pharmaceutically acceptable salt thereof, to a subject in need thereof, wherein the cancer is selected from the group consisting of EGFR+ non-small cell lung cancer; BRAF-, KRAS-, or NRAS-mutated colorectal carcinoma; persistent or recurrent ovarian carcinoma; BRAF-mutated melanoma, inflammatory breast cancer, and triple negative breast cancer. In some embodiments, the subject may have shown disease progress after receiving one or more prior cancer therapy. For example, the cancer is a resistant, refractory, recurrent, or relapsed cancer. In some embodiments, the one or more prior cancer therapy comprises a hormone therapeutic agent, a chemotherapeutic agent, an immunotherapeutic agent, or a cell surface receptor inhibitor.

In addition, the present disclosure provides a method of treating a cancer, the method comprising administering an effective amount of a compound of structure (I):

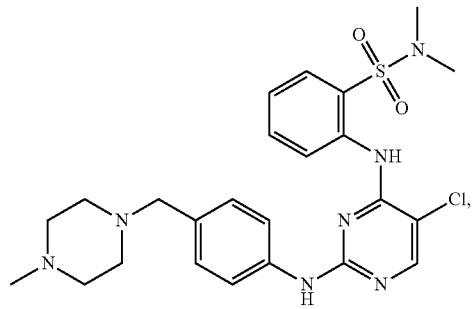

(I)

or a pharmaceutically acceptable salt thereof, to a subject in need thereof, wherein the subject has an advanced solid cancer or hematopoietic cancer, wherein the subject shows disease progression after a chemotherapy, an immunotherapy, or a combination thereof. The subject to be treated by this method can have any of the solid tumor or hematopoietic cancer as disclosed herein. In some embodiments, the chemotherapy or immunotherapy may comprise a hormone therapeutic agent, a chemotherapeutic agent, an immunotherapeutic agent, or a cell surface receptor inhibitor, e.g., those disclosed herein. In some embodiments, the subject is resistant to an immunotherapy and wherein the method further comprising subjecting the subject to the same immunotherapy. In some embodiments, the subject is resistant to a chemotherapy comprising a TKI, and wherein the method further comprising subjecting the subject to the same chemotherapy.

Moreover, provided herein is a method for preparing a compound of structure (I):

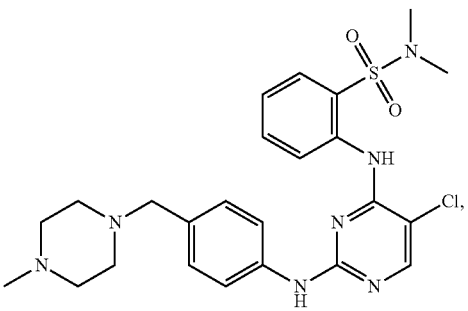

or a pharmaceutically acceptable salt thereof. The method may comprise reacting a compound having the following structure:

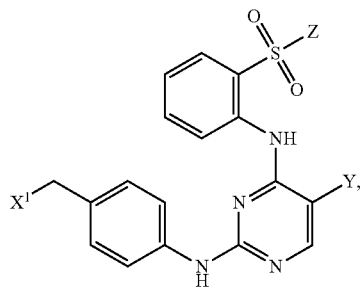

or a pharmaceutically acceptable salt thereof, wherein:
X' is a leaving group;
Y is halo;
Z is halo or —NR$^1$R$^2$; and
R$^1$ and R$^2$ are, each independently, hydrogen or C$_1$-C$_8$ alkyl, with N-methylpiperazine, or a salt thereof, to obtain a compound having the following structure:

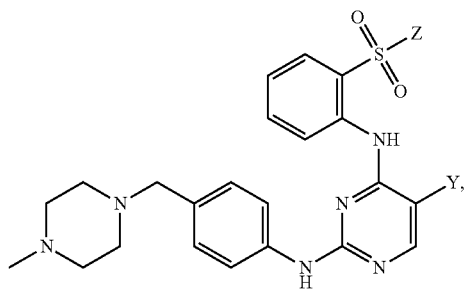

or a pharmaceutically acceptable salt thereof.

In some embodiments, the method may further comprise the step of:

reacting a compound having the following structure:

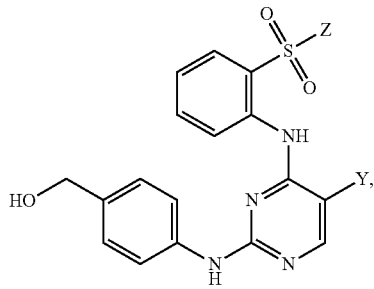

or a pharmaceutically acceptable salt thereof, wherein:
Y is halo;
Z is halo or —NR$^1$R$^2$); and
R$^1$ and R$^2$ are, each independently, hydrogen or C$_1$-C$_8$ alkyl, with an activating agent to obtain the compound having the structure:

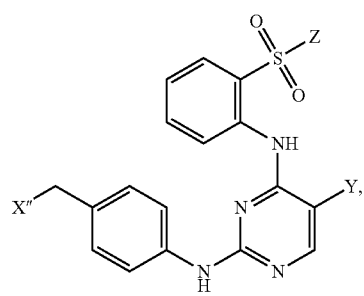

or a pharmaceutically acceptable salt thereof.

In some embodiments, the activating agent comprises a sulfonyl chloride functional group. In some embodiments, X' is halo or sulfonate (e.g., chloro). Alternatively or in addition, the activating agent is thionyl chloride.

In some embodiments the method may further comprise the step:

reacting a compound having the following structure:

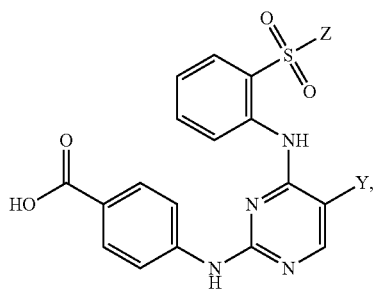

or a pharmaceutically acceptable salt thereof, wherein:
Y is halo;
Z is halo or —NR$^1$R$^2$); and
R$^1$ and R$^2$ are, each independently, hydrogen or C$_1$-C$_8$ alkyl, with a reducing agent to obtain the compound having the structure:

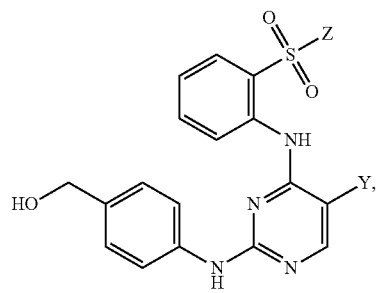

In some examples, the reducing agent is lithium aluminum hydride, diborane, sodium borohydride, borane, or combinations thereof. In one particular example, the reducing agent is borane.

Any of the methods disclosed herein may further comprise: reacting a compound having the following structure:

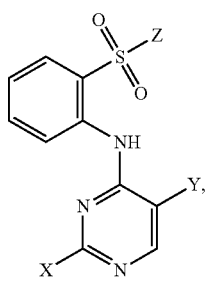

or a pharmaceutically acceptable salt thereof, wherein
X is a leaving group;
Y is halo;
Z is halo or —NR$^1$(R$^2$); and
R$^1$ and R$^2$ are, each independently, hydrogen or C$_1$-C$_8$ alkyl,
with a compound having the following structure:

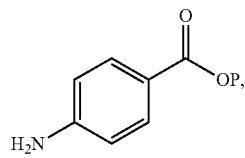

wherein P is H or a protecting group, to obtain a compound having the following structure:

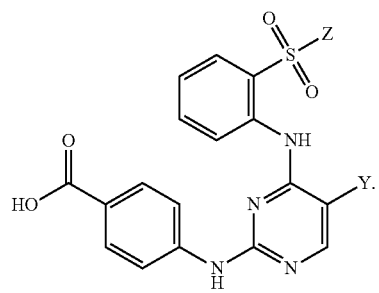

In some embodiments, X can be halo or sulfonate (e.g., chloro). Alternatively or in addition, P can be H; Y can be chloro; Z can be —NR$^1$(R$^2$); R$^1$ can be C$_1$-C$_8$ alkyl (e.g., methyl); and/or R$^2$ can be C$_1$-C$_8$ alkyl (e.g., methyl).

In yet another aspect, the present disclosure provides a method for preparing a tartrate salt of the compound of structure (I):

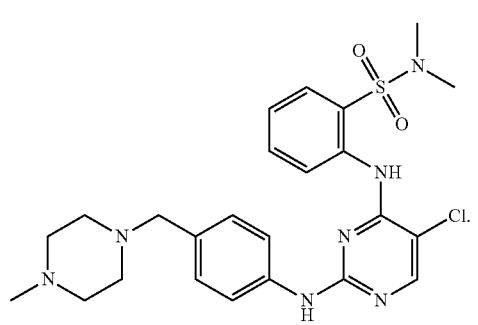

(I)

The method may comprise admixing the compound of structure (I) with tartaric acid. In some examples, the tartaric acid can be L-(+)-tartaric acid. In some embodiments, the tartrate salt is of crystalline Form A, and the method comprises: (a) dissolving the compound of structure (I) in a solvent comprising anisole and ethanol to afford a first solution; (b) adding a solution of (L)-tartaric acid in ethanol to the first solution to afford a second solution; and (c) allowing the tartrate salt of structure (I) to crystallize from the second solution.

In some embodiments, the solvent of step (a) may comprise anisole and ethanol in a ratio of about 2.5:1 (w/w) and/or has a temperature of about 70° C. In some examples, the molar ratio of (L)-tartaric acid in step (b) to the compound of structure (I) in step (a) is about 2:1 and/or wherein the solution of tartaric acid is added to the first solution over the course of about an hour. In any of the methods disclosed herein, the second solution is cooled to about 20° C. and/or is stirred for about 5 hours.

Also within the scope of the present disclosure is a compound having the following structure (III):

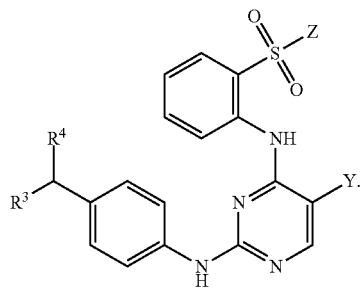

(III)

or a pharmaceutically acceptable salt, stereoisomer or tautomer thereof, wherein:
   Y is halo;
   Z is halo or —NR$^1$(R$^2$);
   R$^1$ and R$^2$ are, each independently, hydrogen or C$_1$-C$_8$ alkyl;
   R$^3$ is halo or OR$^a$;
   R$^4$ is hydrogen or oxo; and
   R$^a$ is hydrogen or C$_1$-C$_8$ alkyl.

In some embodiments, Y can be chloro; Z can be —NR$^1$(R$^2$), in which R$^1$ and R$^2$, in some instances, may be C$_1$-C$_8$ alkyl (e.g., methyl); and/or R$^3$ can be OR$^a$, in which R$^a$ may be H in some instances. In some examples, R$^3$ can be halo (e.g., chloro). In some examples, R$^4$ can be hydrogen. In other examples, R$^4$ can be oxo.

In some embodiments, the compound may have one of the following structures:

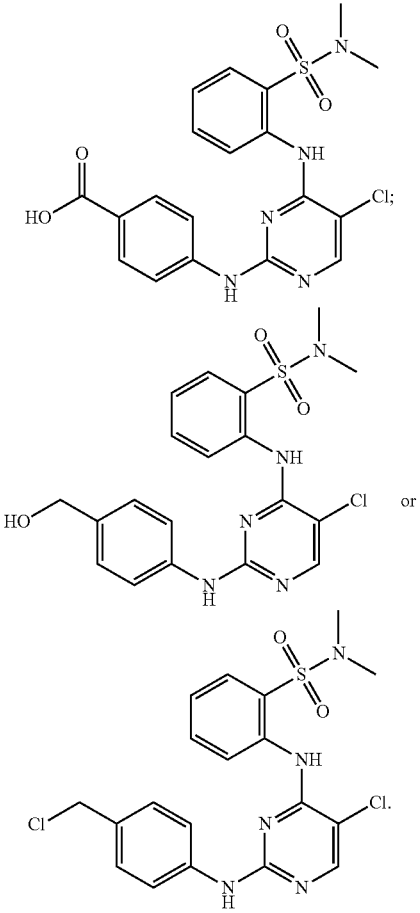

Further, the present disclosure provides a compound having the following structure (I):

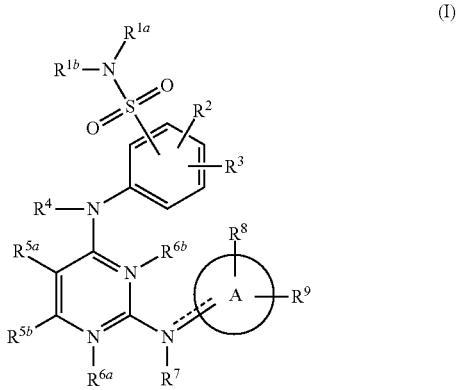

(I)

or a stereoisomer, pharmaceutically acceptable salt, tautomer or prodrug thereof, wherein:

A represents a 6-membered aromatic ring or a 6-membered carbocyclic ring;

$R^{1a}$ and $R^{1b}$ are each independently H, $C_1$-$C_6$ alkyl, or —OH;

$R^2$ and $R^3$ are each independently H, $C_1$-$C_6$ alkyl, or halo;

$R^4$ is H, $C_1$-$C_6$ alkyl, or —OH;

$R^{5a}$ and $R^{5b}$ are each independently H, $C_1$-$C_6$ alkyl, or halo;

$R^{6a}$, $R^{6b}$, $R^{6c}$ and $R^{6d}$ are each independently absent or —O⁻;

$R^7$ is H, $C_1$-$C_6$ alkyl, —OH or absent;

$R^8$ is absent or has the following structure:

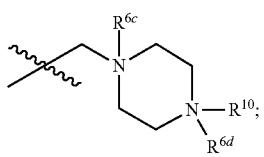

$R^9$ is absent or alkenyl, provided that at least one of $R^8$ or $R^9$ is present;

$R^{10}$ is H or $C_1$-$C_6$ alkyl; and

===== represents a double or single bond; and all valencies are satisfied;

provided that if $R^{1a}$ and $R^{1b}$ are both methyl, then:

a. at least one of $R^{6a}$, $R^{6b}$, $R^{6c}$, $R^{6d}$ and $R^9$ is —O⁻;

b. $R^7$ is $C_1$-$C_6$ alkyl, —OH or absent; and/or c. $R^{10}$ is H.

In some embodiments, the compound may be one of the following:

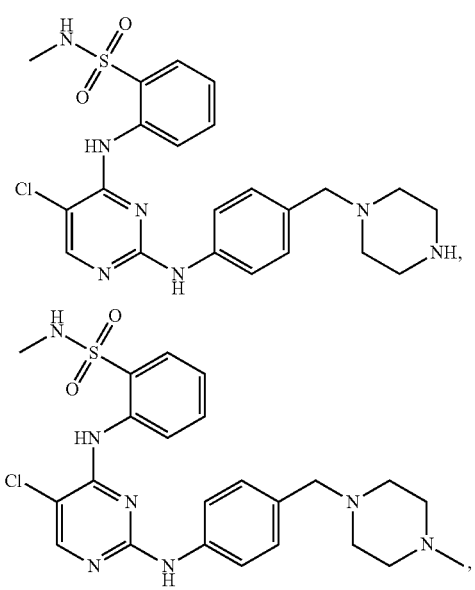

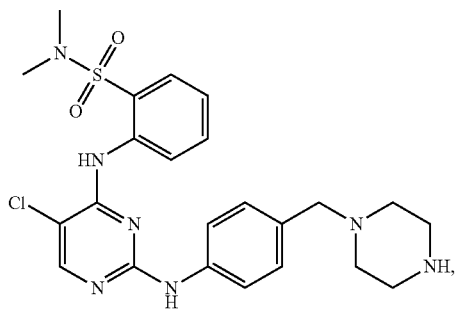

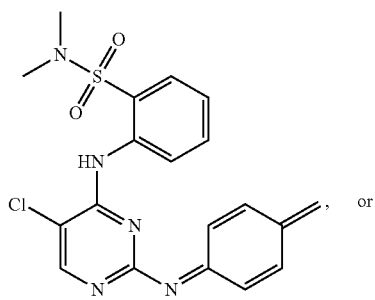

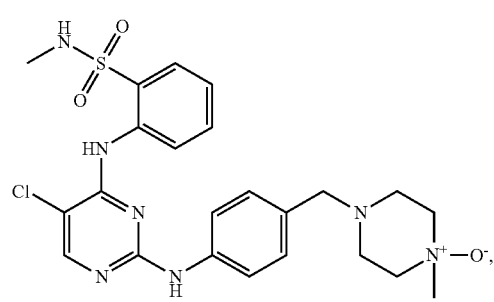

or pharmaceutically acceptable salts thereof.

Further, the present disclosure provides a pharmaceutical composition comprising any of the compounds disclosed herein, or a stereoisomer, pharmaceutically acceptable salt, tautomer or prodrug thereof, and a pharmaceutically acceptable carrier, diluent or excipient.

Also within the scope of the present disclosure is a method of treating cancer in a subject, the method comprising administering an effective amount of any of the compounds disclosed herein, or a stereoisomer, pharmaceutically acceptable salt, tautomer or prodrug thereof, or a pharmaceutical composition as also disclosed herein.

Further, provided herein is a method for determining a metabolic profile of a subject, the method comprising: contacting a population of cells of the subject with a therapeutic agent; and determining a concentration of a first metabolite that is any of the compounds disclosed herein. In some embodiments, the therapeutic agent can be a compound that has the following structure (VI):

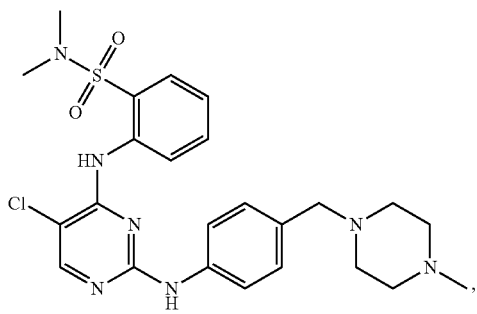

(VI)

or a pharmaceutically acceptable salt or crystalline form thereof. In some embodiments, the cancer is melanoma (e.g., metastatic melanoma), breast cancer (e.g., inflammatory breast cancer and/or triple negative breast cancer), or brain tumor (e.g., gliblastoma multiforme (GBM)). In some embodiments, the subject shows disease progression, recurrence, or relapse after treatment with an immunotherapy.

The method disclosed herein may further comprise administering an immunotherapeutic agent to the subject. In some embodiments, the immunotherapy is a checkpoint inhibitor or a CTLA-4 inhibitor. For example, the immunotherapeutic agent is pembrolizumab. In some embodiments, the method can be performed under one or more of the conditions disclosed herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

FIG. 11A shows tumor volumes and FIG. 11B shows body weights for animals on study.

FIG. 29 shows a selected list of genes that respond to RA and a compound of structure (I).

FIG. 94 shows XRPD peaks characteristic of Form B.

FIG. 96 shows XRPD peaks characteristic of Form D.

FIG. 104A shows KRAS mutation status of selected CRC cell lines. FIG. 104B shows CRC cell viability determination following 72 hrs treatment with the compound of structure (I) and assessment via CellTiter-Glo. The compound of structure (I) demonstrated potency independent of the KRAS mutation status with $IC_{50}$ between 4.5 nM and 123 nM.

FIG. 105A shows mRNA expression levels were quantified via RT-qPCR. FIG. 105B shows protein expression levels were analyzed via western blot. Snail expression was suppressed by 7.6 fold (m-RNA) and 4.9 fold (protein) with 500 nM compound of structure (I).

Figure 113:
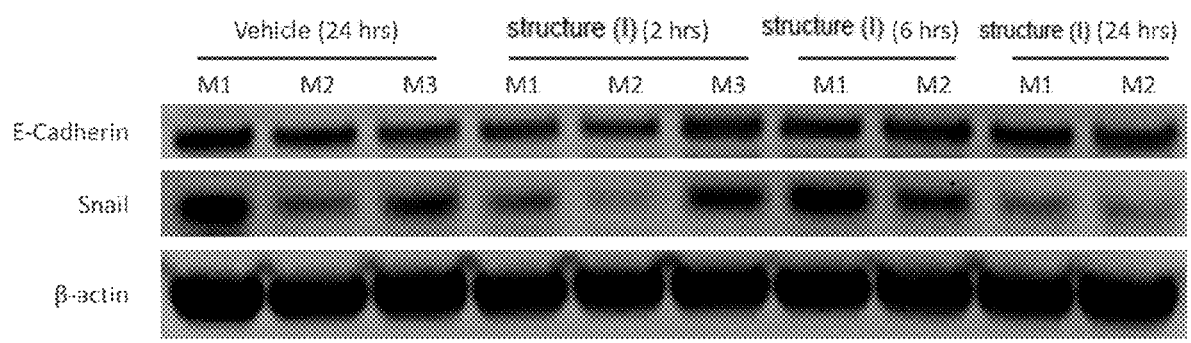

FIG. 113 shows snail protein expression in the compound of structure (I)-treated H1650 xenograft mice. H1650 xenograft tumor bearing mice were treated with the compound of structure (I) (40 mg/kg) by oral gavage, following which tumors were harvested at varying timepoints following dosing. Slug and E-cadherin protein expression was assessed by standard immunoblotting technique.

Figure 114:
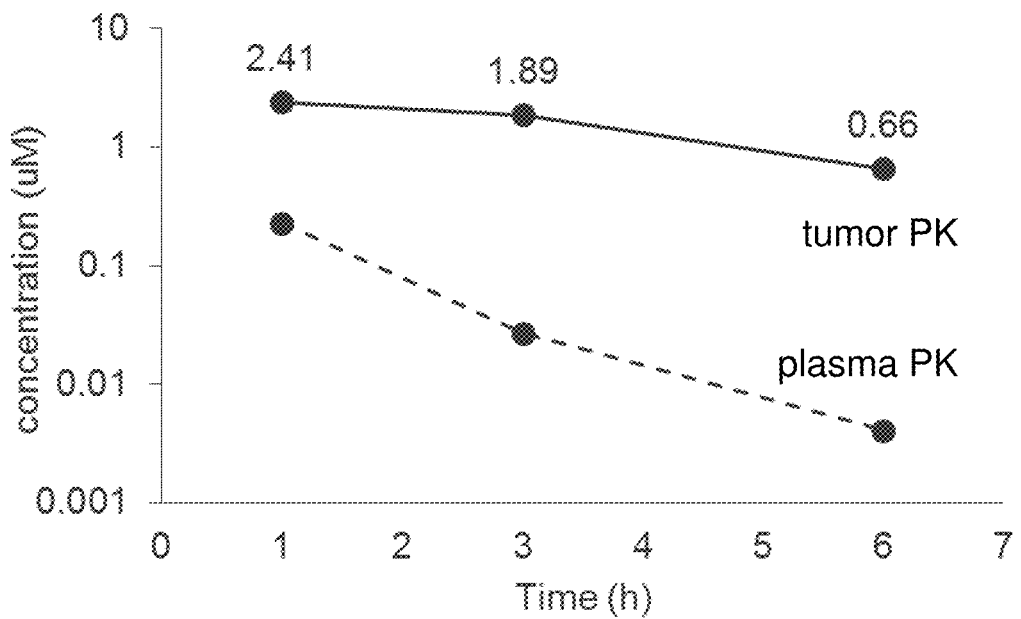

FIG. 114 shows pharmacokinetic profile of the compound of structure (I) in 4T1 model. 4T1 bearing mice were treated with 60 mpk of the compound of structure (I) tartrate p.o. Tumor and blood were collected at the indicated time points.

Figure 115:
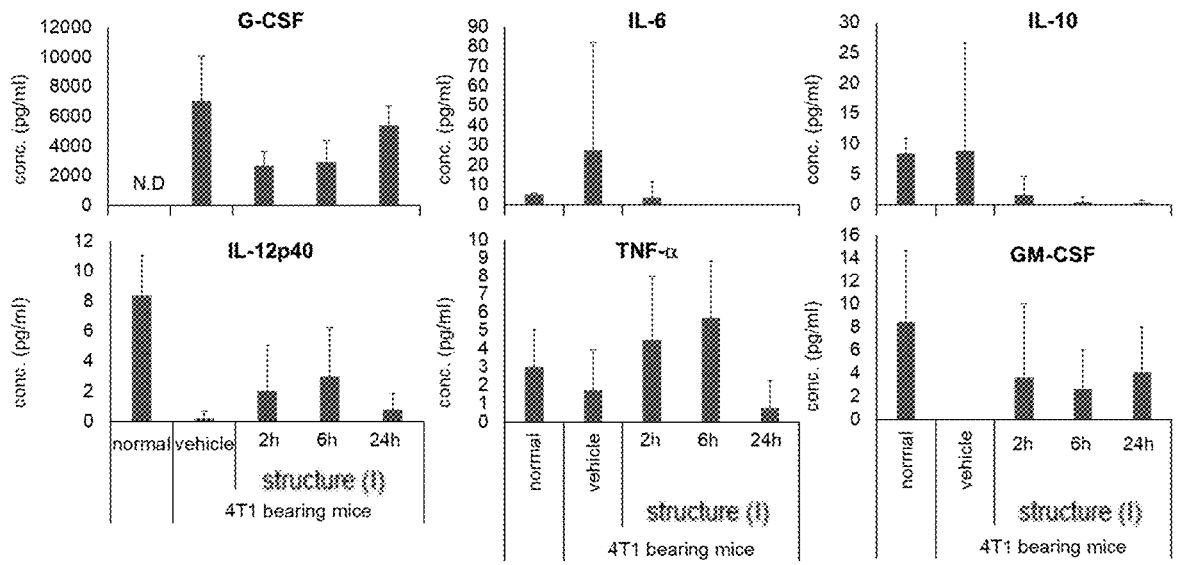

FIG. 115 shows effect of the compound of structure (I) on cytokines in serum. Balb/c mice were transplanted with 4T1 cells orthotopically. 7 days after transplantation, the compound of structure (I) tartrate was administered (60 mg/kg, p.o., Q.D.). Whole blood was collected 2, 6, and 24 hour after the last dosage on Day12. Cytokines in serum were measured with Milliplex assay. Normal indicates healthy mouse without tumor, n=6 (vehicle: n=5, normal: n=3). Error Bar indicates SD. N.D indicates "no data".

Figure 116:
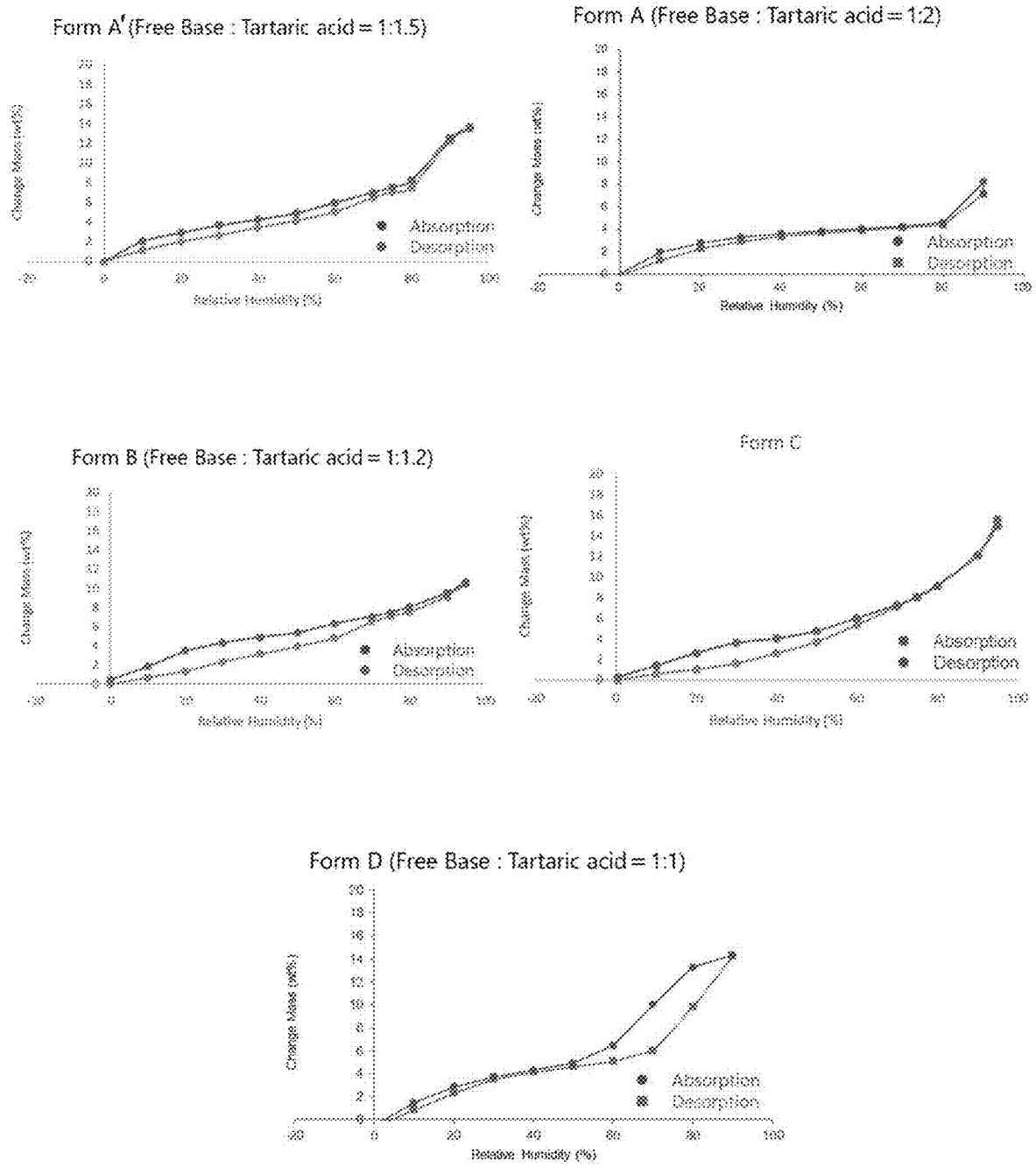

FIG. 116 shows moisture sorption isotherms for Forms A', A, B, C, and D.

Figure 117:
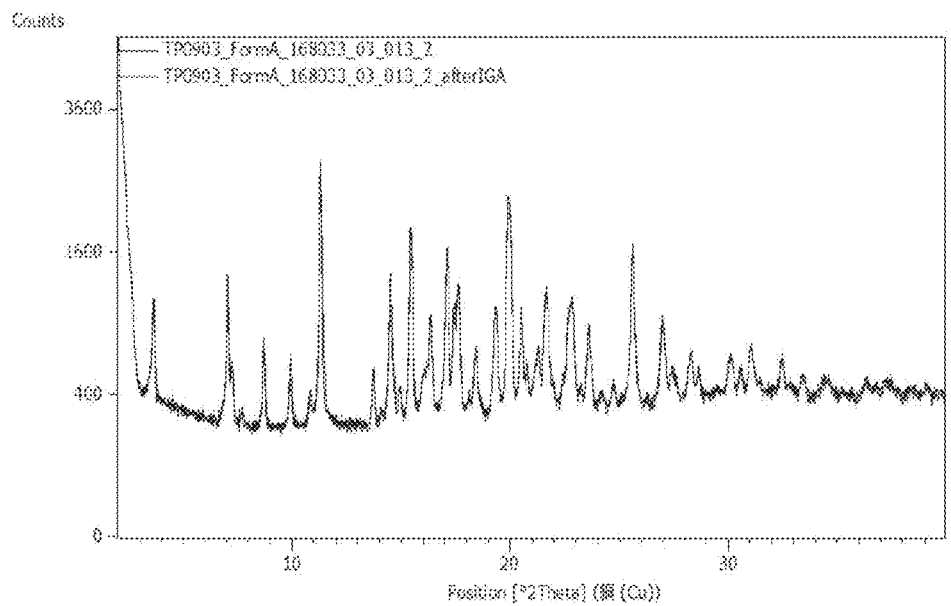
Figure 117:
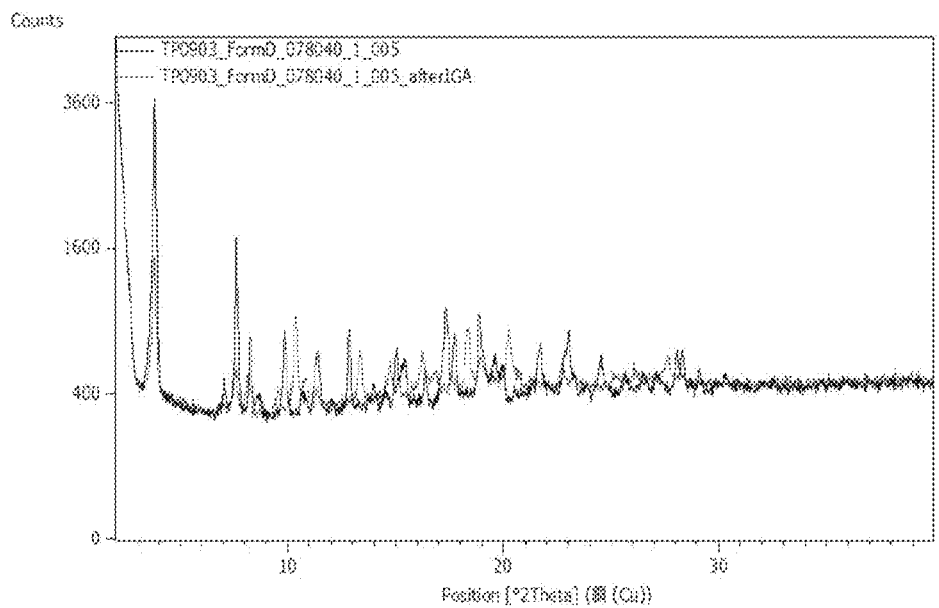

FIG. 117 shows the comparison of XRPD patterns of Form A and Form D between before and after moisture sorption isotherm.

Figure 118:
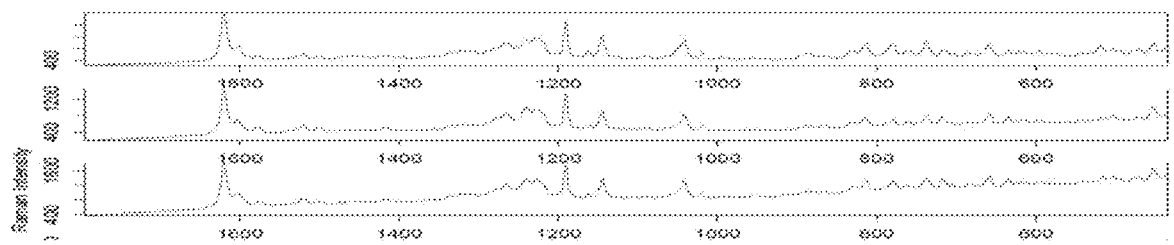
Figure 118:
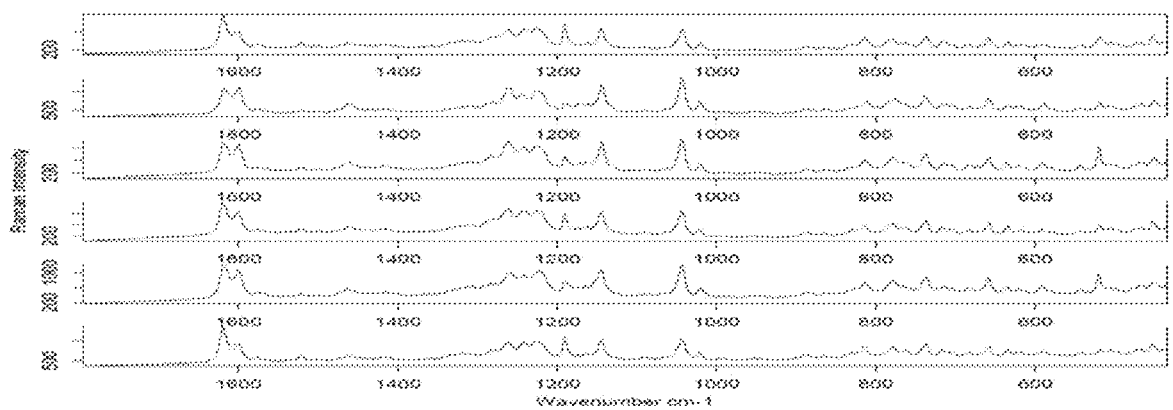
Figure 118:
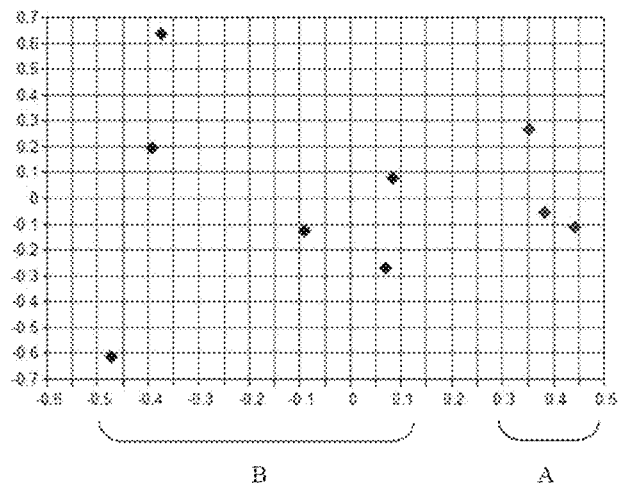

FIG. 118 shows Raman spectra and its PCA data for Form A and Form B.

DETAILED DESCRIPTION OF THE INVENTION

A. Definitions

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an", and "the" include plural references unless the context clearly dictates otherwise.

"Oxo" refers to the =O substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds such as ethynyl and the like). Unless stated otherwise specifically in the specification, an alkyl group is optionally substituted.

"Halo" or "halogen" refers to bromo, chloro, fluoro or iodo.

The term "substituted" as used herein means at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, in some embodiments "substituted" means one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "effective amount" or "therapeutically effective amount" refers to that amount of compound (e.g., a compound of structure (I) or a pharmaceutically acceptable salt, such as a tartrate salt, of the compound of structure (I)) described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

A "cancer," including a "tumor," refers to an uncontrolled growth of cells and/or abnormal increased cell survival and/or inhibition of apoptosis which interferes with the normal functioning of the bodily organs and systems. "Cancer" (e.g., a tumor) includes solid and non-solid cancers. A subject that has a cancer or a tumor has an objectively measurable number of cancer cells present in the subject's body. "Cancers" include benign and malignant cancers (e.g., benign and malignant tumors, respectively), as well as dormant tumors or micrometastases.

A cancer that is "resistant" to a particular therapy refers to a cancer that demonstrates persistent disease or complete remission for less than 6 months after administration of the therapy. In some embodiments, a subject that has a cancer that is resistant to a particular therapy shows no statistically significant objective response to the therapy. A subject is considered to be in "complete remission" if the subject has a normal CA-125 level (e.g., less than 46 U/mL) and a normal CT scan. In some embodiments, a cancer is resistant to a particular therapy if the cancer progresses while receiving the therapy or within six months of the last administration of the therapy.

A recurrent cancer refers to a cancer that appears in a site where it was eradicated or disappeared. A treatment resistant cancer (e.g., platinum-resistant) is "recurrent" if the cancer has progressed (e.g., confirmed by imaging) if the subject had recurrence within six months of the last receipt of the treatment. For example, platinum-resistant cancer is recurrent if the subject had recurrence within 6 months of the last receipt of platinum-based chemotherapy.

As used herein, the term "refractory" with respect to a subject having AML has its ordinary meaning in the art and may refer to a subject that has residual leukemic cells in their marrow after treatment, e.g., within one week, within two weeks, within four weeks, or within two months after treatment.

A cancer is "persistent" if the cancer exists or remains in the same state for an indefinitely long time.

As used herein, the term "relapse" has its ordinary meaning in the art and may refer to the return of AML or the signs and symptoms of an AML after a period of complete remission (e.g., initial complete remission) due to treatment. In some embodiments, relapse may refer to the recurrence of disease after complete remission, which a may be determined by a physician upon clinical assessment.

A cancer is "partially sensitive" to a therapy (e.g., partially platinum sensitive) if the cancer progresses between 6 and 12 months after the last administration of the therapy.

A cancer is "sensitive" to a therapy (e.g., platinum sensitive) if the cancer progresses more than 12 months after the last administration of the therapy. "Metastasis" refers to the spread of cancer from its primary site to other places in the body. "Metastases" are cancers which migrate from their original location and seed vital organs, which can eventually lead to the death of the subject through the functional deterioration of the affected organs. Metastasis is a sequential process, where cancer cells can break away from a primary tumor, penetrate into lymphatic and blood vessels, circulate through the bloodstream, and grow in a distant focus (metastasize) in normal tissues elsewhere in the body. At the new site, the cells establish a blood supply and can grow to form a life-threatening mass. Metastasis can be local or distant. Both stimulatory and inhibitory molecular pathways within the tumor cell regulate this behavior, and interactions between the tumor cell and host cells in the new site are also significant.

A subject having at least "stable disease" refers to a subject having stable disease, partial response or complete response to a therapy according to iRECIST.

As used herein, "treatment" or "treating" refers to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

As used herein, the term "treatment cycle" has its ordinary meaning in the art and may refer to one or more course of treatments that are repeated on a regular schedule, including periods of rest.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid (e.g., L-(+)-tartaric acid), thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

In some embodiments, pharmaceutically acceptable salts include quaternary ammonium salts such as quaternary amine alkyl halide salts (e.g., methyl bromide).

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP, or high-energy radiation, including without limitation x-rays, gamma rays, and neutrons.

"Prodrug" is meant to indicate a compound that may be converted under physiological conditions or by solvolysis to a biologically active salt described herein (e.g., the tartrate salt of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

"About" and "approximately," when used in connection with a numeric value or range of values which is provided to describe a particular solid form, e.g., a specific temperature or temperature range, such as, for example, that describing a melting, dehydration, desolvation or glass transition; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid state form. Specifically, the terms "about" and "approximately," when used in this context, indicate that the numeric value or range of values may vary by 20%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or 0.01% of the recited value or range of values while still describing the particular composition or solid state form.

"Substantially identical" as used herein refers to measured physical characteristics that are comparable in value or data traces that are comparable in peak position and amplitude or intensity within the scope of variations that are typically associated with sample positioning or handling or the identity of the instrument employed to acquire the traces or physical characteristics or due to other variations or fluctuations normally encountered within or between laboratory environments or analytical instrumentation.

"Substantially pure" as used herein refers to a solid state form of a compound described herein that contains less than about 3% or less than about 2% by weight total impurities, or more preferably less than about 1% by weight water, and/or less than about 0.5% by weight impurities such as decomposition or synthesis by-products or residual organic solvent.

"Essentially pure" as used herein refers to a form of a compound described herein wherein the sum of impurities or related substance in the form is less than 1%, preferably less than 0.75%, more preferably less than 0.5% and that the residual solvents and water are less than 1%, preferably less than 0.75%, more preferably less than 0.5% and still more preferably less than 0.25% by weight.

The term "crystalline forms" and related terms herein refers to the various crystalline states of a given substance, including, but not limited to, polymorphs, solvates, hydrates, mixed solvates, co-crystals and other molecular complexes. A crystalline form may also be, but is not necessarily, a mixture of various crystalline states of a given substance such as a combination of pseudopolymorph or polymorph forms, a combination of one or more polymorph forms with one or more pseudopolymorph or a combination of such forms with amorphous or non-solid state forms of the substance. Typical combinations are of two or more polymorph or pseudo polymorph forms, such a mixture of a polymorph form with a pseudopolymorph form or a mixture of a polymorph or pseudopolymorph form with amorphous material. Typically crystalline forms are typically distinguishable from each other by their XRPD patterns. Solid state forms having different crystal morphologies but essentially identical XRPD patterns are considered to be different crystalline forms, since different morphologies can exhibit different properties related to physical shape. Properties related to physical shape include dissolution rate, stability, hygroscopicity, mechanical properties such hardness, tensile strength, compatibility (tableting) and those related to handling, e.g., flow, filtering, blending and other physical or pharmaceutical properties as described herein for different polymorphs.

Embodiments of the invention disclosed herein are also meant to encompass pharmaceutically acceptable salts of a compound of structure (I) being isotopically-labelled by having one or more atoms replaced by an atom having a different atomic mass or mass number (i.e., an "isotopic form" of the pharmaceutically acceptable salts of a compound of structure (I)). Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled pharmaceutically acceptable salts of compounds of structure (I), for example, those incorporating a radioactive isotope, are useful in drug and/or substrate tissue distribution studies. The radioactive isotopes tritium (i.e. $^3H$), and carbon-14 (i.e., $^{14}C$) are particularly useful for this purpose in view of their ease of incorporation and ready means of detection.

Substitution with heavier isotopes such as deuterium (i.e., $^2H$) may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled salts of compounds of structure (I) can generally be prepared by conventional techniques known to those skilled in the art or by processes analogous to those described in the Examples as set out below using an appropriate isotopically-labeled reagent in place of the non-labeled reagent previously employed.

It is understood that in the present description, combinations of substituents and/or variables of the depicted formulae are permissible only if such contributions result in stable compounds. "Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Zwitterionic form" refers to a form of a compound (e.g. structure (II')), wherein at least one functional group has a positive charge, one functional group has a negative electrical charge, and the net charge of the entire molecule is zero. For example, a phosphate group (—PO$_3$H$_2$) may exist in an anionic form (e.g., —PO$_3$H⁻), and a nitrogen atom within the same molecule may exist in the protonated (cationic form).

A "tautomer" refers to a proton shift from one atom of a molecule to another atom of the same molecule. Embodiments thus include tautomers of the disclosed compounds.

A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

B. TARTRATE SALTS OF COMPOUND OF STRUCTURE (I)

In one aspect, the present disclosure provides a tartrate salt of a compound of structure (I):

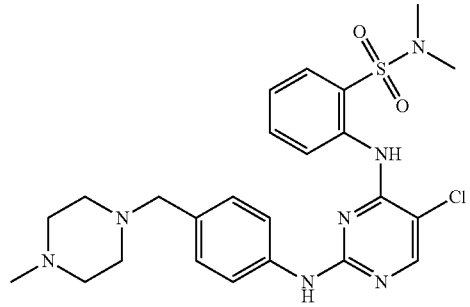

(I)

In certain embodiments, the tartrate salt is a salt of L-(+)-tartaric acid. In certain particular embodiments, the tartrate salt of the compound of structure (I) is a crystalline or partially crystalline solid.

Other salt forms of the compound of structure (I) are provided. The salt may be a pharmaceutically acceptable salt. The pharmaceutically acceptable salt of a compound of structure (I) can be represented by the following structure:

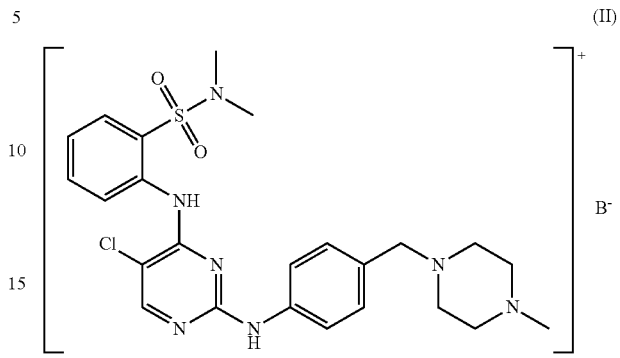

(II)

wherein B— is the conjugate base of the acid used for salt formation. In certain embodiments, the pharmaceutically acceptable salt is a phosphoric acid salt. In certain embodiments, the pharmaceutically acceptable salt is a malate salt. In certain embodiments, the pharmaceutically acceptable salt is a succinate salt. In certain embodiments, the pharmaceutically acceptable salt is a benzenesulfonate salt.

Several salts of the compound of structure (I) were screened, as described in Example 1. The tartrate salt exhibits favorable pharmacokinetic properties, such as bioavailability, as described in Examples 2 and 3.

1. Stoichiometric and Crystalline Forms

In some embodiments, the molar ratio of tartaric acid to the compound of structure (I) ranges from about 4:1 to about 1:4, from about 3.5:1 to about 1:3.5, from about 3.2:1 to about 1:3.2, from about 3:1 to about 1:3, from about 2.7:1 to about 1:2.7, from about 2.5:1 to about 1:2.5, from about 2.2:1 to about 1:2.2, from about 2:1 to about 1:2.2, from about 1.8:1 to about 1:2.2, from about 1.5:1 to about 1:2.2, from about 1.2:1 to about 1:2.2, from about 1.1:1 to about 1:2.2, from about 0.8:1 to about 1:2.2, from about 0.5:1 to about 1:2.2, from about 0.2:1 to about 1:2.2, from about 0.1:1 to about 1:2.2, or from about 2:1 to about 1:2.5.

In certain embodiments, the molar ratio of tartaric acid to the compound of structure (I) is about 1:1; e.g., from about 0.8:1 to about 1.2:1. In certain embodiments, the molar ratio is 0.8:1, 0.9:1, 1:1:, 1.1:1, or 1.2:1. In a particular embodiment, the molar ratio is 1:1. In another particular embodiment, the molar ratio is 1.2:1. A specific embodiment provides a tartrate salt having the following structure (IIa):

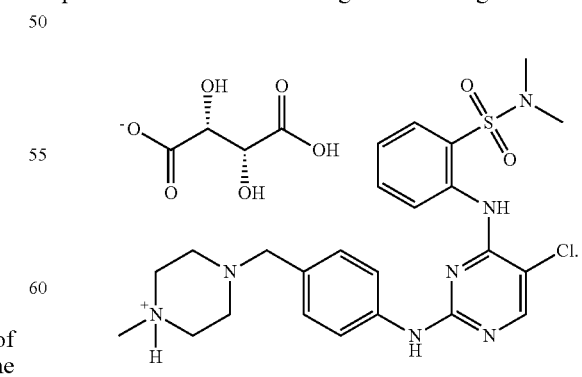

In certain embodiments, the tartrate salt of a compound of structure (I) has one of the following structures (IIb), (IIc), (IId), (IIe), (IIf) or (IIg):

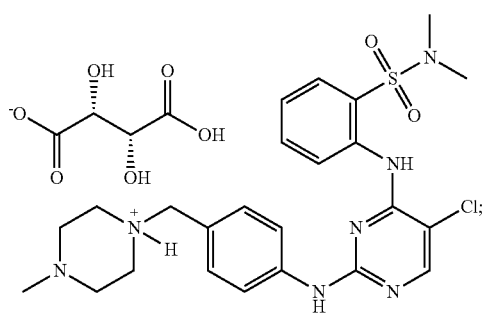

(IIb)

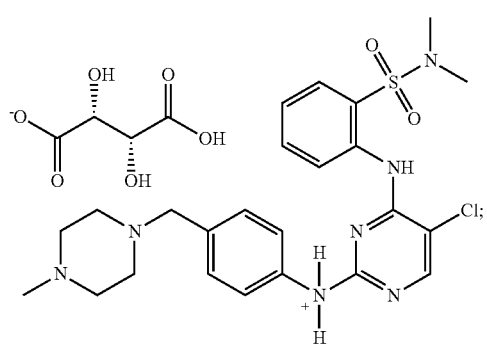

(IIc)

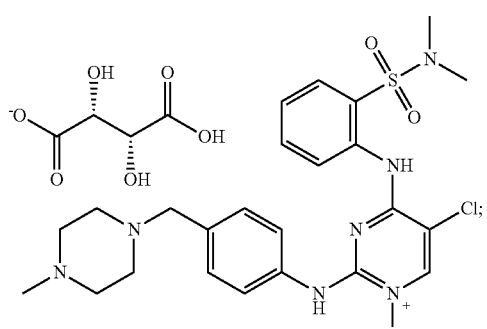

(IId)

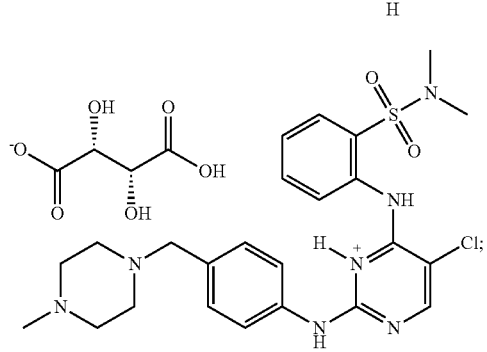

(IIe)

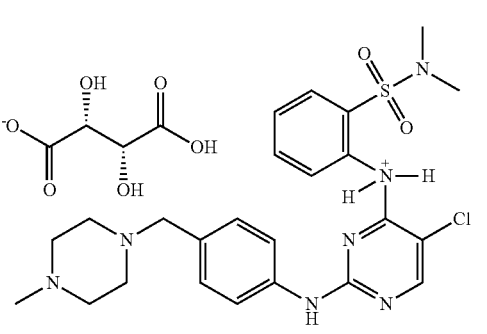

(IIf)

or

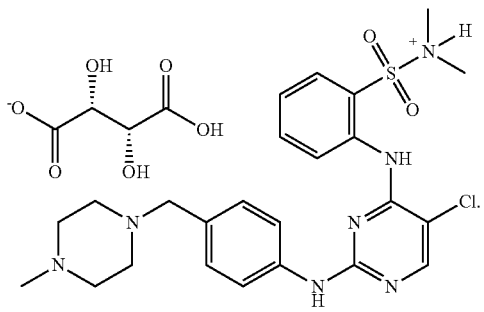

(IIg)

a. Form B

In certain embodiments, a tartrate salt having a stoichiometry of about 1:1 is of crystalline Form B, and is characterized by one or more of X-ray powder diffraction (XRPD), Differential Scanning Calorimetry (DSC), and Thermogravimetric Analysis (TGA). In a particular embodiment, Form B has a molar ratio of tartaric acid to the compound of Structure (I) of 1:1. In another particular embodiment, Form B has a molar ratio of tartaric acid to the compound of Structure (I) of 1.2:1.

In certain embodiments, Form B is characterized by an XRPD pattern comprising two or more peaks, in units of 2-theta, selected from 7.5±0.2, 10.3±0.2, 18.9±0.2, and 19.0±0.2 at a temperature of about 22° C. In certain embodiments, the XRPD pattern of Form B comprises 2, 3, or 4 peaks selected from 7.5±0.2, 10.3±0.2, 18.9±0.2, and 19.0±0.2. In certain embodiments, the XRPD pattern is substantially identical to that of FIG. 62. In certain embodiments, the XRPD pattern comprises one or more (e.g., 1, 2, 3, 4, or 5) additional peaks selected from the peaks listed in FIG. 94.

Figure 95:
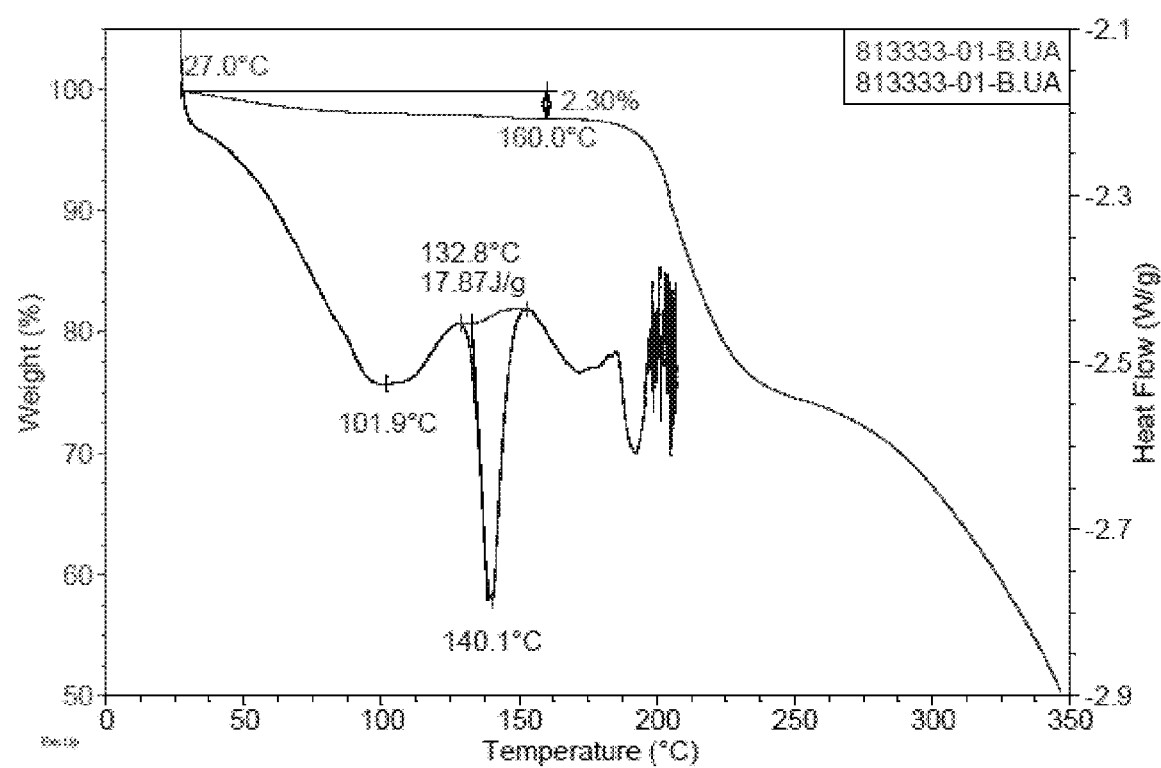
FIG. 95 shows TGA/DSC curves of Form B.

In certain embodiments, Form B is characterized by a DSC thermogram comprising an endotherm peak in units ° C. at about 101.9. In certain embodiments, the DSC thermogram comprises an endotherm peak in units ° C. at about 140.1. In certain embodiments, the DSC thermogram comprises endotherm peaks in units ° C. at about 101.9 and 140.1. In a particular embodiment, the DSC thermogram is substantially identical to that of FIG. 95.

In certain embodiments, Form B is characterized by a TGA thermogram showing weight loss of about 2.3% at 160° C. In a particular embodiment, the TGA thermogram is substantially identical to the thermogram shown in FIG. 95.

Physical and chemical properties of Form B are described in Example 26, Table 17. Toxicokinetic and toxicology profiles of Form B are described in Example 27.

b. Form D

In certain embodiments, a tartrate salt having a stoichiometry of about 1:1 is of crystalline Form D, and is characterized by one or more of XRPD, DSC, and TGA. In a particular embodiment, Form D has a molar ratio of tartaric acid to the compound of Structure (I) of 1:1.

In certain embodiments, Form D is characterized by an XRPD pattern comprising peaks, in units of 2-theta, at 12.8±0.2 and 18.9±0.2 at a temperature of about 22° C. In certain embodiments, the XRPD pattern is substantially identical to that of FIG. 63. In certain embodiments, the XRPD pattern comprises one or more (e.g., 1, 2, 3, 4, or 5) additional peaks selected from the peaks listed in FIG. 96.

Figure 97:
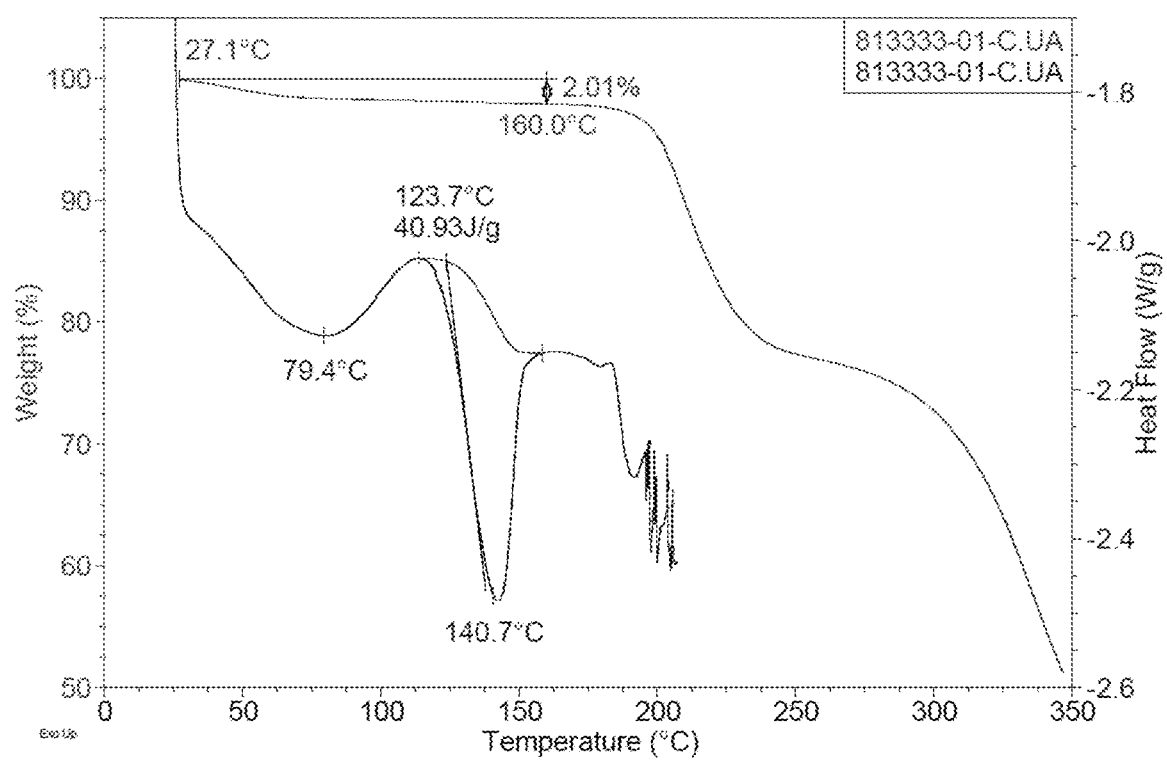
FIG. 97 shows TGA/DSC curves of Form D.

In certain embodiments, Form D is characterized an endotherm peak in units ° C. at about 79.4. In certain embodiments, the DSC thermogram comprises an endotherm peak in units ° C. at about 140.7. In certain embodiments, the DSC thermogram comprises endotherm peaks in units ° C. at about 79.4 and 140.7. the DSC thermogram is substantially identical to that of FIG. 97.

In certain embodiments, Form D is characterized by a TGA thermogram showing weight loss of about 2.0% at 160° C. In a particular embodiment, the TGA thermogram is substantially identical to that of FIG. 97.

In certain embodiments, a tartrate salt having a stoichiometry of about 1:1 comprises Form D. In certain embodiments, a tartrate salt having a stoichiometry of about 1:1 consists essentially of Form D. In certain embodiments, Form D is essentially pure.

Physical and chemical properties of Form B are described in Example 26, Table 17. Toxicokinetic and toxicology profiles of Form B are described in Example 27.

c. Form A'

In certain embodiments, a tartrate salt having a stoichiometry of about 1.5:1 is of crystalline Form A', and is characterized by one or more of XRPD, DSC, and TGA. In certain embodiments, the molar ratio of tartaric acid to the compound of structure (I) is about 1.5:1; e.g., from about 1.4:1 to about 1.6:1. In certain embodiments, the molar ratio is 1.4:1, 1.5:1, or 1.6:1. In a particular embodiment, the molar ratio is 1.5:1. In certain embodiments, crystalline Form A' is characterized by a DSC thermogram comprising an endotherm peak at about 182.3° C. In certain embodiments, the endotherm peak has an onset temperature of about 170.5° C.

In certain embodiments, a tartrate salt having a stoichiometry of about 1.5:1 comprises Form A'. In certain embodiments, a tartrate salt having a stoichiometry of about 1.5:1 consists essentially of Form A'. In certain embodiments, Form A' is essentially pure.

d. Form A

Figure 61A:
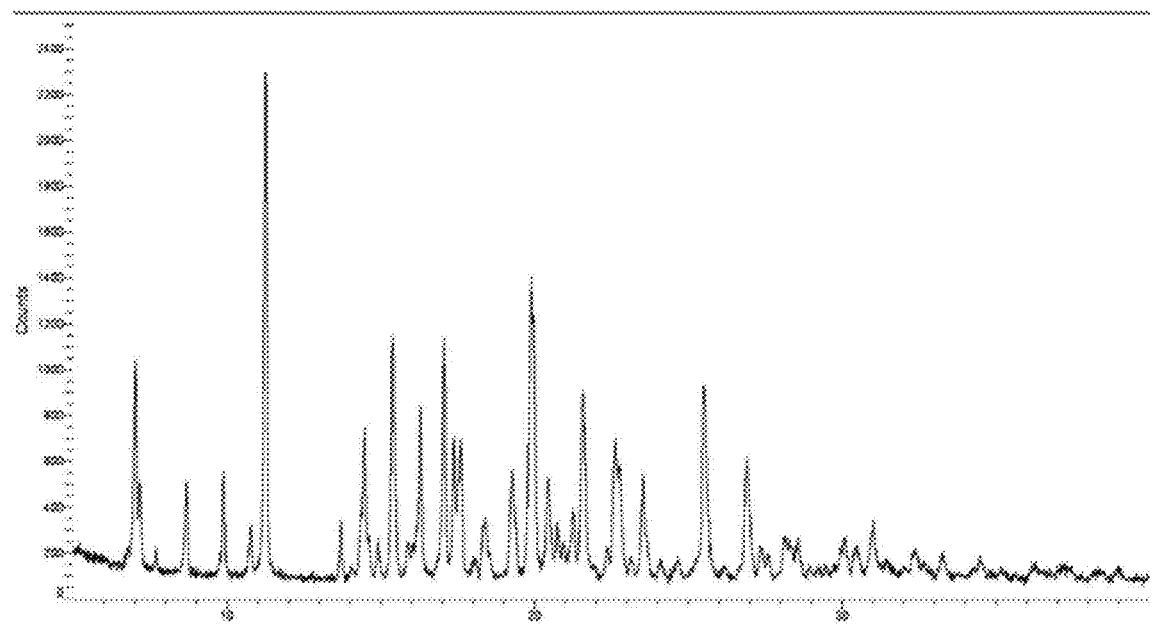
FIG. 61A illustrates an x-ray diffractogram obtained from XRPD analysis for crystalline Form A.
Figure 61B:
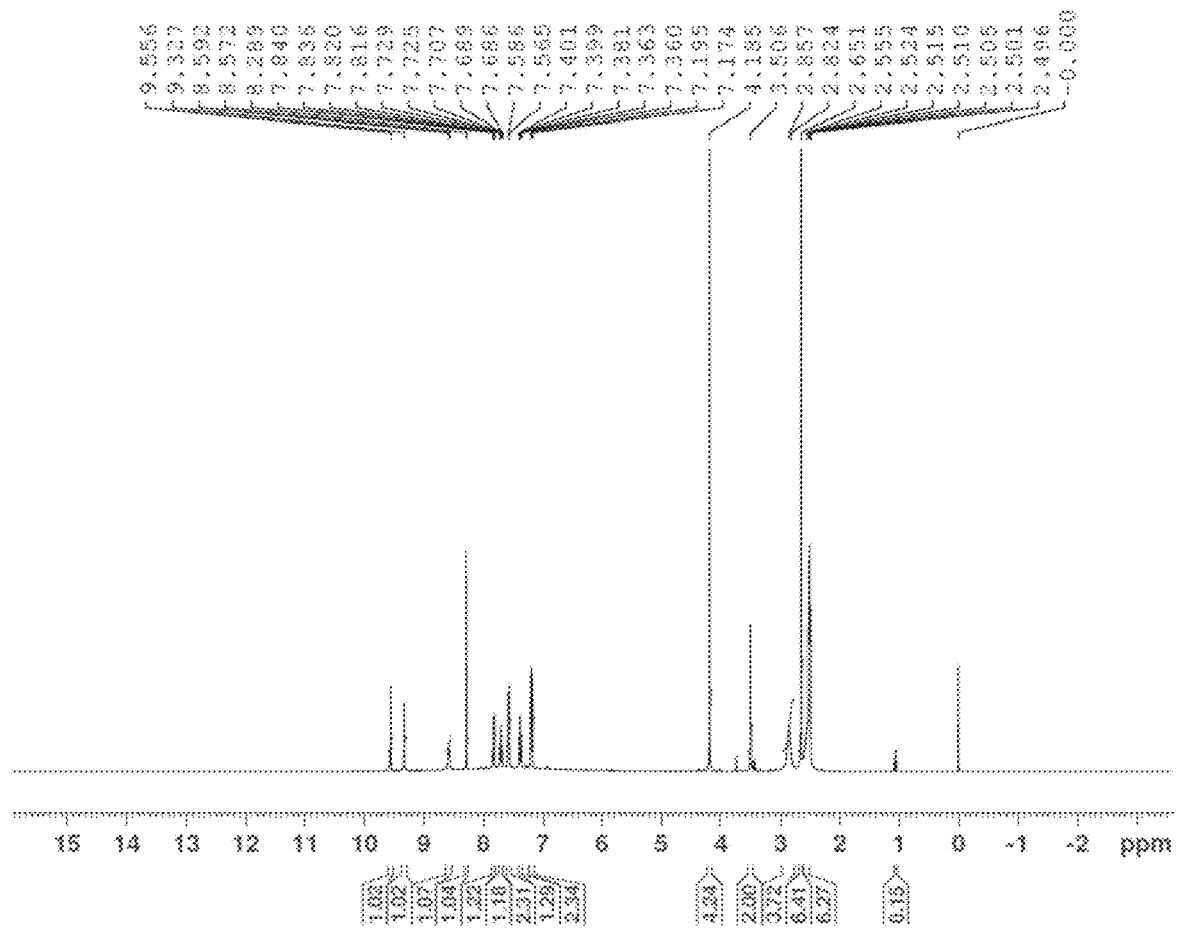
FIG. 61B illustrates an $^1$HNMR spectrum of crystalline Form A.
Figure 61C:
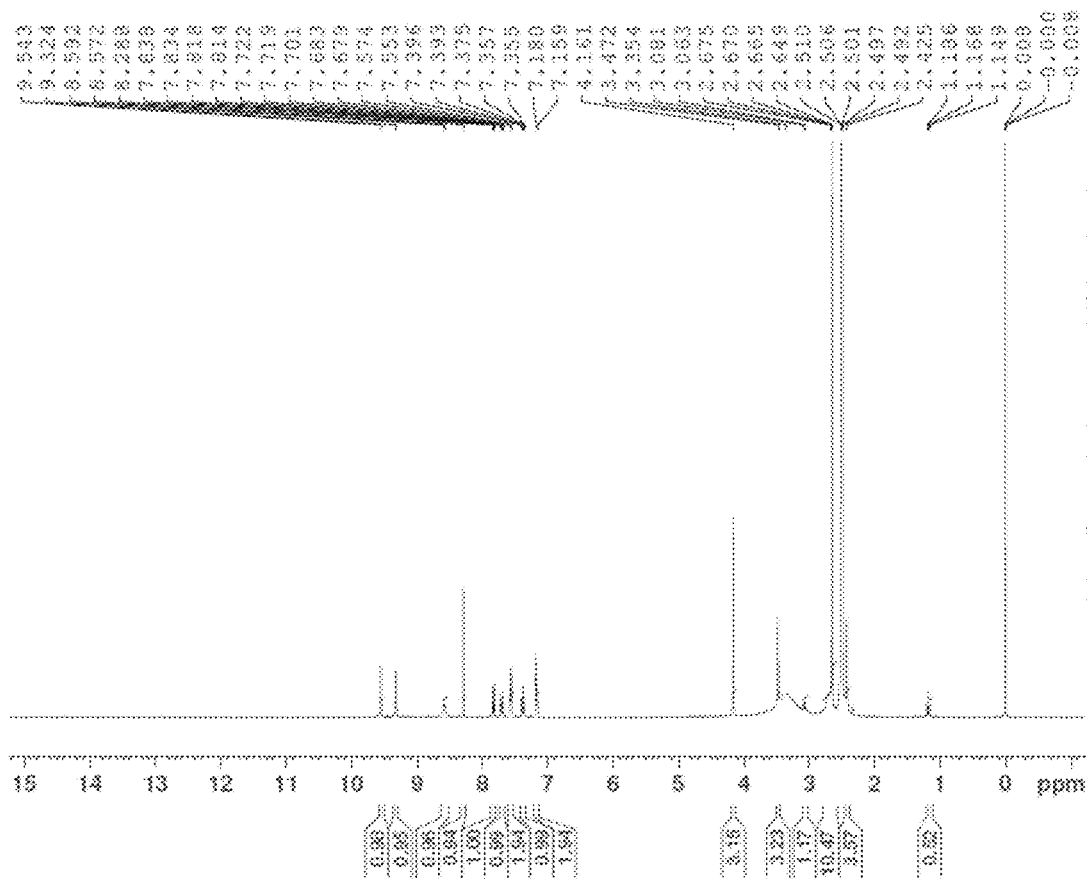
FIG. 61C illustrates an $^1$HNMR spectrum of crystalline Form A'.

In certain embodiments, a tartrate salt having a stoichiometry of about 2:1 is of crystalline Form A, and is characterized by one or more of XRPD, DSC, and TGA. In certain embodiments, the molar ratio of tartaric acid to the compound of structure (I) ranges from about 2.2:1 to about 1.9:1. In a particular embodiment, the molar ratio is 2:1. In certain embodiments, Form A is characterized by an XRPD pattern comprising three or more peaks, in units of 2-theta, selected from 7.0±0.2, 11.2±0.2, 15.4±0.2, 16.3±0.2, 17.1±0.2, 19.9±0.2, 21.6±0.2, and 25.5±0.2 at a temperature of about 22° C. In certain embodiments, the XRPD pattern of Form A comprises 3, 4, 5, 6, 7, or 8 peaks selected from 7.0±0.2, 11.2±0.2, 15.4±0.2, 16.3±0.2, 17.1±0.2, 19.9±0.2, 21.6±0.2, and 25.5±0.2. In certain embodiments, the XRPD pattern is substantially identical to that of FIG. 61. In certain embodiments, the XRPD pattern comprises one or more (e.g., 1, 2, 3, 4, or 5) additional peaks selected from the peaks listed in Table 1.

Table 1

Tabulated X-ray Powder Diffractogram data from Form A

| Angle | D Value | Net Intensity | Gross Intensity | Relative Intensity |
|---|---|---|---|---|
| 7.016 | 12.58927 | 872 | 1003 | 39.7% |
| 7.137 | 12.37531 | 283 | 413 | 12.9% |
| 7.671 | 11.51594 | 89.1 | 210 | 4.1% |
| 8.655 | 10.20899 | 379 | 489 | 17.3% |
| 9.869 | 8.95559 | 442 | 542 | 20.1% |
| 10.751 | 8.22221 | 215 | 312 | 9.8% |
| 11.241 | 7.86498 | 2195 | 2290 | 100.0% |
| 13.701 | 6.45790 | 223 | 312 | 10.2% |
| 14.070 | 6.28943 | 34.2 | 128 | 1.6% |
| 14.457 | 6.12183 | 595 | 692 | 27.1% |
| 14.914 | 5.93526 | 129 | 229 | 5.9% |
| 15.402 | 5.74823 | 990 | 1093 | 45.1% |
| 15.921 | 5.56201 | 114 | 222 | 5.2% |
| 16.286 | 5.43814 | 666 | 776 | 30.4% |
| 17.046 | 5.19745 | 1012 | 1124 | 46.1% |
| 17.392 | 5.09476 | 473 | 585 | 21.5% |
| 17.562 | 5.04590 | 505 | 616 | 23.0% |
| 18.035 | 4.91450 | 65.4 | 173 | 3.0% |
| 18.371 | 4.82545 | 226 | 330 | 10.3% |
| 19.280 | 4.60009 | 427 | 532 | 19.5% |
| 19.910 | 4.45589 | 1229 | 1339 | 56.0% |
| 20.445 | 4.34050 | 406 | 517 | 18.5% |
| 20.752 | 4.27683 | 172 | 282 | 7.8% |
| 20.915 | 4.24395 | 130 | 239 | 5.9% |
| 21.235 | 4.18071 | 279 | 387 | 12.7% |
| 21.579 | 4.11474 | 799 | 904 | 36.4% |
| 21.909 | 4.05363 | 38.7 | 139 | 1.8% |
| 22.383 | 3.96882 | 110 | 208 | 5.0% |
| 22.665 | 3.91998 | 512 | 609 | 23.3% |
| 23.147 | 3.83948 | 78.3 | 174 | 3.6% |
| 23.538 | 3.77658 | 417 | 509 | 19.0% |
| 24.111 | 3.68807 | 64.8 | 149 | 3.0% |
| 24.670 | 3.60583 | 95.8 | 180 | 4.4% |
| 25.533 | 3.48590 | 789 | 880 | 36.0% |
| 26.170 | 3.40239 | 44.5 | 137 | 2.0% |
| 26.904 | 3.31131 | 518 | 614 | 23.6% |
| 27.366 | 3.25638 | 114 | 213 | 5.2% |
| 27.575 | 3.23223 | 78.8 | 180 | 3.6% |
| 28.167 | 3.16561 | 163 | 266 | 7.4% |
| 28.282 | 3.15301 | 146 | 250 | 6.7% |
| 28.542 | 3.12484 | 146 | 250 | 6.7% |
| 28.960 | 3.08070 | 32.3 | 137 | 1.5% |
| 29.228 | 3.05304 | 33.5 | 138 | 1.5% |
| 29.485 | 3.02701 | 28.9 | 135 | 1.3% |
| 30.066 | 2.96986 | 155 | 265 | 7.0% |
| 30.461 | 2.93226 | 104 | 215 | 4.8% |
| 31.002 | 2.88223 | 189 | 299 | 8.6% |
| 31.440 | 2.84310 | 62.4 | 169 | 2.8% |
| 32.056 | 2.78984 | 34.6 | 139 | 1.6% |
| 32.362 | 2.76416 | 90.1 | 195 | 4.1% |
| 33.279 | 2.69008 | 99.6 | 202 | 4.5% |
| 34.511 | 2.59683 | 59.1 | 157 | 2.7% |
| 36.261 | 2.47542 | 46.4 | 136 | 2.1% |
| 37.084 | 2.42233 | 45.3 | 136 | 2.1% |
| 37.386 | 2.40348 | 33.8 | 123 | 1.5% |
| 38.983 | 2.30860 | 46.3 | 126 | 2.1% |

In certain embodiments, Form A is characterized by a DSC thermogram comprising an endotherm peak value at about 185.0° C.-194.0° C. In some embodiments, the endotherm peak value is at a temperature ranging from about 186.0° C.-193.0° C., from about 187.0° C.-192.0° C., or from about 188.0° C.-191.0° C. In some more specific embodiments, the endotherm peak value is at about 189.1° C.

In certain embodiments, Form A is characterized by a DSC thermogram comprising an endotherm peak value at about 148.0° C.-155.0° C. In some embodiments, the endotherm peak value is at a temperature ranging from about 150.0° C.-154.0° C., from about 151.0° C.-153.0° C., or from about 151.5° C.-152.5° C. as determined by differential scanning calorimetry. In some more specific embodiments, the endotherm peak value is at about 152.1° C.

In certain embodiments, Form A is characterized by a DSC thermogram comprising endotherm peak values at about 185.0° C.-194.0° C. and at about 148.0° C.-155.0° C. In some embodiments, the endotherm peak values are at a temperature ranging from about 186.0° C.-193.0° C., from about 187.0° C.-192.0° C., or from about 188.0° C.-191.0° C. and from about 150.0° C.-154.0° C., from about 151.0° C.-153.0° C., or from about 151.5° C.-152.5° C. In some more specific embodiments, the endotherm peak values are at about 189.1° C. and at about 152.1° C.

Figure 64:
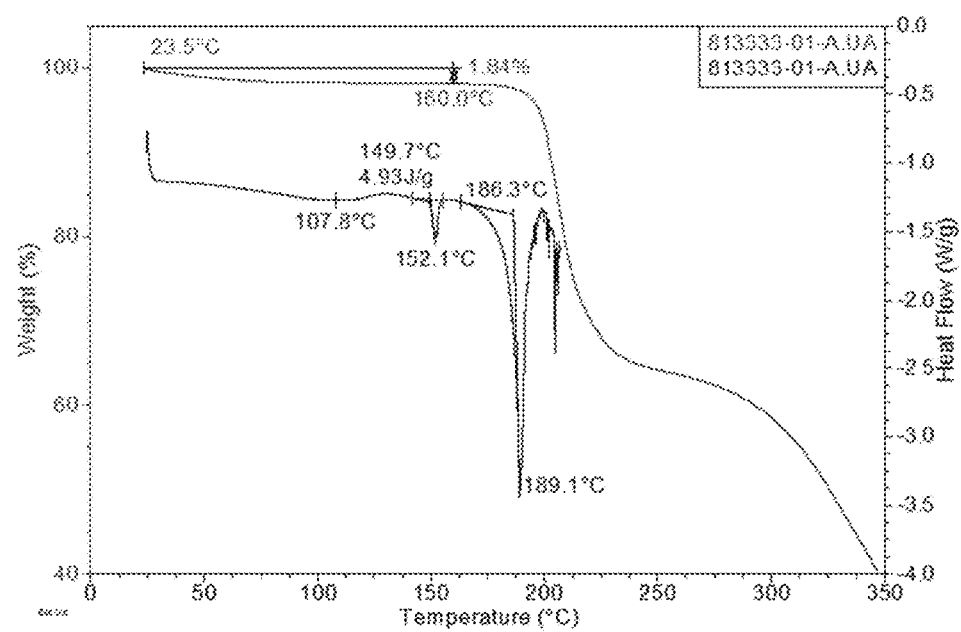
FIG. 64 shows a TGA and DSC plot obtained for crystalline Form A.

In certain embodiments, Form A is characterized by a DSC thermogram comprising an endotherm peak in units ° C. at about 107.8. In certain embodiments, the DSC thermogram comprises an endotherm peak in units ° C. at about 152.1. In certain embodiments, the DSC thermogram comprises an endotherm peak in units ° C. at about 189.1. In certain embodiments, the DSC thermogram comprises endotherm peaks in units ° C. at about 107.8, about 152.1, and about 189.1. In certain embodiments, the DSC thermogram is substantially identical to that of FIG. 64.

In certain embodiments, Form A is characterized by a TGA thermogram showing weight loss of about 1.8% at 160° C. In certain embodiments, the TGA thermogram is substantially identical to that of FIG. 64.

In certain embodiments, a tartrate salt having a stoichiometry of about 2:1 comprises Form A. In certain embodiments, a tartrate salt having a stoichiometry of about 2:1 consists essentially of Form A. In certain embodiments, Form A is essentially pure. Physical and chemical properties of Form A are described in Example 26, Table 17. Toxicokinetic and toxicology profiles of Form A are described in Example 27.

e. Forms C, E, F, G, H, and I

The tartrate salt of the compound of Structure (I) exists in other crystalline forms, as summarized in Table 2.

TABLE 2

Crystalline forms of tartrate salts of Structure (I)

| Crystal form | Solvent screen from Form A | Slurry screen from Form A | Slurry screen from Form D | Stoichiometry | Stability by HPLC | DSC Onset (° C.) | Moisture sorption isotherm |
|---|---|---|---|---|---|---|---|
| A | +++ | +++ | Not formed | 1:1.5 | Stable | 170.52 | hygroscopic |
|   |     |     |            | 1:2   | Stable | 187.06 | hygroscopic |
| B | +   | +   |            | 1:1.2 |        | 131.62 | hygroscopic |
| C | +   | Not formed |     |       |        | 165.76 | hygroscopic |
| D | Not formed |  | ++       | 1:1   | Stable | 127.43 | hygroscopic |
| E |     |     | +          |       |        | 102.33 |             |
| F |     |     | ++         |       |        | 61.06  |             |
| G |     |     | +          |       |        | 128.61 |             |
| H |     |     | +          |       |        | 139.36 |             |
| I |     |     | +          |       |        | 118.60 |             |

Figure 98:
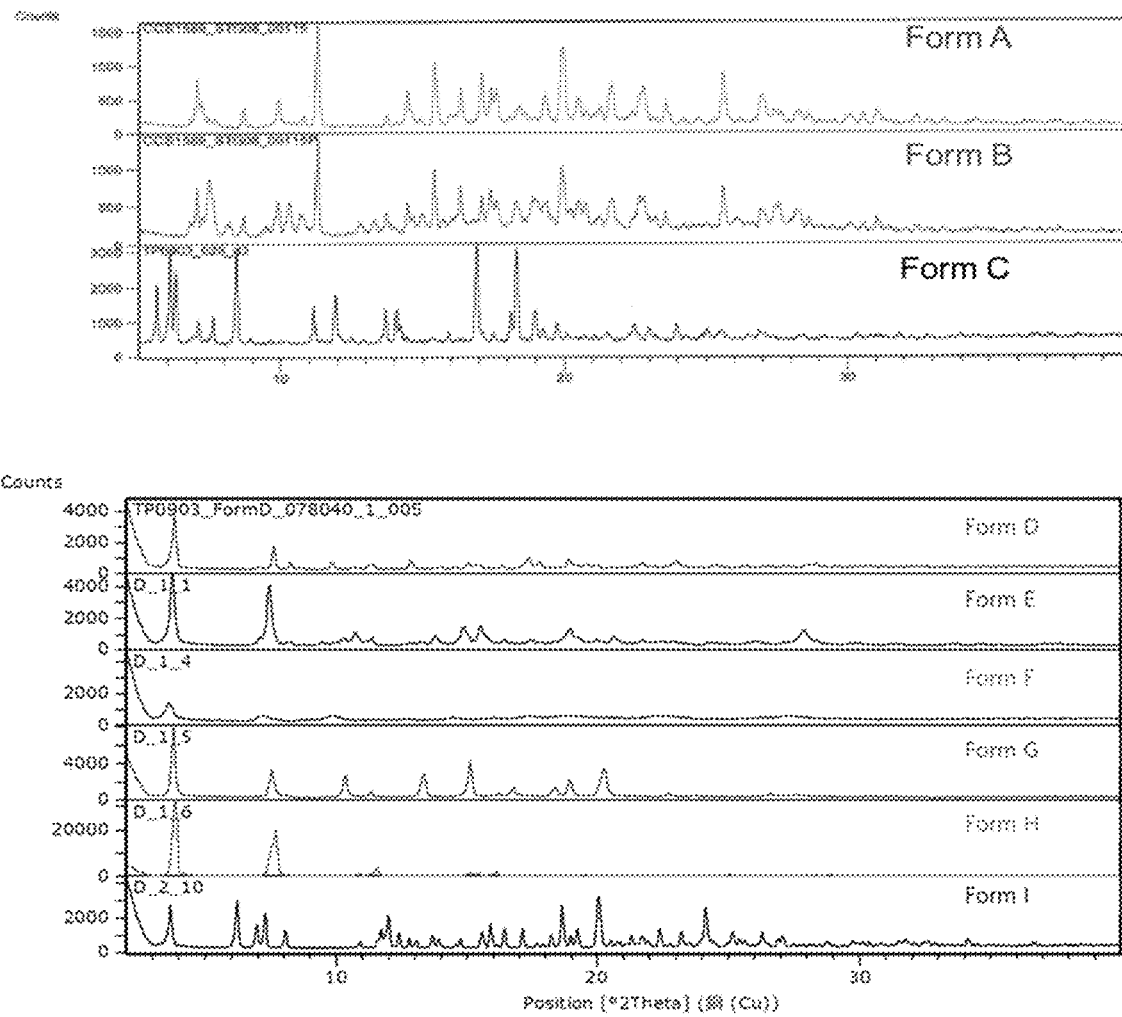
FIG. 98A shows a comparison between XRPD diffractograms of crystalline Forms A, B, and C.
FIG. 98B shows a comparison between XRPD diffractograms of crystalline Forms D, E, F, G, H, and I.

+++: Formed in three solvent systems or more
++: Formed in a few solvent systems
+: Formed in one solvent systms or only at the higher temperature From polymorph screening studies, ten crystal forms, Form A (1:2), A' (1:1.5), B, C, D, E, F, G, H and I, were assigned by XRPD patterns as shown in FIG. 98. The thermal behavior (DSC/TGA charts) for these crystalline forms are shown in FIGS. 99A-99I.

The Slurry Screens and Solvent Screens described below were performed according to the methods of Example 51.

TABLE 3

Slurry Screening of Form A

| | Room Temperature | | 50° C. | |
|---|---|---|---|---|
| Run | Solvent | Crystal Form | Run | Solvent | Crystal Form |
| 1-1 | Methanol | A | 2-1 | Methanol | A |
| 1-2 | Ethanol | A | 2-2 | Ethanol | A |
| 1-3 | 2-Propanol | A | 2-3 | 2-Propanol | A |
| 1-4 | 2-Propanol-H$_2$O(5:1) | A | 2-4 | 2-Propanol-H$_2$O(5:1) | A |
| 1-5 | H$_2$O | B | 2-5 | H$_2$O | — |
| 1-6 | Methanol-H$_2$O(5:1) | A | 2-6 | Methanol-H$_2$O(5:1) |   |
| 1-7 | Ethanol-H$_2$O(5:1) | A | 2-7 | Ethanol-H$_2$O(5:1) | A |
| 1-8 | Methanol-H$_2$O(10:1) | A | 2-8 | Methanol-H$_2$O(10:1) | A |
| 1-9 | Acetonitrile-H$_2$O(1:1) | — | 2-9 | Acetonitrile-H$_2$O(1:1) | — |
| 1-10 | Acetonitrile-H$_2$O(10:1) | A | 2-10 | Acetonitrile-H$_2$O(10:1) | A |

TABLE 4

Solvent Screen of Form A'

| Run | Crystal Form | Solvent | Run | Crystal Form | Solvent |
|---|---|---|---|---|---|
| 001 | B | H$_2$O | 016 | A | Chlorobenzene |
| 002 | — | Methanol | 017 | A | Toluene |
| 003 | A | Ethanol | 018 | A + C | H$_2$O-Methanol(1:1) |
| 004 | A | 2-Propanol | 019 | — | H$_2$O-Ethanol(1:1) |
| 005 | A | 2-Butanol | 020 | C | H$_2$O-2-Propanol (1:1) |
| 006 | A | Chloroform | 021 | — | H$_2$O-Acetonitrile(1:1) |
| 007 | A | Acetonitrile | 022 | — | H$_2$O-Acetone(1:1) |
| 008 | A | 1,2-Dimethoxyethane | 023 | Amorphous | H$_2$O-Methanol(1:10) |
| 009 | A | Tetrahydrofuran | 024 | Amorphous | H$_2$O-Ethanol(1:10) |
| 010 | A | Butyl methyl ether | 025 | Amorphous + A | H$_2$O-2-Propanol (1:10) |
| 011 | A | Cyclopentyl methyl ether | 026 | Amorphous + A | H$_2$O-Acetonitrile(1:10) |
| 012 | A | Ethyl acetate | 027 | Amorphous + A | H$_2$O-Acetone(1:10) |
| 013 | A | Propyl acetate | 028 | C | H$_2$O-2-Propanol (1:5) |
| 014 | A | Acetone | 029 | — | H$_2$O-Acetonitrile(1:5) |
| 015 | A | Heptane | 030 | — | H$_2$O-Acetone(1:5) |

TABLE 5

Slurry Screen of Form A'

| | Room Temperature | | | 50° C. | |
|---|---|---|---|---|---|
| Run | Solvent | Crystal Form | Run | Solvent | Crystal Form |
| 1-1 | Methanol | A | 2-1 | Methanol | A |
| 1-2 | Ethanol | A | 2-2 | Ethanol | A |
| 1-3 | 2-Propanol | A | 2-3 | 2-Propanol | A |
| 1-4 | Acetone | A | 2-4 | Acetone | A |
| 1-5 | Acetonitrile | A | 2-5 | Acetonitrile | A |
| 1-6 | 2-Propanol-H$_2$O(10:1) | A | 2-6 | 2-Propanol-H$_2$O(10:1) | A |
| 1-7 | 2-Propanol-H$_2$O(5:1) | A | 2-7 | 2-Propanol-H$_2$O(5:1) | A |
| 1-8 | Methyl tert-butyl ether | A | 2-8 | Methyl tert-butyl ether | A |
| 1-9 | 2-Propanol-H$_2$O(1:1) | A | 2-9 | 2-Propanol-H$_2$O(1:1) | — |

TABLE 6

Slurry Screen of Form D

| | Room Temperature | | | 50° C. | |
|---|---|---|---|---|---|
| Run | Solvent | Crystal Form | Run | Solvent | Crystal Form |
| 1-1 | Methanol | E | 2-1 | Methanol | F |
| 1-2 | Ethanol | D | 2-2 | Ethanol | D |
| 1-3 | 2-Propanol | D | 2-3 | 2-Propanol | D |
| 1-4 | 2-Propanol-H$_2$O(5:1) | F | 2-4 | 2-Propanol-H$_2$O(5:1) | F |
| 1-5 | H$_2$O | G | 2-5 | H$_2$O | G |
| 1-6 | Methanol-H$_2$O(5:1) | H | 2-6 | Methanol-H$_2$O(5:1) | — |
| 1-7 | Ethanol-H$_2$O(5:1) | F | 2-7 | Ethanol-H$_2$O(5:1) | F |
| 1-8 | Ethanol-H$_2$O(10:1) | D + F | 2-8 | Ethanol-H$_2$O(10:1) | F |
| 1-9 | Acetonitrile-H$_2$O(1:1) | — | 2-9 | Acetonitrile-H$_2$O(1:1) | — |
| 1-10 | Acetonitrile-H$_2$O(10:1) | F | 2-10 | Acetonitrile-H$_2$O(10:1) | I |

Figure 99A:
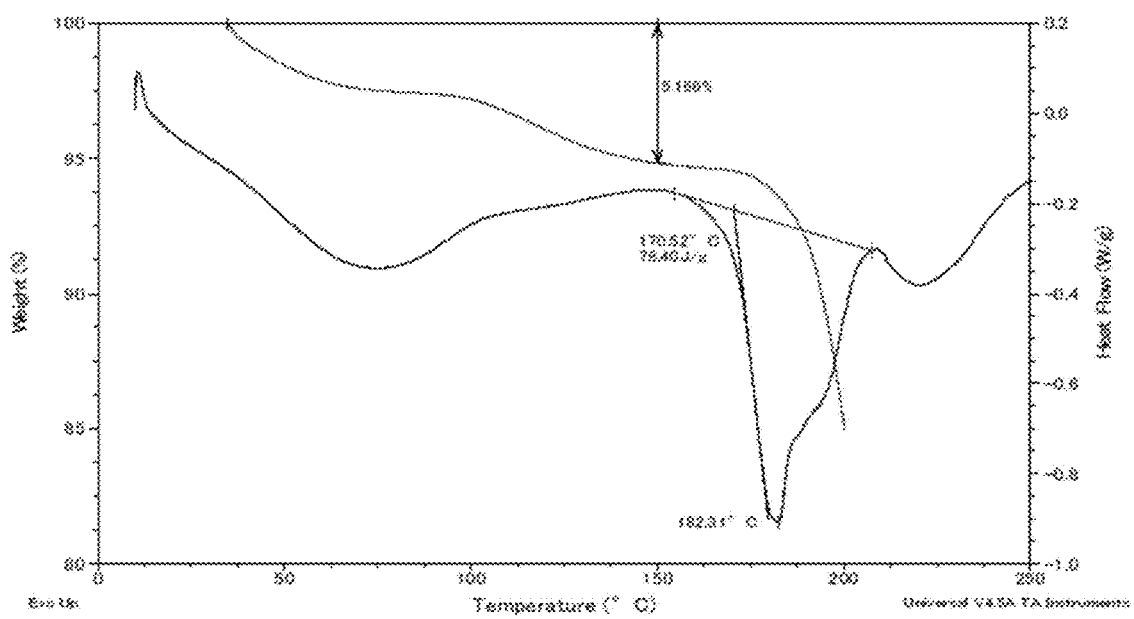
FIGS. 99A-99I shows thermal behavior (DSC/TGA charts) for crystalline Forms A through I.
Figure 99A:
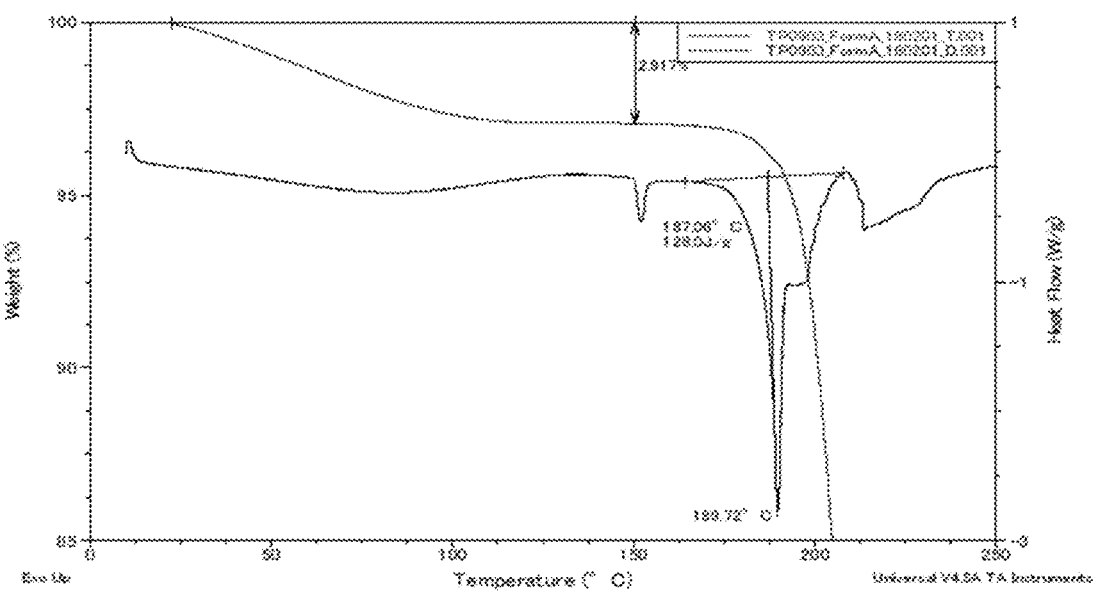
Figure 99B:
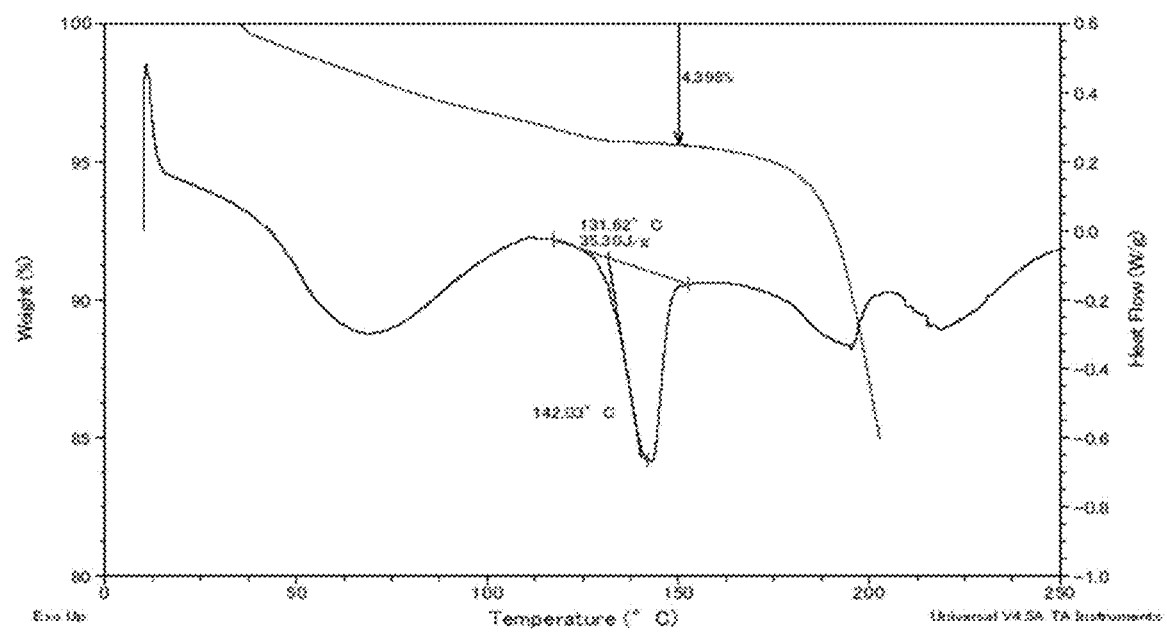
Figure 99C:
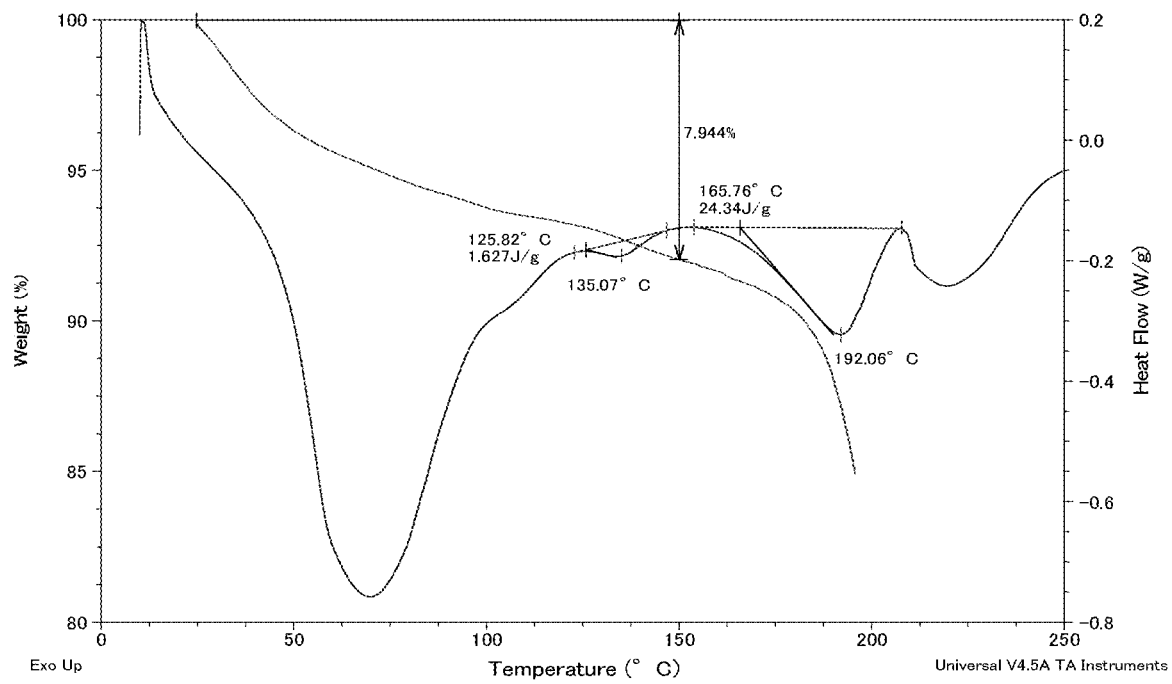

In the solvent screen shown in Table 4 (above), Form C was formed by the recrystallization of Form A' with the mixture of H$_2$O and alcohol, such as methanol and 2-propanol. About 10% weight loss and a broad endotherm peak was observed in the thermal analysis chart as shown in FIG. 99C. That suggested that Form C might be a solvate with alcohol and the alcohol was eliminated depending on the increase of temperature.

Figure 99D:
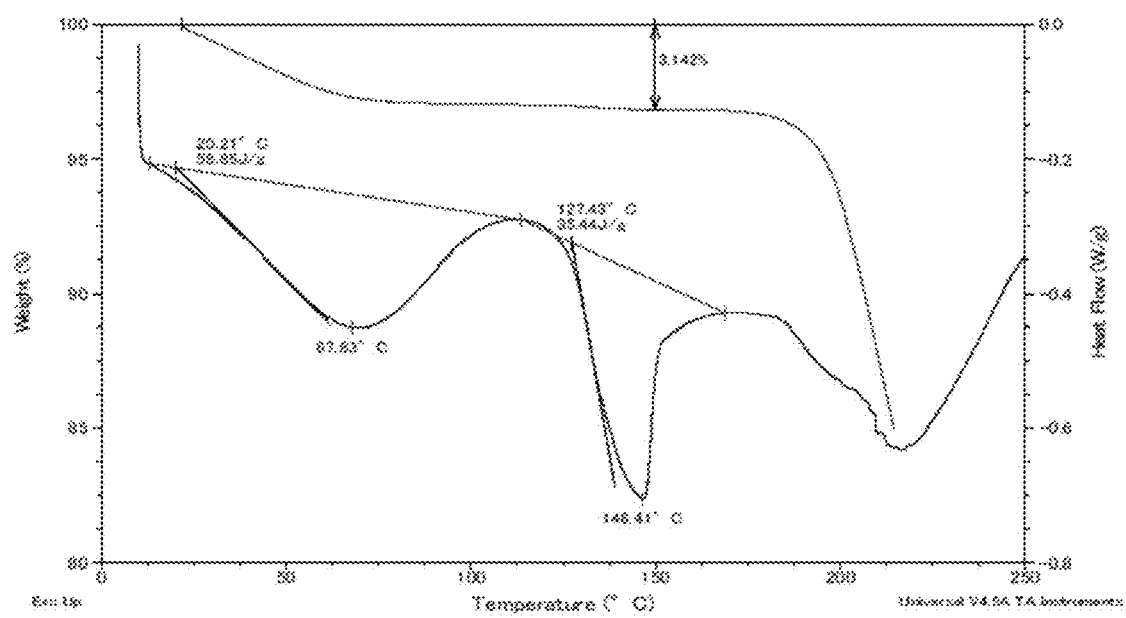
Figure 99E:
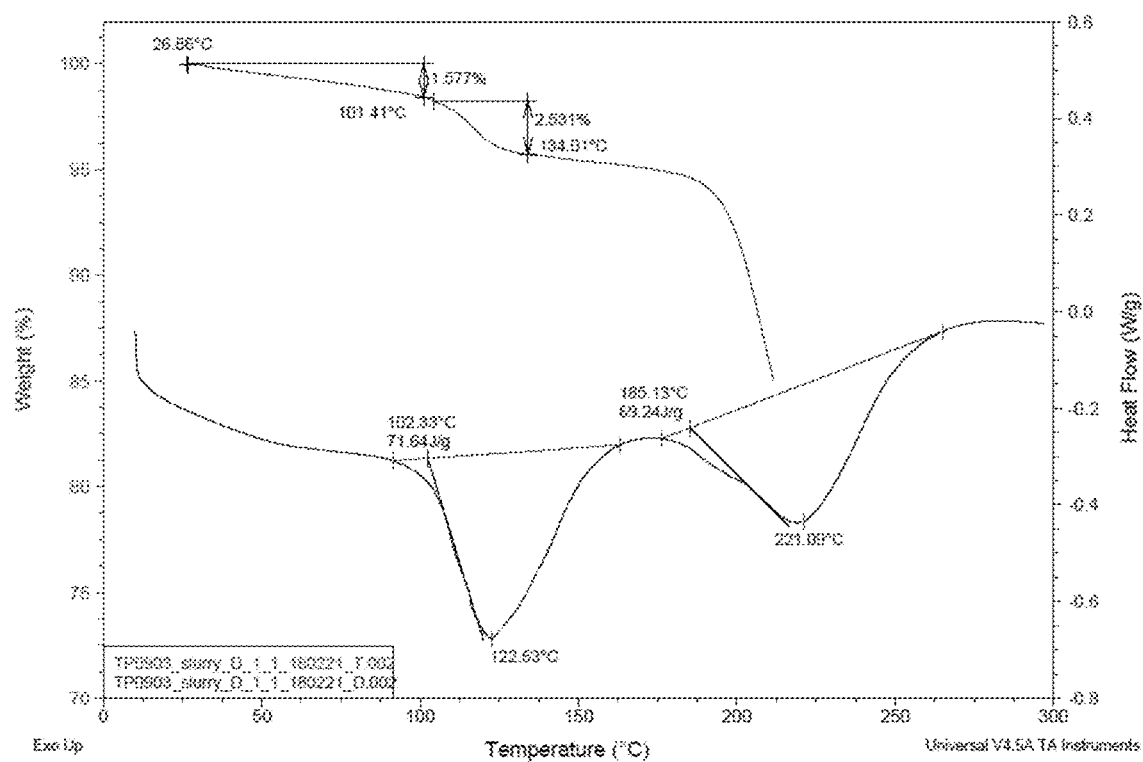

Form E was formed in the slurry screen from Form D only in methanol at room temperature, as shown in Table 6. About 4% weight loss was observed in the thermal analysis chart as shown in FIG. 99E.

Figure 99F:
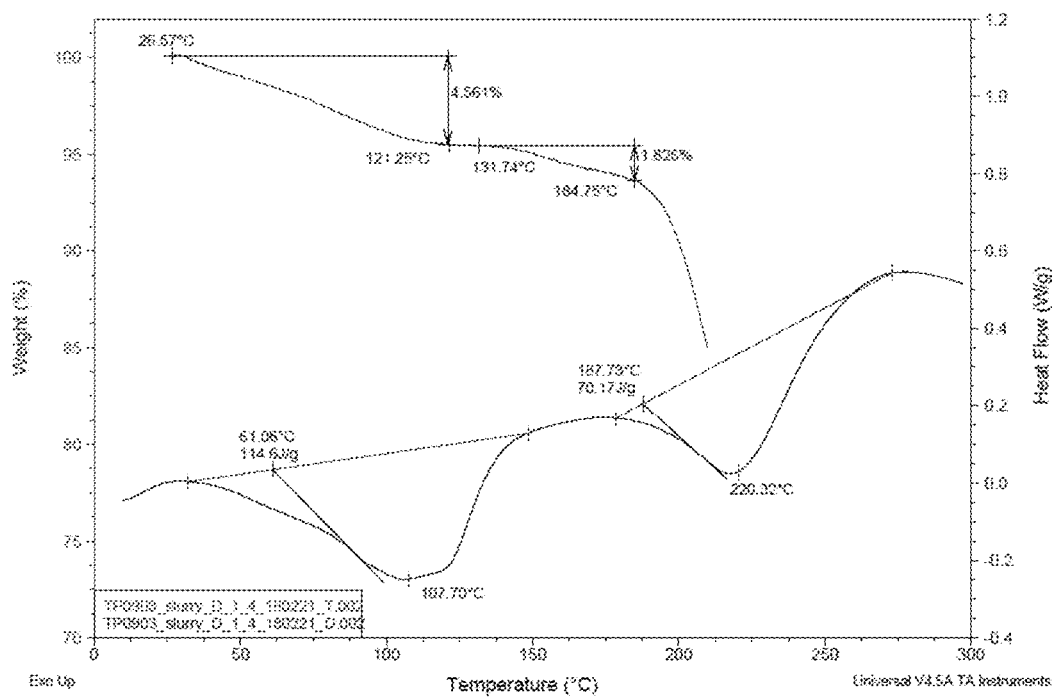
Figure 99G:
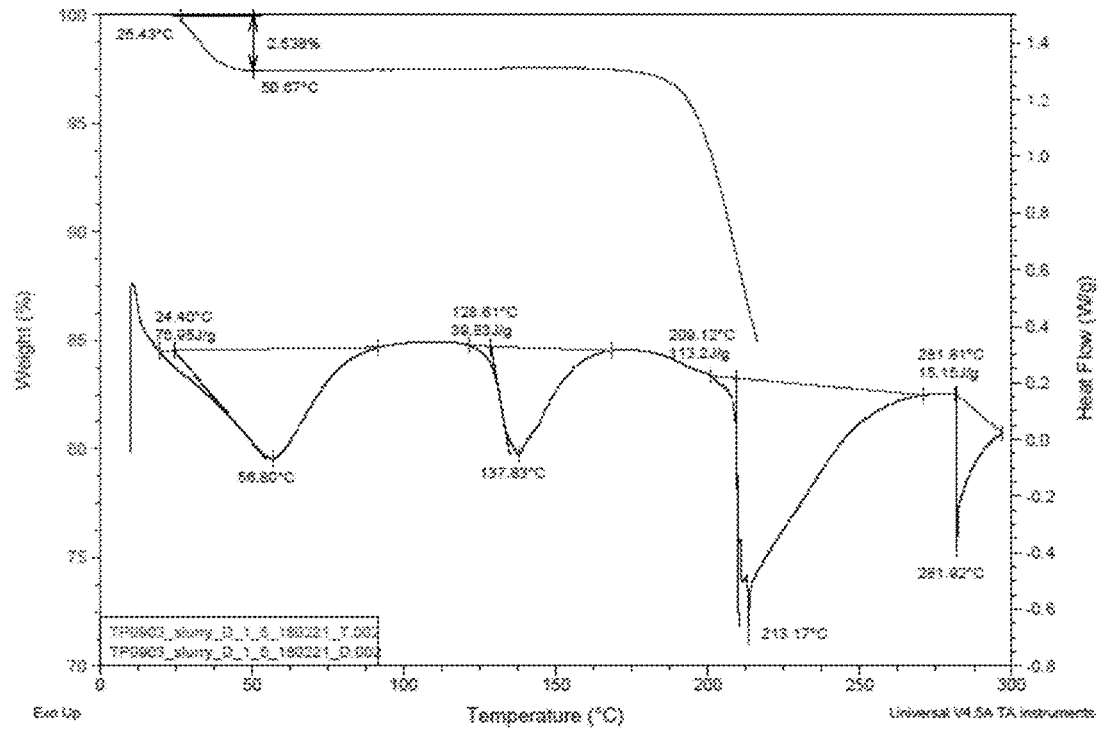
Figure 99H:
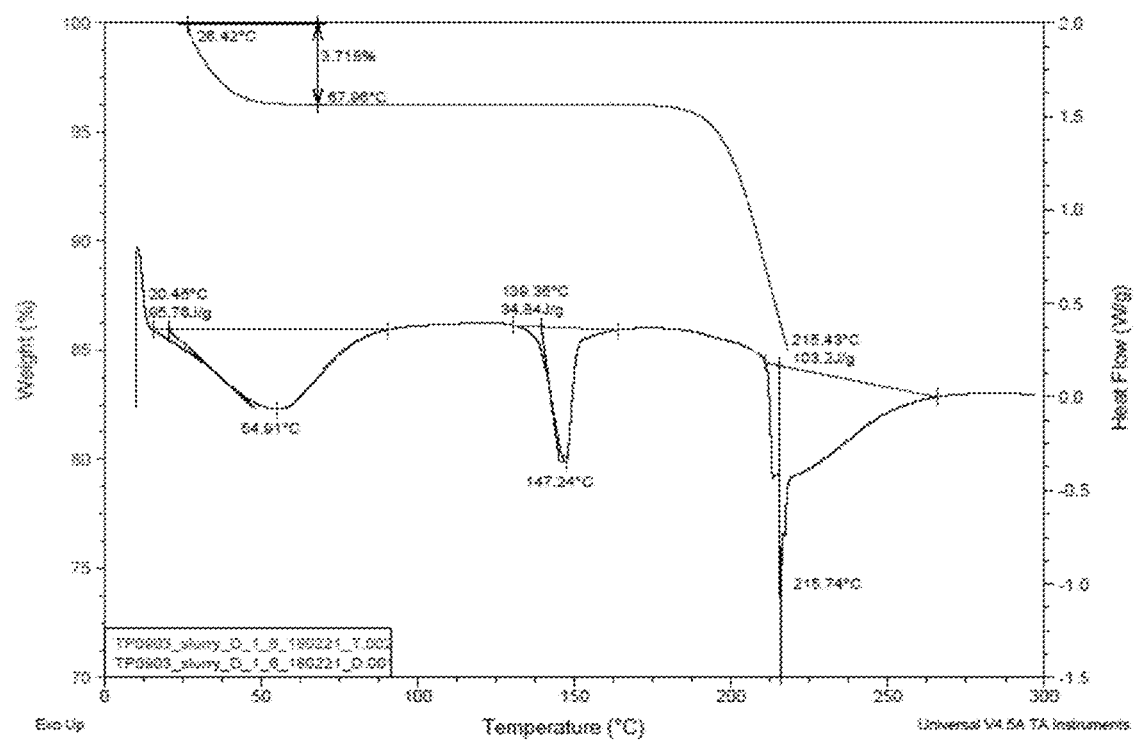
Figure 99I:
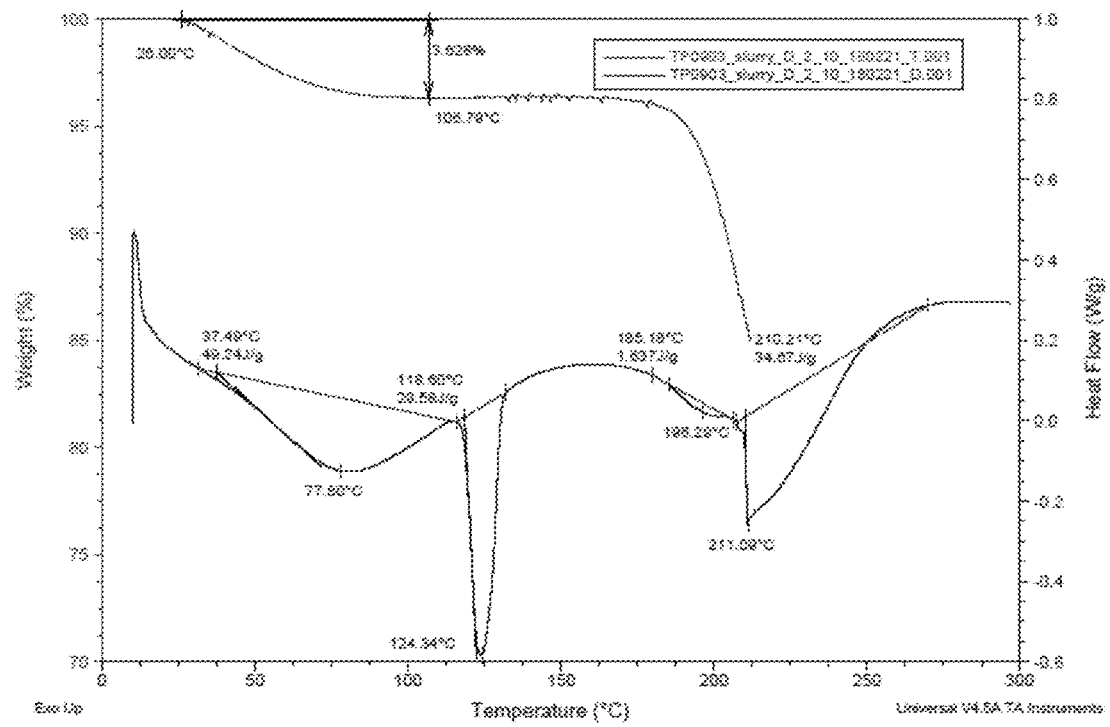

Form F was formed in the slurry screen from Form D in the mixture of alcohol and H$_2$O at room temperature and 50° C. as shown in Table 6. About 6%-weight loss was observed in the thermal analysis chart as shown in FIG. 99F.

Form G was formed in the slurry screen from Form D in H$_2$O at room temperature and 50° C. as shown in Table 6. The thermal analysis chart was provided in FIG. 99G.

Form H was formed in the slurry screen from Form D only in Methanol-H$_2$O (5:1) at room temperature, as shown in 6. The thermal analysis chart is provided in FIG. 99H.

Form I was formed in the slurry screen from Form D only in acetonitrile-H$_2$O (10:1) at 50° C., as shown in Table 6. Thermal analysis data is provided in FIG. 99I.

C. Pharmaceutical Compositions

In another aspect, the present disclosure provides pharmaceutical compositions comprising one or more compounds described herein, such as a pharmaceutically acceptable salt (e.g., a tartrate salt) of the compound of structure (I), or a crystalline form thereof (e.g., Form A), or a compound of structure (IV), or a pharmaceutically acceptable salt thereof, and a pharmaceutically acceptable carrier or excipient. As used herein, "a compound of structure (I)" is intended to refer to either the compound per se (i.e., freebase), or a pharmaceutically acceptable salt such as a tartrate salt of the compound of structure (I), or a crystalline form thereof (e.g., Form A), unless it is specified otherwise. As used herein, "a compound of structure (IV)" is intended to refer to the compound per se, or an embodiment thereof as described herein, including pharmaceutically acceptable salts thereof (e.g., a tartrate salt). In some embodiments, the pharmaceutical composition is formulated for oral administration. For example, in some embodiments, the pharmaceutical composition comprises an oral capsule. In other embodiments, the pharmaceutical composition is formulated for injection. In some more specific embodiments, the carrier or excipient is selected from the group consisting of cellulose, lactose, carboxymethylcellulose and magnesium stearate.

In still more embodiments, the pharmaceutical compositions comprise a compound of structure (I), or a pharmaceutically acceptable salt thereof (e.g., tartrate salt), or a compound of structure (IV), and an additional therapeutic agent (e.g., anticancer agent). Non-limiting examples of such therapeutic agents are described herein below (e.g., Ibrutinib or Alvocidib).

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, the pharmaceutically acceptable salt (e.g., tartrate salt) of the compound of structure (I), or the compound of structure (IV), as described herein is administered in a local rather than systemic manner, for example, via injection directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound of structure (I) or pharmaceutically acceptable salt thereof (e.g., a tartrate salt), or the compound of structure (IV), as described herein is provided in the form of a rapid release formulation, in the form of an extended release formulation, or in the form of an intermediate release formulation. In yet other embodiments, the compound of structure (I) or pharmaceutically acceptable salt thereof (e.g., a tartrate salt), or the compound of structure (IV), as described herein is administered topically.

The compound of structure (I) or pharmaceutically acceptable salt of the compound of structure (I) (e.g., a tartrate salt), or the compound of structure (IV), according to certain embodiments is effective over a wide dosage range. For example, in the treatment of adult humans, dosages from 0.01 to 1000 mg, from 0.5 to 100 mg, from 5 to 100 mg, from 20 to 100 mg, from 25 to 75 mg, from 1 to 50 mg per day, and from 5 to 40 mg per day are examples of dosages that are used in some embodiments. An exemplary dosage is 10 to 30 mg per day. In various embodiments, the dosage is 3, 6, 9, 12, 16, 21, 28, 32, 42, or 50 mg per day. The exact dosage will depend upon the route of administration, the form in which the compound of structure (I) or pharmaceutically acceptable salt thereof (e.g., a tartrate salt), or the compound of structure (IV), is administered, the subject to be treated, the body weight of the subject to be treated, and the preference and experience of the attending physician.

In certain embodiments, the dosage of the compound of structure (I) or pharmaceutically acceptable salt thereof (e.g., a tartrate salt) is about 1-37 mg/m$^2$ (e.g., 1-25 mg/m$^2$) or about 1-75 mg (e.g., 1-50 mg) daily.

In certain embodiments, the daily dosage of the compound of structure (I) (e.g., freebase, or a pharmaceutically acceptable salt thereof such as a tartrate salt), or the compound of structure (IV) can be about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In some embodiments, the compound of structure (I) or pharmaceutically acceptable salt thereof (e.g., a tartrate salt), or the compound of structure (IV), is administered in a single dose. Typically, such administration will be by injection, e.g., intravenous injection, in order to introduce the agent quickly. However, other routes are used as appropriate. A single dose of the compound of structure (I) or pharmaceutically acceptable salt thereof (e.g., a tartrate salt), or the compound of structure (IV), may also be used for treatment of an acute condition.

In some embodiments, the compound of structure (I) or pharmaceutically acceptable salt thereof (e.g., a tartrate salt), or the compound of structure (IV), is administered in multiple doses. In some embodiments, dosing is about once, twice, three times, four times, five times, six times, or more than six times per day. In other embodiments, dosing is about once a month, once every two weeks, once a week, or once every other day. In another embodiment the compound of structure (I) or pharmaceutically acceptable salt thereof (e.g., a tartrate salt), or the compound of structure (IV), and another agent (e.g., Ibrutinib or Alvocidib) are administered together about once per day to about 6 times per day. In another embodiment the administration of the compound of structure (I) or pharmaceutically acceptable salt thereof (e.g., a tartrate salt), or the compound of structure (IV), and an agent continues for less than about 7 days. In yet another embodiment the administration continues for more than about 6, 10, 14, 28 days, two months, six months, or one year. In some cases, continuous dosing is achieved and maintained as long as necessary.

Administration of the compound of structure (I) or pharmaceutically acceptable salt thereof (e.g., a tartrate salt), or the compound of structure (IV), may continue as long as necessary. In some embodiments, the compound of structure (I) or pharmaceutically acceptable salt thereof (e.g., a tartrate salt), or the compound of structure (IV), is administered for more than 1, 2, 3, 4, 5, 6, 7, 14, or 28 days. In some embodiments, the compound of structure (I) or pharmaceutically acceptable salt thereof (e.g., a tartrate salt), or the compound of structure (IV), is administered for less than 28, 14, 7, 6, 5, 4, 3, 2, or 1 day. In some embodiments, the compound of structure (I) or pharmaceutically acceptable salt thereof (e.g., a tartrate salt), or the compound of structure (IV), is administered chronically on an ongoing basis, e.g., for the treatment of chronic effects. In some embodiments, the compound of structure (I) or pharmaceutically acceptable salt thereof (e.g., a tartrate salt), or the compound of structure (IV), is administered once daily for the first 21 out of a 28 day cycle.

In some embodiments, a compound of structure (I) or a pharmaceutically acceptable salt thereof is administered for 1, 2, 3, 4, 5, 6, or more cycles. In some embodiments, a compound of structure (I) or a pharmaceutically acceptable salt thereof is administered in treatment cycles until the subject presents progressive disease or no longer tolerates treatment. In some embodiments, a compound of structure (I) or a pharmaceutically acceptable salt thereof is administered in treatment cycles until the subject presents no detectable disease. In some embodiments, a compound of structure (I) or a pharmaceutically acceptable salt thereof is administered chronically on an ongoing basis, e.g., for the treatment of chronic effects.

Dosage amount and interval may be adjusted individually to provide plasma levels of the active species which are sufficient to maintain desired pharmacological effects. These plasma levels are referred to as minimal effective concentrations (MECs). Dosages necessary to achieve the MEC will depend on individual characteristics and route of administration. HPLC assays or bioassays can be used to determine plasma concentrations.

Dosage intervals can also be determined using MEC value. In some embodiments, methods of treatment comprise maintaining plasma levels above the MEC for 10-90% of the time. In some embodiments, plasma levels are maintained between 30-90%. In some embodiments, plasma levels are maintained between 50-90%. For example, in certain embodiments, effective amounts of a therapeutic agent may range from approximately 2.5 mg/m2 to 1500 mg/m2 per day. Additional illustrative amounts range from 0.2-1000 mg/qid, 2-500 mg/qid, and 20-250 mg/qid.

In some embodiments, the compound of structure (I) or pharmaceutically acceptable salt thereof (e.g., a tartrate salt), or a compound of structure (IV), is administered in dosages. It is known in the art that due to inter subject variability in compound pharmacokinetics, individualization of dosing regimen is necessary for optimal therapy. Dosing for the compound of structure (I) or pharmaceutically acceptable salt thereof (e.g., a tartrate salt), or a compound of structure (IV), may be found by routine experimentation in light of the instant disclosure.

In some embodiments, the compound of structure (I) or pharmaceutically acceptable salt thereof (e.g., a tartrate salt), or a compound of structure (IV), is formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

In certain embodiments, the compound of structure (I) or pharmaceutically acceptable salt thereof (e.g., a tartrate salt), or a compound of structure (IV), described are administered as pharmaceutical compositions in which the compound of structure (I) or pharmaceutically acceptable salt thereof (e.g., a tartrate salt), or a compound of structure (IV), is mixed with other active ingredients, as in combination therapy. Encompassed herein are all combinations of actives set forth in the combination therapies section below and throughout this disclosure.

A pharmaceutical composition, as used herein, refers to a mixture of the compound of structure (I) or pharmaceutically acceptable salt thereof (e.g., a tartrate salt), or a compound of structure (IV), with other chemical components, such as carriers, stabilizers, diluents, dispersing agents, suspending agents, thickening agents, and/or excipients. In certain embodiments, the pharmaceutical composition facilitates administration of the compound of structure (I) or pharmaceutically acceptable salt thereof (e.g., a tartrate salt), or the compound of structure (IV), to a subject. In some embodiments, practicing the methods of treatment or use provided herein, therapeutically effective amounts of the compound of structure (I) or pharmaceutically acceptable salt thereof (e.g., a tartrate salt), or the compound of structure (IV), provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compound of structure (I) or pharmaceutically acceptable salt thereof (e.g., a tartrate salt), or the compound of structure (IV), described herein is used singly or in combination with one or more therapeutic agents as components of mixtures.

In some embodiments, the mammal (e.g., a human) is older than 18 years old. In some embodiments, the mammal (e.g., a human) has a life expectancy of ≥3 months, is not pregnant or cannot become pregnant, have acceptable liver function (e.g., bilirubin≤1.5× the upper limit of normal, or <3.0× the upper limit of normal for patients receiving immunotherapy, aspartate aminotransferase, alanine aminotransferase and alkaline phosphatase ≤2.5× the upper limit of normal), have acceptable renal function (e.g., calculated creatine clearance ≥30 mL/minute), have acceptable hematologic status (e.g., granulocyte ≥1500 cells/mm$^3$, platelet count ≥100,000 platelets/mm$^3$ or hemoglobin ≥9 g/dL), have no clinically significant abnormalities on urinalysis, have acceptable coagulation status (e.g., prothrombin time within 1.5× normal limits or activated partial thromboplastin time within 1.5× normal limits), or any combination thereof.

In one embodiment, one or more of the compound of structure (I) or pharmaceutically acceptable salt thereof (e.g., a tartrate salt), or the compound of structure (IV), is formulated in an aqueous solution. In specific embodiments, the aqueous solution is selected from, by way of example only, a physiologically compatible buffer, such as Hank's solution, Ringer's solution, or physiological saline buffer. In other embodiments, the compound of structure (I) or pharmaceutically acceptable salt thereof (e.g., a tartrate salt), or the compound of structure (IV), is formulated for transmucosal administration. In specific embodiments, transmucosal formulations include penetrants that are appropriate to the barrier to be permeated. In still other embodiments wherein the compounds described herein are formulated for other parenteral injections; appropriate formulations include aqueous or non-aqueous solutions. In specific embodiments, such solutions include physiologically compatible buffers and/or excipients.

In another embodiment, the compound of structure (I) or pharmaceutically acceptable salt thereof (e.g., a tartrate salt), or the compound of structure (IV), described herein is formulated for oral administration. Compounds described herein are formulated by combining the active compounds with, e.g., pharmaceutically acceptable carriers or excipients. In various embodiments, the compound of structure (I) or pharmaceutically acceptable salt thereof (e.g., a tartrate salt), or the compound of structure (IV), described herein is formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with the compound of structure (I) or pharmaceutically acceptable salt thereof (e.g., a tartrate salt), or the compound of structure (IV), described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of the compound of structure (I) or pharmaceutically acceptable salt thereof (e.g., a tartrate salt), or the compound of structure (IV), described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain the compound of structure (I) or pharmaceutically acceptable salt thereof (e.g., a tartrate salt), or the compound of structure (IV), that is dissolved or suspended in a suitable liquid. Suitable liquids include, by way of example only, one or more fatty oil, liquid paraffin, or liquid polyethylene glycol. In addition, stabilizers are optionally added.

In other embodiments, a therapeutically effective amount of the compound of structure (I) or pharmaceutically acceptable salt thereof (e.g., a tartrate salt), or the compound of structure (IV), described herein is formulated for buccal or sublingual administration. Formulations suitable for buccal or sublingual administration include, by way of example only, tablets, lozenges, or gels. In still other embodiments, the compound of structure (I) or pharmaceutically acceptable salt thereof (e.g., a tartrate salt), or the compound of structure (IV), described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the compound of structure (I) or pharmaceutically acceptable salt thereof (e.g., a tartrate salt), or the compound of structure (IV), are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compound of structure (I) or pharmaceutically acceptable salt thereof (e.g., a tartrate salt), or the compound of structure (IV), is administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compound of structure (I) or pharmaceutically acceptable salt thereof (e.g., a tartrate salt), or the compound of structure (IV), is formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compound of structure (I) or pharmaceutically acceptable salt thereof (e.g., a tartrate salt), or the compound of structure (IV), is accomplished by means of iontophoretic patches and the like. In certain embodiments, transdermal patches provide controlled delivery of the compound of structure (I) or pharmaceutically acceptable salt thereof (e.g., a tartrate salt), or the compound of structure (IV). In specific embodiments, the rate of absorption is slowed by using rate-controlling membranes or by trapping the compound of structure (I) or pharmaceutically acceptable salt thereof (e.g., a tartrate salt), or the compound of structure (IV), within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound of structure (I) or pharmaceutically acceptable salt thereof (e.g., a tartrate salt), or the compound of structure (IV), optionally with carriers, optionally a rate controlling barrier to deliver the compound of structure (I) or pharmaceutically acceptable salt thereof (e.g., a tartrate salt), or the compound of structure (IV), to the skin of the host at a controlled and predetermined rate over a prolonged period of time, and means to secure the device to the skin.

In other embodiments, the compound of structure (I) or pharmaceutically acceptable salt thereof (e.g., a tartrate salt), or the compound of structure (IV), is formulated for administration by inhalation. Various forms suitable for administration by inhalation include, but are not limited to, aerosols, mists or powders. Pharmaceutical compositions of any of the compound of structure (I) or pharmaceutically acceptable salt thereof (e.g., a tartrate salt), or the compound of structure (IV), are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound of structure (I) or pharmaceutically acceptable salt thereof (e.g., a tartrate salt), or the compound of structure (IV), and a suitable powder base such as lactose or starch.

In still other embodiments, the compound of structure (I) or pharmaceutically acceptable salt thereof (e.g., a tartrate salt), or the compound of structure (IV), is formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising the compound of structure (I) or pharmaceutically acceptable salt thereof (e.g., a tartrate salt), or the compound of structure (IV), are manufactured in a conventional manner, such as, by way of example only, by means of conventional mixing, dissolving, granulating, dragee-making, levigating, emulsifying, encapsulating, entrapping or compression processes.

Additionally, the compound of structure (I) or pharmaceutically acceptable salt thereof (e.g., a tartrate salt), or the compound of structure (IV), described herein encompass unsolvated as well as solvated forms with pharmaceutically acceptable solvents such as water, ethanol, and the like. The solvated forms of the compound of structure (I) or pharmaceutically acceptable salt thereof (e.g., a tartrate salt), or the compound of structure (IV), presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compound of structure (I) or pharmaceutically acceptable salt thereof (e.g., a tartrate salt), or the compound of structure (IV), described herein include formulating the compound of structure (I) or pharmaceutically acceptable salt thereof (e.g., a tartrate salt), or the compound of structure (IV), with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which the compound of structure (I) or pharmaceutically acceptable salt thereof (e.g., a tartrate salt), or the compound of structure (IV), is dissolved, emulsions comprising a compound, or a solution containing liposomes, micelles, or nanoparticles comprising the compound of structure (I) or pharmaceutically acceptable salt thereof (e.g., a tartrate salt), or the compound of structure (IV), as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, the pharmaceutical composition comprising the compound of structure (I) or pharmaceutically acceptable salt thereof (e.g., a tartrate salt), or the compound of structure (IV), illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of the compound of structure (I) or pharmaceutically acceptable salt thereof (e.g., a tartrate salt), or the compound of structure (IV). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose redo sable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of the compound of structure (I) or pharmaceutically acceptable salt thereof (e.g., a tartrate salt), or the compound of structure (IV), provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of structure (I) or pharmaceutically acceptable salt thereof (e.g., a tartrate salt), or the compound of structure (IV), is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound of structure (I) or pharmaceutically acceptable salt thereof (e.g., a tartrate salt), or the compound of structure (IV), is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of the compound of structure (I) or pharmaceutically acceptable salt thereof (e.g., a tartrate salt), or the compound of structure (IV), is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

Pharmaceutical compositions comprising a pharmaceutically acceptable salt (e.g., tartrate salt) of the compound of structure (I), as described above, may comprise a crystalline form as described herein (e.g., Form A). A polymorph of the present disclosure is typically formulated into pharmaceutical dosage forms to provide an easily controllable dosage of the drug and to give the subject an elegant and ergonomic product. The dosage regimen for the polymorphs of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the subject, and the effect desired. Polymorphs of this disclosure may be administered in a single daily dose, or the total daily dosage may be administered in divided doses of two, three, or four times daily.

In some embodiments, the pharmaceutical composition comprises the polymorph in a concentration ranging from about 0.5 wt. % to about 5.0 wt. %. In other specific embodiments, the pharmaceutical composition comprises the polymorph in a concentration ranging from about 1.8 wt. % to about 2.8 wt. %.

In some embodiments, the pharmaceutical composition comprises the polymorph in a concentration ranging from about 10.0 wt. % to about 20.0 wt. %. In other specific embodiments, the pharmaceutical composition comprises the polymorph in a concentration ranging from about 13.7 wt. % to about 15.7 wt. %.

In some embodiments, the pharmaceutical composition comprises the polymorph in a concentration ranging from about 16.3 wt. % to about 36.3 wt. %. In other specific embodiments, the pharmaceutical composition comprises the polymorph in a concentration ranging from about 21.3 wt. % to about 31.3 wt. %.

In more specific embodiments, the pharmaceutical composition comprises about 2.35 wt. % of the polymorph. In other specific embodiments, the pharmaceutical composition comprises about 14.7 wt. % of the polymorph. In still other specific embodiments, the pharmaceutical composition comprises about 26.3 wt. % of the polymorph.

In some more specific embodiments, the pharmaceutical composition comprises about 4 milligram (mg) of the polymorph. In other specific embodiments, the pharmaceutical composition comprises about 25 mg of the polymorph. In some embodiments, the pharmaceutical composition comprises about 100 mg of the polymorph.

In some embodiments, the excipient is lactose (e.g., lactose monohydrate), microcrystalline cellulose, croscarmellose sodium, magnesium stearate, or a combination thereof. In more specific embodiments, the excipient comprises lactose monohydrate. In some embodiments, the excipient comprises microcrystalline cellulose. In some embodiments, the excipient comprises croscarmellose sodium. In some embodiments, the excipient comprises magnesium stearate. In some embodiments, the excipient comprises microcrystalline cellulose, lactose monohydrate, croscarmellose sodium, and magnesium stearate.

In some of the foregoing embodiments, the pharmaceutical composition comprises the excipient in a concentration ranging from about 95.0 wt. % to about 99.5 wt. %. In more specific embodiments, the pharmaceutical composition comprises the excipient in a concentration ranging from about 97.2 wt. % to about 98.2 wt. %. In some embodiments, the pharmaceutical composition comprises about 97.65 wt. % of the excipient.

In some of the foregoing embodiments, the pharmaceutical composition comprises the excipient in a concentration ranging from about 80.0 wt. % to about 90.0 wt. %. In more specific embodiments, the pharmaceutical composition comprises the excipient in a concentration ranging from about 84.3 wt. % to about 86.4 wt. %. In some embodiments, the pharmaceutical composition comprises about 85.3 wt. % of the excipient.

In some of the foregoing embodiments, the pharmaceutical composition comprises the excipient in a concentration ranging from about 63.7 wt. % to about 88.7 wt. %. In more specific embodiments, the pharmaceutical composition comprises the excipient in a concentration ranging from about 68.7 wt. % to about 83.7 wt. %. In some embodiments, the pharmaceutical composition comprises about 73.7 wt. % of the excipient.

The polymorph of a tartaric acid salt of a compound of structure (I) according to certain embodiments is effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. In various embodiments, the dosage is 3, 6, 9, 12, 16, 21, 28, 32, 42, or 50 mg per day. The exact dosage will depend upon the route of administration, the form in which the polymorph of a tartaric acid salt of a compound of structure (I) is administered, the subject to be treated, the body weight of the subject to be treated, and the preference and experience of the attending physician.

Some particular embodiments provide a unit dose form comprising a pharmaceutical composition as described herein. In various embodiments, the unit dose form is formulated for oral administration. In some embodiments, the unit dose form is a capsule. In some embodiments, the unit dose form is a tablet.

In some embodiments, the unit dose form comprises the polymorph in a concentration ranging from about 0.5 wt. % to about 5.0 wt. %. In other specific embodiments, the unit dose form comprises the polymorph in a concentration ranging from about 1.8 wt. % to about 2.8 wt. %.

In some embodiments, the unit dose form comprises the polymorph in a concentration ranging from about 10.0 wt. % to about 20.0 wt. %. In other specific embodiments, the unit dose form comprises the polymorph in a concentration ranging from about 13.7 wt. % to about 15.7 wt. %.

In some embodiments, the unit dose form comprises the polymorph in a concentration ranging from about 16.3 wt. % to about 36.3 wt. %. In other specific embodiments, the unit dose form comprises the polymorph in a concentration ranging from about 21.3 wt. % to about 31.3 wt. %.

In more specific embodiments, the unit dose form comprises about 2.35 wt. % of the polymorph. In other specific embodiments, the unit dose form comprises about 14.7 wt. % of the polymorph. In still other specific embodiments, the unit dose form comprises about 26.3 wt. % of the polymorph.

In some more specific embodiments, the unit dose form comprises about 4 milligram (mg) of the polymorph. In other specific embodiments, the unit dose form comprises about 25 mg of the polymorph. In some embodiments, the unit dose form comprises about 100 mg of the polymorph.

In some of the foregoing embodiments, the unit dose form comprises the excipient in a concentration ranging from about 95.0 wt. % to about 99.5 wt. %. In more specific embodiments, the unit dose form comprises the excipient in a concentration ranging from about 97.2 wt. % to about 98.2 wt. %. In other embodiments, the unit dose form comprises about 97.65 wt. % of the excipient.

In some of the foregoing embodiments, the unit dose form comprises the excipient in a concentration ranging from about 80.0 wt. % to about 90.0 wt. %. In more specific embodiments, the unit dose form comprises the excipient in a concentration ranging from about 84.3 wt. % to about 86.4 wt. %. In other embodiments, the unit dose form comprises about 85.3 wt. % of the excipient.

In some of the foregoing embodiments, the unit dose form comprises the excipient in a concentration ranging from about 63.7 wt. % to about 88.7 wt. %. In more specific embodiments, the unit dose form comprises the excipient in a concentration ranging from about 68.7 wt. % to about 83.7 wt. %. In other embodiments, the unit dose form comprises about 73.7 wt. % of the excipient.

The pharmaceutical composition or combination of the present disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound (e.g., a polymorph), the pharmaceutical composition, or the combinations thereof, is dependent on the species of the subject, the body weight, age and individual condition, the disorder or disease or the severity thereof being treated. A physician, clinician or veterinarian of ordinary skill can readily determine the therapeutically effective amount of each of the active ingredients necessary to prevent, treat or inhibit the progress of the disorder or disease.

D. Therapeutic Uses and Methods of Treatment

1. Methods of Treating Cancer

Certain embodiments provide a method for treatment of cancer, the method comprising administering an effective amount of a pharmaceutical composition comprising a compound of structure (I) or a pharmaceutically acceptable salt of a compound of structure (I) (e.g., a tartrate salt) as described herein to a subject in need thereof. In some embodiments, the methods comprising administering an effective amount of a pharmaceutical composition comprising a compound of structure (I) to a subject in need thereof. In some different embodiments, the methods described herein comprise administering an effective amount of a pharmaceutical composition comprising a pharmaceutically acceptable salt of a compound of structure (I) (e.g., a tartrate salt) to a subject in need thereof. In some more specific embodiments, the cancer is a hematological cancer. In some embodiments, the cancer is a chronic lymphocytic leukemia.

In some specific embodiments, a method for treatment of cancer is provided, wherein the method comprises administering a compound of structure (I) or a pharmaceutically acceptable salt of a compound of structure (I) (e.g., tartrate salt), or a pharmaceutical composition comprising the same, to a subject in need thereof. In some more specific embodiments, the cancer is a hematological cancer, and the methods comprise administering a pharmaceutically acceptable salt of a compound of structure (I) (e.g., tartrate salt) to the subject. In some embodiments, the cancer is a chronic lymphocytic leukemia.

In some embodiments, a method for treatment of cancer is provided, the method comprising administering an effective amount of any of the foregoing pharmaceutical compositions comprising a compound of structure (I), or pharmaceutically acceptable salt of a compound of structure (I), for example a tartrate salt of a compound of structure (I), to a subject in need thereof. In some embodiments, the cancer is mediated by an AXL kinase. In some embodiments, the cancer is breast cancer (e.g., triple negative breast cancer), pancreatic cancer, renal carcinoma, colon cancer, thyroid carcinoma, colorectal cancer (e.g., BRAF, KRAS, or NRAS-mutated colorectal carcinoma), ovarian cancer, melanoma (e.g., BRAF-mutated melanoma) or lung cancer (e.g., EGFR+ non-small cell lung cancer). In certain embodiments, the cancer is selected from the group consisting of chronic lymphocytic leukemia (CLL), breast cancer, and colon cancer. In particular embodiments, the cancer is an advanced solid tumor, triple negative breast cancer, EGFR+ non-small cell lung cancer, colorectal carcinoma, recurrent ovarian carcinoma, or BRAF-mutated melanoma.

In some embodiments, the cancer is an advanced solid tumor (e.g., an advanced solid tumor that has progressed despite immunotherapy). In some embodiments is provided, a method for treating an advanced solid tumor comprising administering an effective amount a compound of structure (I) or a pharmaceutically acceptable salt thereof (e.g., a tartrate salt). In some embodiments the advanced solid tumor is an advanced metastatic or progressive solid tumor. In some embodiments, the cancer (e.g., a tumor) has progressed despite immunotherapy.

One embodiment provides a method for modulating a tumor immune response in a subject in need thereof, wherein the method comprises administering a compound of structure (I) or a pharmaceutically acceptable salt of a compound of structure (I) (e.g., a tartrate salt), or a pharmaceutical composition comprising the same, to the subject in need thereof thereby modulating a tumor immune response. In some embodiments, the immune response is increased. In some embodiments, the tumor is a solid tumor. In some embodiments, the modulating comprises inhibiting TAM kinase activity. In some embodiments, the modulating comprises increasing activated dendritic cells and/or increasing tumor infiltration by dendritic cells. In some embodiments, the modulating comprises reducing neutrophils, regulator T-cells or combinations thereof. In some embodiments, the modulating comprises reducing immunosuppressive cytokines (e.g., IL-6, G-CSF) in the tumor microenvironment. In some embodiments, the method further comprises administering a therapeutically effective amount of an additional agent, for example, an immune checkpoint inhibitor described herein or known in the art.

One embodiment provides a method for modulating an immune response in a subject in need thereof, wherein the method comprises administering a compound of structure (I) or a pharmaceutically acceptable salt of a compound of structure (I) (e.g., a tartrate salt), or a pharmaceutical composition comprising the same, to the subject in need thereof. In some embodiments, modulating an immune response includes modulating of immune cell populations (e.g., neutrophils, regulatory T-cells, and dendritic cells in a tumor).

One embodiment provides a method for enhancing host immunity in a subject in need thereof, wherein the method comprises administering a compound of structure (I) or a pharmaceutically acceptable salt of a compound of structure (I) (e.g., a tartrate salt), or a pharmaceutical composition comprising the same, to the subject in need thereof.

One embodiment provides a method for suppressing a mesenchymal phenotype in a subject in need thereof, wherein the method comprises administering a compound of structure (I) or a pharmaceutically acceptable salt of a compound of structure (I) (e.g., a tartrate salt), or a pharmaceutical composition comprising the same, to the subject in need thereof. Suppressing a mesenchymal phenotype may include reversing a mesenchymal phenotype. Suppressing (e.g., reversing a mesenchymal phenotype) may be useful, for example, for treating a wide variety of cancers linked to a mesenchymal phenotype, such as metastatic colorectal cancer. A mesenchymal phenotype may be evidenced by the expression of mesenchymal markers, such as Snail and Slug. In particular embodiments of the method for suppressing a mesenchymal phenotype, a compound of structure (I) is administered to a subject with metastatic colorectal cancer. In particular embodiments of the method for suppressing a mesenchymal phenotype, a compound of structure (I) is administered to a subject with non-metastatic colorectal cancer, thereby preventing or reducing the likelihood of metastasis of the colorectal cancer.

One embodiment provides a method for creating a tumor microenvironment amenable to an immune response in a subject in need thereof, wherein the method comprises administering a compound of structure (I) or a pharmaceutically acceptable salt of a compound of structure (I) (e.g., a tartrate salt), or a pharmaceutical composition comprising the same, to the subject in need thereof. In certain embodiments, creating a tumor microenvironment amenable to an immune response includes reducing local levels of immunosuppressive cytokines and chemokines, such as IL-6 and G-CSF. In certain embodiments, creating a tumor microenvironment amenable to an immune response includes increased infiltration and activation of dendritic cells (DCs) in the tumor.

One embodiment provides a method for treating cancer comprising administering an effective amount a compound of structure (I) or a pharmaceutically acceptable salt thereof (e.g., a tartrate salt) in combination with an immunotherapy. Another embodiment provides a method for treating cancer comprising administering an effective amount a compound of structure (I) or a pharmaceutically acceptable salt thereof (e.g., a tartrate salt) in combination with a tyrosine kinase inhibitor.

In embodiments, the cancer is breast cancer. Breast cancer is categorized into four major molecular subtypes: (a) luminal A, which is hormone receptor positive (estrogen receptor positive and/or progesterone receptor positive), human epidermal growth factor receptor 2 (HER2) negative, and has low expression of Ki-67 (a cellular marker for proliferation); (b) luminal B, which is hormone receptor positive, may be HER2 positive or negative, and has high expression of Ki-67; (c) HER2-enriched, which is hormone receptor negative and HER2 positive; and (d) triple negative, which is hormone receptor negative and HER2 negative.

In some embodiments, the breast cancer is hormone receptor positive. Hormone receptor positive breast cancer refers to breast cancer that is positive for expression of estrogen receptor and/or progesterone receptor. In some embodiments, the breast cancer is luminal A or luminal B breast cancer. In particular embodiments, a method for treating hormone receptor positive breast cancer (e.g., luminal A or luminal B breast cancer) comprises administering an effective amount a compound of structure (I) or a pharmaceutically acceptable salt thereof (e.g., a tartrate salt) and administering an effective amount of a hormone therapy. Hormone therapy for breast cancer can refer to a therapy that reduces estrogen binding to estrogen receptor, and/or reduces progesterone binding to progesterone receptor. In particular embodiments, the hormone therapy comprises tamoxifen, toremifene, fulvestrant, or an aromatase inhibitor. Examples of aromatase inhibitors used to treat hormone receptor positive breast cancer include anastrozole, exemestane, and letrozole.

In some embodiments, the breast cancer is HER2 positive. HER2 positive breast cancer is a breast cancer that tests positive for expression of HER2, such as luminal B or HER2 enriched breast cancer. In some embodiments, a method for treating HER2 positive breast cancer comprises administering an effective amount a compound of structure (I) or a pharmaceutically acceptable salt thereof (e.g., a tartrate salt) and administering an effective amount of HER2 inhibitor. In some embodiments, the HER2 inhibitor is selected from trastuzumab, pertuzumab, trastuzumab emtansine (i.e., TDM1), lapatinib, and neratinib. In particular embodiments, the HER2 inhibitor is trastuzumab or trastuzumab emtansine.

In some embodiments, the breast cancer is triple negative breast cancer. Triple negative breast cancer is the most aggressive molecular subtype of breast cancer, and is not responsive to hormone therapy regimens or HER2 inhibitors.

Breast cancer can also be categorized as inflammatory breast cancer or non-inflammatory breast cancer. Inflammatory breast cancer is a rare, highly aggressive form of breast cancer, which is diagnosed based on clinical presentation with inflammatory-like symptoms in the breast including erythema, oedema, tenderness, warmth, and/or skin dimpling. Inflammatory breast cancer may present with the any of the molecular subtypes of breast cancer (i.e., may be hormone receptor positive and/or HER2 positive, or may be triple negative).

In some embodiments, the cancer is inflammatory breast cancer. Inflammatory breast cancer may be hormone receptor positive and/or HER2 positive, or triple negative. Inflammatory breast cancer may be, in certain cases, responsive to hormone therapy and or HER2 inhibitors, depending on the molecular subtype. Given that inflammatory breast cancer is highly aggressive, treatment often includes radical mastectomy in combination with chemotherapy and/or radiation.

In embodiments, methods for treating breast cancer (e.g., triple negative breast cancer or inflammatory breast cancer) comprise administering an effective amount a compound of structure (I) or a pharmaceutically acceptable salt thereof (e.g., a tartrate salt) and administering an effective amount of a further therapy to a subject in need thereof. The further therapy may be, for example, radiation, surgical (e.g., mastectomy), or a therapeutic agent (e.g., a chemotherapeutic agent. In particular embodiments, the further therapy is at least one of: an immune checkpoint inhibitor, a PARE inhibitor, a WEE1 inhibitor, an EGER targeting agent, a CDK4/6 inhibitor, a PI3K inhibitor, a TORC1/2 inhibitor, an anthracycline, or a taxane.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of an immune checkpoint inhibitor to a subject in need thereof. In particular embodiments, the immune checkpoint inhibitor is a PD-L1 inhibitor, a PD-1 inhibitor, a CTLA-4 inhibitor, a LAG-3 inhibitor, a Tim-3 inhibitor, or a combination thereof.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of a PARP inhibitor to a subject in need thereof. In some embodiments, the PARP inhibitor is selected from olaparib, niraparib, talazoparib, and velaparib. In particular embodiments, the PARP inhibitor is olaparib.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of a WEE1 inhibitor to a subject in need thereof. WEE1 is a nuclear kinase that regulates cell cycle progression, and inhibition of WEE1 has anti-cancer effects and may sensitive cancer cells to other treatments, such as cisplatin or radiation. In particular embodiments, the WEE1 inhibitor comprises AZD1775.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of an EGER targeting agent to a subject in need thereof. In particular embodiments, the EGFR-targeting agent is lapatinib, panitumumab, cetuximab or erlotinib, gefetinib, or a combination thereof.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of a CDK4 or CDK6 inhibitor to a subject in need thereof. In some embodiments, the CDK4 or CDK6 inhibitor is palbociclib, abemaciclib, ribociclib, or a combination thereof. In particular embodiments, the CDK4 or CDK6 inhibitor is palbociclib.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of a PI3K inhibitor to a subject in need thereof. The PI3K-AKT-mTOR pathway is commonly activated in a variety of cancers and contributes to cancer cell survival in proliferation. In some embodiments, the PI3K inhibitor is AZD8186, GDC-0941, GDC-0980, idelalisib (CAL-101), alpelisib (BYL719), buparlisib (BKM120), or a combination thereof. In particular embodiments, the PI3K inhibitor is AZD8186.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of a TORC1/2 inhibitor to a subject in need thereof. In some embodiments, the TORC1/2 inhibitor is AZD2014 (vistusertib), TAK228 (INK 128, MLN0128), or both.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of an anthracycline to a subject in need thereof. "Anthracycline" refers to a chemical class of compounds with intercalating activity, and include daunorubicin, doxorubicin, epirubicin, idarubicin, nemorubicin, pixantrone, sabarubicin, and valrubicin. In particular embodiments, the anthracycline is doxorubicin, Daunorubicin, or both.

In certain embodiments, a method for treating breast cancer (e.g., triple negative breast cancer or inflammatory breast cancer) comprises administering an effective amount a compound of structure (I) or a pharmaceutically acceptable salt thereof (e.g., a tartrate salt) and administering an effective amount of a taxane to a subject in need thereof. Taxanes used to treat cancer are di-terpene molecules that inhibit microtubule formation. In some embodiments, the taxane comprises paclitaxel, docetaxel, or both.

In some embodiments, the cancer is pancreatic cancer. In some embodiments, the cancer is renal carcinoma. In some embodiments, the cancer is colon cancer. In some embodiments, the cancer is thyroid cancer. In some embodiments, the cancer is lung cancer.

In some embodiments, the cancer is non-small cell lung cancer. In certain embodiments, a method for treating non-small cell lung cancer (e.g., EGRF+non-small cell lung cancer) comprises administering an effective amount a compound of structure (I) or a pharmaceutically acceptable salt thereof (e.g., a tartrate salt). In some embodiments, the compound of structure (I) or a pharmaceutically acceptable salt thereof (e.g., a tartrate salt) is administered in combination with an EGRF inhibitor, an immunotherapy and/or a tyrosine kinase inhibitor (e.g., CDK9 inhibitor). In some embodiments, the non-small cell lung cancer comprises an immunotherapy-resistant tumor. In some embodiments, the non-small cell lung cancer (e.g., EGRF+non-small cell lung cancer) has progressed after administering ≤2 lines of tyrosine kinase inhibitors (e.g., oral tyrosine kinase inhibitors).

In some embodiments, the cancer is colorectal cancer. In certain embodiments, the colorectal cancer includes tumor(s) that express mutated BRAF, KRAS or NRAS. In certain embodiments, a method for treating colorectal cancer comprising administering an effective amount a compound of structure (I) or a pharmaceutically acceptable salt thereof (e.g., a tartrate salt) in combination with an EGFR inhibitor. In some embodiments, the method comprises administering an immune checkpoint inhibitor (e.g., PD-L1-, PD-1-, CTLA-4-, LAG-3- or Tim-3-targeted agents). In some specific embodiments, the colorectal cancer is BRAF-, KRAS- or NRAS-mutated colorectal carcinoma. In particular embodiments, the colorectal cancer is KRAS-mutated colorectal carcinoma. In some embodiments, the administration is after standard therapies have been administered.

In some embodiments, the cancer is ovarian cancer. In some embodiments, a method for treating ovarian cancer comprising administering an effective amount a compound of structure (I) or a pharmaceutically acceptable salt thereof (e.g., a tartrate salt). Some embodiments the ovarian cancer is persistent or recurrent. In some specific embodiments, the ovarian cancer is platinum refractory/resistant. In some embodiments, the method for treating ovarian cancer further comprises administering a platinum compound. In some embodiments, the administering is following administration of any number of lines of prior therapies.

In some embodiments, the cancer is melanoma (e.g., BRAF-mutated melanoma). In certain embodiments, a method for treating melanoma (e.g., BRAF-mutated melanoma) comprising administering an effective amount a compound of structure (I) or a pharmaceutically acceptable salt thereof (e.g., a tartrate salt). In some embodiments, the method further comprises administrating the compound of structure (I) or a pharmaceutically acceptable salt thereof (e.g., a tartrate salt) in combination with an immunotherapy or a combination BRAF and MEK inhibitor. In some embodiments, the melanoma (e.g., BRAF-mutated melanoma) has not responded to immunotherapy or a combination of a BRAF/MEK inhibitor.

One particular embodiment provides a method of treating a disease, the method comprising administering an effective amount of the compound of structure (I) or a pharmaceutically acceptable salt thereof (e.g., a tartrate salt) or a pharmaceutical composition comprising the compound of structure (I) or a pharmaceutically acceptable salt thereof (e.g., a tartrate salt) to a subject in need thereof, wherein the disease is selected from the group consisting of an advanced solid tumor, EGFR+non-small cell lung cancer, colorectal carcinoma, recurrent ovarian carcinoma, and BRAF-mutated melanoma.

In another embodiment the disclosure provides a method for inhibiting tumor metastasis, the method comprising administering an effective amount a compound of structure (I) or a pharmaceutically acceptable salt thereof (e.g., a tartrate salt) or a pharmaceutical composition of comprising a compound of structure (I) or pharmaceutically acceptable salt of a compound of structure (I), for example a tartrate salt of a compound of structure (I) and a pharmaceutically acceptable carrier to a subject in need thereof.

One embodiment provides a method of treating a disease, the method comprising administering an effective amount of the compound of structure (I) or a pharmaceutically acceptable salt thereof (e.g., a tartrate salt) or a pharmaceutical composition comprising the compound of structure (I) or a pharmaceutically acceptable salt thereof (e.g., a tartrate salt) to a subject in need thereof, wherein the disease is colorectal cancer, for example, colorectal carcinoma. In some embodiments, the colorectal cancer is resistant to EGFR-targeted therapies.

Hematologic malignancies that can be treated with a compound of structure (I) or a pharmaceutically acceptable salt thereof (e.g., a tartrate salt) include, but are not limited to leukemias and lymphomas. For example, the presently disclosed compounds and compositions can be used for treatment of diseases such as Acute lymphoblastic leukemia (AFF), Acute myelogenous leukemia (AMF), Chronic lymphocytic leukemia (CFF), small lymphocytic lymphoma (SEE), Chronic myelogenous leukemia (CMF), Acute monocytic leukemia (AMoF) and/or other leukemias. In other embodiments, the compound of structure (I) or a pharmaceutically acceptable salt thereof (e.g., a tartrate salt) is useful for treatment of lymphomas such as all subtypes of Hodgkin's lymphoma or non-Hodgkin's lymphoma. In specific embodiments, the presently disclosed compounds and compositions can be used for treatment of CFF and/or SEE. In some particular embodiments, the presently disclosed compounds and compositions can be used for treatment of CFF. In some particular embodiments, the presently disclosed compounds and compositions can be used for treatment of SEE.

A wide variety of cancers, including solid tumors and leukemias (e.g., acute myeloid leukemia and chronic lymphocytic leukemia) are amenable to the methods disclosed herein. Types of cancer that may be treated in various embodiments include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); histiocytic disorders; leukemia; histiocytosis malignant; Hodgkin's disease; immunoproliferative small; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor; adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma non-chromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a still further aspect, the cancer is selected from cancers of the brain, genitourinary tract, endocrine system, gastrointestinal tract, blood, rectum, kidney, lymphatic system, stomach, and skin.

In some embodiments, the cancer is selected from cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cancer in adolescents, cervical cancer, childhood cancers, chordoma, cardiac tumors, chronic myeloproliferative disorders, colon cancer, colorectal cancer (e.g., colorectal cancer that is resistant to EGFR-targeted therapies), craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal stromal tumors (GIST), gastrointestinal carcinoid tumor, germ cell tumor, gestational trophoblastic tumor, hairy cell leukemia, head and neck cancer, heart cancer, liver cancer, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, such as myelofibrosis, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, Viral-Induced cancer, acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, choroid plexus carcinoma, choroid plexus papilloma, craniopharyngioma, dysembryoplastic neuroepithelial tumor, gangliocytoma, germinoma, hemangioblastoma, hemangiopercytoma, metastatic brain tumor cell, and glioma (e.g., glioblastoma multiforme, ependymoma, astrocytoma, oligodendroglioma, oligoastrocytoma, juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, paraganglioma, or ganglioglioma cell).

Embodiments of the invention also include a method of treating a hyperproliferative disorder in a mammal that comprises administering to said mammal a therapeutically effective amount of a compound of structure (I) or a pharmaceutically acceptable salt of a compound of structure (I) (e.g., a tartrate salt). In some embodiments, the method relates to the treatment of a non-cancerous hyperproliferative disorder such as benign hyperplasia of the skin (e.g., psoriasis), restenosis, or prostate (e.g., benign pro static hypertrophy (BPH)). In some embodiments the method relates to use of a compound of structure (I) or a pharmaceutically acceptable salt of a compound of structure (I) (e.g., a tartrate salt) for treatment of fibrosis including, but not limited to pulmonary fibrosis (e.g., idiopathic pulmonary fibrosis) and liver fibrosis.

In some embodiments, the invention provides methods of inhibiting kinase activity in a cell by contacting said cell with an amount of a compound of structure (I) or a pharmaceutically acceptable salt of a compound of structure (I) (e.g., a tartrate salt) sufficient to inhibit the activity of AXL kinase. In some embodiments, the invention provides methods of inhibiting AXL kinase activity in a tissue by contacting said tissue with an amount of a compound of structure (I) or a pharmaceutically acceptable salt of a compound of structure (I) (e.g., a tartrate salt) sufficient to inhibit the activity of the AXL kinase in said tissue. In some embodiments, the invention provides methods of inhibiting AXL kinase activity in an organism by contacting said organism with an amount of a compound of structure (I) or a pharmaceutically acceptable salt of a compound of structure (I) (e.g., a tartrate salt) sufficient to inhibit the activity of the AXL kinase in said organism. In some embodiments, the invention provides methods of inhibiting AXL kinase activity in an animal by contacting said animal with an amount of a compound of structure (I) or a pharmaceutically acceptable salt of a compound of structure (I) (e.g., a tartrate salt) sufficient to inhibit the activity of the AXL kinase in said animal. In some embodiments, the invention provides methods of inhibiting AXL kinase activity in a mammal by contacting said mammal with an amount of a pharmaceutically acceptable salt of a compound of structure (I) or a pharmaceutically acceptable salt of a compound of structure (I) (e.g., a tartrate salt) sufficient to inhibit the activity of AXL kinase in said mammal. In some embodiments, the invention provides methods of inhibiting AXL kinase activity in a human by contacting said human with an amount of a compound of structure (I) or a pharmaceutically acceptable salt of a compound of structure (I) (e.g., a tartrate salt) sufficient to inhibit the activity of AXL kinase in said human. In other embodiments, the present invention provides methods of treating a disease mediated by AXL kinase activity in a subject in need of such treatment.

In some specific embodiments, the present disclosure provides a method of treating chronic lymphocytic leukemia (CLL) by administering an AXL kinase inhibitor, such as a compound of structure (I), or a pharmaceutically acceptable salt thereof (e.g., tartrate salt), to a subject in need thereof. In some embodiments, methods of the disclosure treat CLL and small lymphocytic lymphoma (SLL). In some embodiments, the subject has been previously treated for CLL, yet still displays symptoms of detectable minimal residual disease (MRD). Accordingly, one embodiment provides a method for treating CLL in a subject, comprising administering an effective amount of an AXL kinase inhibitor to the subject, wherein the subject has received a prior treatment regimen for CLL, and the subject was refractory after the prior treatment regimen, the subject has relapsed CLL after a response to the prior treatment regimen, or the subject has detectable minimal residual disease (MRD).

According to the revised IWCLL guidelines a subject diagnosed with CLL is considered to be in "complete remission" if peripheral blood (circulating) lymphocyte counts are normal, absence of significant lymphadenopathy (e.g., lymph nodes >1.5 cm in diameter) by physical examination, normal liver size and spleen size <13 cm, absence of constitutional symptoms, platelet count greater than or equal to 100,000/µL, hemoglobin greater than or equal to 11.0 g/dL (untransfused and without erythropoietin), and normocellular bone marrow (no CLL cells, no B-lymphoid nodules). A subject diagnosed with CLL meets the criteria of "partial remission" if peripheral blood (circulating) lymphocyte counts decrease ≥50% from baseline, lymph nodes decrease ≥50% from baseline, liver and spleen sizes decrease ≥50% from baseline, platelet count greater than or equal to 100,000/µL or increase ≥50% from baseline, hemoglobin greater than or equal to 11.0 g/dL or increase ≥50% from baseline, yet still has the presence of CLL cell or B-lymphoid nodules in the bone marrow. For a "partial remission" at least one parameter of the first three parameters needs to be met and one parameter of the second three parameters needs to be met. The term "relapse" refers to disease progression in a patient who has previously achieved the above criteria of a CR or PR for a period of six or more months. In particular embodiments, the subject was refractory after the prior treatment regimen. In particular embodiments, the subject was relapsed CLL after a response to the prior treatment regimen. In particular embodiments, the subject has detectable minimal residual disease (MRD).

In some embodiments, the subject has been previously treated for CLL and/or SLL. In some embodiments, a subject is intolerant to the prior treatment regimen. As used herein "intolerant" means that the subject is unable or unwilling to tolerate the adverse effects of an effective amount of therapeutic agent.

Detectable MRD refers to a disease state in which the subject has at least 1 CLL cell per 10,000 leukocytes in a sample of peripheral blood or bone marrow. Percent MRD refers to the percent of CLL cells relative to leukocytes in a sample of peripheral blood or bone marrow. For example, a subject having 1 CLL cell per 10,000 leukocytes is classified as having 0.01% MRD. MRD can be determined from peripheral blood and/or bone marrow using techniques known in the art, for example immunophenotyping (e.g., flow cytometry) or molecular based assays (e.g., polymerase chain reaction and next-generation sequencing), as disclosed in *JAMA Oncology, March* 2018, *Volume* 4, *Number* 3, *P.* 394-400, *and Blood, March* 2018, *blood*-2017-09-806398, which are hereby incorporated by reference.

Exemplary AXL kinase inhibitors useful in treating CLL and/or SLL, such as CLL with detectable MRD, and other embodiments of the invention are known in the art, for example as disclosed in WO 2012/135800 and WO 2008/128072, the full disclosures of which are hereby incorporated by reference in their entirety. Exemplary AXL kinase inhibitors include compounds having the following structure (I'):

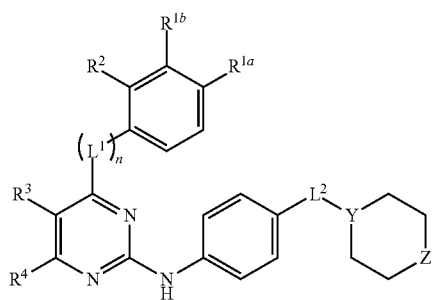

or a pharmaceutically acceptable salt, hydrate, solvate, or polymorph thereof, wherein:

$L^1$ is selected from O and $NR^5$, wherein $R^5$ is selected from hydrogen and C1-C6 alkyl;

$L^2$ is selected from $CH_2$ and $NCH_3$, provided that $L^2$ is $CH_2$ when Y is N;

Y is selected from CH and N;

Z is selected from O, $NR^6$ and $CH_2$, wherein $R^6$ is selected from hydrogen and $CH_3$;

each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$, $R^7$ is selected from hydrogen and C1-C6 alkyl;

$R^2$ is selected from hydrogen, C1-C6 alkyl, $SO_2R^8$, and $(C=O)R^8$, wherein $R^8$ is selected from hydrogen, C1-C6 alkyl, C3-C6 cycloalkyl, C3-C6 heterocycloalkyl, and $NR^{10}R^{11}$, wherein: a) $R^{10}$ is selected from hydrogen, C1-C6 alkyl, and C3-C6 cycloalkyl; and $R^{11}$, when present, is selected from hydrogen and C1-C6 alkyl; or b) $R^{10}$ and $R^{11}$ are covalently bonded and, together with the intermediate nitrogen, comprise an optionally substituted 3-7 membered heterocycloalkyl ring;

$R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl;

$R^4$ is selected from hydrogen, halogen, $Ar^1$, C1-C6 alkyl, C3-C6 cycloalkyl, and C3-C6 heterocycloalkyl, wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; or $Ar^1$ is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino, wherein $R^{12}$ is selected from C1-C6 alkyl and C3-C6 cycloalkyl; and n is 0 or 1.

Substituents for compounds of structure (I') are as defined in WO 2012/135800.

In some embodiments, exemplary AXL kinase inhibitors are selected from the following, or a pharmaceutically acceptable salt thereof:

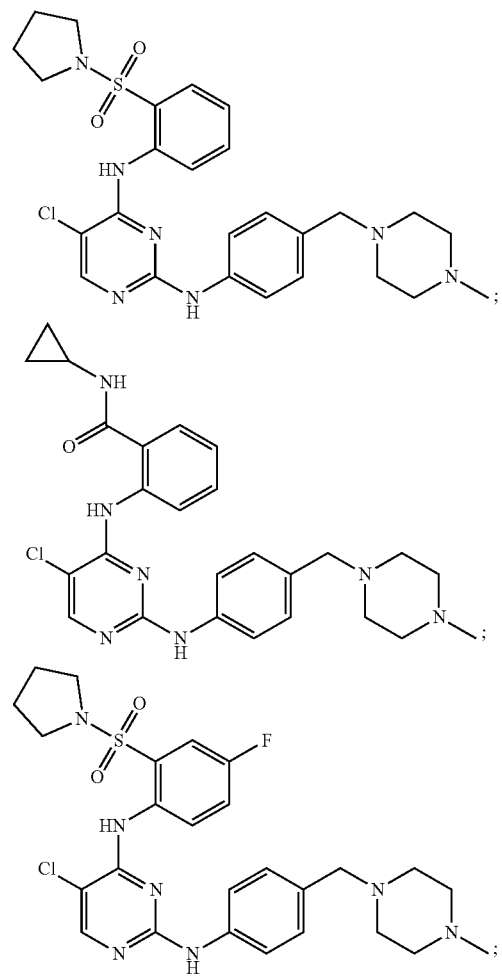

63
-continued
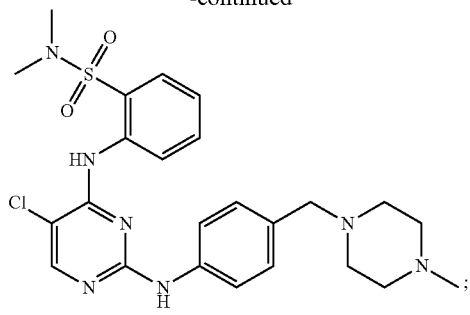
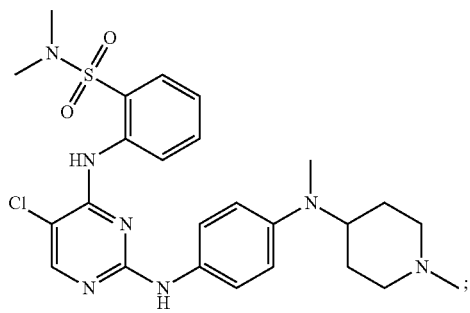
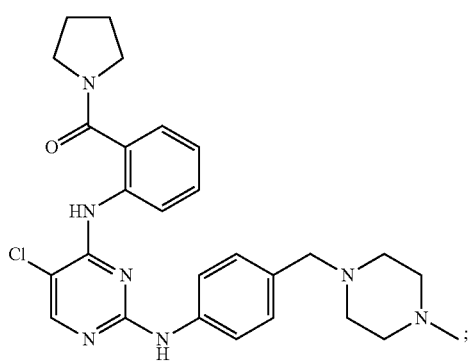
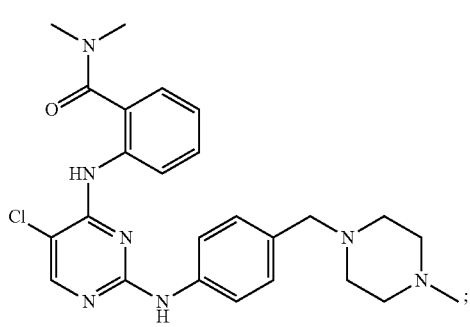
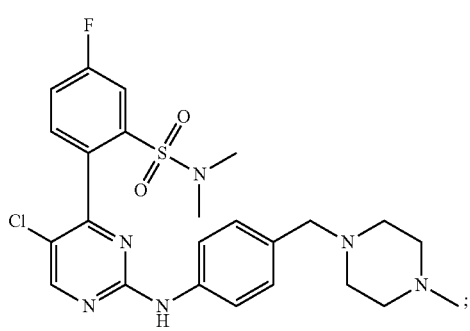
64
-continued
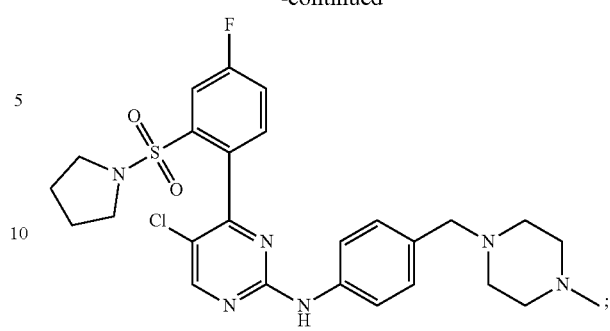
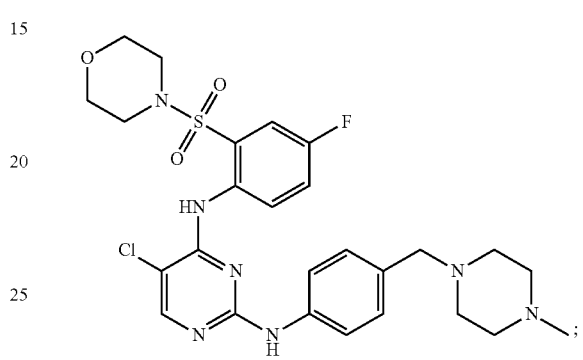
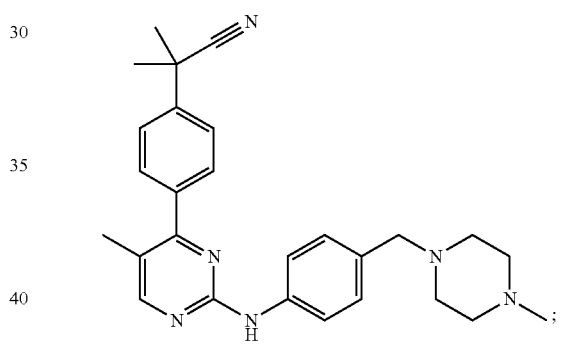
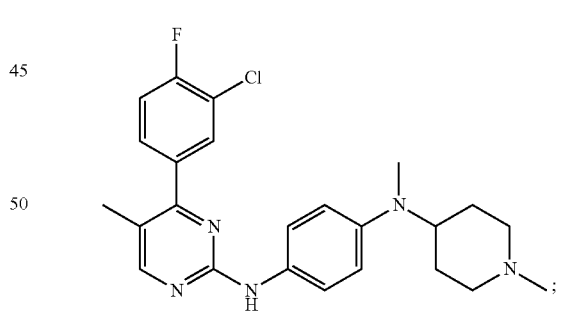
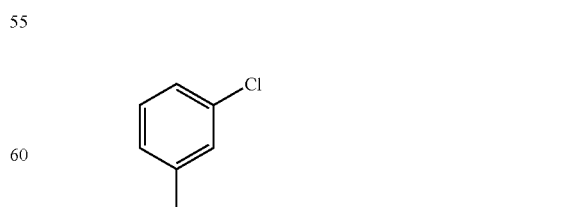
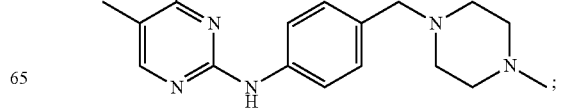

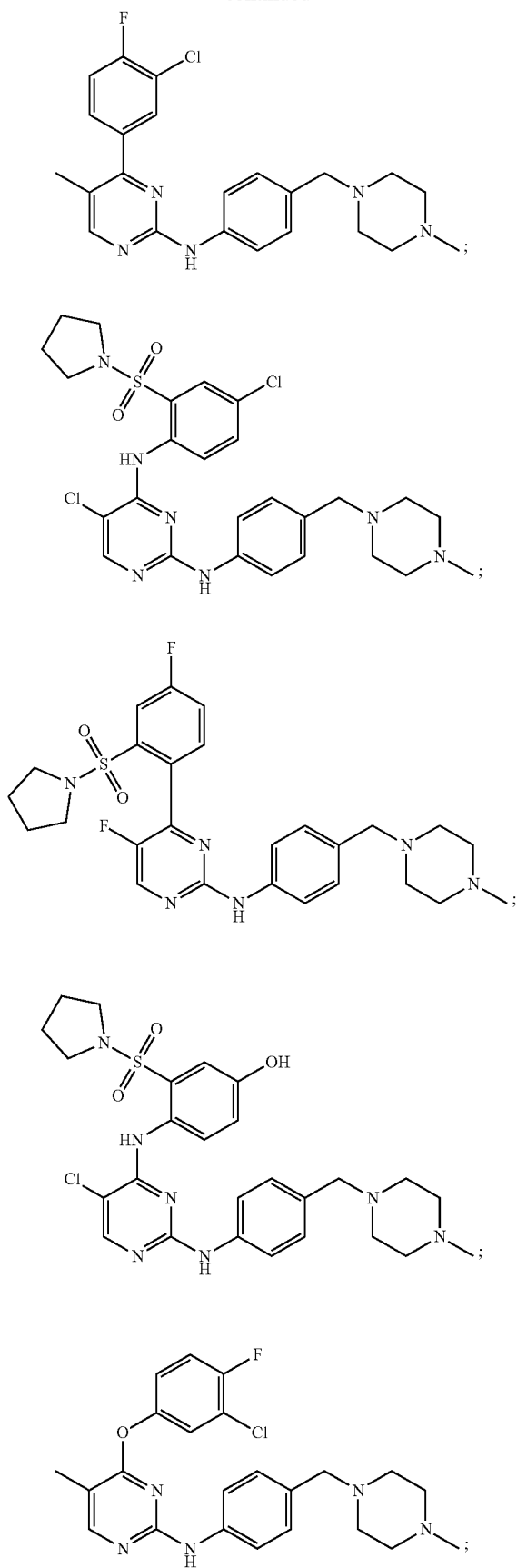
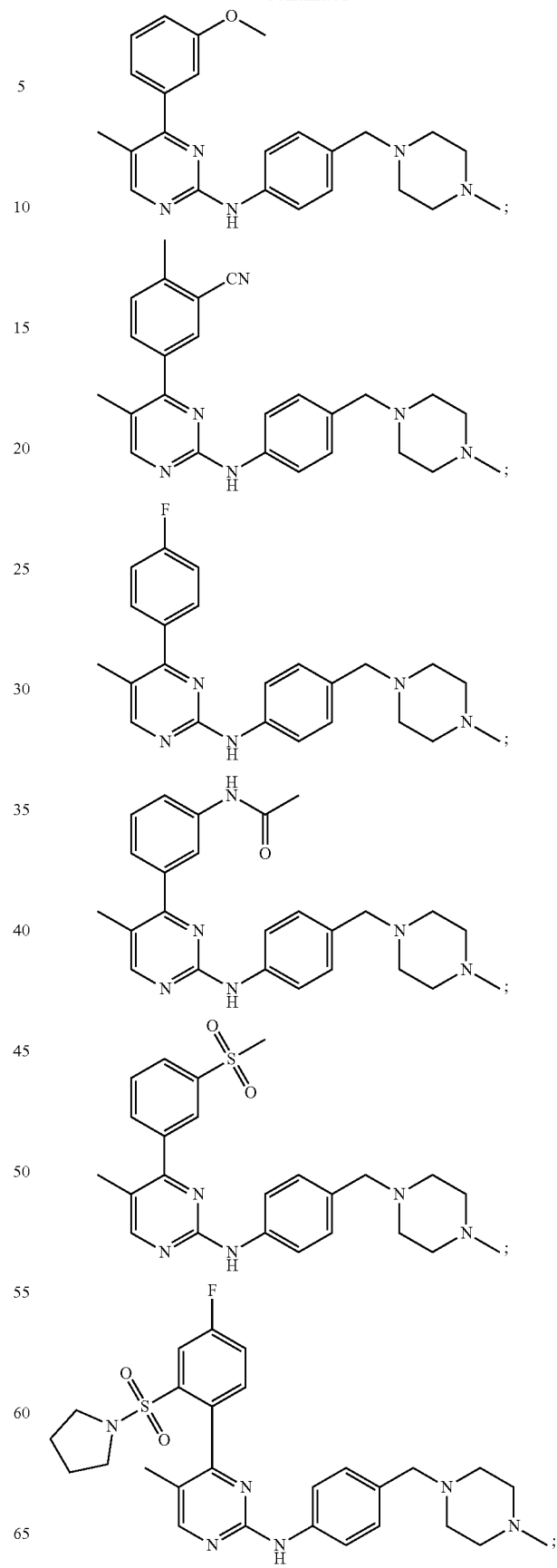

-continued

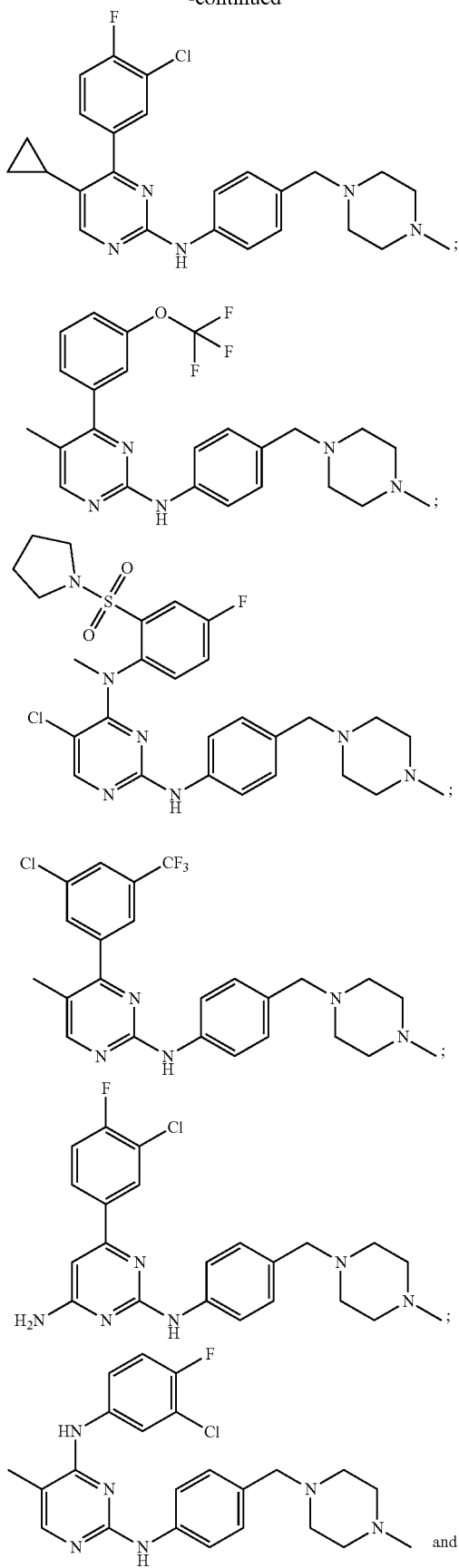

-continued

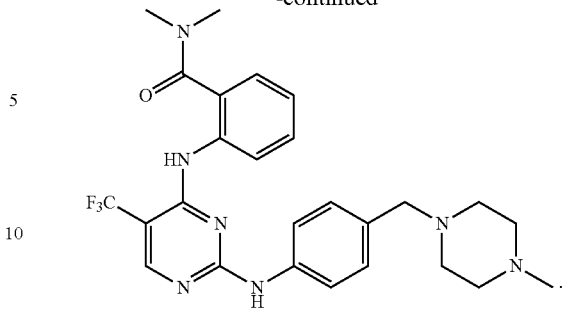

In certain more specific embodiments, the AXL kinase inhibitor is a compound of structure (I) or a pharmaceutically acceptable salt thereof. In certain embodiment, the AXL kinase inhibitor is the tartrate salt of the compound of structure (I) as disclosed herein.

In certain embodiments of the foregoing, the prior treatment regimen comprises treatment with a B-cell receptor signaling antagonist (e.g., a Bruton's tyrosine kinase (BTK), SYK or PI3K inhibitor) or a Bcl-2 inhibitor, or both. In other embodiments, the subject is ineligible for treatment with a B-cell receptor signaling antagonist or a Bcl-2 inhibitor, or both. In different embodiments, the subject is intolerant to treatment with a B-cell receptor signaling antagonist or a Bcl-2 inhibitor, or both.

In certain embodiments, the B-cell receptor signaling antagonist is a BTK inhibitor. Exemplary BTK inhibitors, which may be included in certain embodiments of the prior treatment regimen, include those known in the art, such as those described in PCT Pub. Nos: WO 2014/052365; WO 2015/048689; WO 2015/002894; WO 2014/168975; WO 2014/159745; WO 2014/130693; WO 2014/078578; WO 2014/018567; WO 2013/184572; WO 2013/173518; WO 2013/116382; WO 2013/102059; WO 2013/059738; WO 2013/010136; WO 2011/153514; WO 2011/046964; WO 2010/009342; WO 2008/121742; WO 2008/054827; WO 2008/039218; WO 2007/087068; and in U.S. Pub. Nos: 2015/0018336; 2014/0336206; 2014/0243355; 2014/0212485; 2014/0194446/2014/0187564; 2014/0135347; 2014/0128414; 2014/0187565; 2014/0171453; 2014/0163027; 2014/01663046; 2014/0142126; 2014/0142123; 2014/0128413; 2014/0079690; 2014/0080844; 2014/0057907; 2014/0039168; 2013/0338172; 2013/0310402; 2013/0273030; 2013/0197014; 2013/0035334; 2013/0012525; 2012/0283277; 2012/0283276; 2012/0277254; 2012/0252821; 2010/0331350, the full disclosures of which are hereby incorporated by reference in their entireties.

In some embodiments, the BTK inhibitor is ONO-4059, AVL-292, SNS-062, CNX-774, CGI-1746, RN486 or ACP-196, which compounds are known in the art. In some specific embodiments, the BTK inhibitor is Ibrutinib.

In certain embodiments, the B-cell receptor signaling antagonist is a SYK inhibitor or a PI3Kgamma/delta inhibitor. In some embodiments, the SYK inhibitor is fostamatinib, entospletinib, cerdulatinib, or TAK-659. In some embodiments, the PI3Kgamma/delta inhibitor is idelalisib, duvelisib, TGR-1202, or ACP-319/AMG-319.

The Bcl-2 inhibitor, which may be included in certain embodiments of the prior treatment regimen, includes those known in the art. For example, in some of the foregoing embodiments, the BCL-2 inhibitor is Venetoclax (i.e., ABT-199). In some other embodiments the Bcl-2 inhibitor is an antisense oligonucleotide drug (e.g., oblimersen), a BH3 mimetic (e.g., ABT-737, ABT-737-d8 or navitoclax/ABT- 263 or ABT-263-d8), a novel non-peptide inhibitor (e.g., TW-37), a pan-BCL-2 inhibitor (e.g., Sabutoclax, Obatoclax), a Bcl-2 xl/BH3 domain interaction inhibitor (e.g., BH3I-1), a BCL-xl inhibitor (e.g., A-1331852 or A-1155463), a non-peptidic ligand of BCL-2 (e.g., HA14-1), a Bax activator (e.g., BAM7), a small molecule BCL-2/BH4 domain antagonist (e.g., BDA-366), a flavonoid (e.g., Licochalcone A). In certain specific embodiments the BCL-2 inhibitor is FX1, AT-101, A-1210477, gambogic acid, UMI-77, Gossypol, (−)-Epigallocatechin Gallate, EM20-25, Nilotinib or Nilotinib-d3, YC137, AG 1024, 3-bromopyruvic acid, Fluvastatin, Piperlongumine, 2,3-DCPE, 2-methoxyantimycin A3 or Marinopyrrole A (i.e., Maritoclax).

In various different embodiments, the subject has greater than 0.01% MRD as determined by immunophenotypic (e.g., flow cytometry) or molecular based (e.g., polymerase chain reaction and next-generation sequencing) analysis of a peripheral blood or bone marrow sample from the subject. In some embodiments, the subject has greater than 0.1% MRD as determined by immunophenotypic or molecular based analysis of a peripheral blood or bone marrow sample from the subject. In different embodiments, the subject has greater than 1.0% MRD as determined by immunophenotypic or molecular based analysis of a peripheral blood or bone marrow sample from the subject. In still more embodiments, the subject has from 0.01% to 1.0% MRD as determined by immunophenotypic or molecular based analysis of a peripheral blood or bone marrow sample from the subject.

In some embodiments, MRD is determined based on % MRD in peripheral blood. In other embodiments, MRD is determined based on % MRD in bone marrow.

The method for treating CLL with detectable MRD may further comprise determining the number of CLL cells and leukocytes in a peripheral blood or bone marrow sample from the subject. The determining step can be performed according to an in vitro method as known in the art and described above. Alternatively, the determining is based on review of data obtained from an in vitro method described above.

The method may also further comprise categorizing the patient as having MRD if the number of CLL cells per 10,000 leukocytes is greater than 1 or categorizing the patient as having MRD if the number of CLL cells per 10,000 leukocytes is from 1 to 100.

2. Biomarkers

In various embodiments, methods of the present disclosure comprise determining expression levels, tissue concentrations, or the presence of one or more markers. In some embodiments, the markers comprise one or more of Snail, Slug, AXL (e.g., AXL, Phospho AXL, Phospho/Total AXL, soluble AXL, etc.), AKT (e.g., Phospho/Total AKT), MMP, mTOR, PI3K, p38, JAK, STAT, SOCS1, SOCS3, PTEN, ERK, H2AX, CCNE, β-Catenin, P-Glycoprotein 1, GAS6, Retinoic acid, protein S, sMerTK, interleukin (IL)1β, IL2r/CD25, IL2, IL4, IL5, IL6, IL8, IL10, IL12, IL13, IL17, TNF-α, IFNγ, CSF2, CSF3, CCL2, sPD-L1/PD-L1, sPD-1/PD-1, sPD-L1/sPD-1, sCD163/CD163, E-cadherin, N-cadherin, Twist, FLT3, CDH1, CDH2, ZEB1, ADH1A, APOA2, ALDH1A2, CD38, CYP26A1, CYP26B1, DHRS3, DLX5, LGR1, FOXA1, HNP1B, HSD17B2, ISL1, LHX1, PPARG, RARA, RARE, RBP4, RXRG, SHH, STRA6, TGM2, and UCPI. In some embodiments, methods of the present disclosure may comprise determining expression levels, tissue concentrations, or the presence of one or more of ADH1A, APOA2, ALDH1A2, CD38, CYP26A1, CYP26B1, DHRS3, DLX5, LGR1, FOXA1, HNP1B, HSD17B2, ISL1, LHX1, PPARG, RARA, RARE, RBP4, RXRG, SHH, STRA6, TGM2, and UCPI. In particular embodiments, the one or more markers comprise AXL and/or GAS6. In some embodiments, the one or more markers comprise AXL. In particular embodiments, the one or more markers comprise soluble AXL. In some embodiments, the one or more markers comprise GAS6. In some embodiments, the one or more markers comprise soluble GAS6.

In some embodiments, methods of the present disclosure may comprise determining expression of markers of activated cells (e.g., dendritic cells, such as CD86, and CD11c). In some embodiments, the method of the present disclosure may comprise determining expression of markers specific to detection of CLL including CD5, CD19, CD20, CD23, CD38, CD43, CD45, CD79b, CD81, kappa light chains, lambda light chains, and serum β2-microglobulin. In some embodiments, the method of the present disclosure may comprise determining mutations in genes associated with CLL including del(17p), TP53, and IGHV. In some embodiments, marker level is measured in any suitable tissue sample. For example, marker level may be measured in one or more of a subject's blood products (e.g., blood plasma, blood serum, peripheral blood mononuclear cells, tumor DNA species circulating as cell free DNA (cfDNA), circulating tumor cells (CTC), circulating tumor DNA (ctDNA), circulating miRNA and the like). In particular embodiments, the sample is a whole blood sample, a serum sample, or a plasma sample. In specific embodiments, the sample is a whole blood sample. In other embodiments, the sample is a serum sample. In other embodiments, the sample is a plasma sample.

Expression levels, tissue concentrations, or the presence of markers may be measured using any suitable techniques, such as enzyme-linked immunoassays (ELISA), mass spectrometry (MS), real-time quantitative PCR (RT-qPCR), flow cytometry, nucleic acid (i.e., DNA, RNA, etc.) sequencing, amino acid (i.e., peptide, protein, etc.) sequencing, molecular cytogenetics fluorescence in situ hybridization (FISH), and the like.

In various embodiments, one or more of the markers described herein may be up-regulated. "Up-regulation" or "up-regulated" refers to an increase in the presence of a protein and/or an increase in the expression of its gene. In various embodiments, one or more markers may be down-regulated. "Down-regulation" or "down-regulated" refers to a decrease in the presence of a protein and/or a decrease in the expression of its gene. Additionally, the function of a protein can be assayed by a relevant activity assay. Exemplary activity assays include binding assays, enzyme activity assays including, for example, protease assays, kinase assays, phosphatase assays, reductase assays, etc.

Up- or down-regulation of the markers can be assessed by comparing a value to a relevant reference level. For example, the quantity of one or more markers can be indicated as a value, which can be derived, e.g., by measuring level(s) of the marker/s) in the sample by an assay performed. In the broadest sense, the value may be qualitative or quantitative. Where detection is qualitative, the systems and methods provide a reading or evaluation, e.g., assessment, of whether or not the marker is present in the sample being assayed. In yet other embodiments, the systems and methods provide a quantitative detection of whether the marker is present in the sample being assayed, i.e., an evaluation or assessment of the actual amount or relative abundance of the marker in the sample being assayed. In such embodiments, the quantitative detection may be absolute or, if the method is a method of detecting two or more different markers in a sample, relative. Accordingly, the term "quantifying" when used in the context of quantifying a marker in a sample can refer to absolute or to relative quantification. Absolute quantification can be accomplished by inclusion of known concentration(s) of one or more control markers and referencing, e.g., normalizing, the detected level of the marker with the known control markers (e.g., through generation of a standard curve). Relative quantification can be accomplished by comparison of detected levels or amounts between the marker and a control (e.g., GAPDH or actin), to provide a relative quantification of the marker, e.g., relative to the control. Alternatively, relative quantification can be accomplished by comparison of detected levels or amounts between two or more different markers to provide a relative quantification of each of the two or more markers, e.g., relative to each other.

In some embodiments, the biomarker for identifying suitable patients to be treated by any of the methods disclosed herein can be soluble AXL, GAS6, or a mesenchymal transcription factor. A patient having an elevated level of one or more of the biomarkers relative to a reference level may be identified as suitable for the treatment disclosed herein. A reference level can be the level of the corresponding biomarker in a control sample, which may be measured using the same method for measuring the biomarker in a sample of a candidate patient. The control may be (or may be derived from) a normal subject (or normal subjects). Normal subjects, as used herein, refer to subjects that are apparently healthy and show no signs or symptoms of a target cancer as disclosed herein. The population of control subjects may therefore be a population of normal subjects. Alternatively, the control sample may be (or may be derived from) a subject or subjects having a target cancer who is/are not responsive to one or more prior cancer therapies, e.g., those described herein. In some embodiments, the control sample may be (or may be derived from) the subject being assessed for responsiveness to an anti-cancer therapy (e.g., those disclosed herein).

In specific examples, the biomarker is soluble AXL. The reference level may be a cutoff value of serum concentration of soluble AXL indicative of disease prognosis and/or suitability to the treatment regimens disclosed herein. In some examples, the cutoff value of soluble AXL can be less than 41,000 pg/ml, which can be indicative of a high risk of progressive disease. In other examples, the cutoff value can be greater than about 42,000 pg/ml, which can be indicative of a likelihood of stable disease. The cutoff values can be used to identify patients having specific prognostic features for treatment.

Measurement of the markers (i.e., the marker level) can be determined at the protein or nucleic acid level using any method known in the art. In certain embodiments, the measuring comprises measuring an mRNA level or a protein level. In particular embodiments, the measuring comprises measuring an mRNA level.

In some embodiments, a marker is detected by contacting a sample with reagents (e.g., antibodies or nucleic acid primers), generating complexes of reagent and marker(s), and detecting the complexes. Antibodies can be conjugated to a solid support suitable for a diagnostic assay in accordance with known techniques, such as passive binding. Antibodies can be conjugated to cell surface antigens for a diagnostic assay in accordance with known techniques, such as flow cytometry, including multi-color flow cytometry. Antibodies or nucleic acid primers can be conjugated to detectable labels or groups such as radiolabels, enzyme labels, and fluorescent labels in accordance with known techniques.

Examples of suitable immunoassays include immunoblotting, immunoprecipitation, immunofluorescence, chemiluminescence, electro-chemiluminescence (ECL), and ELISA. Up- or down-regulation of markers also can be detected using, for example, cDNA arrays, clone hybridization, differential display, differential screening, FRET detection, liquid microarrays, PCR, RT-PCR, Sanger sequencing, mass-parallel (next-generation) sequencing, molecular beacons, microelectric arrays, oligonucleotide arrays, polynucleotide arrays, serial analysis of gene expression (SAGE), and/or subtractive hybridization.

Examples of anti-AXL antibodies include AF154 (available from R&D SYSTEMS®), and MM0098-2N33 (available from ABCAM®). Examples of anti-GAS6 antibodies include A-9 (available from SANTA CRUZ BIOTECHNOLOGY®), and AF986 (available from R&D SYSTEMS®). Nucleic acid primers may be designed using known techniques, based on the gene sequence of AXE (NCBI Gene ID: 558) or GAS6 (NCBI Gene ID: 2621).

Marker level may be determined in a sample collected from a subject prior to treatment. In such embodiments, marker levels may be used to predict responsiveness to a particular treatment. In some embodiments, a subject's marker level may be used to select an appropriate treatment regimen. In some embodiments, levels may be used, at least in part, to determine a treatment administered to a subject. In some embodiments, a pre-treatment sample is collected on day 1 of a first cycle of treatment, pre-dose. In some embodiments a pre-treatment sample may be collected one month, three weeks, two weeks, one week, six days, five days, four days, three days, two days, or one day prior to administration of the first dose of the treatment regimen.

In embodiments, the sample is a whole blood sample, a serum sample, or a plasma sample. In certain embodiments, the expression level is an mRNA level or a protein level. In particular embodiments, the expression level is an mRNA level.

In some embodiments, a sample may be collected after a dose of a treatment is administered to a subject. In specific embodiments, a sample is collected on day 1 of a first cycle of treatment, predose, two hours after dosing, six hours after dosing, and 24 hours after dosing. In another specific embodiment, a sample is also collected on day 8 of the first cycle of treatment, predose. In another specific embodiment, a sample is also collected on day 1 of the second cycle of treatment, predose. In further specific embodiment, a sample is also collected on day 1 of any additional cycles of treatment (e.g., third, fourth, fifth, etc.), predose. In another specific embodiment, a sample is also collected after treatment is completed.

A predetermined marker level may be measured from a sample collected from a subject prior to treatment. In such embodiments, the marker level may be used to inform selection of a treatment regimen and/or predict responsiveness to a particular treatment. In some embodiments, the marker level may be used, at least in part, to determine a treatment regimen for a subject.

Accordingly, embodiments of the present disclosure include methods for selecting a treatment regimen for a subject in need thereof, the method comprising: obtaining a pre-treatment sample derived from the subject; measuring a marker in the sample; comparing the marker level to a threshold marker level; and selecting a treatment regimen based on the same.

Embodiments of the present application include methods for selecting a treatment regimen for a subject in need thereof, the methods comprising: obtaining a pre-treatment sample derived from the subject; measuring a marker level in the sample; comparing the marker level to a threshold marker level; and selecting a treatment regimen comprising an effective amount of a compound of structure (I) or a pharmaceutically acceptable salt thereof based on the comparison.

Further embodiments of the present application include methods for selecting a treatment regimen for a subject in need thereof, the methods comprising: obtaining a pre-treatment sample derived from the subject; measuring a marker level of a marker in the sample; and selecting a treatment regimen comprising an effective amount of a compound of structure (I) or a pharmaceutically acceptable salt thereof if the marker level is above a threshold marker level.

Particular embodiments of the disclosure include methods for selecting a treatment regimen for a subject in need thereof, the method comprising: obtaining a pre-treatment sample derived from the subject; measuring a marker comprising AXL or GAS6 proteins in the sample; comparing the marker levels of the marker to a threshold marker level; and selecting a treatment regimen based on the comparison. In certain embodiments, the treatment regimen comprises administering a pharmaceutical composition comprising a compound of structure (I) or a pharmaceutically acceptable salt of a compound of structure (I) (e.g., a tartrate salt).

Further embodiments include administering a treatment regimen to a subject based on a predetermined level of a marker. Accordingly, embodiments of the disclosure include methods for treating a cancer in a subject, the method comprising: administering an effective amount of a compound of structure (I), or a pharmaceutically acceptable salt thereof to a subject having a predetermined level of a marker that is above a threshold marker level.

Further embodiments of the disclosure include methods for treating a cancer in a subject, the method comprising: administering an effective amount of a compound of structure (I) or a pharmaceutically acceptable salt thereof to a subject having a predetermined level of a marker comprising AXL or GAS6 proteins, wherein the predetermined level is above a threshold marker level.

In some embodiments, the threshold marker level is associated with a disease outcome. Additionally, the threshold marker level may be determined from a population grouped according to disease outcome. In some embodiments, the population was treated for cancer. In certain embodiments, the cancer was a solid tumor. In embodiments, the cancer was a hematologic cancer. In particular embodiments, the population was treated for the same type of disease (e.g., the same type of cancer) as the subject.

In embodiments, the population has the same type of disease (e.g., the same type of cancer) as the subject. In particular embodiments, the population has the same type of cancer as the subject.

In some of the foregoing embodiments, the population had disease progression following treatment with a compound of structure (I) or a pharmaceutically acceptable salt thereof. Progressive disease may refer to disease that has progressed in severity following initiation of treatment. Accordingly, in particular embodiments, the threshold marker level is associated with a progressive disease outcome.

In some embodiments, the population had non-progression (e.g., stable disease) following treatment with a compound of structure (I) or pharmaceutically acceptable salt thereof. Non-progression may refer to disease that has improved (e.g., remission) or disease that has not progressed during the course of treatment (e.g., a tumor has not significantly grown or has decreased in size; and/or the cancer staging has not increased or has decreased). In particular embodiments, the non-progression is stable disease. Stable disease may refer to disease that has not improved but has not progressed during the course of treatment. Accordingly, in other embodiments, the threshold marker level is associated with non-progression.

In some embodiments, the population is a group comprising about 2, about 5, about 10, about 25, about 50, about 75, or about 100 subjects. In some embodiments, the population is a group comprising about 200, about 300, about 500, about 1,000, about 1,500, about 2,000, about 3,000, about 5,000, or about 10,000 subjects. In some embodiments, the population is a group comprising less than about 10,000 subjects. In other embodiments, the population is a group comprising greater than about 10,000 subjects.

In certain embodiments, the subject's marker level is higher than a threshold marker level associated with progressive disease. In embodiments, the subject's marker level is greater than or equal to a threshold marker level associated with non-progression.

In embodiments, the threshold marker level of AXL protein is about 35,000 picograms per milliliter (pg/mL). In some embodiments, the threshold marker level of AXL protein is about 36,000 pg/mL. In some embodiments, the threshold marker level of AXL protein is about 37,000 pg/mL. In some embodiments, the threshold marker level of AXL protein is about 37,500 pg/mL. In some embodiments, the threshold marker level of AXL protein is about 38,000 pg/mL. In some embodiments, the threshold marker level of AXL protein is about 38,500 pg/mL. In some embodiments, the threshold marker level of AXL protein is about 39,000 pg/mL. In some embodiments, the threshold marker level of AXL protein is about 39,500 pg/mL. In some embodiments, the threshold marker level of AXL protein is about 40,000 pg/mL. In some embodiments, the threshold marker level of AXL protein is about 40,500 pg/mL. In some embodiments, the threshold marker level of AXL protein is about 41,000 pg/mL. In some embodiments, the threshold marker level of AXL protein is about 41,500 pg/mL. In some embodiments, the threshold marker level of AXL protein is about 42,000 pg/mL. In particular embodiments, the threshold marker level of AXL protein is about 43,000 pg/mL. In some embodiments, the threshold marker level of AXL protein is about 44,000 pg/mL. In certain embodiments, the threshold marker level of AXL protein is about 45,000 pg/mL. In some embodiments, the threshold marker level of AXL protein is about 46,000 pg/mL. In some embodiments, the threshold marker level of AXL protein is about 47,000 pg/mL.

In some embodiments, the threshold marker level of GAS6 protein is about 8,000 pg/mL. In some embodiments, the threshold marker level of GAS6 protein is about 9,000 pg/mL. In some embodiments, the threshold marker level of GAS6 protein is about 10,000 pg/mL. In particular embodiments, the threshold marker level of GAS6 protein is about 10,500 pg/mL. In some embodiments, the threshold marker level of GAS6 protein is about 11,000 pg/mL. In particular embodiments, the threshold marker level of GAS6 protein is about 11,500 pg/mL. In some embodiments, the threshold marker level of GAS6 protein is about 12,000 pg/mL. In certain embodiments, the threshold marker level of GAS6 protein is about 12,500 pg/mL. In particular embodiments, the threshold marker level of GAS6 protein is about 13,000 pg/mL. In some embodiments, the threshold marker level of GAS6 protein is about 13,500 pg/mL. In some embodiments, the threshold marker level of GAS6 protein is about 14,000 pg/mL. In certain embodiments, the threshold marker level of GAS6 protein is about 14,500 pg/mL. In particular embodiments, the threshold marker level of GAS6 protein is about 15,000 pg/mL. In particular embodiments, the threshold marker level of GAS6 protein is about 15,500 pg/mL. In particular embodiments, the threshold marker level of GAS6 protein is about 16,000 pg/mL. In certain embodiments, the threshold marker level of GAS6 protein is about 16,500 pg/mL.

Accordingly, embodiments of the present disclosure include methods of selecting a treatment regimen for a cancer in a subject, the method comprising: obtaining a pre-treatment sample derived from the subject; measuring the level of a marker comprising AXL or GAS6 in the sample; and selecting a treatment regimen comprising an effective amount of an AXL inhibitor if: (A) the level of AXL protein is at least about 35,000 picograms per milliliter (pg/mL); (B) the level of GAS6 protein is at least about 8,000 pg/mL; or (C) both.

Accordingly, embodiments of the present disclosure include methods of selecting a treatment regimen for a cancer in a subject, the method comprising: obtaining a pre-treatment sample derived from the subject; measuring the level of a marker comprising AXL or GAS6 in the sample; and selecting a treatment regimen comprising an effective amount of an AXL inhibitor if: (A) the level of AXL protein is at least about 45,000 picograms per milliliter (pg/mL); (B) the level of GAS6 protein is at least about 13,500 pg/mL; or (C) both.

Particular embodiments of the present disclosure include methods of selecting a treatment regimen for a cancer in a subject, the method comprising: obtaining a pre-treatment sample derived from the subject; measuring the level of a marker comprising AXL or GAS6 in the sample; and selecting a treatment regimen comprising an effective amount of a compound of structure (I):

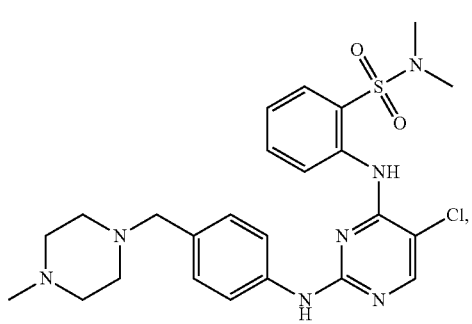

(I)

or a pharmaceutically acceptable salt thereof if: (A) AXL protein is present at a level of at least about 45,000 pg/mL; (B) GAS6 protein is present at a level of at least about 13,500 pg/mL; or (C) both In embodiments, a subject's marker level is pre-determined.

Accordingly, embodiments of the present disclosure include methods for treating a cancer in a subject, the method comprising: administering an effective amount of an AXL inhibitor to a subject having a predetermined level of a marker comprising AXL or GAS6, wherein: (A) the predetermined level of AXL protein is at least 45,000 pg/mL; (B) the predetermined level of GAS6 protein is at least 13,500 pg/mL; or (C) both.

Further embodiments of the present disclosure include methods for treating a cancer in a subject, the method comprising: administering an effective amount of a compound of structure (I):

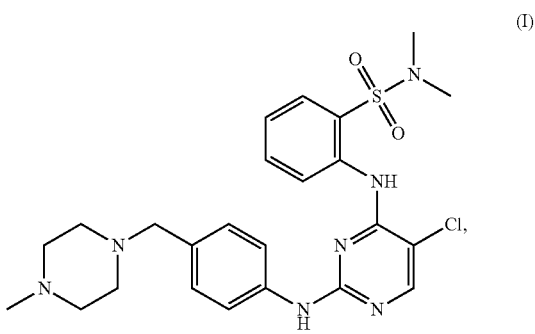

(I)

or a pharmaceutically acceptable salt thereof to a subject having a predetermined level of a marker comprising AXL or GAS6, wherein: (A) the predetermined level of AXL protein is at least 35,000 pg/mL; (B) the predetermined level of GAS6 protein is at least 8,000 pg/mL; or (C) both.

In still further embodiments of the present disclosure include methods for treating a cancer in a subject, the method comprising: administering an effective amount of a compound of structure (I):

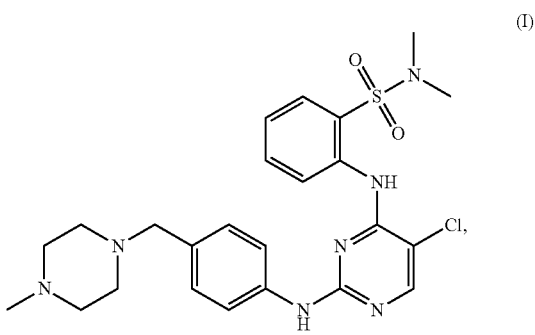

(I)

or a pharmaceutically acceptable salt thereof to a subject having a predetermined level of a marker comprising AXL or GAS6, wherein: (A) the predetermined level of AXL protein is at least 45,000 pg/mL; (B) the predetermined level of GAS6 protein is at least 13,500 pg/mL; or (C) both.

3. Combination Therapies

In still another embodiment, an AXL kinase inhibitor, such as a compound of structure (I) or a pharmaceutically acceptable salt of a compound of structure (I) (e.g., a tartrate salt), is administered to a subject in need thereof in combination with a B-cell receptor signaling antagonist (e.g., a Bruton's tyrosine kinase (BTK) inhibitor, such as Ibrutinib). Accordingly, methods of the present disclosure include methods for treating cancer comprising administering an effective amount of an AXL kinase inhibitor and a Bruton's tyrosine kinase (BTK) inhibitor to a subject in need thereof. The administration may be before, concurrently or after administration of the B-cell receptor signaling antagonist (e.g., the BTK inhibitor). In some embodiments, the AXL kinase inhibitor and BTK inhibitor are co-administered. In other embodiments, the AXL kinase inhibitor is administered after the BTK inhibitor. In still different embodiments, the AXL kinase inhibitor is administered before the BTK inhibitor.

In various embodiments, the BTK inhibitor is Ibrutinib. In some particular embodiments, the cancer is chronic lymphocytic leukemia (CLL), small lymphocytic lymphoma (SLL), or both. In some embodiments, the subject has received a prior treatment regimen for CLL, SLL, or both. In some embodiments, the subject was refractory after the prior treatment regimen, the subject has relapsed CLL, SLL, or both after a response to the prior treatment regimen, or the subject has detectable minimal residual disease (MRD).

In certain embodiments the subject is insensitive to treatment with a B-cell receptor signaling antagonist (e.g., a BTK inhibitor), is ineligible for treatment with a B-cell receptor signaling antagonist (e.g., a BTK inhibitor) or has relapsed after treatment with a B-cell receptor signaling antagonist (e.g., a BTK inhibitor). In one specific embodiment, a compound of structure (I) or a pharmaceutically acceptable salt of a compound of structure (I) (e.g., a tartrate salt), is administered to a subject in need thereof in combination with a BTK inhibitor, such as Ibrutinib for treatment of leukemia (e.g., CLL, SLL, or both).

In another embodiment, an AXL kinase inhibitor, such as a compound of structure (I) or a pharmaceutically acceptable salt of a compound of structure (I) (e.g., a tartrate salt), is administered to a subject in need thereof in combination with a Bcl-2 inhibitor, such as venetoclax. The administration may be before, concurrently or after administration of the Bcl-2 inhibitor. In certain embodiments the subject is insensitive to treatment with a Bcl-2 inhibitor, is ineligible for treatment with a Bcl-2 inhibitor or has relapsed after treatment with a Bcl-2 inhibitor In one specific embodiment, a compound of structure (I) or a pharmaceutically acceptable salt of a compound of structure (I) (e.g., a tartrate salt), is administered to a subject in need thereof in combination with a Bcl-2 inhibitor, such as venetoclax for treatment of leukemia (e.g., CLL, SLL, or both).

In still another embodiment, an AXL kinase inhibitor, such as a compound of structure (I) or a pharmaceutically acceptable salt of a compound of structure (I) (e.g., a tartrate salt), is administered to a subject in need thereof in combination with an immune checkpoint inhibitor (e.g., a PD-1 inhibitor (such as Pembrolizumab or Nivolumab), a PD-L1 inhibitor (such as Atezolizumab, Avelumab, or Durvalumab), a CTLA-4 inhibitor, a LAG-3 inhibitor, or a Tim-3 inhibitor). Accordingly, methods of the present disclosure include methods for treating cancer comprising administering an effective amount of an AXL kinase inhibitor and an immune checkpoint inhibitor to a subject in need thereof. The administration of the AXL kinase inhibitor may be before, concurrently or after administration of the immune checkpoint inhibitor (e.g., a PD-1 inhibitor (such as Pembrolizumab or Nivolumab), a PD-L1 inhibitor (such as Atezolizumab, Avelumab, or Durvalumab), a CTLA-4 inhibitor, a LAG-3 inhibitor, or a Tim-3 inhibitor).

In some embodiments, the AXL kinase inhibitor and immune checkpoint inhibitor are co-administered. In other embodiments, the AXL kinase inhibitor is administered after the immune checkpoint inhibitor. In still different embodiments, the AXL kinase inhibitor is administered before the immune checkpoint inhibitor.

In various embodiments, the immune checkpoint inhibitor is a PD-1 inhibitor. In specific embodiments, the PD-1 inhibitor is Pembrolizumab, Nivolumab, or a combination thereof. In particular embodiments, the PD-1 inhibitor is Pembrolizumab. In particular embodiments, the PD-1 inhibitor is Nivolumab. In some other embodiments, the PD-1 inhibitor is CBT-501 (CBT Pharmaceuticals), CBT-502 (CBT Pharmaceuticals), JS001 (Junshi Biosciences), IB1308 (Innovent Biologies), SHR-1210 (Hengrui Medicine), BGB-A317 (Beigene), BAT-1306 (Bio-Thera Solutions), GLS-010 (Gloria Pharmaceuticals; WuXi Biologies), AK103, AK104, AK105 (Akesio Biopharma; Hangzhou Hansi Biologies; Hanzhong Biologies), LZM009 (Livzon), HLX-10 (Henlius Biotech), or CS1003 (CStone Pharmaceuticals). In some embodiments, the PD-1 inhibitor is a monoclonal antibody (e.g., made by Genor Biopharma and in Phase I of clinical trials as of this filing; as made by Shenzhou Gongcheng and applying for clinical trials as of this filing; as made by Lunan Hope Pharmaceuticals and applying for clinical trials as of this filing).

In some embodiments, the immune checkpoint inhibitor is a PD-L1 inhibitor. In some such embodiments, the PD-L1 inhibitor is Atezolizumab, Avelumab, Durvalumab, or a combination thereof. In particular embodiments, the PD-L1 inhibitor is Atezolizumab. In particular embodiments, the PD-L1 inhibitor is Avelumab. In particular embodiments, the PD-L1 inhibitor is Durvalumab. In certain embodiments, the PD-L1 inhibitor is KN035 (Alphamab; 3DMed), CS1001 (CStone Pharmaceuticals), SHR-1316 (Hengrui Medicine), TQB2450 (Chiatai Tianqing), STI-A1014 (Zhaoke Pharm; Lee's Pharm), BGB-A333 (Beigene), MSB2311 (Mabspace Biosciences), or HLX-20 (Henlius Biotech). In some embodiments, the PD-L1 inhibitor is a monoclonal antibody (e.g., as made by Hisun Pharm and applying for clinical trials as of this filing).

In some embodiments, the immune checkpoint inhibitor is a CTLA-4 inhibitor. In certain embodiments, the CTLA-4 inhibitor is ipilimumab. In other embodiments, the CTLA-4 inhibitor is tremelimumab.

In embodiments, an AXL kinase inhibitor, such as a compound of structure (I) or a pharmaceutically acceptable salt of a compound of structure (I) (e.g., a tartrate salt), is administered to a subject in need thereof in combination with a bromodomain inhibitor, a histone deacetylase (HDAC), or both.

A bromodomain inhibitor inhibits at least one bromodomain protein, such as Brd2, Brd3, Brd4 and/or BrdT, for example Brd4. In some of these embodiments, the bromodomain inhibitor is JQ-1 (Nature 2010 Dec. 23; 468(7327): 1067-73), B12536 (ACS Chem. Biol. 2014 May 16; 9(5): 1160-71; Boehringer Ingelheim), TG101209 (ACS Chem. Biol. 2014 May 16; 9(5): 1160-71), OTX015 (Mol. Cancer Ther. November 201372; C244; Oncoethix), IBET762 (J Med Chem. 2013 Oct. 10; 56(19):7498-500; GlaxoSmithKline), IBET151 (Bioorg. Med. Chem. Lett. 2012 Apr. 15; 22(8):2968-72; GlaxoSmithKline), PFI-1 (J. Med. Chem. 2012 Nov. 26; 55(22):9831-7; Cancer Res. 2013 Jun. 1; 73(11):3336-46; Structural Genomics Consortium) of CPI-0610 (Constellation Pharmaceuticals). In some embodiments, the bromodomain inhibitor is TG101209, B12536, OTX015, C244, IBET762, IBET151, or PFI-1.

A HD AC inhibitor inhibits at least one HD AC protein. HD AC proteins may be grouped into classes based on homology to yeast HD AC proteins with Class I made up of HDAC1, HDAC2, HD AC 3 and HD AC 8; Class Ha made up of HDAC4, HDAC5, HDAC7 and HD AC 9; Class lib made up of HD AC 6 and HD AC 10; and Class IV made up of HD AC 11. In some of these embodiments, the HD AC inhibitor is trichostatin A, vorinostat (Proc. Natl. Acad. Sci. U.S.A. 1998 Mar. 17; 95(6):3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19):5494-504), quisinostat (Clin. Cancer Res. 2013 Aug. 1; 19(15):4262-72), depsipeptide (Blood. 2001 Nov. 1; 98(9):2865-8), entinostat (Proc. Natl. Acad. Sci. U.S.A. 1999 Apr. 13; 96(8): 4592-7), mocetinostat (Bioorg. Med. Chem. Lett. 2008 Feb. 1; 18(3): 1067-71) or valproic acid (EMBO J. 2001 Dec. 17; 20(24):6969-78). For example, in some embodiments the HDAC inhibitor is panobinostat, vorinostat, MS275, belmosiat, or LBH589. In some embodiments, the HDAC inhibtior is panobinostat or SAHA.

In some embodiments, methods of the present disclosure further comprise administering radiation therapy to the subject.

In some of the foregoing embodiments, the method is for treating liver cancer, refractory cancers (e.g., non-small cell lung cancer), lung cancer, esophageal cancer, Hodgkin's lymphoma, NK/T-cell lymphoma, or melanoma. In some specific embodiments, the method is for treating esophageal squamous cell carcinoma, gastric cancer, lung cancer, nasopharyngeal carcinoma, bladder cancer, soft tissue sarcoma, diffuse large B-cell lymphoma, head and neck squamous cell carcinomas, kidney cancer, urothelial carcinoma, ovarian cancer, uterine cancer, or pancreatic cancer.

Other embodiments provide methods for combination therapies in which an agent known to modulate other pathways, or other components of the same pathway, or even overlapping sets of target enzymes are used in combination with a compound of structure (I) or a pharmaceutically acceptable salt of a compound of structure (I) (e.g., a tartrate salt). In one aspect, such therapy includes but is not limited to the combination of a compound of structure (I) or a pharmaceutically acceptable salt of a compound of structure (I) (e.g., a tartrate salt) with chemotherapeutic agents, therapeutic antibodies, and radiation treatment, to provide a synergistic or additive therapeutic effect.

Many chemotherapeutics are presently known in the art and can be used in combination with a compound of structure (I) or a pharmaceutically acceptable salt of a compound of structure (I) (e.g., a tartrate salt). In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomeRASe inhibitors, biological response modifiers, anti-hormones, angiogenesis inhibitors, and anti-androgens.

Non-limiting examples of therapeutic agents that can be used in combinations with a compound of structure (I) or a pharmaceutically acceptable salt of a compound of structure (I) (e.g., a tartrate salt) are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; tempo side; daunomycin; aminopterin; xeloda; ibandronate; camptothecin-11 (CPT-11); topoisomeRASe inhibitor RES 2000; difluoromethylornithine (DMFO). Where desired, the compound of structure (I) or a pharmaceutically acceptable salt of a compound of structure (I) (e.g., a tartrate salt) or a pharmaceutical composition thereof can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

In one embodiment, a compound of structure (I), is administered to a subject in need thereof in combination with a CDK9 inhibitor, such as Alvocidib. In a related embodiment, a pharmaceutically acceptable salt of a compound of structure (I) (e.g., a tartrate salt) is administered to a subject in need thereof in combination with a CDK9 inhibitor, such as Alvocidib. The administration may be before, concurrently or after administration of the CDK9 inhibitor. In one specific embodiment, a compound of structure (I) is administered to a subject in need thereof in combination with a CDK9 inhibitor, such as Alvocidib for treatment of pancreatic cancer. In a related specific embodiment, a pharmaceutically acceptable salt of a compound of structure (I) (e.g., a tartrate salt) is administered to a subject in need thereof in combination with a CDK9 inhibitor, such as Alvocidib for treatment of pancreatic cancer. In some of the foregoing embodiments, the salt is a tartrate salt. In some of the foregoing embodiments, the CDK9 inhibitor is Alvocidib. In some embodiments, the salt is a tartrate salt and the CDK9 inhibitor is Alvocidib.

In certain other embodiments, a method for treating cancer is provided, the method comprising administering an effective amount of an AXL kinase inhibitor and a CDK inhibitor to a subject in need thereof. The AXL kinase inhibitor and CDK inhibitor may be any of the AXL kinase or CDK inhibitors known in the art.

In certain embodiments, the AXL kinase inhibitor is a compound of structure (I), or a pharmaceutically acceptable salt thereof. For example, in some specific embodiments, the AXL kinase inhibitor a tartrate salt of a compound of structure (I) as disclosed herein.

In embodiments, the CDK inhibitor is a CDK2, CDK4, CDK6, CDK7, CDK8, CDK9, CDK10, and/or CDK11 inhibitor. In some embodiments, the CDK inhibitor is a CDK7, CDK9 inhibitor, or both. In some embodiments, the CDK inhibitor is dinaciclib (ACS Med. Chem. Lett. 2010 May 17; 1(5):204-8; Mol. Cancer Ther. 2010 August; 9(8):2344-53; Merck, Sharp and Dohme), AT7519 (J. Med. Chem. 2008 Aug. 28; 51(16):4986-99; Astex Pharmaceutical) or palbociclib (J. Med. Chem. 2005 Apr. 7; 48(7):2388-406; Pfizer). In certain embodiments, the CDK inhibitor is a CDK9 inhibitor, such as alvocidib. The alvocidib may be administered as the free bases, as a pharmaceutically acceptable salt or as a prodrug. In certain embodiments, the CDK9 inhibitor is alvocidib. in other embodiments, the CDK9 inhibitor is a pharmaceutically acceptable salt of alvocidib. In other embodiments, the CDK9 inhibitor is a prodrug of alvocidib. Prodrugs of alvocidib include those disclosed in WO 2016/187316, the full disclosure of which is hereby incorporated by reference in its entirety. For example, in some embodiments the prodrug of alvocidib has the following structure (II):

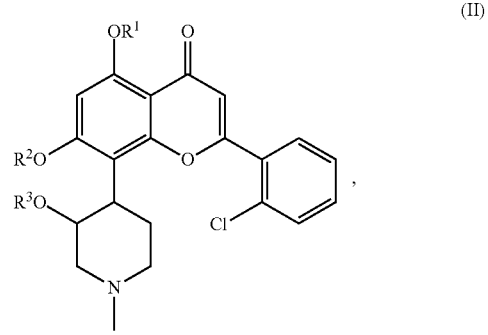

or a stereoisomer, tautomer or pharmaceutically acceptable salt thereof, wherein: one of $R^1$, $R^2$ or $R^3$ is —P(=O)(OH)$_2$, and the other two of $R^1$, $R^2$ and $R^3$ are each H.

In certain specific embodiments, the prodrug of alvocidib has the following structure:

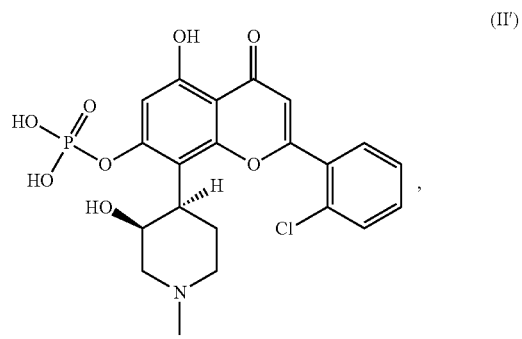 [SMILES: CN1CC[C@H](c2c(OP(=O)(O)O)cc(O)c3c(=O)cc(-c4ccccc4Cl)oc23)[C@H](O)C1]

or a pharmaceutically acceptable salt or zwitterionic form thereof.

In some embodiments, the AXL kinase inhibitor and CDK inhibitor are co-administered. In other embodiments, the AXL kinase inhibitor is administered after the CDK inhibitor. In still different embodiments, the AXL kinase inhibitor is administered before the CDK inhibitor.

Various different cancers can be treated with the combination of an AXL kinase inhibitor and CDK inhibitor. In some embodiments, the cancer is a hematologic cancer or solid tumor, for example any of the hematologic cancers or solid tumors disclosed herein or known in the art.

In some specific embodiments, the cancer is a hematologic cancer, such as multiple myeloma, myelodysplastic syndrome (MDS), acute myelogenous leukemia (AML), acute lymphoblastic leukemia (ALL), acute lymphocytic leukemia, chronic lymphogenous leukemia, chronic lymphocytic leukemia (CLL), mantle cell lymphoma, diffuse large B-cell lymphoma, follicular lymphoma, or non-Hodgkin's lymphoma. In some specific embodiments, the hematologic cancer is CLL, SLL, or both. In some specific embodiments, the hematologic cancer is CLL. In some specific embodiments, the hematologic cancer is SLL.

In some other specific embodiments, the cancer treated by the combination of an AXL kinase inhibitor and a CDK inhibitor is a solid tumor, such as a pancreatic, colon or lung cancer.

Embodiments further relate to a method of administering a compound of structure (I) or a pharmaceutically acceptable salt of a compound of structure (I) (e.g., a tartrate salt), to a subject in need thereof in combination with a BTK inhibitor (e.g., Ibrutinib) or a CDK9 inhibitor (e.g., Alvocidib) provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of a pharmaceutically acceptable salt of a compound of structure (I), for example a tartrate salt of a compound of structure (I) in this combination therapy can be determined as described herein.

In one embodiment, a compound of structure (I), is administered to a subject in need thereof in combination with an ATR inhibitor, such as AZD6738 or VX-970. In a related embodiment, a pharmaceutically acceptable salt of a compound of structure (I) (e.g., a tartrate salt) is administered to a subject in need thereof in combination with an ATR inhibitor, such as AZD6738 or VX-970. The administration may be before, concurrently or after administration of the ATR inhibitor. In one specific embodiment, a compound of structure (I) is administered to a subject in need thereof in combination with an ATR inhibitor, such as AZD6738 or VX-970 for treatment of non-small cell lung cancer. In a related specific embodiment, a pharmaceutically acceptable salt of a compound of structure (I) (e.g., a tartrate salt) is administered to a subject in need thereof in combination with an ATR inhibitor, such as AZD6738 or VX-970 for treatment of non-small cell lung cancer. In some of the foregoing embodiments, the salt is a tartrate salt. In some of the foregoing embodiments, the ATR inhibitor is AZD6738. In some of the foregoing embodiments, the ATR inhibitor is VX-970. In some embodiments, the salt is a tartrate salt and the ATR inhibitor is AZD6738. In some embodiments, the salt is a tartrate salt and the ATR inhibitor is VX-970. In some of the foregoing embodiments, the ATR inhibitor is a combination of AZD6738 and VX-970.

In some of the foregoing embodiments, the non-small cell lung cancer comprises TCGA lung adenocarcinoma, one or more LUAD tumors, TCGA lung squamous cell carcinoma, one or more LUSC tumors, one or more MDACC PROSPECT tumors, one or more MDACC BATTLE1 tumors, one or more BATTLE2 tumors, or combinations thereof. In some embodiments, the non-small cell lung cancer comprises TCGA LUAD tumors, for example, tumors enriched in ALK translocations. In some embodiments, the non-small cell lung cancer comprises TCGA LUAD tumors, for example, tumors comprising one or more EGER mutations.

In one embodiment, a compound of structure (I), is administered to a subject in need thereof thereby sensitizing the subject to administration of an ATR inhibitor, such as AZD6738 or VX-970. In a related embodiment, a pharmaceutically acceptable salt of a compound of structure (I) (e.g., a tartrate salt) is administered to a subject in need thereof thereby sensitizing the subject to administration of an ATR inhibitor, such as AZD6738 or VX-970. In one specific embodiment, a compound of structure (I) is administered to a subject in need thereof thereby sensitizing the subject to administration of an ATR inhibitor, such as AZD6738 or VX-970 for treatment of non-small cell lung cancer. In a related specific embodiment, a pharmaceutically acceptable salt of a compound of structure (I) (e.g., a tartrate salt) is administered to a subject in need thereof thereby sensitizing the subject to administration of an ATR inhibitor, such as AZD6738 or VX-970 for treatment of non-small cell lung cancer. In some of the foregoing embodiments, the salt is a tartrate salt. In some of the foregoing embodiments, the ATR inhibitor is AZD6738. In some of the foregoing embodiments, the ATR inhibitor is VX-970. In some embodiments, the salt is a tartrate salt and the ATR inhibitor is AZD6738. In some embodiments, the salt is a tartrate salt and the ATR inhibitor is VX-970. In some of the foregoing embodiments, the ATR inhibitor is a combination of AZD6738 and VX-970.

Radiation therapy can be administered in combination with a compound of structure (I) or a pharmaceutically acceptable salt of a compound of structure (I) (e.g., a tartrate salt) in some embodiments. Exemplary radiation therapies include external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu). Suitable radiation sources for use as a cell conditioner of the present invention include both solids and liquids. By way of non-limiting example, the radiation source can be a radionuclide, such as $I^{125}$, $I^{131}$, $Yb^{169}$, $Ir^{192}$ as a solid source, $I^{125}$ as a solid source, or other radionuclides that emit photons, beta particles, gamma radiation, or other therapeutic rays. The radioactive material can also be a fluid made from any solution of radionuclide(s), e.g., a solution of $I^{125}$ or $I^{131}$, or a radioactive fluid can be produced using a slurry of a suitable fluid containing small particles of solid radionuclides, such as $An^{198}$, $Y^{90}$. Moreover, the radionuclide(s) can be embodied in a gel or radioactive micro spheres.

Without being limited by any theory, a compound of structure (I) or a pharmaceutically acceptable salt of a compound of structure (I) (e.g., a tartrate salt) can render abnormal cells more sensitive to treatment with radiation for purposes of killing and/or inhibiting the growth of such cells. Accordingly, some embodiments include a method for sensitizing abnormal cells in a mammal to treatment with radiation which comprises administering to the mammal an amount of a compound of structure (I) or a pharmaceutically acceptable salt of a compound of structure (I) (e.g., a tartrate salt), which amount is effective is sensitizing abnormal cells to treatment with radiation. The amount of a compound of structure (I) or a pharmaceutically acceptable salt of a compound of structure (I) (e.g., a tartrate salt) in this method can be determined according to the means for ascertaining effective amounts of such compounds and salts described herein.

The compound of structure (I) or a pharmaceutically acceptable salt of a compound of structure (I) (e.g., a tartrate salt) can also be used in combination with an amount of one or more substances selected from anti-angiogenesis agents, signal transduction inhibitors, antiproliferative agents, glycolysis inhibitors, or autophagy inhibitors.

Anti-angiogenesis agents include, for example, MMP-2 (matrix-metalloproteinase 2) inhibitors, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Embodiments of MMP-2 and MMP-9 inhibitors include those that have little or no activity inhibiting MMP-1. Other embodiments include those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in some embodiments are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In other embodiments, agents useful in methods for combination therapy with a compound of structure (I) or a pharmaceutically acceptable salt of a compound of structure (I) (e.g., a tartrate salt) include, but are not limited to: Erlotinib, Afatinib, Iressa, GDC0941, MLN1117, BYL719 (Alpelisib), BKM120 (Buparlisib), CYT387, GLPG0634, Baricitinib, Lestaurtinib, momelotinib, Pacritinib, Ruxolitinib, TG101348, Crizotinib, tivantinib, AMG337, cabozantinib, foretinib, onartuzumab, NVP-AEW541, Dasatinib, Ponatinib, saracatinib, bosutinib, trametinib, selumetinib, cobimetinib, PD0325901, R05126766, Axitinib, Bevacizumab, Bostutinib, Cetuximab, Crizotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, Vemurafenib, Irinotecan, Taxol, Docetaxel, Rapamycin or MLN0128.

In embodiments, a compound of structure (I) or a pharmaceutically acceptable salt of a compound of structure (I) (e.g., a tartrate salt) is administered in combination with an epidermal growth factor receptor tyrosine kinase (EGER) inhibitor. Examples of EGER inhibitors include erlotinib, osimertinib, cetuximab, gefitinib, necitumumab, lapatinib, neratinib, panitumumab, vandetanib, and necitumumab. A combination of a compound of structure (I) and an EGER inhibitor may be useful, for example, in the treatment of cancers that are related to EGER dysregulation, such as non-small-cell lung cancer (NSCLC), pancreatic cancer, breast cancer, and colon cancer. EGER may be dysregulated, for example, due to activating mutations in exons 18, 19, 20, or 21. As shown in Examples 9, 10, and 19, combinations of a compound of structure (I) and EGER inhibitors show synergy in preclinical models of EGFR-mutated cancer. In particular embodiments, the EGER inhibitor is erlotinib or osimertinib. In particular embodiments, the combination of a compound of structure (I) and an EGER inhibitor is used to treat EGFR-mutated NSCLC. In particular embodiments, the combination of a compound of structure (I) and an EGER inhibitor is used to treat an EGER inhibitor-resistant cancer, and the compound of structure (I) sensitized the cancer to the EGER inhibitor.

In certain embodiments, a compound of structure (I) or a pharmaceutically acceptable salt of a compound of structure (I) (e.g., a tartrate salt) is administered in combination with Erlotinib. In some embodiments, such a combination is used to treat pancreatic cancer. In other embodiments, such a combination is used to treat lung cancer. In further embodiments, the lung cancer is non-small cell lung cancer.

In certain embodiments, a compound of structure (I) or a pharmaceutically acceptable salt of a compound of structure (I) (e.g., a tartrate salt) is administered in combination with osmertinib. In some embodiments, such a combination is used to treat lung cancer. In further embodiments, the lung cancer has an EGFR mutation.

When used in combination therapy, a compound of structure (I) or a pharmaceutically acceptable salt of a compound of structure (I) (e.g., a tartrate salt), is administered with the second agent simultaneously or separately. This administration in combination can include simultaneous administration of the two agents in the same dosage form, simultaneous administration in separate dosage forms, and separate administration. That is, a compound of structure (I) or a pharmaceutically acceptable salt of a compound of structure (I) (e.g., a tartrate salt), and any of the agents described above (e.g., Ibrutinib or Alvocidib) can be formulated together in the same dosage form and administered simultaneously. Alternatively, a compound of structure (I) or a pharmaceutically acceptable salt of a compound of structure (I) (e.g., a tartrate salt), and any of the agents described above (e.g., Ibrutinib or Alvocidib) can be simultaneously administered, wherein both the agents are present in separate formulations. In another alternative, a compound of structure (I) or a pharmaceutically acceptable salt of a compound of structure (I) (e.g., a tartrate salt), can be administered just followed by and any of the agents described above, or vice versa. In some embodiments of the separate administration protocol, a compound of structure (I) or a pharmaceutically acceptable salt of a compound of structure (I) (e.g., a tartrate salt), and any of the agents described above are administered a few minutes apart, or a few hours apart, or a few days apart.

A compound of structure (I) or a pharmaceutically acceptable salt thereof (e.g., a tartrate salt) used in embodiments of the disclosure may also be administered simultaneously with, prior to, or after administration of one or more other therapeutic agents. For example, a compound of structure (I) or a pharmaceutically acceptable salt thereof (e.g., a tartrate salt) can be administered and after a sufficient period of time a second therapeutic agent is administered. In such embodiments, the period of time between the administration of a compound of structure (I) or a pharmaceutically acceptable salt thereof (e.g., a tartrate salt) and the second therapeutic agent may be referred to as a "treatment break." In some embodiments, such a treatment break ranges from about 12 hours to about 48 hours. In some embodiments, such a treatment break ranges from about 18 to about 40 hours. In some embodiments, such a treatment break ranges from about 18 to about 36 hours. In some embodiments, such a treatment break ranges from about 24 to about 48 hours. One of ordinary skill in the art can derive an appropriate dosing schedule based on common techniques and knowledge.

In embodiments, a compound of structure (I) or a pharmaceutically acceptable salt thereof (e.g., a tartrate salt) and a second therapeutic agent are administered sequentially. In some embodiments, there is a treatment break between administering a compound of structure (I) or a pharmaceutically acceptable salt thereof (e.g., a tartrate salt) and administering the second therapeutic agent. In more specific embodiments, the treatment break is at least about 24 to about 48 hours. In particular embodiments, the treatment break is about 48 hours. In some embodiments, the treatment break is at least about 120 hours.

4. Treatment of Ovarian Cancer

In embodiments, methods of the disclosure are useful for treating cancer in a subject. Such methods of treating a cancer (e.g., (i) arrest the cancer's development; (ii) cause regression of the cancer; or (iii) relieve the symptoms resulting from the cancer) include administering a tartrate salt of a compound of structure (I), as described herein. In embodiments, the cancer is ovarian clear cell carcinoma.

Additionally, in various embodiments, methods of the disclosure are useful for treating ascites caused by a cancer in a subject. Accordingly, embodiments of the methods of treatment disclosed herein comprise treating ascites in a subject in need thereof, the method comprising: administering a compound of structure (I), or a pharmaceutically acceptable salt thereof (e.g., a tartrate salt), wherein the ascites is caused by a cancer. In some embodiments, the cancer is ovarian cancer.

In embodiments, the cancer is sensitive to a treatment. In embodiments, the cancer is partially sensitive to a treatment. In some embodiments, the cancer is refractory with regard to a treatment. In some embodiments, the cancer is recurrent. In embodiments, the cancer is resistant to a treatment. In embodiments, the cancer is treatment-resistant ovarian cancer.

In some embodiments, the treatment-resistant ovarian cancer is recurrent treatment-resistant ovarian cancer. In some embodiments, the ovarian cancer is drug-resistant ovarian cancer. In embodiments, the ovarian cancer is resistant to a drug selected from the group consisting of a hormone therapeutic agent, a chemotherapeutic agent, an immunotherapeutic agent, or a cell growth factor and an agent to inhibit its receptor action.

In various embodiments, the drug is a hormone therapeutic agent. Examples of hormone therapeutic agents include fosfestrol, diethylstilbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, tadenan, mepartricin, raloxifene, ormeloxifene, levormeloxifene, antiestrogen (e.g., tamoxifen citrate, toremifene citrate, and the like), a pill formulation, mepitiostane, testololactone, aminoglutethimide, LH-RH derivatives (LH-RH agonist (e.g., goserelin acetate, buserelin, leuprorelin, and the like), LH-RH antagonist), droloxifene, epitiostanol, ethinyl estradiol sulfonate, aromatase inhibitors (e.g., fadrozole hydrochloride, anastrozole, letrozole, exemestane, vorozole, formestane, and the like), antiandrogens (e.g., flutamide, bicalutamide, nilutamide, and the like), adrenocortical hormone-based agents (e.g., dexamethasone, prednisolone, betamethasone, triamcinolone, and the like), androgen synthesis inhibitors (e.g., abiraterone and the like), retinoid and an agent to retard the metabolism of retinoid (e.g., liarozole and the like), and the like.

In various embodiments, the drug is a chemotherapeutic agent. In various embodiments, the chemotherapeutic agent is an alkylating agent, an antimetabolite, an anti-cancer antibiotic, or a plant-derived anti-cancer agent. In particular embodiments, the chemotherapeutic agent is an alkylating agent. Examples of alkylating agents include nitrogen mustard, nitrogen mustard N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylene melamine, carmustine, lomustine, streptozocin, pipobroman, ethoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulfan, trophosphamide, zinostatin stimalamer, adozelesin, cystemustine, bizelesin and DDS formulations thereof, and the like. In specific embodiments, the alkylating agent is selected from the group consisting of carboplatin, cisplatin, miboplatin, nedaplatin, and oxaliplatin. In certain embodiments, the alkylating agent is a cisplatin.

In embodiments, the chemotherapeutic agent is an antimetabolite. Examples of antimetabolites include mercaptopurine, 6-mercaptopurine riboside, thioinosine, methotrexate, pemetrexed, enocitabine, cytarabine, cytarabine ocfosphate, ancitabine hydrochloride, 5-FU based agent (e.g., fluorouracil, tegafur, UFT, doxifluridine, carmofur, galocitabine, emitefur, capecitabine, and the like), aminopterin, nelzarabine, leucovorin calcium, Tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine, and DDS formulations thereof, and the like.

In embodiments, the chemotherapeutic agent is an anti-cancer antibiotic. Examples of anti-cancer antibiotics include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and DDS formulations thereof, and the like.

In embodiments, the chemotherapeutic agent is a plant-derived anti-cancer agent. Examples of plant-derived anti-cancer agents include etoposide, etoposide phosphate, vinblastine sulfate, vincristine sulfate, vindesine sulfate, teniposide, paclitaxel, docetaxel, DJ-927, vinorelbine, irinotecan, topotecan, and DDS formulations thereof, and the like. Chemotherapeutic agents also include sobuzoxane.

In various embodiments, the drug is an immunotherapeutic agent. Examples of immunotherapeutic agents include picibanil, krestin, schizophyllan, lentinan, ubenimex, interferon, interleukin, macrophage colony-stimulating factor, granulocyte colony stimulating factor, erythropoietin, lymphotoxin, BCG vaccine, *Corynebacterium parvum*, levamisole, polysaccharide K, procodazole, anti-CTLA4 antibody, PD-1 antibody, and Toll-like Receptors agonist (e.g., TLR7 agonist, TLR8 agonist, TLR9 agonist, and the like). In various embodiments, the drug is a cell growth factor. A cell growth factor may be any substance as long as the substance promotes cell growth. Commonly, it includes a factor that is a peptide having a molecular weight of 20,000 or less and exhibits an effect at a low concentration by binding with the receptor. Specifically, epidermal growth factor (EGF) or substances having substantially the same activity (e.g., TGFalpha and the like), insulin or substances having substantially the same activity (e.g., insulin, insulin-like growth factor (IGF)-1, IGF-2, and the like), fibroblast growth factor (FGF) or substances having substantially the same activity (e.g., acidic FGF, basic FGF, keratinocyte growth factor (KGK), FGF-10, and the like), and other cell growth factors (e.g., colony stimulating factor (CSF), erythropoietin (EPO), interleukin-2 (IF-2), nerve growth factor (NGF), platelet-derived growth factor (PDGF), transforming growth factor beta (TGF-beta), hepatocyte growth factor (HGF), vascular endothelial growth factor (VEGF), heregulin, angiopoietin, and the like).

In various embodiments, the subject being treated has been previously treated with the treatment to which the ovarian cancer is resistant. In embodiments, the ovarian cancer is refractory with regard to the treatment.

In embodiments, the subject being treated has been previously treated e.g., with a first-line therapy. In some embodiments, the subject's cancer is resistant to the first-line therapy (e.g., surgical resection, platinum based therapy, etc.). In some embodiments, the first-line therapy is a platinum-based therapy. In certain embodiments, the platinum-based therapy includes administering cisplatin to the subject. In various embodiments, the cancer is refractory with regard to the first-line therapy.

In various embodiments, effective amounts of a compound of structure (I), or a pharmaceutically acceptable salt thereof (e.g., a tartrate salt), can decrease the number of tumor cells, decrease the number of metastases, decrease tumor volume, induce apoptosis of cancer cells, induce cancer cell death, induce radio-sensitivity in cancer cells, inhibit angiogenesis near cancer cells, inhibit cancer cell proliferation, inhibit tumor growth, prevent metastasis, reduce the number of metastases, increase life expectancy, prolong a subject's life, reduce cancer-associated pain, and/or reduce relapse or re-occurrence of the cancer following treatment.

In embodiments, effective amounts of a compound of structure (I), or a pharmaceutically acceptable salt thereof (e.g., a tartrate salt), can slow or reverse weight gain, reduce swelling of the abdomen, reduce difficulty breathing, eliminate the need or decrease the frequency to reduce ascites volume by paracentesis or a similar procedure, increase appetite, decrease abdominal pain, decrease bloating, decrease nausea, decrease vomiting, and/or decrease heartburn following treatment.

In some embodiments, administration of a compound of structure (I), or a pharmaceutically acceptable salt thereof (e.g., a tartrate salt), to a subject results in complete remission. In some embodiments, administration of a compound of structure (I), or a pharmaceutically acceptable salt thereof (e.g., a tartrate salt), to a subject results in minimal residual disease (MRD; deposits of residual tumor <1 cm). In some embodiments, administration of a compound of structure (I), or a pharmaceutically acceptable salt thereof (e.g., a tartrate salt), to a subject results in no residual disease (NRD; no detectable residual deposits). In some embodiments, administration of a compound of structure (I), or a pharmaceutically acceptable salt thereof (e.g., a tartrate salt), to a subject results in gross residual disease (GRD; deposits of residual tumor >1 cm), but with a statistically significant decrease in overall tumor volume as compared to earlier measurements. In particular embodiments, administration of a compound of structure (I), or a pharmaceutically acceptable salt thereof (e.g., a tartrate salt), to a plurality of subjects results in an increase in one or more of progression free survival, complete remission rate, event free survival, and/or overall survival relative to an untreated plurality of subjects. In embodiments, administration of a compound of structure (I), or a pharmaceutically acceptable salt thereof (e.g., a tartrate salt), to a subject results in reversing epithelial-to-mesenchymal transition (EMT).

The compound of structure (I) may be in free-acid or free-base form, or in a pharmaceutically acceptable salt form. In embodiments of the methods of treatment disclosed herein comprise administering a tartrate salt (e.g., di-tartrate salt) of the compound of structure (I). In some embodiments, the tartrate salt is a di-tartrate salt. In some embodiments, the compound of structure (I) is present as a prodrug.

5. Additional Methods for Treating Solid Cancers

Provided herein are methods of treating a solid tumor in a subject, wherein the solid tumor has progressed on immunotherapy. In certain embodiments, the tumor has progressed after achieving a best documented response of at least stable disease (i.e., SD, PR, or CR) following immunotherapy. In certain embodiments, the tumor has progressed after achieving a best documented response of at least stable disease (i.e., SD, PR, or CR) following at least 2 cycles (e.g., 8 weeks) of immunotherapy. In certain embodiments, the method comprises administering to the subject a compound of structure (I) (e.g., tartrate salt, e.g., Form A). In certain embodiments, the method comprises administering to the subject Form A of the compound of structure (I). In certain embodiments, the subject continues treatment with their previous immunotherapy in combination with a compound of structure (I) (e.g., tartrate salt, e.g., Form A).

Also provided herein are methods of treating EGFR+non-small cell lung cancer (NSCLC) in a subject. In certain embodiments, the subject has demonstrated progression following TKI treatment. In certain embodiments, the subject has demonstrated progression following a best documented response of at least stable disease (i.e., SD, PR, or CR) on ≤2 lines of oral TKIs. In certain embodiments, the subject continues treatment with their TKI regimen in combination with a compound of structure (I) (e.g., tartrate salt, e.g., Form A). In certain embodiments, the method comprises administering to the subject a compound of structure (I) (e.g., tartrate salt). In certain embodiments, the method comprises administering to the subject Form A of the compound of structure (I).

Also provided herein are methods of treating BRAF-, KRAS-, or NR AS-mutated colorectal carcinoma (CRC) in a subject. In certain embodiments, the subject is a patient for whom there is no standard therapy remaining. In certain embodiments, the method comprises administering to the subject a compound of structure (I) (e.g., tartrate salt). In certain embodiments, the method comprises administering to the subject Form A of the compound of structure (I).

Also provided herein are methods of treating persistent and/or recurrent ovarian cancer in a subject. In certain embodiments, the cancer is platinum refractory and/or platinum resistant. In certain embodiments, the cancer is platinum refractory and/or platinum resistant and the subject has been administered any number of lines of prior therapy. In certain embodiments, the method comprises administering to the subject a compound of structure (I) (e.g., tartrate salt). In certain embodiments, the method comprises administering to the subject Form A of the compound of structure (I). Also provided herein are methods of treating BRAF-mutated melanoma in a subject.

In certain embodiments, the subject has progressed on immunotherapy. In certain embodiments, the subject has progressed on a combination BRAF/MEK inhibitor. In certain embodiments, the method comprises administering to the subject a compound of structure (I) (e.g., tartrate salt). In certain embodiments, the method comprises administering to the subject Form A of the compound of structure (I).

The following embodiments are with respect to any of the methods of treatment provided herein. In certain embodiments, the compound of structure (I) (e.g., tartrate salt, e.g., Form A) is administered orally. In certain embodiments, the compound of structure (I) (e.g., tartrate salt, e.g., Form A) is administered orally once daily. In certain embodiments, the compound of structure (I) (e.g., tartrate salt, e.g., Form A) is administered orally once daily for 21 days, followed by 7 drug free days (i.e., 28 day cycle). In certain embodiments, the 28-day cycle is repeated. In certain embodiments, the dose of the compound of structure (I) (e.g., tartrate salt, e.g., Form A) is recalculated at the beginning of each new treatment cycle to reflect changes in the body surface area (BSA) that may have occurred during the previous cycle. In certain embodiments, doses are only adjusted if there is a ≥10% increase or decrease in body weight compared to baseline. In certain embodiments, dosing is repeated every cycle in the absence of disease progression or unacceptable toxicity. In certain embodiments, the compound of structure (I) (e.g., tartrate salt, e.g., Form A) is taken in the morning after an overnight fast with up to 200 mL or 7 fluid ounces of water at least 1 hour before ingesting any food or other medications.

In certain embodiments, the compound of structure (I) (e.g., tartrate salt, e.g., Form A) is administered daily at a dose from 1 $mg/m^2$ to 65 $mg/m^2$, inclusive. In certain embodiments, the compound of structure (I) (e.g., tartrate salt, e.g., Form A) is administered daily at a dose of about 1.5 $mg/m^2$, 3.0 $mg/m^2$, 6.0 $mg/m^2$, 9.0 $mg/m^2$, 12.0 $mg/m^2$, 16.0 $mg/m^2$, 21.0 $mg/m^2$, 28.0 $mg/m^2$, 37.0 $mg/m^2$, 49.0 $mg/m^2$, or 65.0 $mg/m^2$. In certain embodiments, the compound of structure (I) (e.g., tartrate salt, e.g., Form A) is administered daily at a dose greater than 65.0 $mg/m^2$.

In certain embodiments, compound of structure (I) (e.g., tartrate salt, e.g., Form A) is administered at a starting dose of 1.5 $mg/m^2$. In certain embodiments, compound of structure (I) (e.g., tartrate salt, e.g., Form A) is administered at a starting dose of 1.5 $mg/m^2$ for 21 out of 28 days in a 28 day dose cycle. In certain embodiments, the dose of compound of structure (I) (e.g., tartrate salt, e.g., Form A) is increased between dose cycles. In certain embodiments, the dose of compound of structure (I) (e.g., tartrate salt, e.g., Form A) is increased 30-100% between cycles.

In certain embodiments, compound of structure (I) (e.g., tartrate salt, e.g., Form A) is administered at a starting dose of 1.5 $mg/m^2$ for 21 out of 28 days in 3-subject cohorts using a standard 3+3 design. For instance, in certain embodiments, once the first subject in each cohort has completed 14 days of dosing with no DLTs, the second and third subjects are enrolled simultaneously at the same dose. In certain embodiments, once the last subject enrolled has completed Day 28 without observation of a DLT and the next higher the compound of structure (I) dose level has not yet been studied, the dose is increased following a modified Fibonacci dose escalation scheme in a new 3-subject cohort according to the dose levels provided in Table 20.

In certain embodiments, If a DLT is observed in 1 of 3 subjects at a given dose level, up to 3 additional subjects are enrolled and treated at that dose level. In certain embodiments, when up to 3 additional subjects are added to a given dose level, if only 1 out of those 6 subjects experiences a DLT, the dose is increased to the next dose level. In certain embodiments, if ≥2 out of 3-6 subjects at a dose level experience DLTs, the dose is decreased to the previous (lower) dose level and 3 additional subjects will be enrolled at that dose level. In certain embodiments, if 0 or 1 subject in any of the 6 subjects experience a DLT, but the next higher dose level has already been studied, then the current dose is declared the MTD. In certain embodiments, the MTD is defined as the dose at which ≤1 of 6 subjects experience a DLT during Cycle 1 with the next higher dose having at least 2 of 3-6 subjects experiencing a DLT during Cycle 1.

In certain embodiments, compound of structure (I) (e.g., tartrate salt, e.g., Form A) is administered as a flat dose (i.e., instead of according to BSA). In certain embodiments, the flat dose is the MTD.

In certain embodiments, the dosage of the compound of structure (I) or pharmaceutically acceptable salt thereof (e.g., a tartrate salt, e.g., Form A) is about 1-37 $mg/m^2$ (e.g., 1-25 $mg/m^2$) or about 1-75 mg (e.g., 1-50 mg) daily.

In certain embodiments, the compound of structure (I) (e.g., tartrate salt, e.g., Form A) is supplied in oral form as a powder in hard gelatin capsules. In certain embodiments, the compound of structure (I) (e.g., tartrate salt, e.g., Form A) capsules are formulated in 1-mg, 4-mg, 16-mg, 25-mg, or 100 mg strengths. In certain embodiments, the compound of structure (I) (e.g., tartrate salt, e.g., Form A) are packaged into round high-density polyethylene bottles with polyester coils as headspace fillers. In certain embodiments, the bottles are then heat-sealed, fitted with child-resistant caps, and placed in low-density polyethylene bags as secondary packaging.

6. Additional Methods for Treating CLL/SLL

Provided herein are methods of treating chronic lymphocytic leukemia (CLL) and/or small lymphocytic lymphoma (SLL) in a subject. In certain embodiments, the subject is intolerant to, or has shown progressive disease on B-cell receptor antagonists and/or BCL-2 antagonists. In certain embodiments, the subject is intolerant to, or has shown progressive disease on other investigational treatments for CLL/SLL. In certain embodiments, the subject has shown progression of disease on ibrutinib. In certain embodiments, the method comprises administering to the subject a compound of structure (I) (e.g., tartrate salt, e.g., Form A). In certain embodiments, the method comprises administering to the subject Form A of the compound of structure (I).

The following embodiments are with respect to any of the methods of treatment provided herein. In certain embodiments, the compound of structure (I) (e.g., tartrate salt, e.g., Form A) is administered orally. In certain embodiments, the compound of structure (I) (e.g., tartrate salt, e.g., Form A) is administered orally once daily. In certain embodiments, the compound of structure (I) (e.g., tartrate salt, e.g., Form A) is administered orally once daily for a 28 day cycle. In certain embodiments, dosing is repeated for one or more 28-day cycles (e.g., in absence of disease progression or unacceptable toxicity). In certain embodiments, the compound of structure (I) (e.g., tartrate salt, e.g., Form A) is taken in the morning after an overnight fast with up to 200 mL or 7 fluid ounces of water at least 1 hour before ingesting any food or other medications. In certain embodiments, ibrutinib is administered orally once daily in combination with the compound of structure (I) (e.g., tartrate salt, e.g., Form A).

In certain embodiments, the compound of structure (I) (e.g., tartrate salt, e.g., Form A) is administered daily at a flat dose of 20 mg to 100 mg, inclusive. In certain embodiments, the compound of structure (I) (e.g., tartrate salt, e.g., Form A) is administered daily at a flat dose of about 20, 25, 33, 45, 50, 58, 75, or 100 mg. In certain embodiments, the compound of structure (I) (e.g., tartrate salt, e.g., Form A) is administered daily at a flat dose of greater than 100 mg In certain embodiments, the compound of structure (I) (e.g., tartrate salt, e.g., Form A) is administered as a monotherapy. In certain embodiments, the compound of structure (I) (e.g., tartrate salt, e.g., Form A) is administered at a 25 mg flat dose as a monotherapy. In certain embodiments, the compound of structure (I) (e.g., tartrate salt, e.g., Form A) is administered orally once daily at a 25 mg flat dose for 28 days. In certain embodiments, the 28-day cycle is repeated one or more times. In certain embodiments, the subject continues to receive the compound of structure (I) (e.g., tartrate salt, e.g., Form A) in 28-day cycles at the same dose given until they experience unacceptable toxicity or unequivocal disease progression. In certain embodiments, the dose of the compound of structure (I) (e.g., tartrate salt, e.g., Form A) is increased between cycles. In certain embodiments, the dose is increased by about 25-36% between cycles. In certain embodiments, the dose is increased based on the dose escalation levels in Table 22.

In certain embodiments, the compound of structure (I) (e.g., tartrate salt, e.g., Form A) is administered in combination with ibrutinib. In certain embodiments, the compound of structure (I) (e.g., tartrate salt, e.g., Form A) is administered daily at a 20-mg flat dose in combination with ibrutinib. In certain embodiments, the compound of structure (I) (e.g., tartrate salt, e.g., Form A) is administered orally once daily at a 20-mg flat dose for 28 days in combination with ibrutinib. In certain embodiments, ibrutinib is administered at the same dose that they were receiving immediately prior to beginning treatment with the compound of structure (I) (e.g., tartrate salt, e.g., Form A). In certain embodiments, a subject continues with the combination of ibrutinib and the compound of structure (I) (e.g., tartrate salt, e.g., Form A) for at least 3 months after the start of treatment with the compound of structure (I) (e.g., tartrate salt, e.g., Form A). In certain embodiments, ater that time, subjects either continue with combination therapy or discontinue ibrutinib and continue with the compound of structure (I) (e.g., tartrate salt, e.g., Form A) monotherapy. In certain embodiments, ibrutinib administration is stopped and reinitiated. In certain embodiments, subject continues to receive the compound of structure (I) (e.g., tartrate salt, e.g., Form A) in 28-day cycles at the same dose until they experience unacceptable toxicity or unequivocal disease progression. In certain embodiments, the 28-day cycle is repeated one or more times. In certain embodiments, the subject continues to receive the compound of structure (I) (e.g., tartrate salt, e.g., Form A) in 28-day cycles at the same dose given until they experience unacceptable toxicity or unequivocal disease progression.

In certain embodiments, the dose of the compound of structure (I) (e.g., tartrate salt, e.g., Form A) is increased between 28 day cycles. In certain embodiments, the dose is increased by about 25-36% between cycles. In certain embodiments, the dose is increased based on the dose escalation levels in Table 22.

In certain embodiments, as described above, the dose of the compound of structure (I) (e.g., tartrate salt, e.g., Form A) is increased between cycles. In certain embodiments, dose escalation of the compound of structure (I) (e.g., tartrate salt, e.g., Form A) follows a standard 3+3 design with sequential cohorts of 3 subjects treated with incrementally higher doses of the compound of structure (I) (e.g., tartrate salt, e.g., Form A) until a DLT is observed and the MTD is established. In certain embodiments, once the first subject at a dose level is enrolled, the second and third subjects are enrolled after 3 weeks if the initial subject has not experienced a DLT or any unacceptable toxicity.

In certain embodiments, if 1 of 3 subjects in a cohort experiences a DLT, up to 3 additional subjects are treated at that dose level. In certain embodiments, if no additional DLTs are observed in the expanded 3- to 6 subject cohort within 28 days after the last subject was first dosed, the dose is escalated in a new cohort of 3 subjects. In certain embodiments, if 2 or more of 3 to 6 subjects at a given dose level experience a DLT during the first cycle, then the MTD is exceeded and up to a total of 6 subjects will be treated at the previous lower dose level. In certain embodiments, if 0 or 1 of 6 subjects experiences a DLT at this previous lower dose level, this dose is declared the MTD. The MTD is defined as the dose at which ≤1 of 6 subjects experience a DLT during Cycle 1 with the next higher dose having at least 2 of 3 to 6 subjects experiencing a DLT during Cycle 1. In certain embodiments, once the MTD or preliminary recommended phase 2 dose (RP2D) is identified, an expansion cohort of up to six subjects is enrolled in each subject group. In certain embodiments, the MTD is the RP2D.

In certain embodiments, the compound of structure (I) (e.g., tartrate salt, e.g., Form A) is administered at the RP2D orally once daily for 28 days. In certain embodiments, dosing with the compound of structure (I) (e.g., tartrate salt, e.g., Form A) may continue until a subject experiences unacceptable toxicity or unequivocal disease progression.

In certain embodiments, the compound of structure (I) (e.g., tartrate salt, e.g., Form A) is administered at the RP2D orally once daily for 28 days in combination with ibrutinib. In certain embodiments, the subject is administered ibrutinib at the same dose that they were receiving immediately prior to starting treatment with the compound of structure (I) (e.g., tartrate salt, e.g., Form A).

In certain embodiments, the dosage of the compound of structure (I) or pharmaceutically acceptable salt thereof (e.g., a tartrate salt, e.g., Form A) is about 1-37 mg/m$^2$ (e.g., 1-25 mg/m$^2$) or about 1-75 mg (e.g., 1-50 mg) daily. In certain embodiments, the dosage of the compound of structure (I) or pharmaceutically acceptable salt thereof (e.g., a tartrate salt, e.g., Form A) is about 1-37 mg/m$^2$ (e.g., 1-25 mg/m$^2$) or about 1-75 mg (e.g., 1-50 mg) daily in combination with ibrutinib.

In certain embodiments, the compound of structure (I) (e.g., tartrate salt, e.g., Form A) is supplied in oral form as a powder in hard gelatin capsules. In certain embodiments, the compound of structure (I) (e.g., tartrate salt, e.g., Form A) capsules are formulated in 1-mg, 4-mg, 16-mg, 25-mg, and 100 mg strengths. In certain embodiments, the compound of structure (I) (e.g., tartrate salt, e.g., Form A) are packaged into round high-density polyethylene bottles with polyester coils as headspace fillers. In certain embodiments, the bottles are then heat-sealed, fitted with child-resistant caps, and placed in low-density polyethylene bags as secondary packaging.

7. Additional therapeutic uses of the compound of structure (I) (e.g., freebase or a pharmaceutically acceptable salt thereof, such as tartrate salt, e.g., Form A) include treatment of melanoma (e.g., BRAF– melanoma and/or metastatic melanoma), either alone or in combination with one or more checkpoint inhibitors, for example, checkpoint inhibitors of PD-1, PD-L1 or CTLA-4). Any of such checkpoint inhibitors can be co-used with the compound of structure (I) in melanoma treatment. In some examples, the checkpoint inhibitor can be a PD-1 inhibitor such as pembrolizumab. Any of the treatment conditions (e.g., dosage, dosing schedule, administration route, etc.) as disclosed herein can be applied in melanoma treatment as disclosed herein.

8. Additional therapeutic uses of the compound of structure (I) (e.g., freebase or a pharmaceutically acceptable salt thereof, such as tartrate salt, e.g., Form A) also include treatment of brain tumor (e.g., GBM), either alone or in combination with one or more checkpoint inhibitors, for example, checkpoint inhibitors of PD-1, PD-L1 or CTLA-4). Any of such checkpoint inhibitors can be co-used with the compound of structure (I) in melanoma treatment. In some examples, the checkpoint inhibitor can be a PD-1 inhibitor such as pembrolizumab. Any of the treatment conditions (e.g., dosage, dosing schedule, administration route, etc.) as disclosed herein can be applied in melanoma treatment as disclosed herein.

E. Methods of Synthesis

1. Synthesis of Tartrate Salts of the Compound of Structure (I)

It will be appreciated by those skilled in the art that the processes and reactions for preparing the compounds described herein (including the salts of the compound of structure (I)) may be modified in accordance with standard techniques to include alternative reagents and/or reaction conditions. For example, a reaction intermediate having a halo substituent (i.e., F, Cl, Br, I) may alternatively employ a sulfonate. Exemplary sulfonates are also referred to as "pseudohalides" that include, but are not limited to p-toluenesulfonate (OTs), methanesulfonate (OMs) or perfluoroalkylsulfonates (e.g., triflate).

Reducing agents include lithium aluminum hydride, nascent (atomic) hydrogen, hydrogen without or with a suitable catalyst, e.g., a Lindlar catalyst, sodium or zinc amalgam (Na(Hg) or Zn(Hg)), sodium-lead alloy (Na+Pb), diborane, sodium borohydride, borane tetrahydrofuran, iron-based reducing agents (e.g., iron(II) sulfate), tin-based reducing agents (e.g., tin(II) chloride), sulfur dioxide, sulfite compounds, dithionates (e.g., $Na_2S_2O_6$), thiosulfates (e.g., $Na_2S_2O_3$), hydrazine, diisobutylaluminum hydride, oxalic acid, formic acid, ascorbic acid, reducing sugars, phosphites, hypophosphites, dithiothreitol (DTT), tris-2-carboxyethylphosphine hydrochloride (TCEP).

Accordingly, one embodiment (hereinafter "Step A") provides a method for preparing a compound of structure (I):

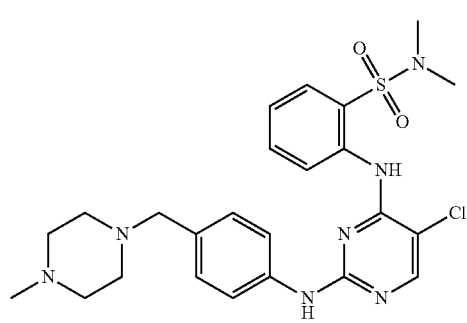

or a pharmaceutically acceptable salt thereof (e.g., a tartrate salt thereof), the method comprising reacting a compound having the following structure:

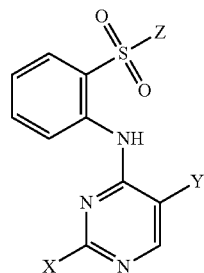

or a pharmaceutically acceptable salt thereof, wherein
X is a leaving group;
Y is halo;
Z is halo or $-NR^1R^2$; and
$R^1$ and $R^2$ are, each independently, hydrogen or $C_1$-$C_8$ alkyl,
with a compound having the following structure:

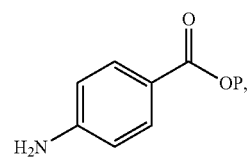

wherein P is H or a protecting group, to obtain a compound having the following structure:

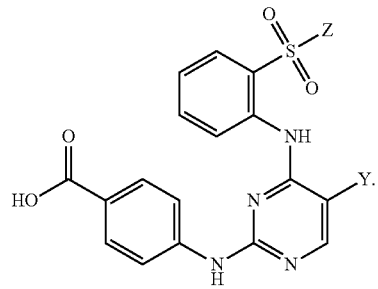

In some embodiments, X is halo or sulfonate. In some specific embodiments, X is fluoro, chloro, bromo, or iodo. In some more specific embodiments, X is chloro.

In some of the foregoing embodiments, P is H. In certain embodiments, P forms a methyl ester, a benzyl ester, a tert-butyl ester, a silyl ester, an ortho-ester or an oxazoline.

Another embodiment (hereinafter "Step B") provides a method for preparing a compound of structure (I):

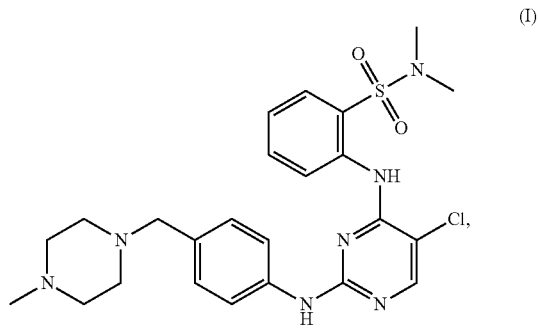

or a pharmaceutically acceptable salt thereof (e.g., a tartrate salt thereof), the method comprising reacting a compound having the following structure:

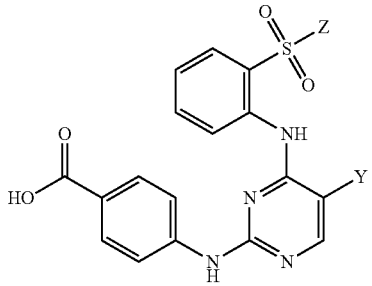

or a pharmaceutically acceptable salt thereof, wherein:

Y is halo;

Z is halo or —NR$^1$(R$^2$); and

R$^1$ and R$^2$ are, each independently, hydrogen or $C_1$-$C_8$ alkyl, with a reducing agent to obtain a compound having the following structure:

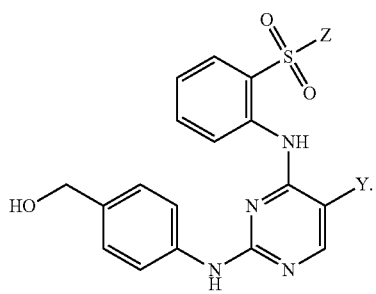

In some embodiments, the reducing agent is lithium aluminum hydride, diborane, sodium borohydride, borane, or combinations thereof. In some more specific embodiments, the reducing agent is borane.

Yet another embodiment (hereinafter "Step C") provides a method for preparing a compound of structure (I):

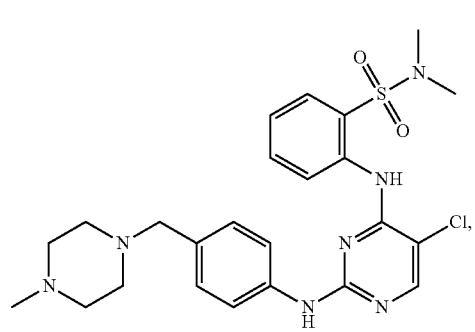

(I)

or a pharmaceutically acceptable salt thereof (e.g., a tartrate salt thereof), the method comprising reacting a compound having the following structure:

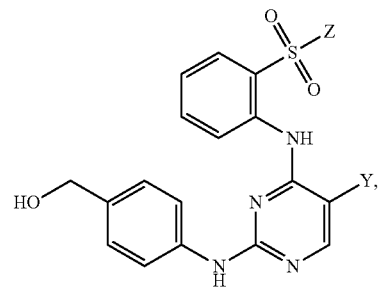

or a pharmaceutically acceptable salt thereof, wherein:

Y is halo;

Z is halo or —NR$^1$(R$^2$); and

R$^1$ and R$^2$ are, each independently, hydrogen or $C_1$-$C_8$ alkyl, with an activating agent to obtain a compound having the following structure:

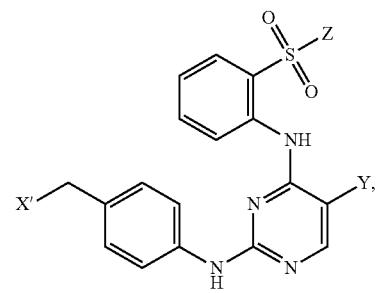

or a pharmaceutically acceptable salt thereof, wherein:

X' is a leaving group.

In some embodiments, the activating agent comprises a sulfonyl chloride functional group. For example, in certain embodiments, the activating compound is thionyl chloride.

Still another embodiment (hereinafter "Step D") provides a method for preparing a compound of structure (I):

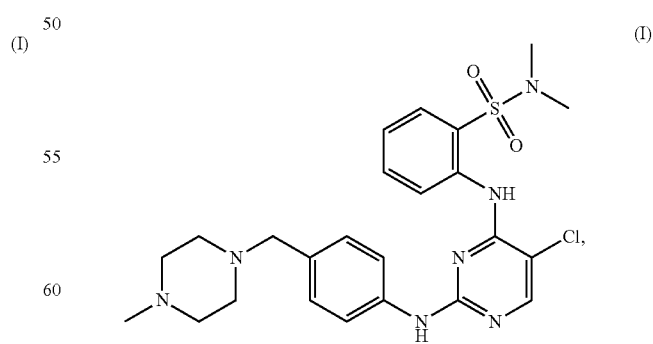

(I)

or a pharmaceutically acceptable salt thereof (e.g., a tartrate salt thereof), the method comprising reacting a compound having the following structure:

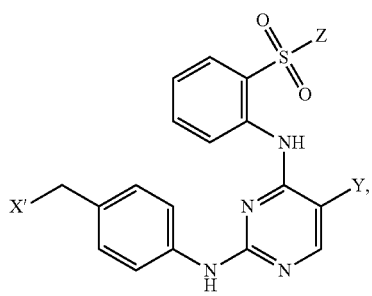

or a pharmaceutically acceptable salt thereof, wherein:
X' is a leaving group;
Y is halo;
Z is halo or —NR$^1$(R$^2$); and
R$^1$ and R$^2$ are, each independently, hydrogen or C$_1$-C$_8$ alkyl,
with N-methylpiperazine, or a salt thereof to obtain a compound having the following structure:

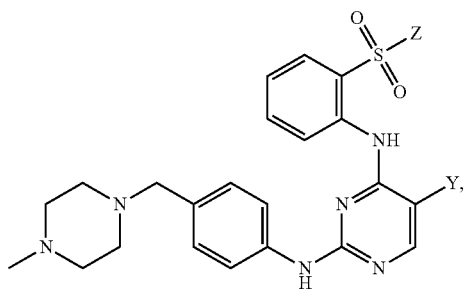

or a pharmaceutically acceptable salt thereof.

In some of the foregoing embodiments, X' is halo or sulfonate. In some embodiments, X' is fluoro, chloro, bromo, or iodo. In certain embodiments, X' is chloro.

In some embodiments, Y is fluoro, chloro, bromo, or iodo. For example, in some specific embodiments, Y is chloro.

In some particular embodiments, Z is —NR$^1$R$^2$). In some more specific embodiments, R$^1$ is C$_1$-C$_8$ alkyl. In other related embodiments, R$^2$ is C$_1$-C$_8$ alkyl. In more specific embodiments, R$^1$ is methyl, ethyl, propyl or isopropyl. For example, in certain embodiments, R$^1$ is methyl. Similarly, in some embodiments, R$^2$ is methyl, ethyl, propyl or isopropyl. For example, in certain embodiments, R$^2$ is methyl.

Another embodiment (hereinafter "Step E") provides a method for preparing a tartrate salt of a compound of structure (I):

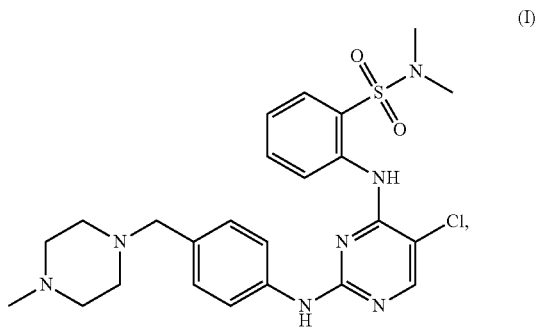

(I)

the method comprising admixing the compound of structure (I) with tartaric acid.

In some embodiments, the method comprises adding tartaric acid to the compound of structure (I). For example, in certain embodiments, the method comprises adding L-(+)-tartaric acid to the compound of structure (I). In certain embodiments, the tartaric acid is added to the compound of structure (I) in a ratio of about 1:1 to about 2:1, e.g., 1:1 or 2:1. In certain embodiments, the tartrate salt is characterized as having a stoichiometry as described above.

Certain embodiments provide a method for preparing a compound of structure (I) or a pharmaceutically acceptable salt thereof (e.g., a tartrate salt thereof) comprising Steps A and B, Steps A, B, and C, Steps A, B, C, and D, Steps A, B, C, D and E, Steps B and C, Steps B, C and D, Steps B, C, D and E, Steps C and D, Steps C, D and E, or Steps D and E. In certain embodiments, the method comprises Steps A and C, Steps A, C, and D, Steps A, C, D and E, Steps A, B, and D, Steps A, B, D and E, Steps A, B, C and E, Steps B and D, Steps B, D and E, Steps A and C, Steps A and D, Steps A and E, Steps B and E or Steps C and E.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include f-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds disclosed herein are included within the scope of embodiments of the invention.

The following General Reaction Scheme illustrates an exemplary method of forming a tartrate salt of a compound of structure (I):

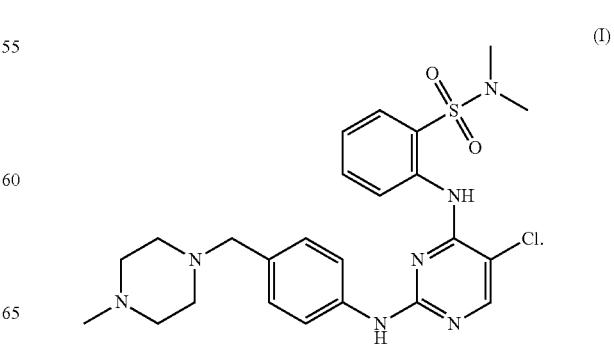

(I)

It is understood that one skilled in the art may be able to make these salts by similar methods or by combining other methods known to one skilled in the art. It is also understood that one skilled in the art would be able to make, in a similar manner as described below, other salts of a compound of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Compounds and salts were analyzed using techniques known in the art, for example, by x-ray powder diffraction (XRPD), dynamic vapor sorption (DVS), thermal gravimetric analysis (TGA), differential scanning calorimetry (DSC), mass spectrometry and/or $^1$H NMR. Synthetic procedures are described in more detail below.

2. Syntheses of Crystalline Forms

Embodiments of the tartaric acid salt of a compound of structure (I) and polymorphs thereof (e.g., Form A) can be prepared according to the General Reaction Scheme below, wherein each occurrence of X is a halide or pseudohalide (e.g., Inflate, nonaflate, mesylate, tosylate, etc.). Certain intermediates useful for preparation of a tartaric acid salt of the compound of structure (I) can be prepared according to methods described in WO 2012/135800, which is incorporated herein by reference in its entirety. As shown in the General Reaction Scheme, compounds of structure A1 can be purchased from commercial sources or prepared according to methods familiar to one of ordinary skill in the art, including those provided in the Examples (see, e.g., Example 6). Reaction of A1 with amine reagent A' (which is prepared according to known methods or purchased from commercial sources) yields A2. Phenyl nitro compound A2 can then be converted to the aniline A3, which is coupled with A4 to yield the pyrimidine containing product A5. The pyrimidine containing A5 is then coupled to aniline compound A6 to afford A7. A7 can then be reduced as necessary (e.g., using BH$_3$.THF) and activated (e.g., using thionyl chloride, Comins' reagent) to yield compound A8 (i.e., structure (I)). The compound A8 is then purified and converted to the desired polymorph/salt by adding the appropriate acid (e.g., tartaric) under the appropriate conditions (e.g., heating cooling following two re-slurry purification steps).

General Reaction Scheme

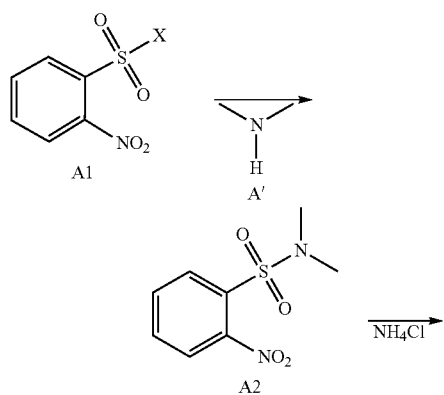

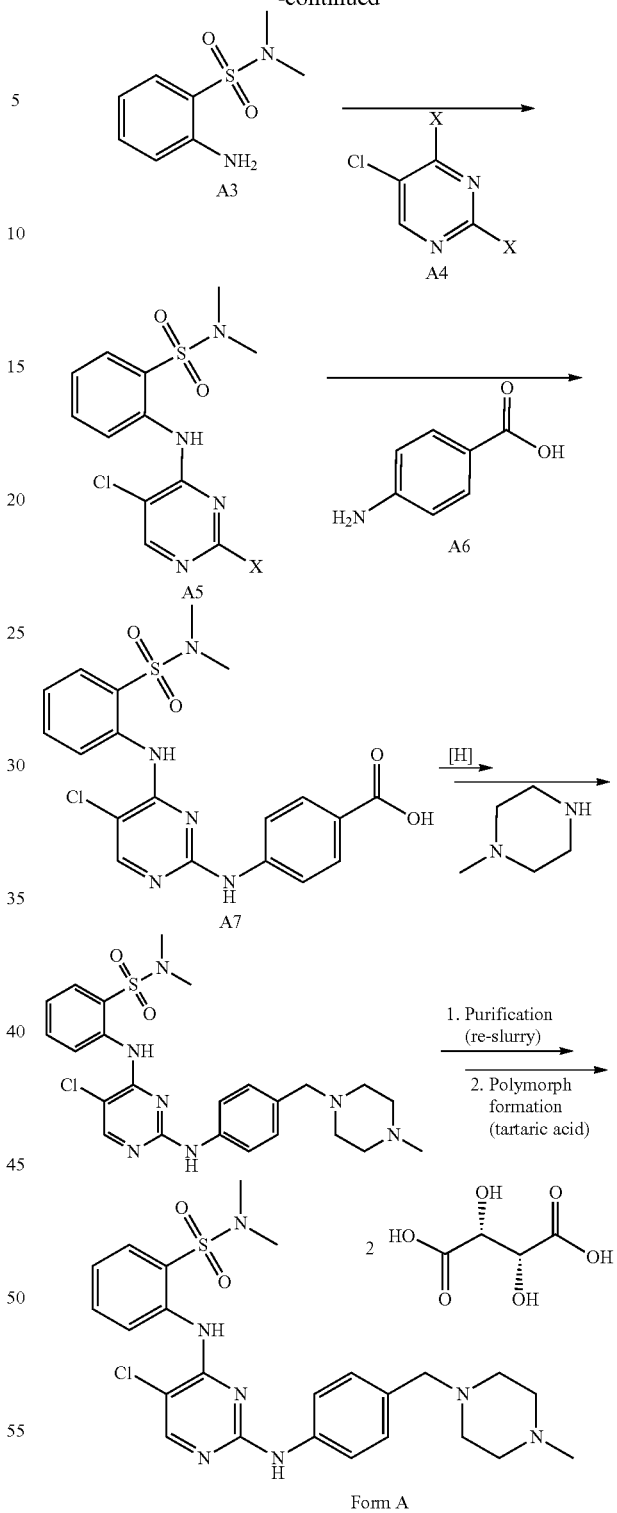

Form A

It should be noted that the General Reaction Scheme only depicts an exemplary method for preparation of a tartaric acid salt of a compound of structure (I) and other methods are available, including methods for preparation of a tartaric acid salt of compounds of structure (I) using different reagents, and/or different intermediates etc.

Other specific embodiments provide methods for preparing the polymorphs from a compound of structure (I). For example, one embodiment provides a method for preparing a polymorph, the method comprising:

a) purifying a free base of a compound having the following structure (I):

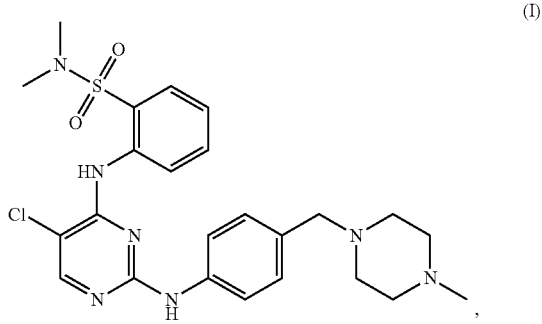 [SMILES: CN1CCN(Cc2ccc(Nc3ncc(Cl)c(Nc4ccccc4S(=O)(=O)N(C)C)n3)cc2)CC1]

thereby isolating a purified free base comprising less than about 30 mol % triethylamine;

b) dissolving the purified free base to form a recrystallization solution comprising the purified free base; and c) treating the recrystallization solution with tartaric acid, thereby forming the polymorph.

In some embodiments, the purified free base comprises less than about 25 mol % triethylamine, less than about 20 mol % triethylamine, less than about 15 mol % triethylamine, less than about 10 mol % triethylamine, less than about 5 mol % triethylamine, less than about 4 mol % triethylamine, less than about 3 mol % triethylamine, less than about 2 mol % triethylamine, less than about 1 mol % triethylamine, or less than about 0.5 mol % triethylamine.

In some specific embodiments, the tartaric acid is L-(+)-tartaric acid.

In some specific embodiments, the tartaric acid is added at a molar ratio ranging from about 2.5:1 to about 0.75:1 relative to the free base. In more specific embodiments, the tartaric acid is added at a molar ratio ranging from about 2.3:1 to about 0.9:1 relative to the free base. In more specific embodiments, the tartaric acid is added at a molar ratio ranging from about 2.2:1 to about 1.5:1 relative to the free base. In certain embodiments, the tartaric acid is added at a molar ratio of about 2:1 relative to the free base.

In some embodiments, the purifying comprises a first purification comprising contacting the free base with a first solvent thereby forming a first suspension. In some embodiments, the first solvent is an organic solvent. In some embodiments, the first solvent is an alcohol (e.g., methanol, ethanol, isopropyl alcohol, n-propyl alcohol, butanol, and the like). In some specific embodiments, the first solvent is ethanol.

In certain embodiments, the first purification further comprises heating the first suspension at a temperature of at least about 50° C. In some more specific embodiments, the first purification further comprises heating the first suspension at a temperature of at least about 65° C. In some more specific embodiments, the first purification further comprises heating the first suspension at a temperature of at least about 45° C., 55° C., 57° C., 60° C., 62° C., 67° C., 70° C., 72° C., or 75° C.

In some embodiments, the first purification further comprises removing the first solvent, thereby forming a solid product.

In some embodiments, the method further comprises a second purification comprising contacting the solid product with a purifying mixture, thereby forming a second suspension. In some embodiments, the purifying mixture comprises a second solvent, a third solvent, and a purifying reagent. In some more specific embodiments, the second solvent is an organic solvent. In some embodiments, the second solvent is an alcohol. In some embodiments, the second solvent is ethanol. In certain embodiments, the third solvent is an organic solvent. In more specific embodiments, the third solvent is chloroform. In certain embodiments, the purifying reagent is activated charcoal.

In some more specific embodiments, the recrystallization solution further comprises a recrystallization solvent. In more specific embodiments, the recrystallization solvent comprises an organic solvent. In some embodiments, the recrystallization solvent comprises an alcohol. In some embodiments, the recrystallization solvent comprises ethanol. In some embodiments, the recrystallization solvent further comprises anisole.

In certain embodiments, the dissolving further comprises heating the recrystallization solution at a temperature of at least about 50° C. In more specific embodiments, the heating is at a temperature of at least about 60° C. In still more specific embodiments, the heating is at a temperature of at least about 65° C. In still more specific embodiments, the heating is at a temperature of at least about 55° C. 57° C. 62° C. 67° C. 70° C. 72° C., or 75° C.

In some embodiments, the method further comprises cooling the recrystallization solution at a temperature below about 25° C. (e.g., below about 20° C. 15° C. 10° C. or 0° C.). In some more specific embodiments, the method further comprises cooling the recrystallization solution at a temperature below about 20° C. In some more specific embodiments, the method further comprises isolating the polymorph as a solid (e.g., a crystalline solid).

In more specific embodiments, the crystalline form has a ratio ranging from about 2.25:1 to about 1.75:1 of tartaric acid to compound of structure (I). In some embodiments, the crystalline form has a ratio ranging from about 2.1:1 to about 1.9:1 of tartaric acid to compound of structure (I). In some embodiments, the polymorph has a ratio of about 2:1 of tartaric acid to compound of structure (I). In certain embodiments, the polymorph is a L-(+)-tartaric acid salt. Certain embodiments provide a polymorph prepared according to the method of any one of the foregoing embodiments.

3. Intermediates

In another aspect, the present disclosure provides a compound of structure (III):

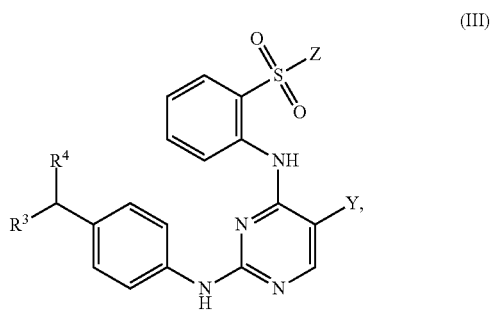

or a pharmaceutically acceptable salt, or tautomer thereof, wherein:

Y is halo;

Z is halo or —NR$^1$(R$^2$);

R¹ and R² are, each independently, hydrogen or $C_1$-$C_8$ alkyl;

R³ is halo or OR$^a$;

R⁴ is hydrogen or oxo; and

R$^a$ is hydrogen or $C_1$-$C_8$ alkyl.

In some embodiments, Y is chloro.

In some embodiments, Z is —NR¹(R²). In some particular embodiments R¹ is $C_1$-$C_8$ alkyl. In some particular embodiments R² is $C_1$-$C_8$ alkyl. In some embodiments, R¹ and R² are $C_1$-$C_8$ alkyl. For example, in some embodiments, R¹ is methyl. In another embodiment, R² is methyl. In yet another embodiment, R¹ and R² are methyl.

In some related embodiments, R³ is OR$^a$. In some embodiments R$^a$ is H. In certain embodiments, R$^a$ is methyl, ethyl or isopropyl. In some embodiments, R³ is halo. In some embodiments, R³ is chloro.

In some embodiments, R⁴ is hydrogen. In some other embodiments, R⁴ is oxo.

In certain specific embodiments, the compound has one of the following structures:

(III-a)

(III-b)

(III-c)

F. Metabolites

1. Compounds

Figure 100:
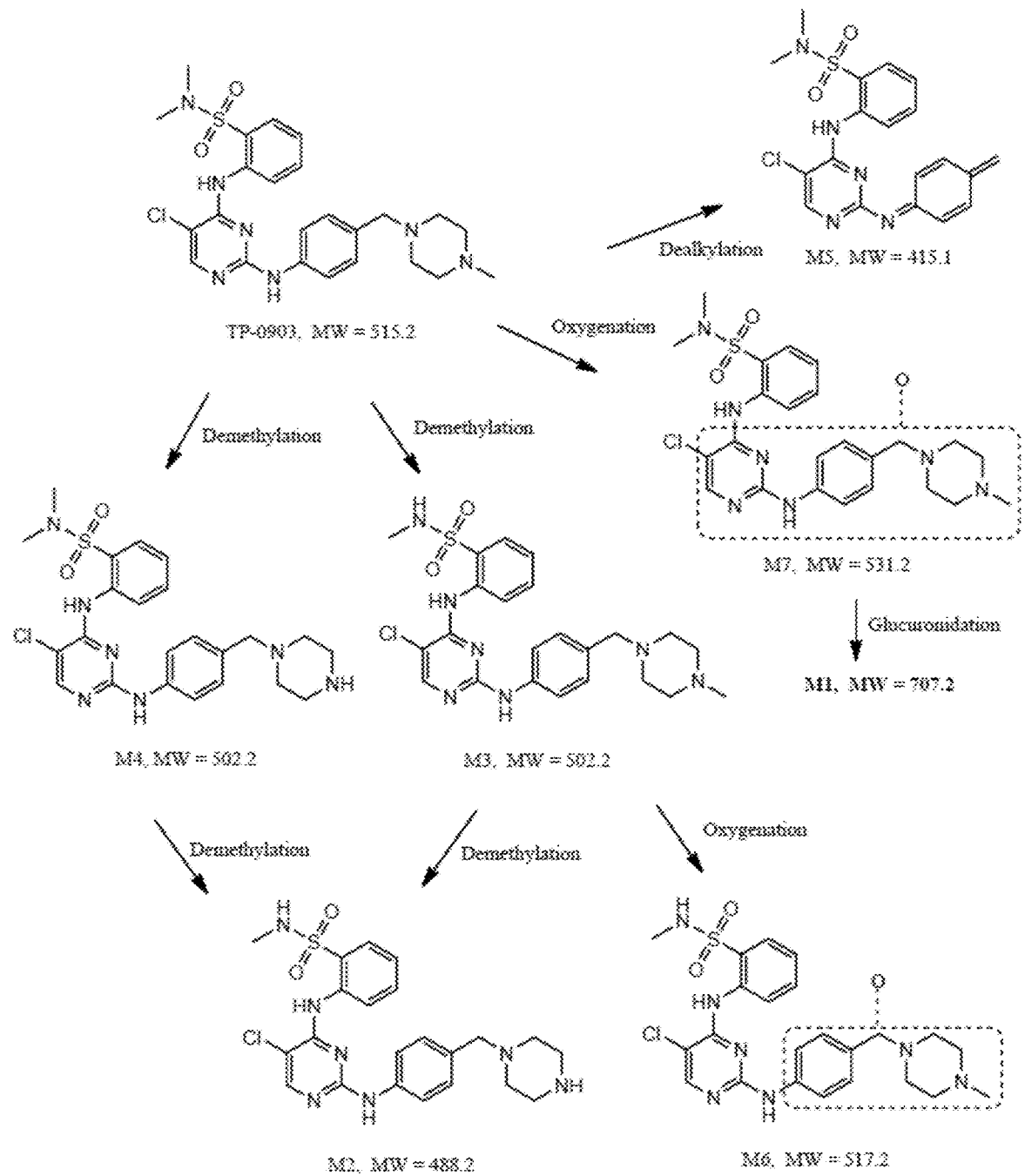
FIG. 100 shows a general scheme outlying how the compound of structure (I) undergoes metabolic conversion into a number of species.

The compound of structure (I) undergoes metabolic conversion into a number of species. See, e.g., FIG. 100. Various embodiments of such compounds are provided as structure (IV), detailed below. Also provided are methods for preparing the same. Some embodiments include compound intermediates useful at least for preparing compounds of structure (IV), all of which are considered to be included as a part of the present disclosure. One embodiment provides a compound having the following structure (IV):

(IV)

or a stereoisomer, pharmaceutically acceptable salt, tautomer or prodrug thereof, wherein:

A represents a 6-membered aromatic ring or a 6-membered carbocyclic ring;

$R^{1a}$ and $R^{1b}$ are each independently H, $C_1$-$C_6$ alkyl, or —OH;

R² and R³ are each independently H, $C_1$-$C_6$ alkyl, or halo;

R⁴ is H, $C_1$-$C_6$ alkyl, or —OH;

$R^{5a}$ and $R^{5b}$ are each independently H, $C_1$-$C_6$ alkyl, or halo;

$R^{6a}$, $R^{6b}$, $R^{6c}$ and $R^{6d}$ are each independently absent or —O⁻;

R⁷ is H, $C_1$-$C_6$ alkyl, —OH or absent;

R⁸ is absent or has the following structure:

R⁹ is absent or alkenyl, provided that at least one of R⁸ or R⁹ is present;

R¹⁰ is H or $C_1$-$C_6$ alkyl; and

===== represents a double or single bond; and all valencies are satisfied;

provided that if $R^{1a}$ and $R^{1b}$ are both methyl, then:

a. at least one of $R^{6a}$, $R^{6b}$, $R^{6c}$, $R^{6d}$ and R⁹ is —O⁻;

b. R⁷ is $C_1$-$C_6$ alkyl, —OH or absent; and/or c. R¹⁰ is H.

In some embodiments, the compound has one of the following structures (V) or (VI):

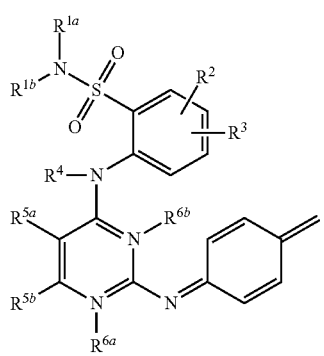

(V)

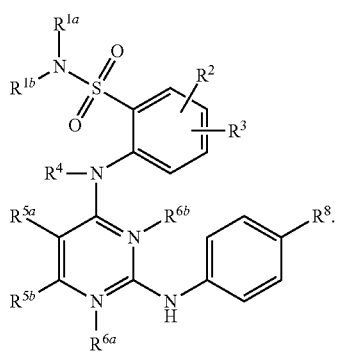

(VI)

In some more specific embodiments, the compound has one of the following structures (IIa) or (IIIa):

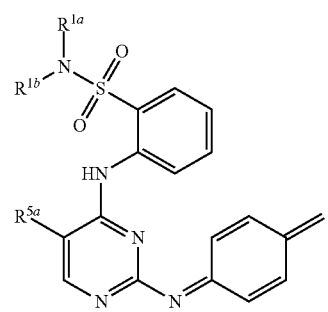

(IIa)

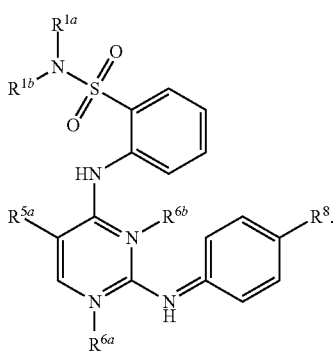

(IIIa)

In more specific embodiments, at least one of $R^{1a}$ or $R^{1b}$ is H. In some embodiments, at least one of $R^{1a}$ or $R^{1b}$ is $C_1$-$C_6$ alkyl. In more specific embodiments, at least one of $R^{1a}$ or $R^{1b}$ is methyl.

In other embodiments, $R^{1a}$ and $R^{1b}$ are both H. In still other embodiments, $R^{1a}$ and $R^{1b}$ are both $C_1$-$C_6$ alkyl, for example, $R^{1a}$ and $R^{1b}$ are both methyl.

In certain embodiments, $R^2$ is H. In related embodiments, $R^3$ is H. In other embodiments, $R^4$ is H. In another embodiment, $R^4$ is absent.

In some embodiments, $R^{5a}$ is halo, for example, F, Cl, Br or I. In some embodiments, $R^{5a}$ is Cl. In certain related embodiments, $R^{5b}$ is H.

In other specific embodiments, at least one of $R^{6a}$, $R^{6b}$, $R^{6c}$ and $R^{6d}$ are —O⁻, for example, $R^{6a}$ is —O⁻, $R^{6b}$ is —O⁻, $R^{6c}$ is —O⁻ or $R^{6d}$ is —O⁻. In some embodiments, $R^{6d}$ is —O⁻.

In other specific embodiments, $R^7$ is H. In another embodiment, $R^7$ is absent. In certain embodiments, $R^{10}$ is H. In another embodiment, $R^{10}$ is $C_1$-$C_6$ alkyl, for example, $R^{10}$ is methyl, ethyl or propyl. In some embodiments, $R^{10}$ is methyl.

In some specific embodiments, $R^8$ has one of the following structures:

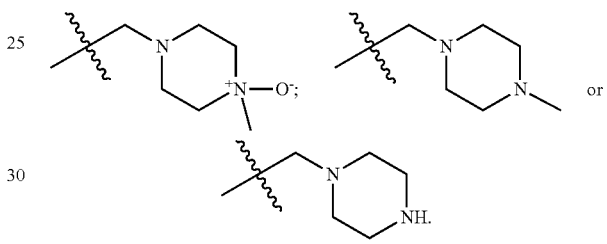

In one particular embodiment, $R^8$ has the following structure:

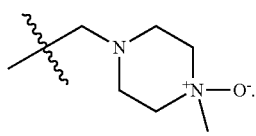

In one particular embodiment, $R^8$ has the following structure:

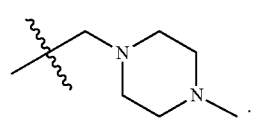 [SMILES: *CN1CCN(C)CC1]

In one particular embodiment, $R^8$ has the following structure:

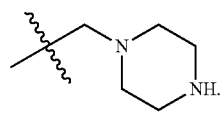

In one embodiment, $R^9$ is absent.

In another embodiment of structure (IV), the compound has one of the following structures (VII) or (VIII):

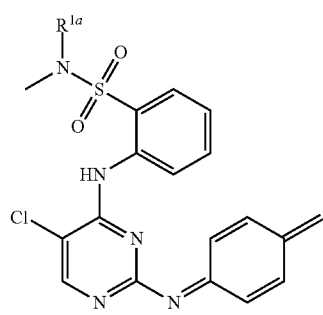 (VII)

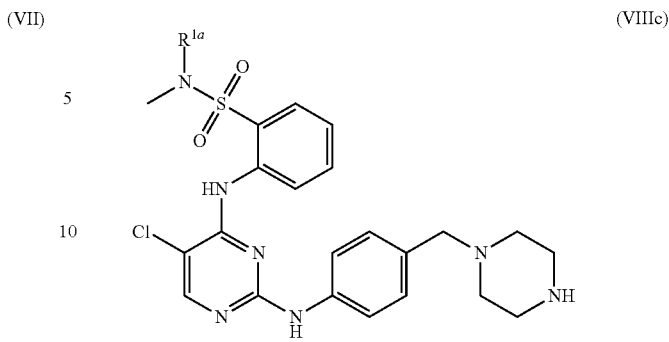 (VIIIc)

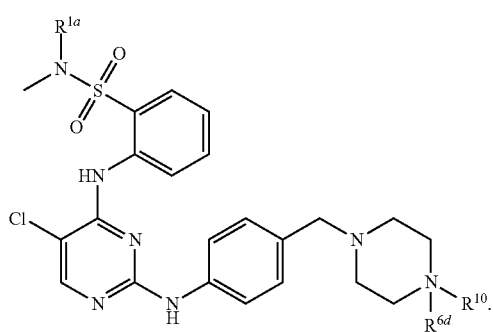 (VIII)

Another embodiment provides a compound having the following structure:

In yet another embodiment of structure (IV), the compound has one of the following structures (VIIIa), (VIIIb) or (VIIIc):

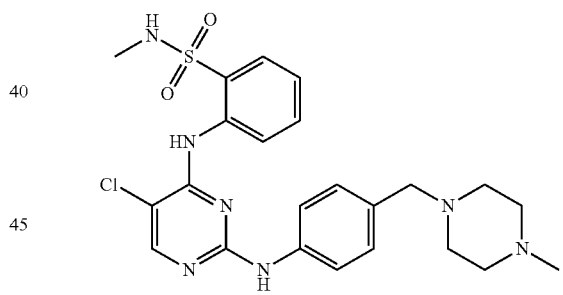

or a stereoisomer, pharmaceutically acceptable salt, tautomer or prodrug thereof.

A different embodiment provides compound having the following structure:

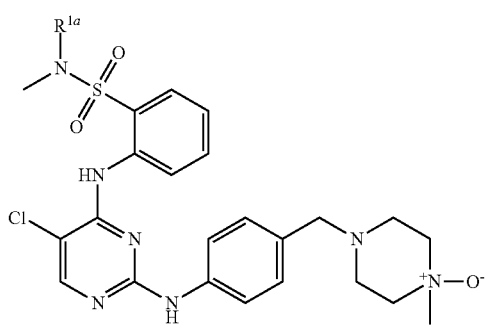 (VIIIa)

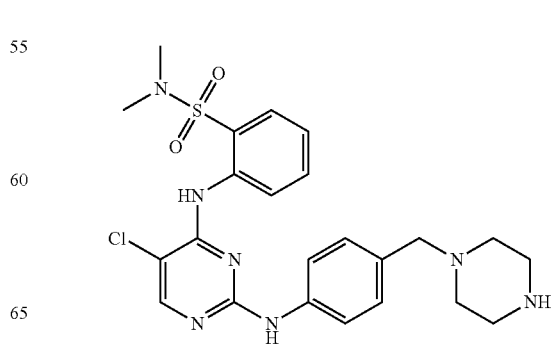

or a stereoisomer, pharmaceutically acceptable salt, tautomer or prodrug thereof.

Yet another embodiment provides a compound having the following structure:

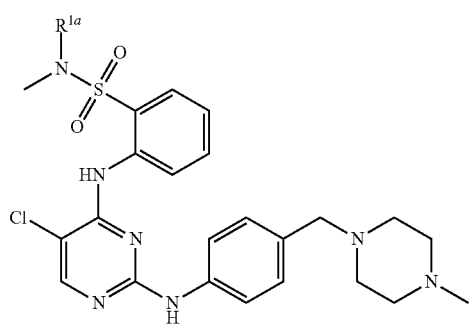 (VIIIb)

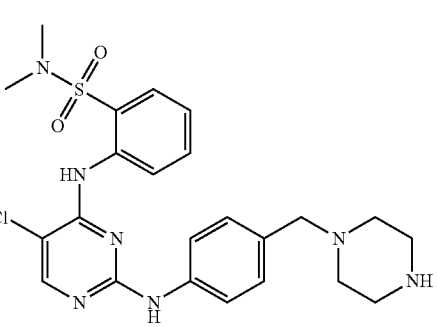

or a stereoisomer, pharmaceutically acceptable salt, tautomer or prodrug thereof, An additional embodiment provides compound having the following structure:

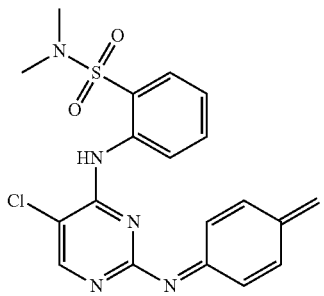

or a stereoisomer, pharmaceutically acceptable salt, tautomer or prodrug thereof.

Yet another embodiment affords compound having the following structure:

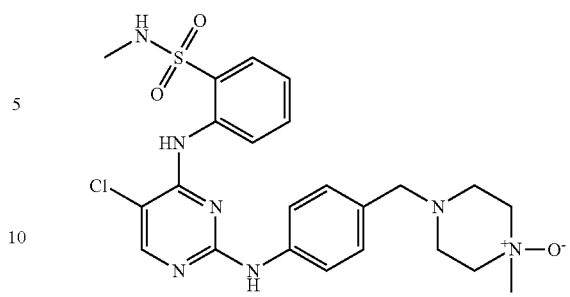

or a stereoisomer, pharmaceutically acceptable salt, tautomer or prodrug thereof.

In certain embodiments of the compound of structure (IV), the compound is isolated using chemical techniques known in the art (e.g., column purification, distillation, recrystallization, etc.). Accordingly, in certain embodiments, the compound of structure (IV) is isolated. In some embodiments, the compound of structure (IV) is purified. In some embodiments, the compound of structure (IV) is isolated and purified.

Some embodiments provide a composition consisting essentially of a compound of structure (IV), that is, a composition that contains substantially no impurities which have an adverse effect on composition as it relates to inhibition of kinase activity as determined using in vitro assays.

In some embodiments, the compound is selected from Table 7, and pharmaceutically acceptable salts thereof.

TABLE 7

Figure 101A:
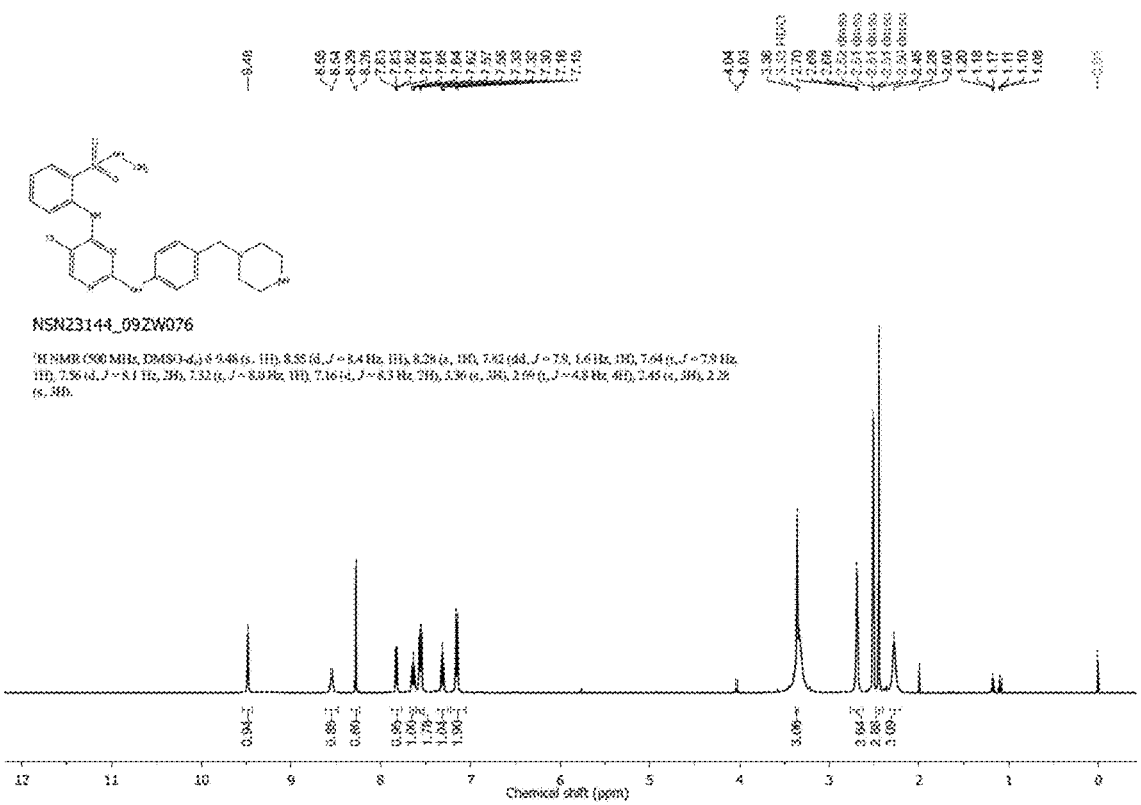
FIGS. 101A-101E show $^1$H (proton) NMR spectra for metabolites M2, M3, M4, M6, and M7.
Figure 101B:
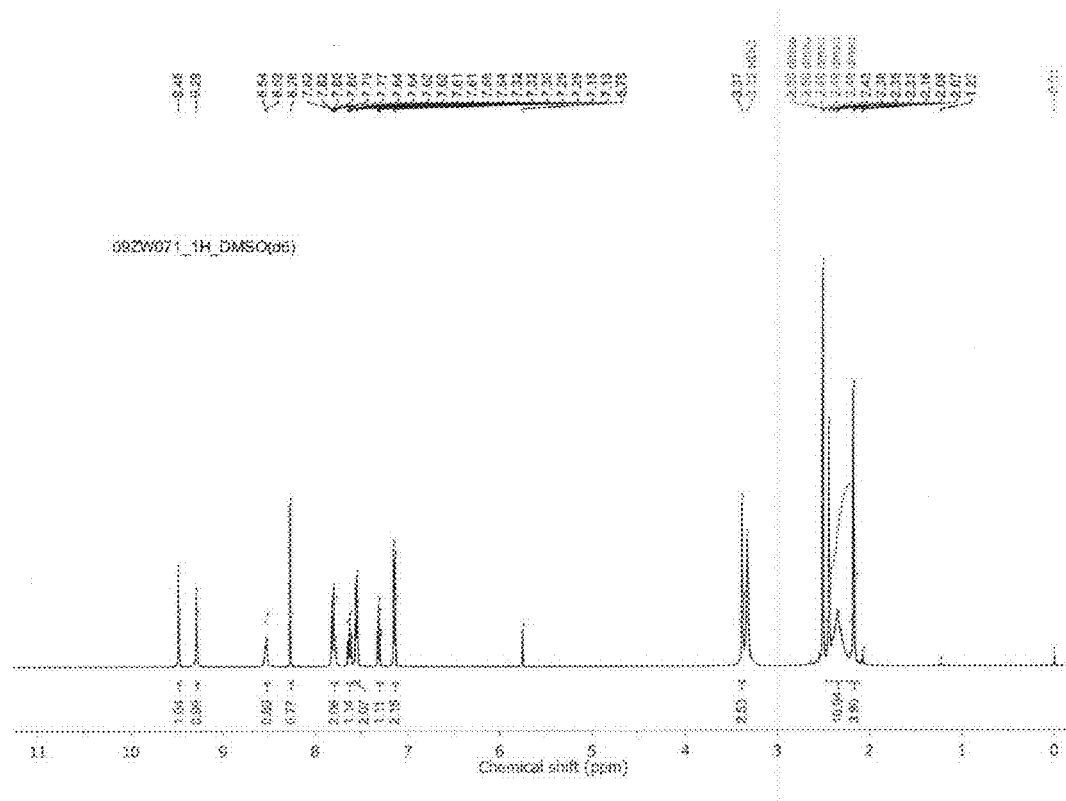

| | Exemplary Compounds of Structure (IV) | | |
|---|---|---|---|
| No. | Structure | m/z [M + H]$^+$ | $^1$HNMR |
| M2 | | 488.2 | FIG. 101A |
| M3 | | 502.2 | FIG. 101B |

TABLE 7-continued

Exemplary Compounds of Structure (IV)

Figure 101C:
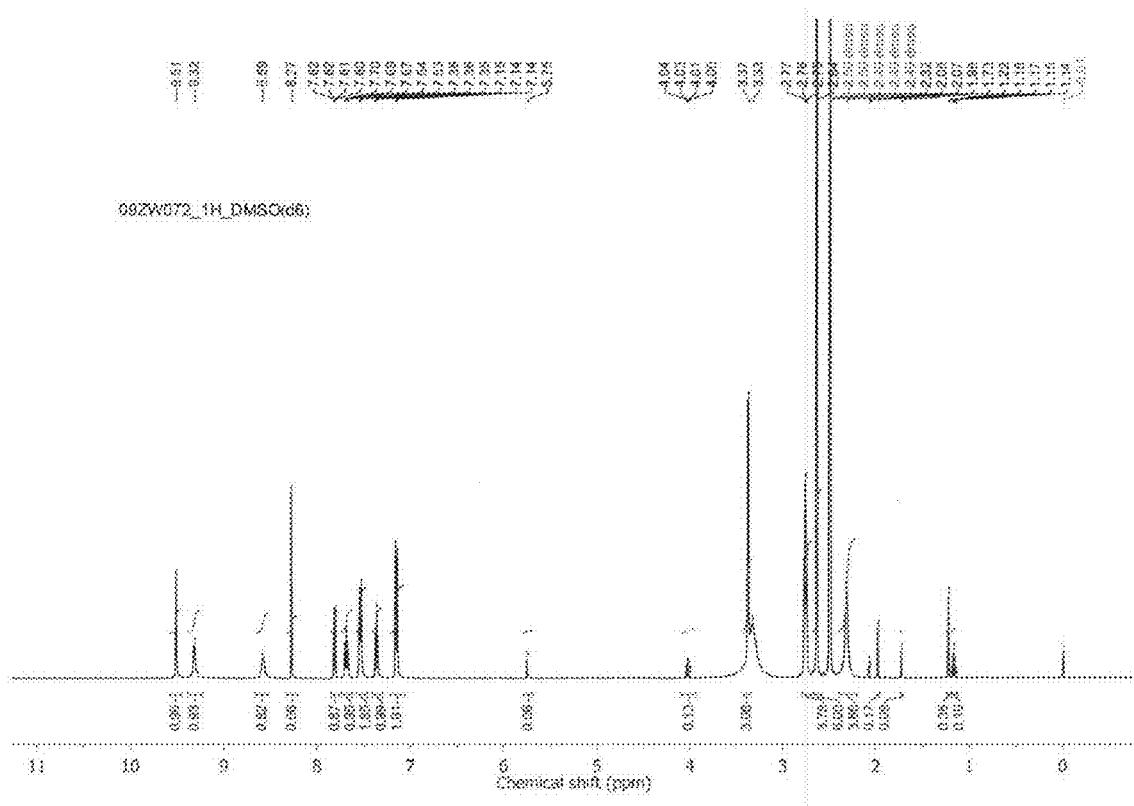
Figure 101D:
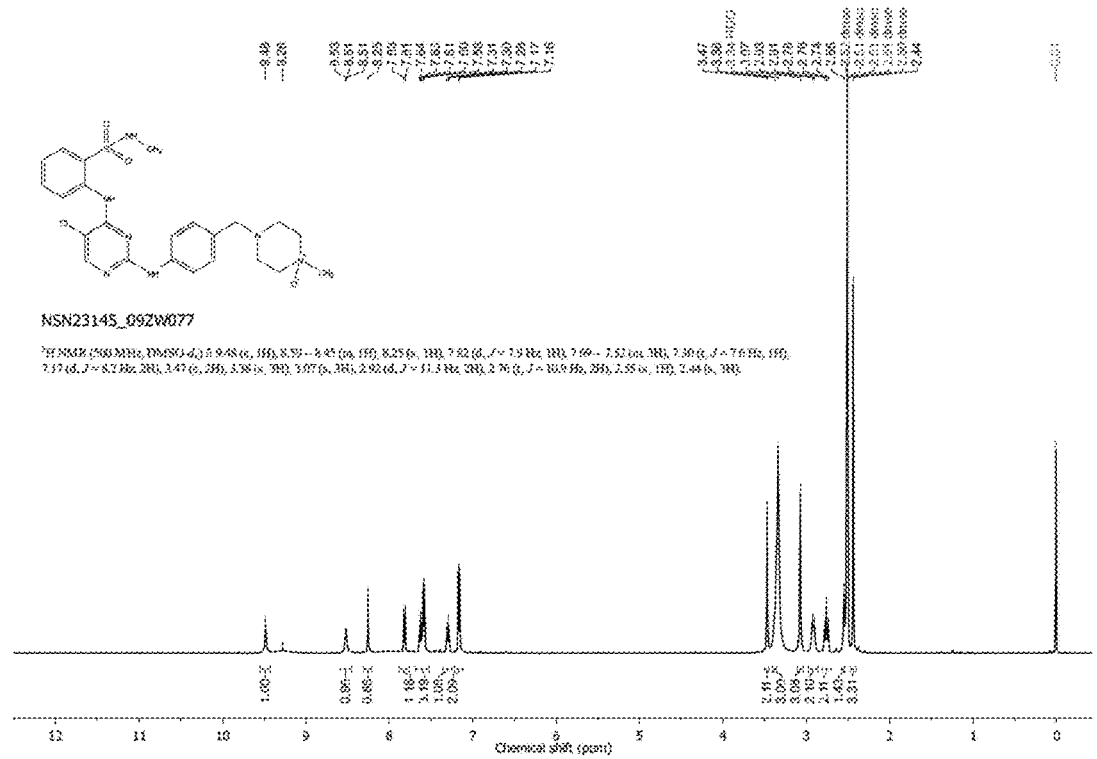
Figure 101E:
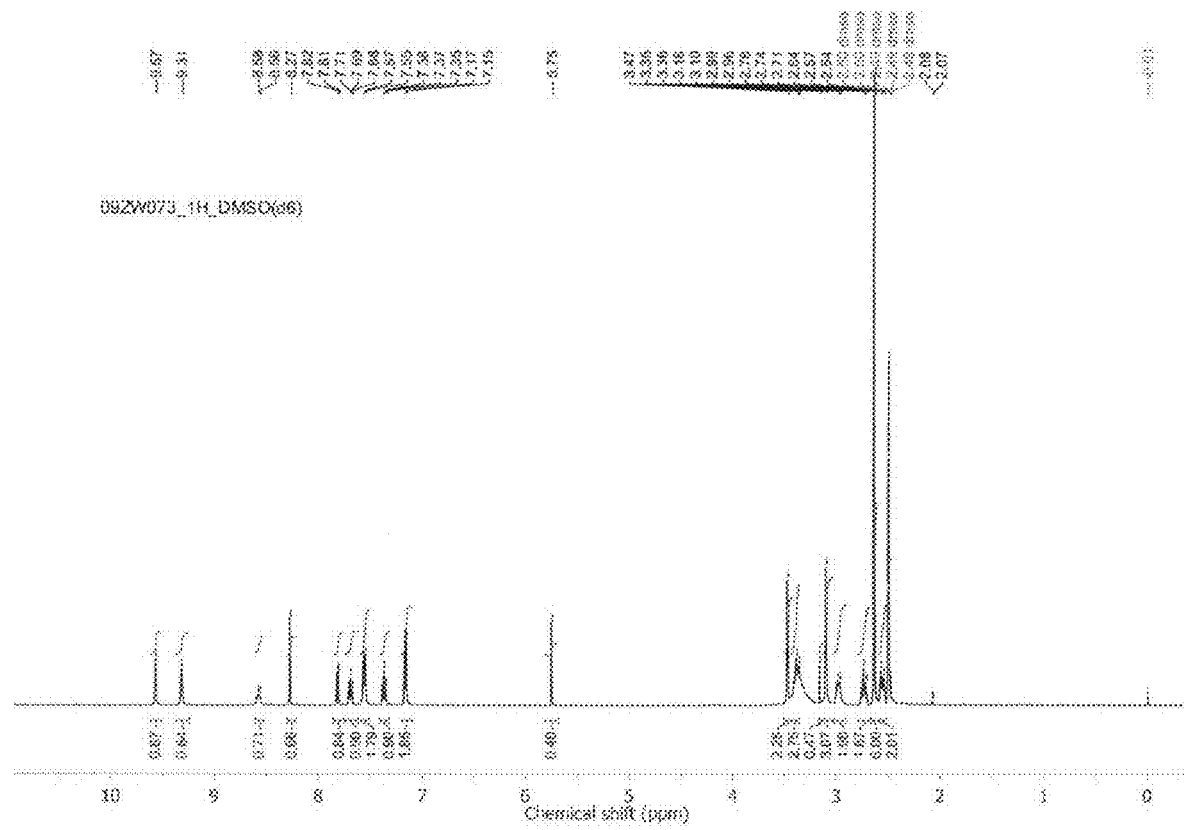

| No. | Structure | m/z [M + H]+ | 1HNMR |
|---|---|---|---|
| M4 | 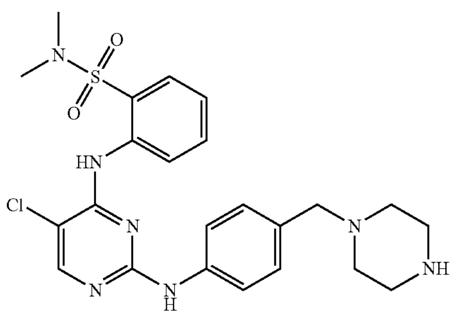 [SMILES: CN(C)S(=O)(=O)c1ccccc1Nc1nc(Nc2ccc(CN3CCNCC3)cc2)ncc1Cl] | 502.2 | FIG. 101C |
| M5 | 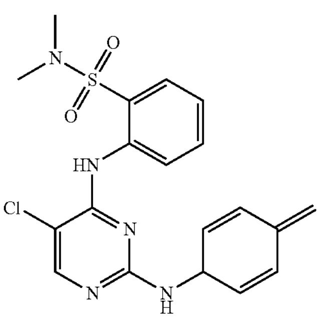 [SMILES: C=C1C=CC(Nc2ncc(Cl)c(Nc3ccccc3S(=O)(=O)N(C)C)n2)C=C1] | 416.1 | |
| M6 | 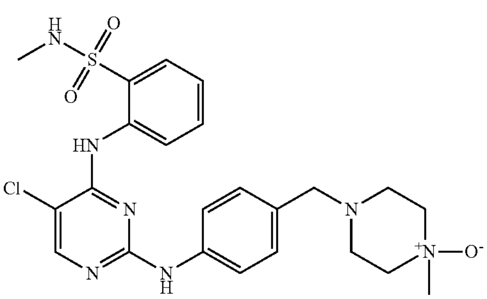 [SMILES: CNS(=O)(=O)c1ccccc1Nc1nc(Nc2ccc(CN3CC[N+](C)([O-])CC3)cc2)ncc1Cl] | 518.2 | FIG. 101D |
| M7 | 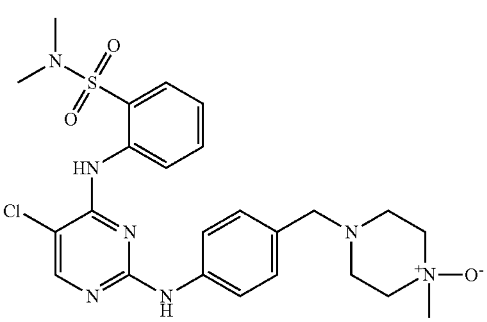 [SMILES: CN(C)S(=O)(=O)c1ccccc1Nc1nc(Nc2ccc(CN3CC[N+](C)([O-])CC3)cc2)ncc1Cl] | 532.2 | FIG. 101E |

Table 7A summarizes AXL inhibition and AUC data for representative metabolites of structure (IV).

TABLE 7A

Metabolite Date

Figure 102A:
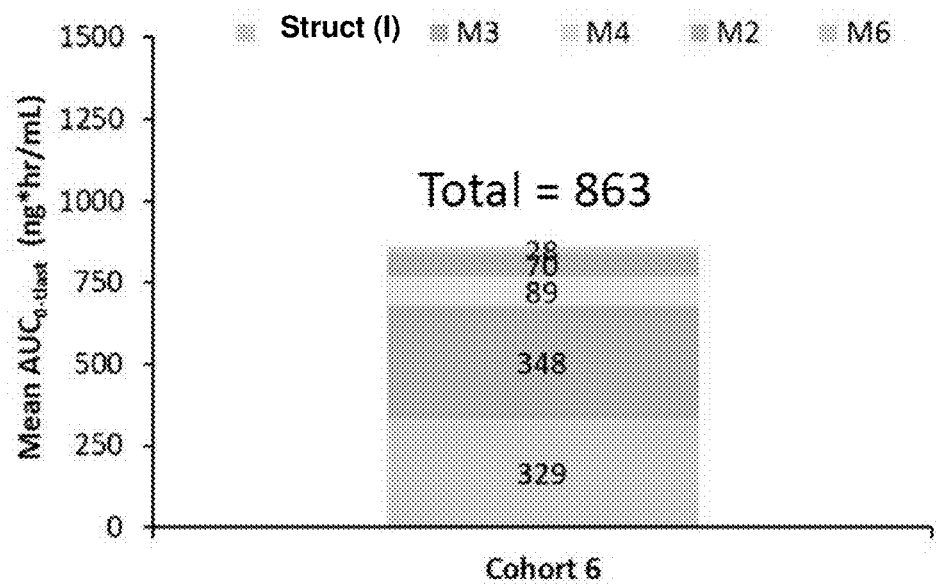
FIGS. 102A-102B show relative amounts of active metabolites after 21 days in two different cohorts.
Figure 102B:
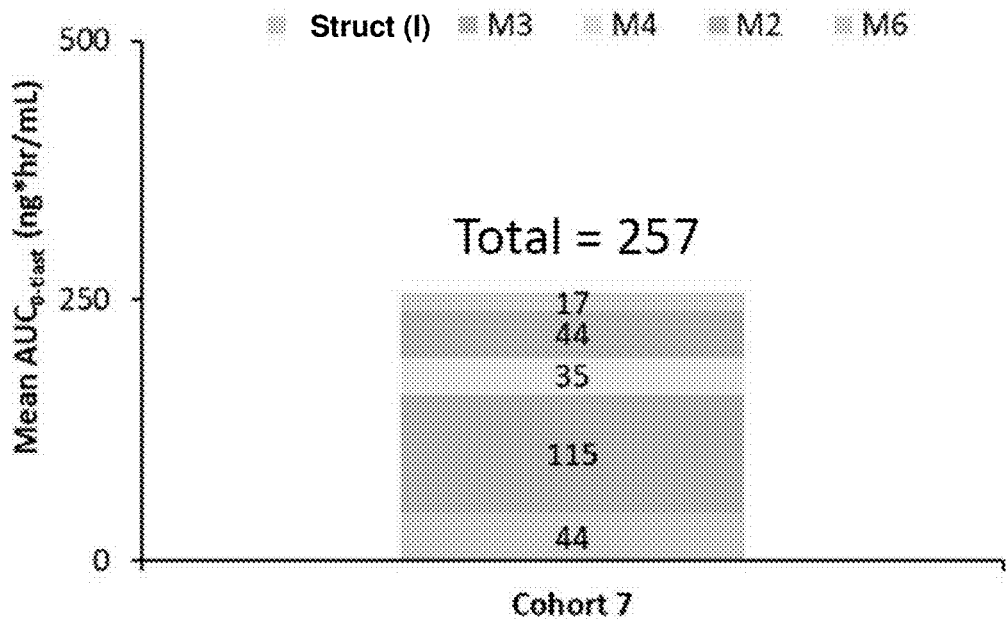

| Cmpd | AXL IC50 (nM) | % after 2 hrs exposure to human hepatocytes | % in plasma at day 21 at 16 mg/M2 dose (FIG. 102A) | % in plasma at day 21 at 21 mg/M2 dose (FIG. 102B) |
|---|---|---|---|---|
| (I) | 4.6 | 55% | 38% | 17% |
| M1 | na | 1% | not detected | not detected |
| M2 | 8.5 | 2% | 8% | 17% |
| M3 | 8.7 | 13% | 40% | 44% |
| M4 | 9.3 | 8% | 10% | 14% |
| M5 | na | 2% | not detected | not detected |
| M6 | 15.7 | 3% | 3% | 7% |
| M7 | 23.4 | 15% | not detected | not detected |

Additionally, the foregoing embodiments include a compound of structure (IV) as a pharmaceutically acceptable salt, for example, an acid addition salt or a base addition salt. In more specific embodiments, the acid addition salt is a hydrochloric salt, a fumaric salt, or a tartrate salt. In certain embodiments, the acid addition salt is a tartrate salt.

2. Methods

Certain methods disclosed herein serve to select a regimen of treatment for a subject in need thereof. That is, this disclosure provides methods for selecting treatment regimens as well as methods of treatment themselves. Additionally, certain embodiments provide a method for selecting treatment regimens and methods of treatment based on a metabolic profile. Other embodiments provide a method for selecting a treatment regimen and for treating cancer in a subject based on the subject having a predetermined genetic profile.

Embodiments provided herein include methods for selecting a treatment regimen for a subject based on the subject's genetic profile. Such genetic profiles may be produced in any suitable manner (e.g., microarrays, reverse transcription polymerase chain reaction (RT-PCR), etc.) In some embodiments, the genetic profile comprises a polymorphism in a gene encoding a cytochrome P450 enzyme. The term "gene" can include not only coding sequences but also regulatory regions such as promoters, enhancers, and termination regions.

The term further can include all introns and other DNA sequences spliced from the mRNA transcript, along with variants resulting from alternative splice sites. Gene sequences encoding the particular protein can be DNA or RNA that directs the expression of the particular protein. These nucleic acid sequences may be a DNA strand sequence that is transcribed into RNA or an RNA sequence that is translated into the particular protein. The nucleic acid sequences include both the full-length nucleic acid sequences as well as non-full-length sequences derived from the full-length protein.

In some embodiments, the particular protein is an enzyme, for example a cytochrome P450 enzyme. Cytochrome P450 (CYP) enzymes are a major source of variability in drug pharmacokinetics and response. In some embodiments the cytochrome P450 enzyme is in the CYP1, CYP2 or CYP3 families. In embodiments, the cytochrome P450 enzyme is CYP1A2, CYP2A6, CYP2C8, CYP2C9, CYP3A43, CYP3A5, CYP4A11, CYP4A22, CYP4B1, CYP4F2, CYP5A1, CYP11A1, CYP11B1, CYP11B2, CYP1A1, CYP1A2, CYP1B1, CYP2A6, CYP2A7, CYP2B6, CYP2C18, CYP2C19, CYP2C19, CYP2C9, CYP2D6, CYP2D6, CYP2E1, CYP2F1, CYP2J2, CYP2R1, CYP2S1, CYP2U1, CYP2W1, CYP3A4, CYP3A5, CYP3A7, CYP3A7, CYP4F11, CYP4F12, CYP4F22, CYP4F3, CYP4F8, CYP4V2, CYP4X1, CYP7A1, CYP7B1, CYP8B1, or CYPF22. In some embodiments, the cytochrome P450 enzyme is CYP1A1, CYP1A2, CYP2C9, CYP2C19, CYP2D6, CYP2A6, CYP3A5, or CYP3A7. In some embodiments, the cytochrome P450 enzyme is CYP3A4, CYP2C9, CYP2C8, CYP2E1, CYP1A2, CYP2A6, CYP2D6, CYP2B6, CYP2C19, CYP3A5, CYP2J2, CYP1A1, or CYP1B1. In some embodiments, the cytochrome P450 enzyme includes CYP2D6, CYP2C19, CYP2C9, CYP2B6, CYP3A5 or CYP2A6. In some embodiments, the cytochrome P450 enzyme is CYP1A1, CYP1A2, CYP2C8, CYP2E1, CYP2J2, or CYP3A4. In some specific embodiments, the cytochrome P450 enzyme is CYP2C19. In various embodiments, the genetic profile comprises information regarding multiple cytochrome P450 enzymes. In some embodiments, the polymorphism is a single nucleotide polymorphism.

In embodiments, the polymorphism results in:

i. an expression level of the cytochrome P450 enzyme that is different than a baseline expression level by at least 10%; and/or ii. an activity of the cytochrome P450 enzyme that is different than a baseline activity by at least 10%.

Expression levels may be measured using any suitable techniques, such as enzyme-linked immunoassays (ELISA), mass spectrometry (MS), real-time quantitative PCR (RT-qPCR), flow cytometry, nucleic acid (i.e., DNA, RNA, etc.) sequencing, amino acid (i.e., peptide, protein, etc.) sequencing, molecular cytogenetics fluorescence in situ hybridization (FISH), and the like.

A baseline level can be derived from a population. A "population" is any grouping of subjects or samples of like specified characteristics. The grouping could be according to, for example, clinical parameters, clinical assessments, therapeutic regimens, disease status, severity of condition, etc.

In some embodiments, the population is selected randomly. In some embodiments, the population is a group comprising about 2, about 5, about 10, about 25, about 50, about 75, or about 100 subjects. In some embodiments, the population is a group comprising about 200, about 300, about 500, about 1,000, about 1,500, about 2,000, about 3,000, about 5,000, or about 10,000 subjects. In some embodiments, the population is a group comprising less than about 10,000 subjects. In other embodiments, the population is a group comprising greater than about 10,000 subjects.

In some embodiments, the population is a group that does not have cancer. In embodiments, the population does not have a hematologic cancer. In some embodiments, the population does not have a solid tumor cancer. In some embodiments, the population does not have liver cancer.

In some embodiments, the population is a group that has cancer. In embodiments, the population has a hematologic cancer. In some embodiments, the population does has a solid tumor cancer. In some embodiments, the population has liver cancer. In some embodiments, the population has a same type of cancer.

In some of the foregoing embodiments, the population is non-responsive to an AXL kinase inhibitor. In some embodiments, the population is refractory after treatment with an AXL kinase inhibitor. In some embodiments, the population is intolerant of treatment with an AXL kinase inhibitor. In some embodiments, the AXL kinase inhibitor is the compound of structure (I), or a pharmaceutically acceptable salt thereof (e.g., a tartrate salt). In some embodiments, the AXL kinase inhibitor is a compound of structure (IV) or a pharmaceutically acceptable salt thereof.

In various embodiments, an expression level of the cytochrome P450 enzyme is greater than a baseline expression level. In embodiments, the expression level of the cytochrome P450 enzyme is at least about 10% greater than the baseline expression level. In some embodiments, the expression level is at least about 1% greater, at least about 2% greater, at least about 3% greater, at least about 4% greater, at least about 5% greater, at least about 7% greater, at least about 12% greater, at least about 15% greater, at least about 17% greater, at least about 20% greater, at least about 22% greater, at least about 25% greater, at least about 27% greater, at least about 30% greater, at least about 32% greater, at least about 35% greater, at least about 37% greater, at least about 40% greater, at least about 45% greater, at least about 50% greater, at least about 75% greater, or at least about 90% greater. In certain embodiments, a cytochrome P450 gene is up-regulated. "Up-regulation" or "up-regulated" refers to an increase in the presence of a protein and/or an increase in the expression of its gene.

In some embodiments, an expression level of the cytochrome P450 enzyme is less than a baseline expression level. In embodiments, the expression level of the cytochrome P450 enzyme is at least 10% less than the baseline expression level. In some embodiments, the expression level is at least about 1% less, at least about 2% less, at least about 3% less, at least about 4% less, at least about 5% less, at least about 10% less, at least about 12% less, at least about 15% less, at least about 17% less, at least about 20% less, at least about 22% less, at least about 25% less, at least about 27% less, at least about 30% less, at least about 32% less, at least about 35% less, at least about 37% less, at least about 40% less, at least about 45% less, at least about 50% less, at least about 75% less, or at least about 90% less. In certain embodiments, a cytochrome P450 gene is down-regulated. "Down-regulation" or "down-regulated" refers to a decrease in the presence of a protein and/or a decrease in the expression of its gene.

Measurement of expression of the markers can be determined at the protein or nucleic acid level using any method known in the art. In some embodiments, a marker is detected by contacting a sample with reagents (e.g., antibodies or nucleic acid primers), generating complexes of reagent and marker(s), and detecting the complexes. Antibodies can be conjugated to a solid support suitable for a diagnostic assay in accordance with known techniques, such as passive binding. Antibodies can be conjugated to cell surface antigens for a diagnostic assay in accordance with known techniques, such as flow cytometry, including multi-color flow cytometry. Antibodies can be conjugated to detectable labels or groups such as radiolabels, enzyme labels, and fluorescent labels in accordance with known techniques.

Examples of suitable immunoassays include immunoblotting, immunoprecipitation, immunofluorescence, chemiluminescence, electro-chemiluminescence (ECL), and ELISA. Up- or down-regulation of markers also can be detected using, for example, cDNA arrays, clone hybridization, differential display, differential screening, FRET detection, liquid microarrays, PCR, RT-PCR, Sanger sequencing, mass-parallel (next-generation) sequencing, molecular beacons, microelectric arrays, oligonucleotide arrays, polynucleotide arrays, serial analysis of gene expression (SAGE), and/or subtractive hybridization. Expression may be determined in a sample collected from a subject prior to treatment.

In such embodiments, expression levels may be used to predict responsiveness to a particular treatment. In some embodiments, expression levels may be used, at least in part, to determine a treatment administered to a subject. In some embodiments, a sample may be collected after a dose of a treatment is administered to a subject. In specific embodiments, a sample is collected on day 1 of a first cycle of treatment, pre-dose, two hours after dosing, six hours after dosing, and 24 hours after dosing. In another specific embodiment, a sample is also collected on day 8 of the first cycle of treatment, pre-dose. In another specific embodiment, a sample is also collected on day 1 of the second cycle of treatment, pre-dose. In further specific embodiment, a sample is also collected on day 1 of any additional cycles of treatment (e.g., third, fourth, fifth, etc.), pre-dose. In another specific embodiment, a sample is also collected after treatment is completed.

Up- or down-regulation can be assessed by comparing a value to a relevant reference level. For example, the quantity of one or more markers can be indicated as a value, which can be derived, e.g., by measuring level(s) of the marker(s) in the sample by an assay performed. In the broadest sense, the value may be qualitative or quantitative. Where detection is qualitative, the systems and methods provide a reading or evaluation, e.g., assessment, of whether or not the marker is present in the sample being assayed. In yet other embodiments, the systems and methods provide a quantitative detection of whether the marker is present in the sample being assayed, i.e., an evaluation or assessment of the actual amount or relative abundance of the marker in the sample being assayed. In such embodiments, the quantitative detection may be absolute or, if the method is a method of detecting two or more different markers in a sample, relative. Accordingly, the term "quantifying" when used in the context of quantifying a marker in a sample can refer to absolute or to relative quantification. Absolute quantification can be accomplished by inclusion of known concentration(s) of one or more control markers and referencing, e.g., normalizing, the detected level of the marker with the known control markers (e.g., through generation of a standard curve). Alternatively, relative quantification can be accomplished by comparison of detected levels or amounts between two or more different markers to provide a relative quantification of each of the two or more markers, e.g., relative to each other.

In various embodiments an activity of the cytochrome P450 enzyme is greater than a baseline activity. The function of a protein can be assayed by a relevant activity assay. Exemplary activity assays include binding assays, enzyme activity assays including, for example, protease assays, kinase assays, phosphatase assays, reductase assays, etc.

In some embodiments, the activity of one or more cytochrome P450 enzymes is at least about 10% greater than the baseline activity. In some embodiments, the activity is at least about 1% greater, at least about 2% greater, at least about 3% greater, at least about 4% greater, at least about 5% greater, at least about 7% greater, at least about 12% greater, at least about 15% greater, at least about 17% greater, at least about 20% greater, at least about 22% greater, at least about 25% greater, at least about 27% greater, at least about 30% greater, at least about 32% greater, at least about 35% greater, at least about 37% greater, at least about 40% greater, at least about 45% greater, at least about 50% greater, at least about 75% greater, or at least about 90% greater.

In some embodiments, an activity of the cytochrome P450 enzyme is less than a baseline activity. In embodiments, the activity of the cytochrome P450 enzyme is at least about 10% less than the baseline activity. In some embodiments, the activity is at least about 1% less, at least about 2% less, at least about 3% less, at least about 4% greater, at least about 5% greater, at least about 7% less, at least about 12% less, at least about 15% less, at least about 17% less, at least about 20% less, at least about 22% less, at least about 25% less, at least about 27% less, at least about 30% less, at least about 32% less, at least about 35% less, at least about 37% less, at least about 40% less, at least about 45% less, at least about 50% less, at least about 75% less, or at least about 90% less.

Accordingly, embodiments of the present disclosure include a method of selecting a treatment regimen for a subject in need thereof, the method comprising: receiving a genetic profile for the subject, the genetic profile comprising a polymorphism in a gene that encodes a cytochrome P450 enzyme; and selecting the treatment regimen based on the genetic profile. In some embodiments, the treatment regimen comprises administering an effective amount of a therapeutic agent. In some embodiments, the treatment regimen comprises withholding a therapeutic agent.

In embodiments, the therapeutic agent is an AXL kinase inhibitor. In some embodiments of the foregoing, the therapeutic agent is the compound of structure (I):

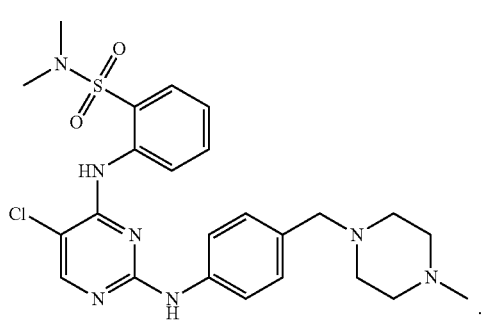

(I)

In related embodiments, the therapeutic agent is an acid addition salt of the following structure (I).

In more specific embodiments, the salt is a tartrate salt.

In embodiments, therapeutic agent is a compound of structure (IV), or a prodrug or pharmaceutically acceptable salt thereof, as described above.

Embodiments of the present disclosure further include a method for treating a cancer in a subject, the method comprising: administering an effective amount of a therapeutic agent to the subject having a predetermined genetic profile comprising a polymorphism in a gene that encodes a cytochrome P450 enzyme. In embodiments, the polymorphism results in:

i. an expression level of the cytochrome P450 enzyme that is different than a baseline expression level by at least 10%; and/or ii. an activity of the cytochrome P450 enzyme that is different than a baseline activity by at least 10%.

In embodiments, the expression level of the cytochrome P450 enzyme is at least 10% greater than the baseline expression level. In embodiments, the activity of the cytochrome P450 enzyme is at least 10% greater than the baseline activity. In embodiments, the expression level of the cytochrome P450 enzyme is at least 10% less than the baseline expression level. In embodiments, the activity of the cytochrome P450 enzyme is at least 10% less than the baseline activity. In embodiments, the therapeutic agent is an AXL kinase inhibitor.

In certain embodiments, the therapeutic agent is the compound of structure (I) or a pharmaceutically acceptable salt thereof. In embodiments, the therapeutic agent is a pharmaceutically acceptable sale of the compound of structure (I). In embodiments, the pharmaceutically acceptable salt of the compound of structure (I) is a tartrate salt. In embodiments, the therapeutic agent is a compound structure (IV), or a prodrug or pharmaceutically acceptable salt thereof, or a composition comprising such a compound, as described above.

In embodiments, a treatment regimen withholding a second therapeutic agent from the subject based on the predetermined genetic profile. In some embodiments, the second therapeutic agent is the compound of structure (I) or a pharmaceutically acceptable salt thereof. In embodiments, the pharmaceutically acceptable salt of the compound of structure (I) is a tartrate salt. In embodiments, the second therapeutic agent is a compound structure (IV), or a prodrug or pharmaceutically acceptable salt thereof, or a composition comprising such a compound, as described above.

In some embodiments, the expression level of one or more cytochrome P450 enzymes is at least about 10% greater than the baseline expression level. In some embodiments, the expression level is at least about 1% greater, at least about 2% greater, at least about 3% greater, at least about 4% greater, at least about 5% greater, at least about 7% greater, at least about 12% greater, at least about 15% greater, at least about 17% greater, at least about 20% greater, at least about 22% greater, at least about 25% greater, at least about 27% greater, at least about 30% greater, at least about 32% greater, at least about 35% greater, at least about 37% greater, at least about 40% greater, at least about 45% greater, at least about 50% greater, at least about 75% greater, or at least about 90% greater.

In some embodiments, the activity of one or more cytochrome P450 enzymes is at least about 10% greater than the baseline concentration. In some embodiments, the activity is at least about 1% greater, at least about 2% greater, at least about 3% greater, at least about 4% greater, at least about 5% greater, at least about 7% greater, at least about 12% greater, at least about 15% greater, at least about 17% greater, at least about 20% greater, at least about 22% greater, at least about 25% greater, at least about 27% greater, at least about 30% greater, at least about 32% greater, at least about 35% greater, at least about 37% greater, at least about 40% greater, at least about 45% greater, at least about 50% greater, at least about 75% greater, or at least about 90% greater.

A baseline level can be derived from a population. A "population" is any grouping of subjects or samples of like specified characteristics. The grouping could be according to, for example, clinical parameters, clinical assessments, therapeutic regimens, disease status, severity of condition, etc.

In some embodiments, the population is selected randomly. In some embodiments, the population is a group comprising about 2, about 5, about 10, about 25, about 50, about 75, or about 100 subjects. In some embodiments, the population is a group comprising about 200, about 300, about 500, about 1,000, about 1,500, about 2,000, about 3,000, about 5,000, or about 10,000 subjects. In some embodiments, the population is a group comprising less than about 10,000 subjects. In other embodiments, the population is a group comprising greater than about 10,000 subjects.

In some embodiments, the population is a group that does not have cancer. In embodiments, the population does not have a hematologic cancer. In some embodiments, the population does not have a solid tumor cancer. In some embodiments, the population does not have liver cancer.

In some embodiments, the population is a group that has cancer. In embodiments, the population has a hematologic cancer. In some embodiments, the population does have a solid tumor cancer. In some embodiments, the population has liver cancer. In some embodiments, the population has a same type of cancer.

In some of the foregoing embodiments, the population is non-responsive to an AXL kinase inhibitor. In some embodiments, the population is refractory after treatment with an AXL kinase inhibitor. In some embodiments, the population is intolerant of treatment with an AXL kinase inhibitor. In some embodiments, the AXL kinase inhibitor is the compound of structure (I) or a pharmaceutically acceptable salt thereof (e.g., a tartrate salt). In some embodiments, the AXL kinase inhibitor is a compound of structure (IV) or a pharmaceutically acceptable salt thereof.

Other embodiments provide a method of determining a metabolic profile of a subject, the method comprising contacting a population of cells (e.g., hepatocytes) of the subject with a therapeutic agent and determining a concentration of a first metabolite which is a compound of any one of the foregoing embodiments or a pharmaceutically acceptable salt of any one of the foregoing embodiments.

In more specific embodiments, the method further comprises determining a concentration of a second metabolite. In some embodiments, the method further comprises determining an expression level of one or more cytochrome P450 enzymes in the population of cells (e.g., hepatocytes). In other embodiments, the method further comprises determining an activity of one or more cytochrome P450 enzymes in the population of cells (e.g., hepatocytes).

In some of the foregoing embodiments, determining the expression level or determining the activity of the one or more cytochrome P450 enzymes based on the concentration of the first metabolite.

In other related embodiments, the method further comprises incubating the population of cells (e.g., hepatocytes) with the therapeutic agent. In some embodiments, the incubating ranges from about 1.5 to about 2.5 hours. For example, in some embodiments the incubating is for about 2 hours. In some specific embodiments, the incubating ranges from about 0.5 to about 20 hours, about 0.25 to about 10 hours, about 0.15 to about 5 hours, about 0.5 to about hours, about 0.5 to about 5 hours, about 0.5 to about 3 hours, about 0.25 to about 20 hours, about 0.25 to about 5 hours, about 0.25 to about 3 hours, about 0.15 to about 10 hours, or about 0.15 to about 3 hours.

In some embodiments, the population of cells comprises hepatocytes, for example, human hepatocytes.

In some embodiments, determining the concentration of the first metabolite comprises performing a mass spectrometry assay (e.g., MS, MS/MS, LC-MS, LC-MS/MS). In more specific embodiments, the mass spectrometry assay comprises collisionally induced dissociation (CID). In some related embodiments, the determining the concentration of the first metabolite further comprises performing a liquid chromatography assay (LC).

The examples and preparations provided below further illustrate and exemplify compounds of structure (I) or pharmaceutically acceptable salts of a compound of structure (I), and methods of preparing the salt. It is to be understood that the scope of the present invention is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

G. Examples

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

The examples and preparations provided below further illustrate and exemplify compounds of structure (I) or pharmaceutically acceptable salts of a compound of structure (I) (e.g., a tartrate salt of the compound of structure (I)), and methods of preparing such a salt. It is to be understood that the scope of the present invention is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

Example 1: Salt Screening 1 mL of solvent was added to 25 pg of the compound of structure (I) and 1 equivalent of the desired acid. The solvents used were water and N-Methyl-2-pyrrolidone (NMP). The salt screen was performed using the Crystal 16 equipment. The program allows heating up to 60° C. followed by controlled cooling to 5° C. with 0.1° C. per minute. Two series of slurry experiments were initiated using water and dichloromethane as a solvent. These experiments were stirred for 3 days at 20° C. If applicable, the solvent were evaporated in a vacuum oven to isolate the solids for XRPD and further analysis as provided below.

X-Ray Powder Diffraction (XRPD)

The X-ray powder diffraction studies were performed using a Bruker AXS D2 PHASER in Bragg-Brentano configuration, equipment #1549. Using a Cu anode at 30 kV, 10 mA; sample stage standard rotating; monochromatisation by a Kβ-filter (0.5% Ni). Slits: fixed divergence slits 1.0 mm (=0.61°), primary axial Seller slit 2.5°, secondary axial Seller slit 2.5°. Detector: Linear detector LYNXEYE with receiving slit 5° detector opening. The standard sample holder (0.1 mm cavity in (510) silicon wafer) has a minimal contribution to the background signal.

Measurement conditions: scan range 5-45° 2θ, sample rotation 5 rpm, 0.5 s/step, 0.010°/step, 3.0 mm detector slit; and all measuring conditions are logged in the instrument control file. As system suitability, corundum sample A26-B26-S (NIST standard) is measured daily.

The software used for data collection is Diffrac.Commander v3.3.35. Data analysis is done using Diffrac.Eva V3.0. No background correction or smoothing is applied to the patterns. The contribution of the Cu-Kα2 is stripped off using the Diffrac.Eva software.

Thermo Gravitational Analysis/Differential Scanning Calorimetry (TGA/DSC)

The TGA/DSC studies were performed using a Mettler Toledo TGA/DSC1 STARe System with a 34-position auto sampler, equipment #1547.

The samples were made using aluminum crucibles (40 μl; pierced). Typically, 5-10 mg of sample was loaded into a pre-weighed aluminum crucible and was kept at 30° C. for 5 minutes, after which it was heated at 10° C./min from 30° C. to 300° C. A nitrogen purge of 40 ml/min was maintained over the sample. As system suitability check Indium and Zinc are used as references.

The software used for data collection and evaluation is STARe Software v10.00 build 2480. No corrections are applied to the thermogram.

Differential Scanning Calorimetry (DSC)

The DSC studies were performed using a Mettler Toledo DSC1 STARe System, equipment #1564.

The samples were made using aluminum crucibles (40 μl; pierced). Typically 1-8 mg of sample was loaded onto a pre-weighed aluminum crucible and was kept at 30° C. for 5 minutes, after which it was heated at 10° C./min from 30° C. to 350° C. and kept at 350° C. again. A nitrogen purge of 40 ml/min was maintained over the sample. As system suitability check Indium and Zinc are used as references.

The software used for data collection and evaluation is STARe Software v10.00 build 2480. No corrections are applied to the thermogram.

Microscopy

The microscopy studies were performed using an Axio-Vert 35M, equipped with an AxioCamERc 5s, equipment #1612. The microscope is equipped with four lenses, being Zeiss A-Plan 5x/0.12, Zeiss A-Plan 10x/0.25, LD A-Plan 20x/0.30 and Achros TIGMAT 32x/0.40. Data collection and evaluation is performed using Carl Zeiss Zen AxioVision Blue Edition Lite 2011 v1.0.0.0 software.

A small amount of sample is loaded on an object glass and spread until a thin layer is obtained.

Dynamic Vapour Sorption (DVS)

The Dynamic Vapour Sorption studies were performed using a Surface Measurement Systems Ltd. DVS-1 No Video, equipment #2126. The sample is loaded into balance pan, typically 20-30 mg, and equilibrated at 0% RH. After the material has dried the RH is increased with 10% per step for 1 hour per increment, ending at 95% RH. After completion of the sorption cycle, the sample was dried using the same method. The software used for data collection is DVS Win v3.01 No Video. Data analysis is performed using DVS Standard Analysis Suite v6.3.0 (Standard).

From these experiments in total 16 unique XRPD patterns, or forms, were obtained. From the salt screen with water as a solvent and controlled cooling with the Crystal 16, 11 unique forms were obtained including salt forms from phosphoric acid, tartaric acid (i.e., (+)-L-tartaric acid), fumaric acid, malic acid (i.e., (−)-L-malic acid), succinic acid, ethane-1,5-disulfonic acid, p-toluenesulfonic acid, methanesulfonic acid, benzenesulfonic acid, ethanesulfonic acid and benzoic acid, respectively. Additional acids were tested yielding the corresponding salt of the compound of structure (I). These additional acids included hydrochloric acid, sulfuric acid, L-aspartic acid, maleic acid, glutamic acid, citric acid, D-glucuronic acid, glycolic acid, D-gluconic acid, L-ascorbic acid, adipic acid, naphthalene-1,5-disulfonic acid and naphthalene-2-sulfonic acid.

A salt screen with NMP as a solvent and controlled cooling with the Crystal 16 did lead to one unique form from sulfuric acid, at low yield and not enough material could be obtained for further analysis.

The slurry experiments with dichloromethane as a solvent lead to 4 new forms from maleic acid, malic acid, succinic acid, and ethane-1,5-disulfonic acid, respectively. The solids from the salt screens were isolated for XRPD analysis, each unique new pattern was analyzed using DSC-TGA, microscopy, FT-IR, $^X$H NMR and HPLC. In this studies, some salt forms were found to be non-reproducible and others showed reduced crystallinity after DVS.

Five forms formed from phosphoric acid, tartaric acid, malic acid, succinic acid, and benzenesulfonic acid were selected for scale up experiments, up to 500 mg, for further analysis.

Upon screening of numerous salt forms of the compound of structure (I), tartrate salt of the compound of structure (I) was identified as a suitable salt form of the compound for pharmaceutical uses. Surprisingly, PK studies showed improved bioavailability of the tartrate salt and the PhysChem properties measured showed the tartrate as having desirable physical properties including good stability. See Examples below.

Example 2: Pharmacokinetic Testing of Salt forms

Figure 1:
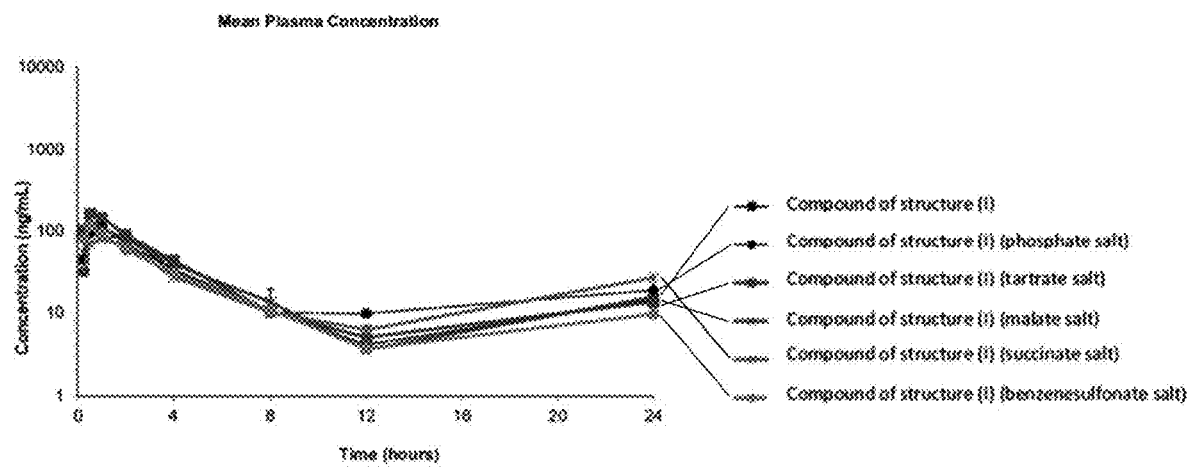
FIG. 1 illustrates PK results comparing salt forms of the compound of structure (I).

The 5 salt forms of structure (I) described in Example 1 (i.e., formed from phosphoric acid, tartaric acid, malic acid, succinic acid and benzenesulfonic acid) were tested to determine their pharmacokinetic (PK) profiles. Fasted male Sprague-Dawley rats were dosed with an oral formulation of each salt form as well as the free base form. Plasma concentration was tested at 5 minutes, 0.25, 0.5 1, 2, 4, 8, 12 and 24 hours post-dose. The mean plasma concentration after PO dosing is illustrated in FIG. 1. The data (mean values) for the 5 different salt forms and the free base is included in Table 8, below.

TABLE 8

PK data comparison for 5 representative salt forms of the compound of structure (I).

| | Compound of Structure (I) | Phosphate Salt | Tartrate Salt | Malate Salt | Succinate Salt | Benzene sulfonate Salt |
|---|---|---|---|---|---|---|
| Dose (PO, mg/kg) | 18.2 | 14.3 | 18.7 | 18.6 | 18.7 | 17.6 |
| $C_{max}$ (ng/mL) | 116 | 103 | 174 | 134 | 79.9 | 117 |
| $T_{max}$ (hours) | 0.833 | 1.00 | 0.667 | 0.500 | 0.833 | 0.667 |

TABLE 8-continued

PK data comparison for 5 representative salt forms of the compound of structure (I).

| | Compound of Structure (I) | Phosphate Salt | Tartrate Salt | Malate Salt | Succinate Salt | Benzene sulfonate Salt |
|---|---|---|---|---|---|---|
| $AUC_{0-24\ hours}$ (ng · h/mL) | 458 | 531 | 581 | 515 | 470 | 408 |
| Bioavailability (%) | 26.9 | 47.2 | 42.9 | 37.3 | 32.9 | 32.4 |

As the data in Table 8 show, the tartrate salt unexpectedly had one of the best overall PK profiles, having the highest $C_{max}$, highest AUC for 0-24 hours, and second highest bioavailability. Because the salt obtained from phosphoric acid showed undesirable stability characteristics, it appears that the tartrate salt has the best overall profile as a drug substance.

Example 3: Pharmacokinetic Study—Free Base v. Tartrate Salt

Fasted male Sprague-Dawley rats were dosed with the free base and the tartrate salt form of structure (I) in 20% solutol. The free base was formulated at 5.0 mg/mL (PO) and dosed by oral gavage (18.2 mg/kg). The tartrate salt of structure (I) was formulated at 6.5 mg/mL to account for the added weight of the tartrate component of the salt and dosed by oral gavage (14.5 mg/kg).

Plasma samples were taken at 0.25, 0.5, 1, 2, 4, 8, 12, and 24 hours post dose and analyzed for the concentration of structure (I) by LC-MS/MS with reference to a previously determined standard curve. Pharmacokinetic parameters were calculated using a non-compartmental approach with Phoenix WinNonlin 6.3 (Pharsight, Mountain View Calif.).

Figure 2:
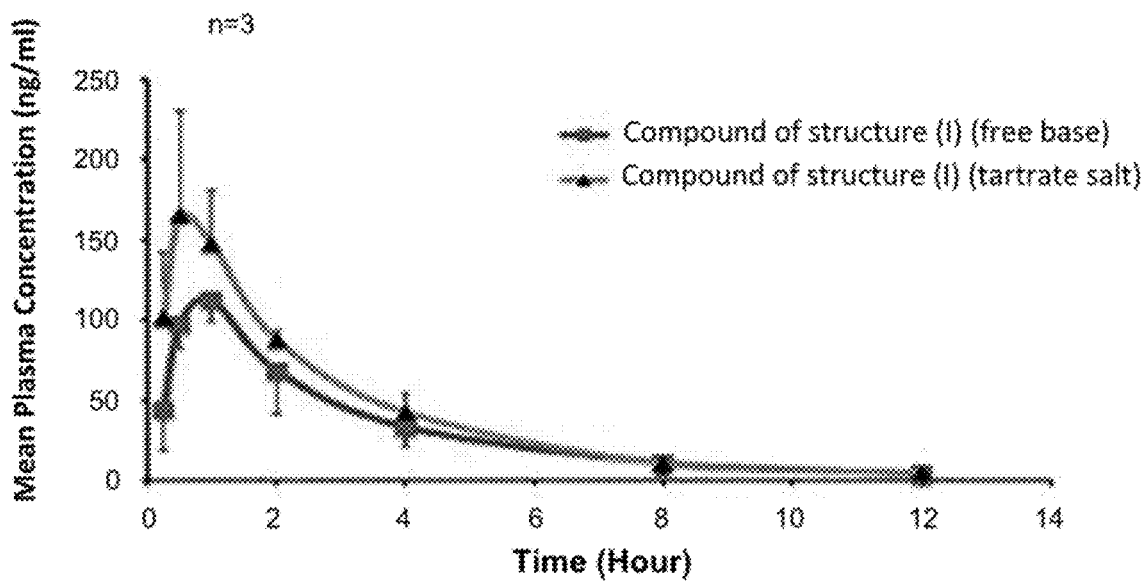
FIG. 2 shows the mean plasma concentration of a compound of structure (I) when administered as a free base and as a tartrate salt.

It was observed that the tartrate salt was superior to the free base having a higher peak of bioavailability than the free base formulation (FIG. 2). These data suggest that the tartrate salt of structure (I) may be more useful in vivo than the free base form. Additionally, the tartrate salt form shows superior $C_{max}$ and AUC parameters (FIG. 2) while maintaining an equivalent toxicity profile to the free base form at equal doses. That is, the tartrate salt of structure (I) allows for higher drug plasma levels without additional toxicity. Pharmacokinetic data for the tartrate salt v. the free base is included in Table 9, below (nominal dose of 20 mg/kg).

TABLE 9

PK data comparing the free base of the compound of structure (I) to the tartrate salt.

| | Free Base | Tartrate Salt |
|---|---|---|
| Dose (PO, mg/kg) | 18.2 | 18.7 |
| $C_{max}$ (ng/mL) | 116 | 174 |
| $T_{max}$ (hours) | 0.833 | 0.667 |
| $AUC_{0-24\ hours}$ (ng · h/mL) | 458 | 581 |
| Bioavailability (%) | 26.9 | 42.9 |

Example 4: Synthesis of a Tartrate Salt of Structure (I)

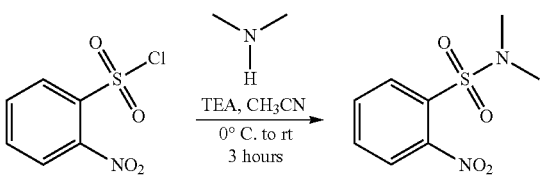

2-nitrobenzenesulfonyl chloride was combined with triethylamine and dimethylamine in acetonitrile under the reaction conditions shown to afford N,N-dimethyl-2-nitrobenzenesulfonamide in 82% yield.

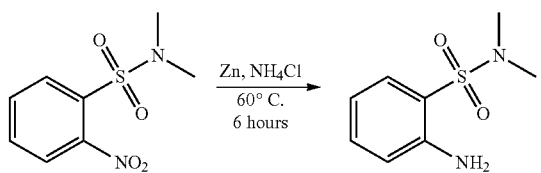

N,N-dimethyl-2-nitrobenzenesulfonamide was combined with zinc and ammonium chloride in methanol under the reaction conditions shown to afford 2-amino-N,N-dimethylbenzenesulfonamide in 99% yield.

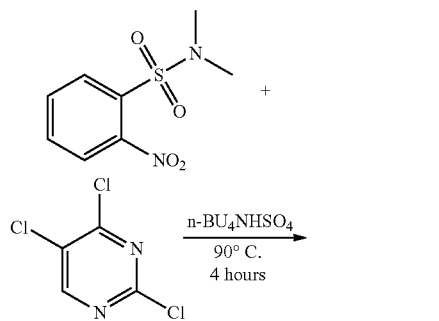

Figure 103A:
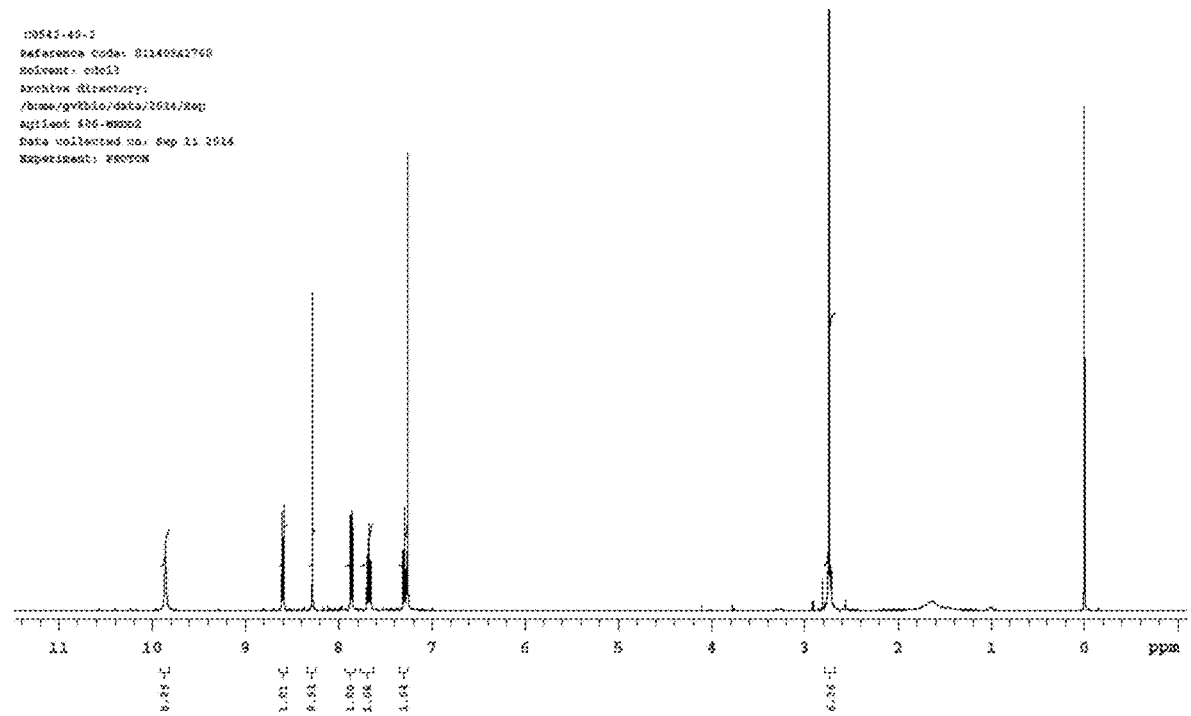
FIGS. 103A-103D show $^1$H (proton) NMR spectra for intermediates in the synthesis of the compound of structure (I).
Figure 103B:
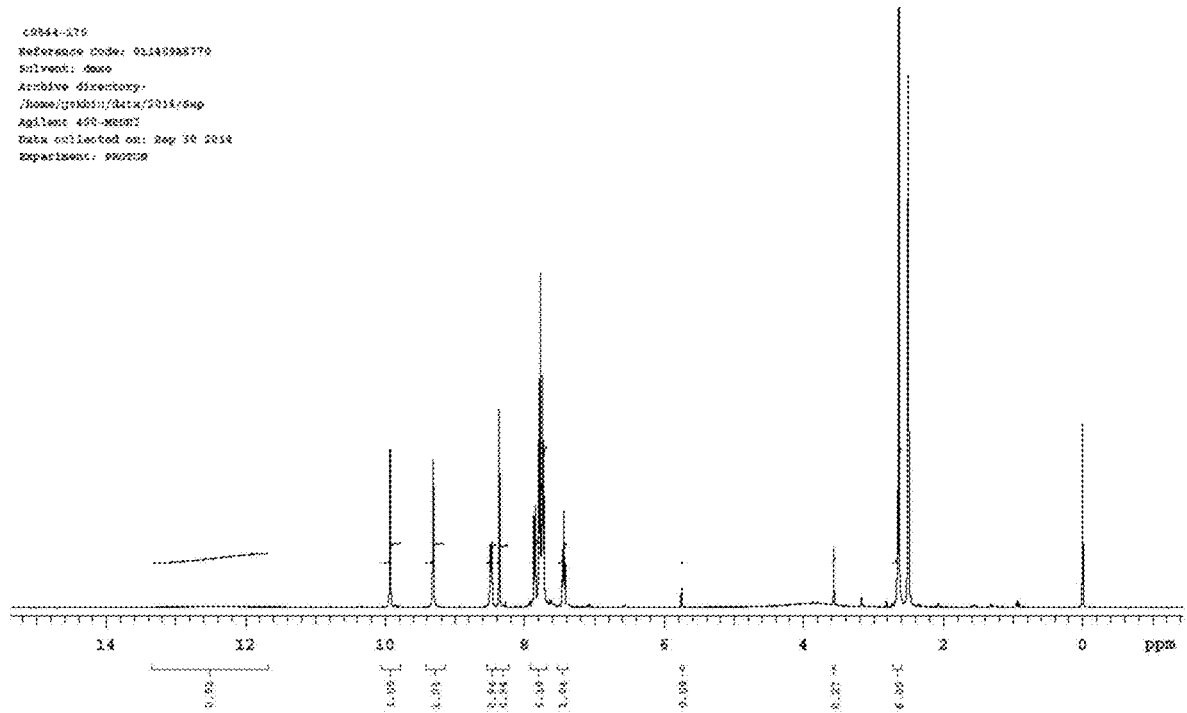
Figure 103C:
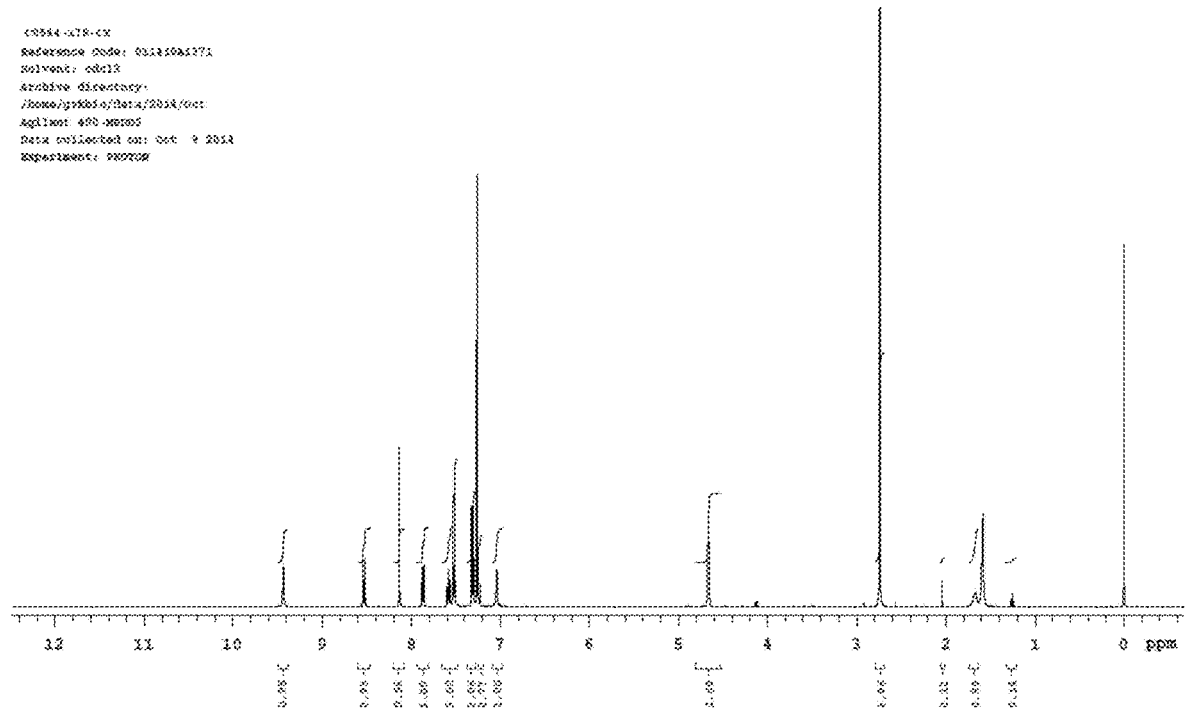

N,N-dimethylbenzenesulfonamide was combined with 2,4,5-trichloropyrimidine and tetrabutylammoniumhydrogen sulfate under the reaction conditions shown to afford 2-((2,5-dichloropyrimidin-4-yl)amino)-N,N-dimethylbenzenesulfonamide in 32% yield. ¹HNMR characterization data is shown in FIG. 103A.

chloric acid under the reaction conditions shown to afford 2-((5-chloro-2-((4-(hydroxymethyl)phenyl)amino)pyrimidin-4-yl)amino)-N,N-dimethylbenzenesulfonamide in 80% yield. ¹HNMR characterization data is shown in FIG. 103C.

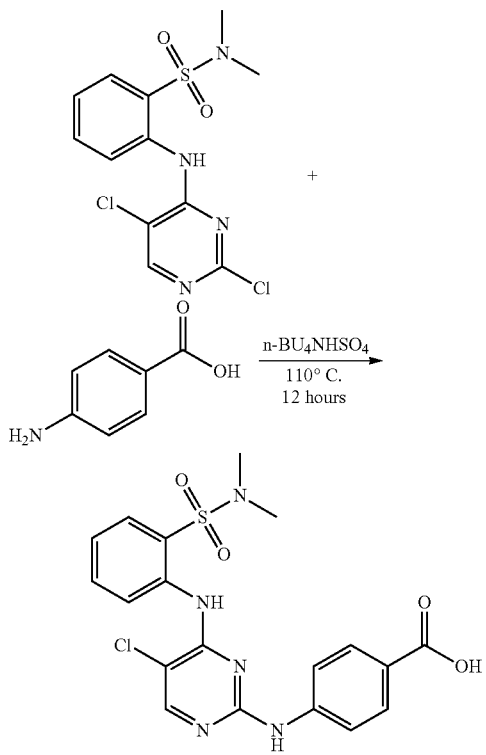

2-((2,5-dichloropyrimidin-4-yl)amino)-N,N-dimethylbenzenesulfonamide was combined with 4-aminobenzoic acid and tetrabutylammoniumhydrogen sulfate under the reaction conditions shown to afford 4-((5-chloro-4-((2-(N,N-dimethylsulfamoyl)phenyl)amino)pyrimidin-2-yl)amino)benzoic acid in 85% yield. ¹HNMR characterization data is shown in FIG. 103B.

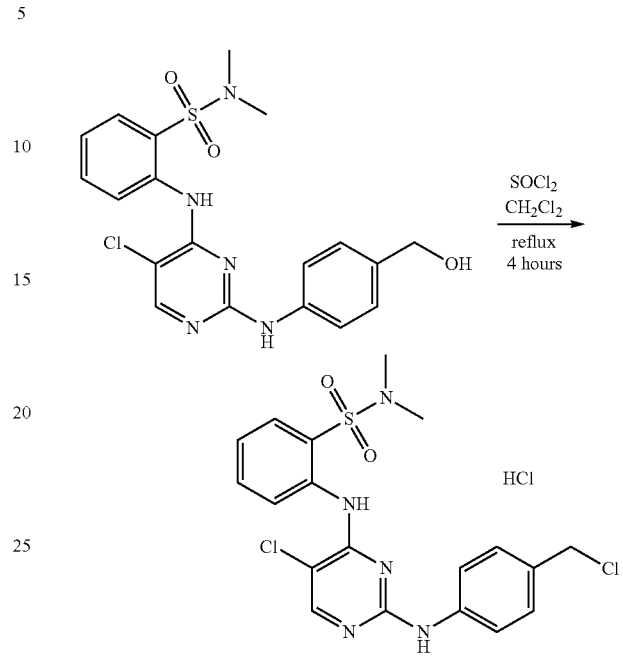

Figure 103D:
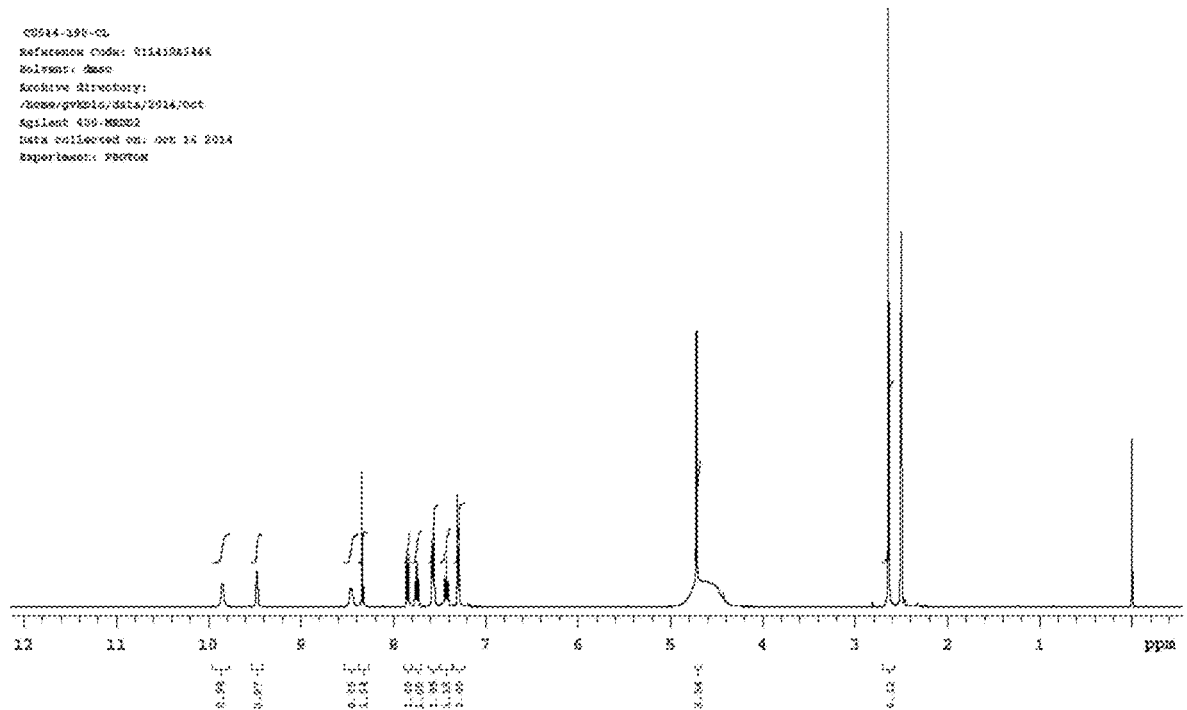

2-((5-chloro-2-((4-(hydroxymethyl)phenyl)amino)pyrimidin-4-yl)amino)-N,N-dimethylbenzenesulfonamide was combined with thionyl chloride in dichloromethane under the reaction conditions shown to afford 2-((5-chloro-2-((4-(chloromethyl)phenyl)amino)pyrimidin-4-yl)amino)-N,N-dimethylbenzenesulfonamide in 90% yield. ¹HNMR characterization data is shown in FIG. 103D.

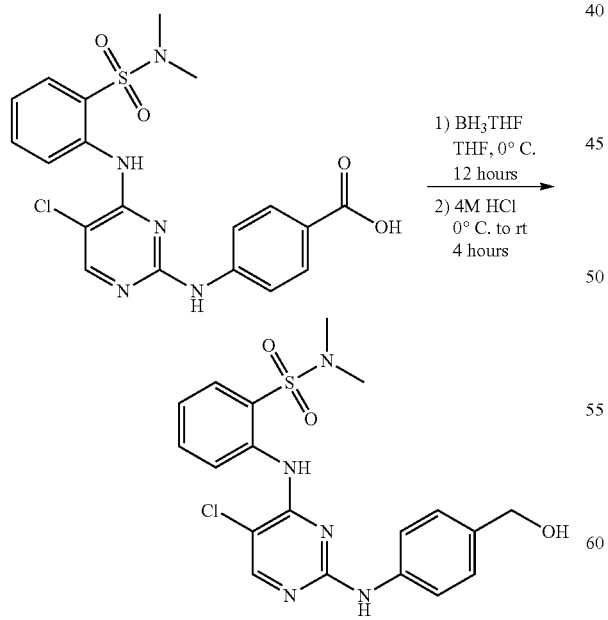

4-((5-chloro-4-((2-(N,N-dimethylsulfamoyl)phenyl)amino)pyrimidin-2-yl)amino)benzoic acid was combined with borane in tetrahydrofuran (1M) under the reaction conditions shown followed by treatment with 4 M hydro-

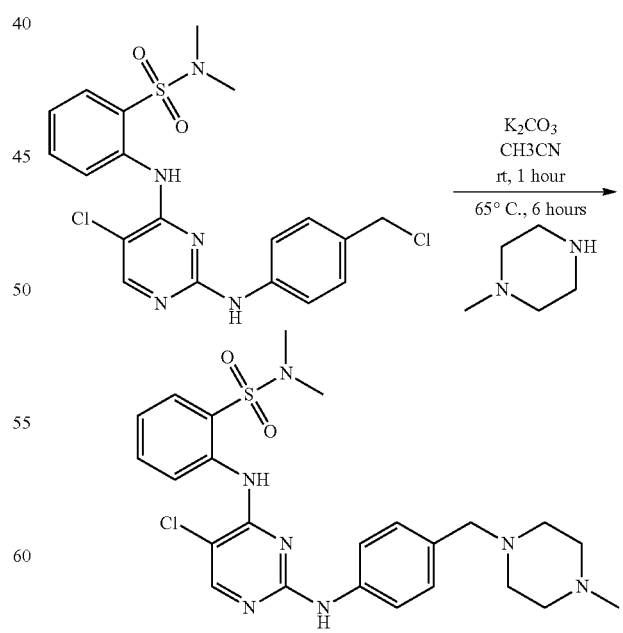

2-((5-chloro-2-((4-(chloromethyl)phenyl)amino)pyrimidin-4-yl)amino)-N,N-dimethylbenzenesulfonamide was combined with potassium carbonate and 1-methylpiperazine in acetonitrile under the reaction conditions shown to afford 2-((5-chloro-2-((4-((4-methylpiperazin-1-yl)methyl)phenyl)amino)pyrimidin-4-yl)amino)-N,N-dimethylbenzenesulfonamide (i.e., structure (I) or Compound 1) in 80% yield.

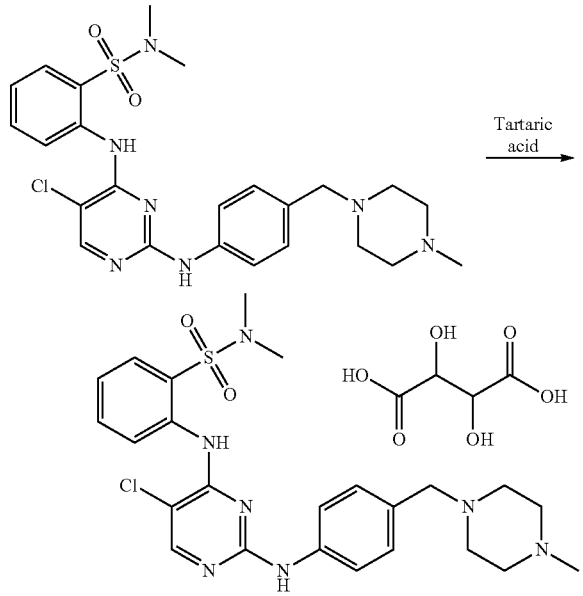

2-((5-chloro-2-((4-((4-methylpiperazin-1-yl)methyl)phenyl)amino)pyrimidin-4-yl)amino)-N,N-dimethylbenzenesulfonamide (i.e., structure (I) or Compound 1) was treated with tartaric acid to afford 2-((5-chloro-2-((4-((4-methylpiperazin-1-yl)methyl)phenyl)amino)pyrimidin-4-yl)amino)-N,N-dimethylbenzenesulfonamide mono-tartrate salt.

Example 5: Determination of Dosage and Treatment Outcomes

Groups of pluralities of patients (e.g., 3) are treated with a compound of structure (I), or a pharmaceutically acceptable salt thereof (e.g., a tartrate salt) using escalated doses until a maximum tolerated dose (MTD) is established ("the MTD expansion safety cohort"). Typically, in the absence of dose limiting toxicities (DLTs) doses are increased using a modified Fibonacci dose escalation scheme.

When the MTD is established, dosages are adjusted to an average dose administered in the MTD expansion safety cohort. Additional cohorts (e.g., 5) of patients with specific tumor types may be treated with a compound of structure (I), or a pharmaceutically acceptable salt thereof (e.g., a tartrate salt) to confirm safety, explore biomarkers, and evaluate potential signals of activity of a compound of structure (I), or a pharmaceutically acceptable salt thereof (e.g., a tartrate salt) is administered to specific groups of heavily pretreated patients (e.g., tumor patients that have progressed despite immunotherapy, EGFR+NSCLC patients that have progressed on ≤2 lines of tyrosine kinase inhibitors, BRAF-, KRAS- or NRAS-mutated colorectal carcinoma patients for whom no standard therapy remains, persistent/recurrent ovarian cancer patients that are or would be platinum refractory/resistant and BRAF-mutated melanoma patients that have not responded to immunotherapy or a combination of BRAF/MEK inhibitor) or given in combination with immunotherapy or a tyrosine kinase inhibitor.

In particular, when the MTD is confirmed, a single daily dose of a compound of structure (I), or a pharmaceutically acceptable salt thereof (e.g., a tartrate salt), is administered orally on days 1-21 of a 28 day cycle based on the average of the dose administered in the MTD expansion safety cohort.

Treatment outcomes may be evaluated by dose limiting toxicities and treatment emergent adverse events. Dose limiting toxicities and treatment emergent adverse events may include Grade 3 or greater febrile neutropenia, Grade 4 ANC for 7 or more consecutive days, Grade 4 thrombocytopenia or Grade 3 thrombocytopenia with clinically significant bleeding or that requires a platelet transfusion, Grade 3 or 4 non-hematologic adverse events including nausea, vomiting, diarrhea, and electrolyte imbalances persisting for more than 48 hours despite optimal medical management.

Treatment outcomes can also be evaluated by measuring plasma concentrations from blood taken from subjects at pre-dose, day 1 and day 21 (derived PK parameters by non-compartment analysis). For example, blood can be collected at 0.5, 1 2, 4, 8, 24 hours post-dose on day 1 and at 48 hours post dose on day 21. Plasma concentration calculated over time can be used to determine an area under the curve for time 0 to infinity, from time 0 to the last measured time point, and peak plasma concentration. Biomarkers in tumor tissue, PBMCs, plasma and serum are also assessed (e.g., using Spearman rank correlation statistic). PBMCs and serum are obtained prior to the first dose on day 1 and at 2, 6, and 24 hours after dosing, and again on day 8. A baseline tumor assessment is also performed and repeated after the 28 day cycle (i.e., cycle 2 and on even cycles thereafter).

Figure 3:
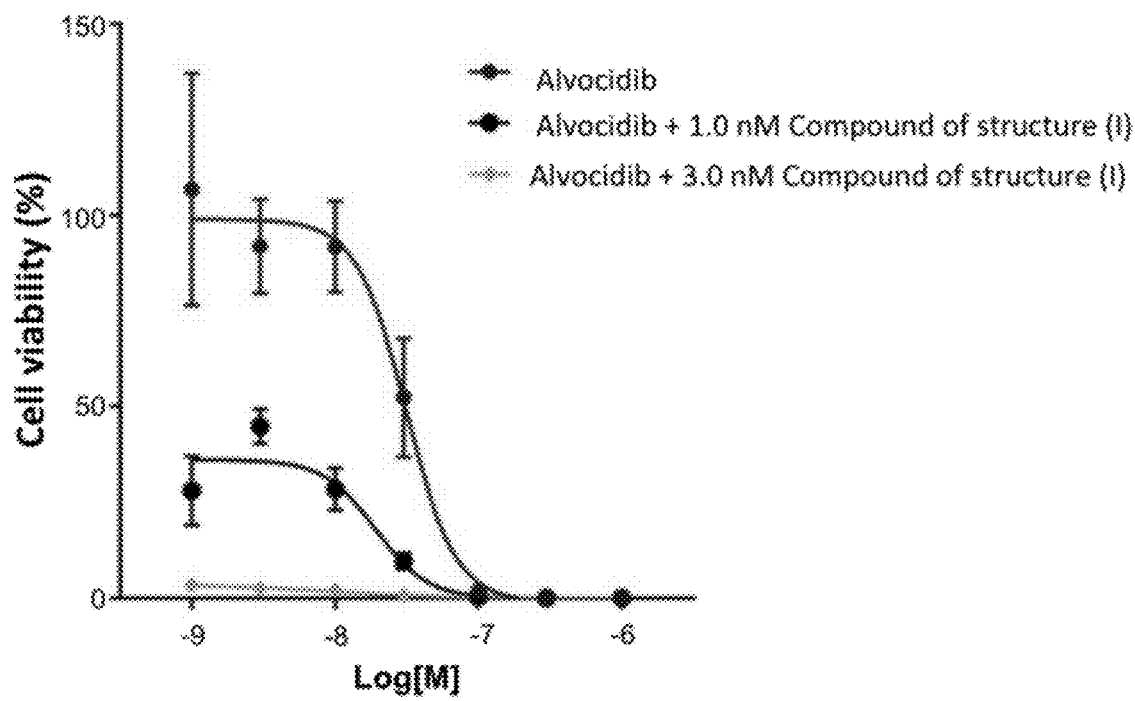
FIG. 3 provides cell viability data for combinations of a CDK inhibitor and an AXL kinase inhibitor in DOHH2 cells.

Example 6: Combination of CDK Inhibitor and AXL Kinase Inhibitor for Treatment of Cancer DOHH2 cells (a B-cell lymphoma cell line) were treated with either alvocidib alone or in combination with a tartare salt of the compound of structure (I) at 1 or 3 nM fixed concentrations and alvocidib at concentrations ranging from 1-1000 nM for 72 hours, as shown in FIG. 3. Single dose concentrations of a tartrate salt of the compound of structure (I) were added to varying alvocidib dilutions. Viability was assessed using CellTiter-Glo according to manufacturer protocol.

Figure 4:
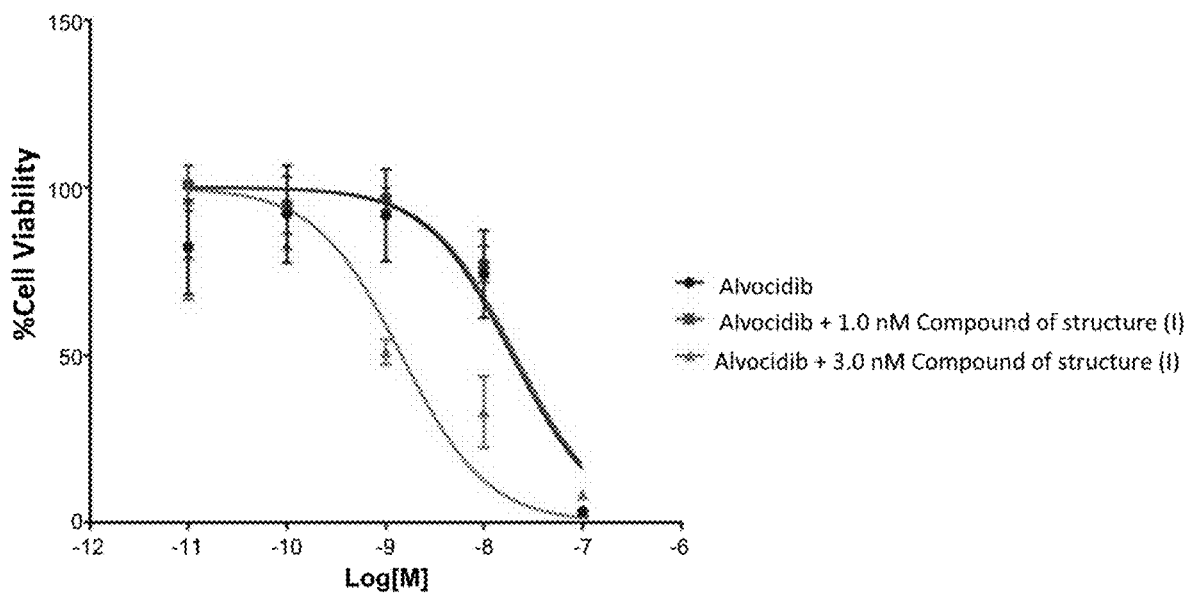
FIG. 4 is additional cell viability for combinations of a CDK inhibitor and an AXL kinase inhibitor in HCT-116 cells.

HCT-116 cells (a KRAS mutant colorectal cancer cell line) were treated with either alvocidib alone or a combination of a tartrate salt of the compound of structure (I) at 1 or 3 nM fixed concentrations and alvocidib at concentrations ranging from 0.01-100 nM for 72 hours as shown in FIG. 4 for 72 hours. Single dose concentrations of a tartrate salt of the compound of structure (I) were added to varying alvocidib dilutions. Viability was assessed using CellTiter-Glo according to manufacturer protocol.

The data in FIGS. 3 and 4 show that a CDK inhibitor, such as alvocidib, synergizes with an AXL kinase inhibitor, such as a tartrate salt of the compound of structure (I), to potently reduce cell viability of cancer cells.

Figure 5:
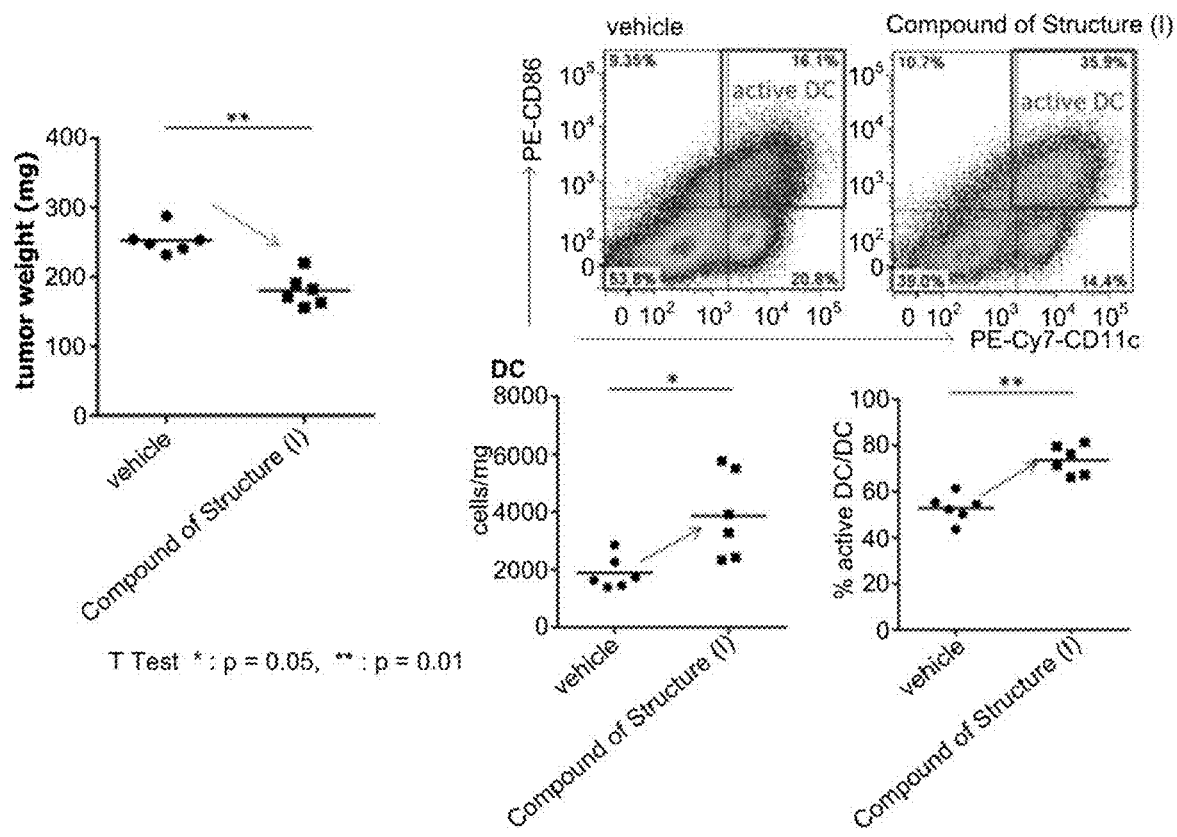
FIG. 5 shows an increased number of active DCs within tumors following administration of an AXL kinase inhibitor.

Example 7: Increased Active DCs in Tumors Following Administration of an AXL Kinase Inhibitor Mice were treated with a tartrate salt of the compound of structure (I) at a concentration of 60 mg/kg. Tumors were assayed by flow cytometry to measure the presence of active DCs using a CD86 antibody and a CD11c antibody. FIG. 5 shows that the percent of activated DCs in tumors cells is increased following treatment with an AXL kinase inhibitor as compared to treatment with a negative control (vehicle).

Example 8: Combination of AXL Kinase Inhibitor and a PD1/PD-L1 Checkpoint Inhibitor for Treatment of Cancer Mice were treated with a tartrate salt of the compound of structure (I) alone (at 60 mg/kg), a PD-L1 antibody alone (200 µg), or both in combination. Tumor volume was measured for fifteen days following inoculation.

Figure 6A:
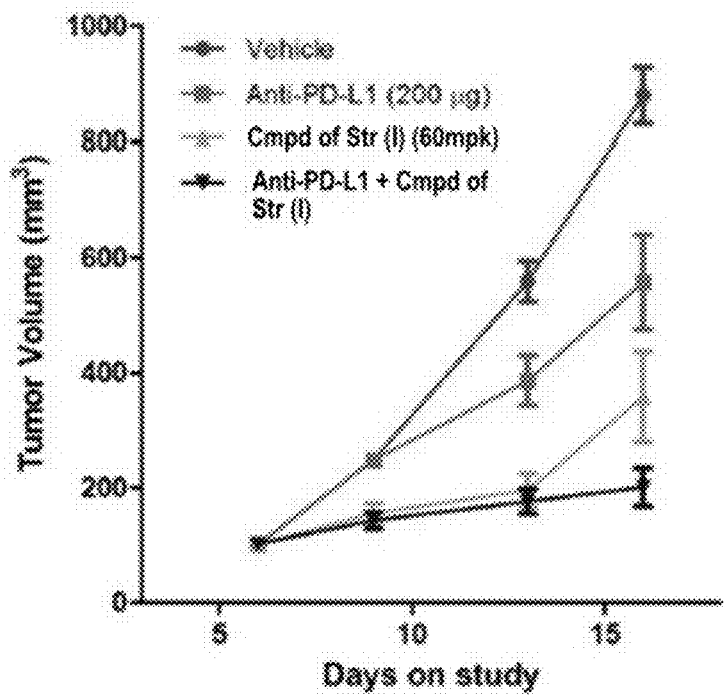
FIG. 6A shows tumor volume and FIG. 6B shows and body weight following treatment with an AXL kinase inhibitor and a PD-L1 antibody in the 4T-1 breast cancer syngraft in mice.
Figure 6B:
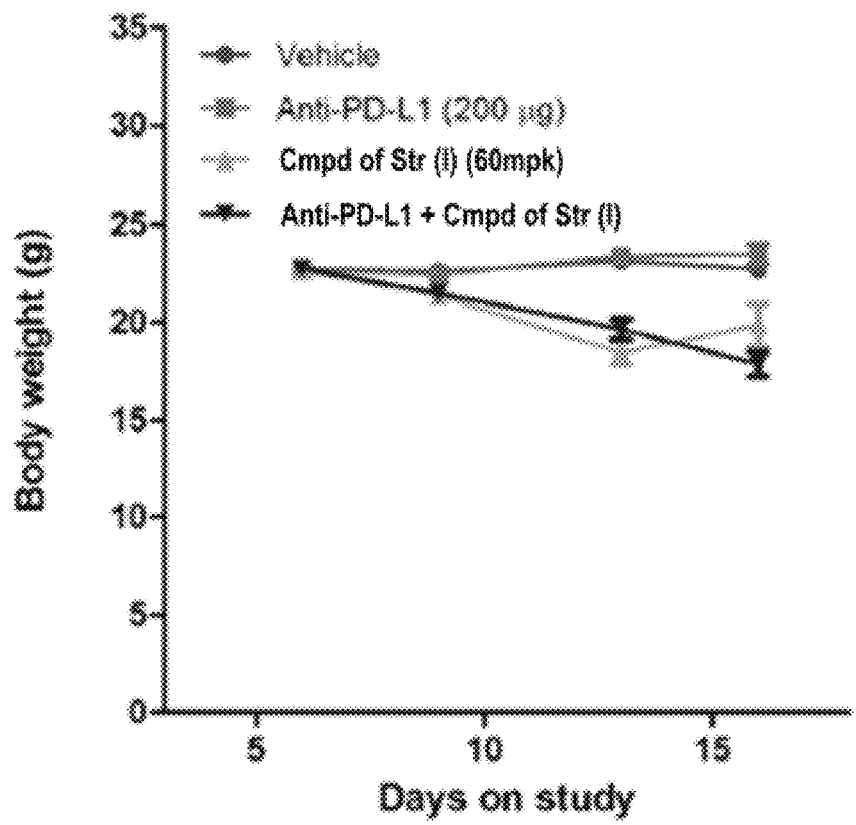

FIGS. 6A and 6B show treatment with a tartrate salt of a compound of structure (I) effects in the 4T1 breast cancer syngraft in mice. (FIG. 6A) Tumor volumes are shown following the treatment of a tartrate salt of a compound of structure (I) at a concentration of 60 mg/kg and/or anti-PD-L1 antibody (200 pg/mouse/dose). Combination treatment appears to have the greatest anti-tumor effect in this model. (FIG. 6B) Comparable body weight losses were observed for single agent using a tartrate salt of a compound of structure (I), and the combination treatment with anti-PD-L1 antibody.

The tartrate salt of the compound of structure (I) achieved a tumor growth inhibition (% TGI) of 67.1% as a single agent, while anti-PD-L1 achieved % TGI of 41.5% in this model. The combination induced a % TGI of 87.3%, over the 16 day treatment schedule.

% TGI is the tumor volume for a given treatment group compared to the vehicle control group, i.e., (1−(TVtreatment/TVvehicle))*100. Tumor volumes were measured in two dimensions using a caliper, and the volume was expressed in mm3 using the formula: V=(L×W×W)/2, where V is tumor volume, L is tumor length (the longest tumor dimension) and W is tumor width (the longest tumor dimension perpendicular to L).

Figure 7:
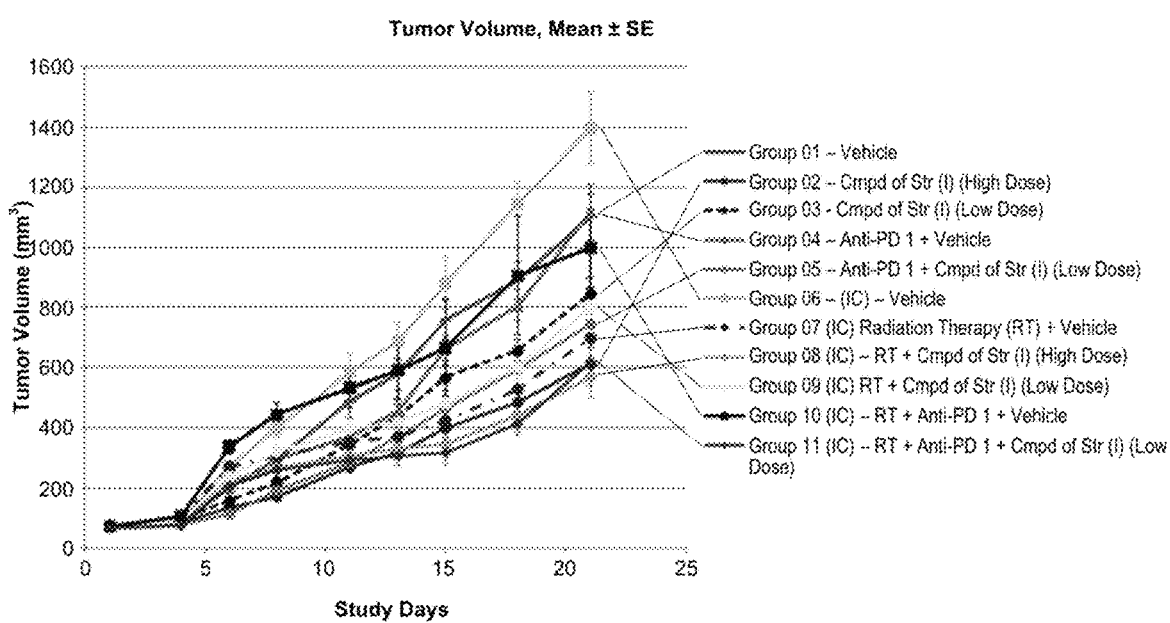
FIG. 7 shows tumor volume following treatment with an AXL kinase inhibitor and a PD1 antibody, with or without radiation therapy, in a mouse breast cancer model.
Figure 8:
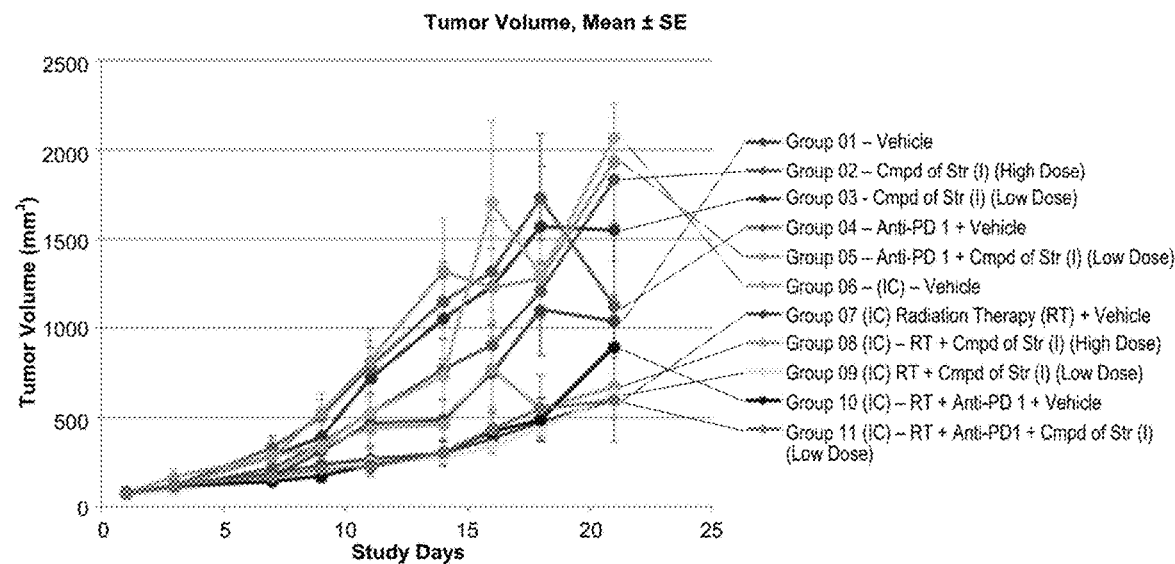
FIG. 8 shows tumor volume following treatment with an AXL kinase inhibitor and a PD1 antibody, with or without radiation therapy, in a mouse melanoma model.
Figure 9:
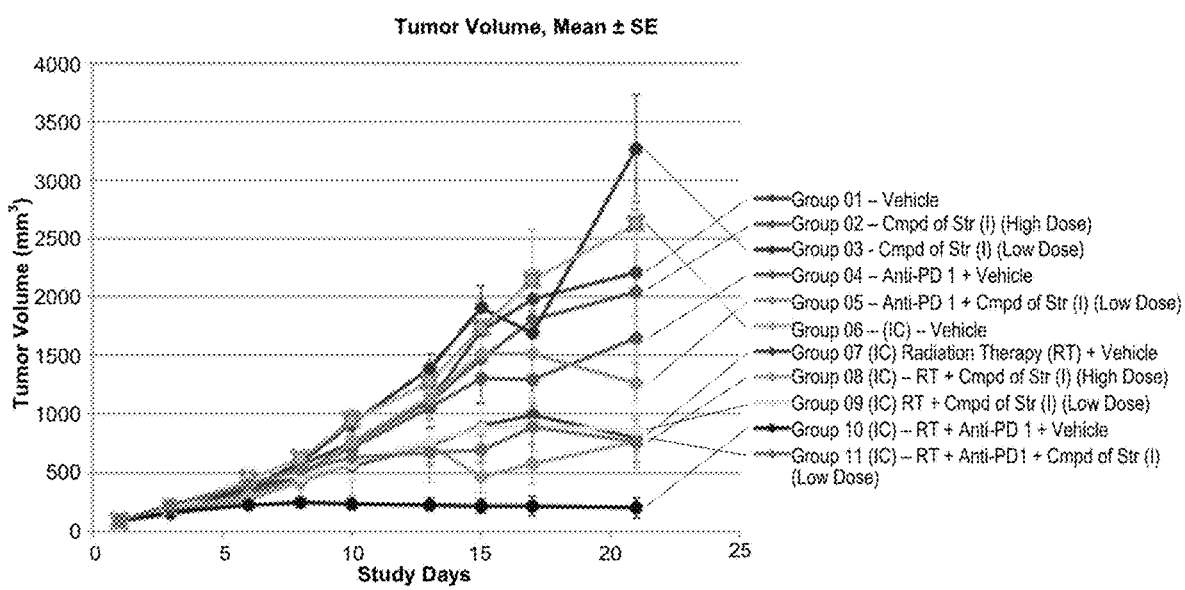
FIG. 9 shows tumor volume following treatment with an AXL kinase inhibitor and a PD1 antibody in a mouse colorectal cancer model.
Figure 10:
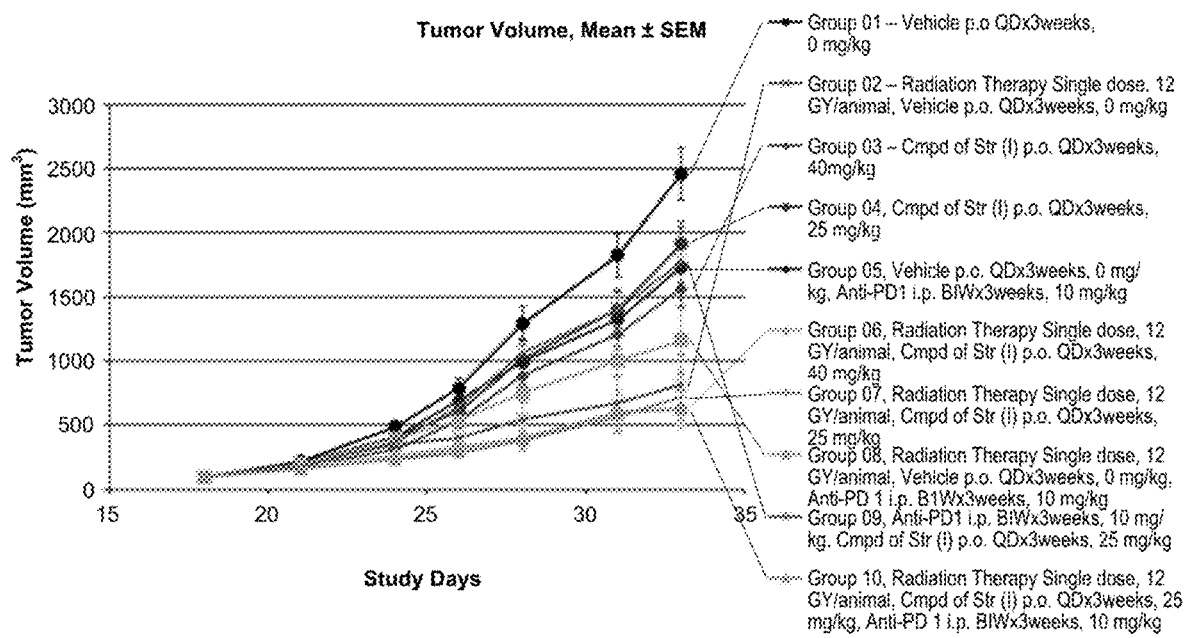
FIG. 10 shows tumor volume following treatment with an AXL kinase inhibitor and a PD1 antibody in a mouse lung cancer model.

In a second set of experiments, mice were treated with a tartrate salt of the compound of structure (I) alone (at 25 mg/kg as the "low dose" and 40 mg/kg as the "high" dose), an anti-PD-1 antibody alone (10 mg/kg), or both in combination, with or without single dose radiation therapy at 12 GY/animal. Tumor volume was measured for several days. FIG. 7 shows the efficacy of the combination treatment in a mouse allograft model of breast cancer (4T1). FIG. 8 shows the efficacy of the combination treatment in a mouse model of melanoma (B16). FIG. 9 shows the efficacy of the combination treatment in a mouse model of colorectal cancer (CT26). FIG. 10 shows the efficacy of the combination treatment in a mouse model of lung cancer (Lewis lung).

Figure 11A:
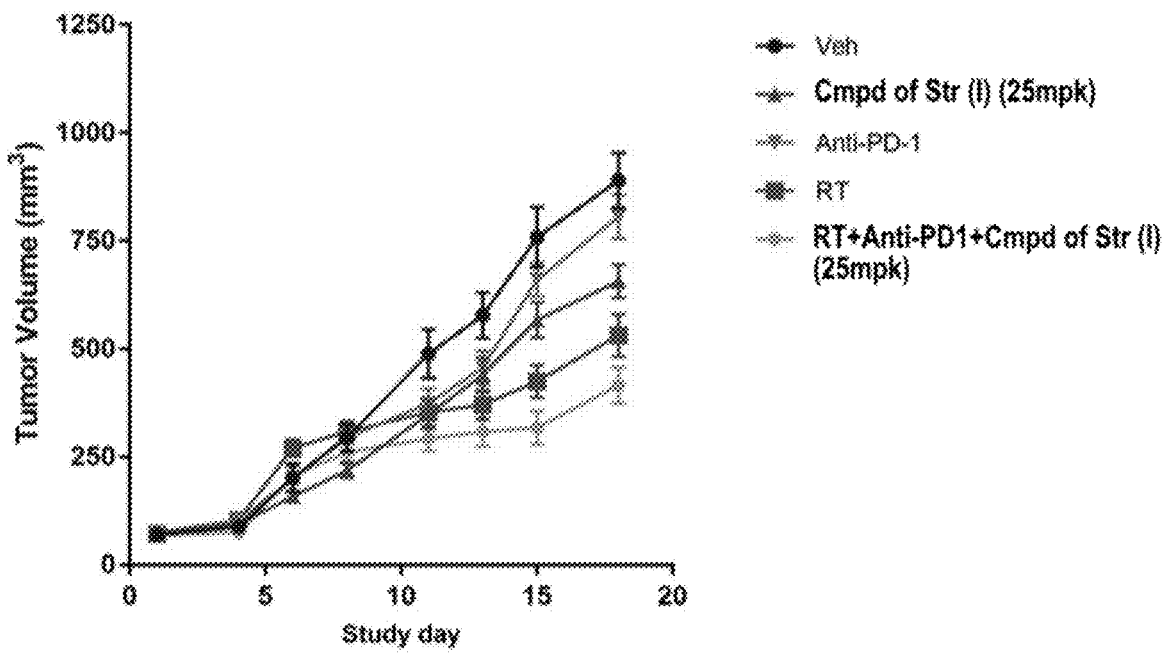
FIG. 11A and FIG. 11B show activity of a compound of structure (I) in a syngeneic mouse model for breast cancer.
Figure 11B:
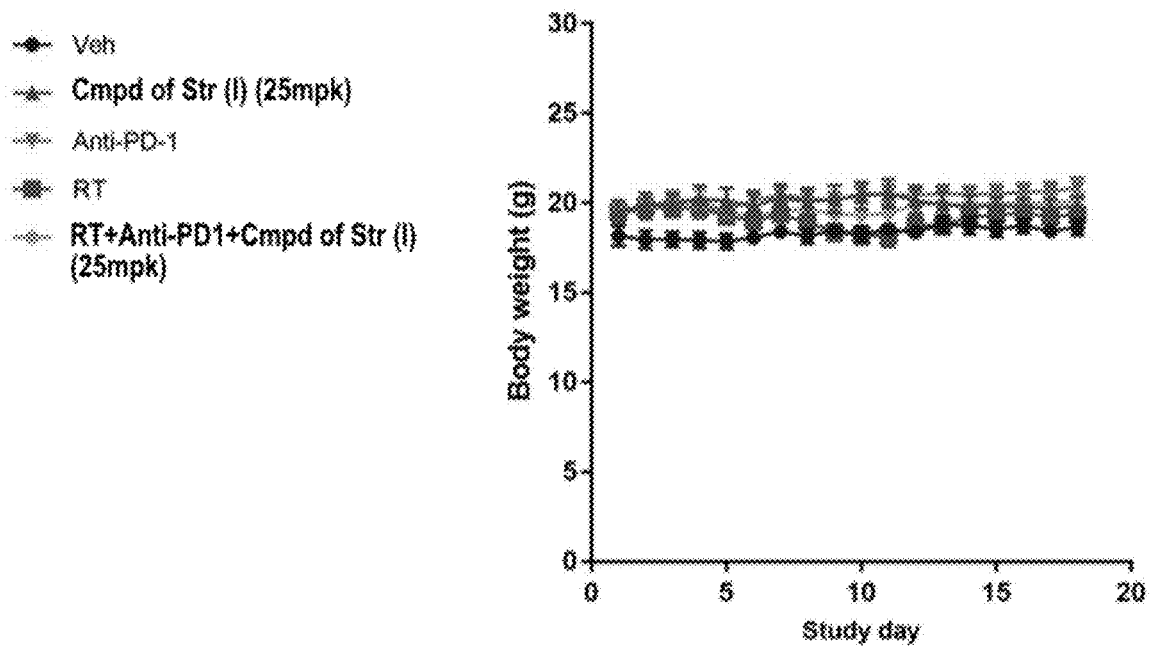

In a third experiment, the in vivo activity of a tartrate salt of the compound of structure (I) as a single agent, and combinations with immune checkpoint blockade (anti-PD-1) and radiation therapy (RT), were assessed in the 4T1 syngeneic (allograft) mouse model for breast cancer. A tartrate salt of the compound of structure (I) was dosed qd by oral gavage at 25 mg/kg. Anti-PD-1 antibody was dosed at 10 mg/kg, biw, intraperitoneally. Mice dosed with radiation were given a single dose of 12 GY. FIG. 11A shows tumor volumes and FIG. 11B shows body weights for animals on study.

A tartrate salt of the compound of structure (I) achieved a tumor growth inhibition (% TGI) of 28.4% as a single agent, while anti-PD-1 and RT each alone achieved % TGI of 10.2% and 43.7%, respectively. However, the combination of all three induced a % TGI of 57.7%, over the 18 day treatment schedule.

The pharmacokinetic profile of a tartrate salt of the compound of structure (I) in a 4T1 model was also assessed. FIG. 114 shows pharmacokinetic profile of a tartrate salt of the compound of structure (I) in 4T1 model. 4T1 bearing mice were treated with 60 mpk of a tartrate salt of the compound of structure (I) tartrate p.o. Tumor and blood were collected at the indicated time points.

The effect of a tartrate salt of the compound of structure (I) on cytokines in serum in a 4T1 model was also assessed (FIG. 115). Balb/c mice were transplanted with 4T1 cells orthotopically. 7 days after transplantation, the compound of structure (I) tartrate was administrated (60 mg/kg, p.o., Q.D.). Whole blood was collected 2, 6, and 24 hour after the last dosage on Day 12. Cytokines in serum were measured with Milliplex assay. Normal indicates healthy mouse without tumor, n=6 (vehicle: n=5, normal: n=3). Error Bar indicates SD. N.D indicates "no data".

Figure 12:
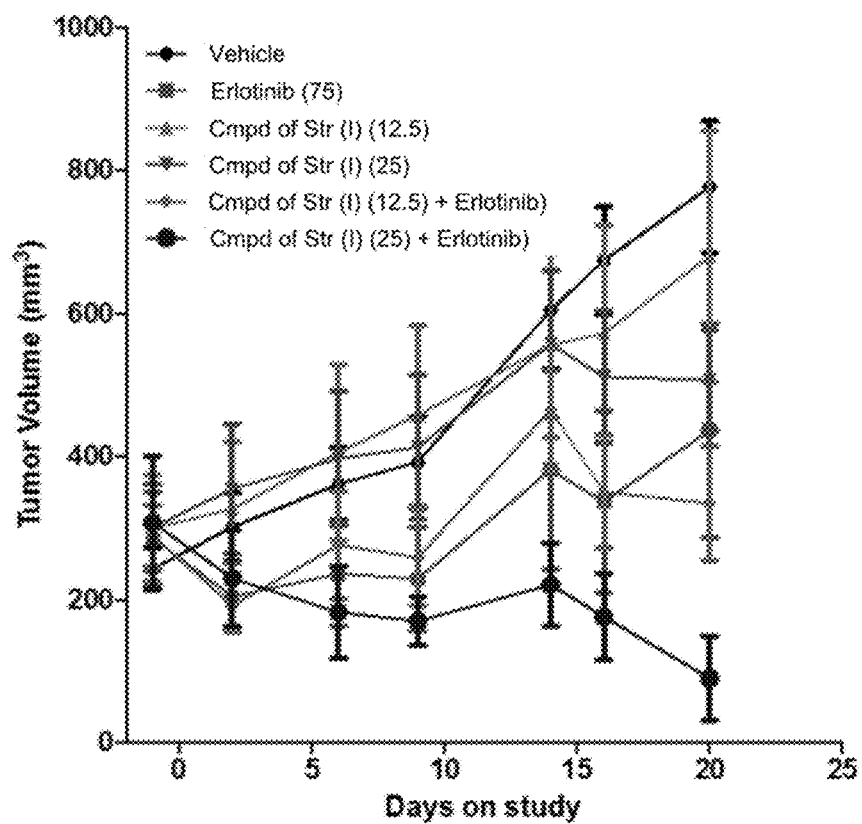
FIG. 12 shows tumor volume following treatment with an AXL kinase inhibitor and an EGFR inhibitor in an EGFR mutated lung cancer model.

Example 9: Combination of AXL Kinase Inhibitor and an EGFR Inhibitor for the Treatment of Cancer Using the H1650 xenograft model, which is an EGFR mutated lung cancer model, mice were treated with a tartrate salt of the compound of structure (I) alone (at 12.5 or 25 mg/kg), an EGFR inhibitor (erlotinib) alone (75 mg/kg), or both in combination. Tumor volume was measured for several days. FIG. 12 shows that a tartrate salt of the compound of structure (I) and the EGFR inhibitor have synergistic effects in an EGFR mutated lung cancer model.

Figure 13:
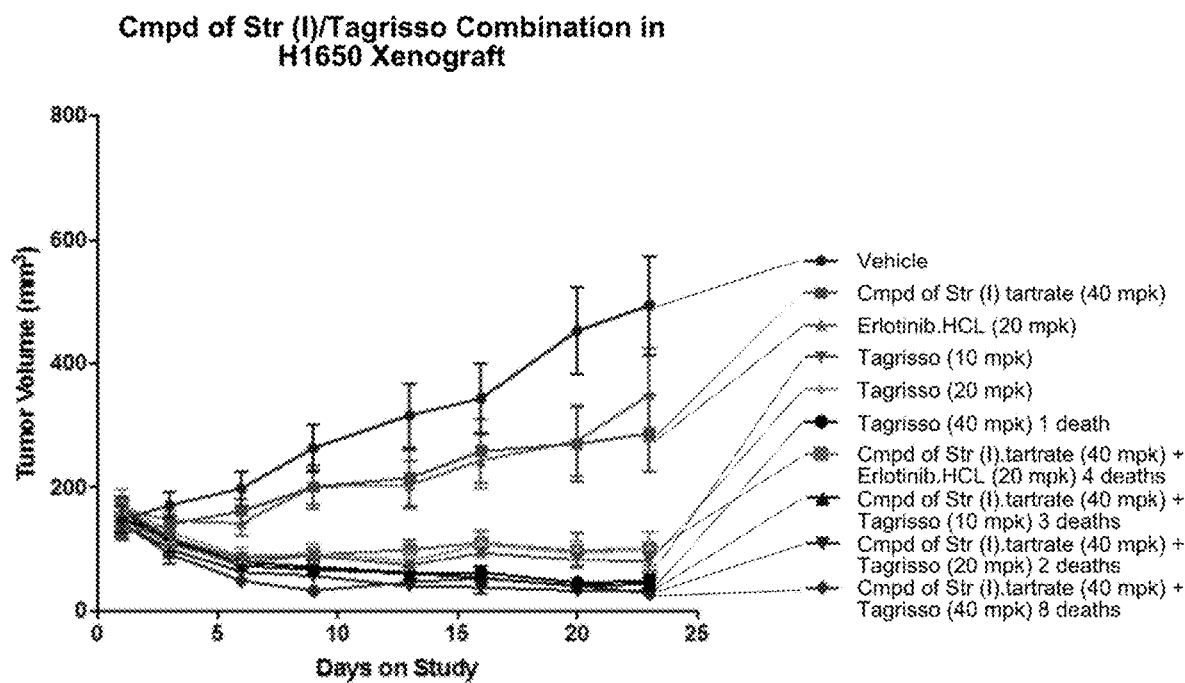
FIG. 13 shows tumor volume following treatment with an AXL kinase inhibitor and two different EGFR inhibitors in an EGFR mutated lung cancer model.

Using the H1650 xenograft model, mice were treated with a tartarate salt of the compound of structure (I) alone (40 mg/kg), an EGFR inhibitor alone (either erlotinib-HCl at 20 mg/kg or osimertinib at 10, 20, or 40 mg/kg), or combinations of the tartarate salt of the compound of structure (I) and the EGFR inhibitors. Tumor volume was measured for several days. FIG. 13 shows the efficacy of the combinations of the tartarate salt of the compound of structure (I) and the EGFR inhibitors.

Example 10: AXE Inhibition Leads to a Reversal of a Mesenchymal Phenotype, Sensitizing Cancer Cells to Targeted Agents and Immuno-Oncology Therapies Mesenchymal properties and the epithelial-to-mesenchymal transition (EMT) contribute to the initiation and progression of many tumor types and ultimately can lead to drug resistance and highly aggressive disease. It was found that a tartrate salt of a compound of structure (I), a potent AXE inhibitor, leads to a reversal of the mesenchymal phenotype in multiple cancer models. Following treatment with a tartrate salt of a compound of structure (I), changes in mRNA expression were observed using RT-qPCR and protein expression using standard immunoblotting that are consistent with a reversal of the mesenchymal phenotype (see, for example, FIGS. 14 and 15).

Figure 14:
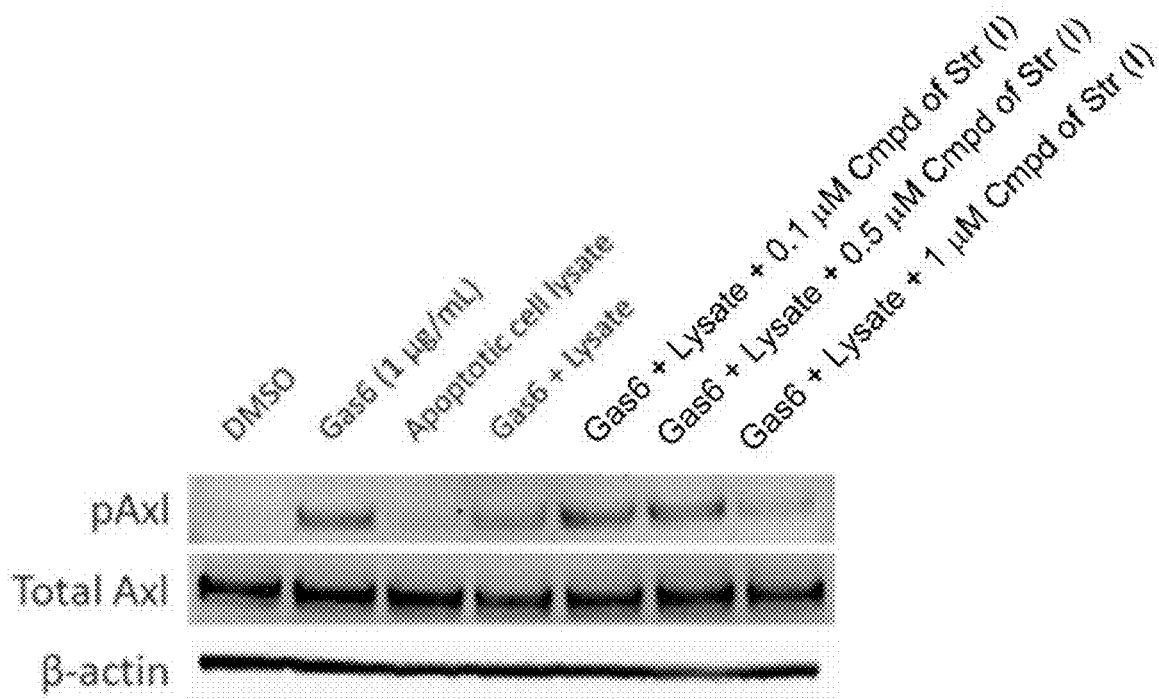
FIG. 14 shows protein expression levels of pAXL and total AXL.

FIG. 14 shows protein levels of pAXF and total AXE. Panc-1 cells were pre-treated with 0.1-1 µM of a tartrate salt of a compound of structure (I) for 1 hour, then AXE phosphorylation was induced by a 10-minute treatment of an apoptotic cell lysate and GAS6. Fysate and GAS6 treatment leads to phosphorylation of AXE. A tartrate salt of a compound of structure (I) inhibits the phosphorylation of AXE in a dose-dependent fashion.

Figure 15A:
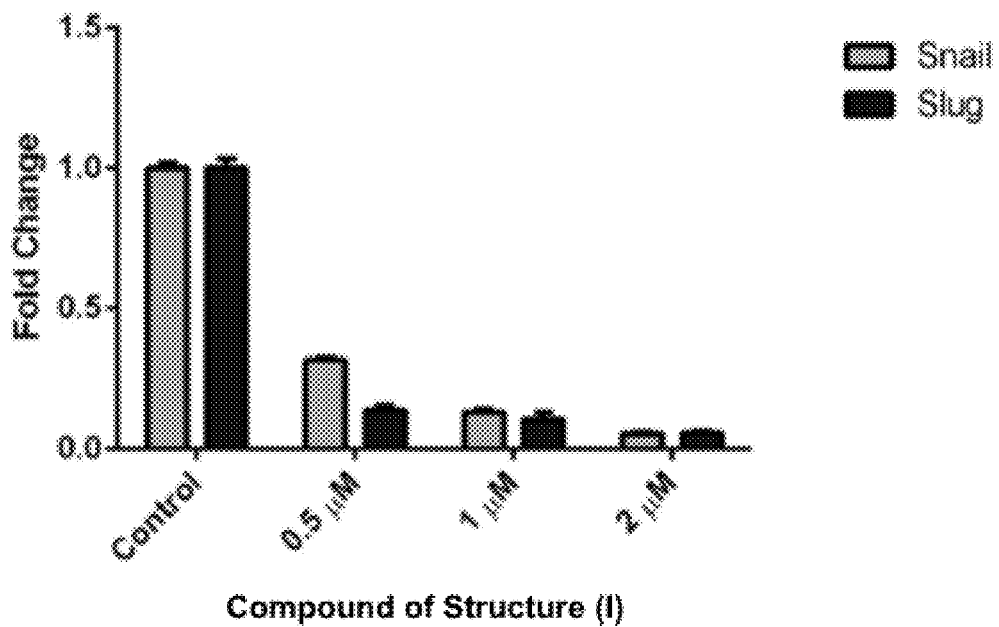
FIG. 15A and FIG. 15B show changes in EMT marker expression after treatment with a compound of structure (I).
Figure 15B:
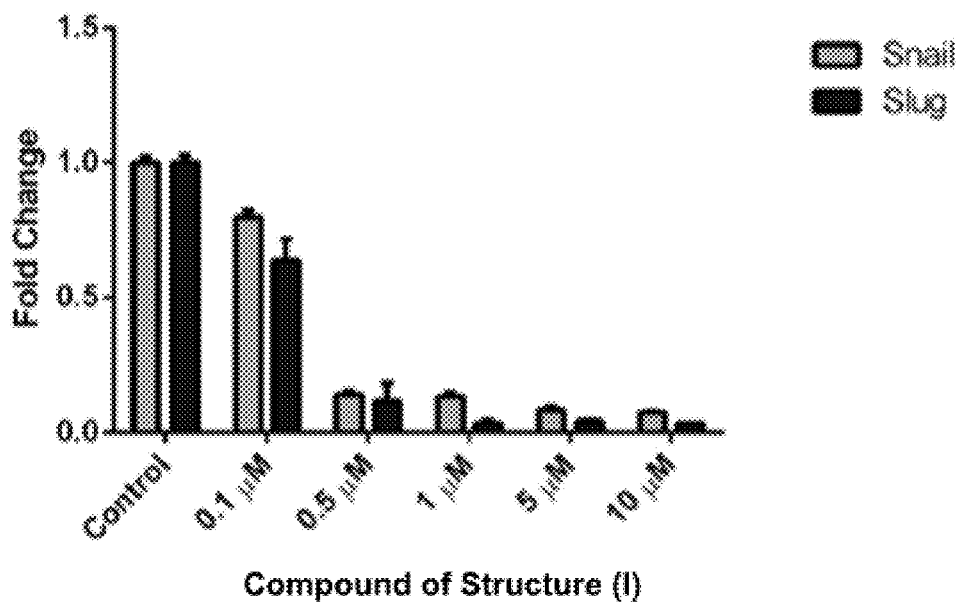

FIG. 15A and FIG. 15B show changes in EMT marker expression after 2 hours of treatment with a tartrate salt of a compound of structure (I). Cells were treated with a single dose of a tartrate salt of a compound of structure (I). Snail (SNAI1) and Slug (SNAI2) levels were measured via RT-qPCR after 2 hours. A concentration-dependent inhibition of expression levels is observed in (FIG. 15A) MV4-11 and (FIG. 15B) A549 cells.

Figure 16A:
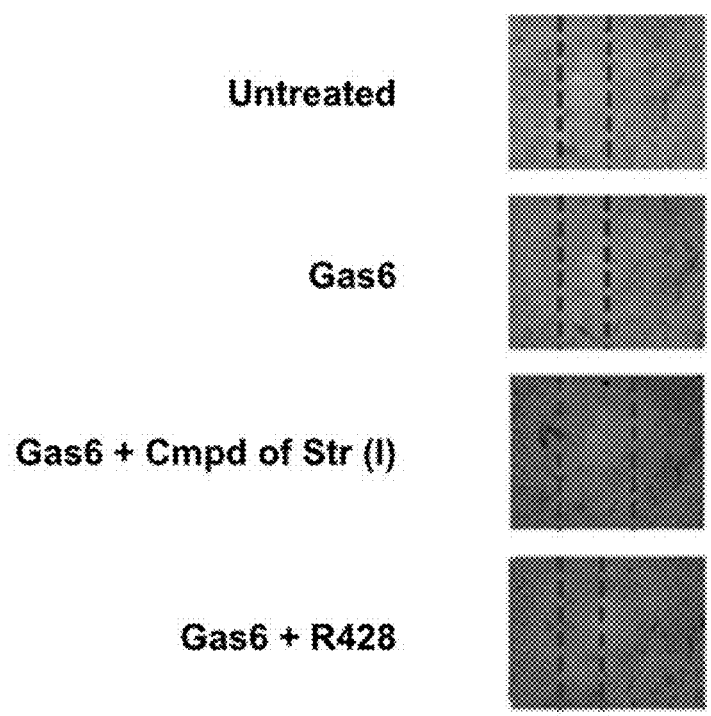
FIG. 16A and FIG. 16B show effects of treatment with a compound of structure (I) on the migration of Panc-1 or Aspc-1 cells.
Figure 16B:
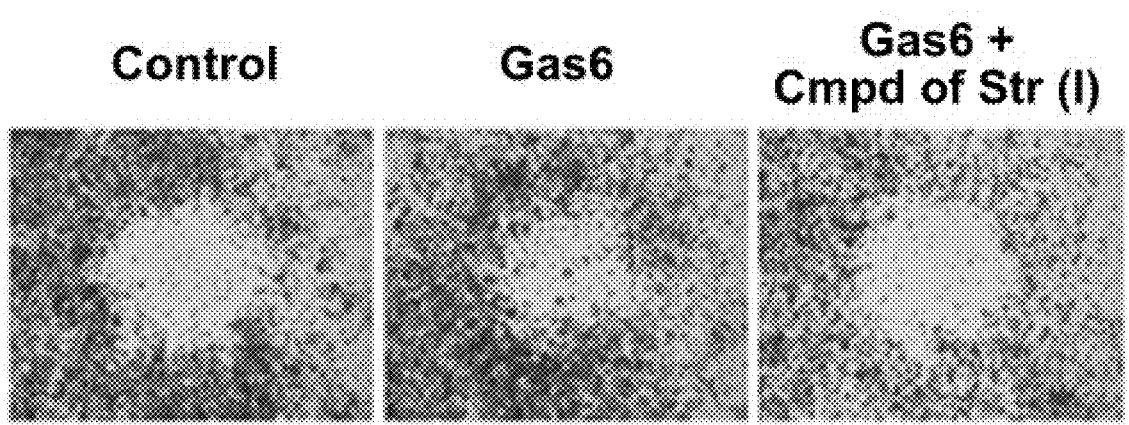

Upon treatment with a tartrate salt of a compound of structure (I), cancer cells possessed lower motility and a decrease in anchorage-independent growth, both hallmarks of a mesenchymal cell (see for example, FIG. 16A and FIG. 16B).

FIG. 16A and FIG. 16B show effects of treatment with a tartrate salt of a compound of structure (I) on the migration of Panc-1 or Aspc-1 cells. (FIG. 16A) The effect of treatment with a tartrate salt of a compound of structure (I) on the migration of Panc-1 cells was assessed in a scratch assay. Confluent cells were scratched, and then treated for 24 hours with GAS6, 0.5 µM of a tartrate salt of a compound of structure (I), or R428. Treatment with a tartrate salt of a compound of structure (I) reduces migration following treatment. (FIG. 16B) The effect of a tartrate salt of a compound of structure (I) treatment on the anchorage independent migratory capability of Aspc-1 cells in a soft agar assay. Treatment with a compound of structure (I) again reduces migration in this assay.

In vivo models of erlotinib-resistant non-small cell lung cancer (NSCLC) were utilized to demonstrate single agent activity of a tartrate salt of a compound of structure (I) in highly mesenchymal models. Additionally, treatment with a tartrate salt of a compound of structure (I) was able to sensitize this highly refractory model to erlotinib (see for example FIGS. 17 and 18).

Figure 17A:
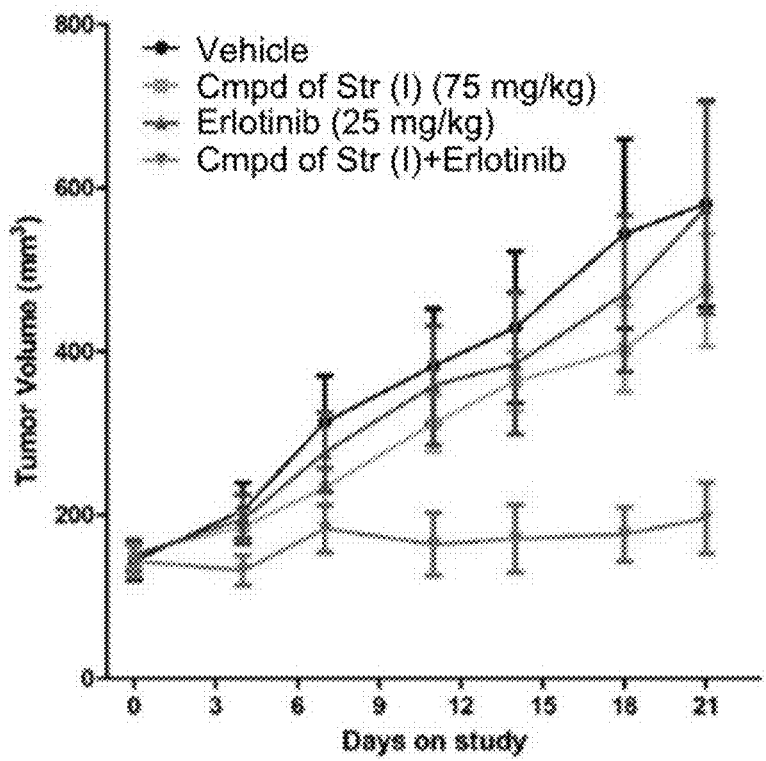
FIG. 17A and FIG. 17B show treatment effects of a compound of structure (I), in combination with erlotinib, in an in vivo xenograft model for lung cancer.
Figure 17B:
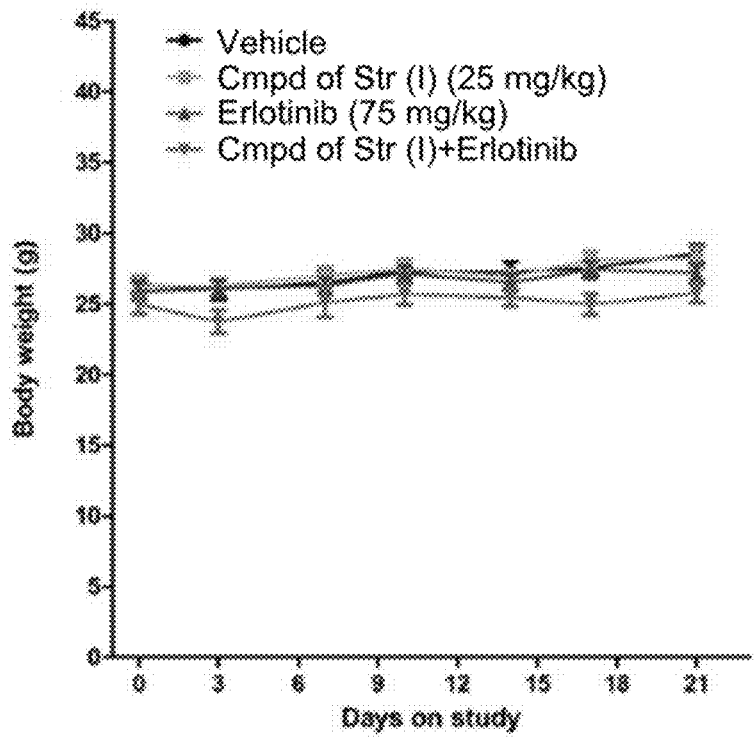

FIG. 17A and FIG. 17B show treatment effects of a tartrate salt of a compound of structure (I), in combination with erlotinib, in an in vivo xenograft model for lung cancer. A549 cells were injected subcutaneously into the hind flank of athymic nude mice at $1\times10^7$ cells/mouse. Once tumor volumes reached 100 mm$^3$, mice were randomized into study arms. Mice were treated with a "two day on, two day off" dosing schedule with a tartrate salt of a compound of structure (I) (75 mg/kg) and/or erlotinib (25 mg/kg). This dosing level and schedule was tolerated well in the animals (FIG. 17B). Combination treatment resulted in maintenance of tumor volumes (FIG. 17A), and was synergistic relative to treatment of either drug as a single agent.

Figure 18A:
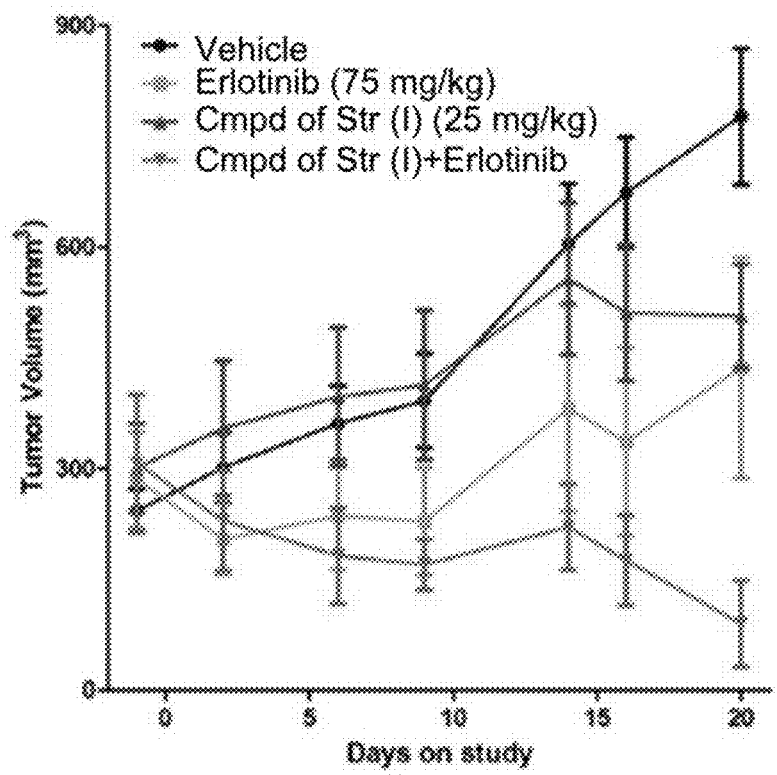
FIG. 18A and FIG. 18B show treatment effects of a compound of structure (I), in combination with erlotinib, in an in vivo xenograft model for lung cancer.
Figure 18B:
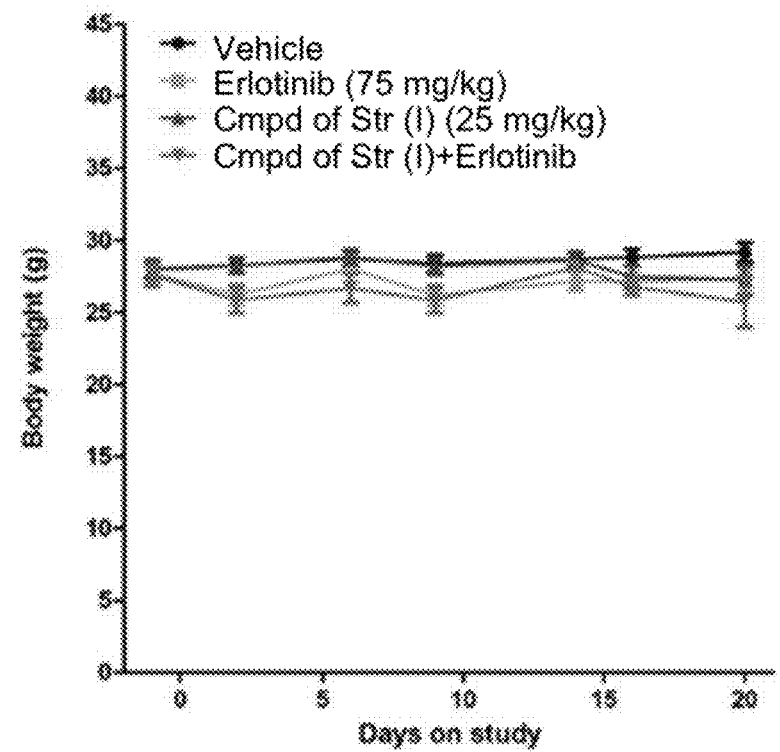

FIGS. 18A and 18B show treatment effects of a tartrate salt of a compound of structure (I), in combination with erlotinib, in an in vivo xenograft model for lung cancer. H1650 cells were injected subcutaneously into the hind flank of athymic nude mice at $1\times10^7$ cells/mouse. Once tumor volumes exceeded 100 mm$^3$, mice were randomized into study arms. Mice were treated with a "three day on, three day off" dosing schedule with a tartrate salt of a compound of structure (I) at a concentration of 12.5 or 25 mg/kg, and/or erlotinib (75 mg/kg). This dosing level and schedule was tolerated well in the animals (FIG. 18B). Combination treatment resulted in significant regression of tumor volumes (FIG. 18A), and was synergistic relative to treatment of either drug as a single agent.

Figure 19A:
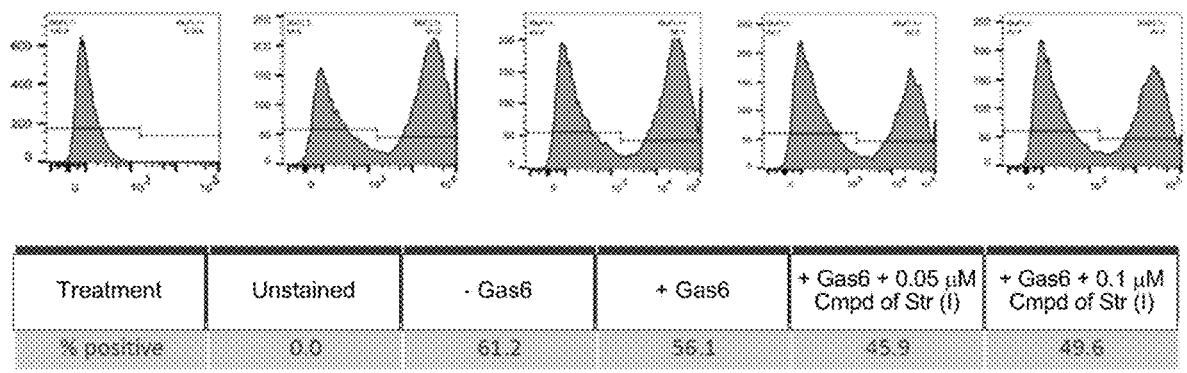
FIG. 19A and FIG. 19B show efferocytosis assays interrogating the effects of a compound of structure (I) treatment in phorbol ester (PMA) treated THP-1 cells (macrophage induction).
Figure 19B:
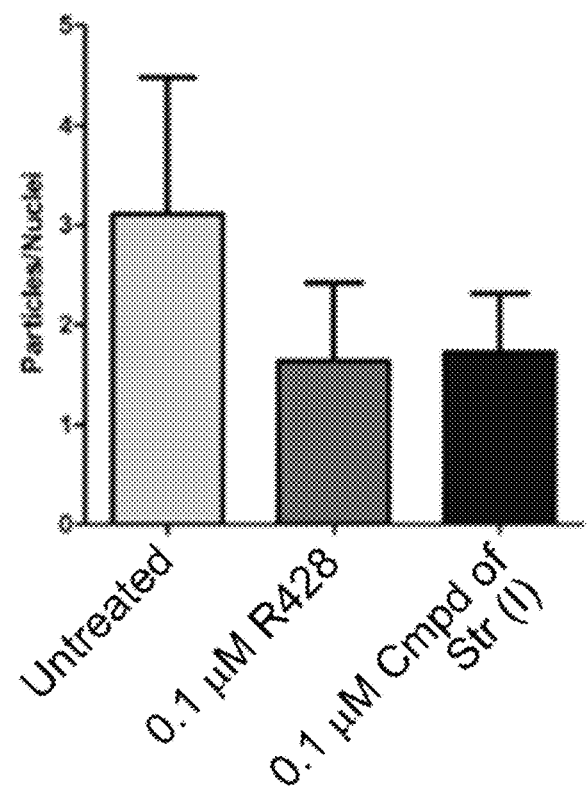

Inhibition of AXL by can inhibit tumor-associated efferocytosis leading to a stronger immunogenic response to the tumor. As shown in FIG. 19A and FIG. 19B, treatment with a tartrate salt of a compound of structure (I) impairs the AXL-mediated phagocytosis of apoptotic bodies. Efferocytosis assays interrogating the effects of a tartrate salt of a compound of structure (I) treatment in phorbol ester (PMA) treated THP-1 cells (macrophage induction) were performed. (FIG. 19A) THP-1 cells were pre-treated with a tartrate salt of a compound of structure (I) and GAS6, followed by treatment with fluorescently labeled apoptotic lysate (staurosporine-treated A549 cell lysate). Following 24-hour incubation, flow cytometry was performed to assess the ability of THP-1 cells to phagocytose apoptotic bodies. (FIG. 19B) A similar experiment is performed using fluorescence microscopy in THP-1 cells. Fluorescently labeled apoptotic bodies were counted in adherent THP-1 cells using ImageJ software on confocal microscopy images (Olympus FV1000).

Furthermore, a tartrate salt of a compound of structure (I) demonstrated synergy when combined with an anti-PD-L1 agent, which is an immune checkpoint inhibitor, in a syngeneic triple negative breast cancer mouse model (see for example, Example 8 and FIGS. 6A and 6B).

Interestingly, during the evaluation of a tartrate salt of a compound of structure (I) in models of EMT, a dramatic change was detected in the expression of the retinoic acid (RA) metabolizing protein CYP26A1 (see for example FIGS. 20-22), suggesting that AXL inhibition leads to changes in RA metabolism.

Figure 20:
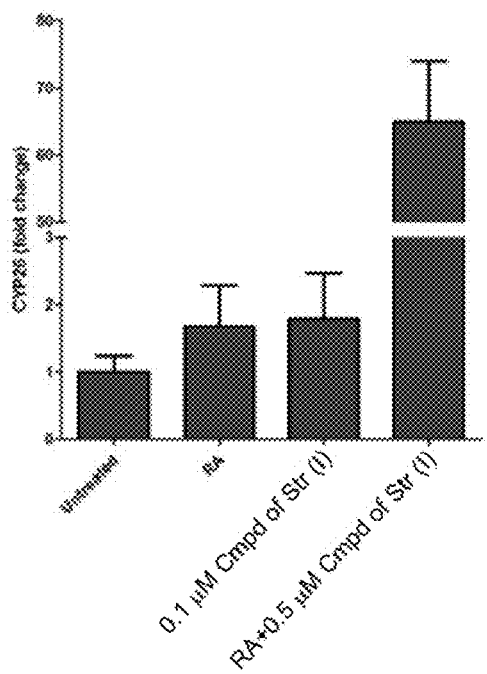
FIG. 20 shows CYP26A1 mRNA levels of RA in cells treated with a compound of structure (I).

FIG. 20 shows CYP26A1 mRNA levels in RA and cell treated with a tartrate salt of a compound of structure (I). Cells were treated with 1 µM Retinyl Acetate (RA) and/or a tartrate salt of a compound of structure (I) at 0.5 µM. Treatment with RA and a tartrate salt of a compound of structure (I) induced RA-dependent expression of CYP26A1.

Figure 21A:
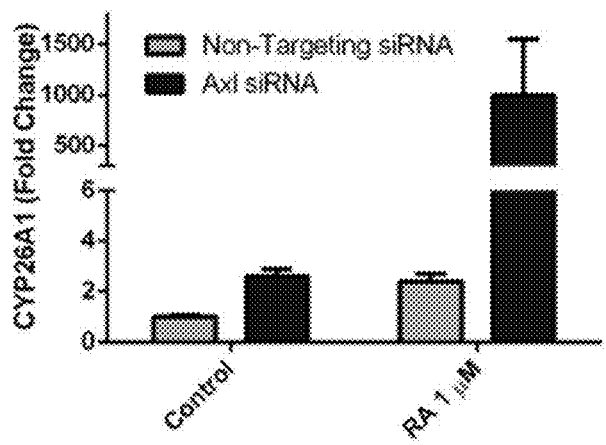
FIG. 21A and FIG. 21B show CYP26A1 mRNA expression in MV4-11 cells.
Figure 21B:

FIGS. 21A and 21B show CYP26A1 mRNA expression in MV4-11 cells. (FIG. 21A) Cells were treated with non-targeting or AXL specific siRNA. Cells were subsequently treated with 1 µM Retinyl Acetate (RA) and a tartrate salt of a compound of structure (I). Treatment with AXL siRNA induced robust increase in CYP26A1 expression in all samples, and the strongest increase in the RA treated sample. (FIG. 21B) Immunoblotting confirmation of protein knockdown by AXL siRNA.

Figure 22A:
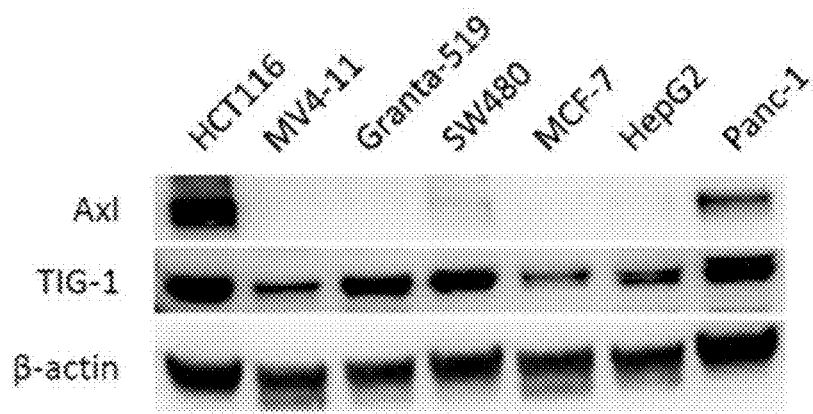
FIG. 22A and FIG. 22B show AXL co-immunoprecipitates with RA import associated gene, Stra6.
Figure 22B:
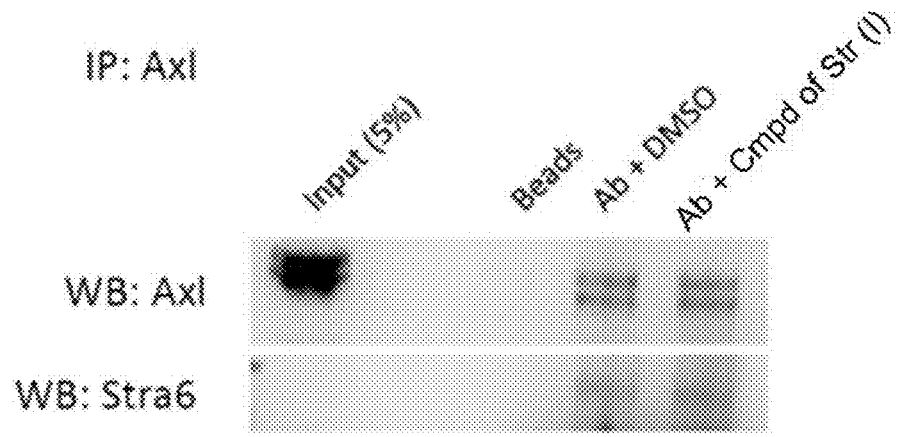

FIGS. 22A and 22B show AXL co-immunoprecipitates with RA import associated gene, Stra6. (FIG. 22A) From a small cell panel, it can be seen that AXL is highly expressed in cells such as HCT116 or Panc-1. (FIG. 22B) Using the HCT116 cell line, it can be seen a co-immunoprecipitation of Stra6 and AXL. Stra6 is a primary cell importer of RA.

These data suggest that AXL induces a transition to a mesenchymal phenotype in cancer cells through the suppression of RA signaling and that a tartrate salt of a compound of structure (I) can rapidly reverse this phenotype causing the cell to revert to a more differentiated state. Thus, a tartrate salt of a compound of structure (I) has single agent activity and combined synergy with targeted anti-cancer agents and immunotherapies.

In summary, a compound of structure (I) inhibits the apoptotic-cell/GAS6-mediated induction of AXL phosphorylation; inhibits expression of mesenchymal genes, Snail and Slug; inhibits the migration of pancreatic cancer cells; the combination of a compound of structure (I) and erlotinib is an active regimen in multiple lung cancer xenograft models; a compound of structure (I) inhibits AXL-mediated endocytosis of apoptotic bodies (efferocytosis); a combination of a compound of structure (I) and Anti-PD-L1 is an active regimen in the 4T1 breast cancer syngraft model; and a compound of structure (I) increases the CYP26A1 induction mediated by RA.

Example 11: Inhibition of AXL Kinase Suppresses Retinoic Acid Metabolism

Retinoic acid (RA), a metabolite of Vitamin A (retinol), has been used as a single-agent treatment in patients with acute promyelocytic leukemia (APL) with roughly 90% of patients attaining a complete remission. However, remissions can be transient and resistance arises within a few months following treatment.

This example aims to determine the role of AXL inhibition as a means of restoring sensitivity to RA treatment. It was hypothesized that treatment with the AXL inhibitor, a compound of structure (I), would disrupt RA metabolism.

Figure 23:
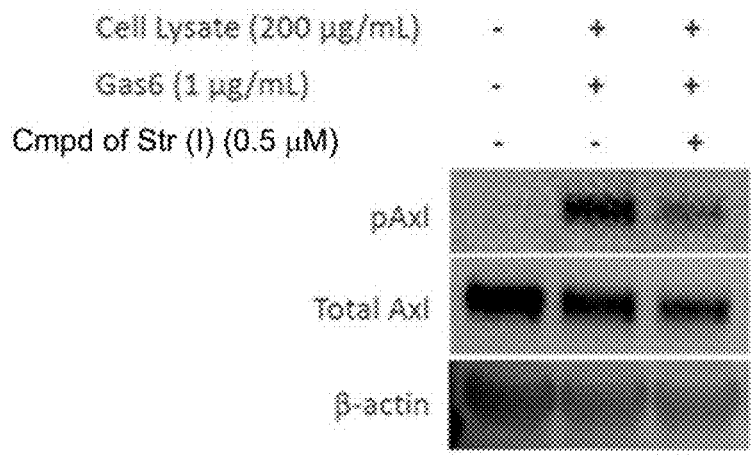
FIG. 23 shows protein levels of pAXL and total AXL.

Following treatment with a tartrate salt of a compound of structure (I), changes in mRNA expression were analyzed using RT-PCR, protein expression using standard immunoblotting, and endogenous RA levels using a competitive ELISA (see, for example FIG. 23). FIG. 23 shows protein levels of pAXL and total AXL. A549 cells were pre-treated with 0.5 µM of a tartrate salt of a compound of structure (I) for 1 hour, then AXL phosphorylation was induced by a 30-minute treatment of an apoptotic cell lysate and GAS6. Lysate and GAS6 treatment leads to phosphorylation of AXL. This result demonstrates that a compound of structure (I) inhibits the phosphorylation of AXL.

RT-PCR was used to measure mRNA expression of CYP26 in cells induced with RA and treated with a tartrate salt of a compound of structure (I). Following treatment, changes in CYP26 expression were assessed at the protein level, using standard western blotting techniques. Endogenous RA levels were measured using a competitive ELISA technique. To determine the effect of a compound of a tartrate salt of structure (I) on tumor growth in an in vivo model, treatment with a tartrate salt of a compound of structure (I) was tested in a MV4-11 xenograft mouse model.

Figure 30A:
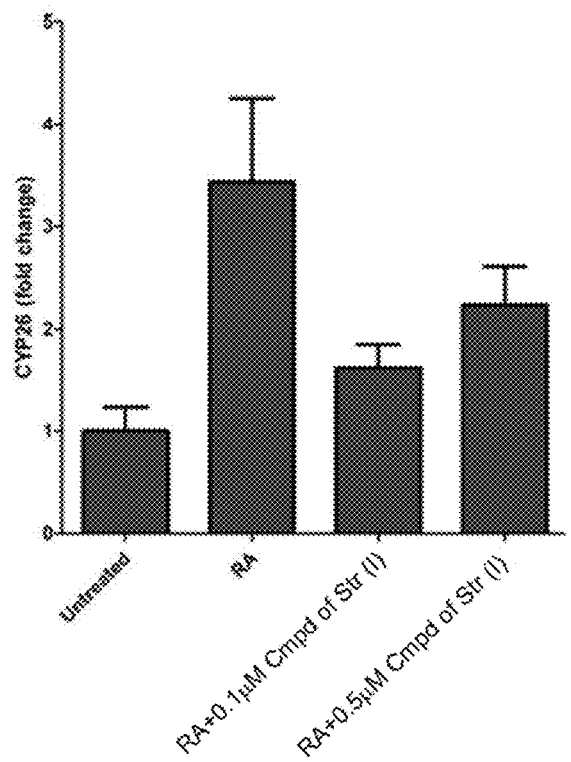
FIG. 30A and FIG. 30B show CYP26A1 mRNA expression in (FIG. 30A) MV4-11 and (FIG. 30B) A549 cells.

A robust induction in mRNA expression levels of CYP26 was observed following 1 µM RA treatment in MV4-11 leukemia cells, reaching nearly 4.3-fold after 6 hours of treatment (FIG. 30A). However, treatment of cells with a tartrate salt of a compound of structure (I) at levels as low as 100 nM inhibited RA-mediated induction of CYP26 mRNA levels by 88.9% in MV4-11 cells at 6 hours (see, for example, FIG. 3). Interestingly, administration of a tartrate salt of a compound of structure (I) also inhibited basal mRNA levels of CYP26 by 94.1% at 6 hours (see, for example, FIGS. 24 and 25).

Changes in neural crest EMT following treatment with a tartrate salt of a compound of structure (I) suggest RA-dependent gene expression (CYP26A1). MV4-11 cells treated with a single dose of a tartrate salt of a compound of structure (I) suggested that a tartrate salt of a compound of structure (I) inhibits EMT in a RA signaling-dependent fashion.

Figure 25:
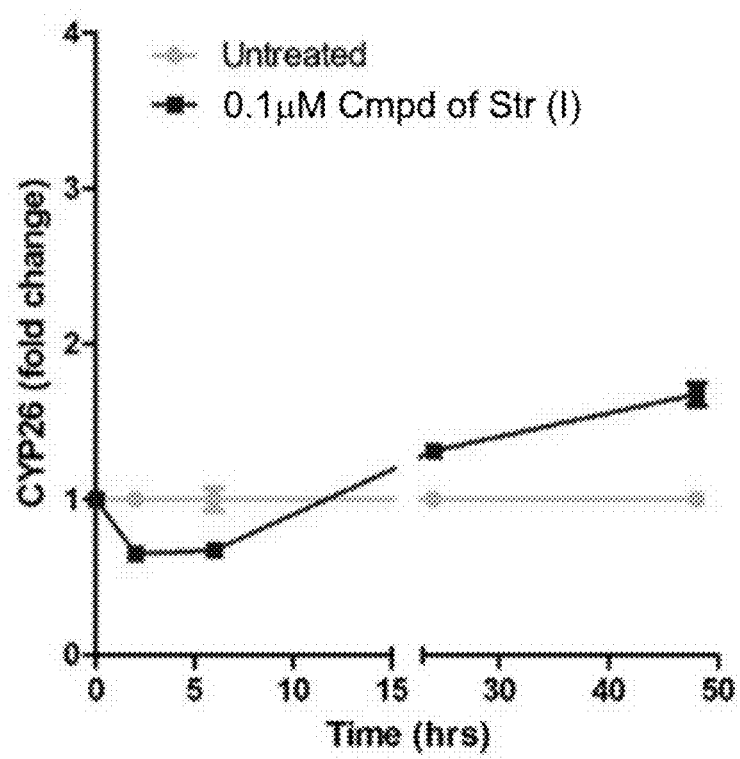
FIG. 25 shows changes in CYP26A1 expression over 24 hours.
Figure 26:
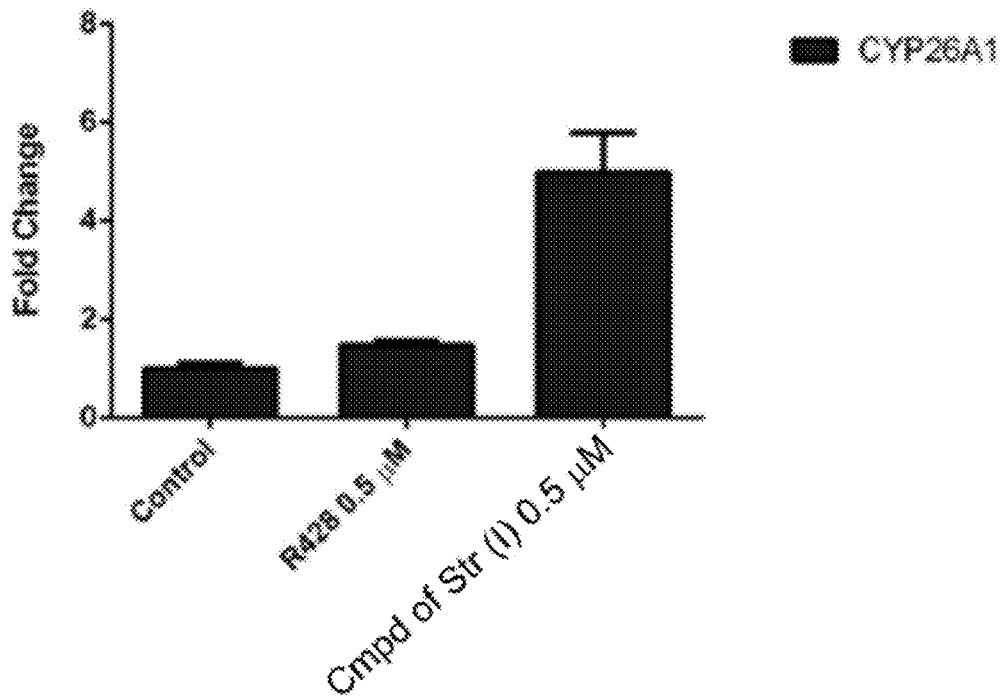
FIG. 26 shows CYP26A1 expression in R428 treated cells.
Figure 33:
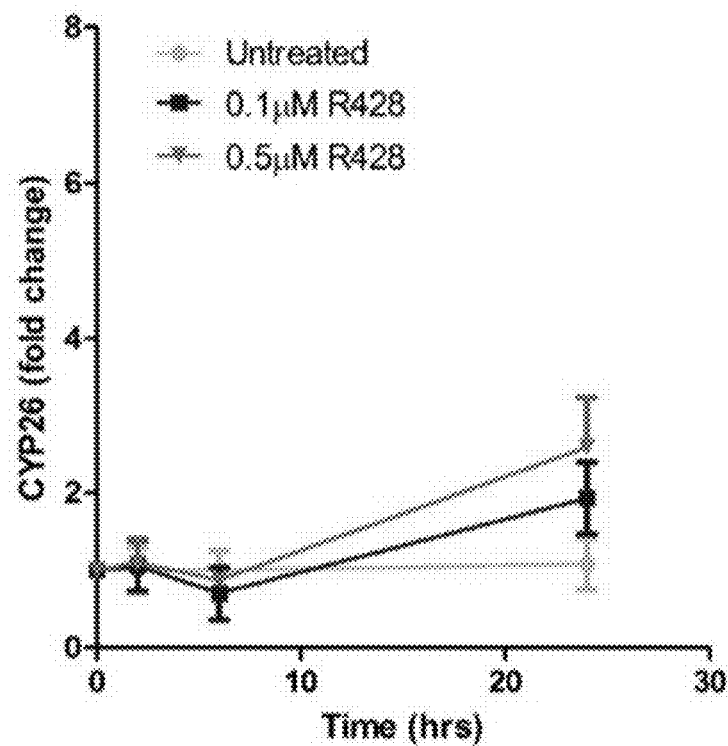
FIG. 33 shows changes in CYP26A1 expression over 24 hours for MV4-11 cells treated with R428.

Similar trends in CYP26A1 expression are observed in additional cell lines (HL60, A549, and H1650; see, for example, FIG. 25 and FIG. 30B), and with an alternative AXL inhibitor, R428, although only at higher concentrations (see, for example, FIGS. 26 and 33).

Figure 24:
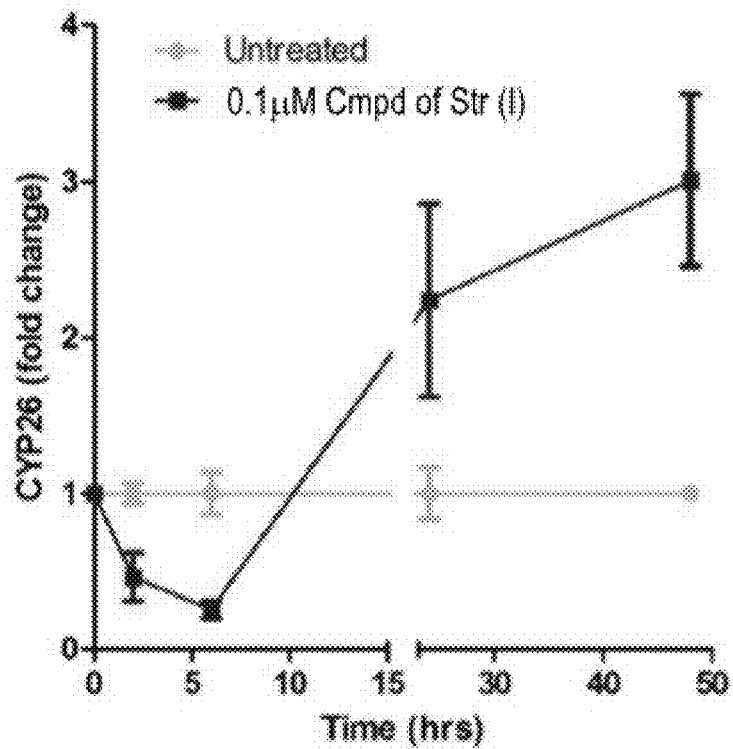
FIG. 24 shows a compound of structure (I) inhibits basal expression of CYP26A1.
Figure 24:
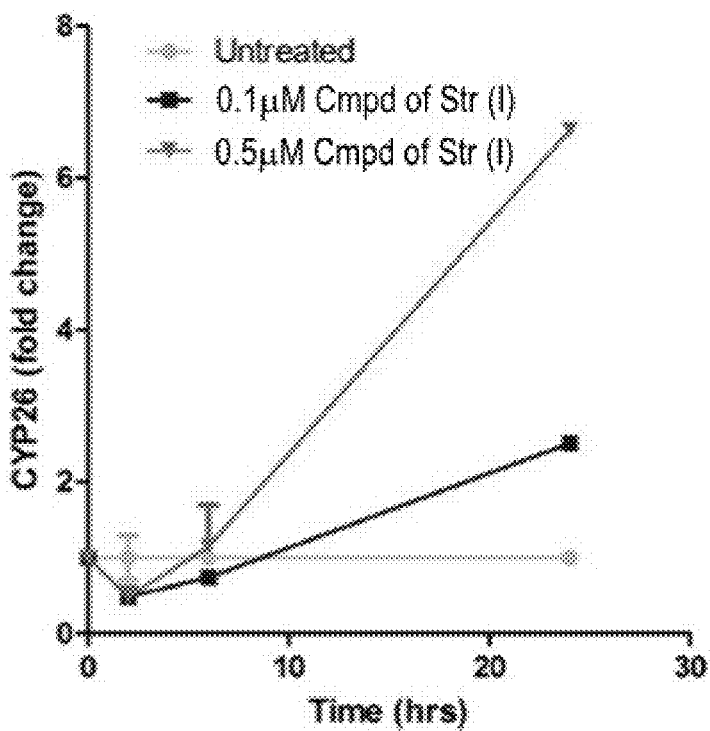

FIG. 24 shows changes in CYP26A1 expression in (top panel) MV4-11 and HL-60 cells (bottom panel) treated with a single dose of a tartrate salt of a compound of structure (I). CYP26A1 mRNA levels were measured via RT-qPCR at several time points. An initial suppression of CYP26A1 expression is followed by a rebounding increase of CYP26A1 expression starting around 24 hours. FIG. 25 shows the same effects observed in A549 cells.

FIG. 26 shows CYP26A1 expression in R428 treated cells. MV4-11 cells were treated with a single dose of R428. CYP26A1 mRNA levels were measured via RT-qPCR at 24 hrs. Induction of CYP26A1 was seen with R428 treatment, though the magnitude was not as large as that seen with a tartrate salt of a compound of structure (I).

Figure 27:
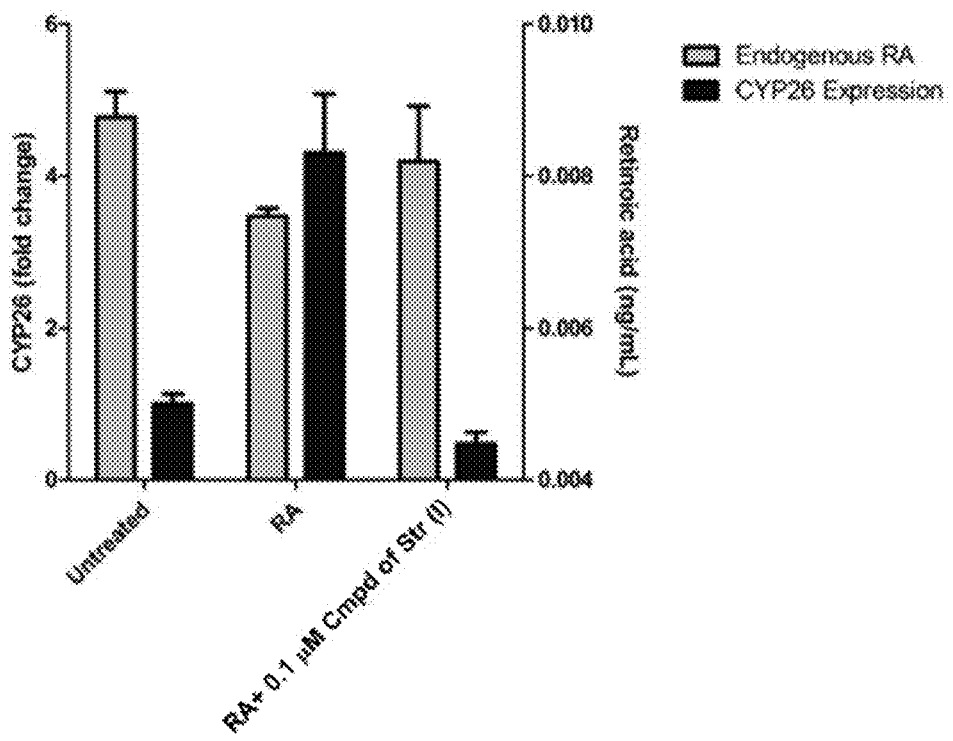
FIG. 27 shows changes in CYP26A1 expression and intracellular RA levels.

As shown in FIG. 27, changes in CYP26A1 expression and intracellular RA levels were analyzed. Cells were treated with a single dose of a tartrate salt of a compound of structure (I) and Retinyl Acetate (RA), and cells were harvested at 6 hrs. CYP26A1 levels were measured via RT-qPCR, and endogenous levels of RA were measured by a competitive ELISA(mybiosource.com). Where CYP26 mRNA is suppressed by treatment with a tartrate salt of a compound of structure (I) at a concentration of 0.1 µM, RA levels were salvaged.

At time points greater than 24 hours, and without re-treatment with a tartrate salt of a compound of structure (I), CYP26 expression exceeded levels observed in induced samples. In cells treated with a tartrate salt of a compound of structure (I), it was observed that RA levels were maintained at time points where CYP26 expression was suppressed. A tartrate salt of a compound of structure (I) strongly inhibited tumor volumes by up to 100% at multiple dose levels and treatment schedules (see for example FIGS. 34A-34D).

Figure 34A:
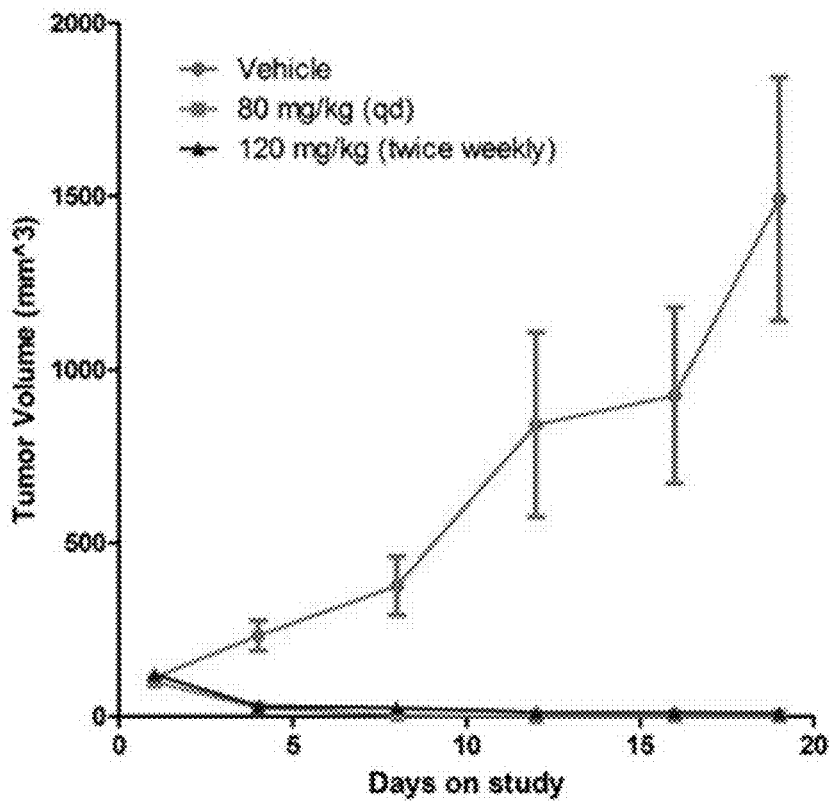
FIGS. 34A-34D show (FIGS. 34A/34B) MV4-11 and (FIGS. 34C/34D) A549 xenograft studies.
Figure 34B:
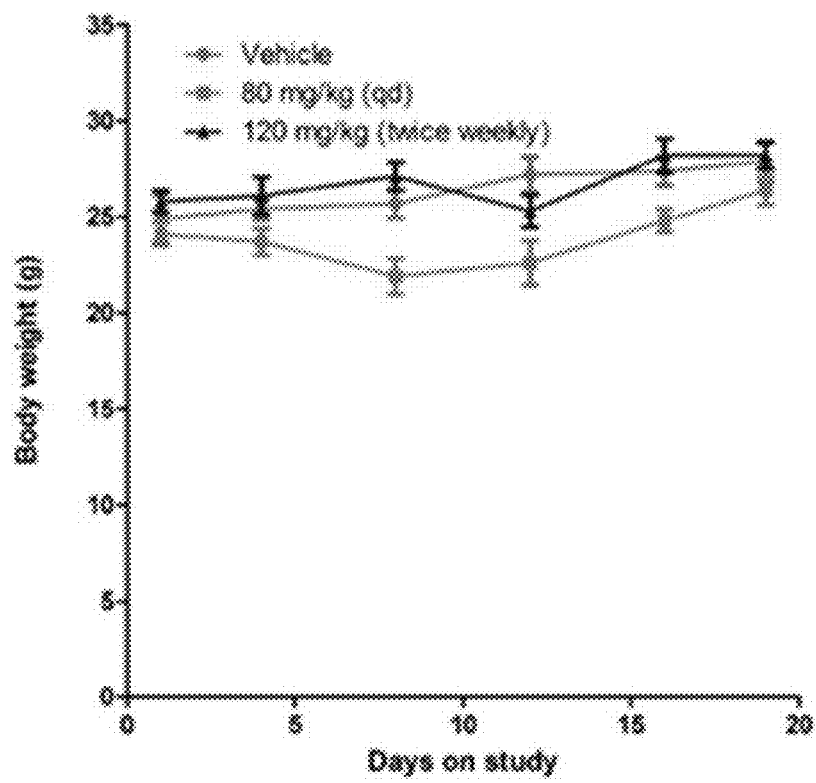
Figure 34C:
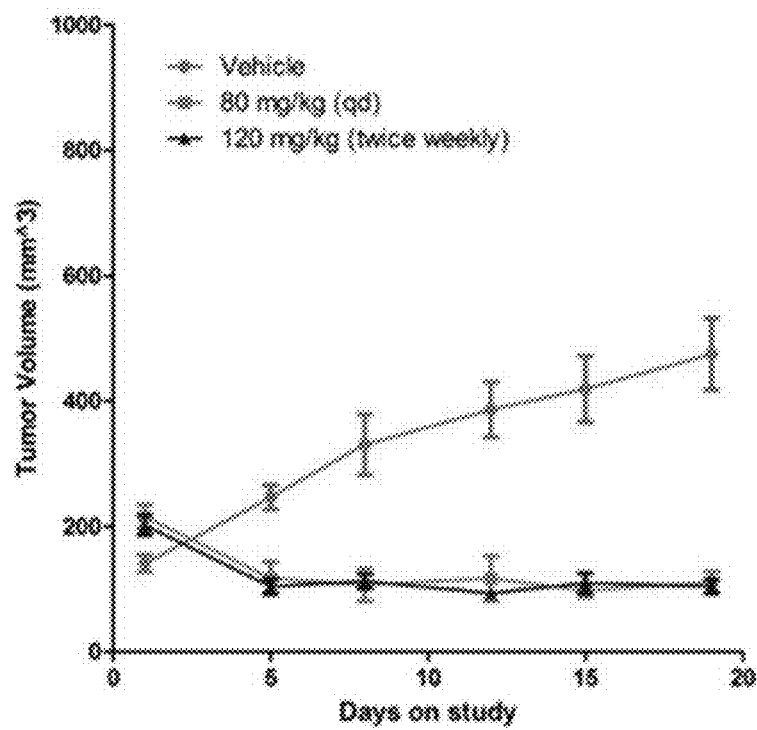
Figure 34D:
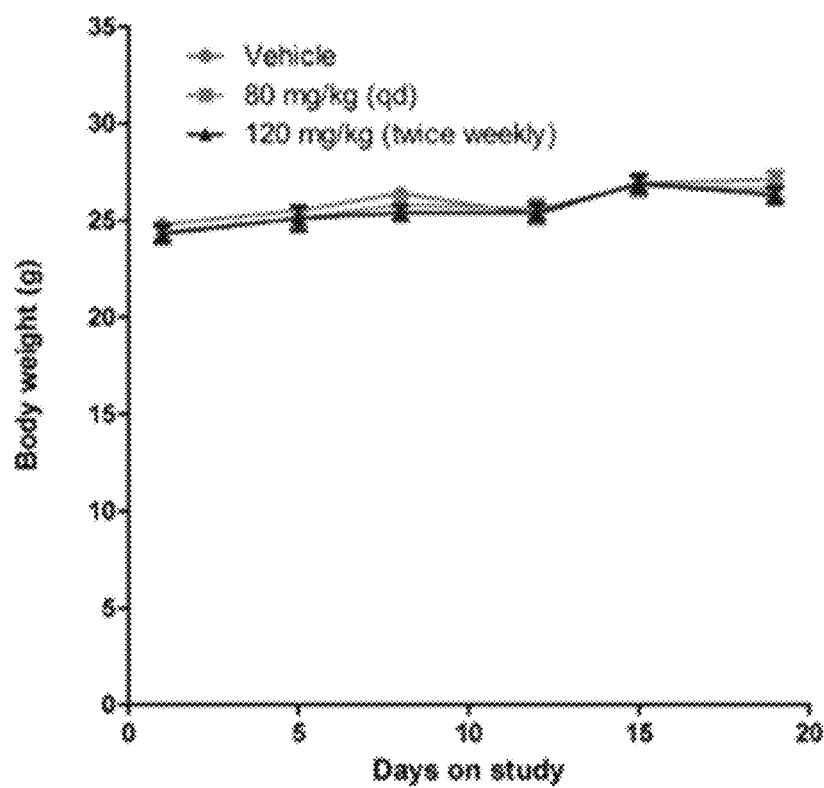

FIG. 34A and FIG. 34B show MV4-11 xenograft studies; and FIG. 34C and FIG. 34D show A549 xenograft studies. Xenograft studies were performed in athymic nude mice with the doses and schedules of a tartrate salt of a compound of structure (I) indicated above. Mice were given food and water ad libitum. Doses shown did not cause significant bodyweight losses in the treated animals. Significant tumor growth inhibition was observed in both tumor models investigated.

Figure 35:
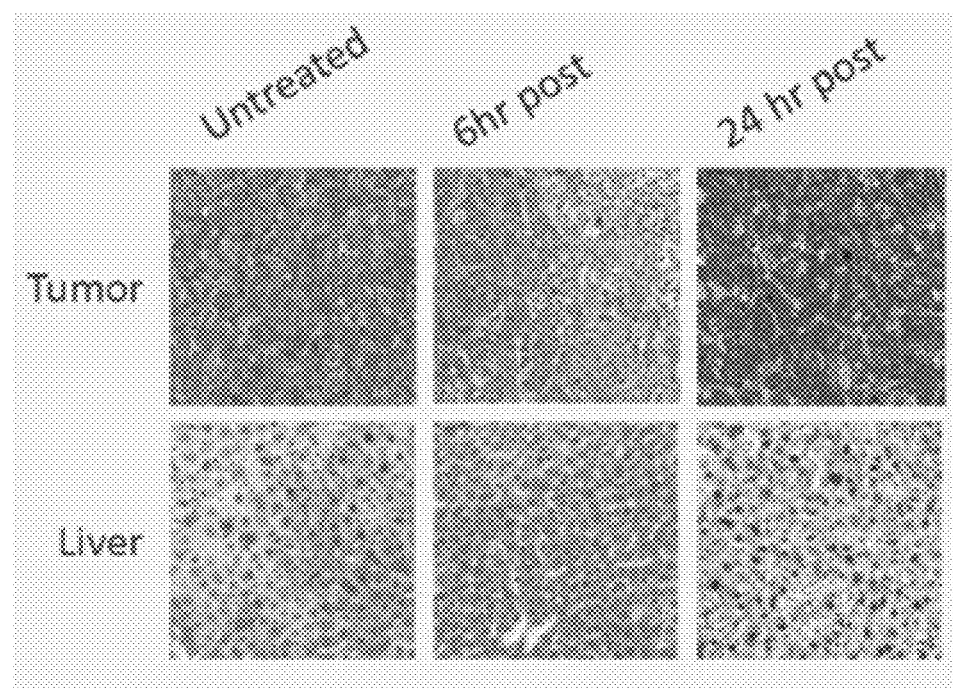
FIG. 35 is a photo showing changes in CYP26A1 expression in vivo before and after treatment.

Changes in CYP26A1 expression in vivo are shown in FIG. 35. Athymic nude mice bearing MV4-11 tumors xenografted subcutaneously were given a single dose of 180 mg/kg of a tartrate salt of a compound of structure (I). Tumors were harvested 6 and 24 hrs post treatment. CYP26 protein expression in tumors and livers is shown in FFPE tissues by standard IHC staining, using fast red chromogen (A). mRNA levels of CYP26 are shown for both tumor (B) and livers (C).

Analysis of CYP26 expression in fixed tissues, and RA levels in plasma will be assessed to determine the effects of a tartrate salt of a compound of structure (I) on physiological levels of CYP26 and RA.

These observations demonstrate that inhibition of AXL kinase by a tartrate salt of a compound of structure (I) suppresses CYP26 and disrupts RA metabolism. Taken together, these data indicate that AXL likely serves as a suitable therapeutic target for addressing cellular responses mediating RA resistance.

In summary, a compound of structure (I) inhibits the apoptotic-cell/GAS6-mediated induction of AXL phosphorylation; a compound of structure (I) inhibits expression of mesenchymal genes, Snail and Slug; a compound of structure (I) phenocopies retinoic acid effects, in an RA-dependent fashion, including inducing expression of CYP26A1 in multiple cell lines; the AXL inhibitor, R428, also induces CYP26A1 expression, though to a lesser degree; compound of structure (I)-mediated modulation of CYP26A1 levels corresponds with altered intracellular RA levels; a compound of structure (I) increases the CYP26A1 induction mediated by RA; AXL siRNA also induces CYP26A1 increases; AXL co-precipitates with Stra6, and may serve as a negative regulator of Stra6; and a compound of structure (I) is an active compound in multiple xenograft tumor models.

Example 12: Inhibition of AXL Kinase Reverses the Mesenchymal Phenotype in Leukemic Cells Following treatment with a tartrate salt of a compound of structure (I), changes in mRNA expression were interrogated using RT-PCR, protein expression was measured using standard immunoblotting, and endogenous RA levels were measured using a competitive ELISA (see for example, FIGS. 28 and 29).

Figure 28:
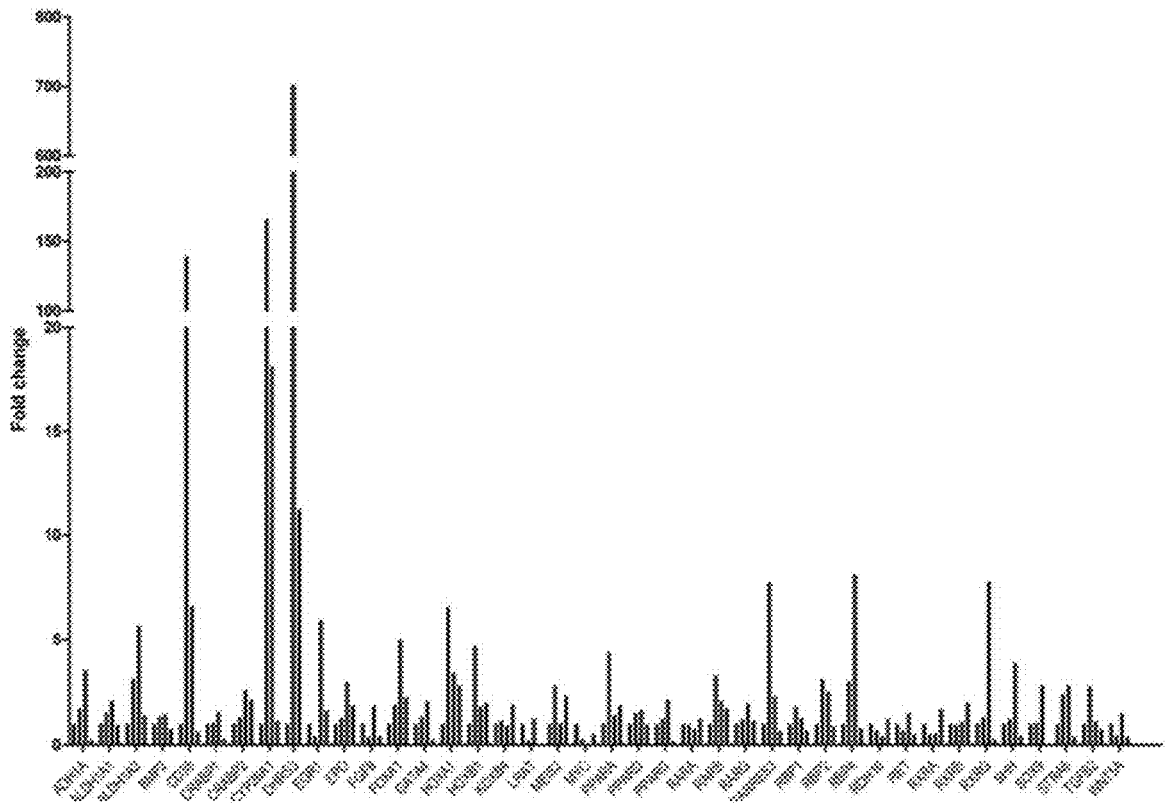
FIG. 28 shows that a compound of structure (I) affects the expression of multiple genes involved in RA synthesis and metabolism.

FIG. 28 shows that a tartrate salt of a compound of structure (I) affects the expression of multiple genes involved in RA synthesis and metabolism. A RT2 Profiler PCR array (Qiagen) was used to profile expression changes with RA and/or 0.1 µM treatment with a tartrate salt of a compound of structure (I). Multiple genes are affected, including CYP26A1, a major CYP involved in RA degradation.

FIG. 29 shows a selected list of genes that respond to RA and a tartrate salt of a compound of structure (I).

Also, the effect of a tartrate salt of a compound of structure (I) on tumor growth was assessed in an in vivo model, assessing efficacy of a tartrate salt of a compound of structure (I) in an MV4-11 xenograft mouse model (see for example, FIG. 30).

Figure 30B:
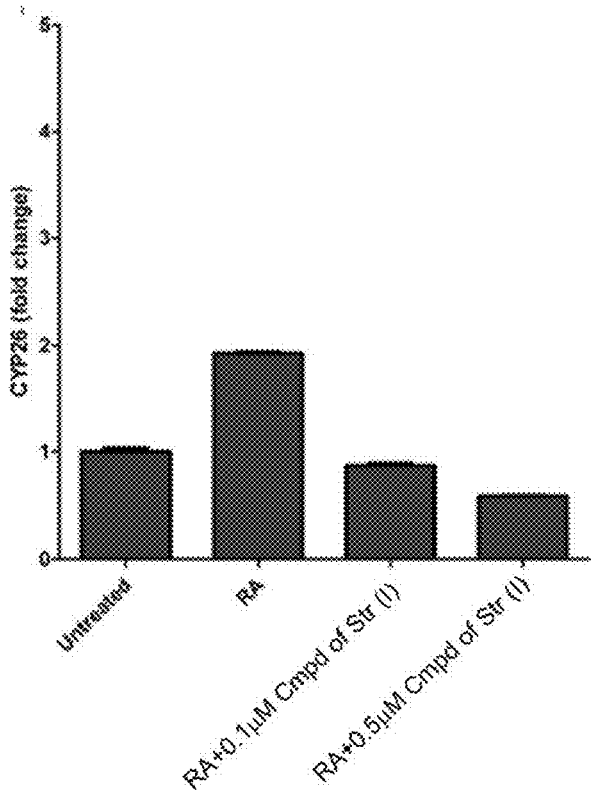

FIGS. 30A and 30B show CYP26A1 mRNA expression in (FIG. 30A) MV4-11 and (FIG. 30B) A549 cells. Cells were treated for 6 hours with 1 µM Retinyl Acetate (RA) and a tartrate salt of a compound of structure (I) at 0.1 µM or 0.5 µM. Treatment with RA and a tartrate salt of a compound of structure (I) suppressed RA induced expression of CYP26. One of the genes that was detected as being dramatically changed by treatment with a tartrate salt of a compound of structure (I) was the RA metabolizing protein CYP26A1 (see for example, FIGS. 31 and 32), suggesting that AXL inhibition indeed leads to changes in RA metabolism.

Figure 31:
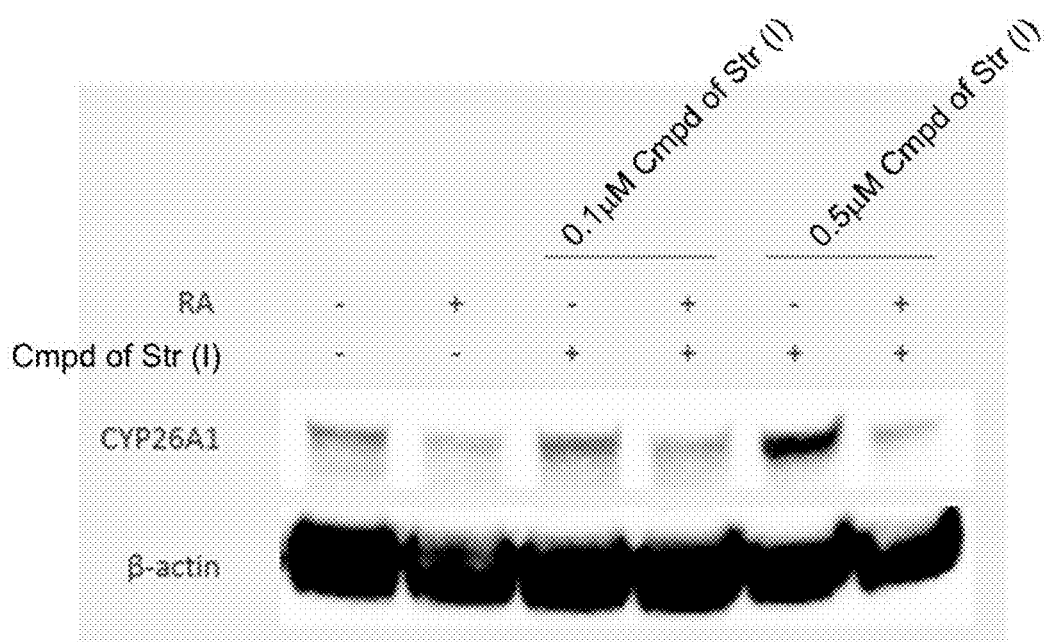
FIG. 31 shows CYP26A1 protein expression in A549 cells treated with RA.

FIG. 31 shows CYP26A1 protein expression in A549 cells. Cells were treated for 24 hours with 1 µM Retinyl Acetate (RA) and a tartrate salt of a compound of structure (I) at 0.1 µM or 0.5 µM. Treatment with RA and a tartrate salt of a compound of structure (I) inhibits expression of CYP26A1 in a dose dependent fashion.

Figure 32:
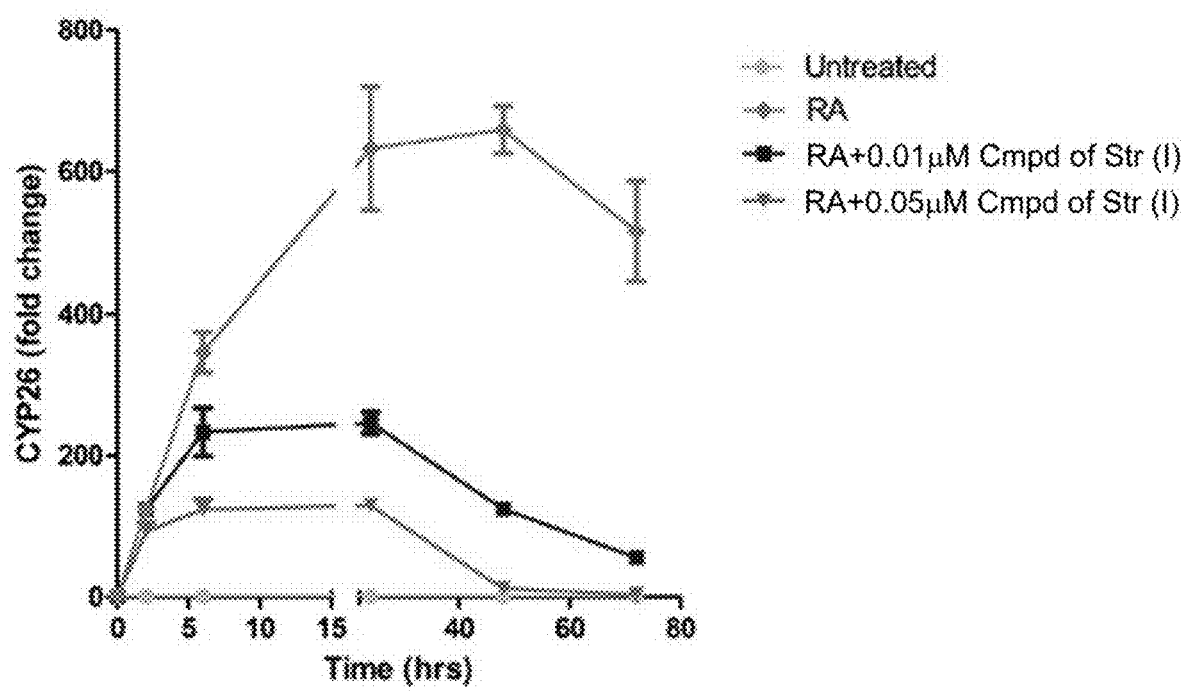
FIG. 32 shows changes in CYP26A1 expression over 72 hours with low-dose treatment with a compound of structure (I).

FIG. 32 shows changes in CYP26A1 expression over 72 hours with low-dose treatment with a tartrate salt of a compound of structure (I). Cells were treated with Retinoic Acid (RA) with/without multiple doses of a tartrate salt of a compound of structure (I), given at 0, 24, and 48 hrs. CYP26A1 levels were measured via RT-PCR. CYP26A1 expression quickly induced by RA, but inhibited by a tartrate salt of a compound of structure (I) at both 0.1 µM and 0.5 µM. Repeated dosing prevents the rebounding expression of CYP26A1 mRNA seen in prior experiments.

A strong induction of CYP26 mRNA expression following RA treatment in MV4-11 leukemia cells was observed, and this effect was also observed in treatment with an AXL inhibitor, a tartrate salt of a compound of structure (I), at levels as low as 100 nM. Activity of a tartrate salt of a compound of structure (I) was also assessed in additional cell lines (HL60, A549, and H1650, see, for example, FIG. 24), and with an alternative AXL inhibitor, R428 (see, for example, FIG. 33). FIG. 33 shows changes in CYP26A1 expression over 24 hours for MV4-11 cells treated with a single dose of R428. CYP26A1 mRNA levels were measured via RTPCR at 24 hrs. An initial suppression of CYP26A1 expression is followed by a rebounding increase of CYP26A1 expression starting around 24 hours. Suppression seen with R428 was not as large as with a tartrate salt of a compound of structure (I).

Treatment with a tartrate salt of a compound of structure (I) correlated with increased CYP26 expression and reduced levels of endogenous RA. In vivo, a tartrate salt of a compound of structure (I) strongly inhibited xenograft tumor volumes by up to 100% with multiple dose levels and treatment schedules (see, for example, FIGS. 34A-34D). CYP26 expression in fixed tissues correlated well with mRNA levels observed in xenograft tumors following treatment (see, for example, FIGS. 35-37).

Figure 36:
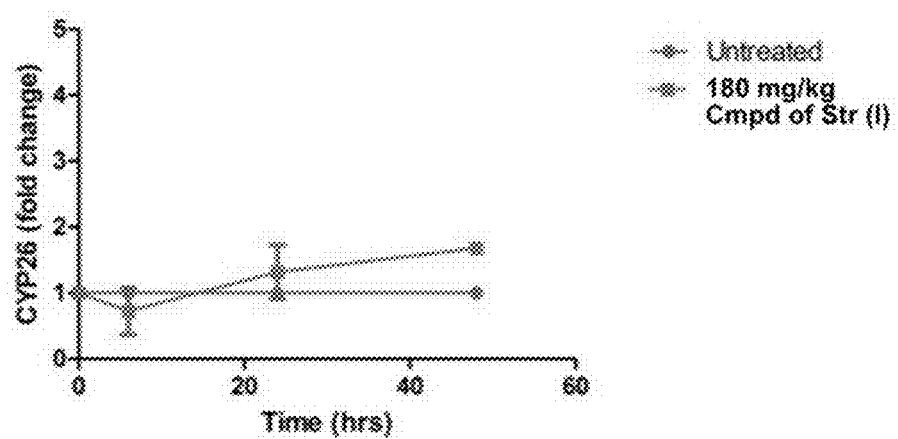
FIG. 36 is a chart showing fold changes of CYP26 in tumors over time in mice treated with compound of structure (I) as relative to untreated mice.
Figure 37:
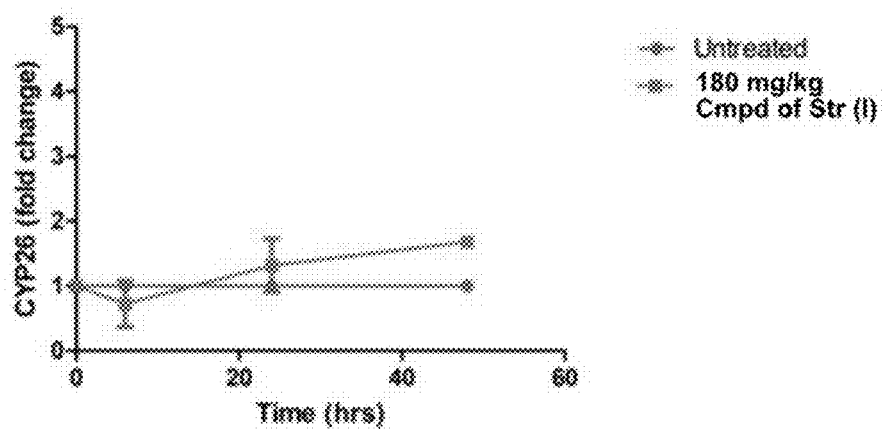
FIG. 37 is a chart showing fold changes of CYP26 in livers over time in mice treated with compound of structure (I) as relative to untreated mice.

FIGS. 35-37 shows changes in CYP26A1 expression in vivo. Athymic nude mice bearing MV4-11 tumors xenografted subcutaneously were given a single dose of 180 mg/kg of a tartrate salt of a compound of structure (I). Tumors were harvested 6 and 24 hrs post treatment. CYP26 protein expression in tumors and livers is shown in FFPE tissues by standard IHC staining, using fast red chromogen (FIG. 35). mRNA levels of CYP26 are shown for both tumor (FIG. 36) and livers (FIG. 37).

Taken together, these observations demonstrate that inhibition of AXL kinase by a tartrate salt of a compound of structure (I) can disrupt RA metabolism by inducing CYP26 expression and this disruption of RA metabolism leads to reversal of the mesenchymal phenotype in leukemic cells.

In summary, a compound of structure (I) alters gene expression of multiple genes involved in RA synthesis, degradation, and signaling; a compound of structure (I) potently inhibits retinyl acetate and retinoic acid-induced expression of the RA degrading CYP protein, CYP26, expression in multiple cell lines; a compound of structure (I) can continually repress CYP26 expression with repeated dosing; a compound of structure (I)-mediated reduction in CYP26 corresponds with higher intracellular RA levels; the AXL-specific inhibitor, R428, induces similar effects, though less potently a compound of structure (I) is an active compound in multiple xenograft tumor models; a compound of structure (I) may synergize with retinoid therapies, including ATRA.

Figure 38:
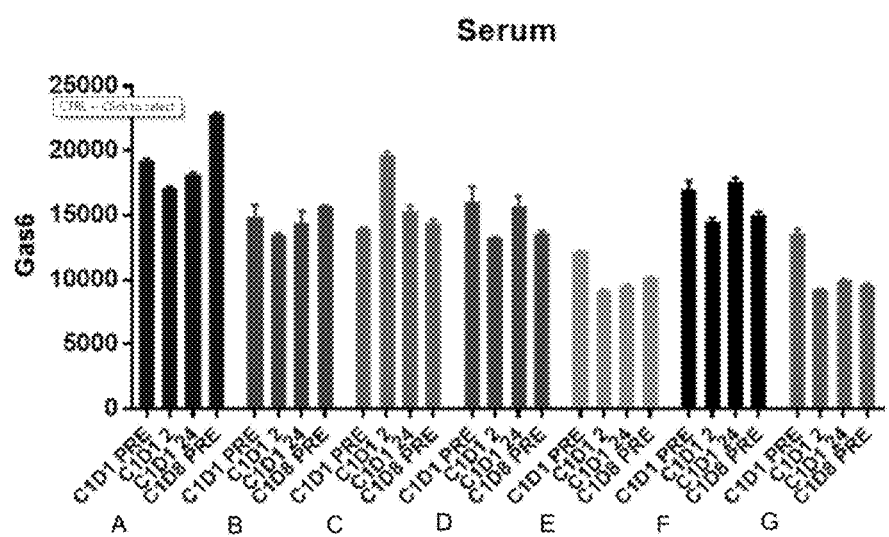
FIGS. 38-40 show serum levels of GAS6 (FIG. 38); and GAS6 and AXL (FIGS. 39 and 40) at the following times: Cycle 1/Day 1 pre-dose ("C1D1 PRE"), and 2 and 24 hours post-dose ("C1D1 2" and "C1D1 24", respectively) and Cycle 1/Day 8 pre-dose ("C1D8 PRE").
Figure 40:
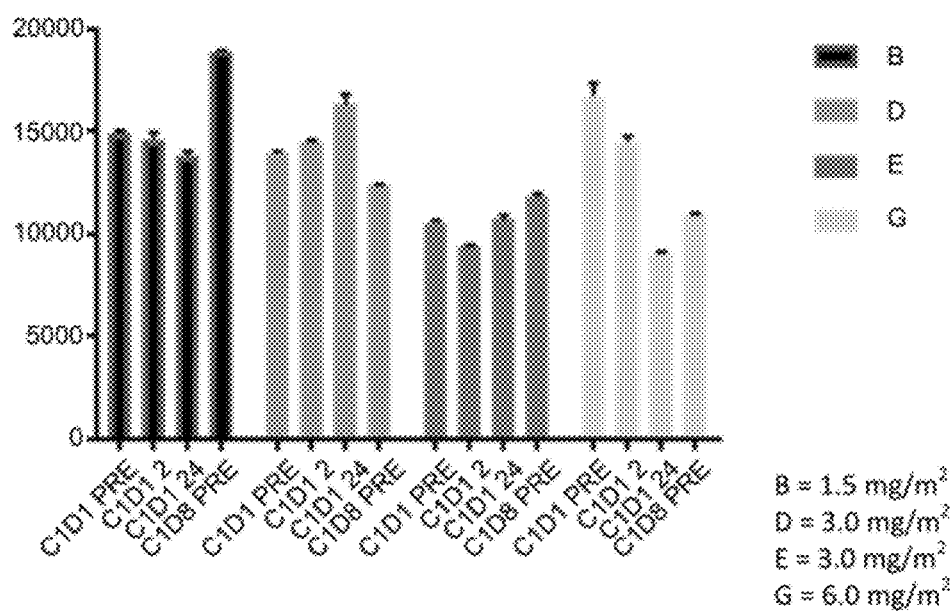

Example 13: Predictive and Pharmacodynamic Biomarkers for Cancer Treated with an AXL Kinase Inhibitor As shown in FIG. 38, serum levels of GAS6 were measured at various time-points during and following treatment with a tartrate salt of the compound of structure (I) for study subjects A-G. Serum levels of GAS6 were measured at the following times: Cycle 1/Day 1 pre-dose ("C1D1 PRE"), and 2 and 24 hours post-dose ("C1D1 2" and "C1D1 24", respectively) and Cycle 1/Day 8 pre-dose ("C1D8 PRE"). As can be seen in FIG. 40, serum levels of AXL and GAS6 were measured at various time-points during and following treatment with a tartrate salt of the compound of structure (I) in study subjects B, D, E, and G. Serum levels of AXL and GAS6 were measured at the following times: Cycle 1/Day 1 pre-dose ("C1D1 PRE"), and 2 and 24 hours post-dose ("C1D1 2" and "C1D1 24", respectively) and Cycle 1/Day 8 pre-dose ("C1D8 PRE"). The dosage administered to each subject is shown in the lower right of the figure.

Figure 39:
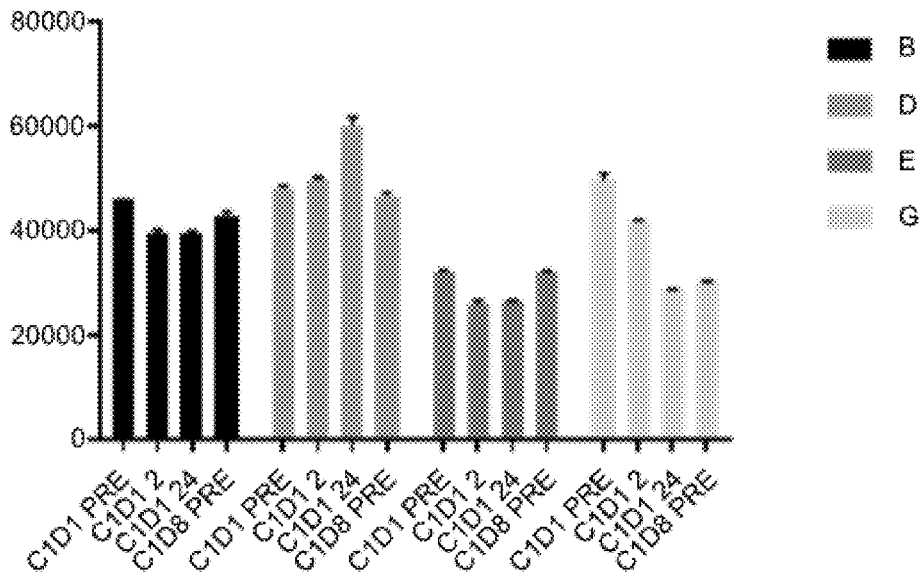

FIGS. 37-40 show results of various immunohistochemistry stains against human patient primary and secondary (metastatic) tumor samples to assess epithelial-to-mesenchymal transition (EMT) markers measured at various timepoints during disease progression. FIG. 37 shows immunostaining for AXL in primary (left) and secondary (right) tumor samples from breast cancer patients X and Y. FIG. 38 shows immuno staining for E-Cadherin in primary (left) and secondary (right) tumor samples from breast cancer patients X and Y. FIG. 39 shows immuno staining for N-Cadherin in primary (left) and secondary (right) tumor samples from breast cancer patients X and Y. FIG. 40 shows immuno staining for phosphorylated AXL ("pAXL") in primary (left) and secondary (right) tumor samples from breast cancer patients X and Y.

Figure 41:
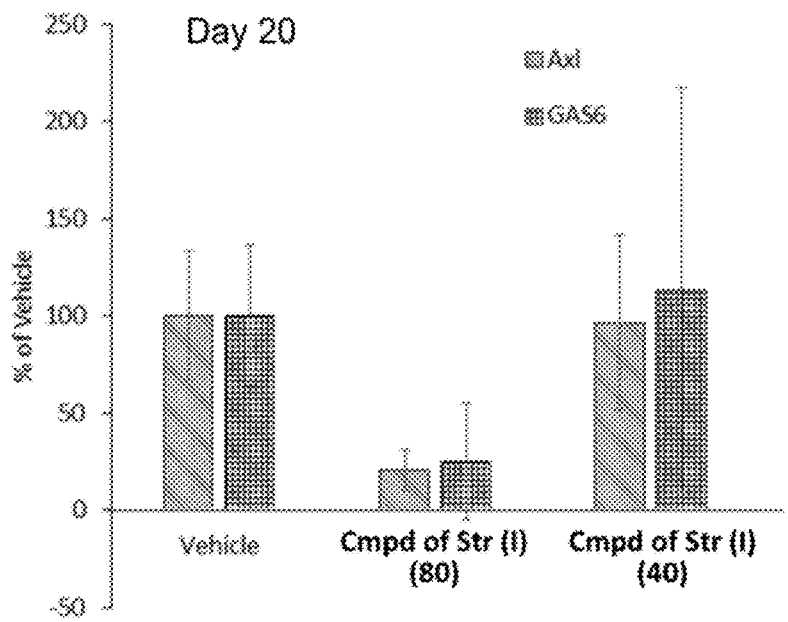
FIG. 41 shows plasma levels of AXL and GAS6 at day twenty (collected four hours post-dosing) of treatment with the compound of structure (I), in a patient-derived xenograft model of colorectal cancer.

FIG. 41 shows plasma levels of AXL and GAS6 at day twenty (collected four hours post-dosing) of treatment with a tartrate salt of the compound of structure (I), in a patient-derived xenograft model of colorectal cancer. Plasma AXL and GAS6 levels were reduced after administration of a tartrate salt of a compound of structure (I) at a concentration of 80 mg/kg.

Figure 42:
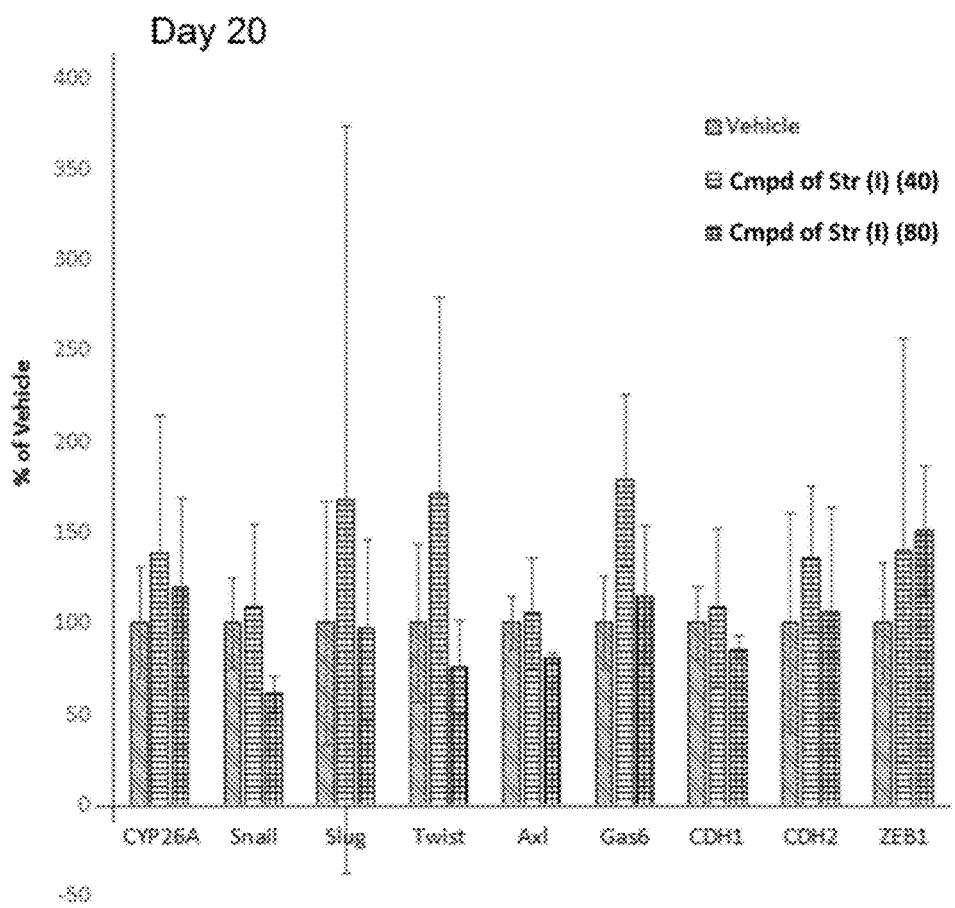
FIG. 42 shows mRNA expression levels of epithelial-to-mesenchymal transition markers at day 20 of treatment with the compound of structure (I), in a patient-derived xenograft model of colorectal cancer.
Figure 43:
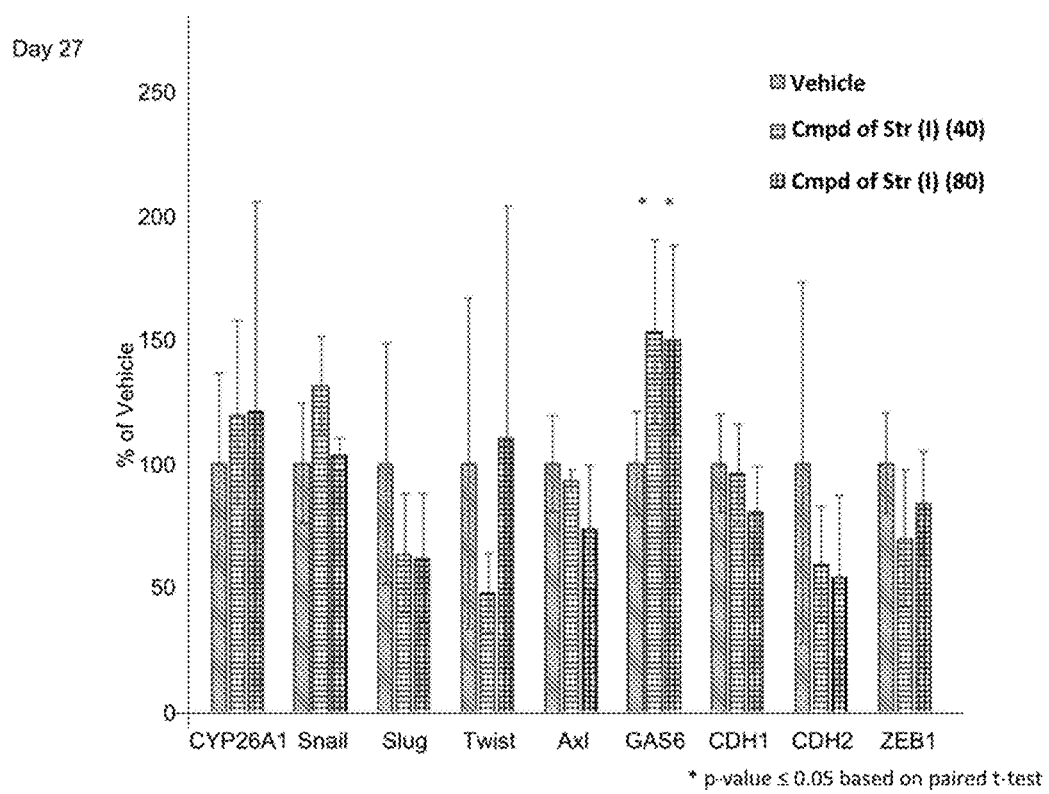
FIG. 43 shows mRNA expression levels of epithelial-to-mesenchymal transition markers at day 27 (one week after the last dosing) of treatment with the compound of structure (I), in a patient-derived xenograft model of colorectal cancer.

Expression levels of mRNA of epithelial-to-mesenchymal transition markers were measured at day 20 (see FIG. 42) and day 27 (one week after the last dosing, see FIG. 43) of treatment with a tartrate salt of the compound of structure (I), in a patient-derived xenograft model of colorectal cancer. At day 20, Snail expression was significantly reduced (p-value ≤0.05, paired t-test) after administration of a tartrate salt of a compound of structure (I) at a concentration of 80 mg/kg. At day 27, GAS6 expression was significantly increased (p-value ≤0.05, paired t-test) after treatment with either 40 mg/kg or 80 mg/kg of a tartrate salt of a compound of structure (I).

Figure 44:
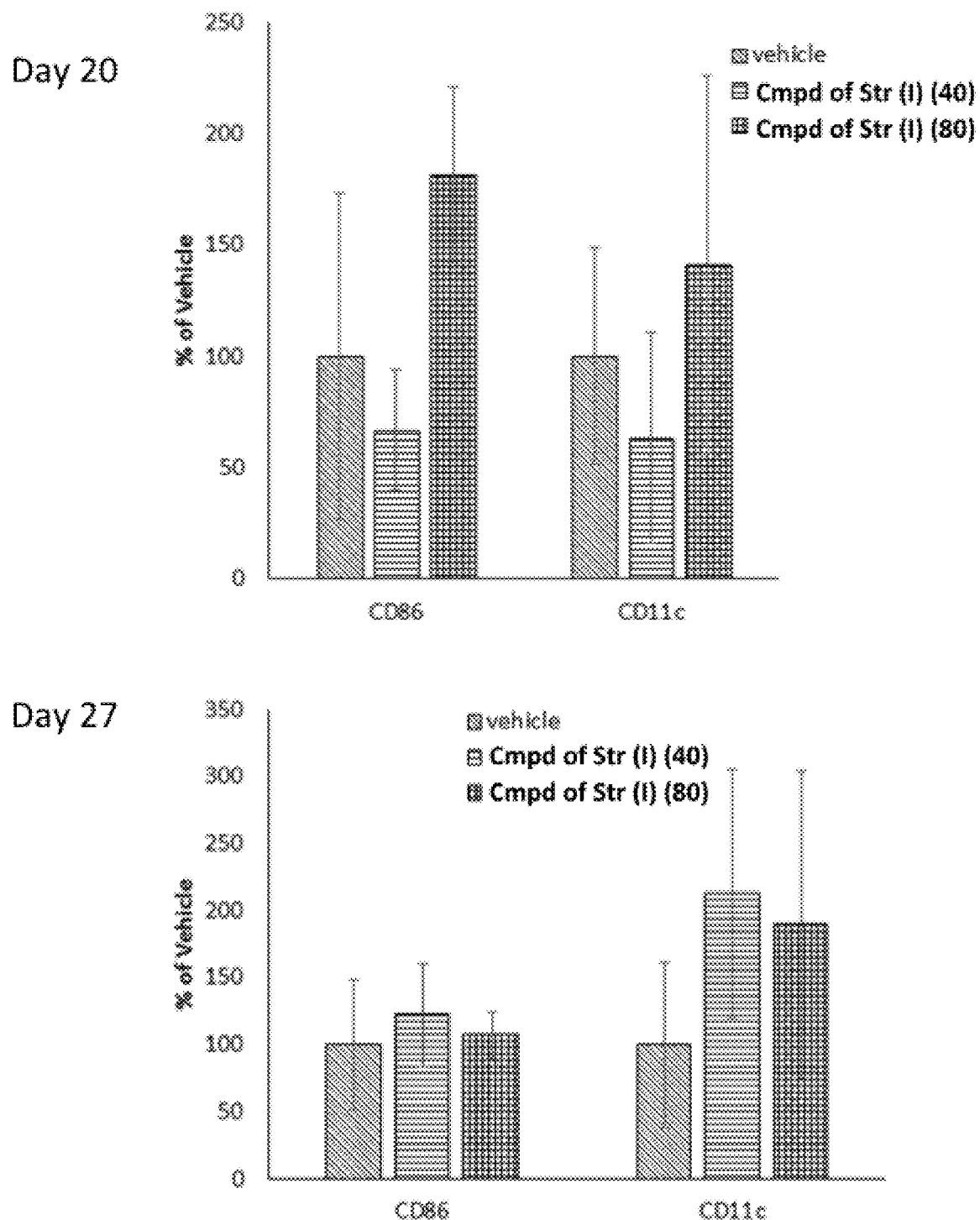
FIG. 44 shows mRNA expression levels of markers of activated dendritic cells (CD86 and CD11c), at day 20 (top panel) and day 27 (one week after the last dosing, bottom panel) of treatment with the compound of structure (I), in a patient-derived xenograft model of colorectal cancer.

FIG. 44 shows mRNA expression level differences of markers of activated dendritic cells (CD86 and CD11c), at day 20 (top panel) and day 27 (one week after the last dosing, bottom panel) of treatment with a tartrate salt of a compound of structure (I), in a patient-derived xenograft model of colorectal cancer.

Example 14: Phase I/II Study of Tartrate Salts of Compound of Structure (I) in Subjects with Previously-Treated CFF This is a combined Phase 1/2 study of tartrate salts of a compound of structure (I) that is orally administered in subjects with previously treated CFF/SLL. In both Phase 1 and Phase 2, study participants will be assigned to one of two defined patient groups:

Group 1 (a tartrate salt of a compound of structure (I) monotherapy): Patients with CFF/SFF who are intolerant to, or have progressed on, B-cell receptor antagonists and/or BCL-2 antagonists Group 2 (a tartrate salt of a compound of structure (I) and ibrutinib combination therapy): Patients with CFF/SFF who have progressed on ibrutinib yet the treating provider considers continuation of ibrutinib therapy to be in the best interest of the patient.

Both groups of patients will be treated identically with a tartrate salt of a compound of structure (I) and will undergo the same study assessments. Patient inclusion criteria include an Eastern Cooperative Oncology Group (ECOG) performance status of ≤2.

Phase 1

Patients will be enrolled in Group 1 and Group 2 in cohorts of 3 to 6 patients simultaneously. Group 2 will start at one dose level below the Group 1 starting dose. In each group, escalation of the dose of a tartrate salt of a compound of structure (I) will follow a standard 3+3 design with sequential cohorts of three patients treated with incrementally higher doses of a tartrate salt of a compound of structure (I) until a dose-limiting toxicity (DLT) is observed and the maximum tolerated dose (MTD) is established. In the absence of DLTs, the dose will be increased using a modified Fibonacci dose escalation scheme.

Once the MTD or preliminary RP2D is identified, an expansion cohort of up to 6 patients will be enrolled in each patient group to confirm safety/suitability of the preliminary RP2D, to collect additional biomarker data, and to further explore efficacy.

It is expected that up to 27 patients will be enrolled in each patient group for a total of up to 54 patients (a tartrate salt of a compound of structure (I) monotherapy and combination therapy with ibrutinib).

Additional dose levels, schedules, or disease indications of a tartrate salt of a compound of structure (I) may be explored, as appropriate, based on the modulation of key biomarkers and the safety profile and clinical signals of activity.

Monotherapy—Group 1:

A tartrate salt of a compound of structure (I) will be administered in a flat dose based on the dose in the current Phase 1 of a solid tumor study at the time of initiation of this study. It is suspected that the dose will be between 33 mg and 45 mg. The study drug will be administered orally once daily for 28 days (each cycle is 28 days; no drug-free period). Patients may continue to receive a tartrate salt of a compound of structure (I) in 28-day cycles at the same dose given during Cycle 1 until they experience unacceptable toxicity or unequivocal disease progression. No intrapatient escalation of the dose of a tartrate salt of the compound of structure (I) is permitted.

Combination Therapy—Group 2:

A tartrate salt of a compound of structure (I) and ibrutinib combination therapy: The starting dose of a tartrate salt of the compound of structure (I) will be one dose level lower than the Group 1 starting dose, administered orally once daily for 28 days (each cycle is 28 days; no drug-free period). Patients will also receive ibrutinib at the same dose that they were receiving immediately prior to study enrollment. Patients should continue with the combination of ibrutinib and a tartrate salt of a compound of structure (I) for at least 3 months after study start.

Phase 2

In Phase 2, patients will be enrolled in Group 1 (a tartrate salt of a compound of structure (I) monotherapy) and Group 2 (a tartrate salt of a compound of structure (I) combination therapy with ibrutinib) based on the Simon 2 stage design. In Stage 1, up to 13 patients will be enrolled into each patient group (total of 26 patients). If there are no responses among these 13 patients in each group, the study will be stopped. Otherwise, Stage 2 will open to enroll 14 additional patients in each group for a total of 27 patients per group. If 4 or more responses are observed among 27 patients, the conclusion will be that the study treatment is worthy of further investigation.

If both patient groups enroll through Stage 2, it is anticipated that the total enrollment for Phase 2 will be 54 patients.

Monotherapy—Group 1:

The starting dose of a tartrate salt of a compound of structure (I) will be the RP2D determined during Phase 1. The tartrate salt of the compound of structure (I) will be administered orally at a fixed dose once daily for 28 days (each cycle is 28 days; no drug-free period) with repeated cycles permitted until a patient experiences unacceptable toxicity or unequivocal disease progression.

Combination Therapy—Group 2:

The starting dose of a tartrate salt of a compound of structure (I) will be the RP2D determined during Phase 1. Patients will also receive ibrutinib at the same dose that they were receiving immediately prior to study enrollment. Both a tartrate salt of a compound of structure (I) and ibrutinib will be administered orally at fixed doses once daily for 28 days (each cycle is 28 days; no drug-free period).

Example 15: Pre-Treatment AXL and GAS6 Levels as Predictors of Disease Progression A phase 1a/1b, first-in-human, open-label, dose-escalation, safety, pharmacokinetics, and pharmacodynamic study is underway for treatment advanced solid tumors using a tartrate salt of a compound of structure (I). The compound is administered once daily for the first 21 out of 28 days. For Phase 1a (dose escalation), sequential cohorts of three (3) patients are treated with escalated doses until the MTD is established. In the absence of dose-limiting toxicities (DLTs), the doses are increased using a modified Fibonacci dose escalation scheme.

Blood samples were collected prior to drug treatment (baseline) and processed for serum. Baseline serum samples were analyzed for soluble AXL and GAS6 using the Biotechne (R&D Systems) Ella platform microfluidic ELISA. Subjects were treated with 1.5-28 mg/m$^2$ of a tartrate salt of a compound of structure (I) for 21 consecutive days followed by a 7 day treatment holiday. Subjects with documented disease assessment (Progressive Disease (PD) or Stable Disease (SD)) were used to compare baseline levels of the analyses. A Wilcoxon rank sum test was used to test the alternative hypothesis (PD<SD) for both AXL and GAS6.

Figure 45A:
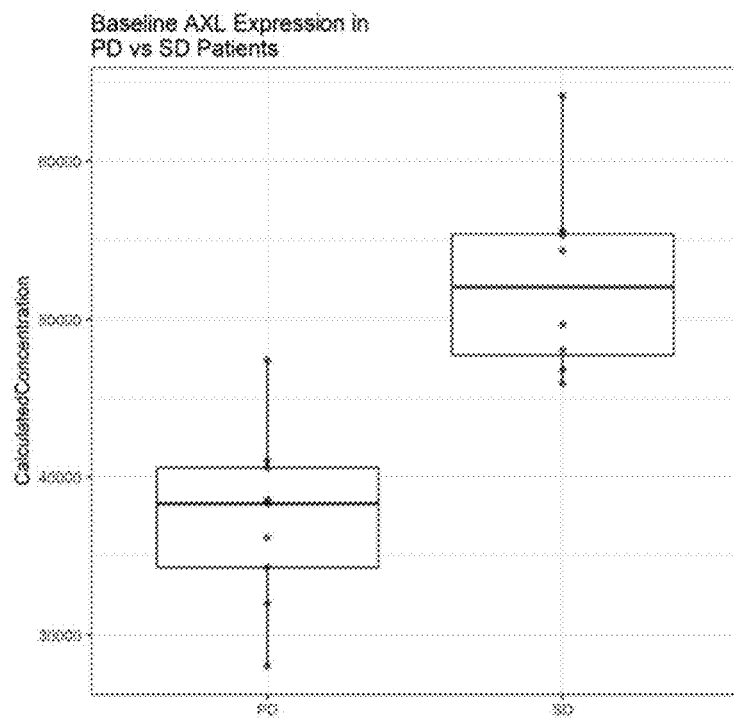
FIG. 45A shows the baseline AXL levels in serum from patients with progressive disease (PD) versus stable disease (SD).
Figure 45B:
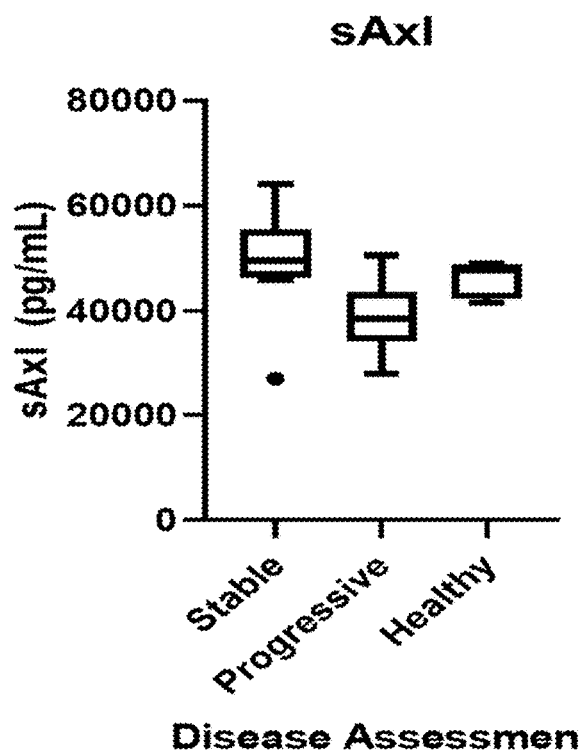
FIG. 45B shows the baseline AXL levels in serum from patients with progressive disease (PD) versus stable disease (SD).
Figure 46A:
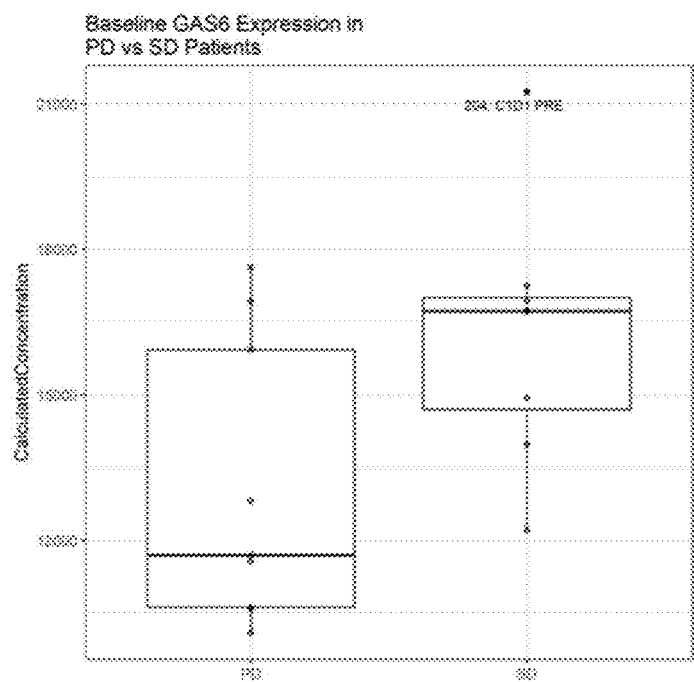
FIG. 46A shows the baseline GAS6 levels in serum from patients with PD versus SD.
Figure 46B:
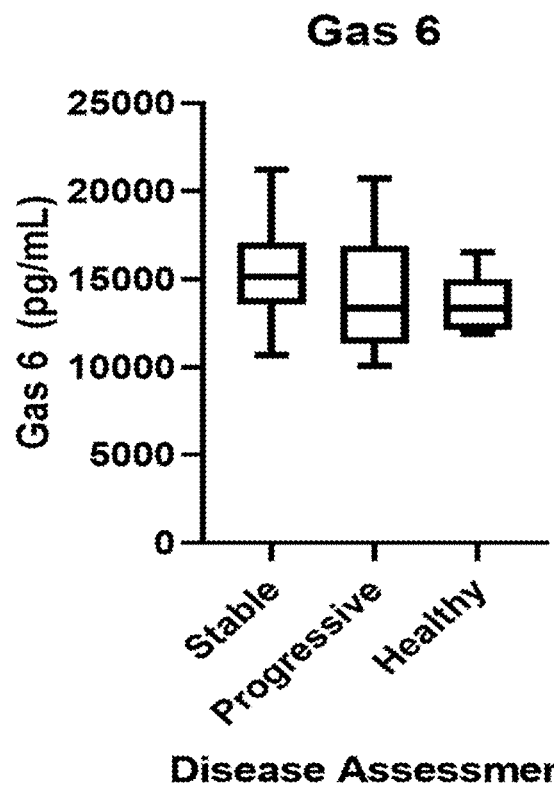
FIG. 46B shows the baseline GAS6 levels in serum from patients with PD versus SD.

FIGS. 45A and 45B show a graph of sAXL protein measured from patients who had PD versus SD during the study. FIG. 45A contains data from 17 patients (9 PD and 8 SD patients), and FIG. 45B contains data from an additional 2 PD patients and an additional 1 SD patient (for a total of 20 patients). This result indicates that patients whose disease progressed during the treatment with a tartrate salt of the compound of structure (I) had significantly lower levels of sAXL protein prior to treatment, as compared to patients who developed SD during the treatment. FIGS. 46A and 46B show a graph of sGAS6 protein measured from patients who had PD versus SD during the study. FIG. 46A contains data from 17 patients (9 PD and 8 SD patients), and FIG. 45B contains data from an additional 2 PD patients and an additional 1 SD patient (for a total of 20 patients). This result indicates that patients whose disease progressed during the treatment with a tartrate salt of the compound of structure (I) had, on average, lower levels of sGAS6 protein prior to treatment, as compared to patients who developed stable disease during the treatment. In summary, both soluble AXL and GAS6 were elevated at baseline in subjects that demonstrated a best response of SD vs PD.

For the Phase 1b expansion study, five groups are enrolled on a flat dosing schedule. Each group includes 20 patients and 10 biopsies will be collected. The study groups include: (1) Progression on Immunotherapy (combined with immunotherapy): (2) EGFR$^+$ Non-small cell lung cancer, Progression after <2 tyrosine kinase inhibitors (TKIs) (combined with a TKI inhibitor); (3) Colorectal cancer, BRAF/KRAS/NRAS mutated; (4) Ovarian cancer, persistent/recurrent (platinum Resistant/Refractory); and (5) Melanoma, BRAF$^-$ mutated.

Example 16: Immune Response Modulation by an AXL Kinase Inhibitor

Figure 47A:
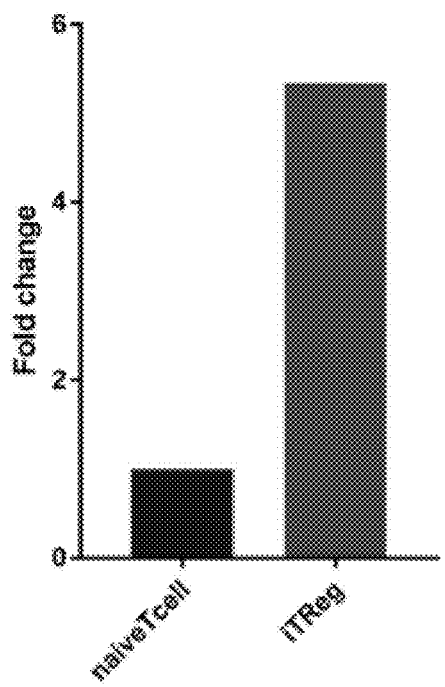
FIGS. 47A-47C show the sensitivity of regulatory T-cells to the compound of structure (I).
Figure 47B:
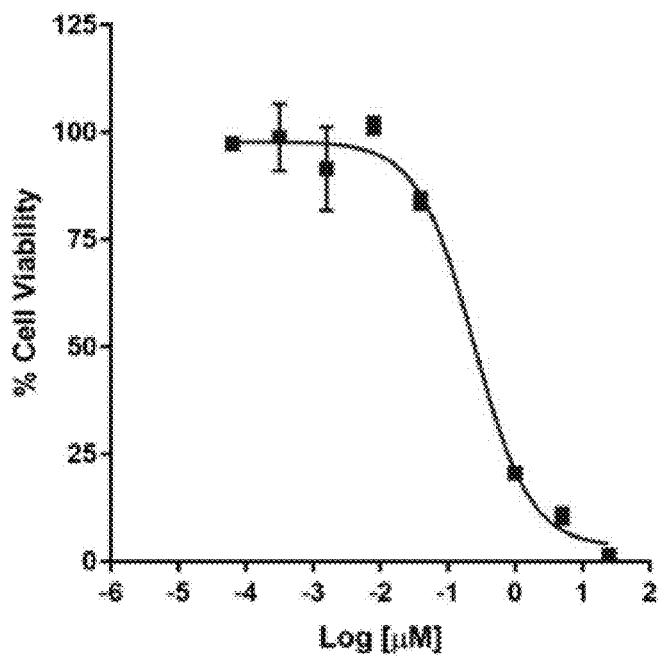
Figure 47C:
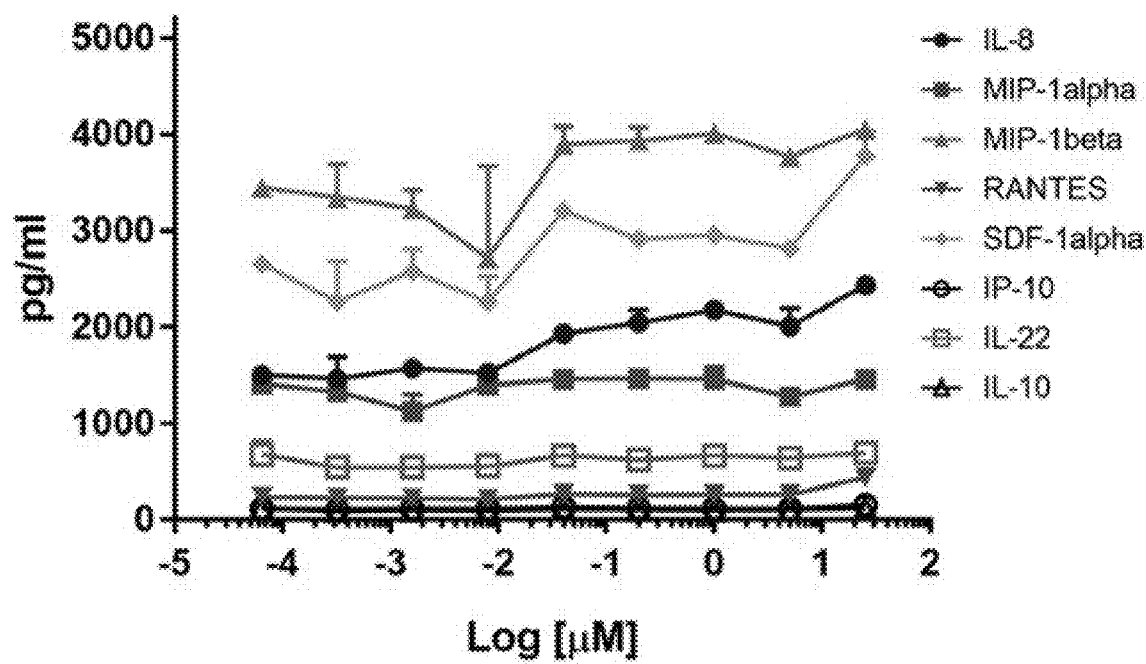
Figure 48:
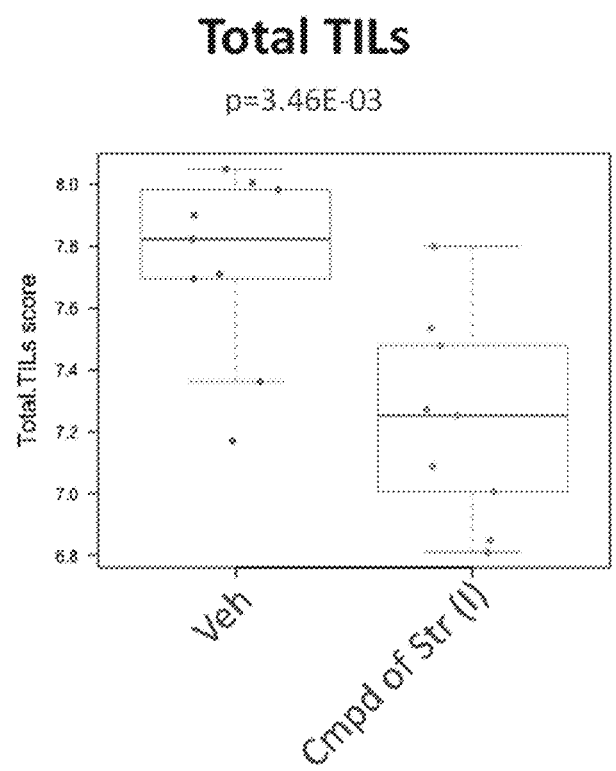
FIG. 48 shows total tumor infiltrating lymphocytes (TILs) found in samples treated with vehicle or 25 milligrams (mg)/kilogram (kg) of a compound of structure (I).
Figure 49:
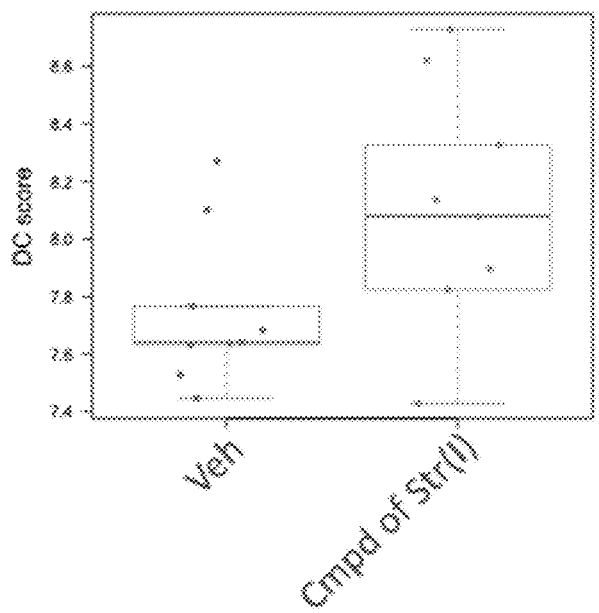
FIG. 49 shows dendritic cells found in samples from a 4T1 model treated with vehicle or 25 mg/kg of a compound of structure (I).
Figure 50:
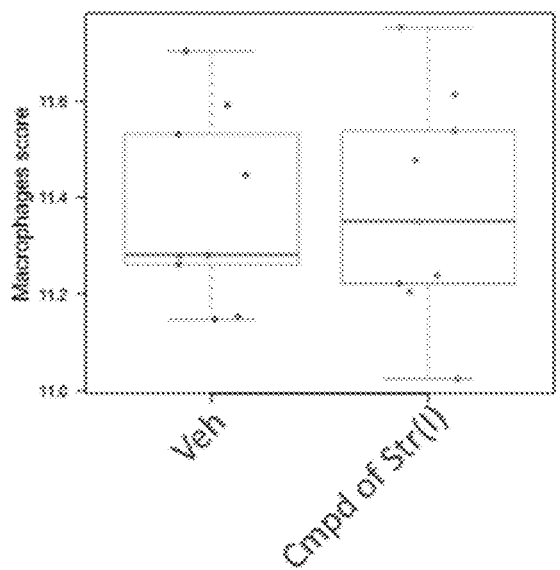
FIG. 50 shows macrophages found in samples from a 4T1 model treated with vehicle or 25 mg/kg of a compound of structure (I).
Figure 51:
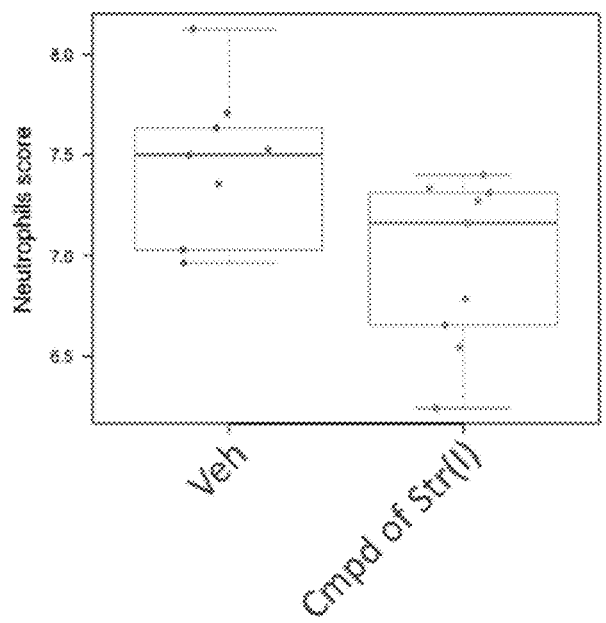
FIG. 51 shows neutrophils found in samples from a 4T1 model treated with vehicle or 25 mg/kg of a compound of structure (I).
Figure 52:
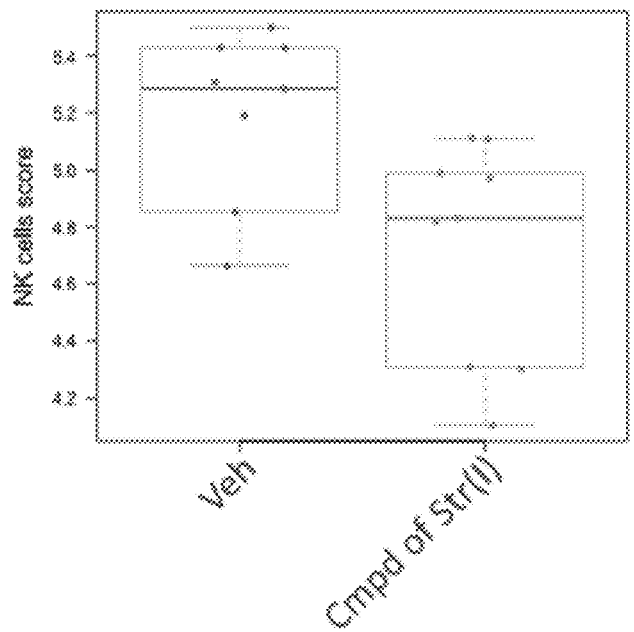
FIG. 52 shows natural killer (NK) cells found in samples from a 4T1 model treated with vehicle or 25 mg/kg of a compound of structure (I).
Figure 53:
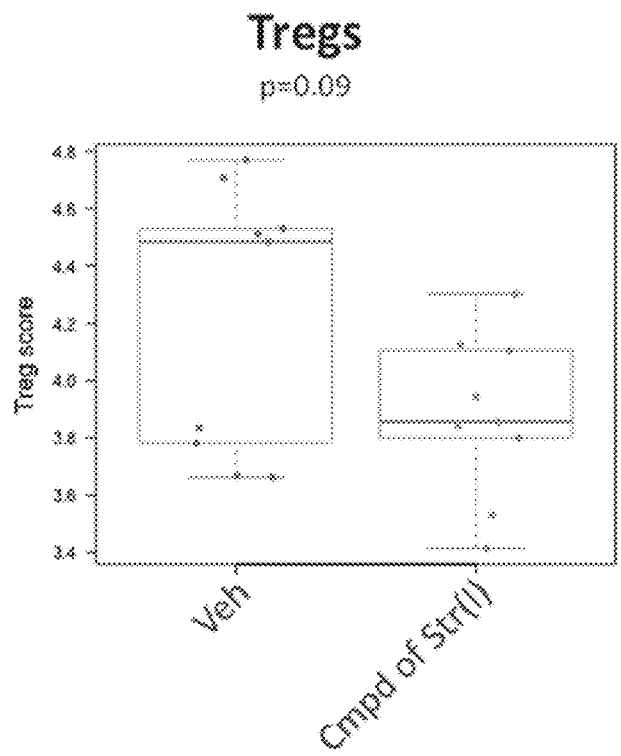
FIG. 53 shows regulatory T cells (Tregs) found in samples from a 4T1 model treated with vehicle or 25 mg/kg of a compound of structure (I).
Figure 54:
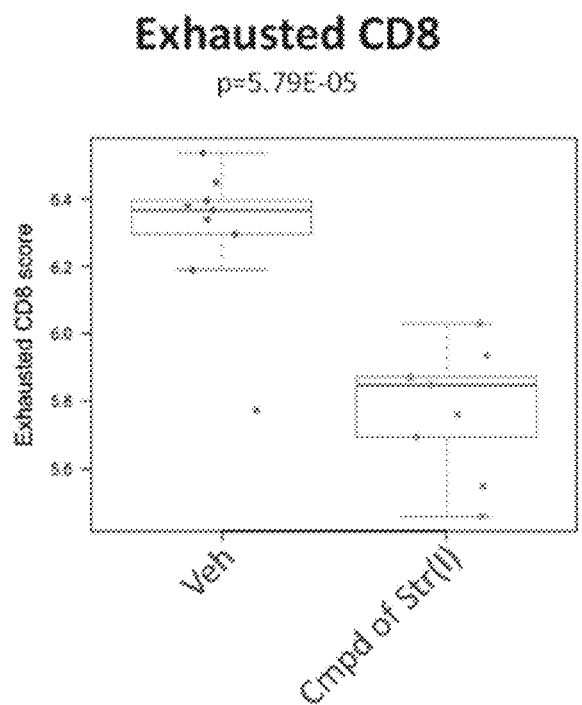
FIG. 54 shows exhausted CD8 T cells found in samples from a 4T1 model treated with vehicle or 25 mg/kg of a compound of structure (I).

To assess the effects of AXL inhibition on the immunosuppressive regulatory T cells (Treg), induced Tregs were treated with a tartrate salt of a compound of structure (I) and both cell viability and cytokine release following treatment were assayed. Treg differentiation was induced from a pooled peripheral blood mononuclear cell (PBMC) sample, using the CellXVivo Human Treg cell differentiation kit (R&D Systems) according to manufacturer protocol, and confirmed differentiation using qPCR for FoxP3 (FIG. 47A). iTregs were then treated with a tartrate salt of the compound of structure (I) at the concentrations indicated (FIG. 47B). iTregs exhibited a cell viability EC$_{50}$ of 245 nM with treatment with a tartrate salt of a compound of structure (I). Using the Luminex assay platform, multiple Treg markers were assessed following treatment with a tartrate salt of a compound of structure (I) (FIG. 47C). Multiple markers were observed to increase following treatment at concentrations up to µM. To assess the effects of treatment with a tartrate salt of a compound of structure (I) on tumor immune cell infiltration, the presence of gene expression signatures representing multiple immune cell types were measured in 4T1 syngeneic breast cancer model tumors. Markers of infiltrating immune cells were assessed on both formalin-fixed and fresh tissues using standard immunohistochemical and real-time PCR techniques. Shown in FIGS. 48-54 are graphical assessments of the immune cell types found in samples treated with vehicle or 25 mg/kg of a tartrate salt of a compound of structure (I). FIG. 48 shows total tumor infiltrating lymphocytes (TILs), FIG. 49 shows dendritic cells, FIG. 50 shows macrophages, FIG. 51 shows neutrophils, FIG. 52 shows natural killer (NK) cells, FIG. 53 shows regulatory T cells (Tregs), and FIG. 54 shows exhausted CD8 T cells.

Tumor samples were harvested at study termination. While a decrease in total tumor infiltrating lymphocytes (TILs) was observed, increased dendritic cell infiltration and a concomitant decrease in the immunosuppressive Tregs were also observed. These results indicate that the immune response affected by a tartrate salt of the compound of structure (I) is associated with dose-related increases in the percent of tumor-infiltrating effector CD4+ and CD8+ T cells and enhanced therapy responses to immune checkpoint inhibitors. In addition, treatment with a compound of structure (I) results in an increase in activated dendritic cells and a reduction in immune-suppressive infiltrating neutrophils and regulatory T-cells. Taken together, these preclinical data support the potential therapeutic activity of a compound of structure (I) as an immune modulating agent capable of enhancing tumor immune response as a single agent and when combined with therapies targeting immune checkpoints.

Example 17: Anti-Tumor Effects of the Compound of Structure (I)

The anti-tumor effects of tartrate salts of the compound of structure (I) have been tested in several mouse models of solid tumors. Table 10 below summarizes the % TGI of a tartrate salt of the compound of structure (I) in several mouse xenograft models, either alone, or in combination with other therapies.

TABLE 10

Single and combination activity of a tartrate salt of a
compound of structure (I) in several xenograft models

| Model | Activity [% TGI (dose level)] |
|---|---|
| KRAS mutant colorectal cancer (HCT-116) | 98.8(90 mg/kg) |
| Colorectal cancer PDX | 65.3(80 mg/kg) |
| Acute myeloid leukemia (MV-4-11) | 108.0(80 mg/kg) |
| Lung cancer (A549) | 111.1(80 mg/kg) |
| Lung cancer (A549, combination with Erlotinib) | 88.0 (75 mg/kg) |
| Lung cancer (H1650, combination with Erlotinib) | 139.3(25 mg/kg) |
| Lung cancer (H1650, combination with Osimertinib) | 130.3(40 mg/kg) |

Figure 55:
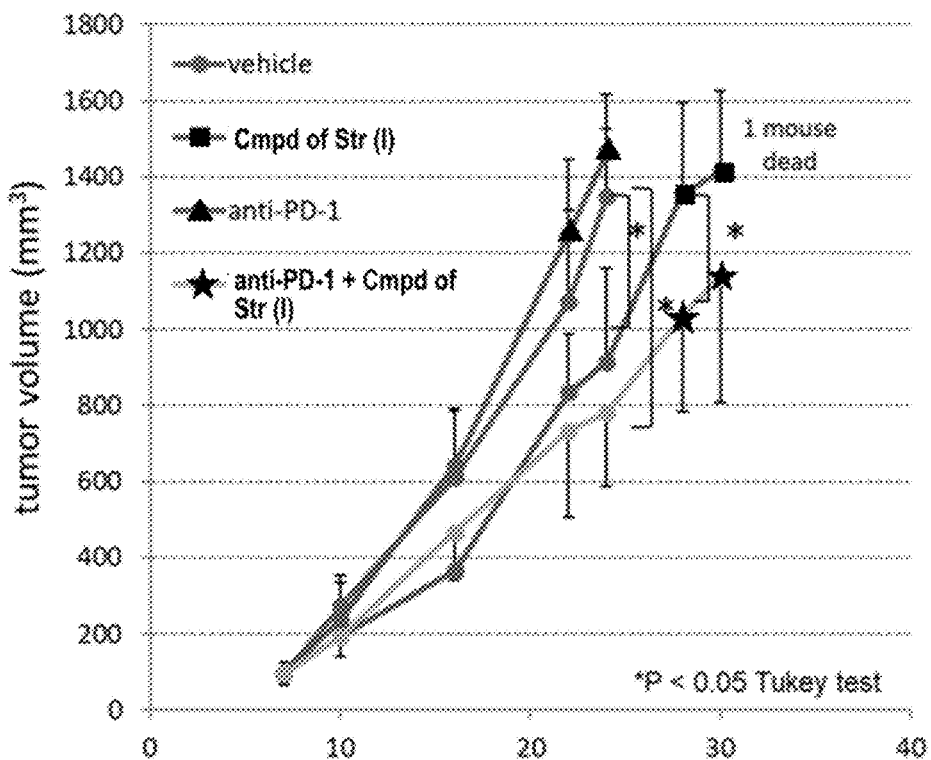
FIG. 55 shows the combination effect of the compound of structure (I) with anti-PD-1 in a 4T1 model.
Figure 56A:
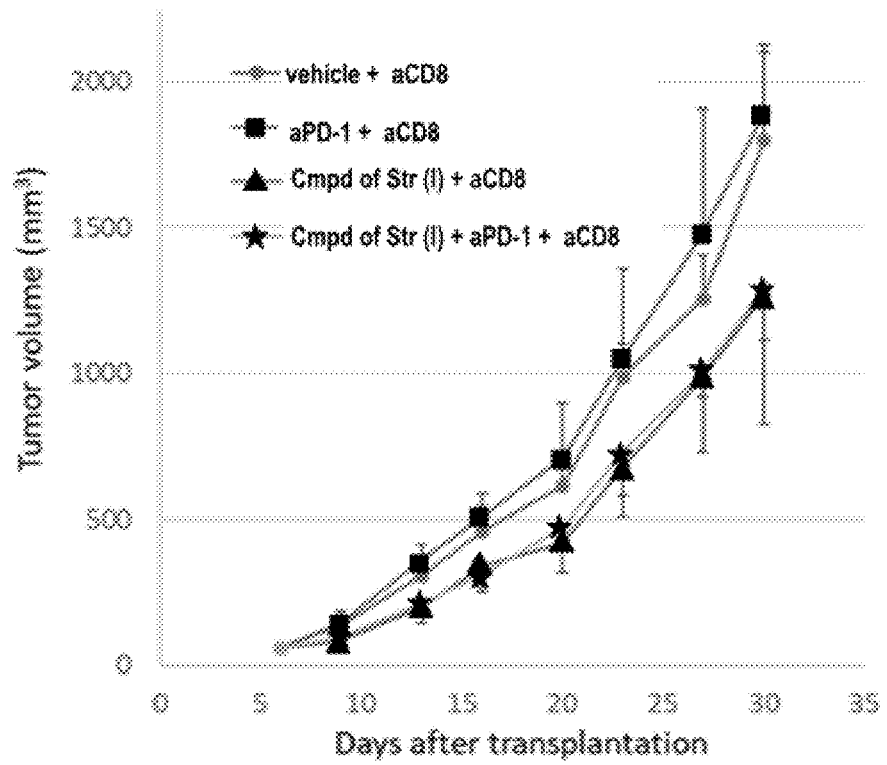
FIG. 56A and FIG. 56B show the anti-tumor effect of the compound of structure (I) in combination with PD-1 in CD8+T depletion mice.
Figure 56B:
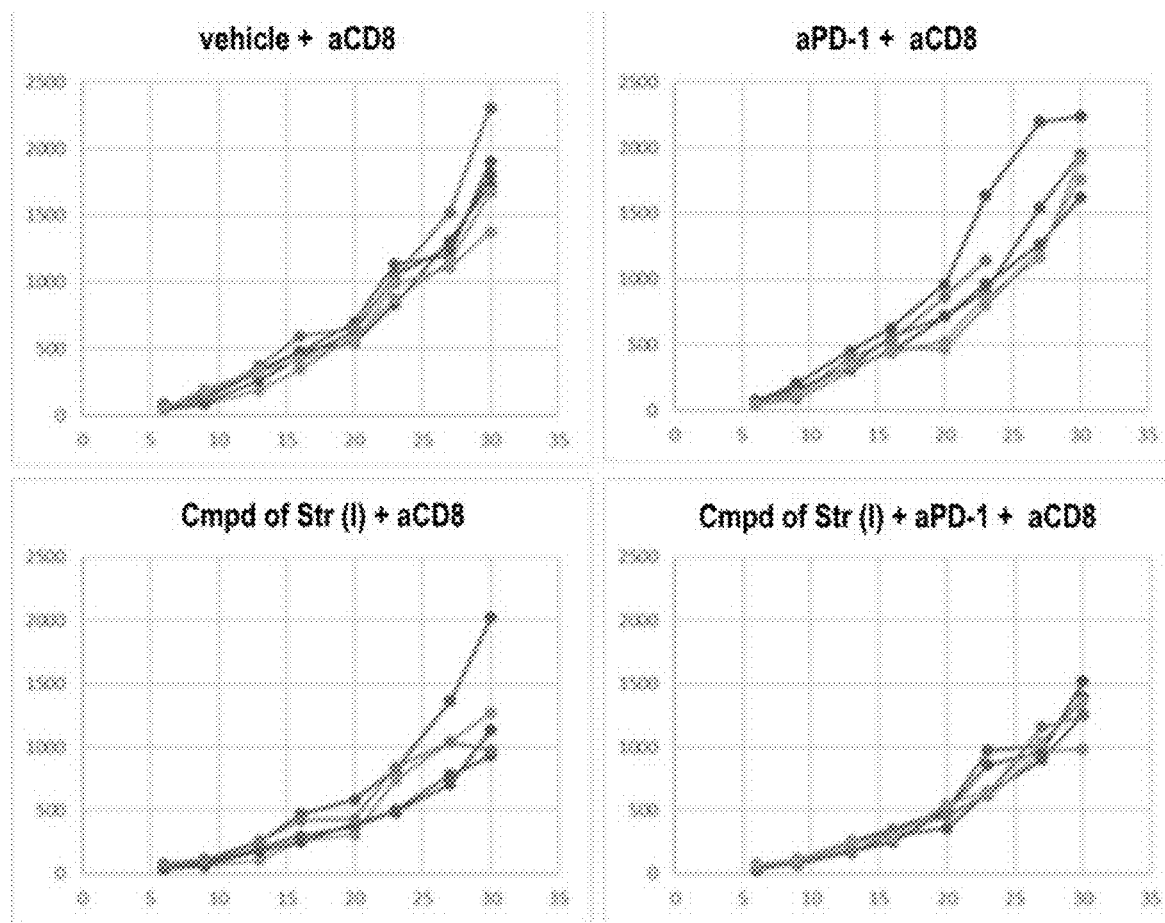
Figure 57:
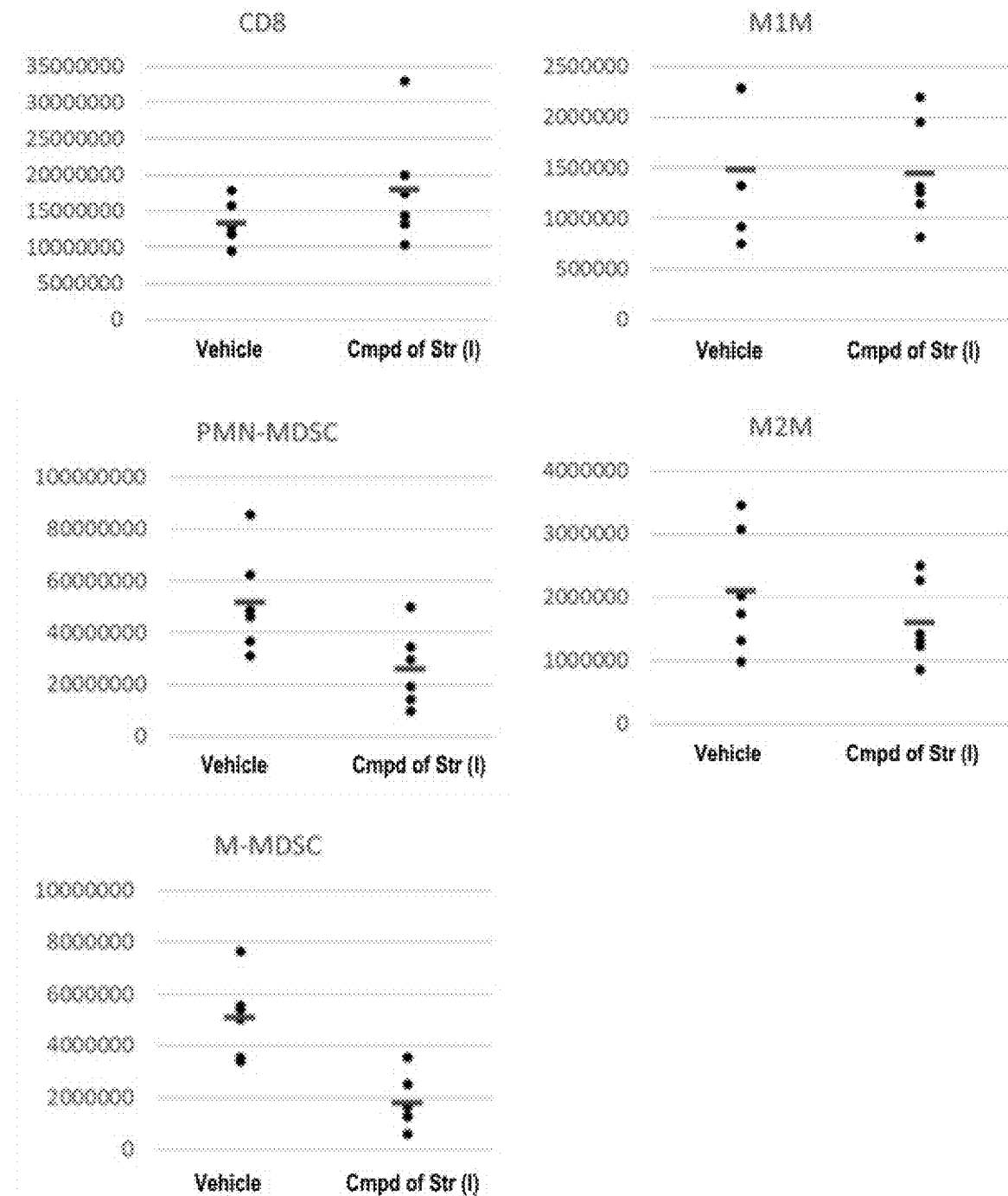
FIG. 57 shows effects of the compound of structure (I) on immune cells in the spleen (depicted as total cells in spleen at Day 16).
Figure 58A:
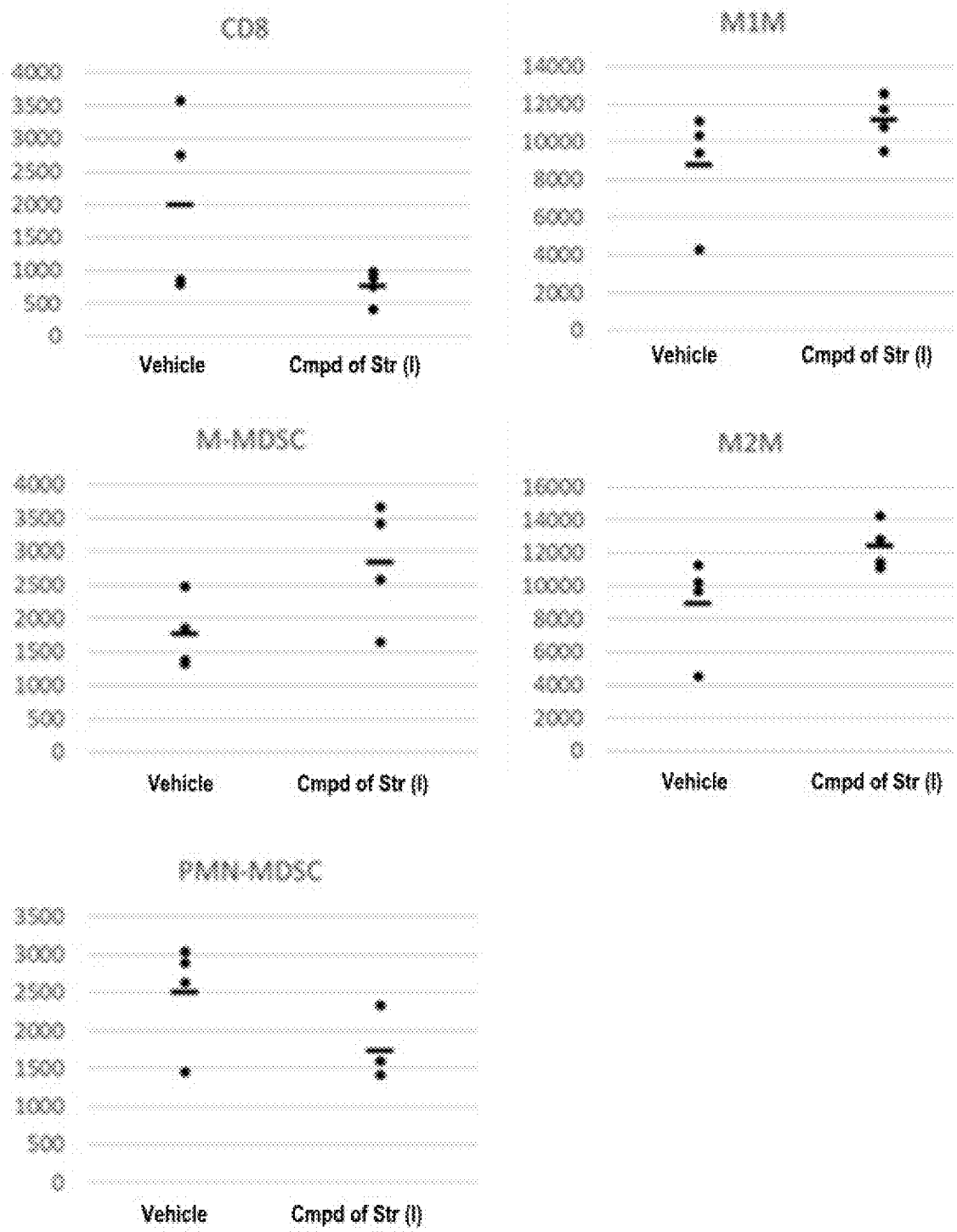
FIGS. 58A and 58B show effects of the compound of structure (I) on immune cells in tumors (depicted as cells/mg tumors at Day 11).
Figure 58B:
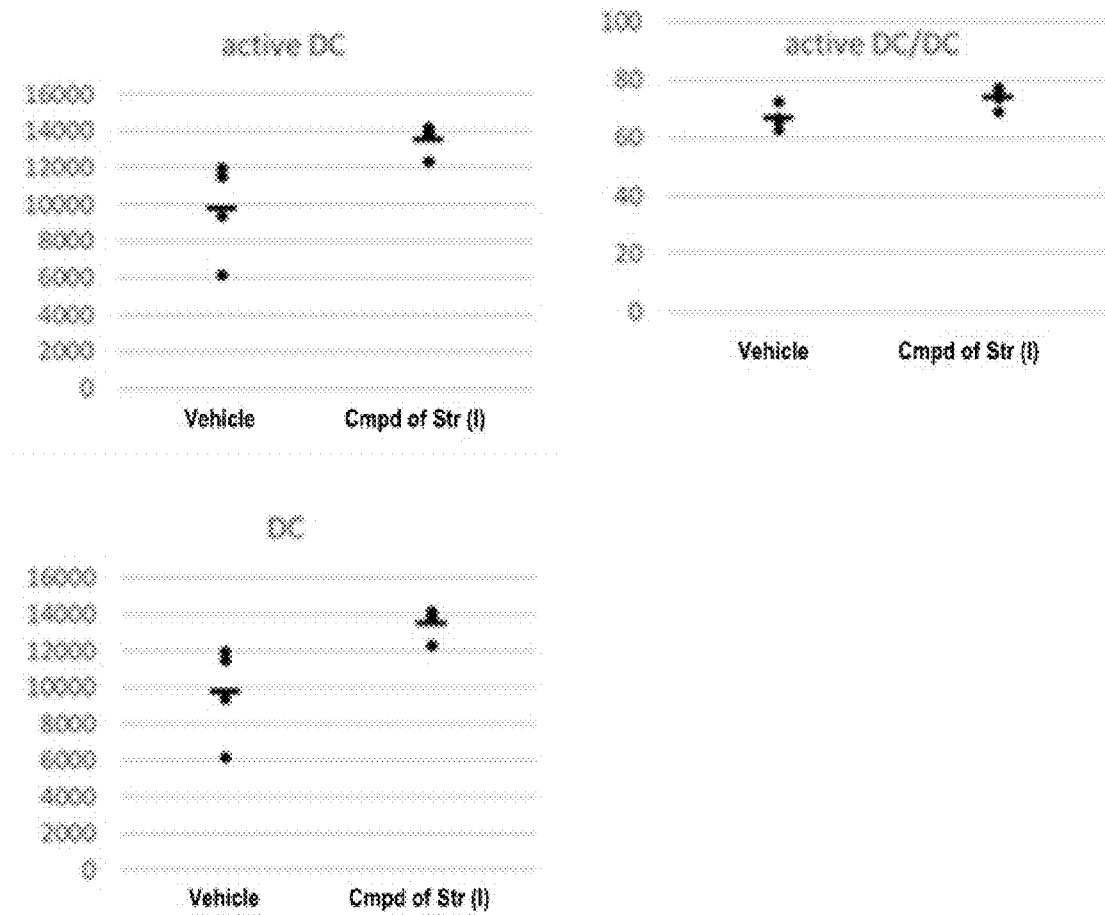
Figure 59:
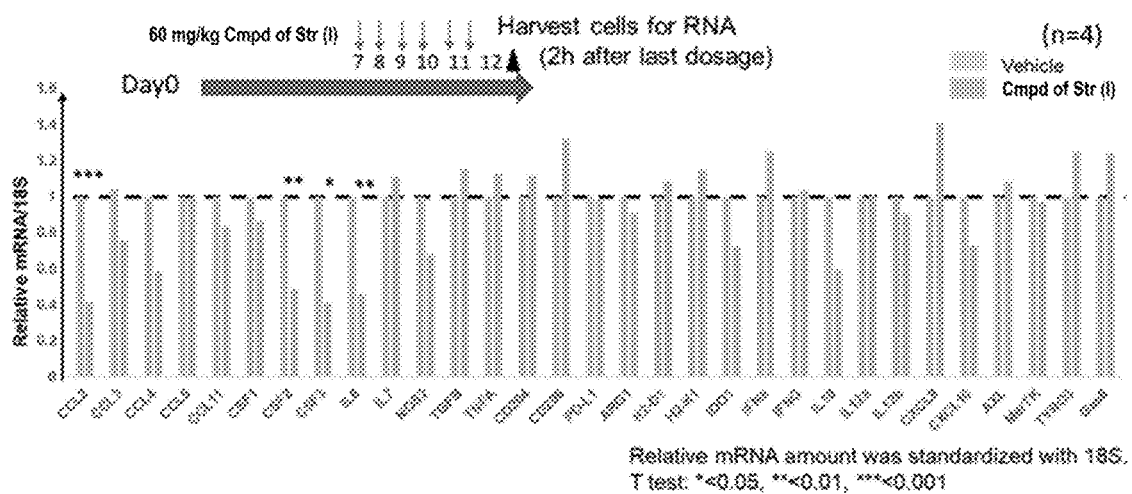
FIG. 59 shows effects of the compound of structure (I) on gene expression of cytokines and chemokines in tumors.
Figure 60:
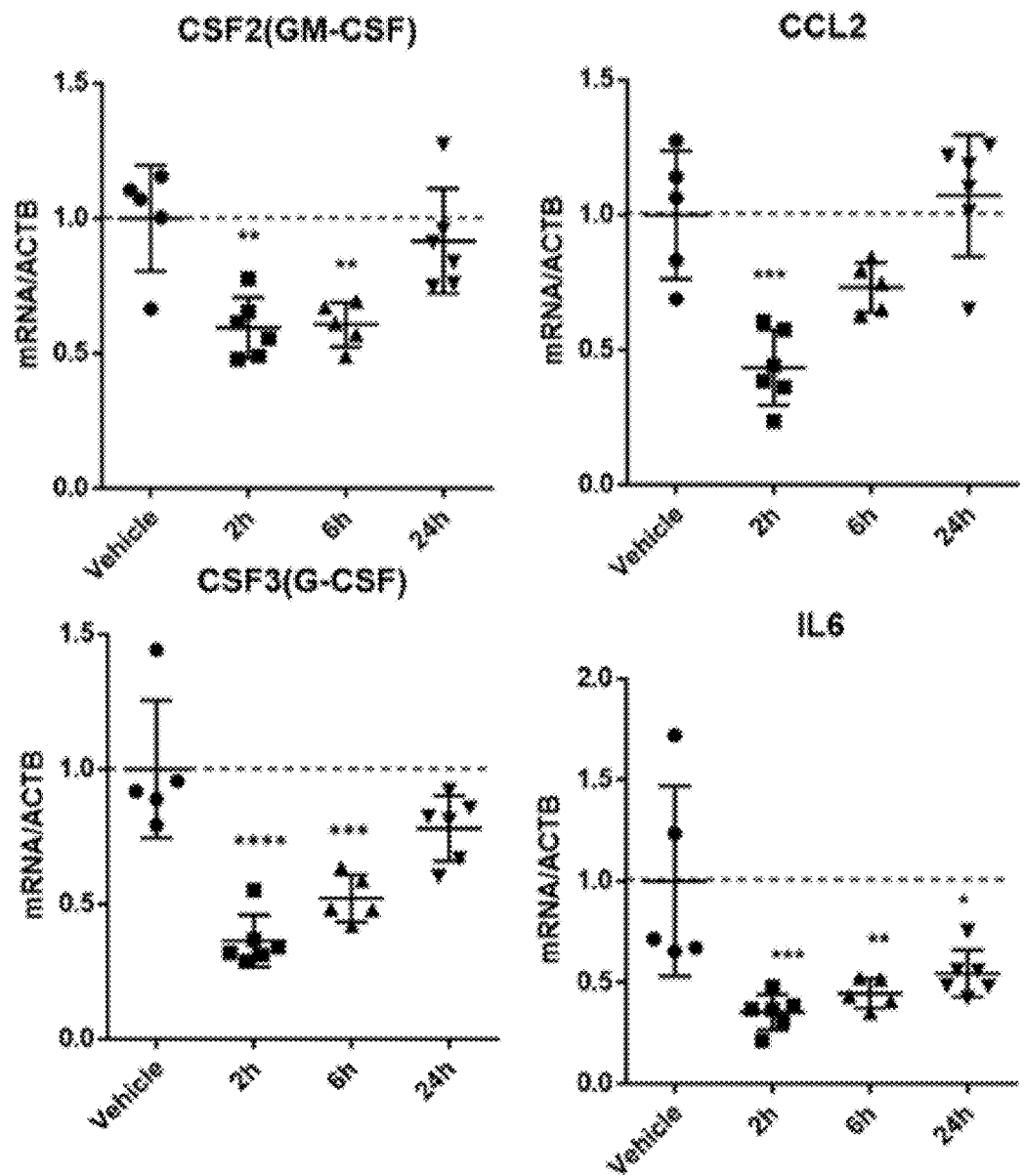
FIG. 60 shows a time course of regulation of cytokines and chemokines in tumors following treatment with the compound of structure (I).

Example 18: Immuno-Oncology Effects of the Compound of Structure (I), in a Syngeneic Breast Cancer Model In this study, tartrate salts of the compound of structure (I) was evaluated in combination with an immune checkpoint inhibitor (ICB) in an ICB-resistant triple negative breast cancer mouse model (4T1). In the 4T1 syngeneic model, anti-PD-1 monotherapy did not inhibit tumor growth indicating that this tumor is resistant to anti-PD-1 treatment, as shown in FIG. 55. On the other hand, the combination of a tartrate salt of the compound of structure (I) and anti-PD-1 resulted in statistically significant tumor growth inhibition versus monotherapy with a tartrate salt of the compound of structure (I) ($p<0.05$). The combination effect was influenced by potential CD8+ T cell depletion (see FIG. 56A and FIG. 56B). However, the effects of a tartrate salt of the compound of structure (I) were further investigated on immune cells in spleen and tumors, which showed the tumor growth inhibition was associated with significant decreases in myeloid-derived suppressor cells (MDSC) in the spleen (see FIG. 57) and an increase in infiltration and activation of dendritic cells (DCs) in the tumor (see FIGS. 58A and 58B). Gene expression analysis revealed that treatment with a tartrate salt of the compound of structure (I) decreased multiple immunosuppressive cytokines and chemokines including IL-6 and G-CSF in vivo (see FIG. 59 and FIG. 60). These results indicate that the compound of structure (I) modulates the immune-suppressive tumor microenvironment (TME) to reinvigorate T cell immunity in anti-PD-1 resistant 4T1 tumors. In conclusion, that AXL inhibition with the compound of structure (I) modulates TME and enhances the effects of ICBs in an anti-PD-1 resistant mice tumor model.

Example 19: The Compound of Structure (I) is Active in Pre-Clinical Models of EGER Positive Non-Small Cell Lung Cancer It was hypothesized that treatment with a tartrate salt of the compound of structure (I) may potentiate EGFRi treatment in cancer, and in particular EGFR mutant NSCLC. To interrogate this hypothesis, cell were treated with a tartrate salt of the compound of structure (I) and cell viability was assessed with the Celltiter-Glo assay, changes in mRNA expression were assayed using RT-qPCR, and protein expression changes were assayed using standard immunoblotting.

Figure 110A:
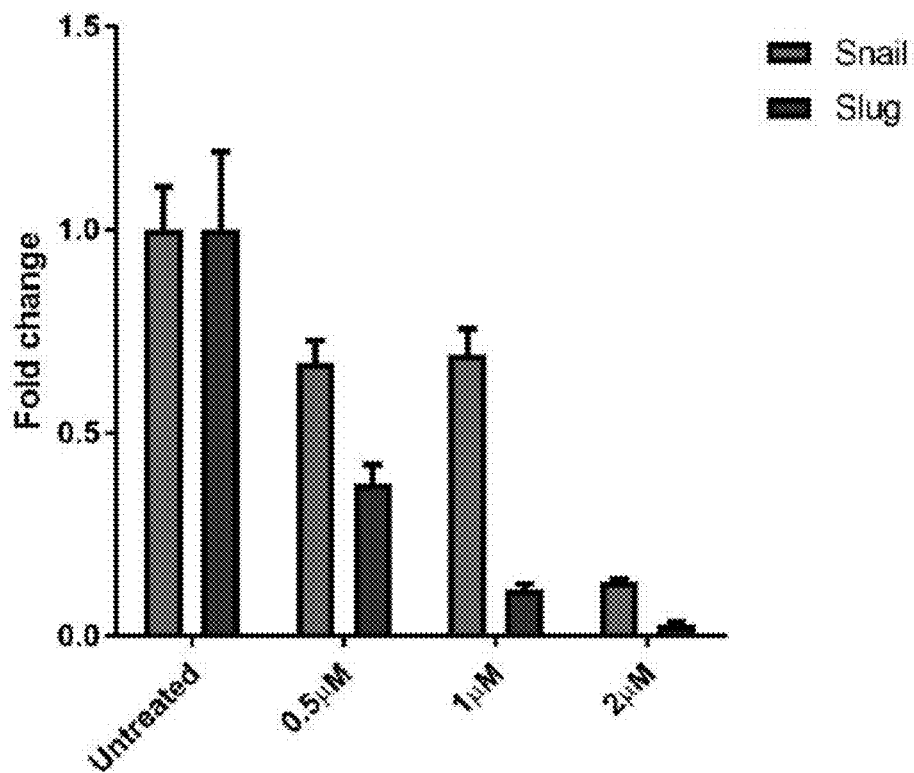
FIGS. 110A-110B shows EMT marker expression in the compound of structure (I)-treated NSCLC cells. H1650 (FIG. 110A) and A549 cells (FIG. 110B) were treated for two hours with the compound of structure (I) at concentrations up to 2 µM, following which snail and slug mRNA expression was assessed using standard qPCR technique.
Figure 110B:
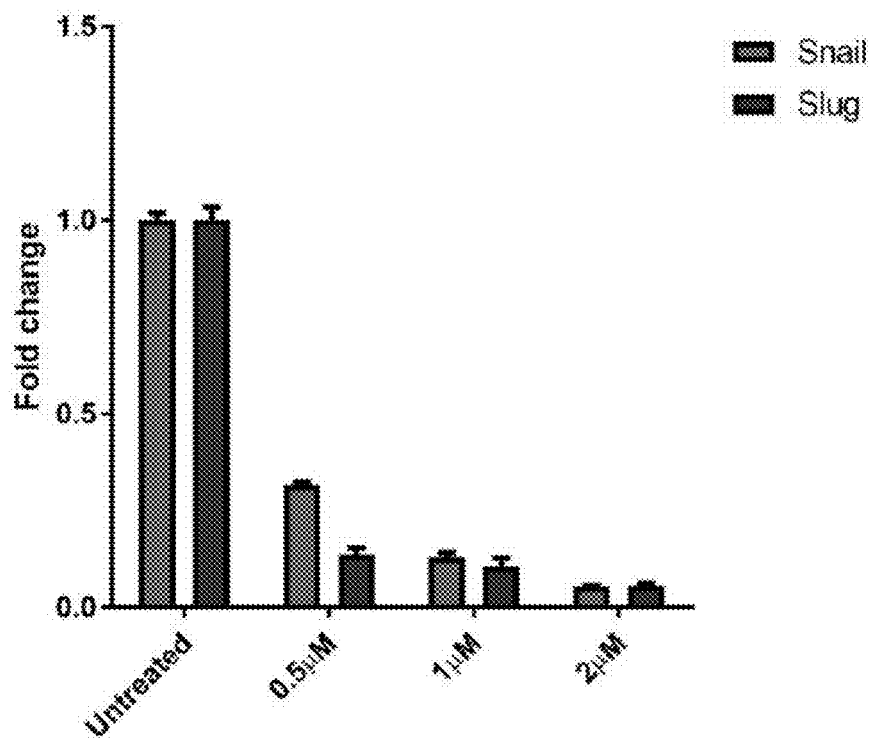

FIGS. 110A-110B shows EMT marker expression in the compound of structure (I)-treated NSCLC cells. H1650 (FIG. 110A) and A549 cells (FIG. 110B) were treated for two hours with a tartrate salt of the compound of structure (I) at concentrations up to 2 μM, following which snail and slug mRNA expression was assessed using standard qPCR technique.

Figure 111A:
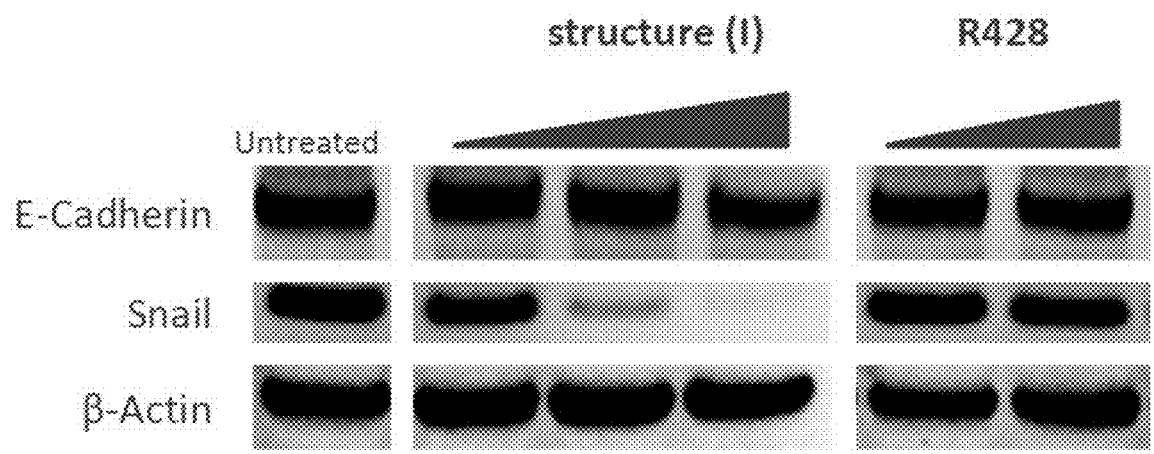
FIGS. 111A-111B show EMT marker protein expression in AXL inhibitor-treated H1650 and A549 cells. H1650 cells were treated with 0.1, 0.5, or 1.0 µM of the compound of structure (I) or R428, for 24 hours, following which cells were harvested and E-cadherin and snail protein expression was assessed using standard western immunblotting technique (FIG. 111A). A549 cells were treated with 0.1, 0.5, or 1.0 µM compound of structure (I) or R428, for 24 hours, following which cells were harvested and E-cadherin and Snail protein expression was assessed using standard western immunblotting technique (FIG. 111B).
Figure 111B:
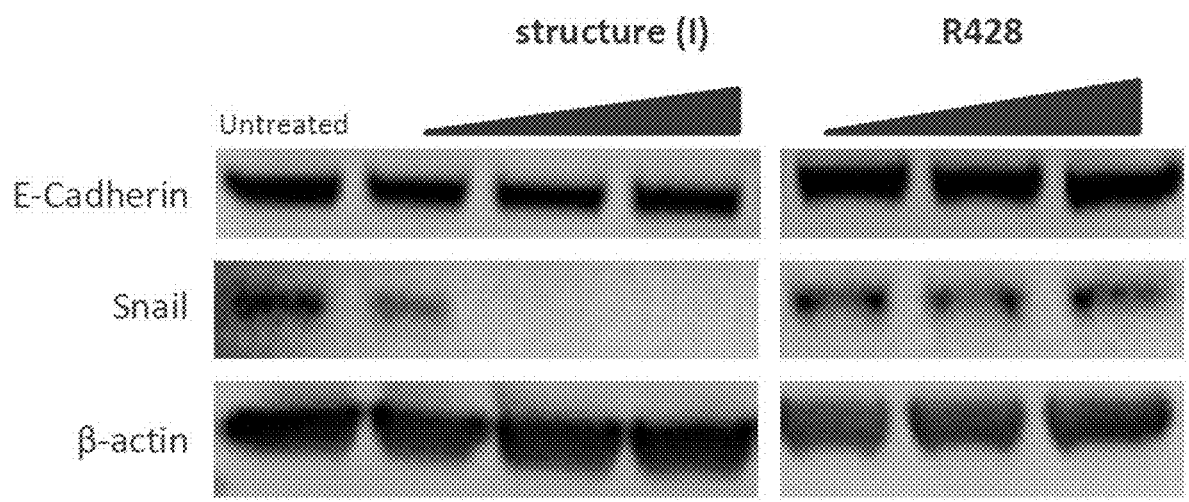

FIGS. 111A-111B show EMT marker protein expression in AXL inhibitor-treated H1650 and A549 cells. H1650 cells were treated with 0.1, 0.5, or 1.0 μM of a tartrate salt of the compound of structure (I) or R428, for 24 hours, following which cells were harvested and E-cadherin and snail protein expression was assessed using standard western immunblotting technique (FIG. 111A). A549 cells were treated with 0.1, 0.5, or 1.0 μM of a tartrate salt of compound of structure (I) or R428, for 24 hours, following which cells were harvested and E-cadherin and Snail protein expression was assessed using standard western immunblotting technique (FIG. 111B).

In mRNA and protein assays, observed changes were consistent with a reversal of the mesenchymal phenotype. Following treatment, Slug mRNA expression was inhibited as much as 3.8-fold. However, E-cadherin expression was increased by 1.6-fold.

Figure 112:
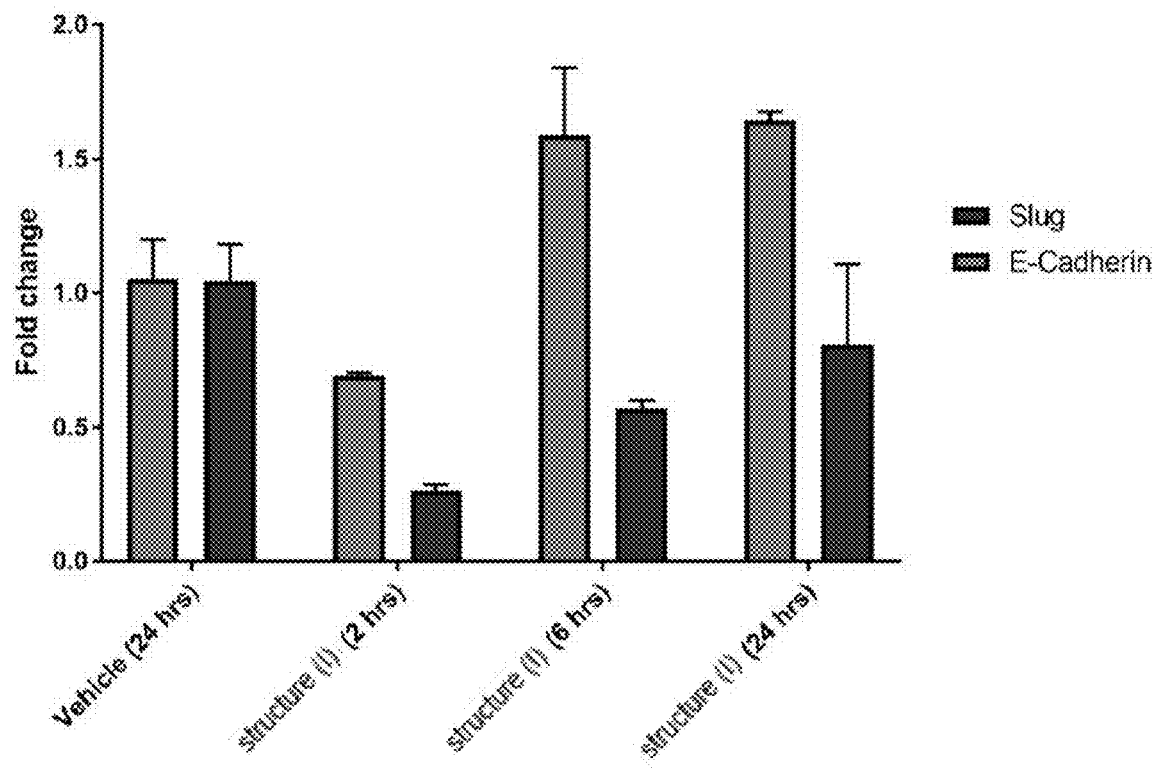
FIG. 112 shows slug mRNA expression in the compound of structure (I) treated H1650 xenograft mice. H1650 xenograft tumor bearing mice were treated with the compound of structure (I) (40 mg/kg) by oral gavage, following which tumors were harvested at varying timepoints following dosing. Slug and E-cadherin mRNA expression was assessed by standard qPCR technique.

To assess the combination in vivo, the H1650 xenograft model for NSCFC was utilized. In pharmacodynamic assessment of EMT markers in vivo, as much as a 56% reduction in Snail protein expression was observed following a single dose of a tartrate salt of the compound of structure (I) (40 mpk, at 24 hrs). FIG. 112 shows slug mRNA expression in a tartrate salt of the compound of structure (I) treated H1650 xenograft mice. H1650 xenograft tumor bearing mice were treated with a tartrate salt of the compound of structure (I) (40 mg/kg) by oral gavage, following which tumors were harvested at varying timepoints following dosing. Slug and E-cadherin mRNA expression was assessed by standard qPCR technique. FIG. 113 shows snail protein expression in the compound of structure (I)-treated H1650 xenograft mice. H1650 xenograft tumor bearing mice were treated with a tartrate salt of the compound of structure (I) (40 mg/kg) by oral gavage, following which tumors were harvested at varying timepoints following dosing. Slug and E-cadherin protein expression was assessed by standard immunoblotting technique.

Figure 18C:
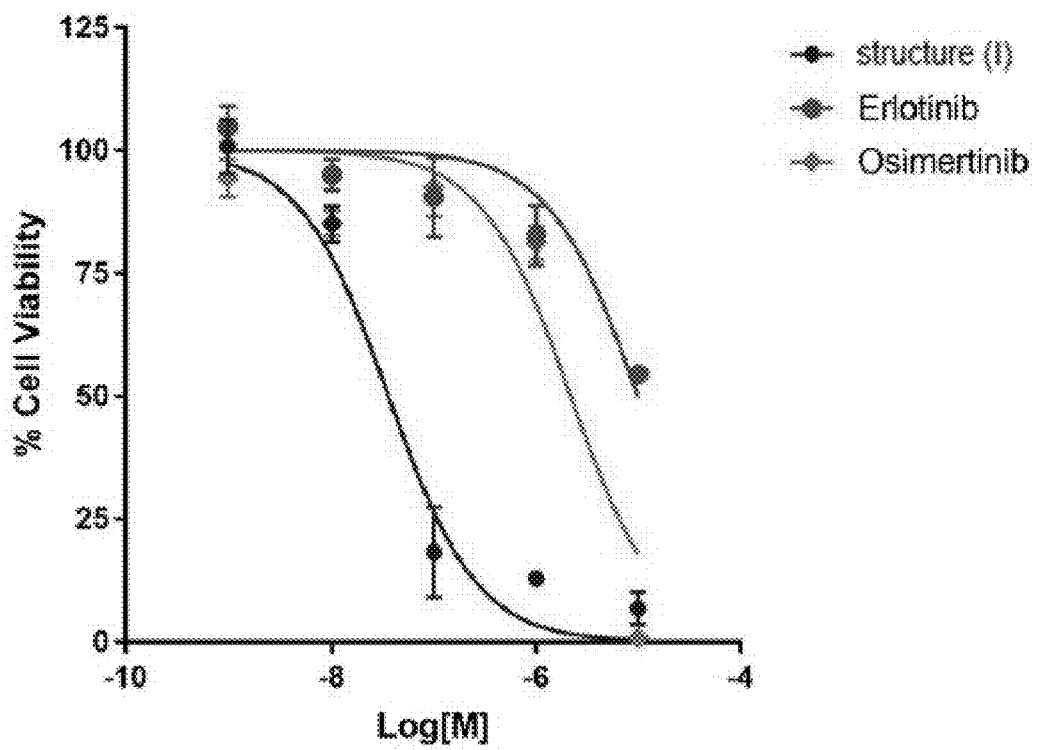
FIG. 18C and FIG. 18D show the compound of structure (I) and EGFRi activity in the H1650 NSCLC cell line. H1650 cells were incubated in the presence of the indicated drugs for 72 hours, following which cell viability was assessed using the CellTiter-Glo reagent according to manufacturer protocol. H1650 cells treated with single-agents ($IC_{50}$): the compound of structure (I) (35.9 nM), erlotinib (9.9 μM), or osimertinib (2.2 μM) (FIG. 18C). H1650 cells were treated with combinations of the compound of structure (I) and erlotinib (FIG. 18D).
Figure 18D:
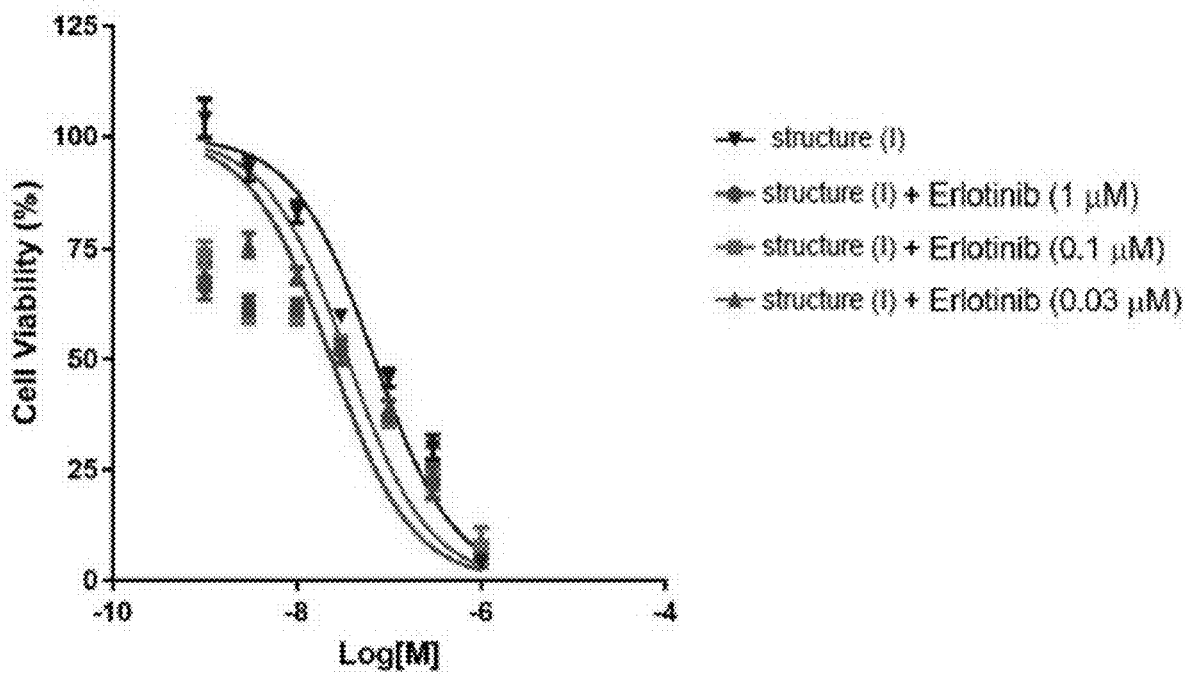

In cell viability assays in the H1650 NSCLC cell line, a tartrate salt of the compound of structure (I) showed an EC so of 39 nM, while osimertinib showed an $EC_{50}$ of 2.2 μM. FIG. 18C and FIG. 18D show a tartrate salt of the compound of structure (I) and EGFRi activity in the H1650 NSCLC cell line. H1650 cells were incubated in the presence of the indicated drugs for 72 hours, following which cell viability was assessed using the CellTiter-Glo reagent according to manufacturer protocol. H1650 cells treated with single-agents ($IC_{50}$): a tartrate salt of the compound of structure (I) (35.9 nM), erlotinib (9.9 μM), or osimertinib (2.2 μM) (FIG. 18C). H1650 cells were also treated with combinations of a tartrate salt of the compound of structure (I) and erlotinib (FIG. 18D).

Figure 18E:
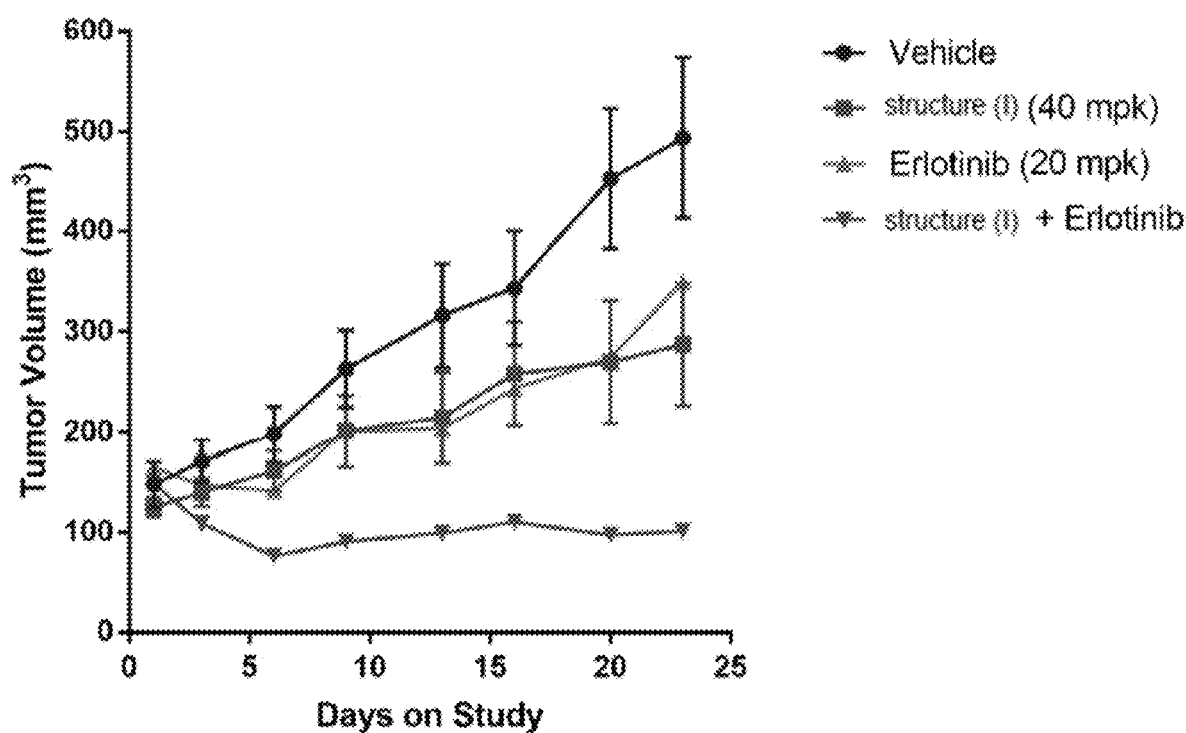
FIG. 18E and FIG. 18F shows combination activity of the compound of structure (I) and erlotinib in the H1650 xenograft model. H1650 xenograft tumor bearing mice were treated daily by oral gavage with either the compound of structure (I) (40 mg/kg), erlotinib (20 mpk), or the combination. Tumor volumes and bodyweights were assessed twice weekly.
Figure 18F:
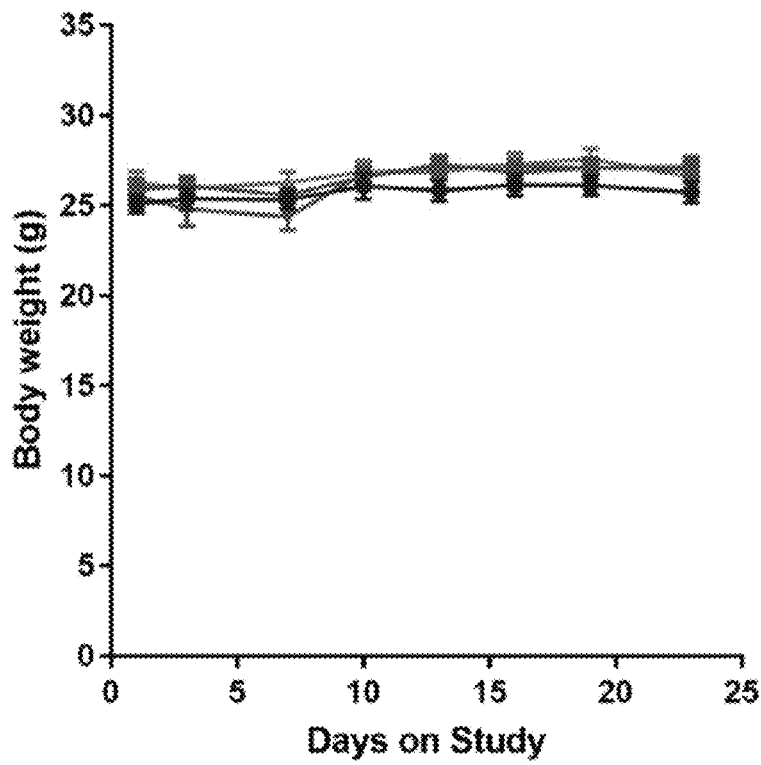

In assessment of treatment efficacy in vivo, and with treatment with a tartrate salt of the compound of structure (I) (40 mpk, qd), 60% tumor growth inhibition (% TGI) was opbserved over the course of a 21-day treatment regimen. FIG. 18E and FIG. 18F also show combination activity of a tartrate salt of the compound of structure (I) and erlotinib in the H1650 xenograft model. H1650 xenograft tumor bearing mice were treated daily by oral gavage with either a tartrate salt of the compound of structure (I) (40 mg/kg), erlotinib (20 mpk), or the combination. Tumor volumes and bodyweights were assessed twice weekly.

Figure 18G:
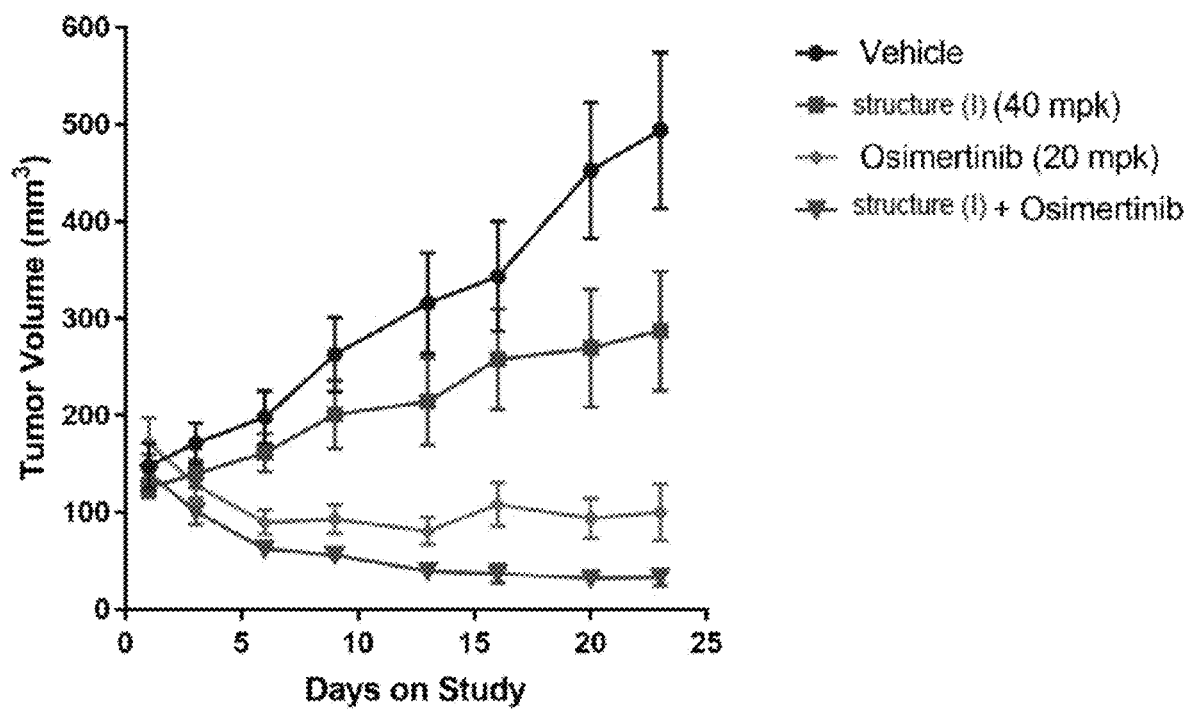
FIG. 18G and FIG. 18H show combination activity of the compound of structure (I) and osimertinib in the H1650 xenograft model. H1650 xenograft tumor bearing mice were treated daily by oral gavage with either the compound of structure (I) (40 mg/kg), osimertinib (20 mpk), or the combination. Tumor volumes and bodyweights were assessed twice weekly.
Figure 18H:
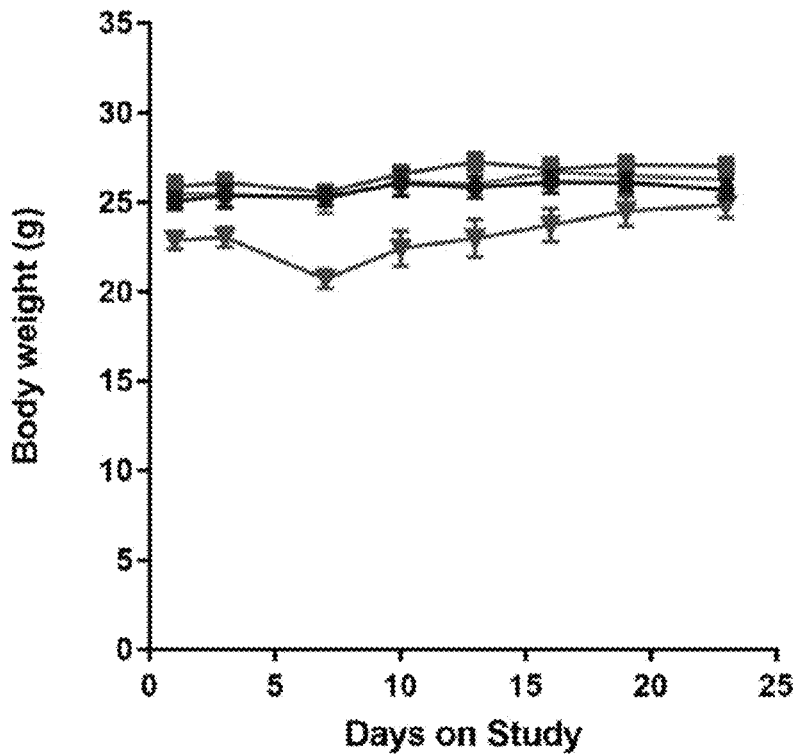

With osimertinib treatment (20 mpk, qd), 121% TGI was observed. However, with the combination, 140% TGI was observed. FIG. 18G and FIG. 18H show combination activity of a tartrate salt of the compound of structure (I) and osimertinib in the H1650 xenograft model. H1650 xenograft tumor bearing mice were treated daily by oral gavage with either a tartrate salt of the compound of structure (I) (40 mg/kg), osimertinib (20 mpk), or the combination. Tumor volumes and bodyweights were assessed twice weekly. Due to its ability to reverse the aggressive mesenchymal phenotype of cancer cells, the compound of structure (I) is a promising agent with the potential to have single agent activity and combined synergy with targeted anti-cancer agents.

Figures 104A, 104B:
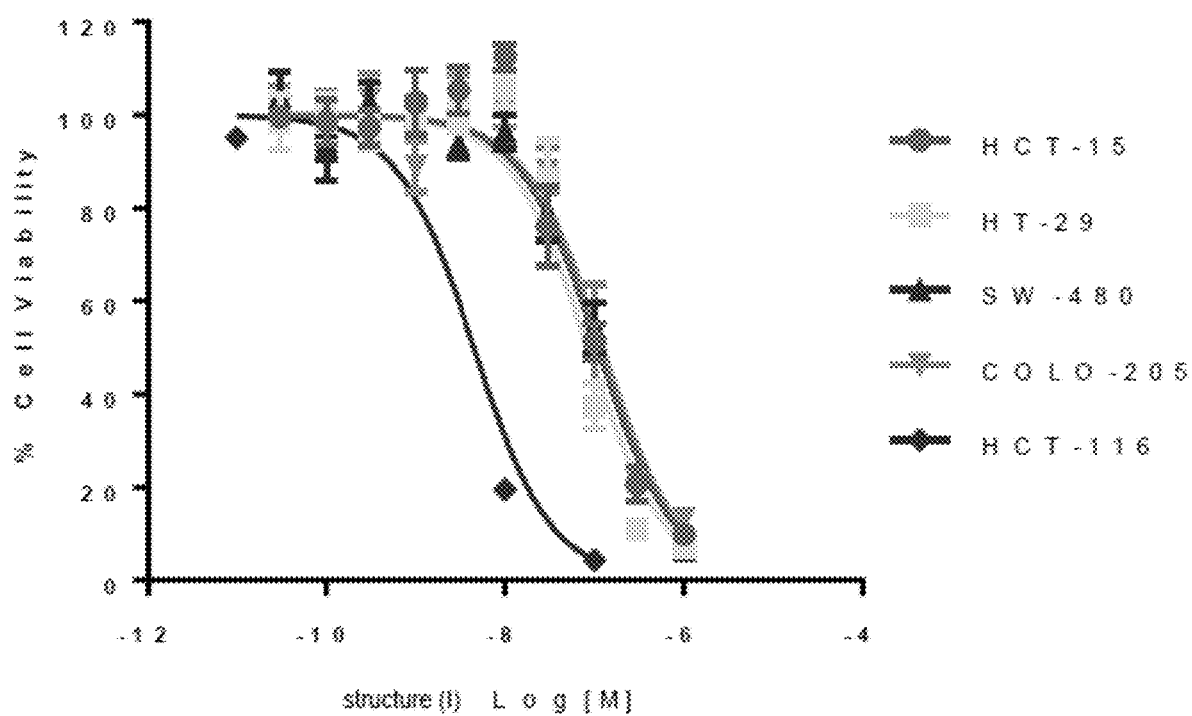
FIGS. 104A-104B illustrate that the compound of structure (I) inhibits cell growth of colorectal carcinoma (CRC) cells lines independent of KRAS mutation status.

Example 20: The Compound of Structure (I) Demonstrates Efficacy in Preclinical Models of Colorectal Cancer Independent of KRAS Mutation Status Tartrate salts of the compound of structure (I) is evaluated for activity against colorectal cancer (CRC). In cell viability assays of CRC lines, treatment with a tartrate salt of the compound of structure (I) resulted in $IC_{50}$ values ranging from 4.5-123 nM. Notably, cell growth inhibition following treatment with a tartrate salt of the compound of structure (I) was independent of KRAS mutation status; the KRAS mutant HCT-116 line was the most sensitive CRC cell line tested. FIG. 104A shows KRAS mutation status of selected CRC cell lines. FIG. 104B shows CRC cell viability determination following 72 hrs treatment with a tartrate salt of the compound of structure (I) and assessment via CellTiter-Glo.

Figure 105A:
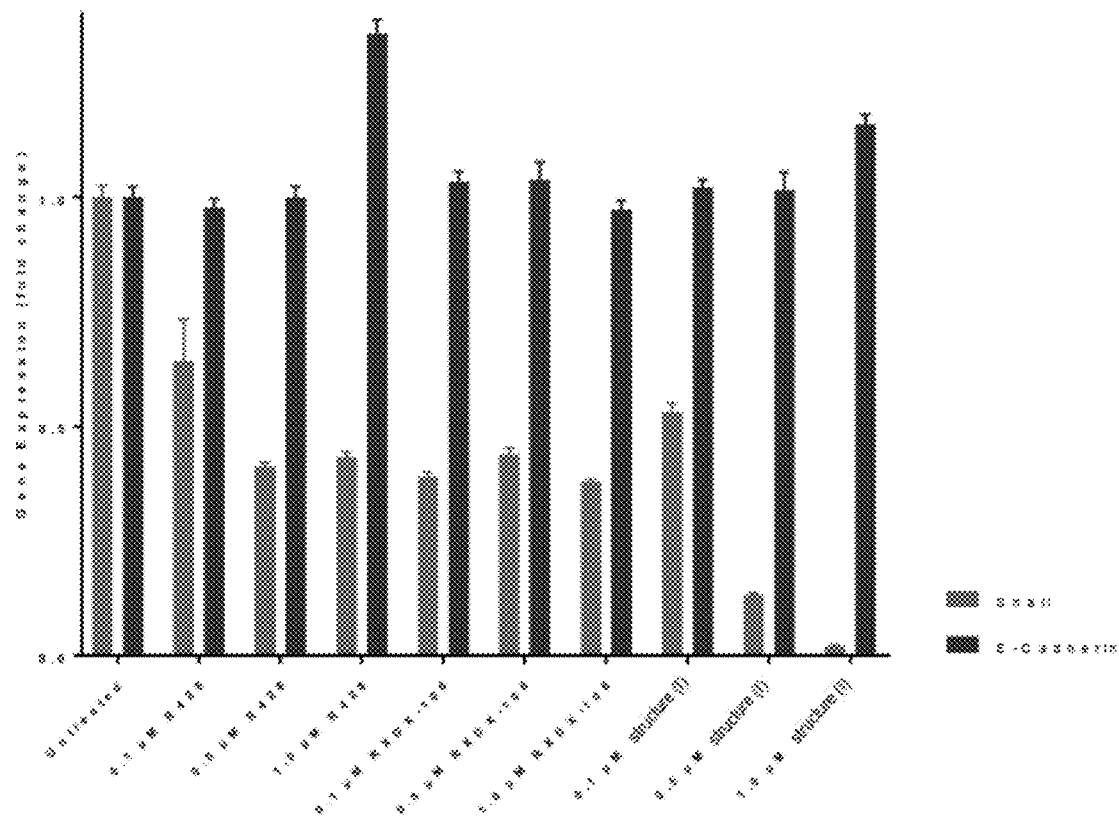
FIGS. 105A-105B shows that the compound of structure (I) suppresses mesenchymal markers without modulating epithelial markers. HCT-116 cells were treated with indicated concentrations of AXL inhibitors: R428, RXDX-106, and the compound of structure (I) for 24 hrs.
Figure 105B:
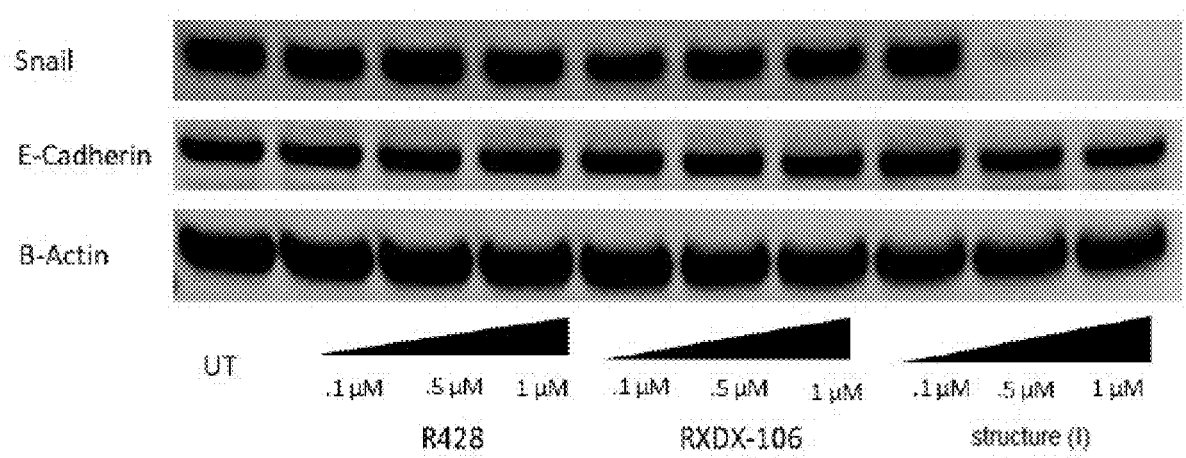

Mesenchymal markers, including Snail, were suppressed by 7.6-fold (mRNA) and 4.9-fold (protein) in the HCT-116 line at 500 nM. For example, FIG. 105A and FIG. 105B show that a tartrate salt of the compound of structure (I) suppresses mesenchymal markers without modulating epithelial markers. HCT-116 cells were treated with indicated concentrations of AXL inhibitors: R428, RXDX-106, and a tartrate salt of the compound of structure (I) for 24 hrs. FIG. 105A shows mRNA expression levels were quantified via RT-qPCR. FIG. 105B shows protein expression levels were analyzed via western blot. Snail expression was suppressed by 7.6 fold (m-RNA) and 4.9 fold (protein) with 500 nM of a tartrate salt of compound of structure (I).

Figure 106A:
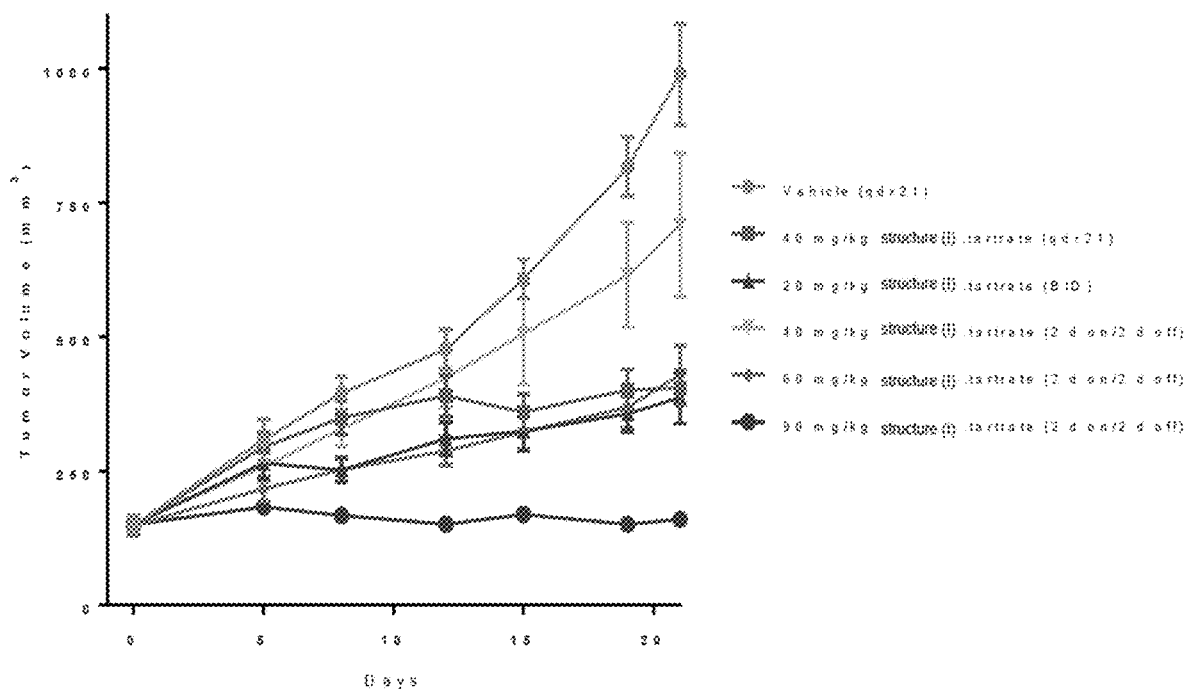
FIGS. 106A-106C shows the compound of structure (I) inhibits tumor growth in the KRAS mutant HCT-116 xenograft model. Athymic nude mice were injected in the hindflank with 10 million cells and stratified into cohorts of 10 mice. Compounds were formulated in 5% (w/v) TPGS and 1% (v/v) PS80 in H20 and administered my oral gavage. Tumor volumes (FIG. 106A) and body weights were measured twice a week (FIG. 106B). Intra-tumoral GAS6 expression was quantified via RT-qPCR. The 40 mg/kg compound of structure (I) cohort achieved 69% TGI without adverse events (FIG. 106C).
Figure 106B:
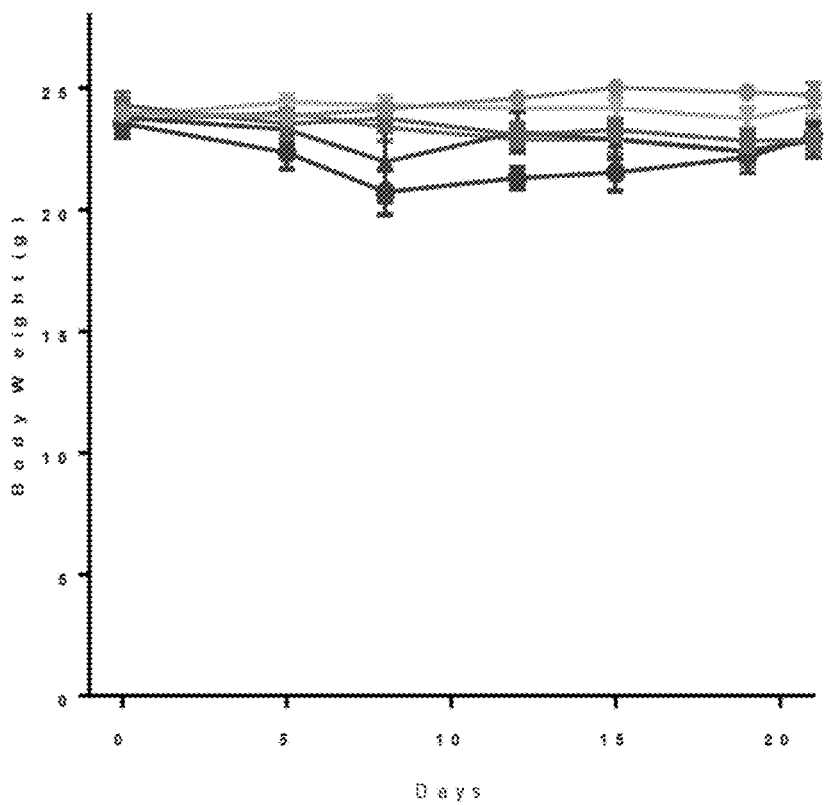
Figure 106C:
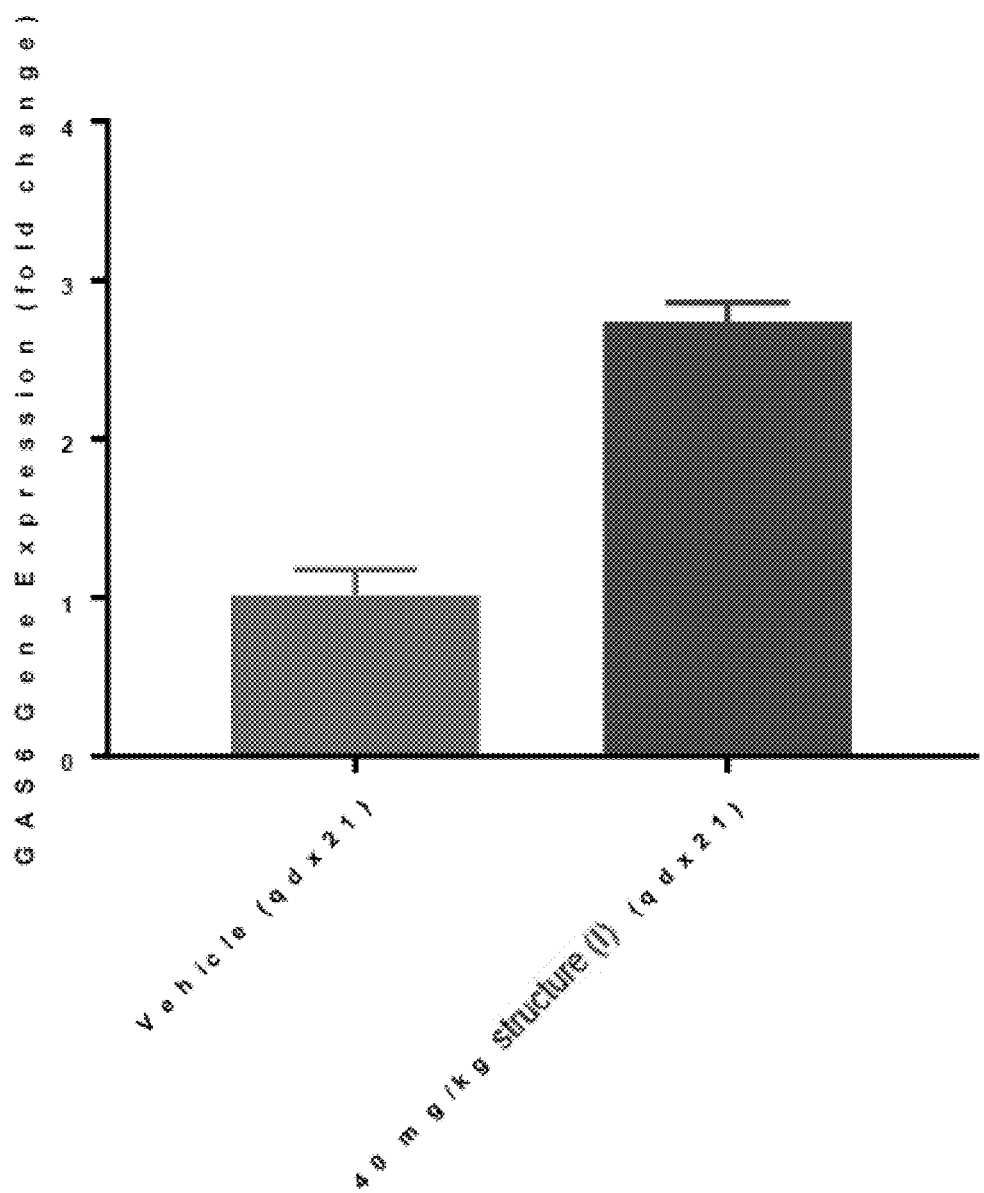

Activity of a tartrate salt of the compound of structure (I) was also assessed in vivo using two KRAS mutant CRC models: HCT-116 and a patient-derived xenograft (PDX) model. In the HCT-116 xenograft model, single agent treatment with a tartrate salt of the compound of structure (I) achieved 69% tumor growth inhibition (% TGI) with an oral dosing schedule at 40 mg/kg. Athymic nude mice were injected in the hind-flank with 10 million cells and stratified into cohorts of 10 mice. Compounds were formulated in 5% (w/v) TPGS and 1% (v/v) PS80 in H20 and administered my oral gavage. Tumor volumes (FIG. 106A) and body weights were measured twice a week (FIG. 106B). Intra-tumoral GAS6 expression was quantified via RT-qPCR. The 40 mg/kg of a tartrate salt of compound of structure (I) cohort achieved 69% TGI without adverse events (FIG. 106C).

Figure 107A:
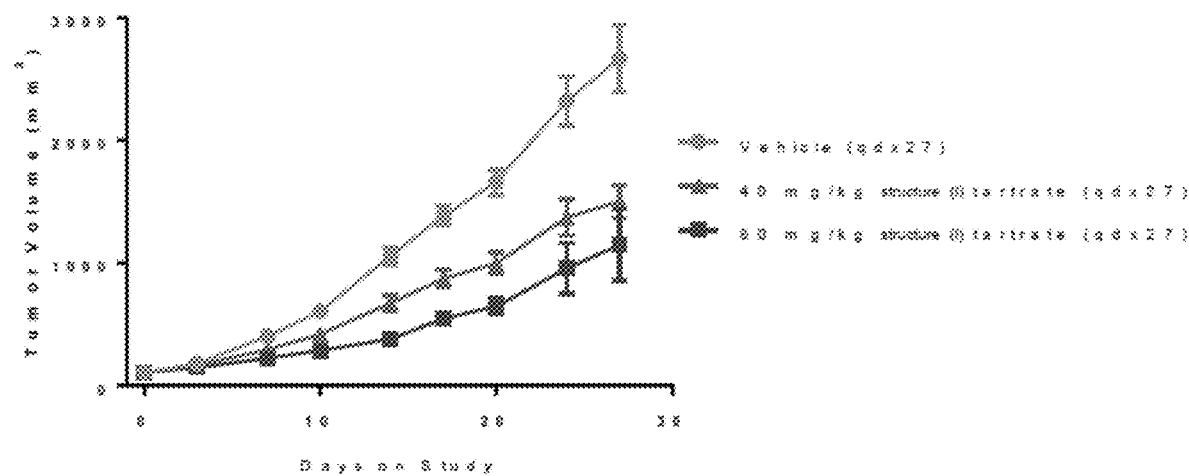
FIGS. 107A-107B show the compound of structure (I) inhibits tumor growth in the KRAS mutant PDX CRC model. Balb/c nude mice were implanted with 2-3 mm fragments of primary human CRC tumors and then stratified into cohorts of 10 mice. The compound of structure (I) was formulated in 5% (w/v) TPGS and 1% (v/v) PS80 in H20 and administered by oral gavage. Tumor volume (FIG. 107A) and bodyweights (FIG. 107B) were measured twice a week. The 40 mg/kg compound of structure (I) cohort-achieved 44% TGI without adverse events.
Figure 107B:
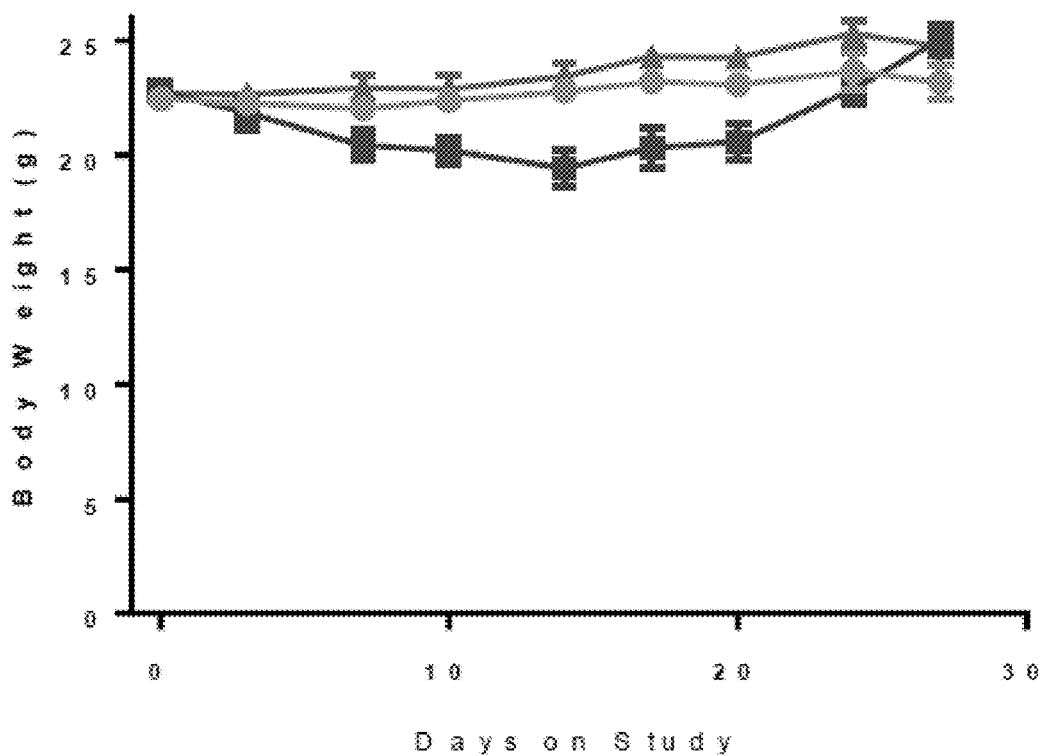
Figure 108A:
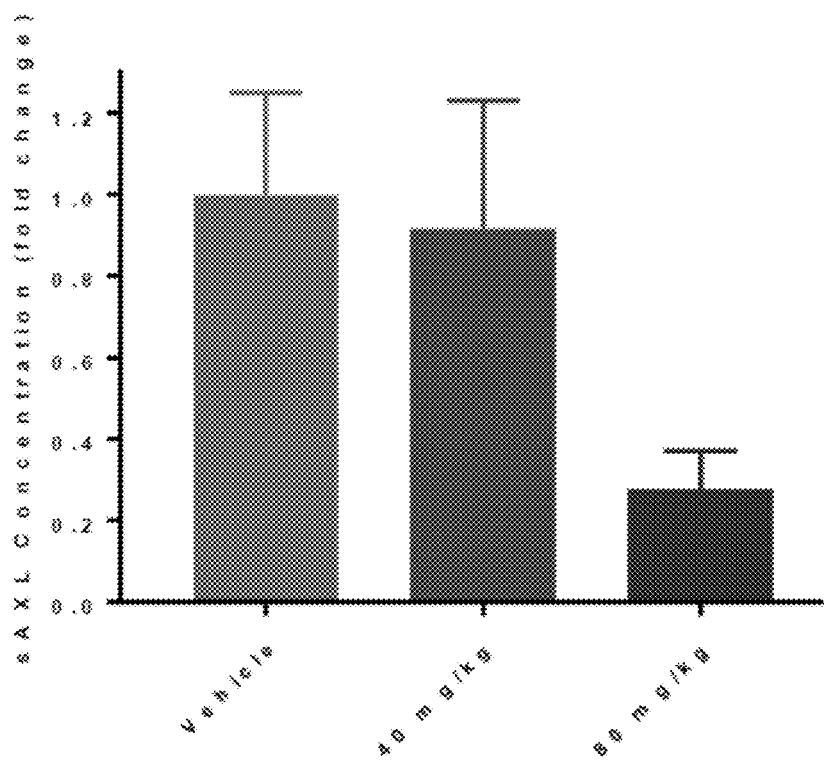
FIGS. 108A-108E show the compound of structure (I) suppresses sAXL/sGAS6 concentrations while down-regulating Wnt/β-catenin regulated genesAxin2/CCND1 in the KRAS mutant PDX CRC model. sAXL (FIG. 108A) and sGAS6 (FIG. 108B) were quantified in the serum via ELISA. Intra-tumoral GAS6 (FIG. 108C), Axin2 (FIG. 108D), and CCND1 (FIG. 108E) were quantified via RT-qPCR. Analyses were performed on mice treated for 27 days (except Axin2; 21 days). Suppression of sAXL and sGAS6 indicate a reversal of EMT. The compound of structure (I)-mediated downregulation of Wnt/β-catenin associated genes further supports a previously reported role for AXL in β-catenin stabilization.
Figure 108B:
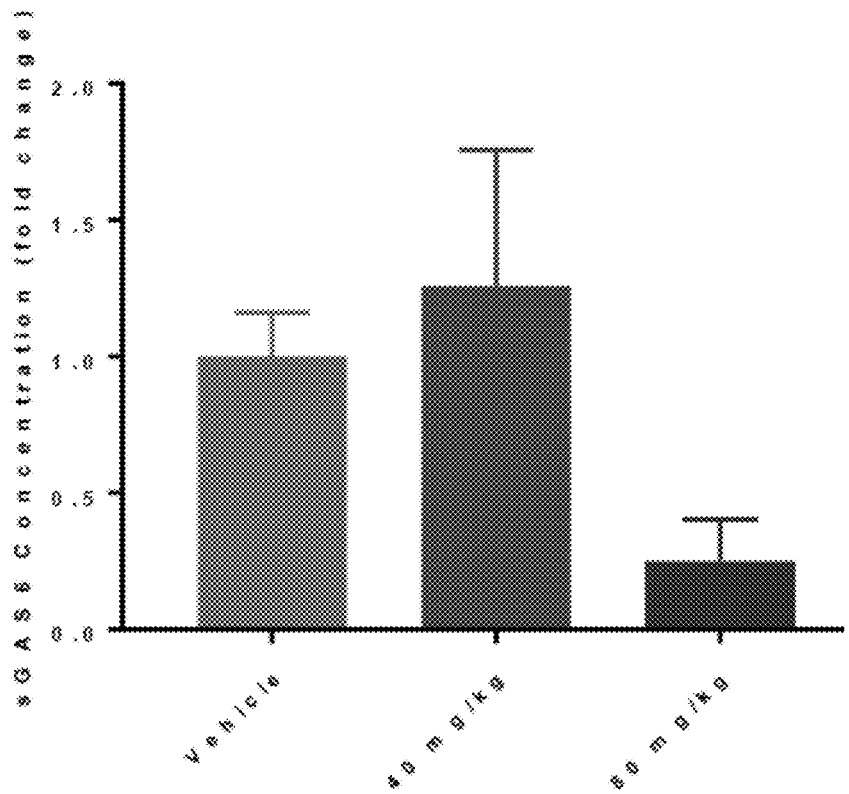
Figure 108C:
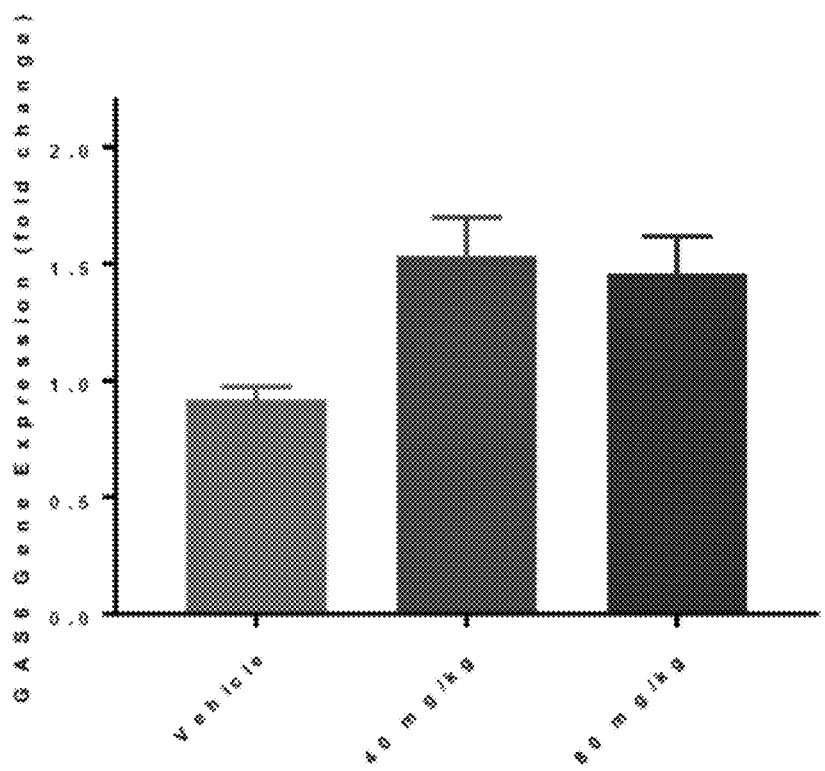
Figure 108D:
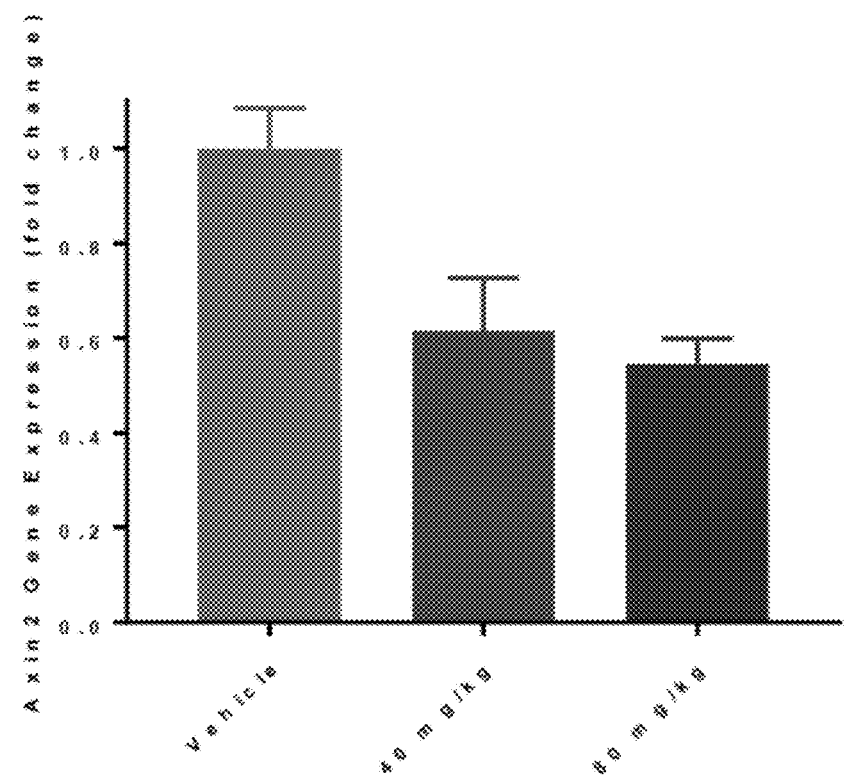
Figure 108E:
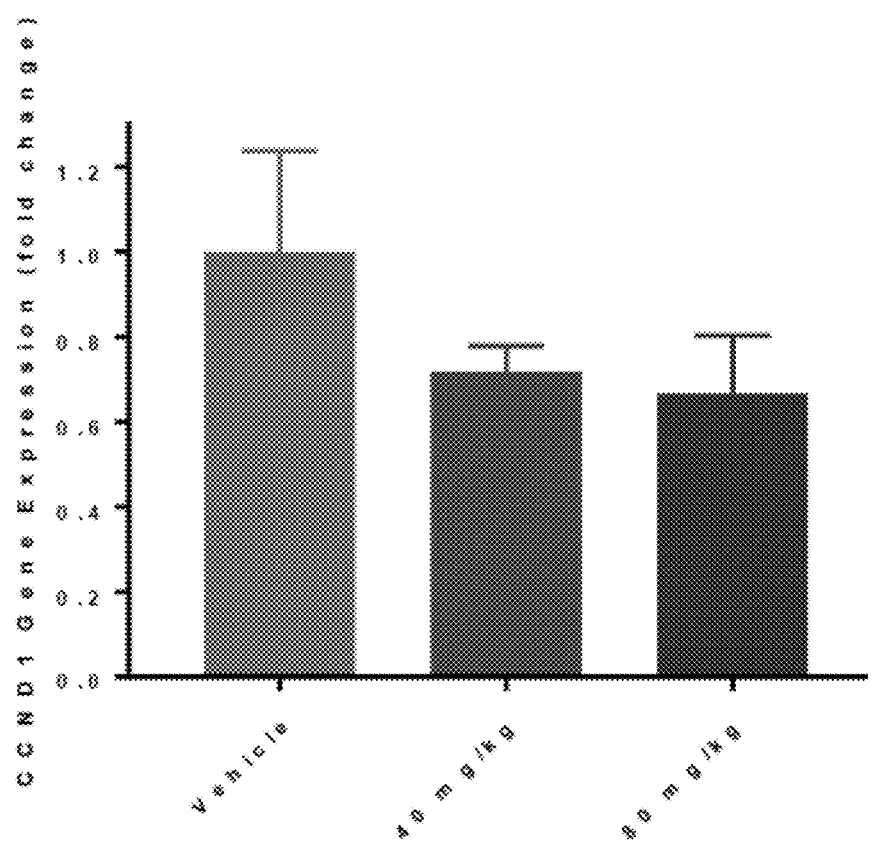

In a KRAS-mutant PDX model, a tartrate salt of the compound of structure (I) achieved 44% TGI when mice were dosed at 40 mg/kg. Balb/c nude mice were implanted with 2-3 mm fragments of primary human CRC tumors and then stratified into cohorts of 10 mice. A tartrate salt of the compound of structure (I) was formulated in 5% (w/v) TPGS and 1% (v/v) PS80 in H20 and administered by oral gavage. Tumor volume (FIG. 107A) and bodyweights (FIG. 107B) were measured twice a week. The 40 mg/kg of a tartrate salt of a compound of structure (I) cohortachieved 44% TGI without adverse events.

Pharmacodynamic analyses were performed on tissues from the HCT-116 and PDX models. The ligand for AXL, GAS6, was significantly upregulated in tissues after treatment with a tartrate salt of the compound of structure (I) in both CRC in vivo models while soluble AXL and GAS6 were significantly downregulated in plasma in the PDX model. Furthermore, Axin2, a Wnt/pcatenin regulated gene, was significantly downregulated by the compound of structure (I) in tumor tissue from the PDX model, suggesting inhibition of the Wnt/pcatenin pathway. These data support a potential role for AXL in the promotion of the mesenchymal phenotype in CRC and show that AXL inhibition by a tartrate salt of the compound of structure (I) suppresses the mesenchymal phenotype and is effective against CRC cells regardless of KRAS mutation status.

FIGS. 108A-108E show a tartrate salt of the compound of structure (I) suppresses sAXL/sGAS6 concentrations while down-regulating Wnt/β-catenin regulated genesAxin2/CCND1 in the KRAS mutant PDX CRC model. sAXL (FIG. 108A) and sGAS6 (FIG. 108B) were quantified in the serum via ELISA. Intra-tumoral GAS6 (FIG. 108C), Axin2 (FIG. 108D), and CCND1 (FIG. 108E) were quantified via RT-qPCR. Analyses were performed on mice treated for 27 days (except Axin2; 21 days). Suppression of sAXL and sGAS6 indicate a reversal of EMT. Compound of structure (I)-mediated downregulation of Wnt/β-catenin associated genes further supports a previously reported role for AXL in β-catenin stabilization.

Figure 109:
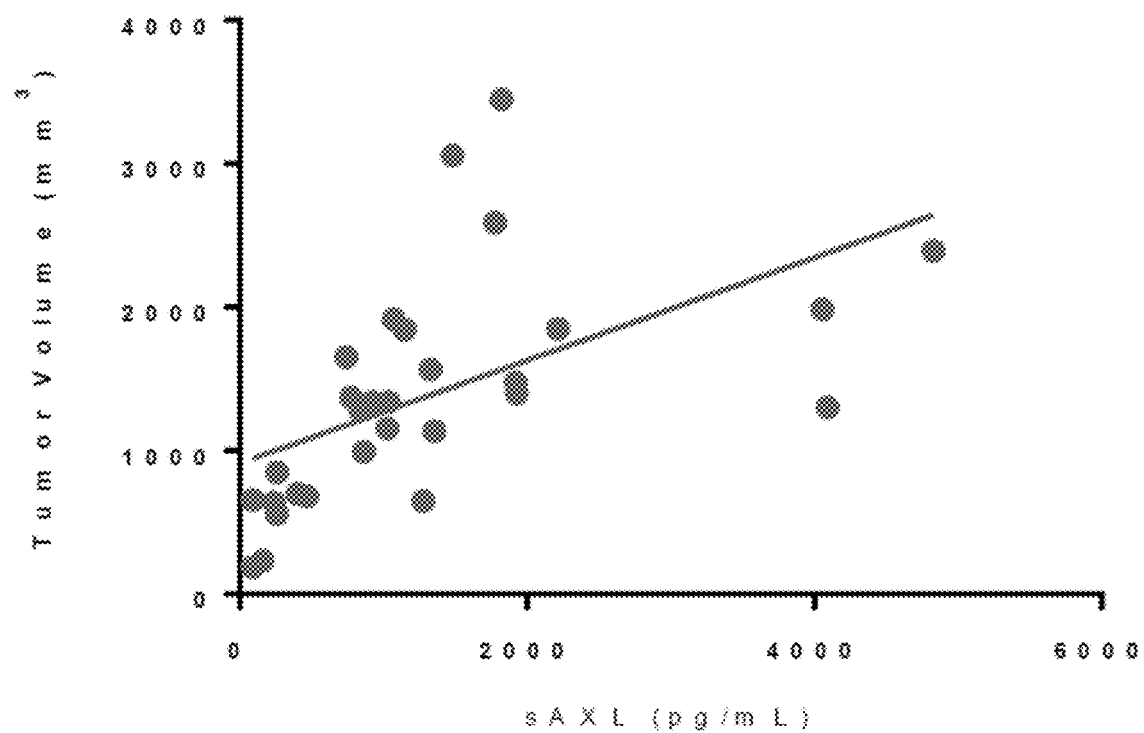
FIG. 109 shows a positive correlation between sAXL/sGAS6 and tumor volume in the KRAS mutant PDX CRC model identifies them as potential biomarkers for disease progression. Soluble concentrations were quantified in each mouse's serum via ELISA followed linear regression analysis. Statistical significance for each correlation: sAXL and tumor volume ($P<0.005$); and sGAS6 and tumor volume ($P<0.0005$).
Figure 109:
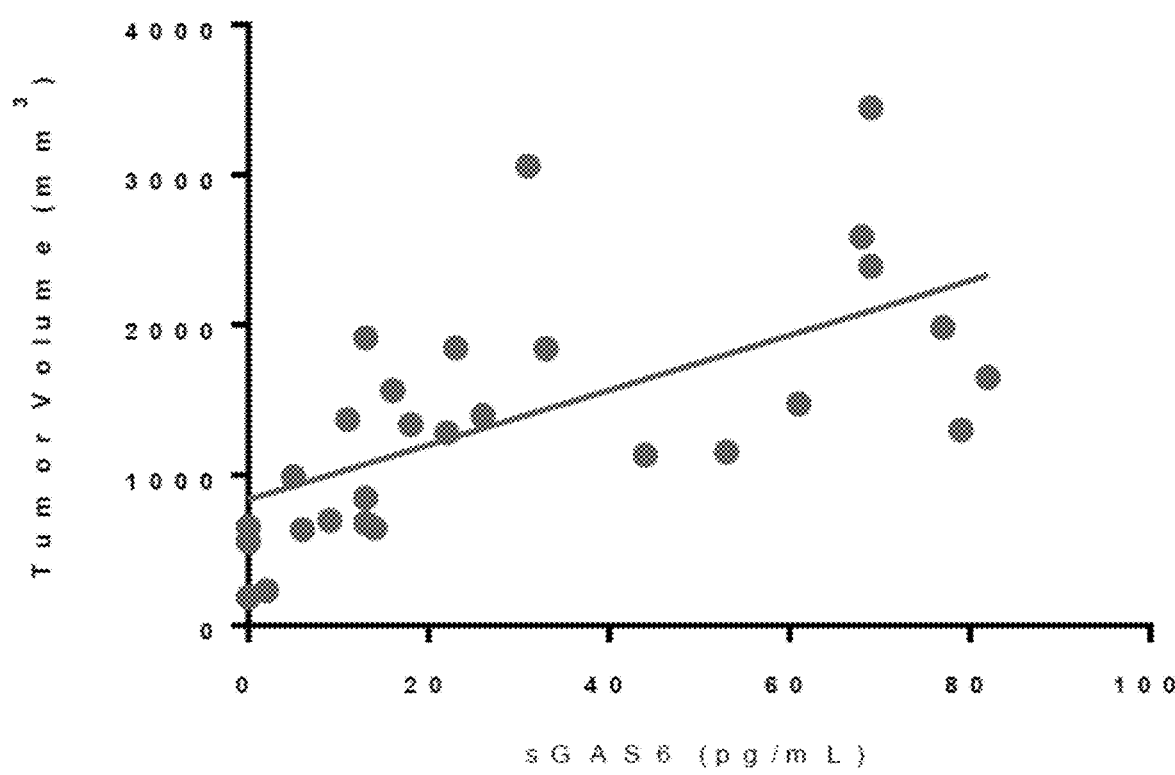

FIG. 109 shows a positive correlation between sAXL/sGAS6 and tumor volume in the KRAS mutant PDX CRC model identifies them as potential biomarkers for disease progression. Soluble concentrations were quantified in each mouse's serum via ELISA followed linear regression analysis. Statistical significance for each correlation: sAXL and tumor volume ($P<0.005$); and sGAS6 and tumor volume ($P<0.0005$).

Example 21: Anti-Tumor Effects of the Compound of Structure (I) on Inflammatory Breast Cancer Tartrate salts of the compound of structure (I) is evaluated for activity against inflammatory breast cancer in cell culture and in a xenograft model.

The activity of a tartrate salt of the compound of structure (I) is evaluated in inflammatory breast cancer cell lines. Cell viability is assessed (e.g., using a CellTiter Glo assay) at a range of doses, and an $IC_{50}$ value is determined. Examples of inflammatory breast cancer cell lines that may be used include SUM149, KPL-4, and SUM190.

The effects of a tartrate salt of the compound of structure (I) are assessed in an inflammatory breast cancer xenograft model. An example of an inflammatory breast cancer xenograft model is described in Wang et al., 2013 *Cancer Research* 73(21): 6516-6525. Athymic BALB/c nu/nu mice are injected into the mammary fat pads with SUM149 cells ($2\times10^6$ cell with 50% Matrigel) and tumors are established. Mice are treated with a tartrate salt of a compound of structure (I) or a vehicle control, for at least two weeks. Tumor volume and body weight are monitored during the course of treatment.

Example 22: Polymorphs of Tartrate Salts of Compound of Structure (I)

The polymorphs of the present disclosure can be prepared in view of the novel methods, reaction schemes and examples provided herein (see, e.g., Example 23), together with synthetic methods known in the art of synthetic organic chemistry, or by variations thereon as appreciated by those skilled in the art. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound or polymorph of the disclosure The starting materials are generally available from commercial sources such as Sigma Aldrich or other commercial vendors, or are prepared as described in this disclosure, or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., Comprehensive Organic Transformations, 2$^{nd}$-ed., Wiley-VCH Weinheim, Germany (1999), or Beilsteins Handbuch der organischen Chemie, 4, Aufl. ed. Springer-Verlag, Berlin, including supplements (also available via the Beilstein online database)).

In the preparation of the polymorphs of the compound of structure (I), protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis*, 4th Ed., Wiley (2007).

Additionally, the polymorphs of present disclosure exhibit valuable pharmacological properties, which can be demonstrated at least by using any one of the following test procedures. Accordingly, polymorphs of the present disclosure were assessed in biochemical assays as set forth below. Data was acquired according to the parameters listed below:

X-Ray Powder Diffraction (XRPD):

PANalytical XRPD instrument. The solid sample was spread on a zero-background Si sample holder. The XRPD parameters used are listed below in Table 11:

TABLE 11

Settings for acquiring XRPD data

| Parameter | Value for Data Acquisition |
|---|---|
| X-Ray Wavelength | Cu, kα |
| | Kα1 (Å): 1.540598 |
| | Kα2: (Å): 1.544426 |
| | Kα2/Kα1 intensity ratio: 0.50 |
| X-ray tube setting | 45kV, 40 mA |
| Divergence slit | 1/8° |
| Scan mode | continuous |
| Scan range (°2θ) | 3°-40° |
| Step Size (°2θ) | 0.263 |
| Scan step time (s) | 50 |
| Test time(s) | ~5 minutes 4 seconds |

TGA and DSC:

TGA data were collected using a TA 5500 TGA from TA Instruments and DSC was performed using a TA 2500 DSC from TA Instruments. Detailed parameters used are listed in Table 12 below.

TABLE 12

Instrument settings for acquiring TGA and DSC data

| Parameters | TGA | DSC |
|---|---|---|
| Method | Ramp | Ramp |
| Sample pan | Aluminum, open | Aluminum, crimped |
| Temperature | RT-desired temperature | 25° C.-desired temperature |
| Heating rate | 10° C./min | 10° C./min |
| Purge gas | N$_2$ | N$_2$ |

HPLC:

Agilent 1260 HPLC was utilized and detailed chromatographic conditions for purity and solubility measurement are listed in Table 13 below.

TABLE 13

HPLC settings for acquiring data

| Parameters | Value | |
|---|---|---|
| HPLC | Agilent 1260 with DAD detector | |
| Column | Ascentis Express C18, 4.6 mm × 100 mm, 2.7 µm | |
| Mobile phase | A: 0.1% H$_3$PO$_4$ in H$_2$O B: Acetonitrile | |
| Gradient table | Time (min) | % B |
| | 0.0 | 10 |
| | 6.0 | 95 |
| | 8.0 | 95 |
| | 8.1 | 10 |
| | 10.0 | 10 |
| Run time | 10.0 min | |
| Post time | 0.0 min | |
| Flow rate | 1.5 mL/min | |
| Injection volume | 10 µL | |
| Detector wavelength | UV at 210 nm | |
| Column temperature | 40° C. | |
| Sampler temperature | ambient | |
| Diluent | acetonitrile:H$_2$O (1:1, v/v) | |

Example 23: Preparation of Crystalline Form A

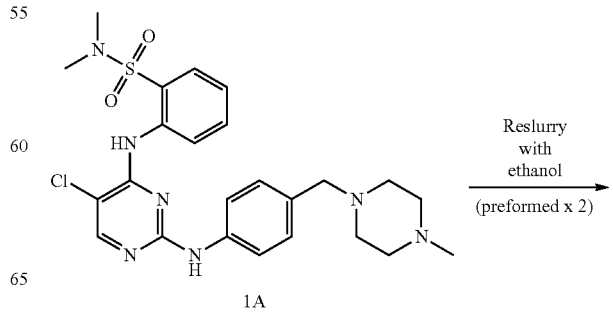

1A

-continued

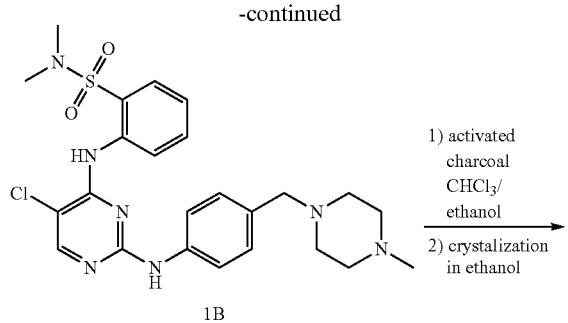

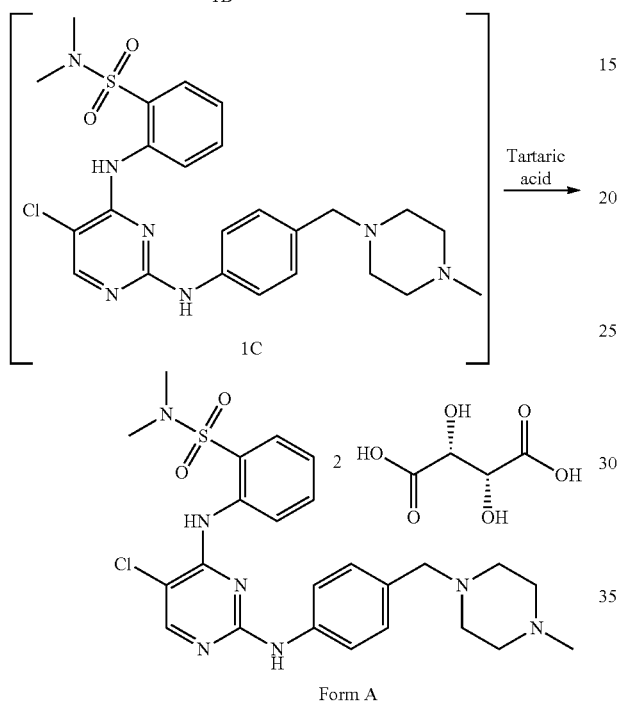

Compound 1A was obtained according to methods known in the art and met purity specifications, however, ¹H-NMR analysis showed that the material included about 30% of triethylamine, which was used in in a previous synthetic step. Applicant discovered that re-slurry in hot ethanol efficiently removed triethylamine. The re-slurry step is performed as follows:

A mixture of 1A and ethanol was heated at 70° C. for 2 hours and then slowly cooled to 20° C. over 5 hours. The slurry was filtered and dried under vacuum to provide purified IB. This isolated crystal was subjected to a reprocessing procedure to provide 1C.

The reprocessing procedure included dissolving 1C in a chloroform and ethanol mixture and activated charcoal was added. The resulting slurry was stirred at room temperature for 1 hour and filtered. The filtered solid was washed, combined with filtrate and the solvents were removed by distillation. Then ethanol was added, and distillation repeated to remove chloroform. After the distillation, resulting slurry was cooled and filtered to give purified 1C. The obtained material was dissolved with mixture of anisole and ethanol at 70° C. Ethanol solution of tartaric acid was then added to this solution and subsequently seeded with Form A. The resulting slurry is cooled to 20° C. and filtered, washed with ethanol, dried to afford the polymorph of a tartaric acid salt of a compound of structure (I). The purity of the desired product was assessed to be 99.5% by HPLC.

¹H NMR (400 MHz, DMSO-d6) δ=9.56 (s, 1H), 9.33 (s, 1H), 8.58 (s, J=8.0 Hz, 1H), 8.29 (s, 1H), 7.83 (dd, J=8.0, 1.6 Hz, 1H), 7.71 (td, J=7.2, 1.4 Hz), 7.57 (d, J=8.4 Hz, 2H), 7.38 (td, J=7.2 Hz, J=1.0 Hz), 7.18 (d, J=8.4 Hz, 2H), 4.19 (s, 4H), 3.51 (s, 2H), 2.86 (bs, 3H), 2.65 (s, 6H), 2.60-2.50 (m, 8H)

Proton signals at 4.19 and 3.51 ppm correspond to tartaric acid. Based on the integration of those peaks, tartaric acid to compound of structure (I) was consistently 2:1.

Example 23A: Preparation of Crystalline Form A

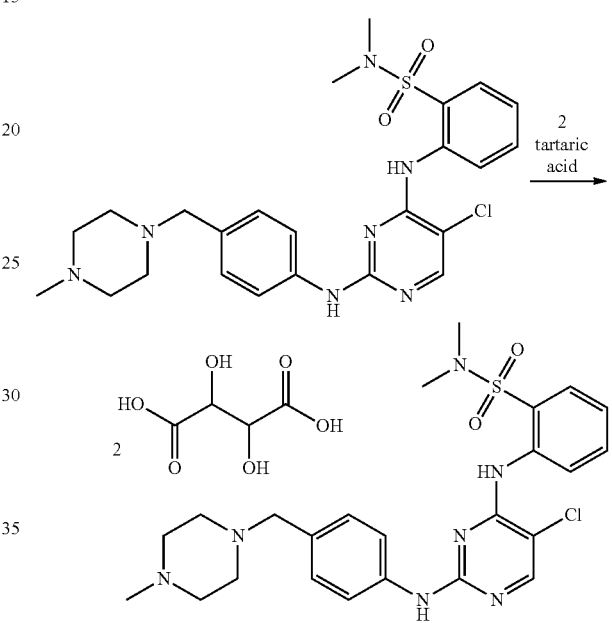

2-((5-chloro-2-((4-((4-methylpiperazin-1-yl)methyl)phenyl)amino)pyrimidin-4-yl)amino)-N,N-dimethylbenzenesulfonamide (5 g, 9.69 mmol) was dissolved in anisole (75 g) and EtOH (30 g) at 70° C. Tartaric acid (2.91 g, 19.38 mmol) dissolved in EtOH (30 g) was added to the mixture over 1 h, then small amount of seed crystal* was added to the solution to initiate the precipitation. The mixture was stirred for 1 h and cooled to 20° C. over 5 h. The solid was collected by filtration, washed with EtOH and dried to afford 2-((5-chloro-2-((4-((4-methylpiperazin-1-yl)methyl)phenyl)amino)pyrimidin-4-yl)amino)-N,N-dimethylbenzenesulfonamide di-tartrate salt as a white solid (7.35 g, 9.01 mmol).

The purity of the desired product was assessed to be 99.5% by HPLC.

¹H NMR (400 MHz, DMSO-d6) δ=9.56 (s, 1H), 9.33 (s, 1H), 8.58 (s, J=8.0 Hz, 1H), 8.29 (s, 1H), 7.83 (dd, J=8.0, 1.6 Hz, 1H), 7.71 (td, J=7.2, 1.4 Hz), 7.57 (d, J=8.4 Hz, 2H), 7.38 (td, J=7.2 Hz, J=1.0 Hz), 7.18 (d, J=8.4 Hz, 2H), 4.19 (s, 4H), 3.51 (s, 2H), 2.86 (bs, 3H), 2.65 (s, 6H), 2.60-2.50 (m, 8H)

Proton signals at 4.19 and 3.51 ppm correspond to tartaric acid. Based on the integration of those peaks, tartaric acid to compound of structure (I) was consistently 2:1.

* Note: Seed crystals of Form A were obtained by combining 2-((5-chloro-2-((4-((4-methylpiperazin-1-yl)methyl)phenyl)amino)pyrimidin-4-yl)amino)-N,N-dimethylbenzenesulfonamide and tartaric acid in anisole/ethanol under the conditions specified above, followed by initiation of crystal formation using one or more techniques such as (1) cooling the solution (e.g., to room temperature, or in a freezer), (2) concentrating the solution (e.g., by slow evaporation, or with a rotart evaporator), and/or (3) scratching the interior of the flask containing the solution. Crystals obtained in this manner were confirmed to be of Form A by $^1$HNMR and XRPD analysis.

Example 23B: Preparation of Crystalline Form B 2-((5-chloro-2-((4-((4-methylpiperazin-1-yl)methyl)phenyl)amino)pyrimidin-4-yl)amino)-N,N-dimethylbenzenesulfonamide mono-tartaric acid salt (1.75 kg, 2.62 mol) was added 5.25 L of EtOH and 4.0 L of solvent distilled under reduced pressure. This was repeated twice until the water content by Karl Fisher Titration is below 0.1%. Then 52.5 L of Ethanol and heated to reflux. Then 0.513 kg of L-(+)-tartaric acid in 17.5 L of ethanol was added slowly over 2 hours and seeded at 70° C. Then stirring was kept for 12 hours at 70° C. and again heated to 80° C. and kept for 2 hours. The slurry was cooled to 20° C. over 6 hours, and then kept stirring for additional 12 hours. The crystals were filtered and then washed with 3.5 L of Ethanol twice. The crystal was dried under reduced pressure to afford 1.8 kg of crystal. Then 1.6 kg of this material was suspended with 16.0 L of methyl t-butyl ether and 0.30 kg of bis(pinacolate) diboron was added at 30° C. Then the mixture was heated at 40-45° C. for 12 hours and cooled to 30° C. and filtered. The filtered solid was washed 8.2 L of methyl t-butyl ether and dried under vacuum to afford 2-((5-chloro-2-((4-((4-methylpiperazin-1-yl)methyl)phenyl)amino)pyrimidin-4-yl)amino)-N,N-dimethylbenzenesulfonamide mono-tartaric acid salt (1.38 kg, 2.07 mol).

Example 23C: Preparation of Crystalline Form D

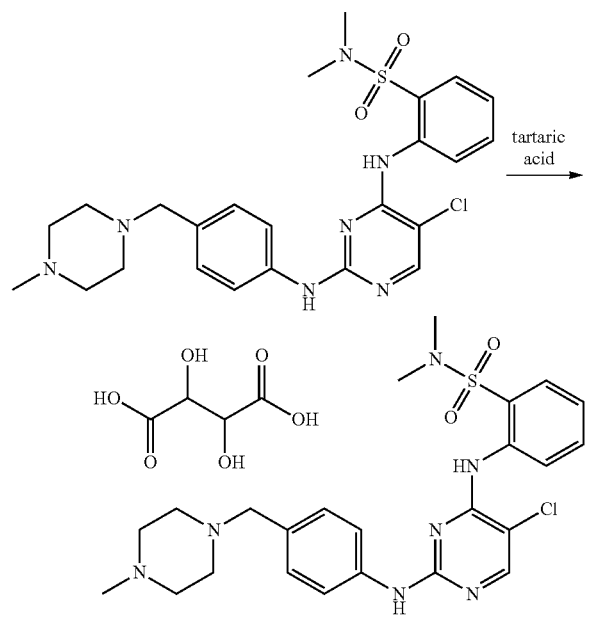

2-((5-chloro-2-((4-((4-methylpiperazin-1-yl)methyl)phenyl)amino)pyrimidin-4-yl)amino)-N,N-dimethylbenzenesulfonamide (5 g, 9.69 mmol) was charged into EtOH (119 g) and the mixture was heated to 80° C. Tartaric acid (1.45 g, 9.69 mmol) dissolved in EtOH (40 g) was added to the mixture over 2 h at the same temperature, then the mixture was cooled to 70° C. before small amount of seed crystal* was added to initiate the precipitation. The mixture was stirred for 2 h and cooled to 20° C. over 5 h. The solid was collected by filtration, washed with EtOH and dried to afford 2-((5-chloro-2-((4-((4-methylpiperazin-1-yl)methyl)phenyl)amino)pyrimidin-4-yl)amino)-N,N-dimethylbenzenesulfonamide mono-tartrate salt as a white solid (5.98 g, 8.98 mmol).

* Note: Seed crystals of Form D were obtained by combining 2-((5-chloro-2-((4-((4-methylpiperazin-1-yl)methyl)phenyl)amino)pyrimidin-4-yl)amino)-N,N-dimethylbenzenesulfonamide and tartaric acid in anisole/ethanol under the conditions specified above, followed by initiation of crystal formation using one or more techniques such as (1) cooling the solution (e.g., to room temperature, or in a freezer), (2) concentrating the solution (e.g., by slow evaporation, or with a rotart evaporator), and/or (3) scratching the interior of the flask containing the solution. Crystals obtained in this manner were confirmed to be of Form D by $^1$HNMR and XRPD analysis.

Example 24: Characterization of Various Polymorphic Forms of Tartrate Salts of Compound of Structure (I)

(i) Stability and Reproducibility

Figure 62A:
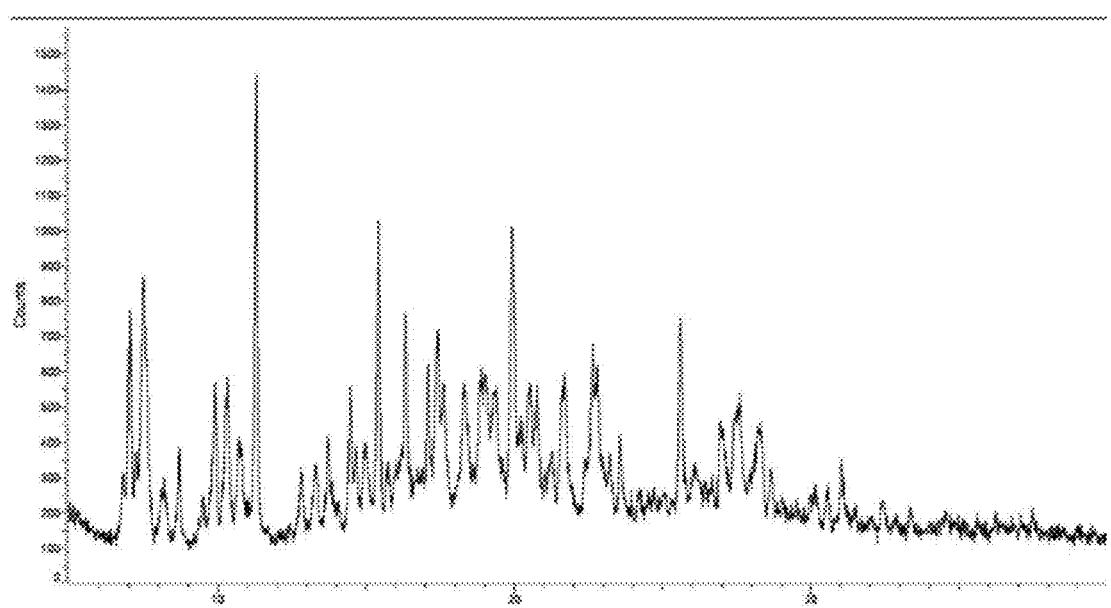
FIG. 62A illustrates an x-ray diffractogram obtained from XRPD analysis for crystalline Form B.
Figure 62B:
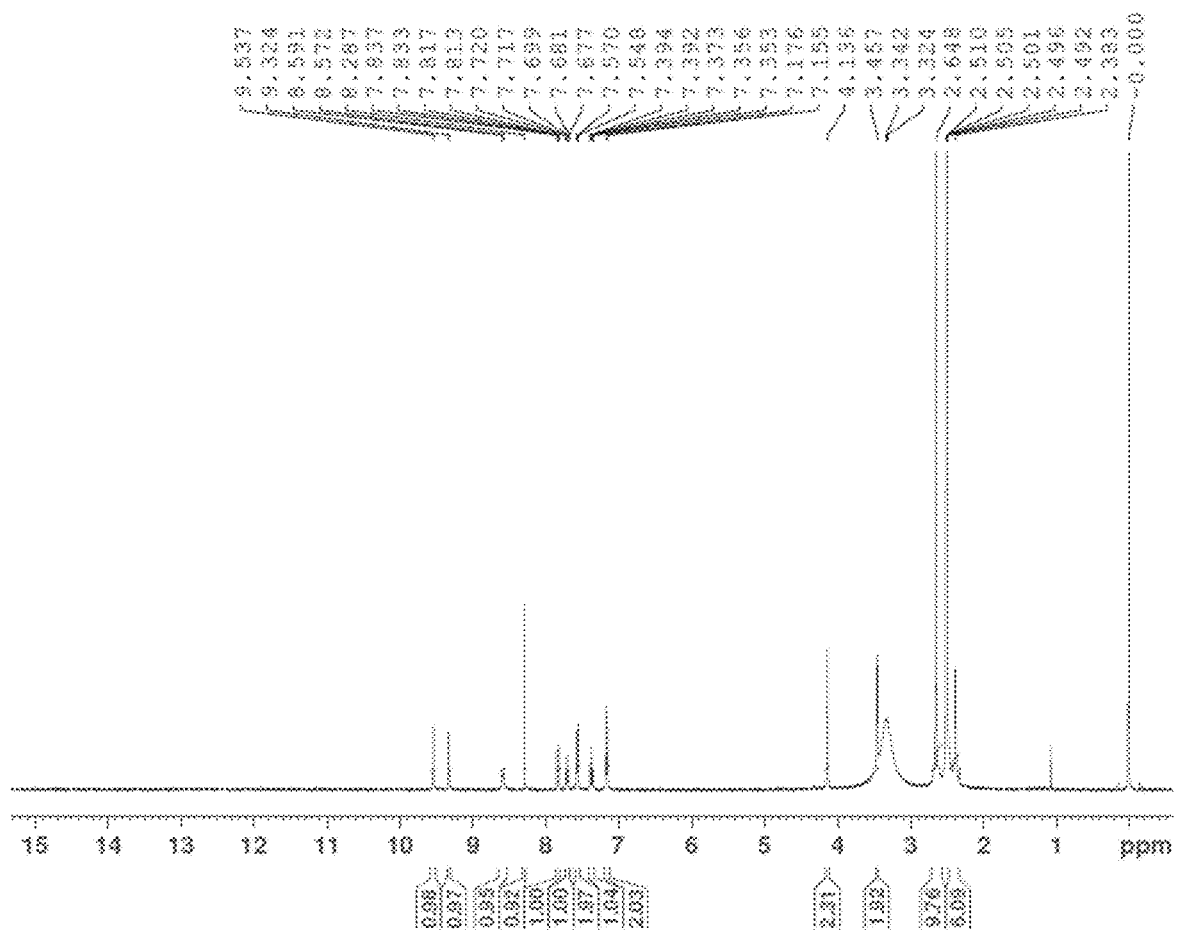
FIG. 62B illustrates an $^1$HNMR spectrum of crystalline Form B.
Figure 63A:
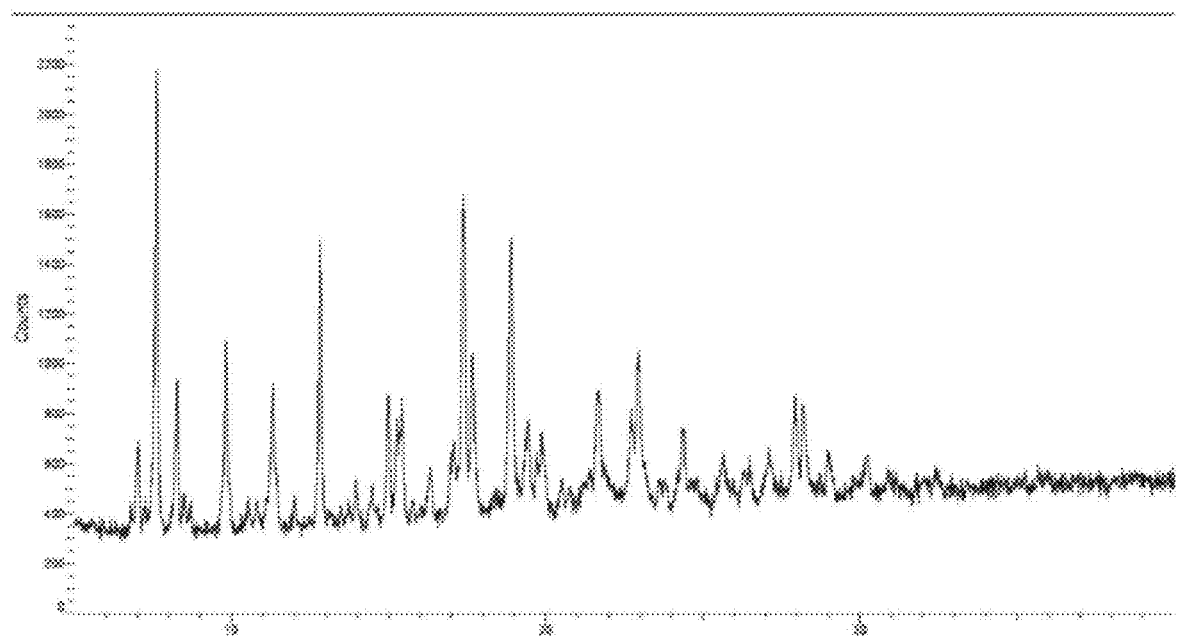
FIG. 63A illustrates an x-ray diffractogram obtained from XRPD analysis for polymorph Form D.
Figure 63B:
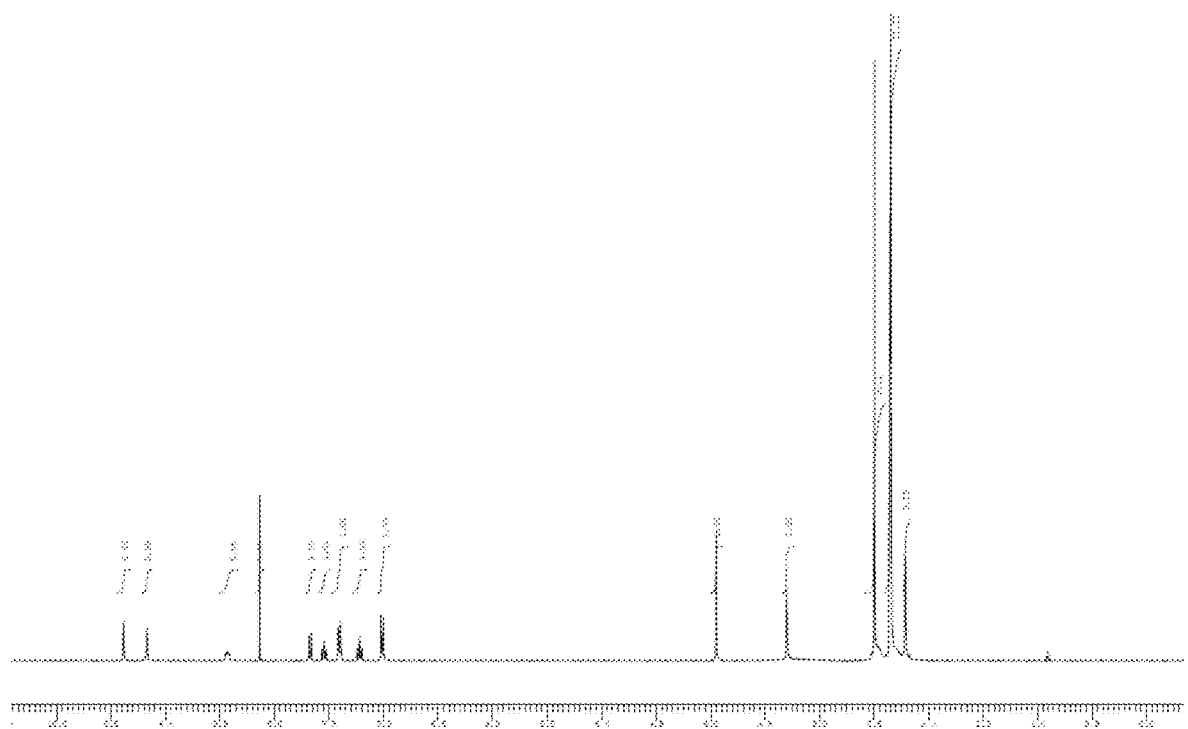
FIG. 63B illustrates an $^1$HNMR spectrum of crystalline Form D.

Other polymorphic forms of the compound of structure (I) were compared for their relative stability under different storage conditions. Other polymorphic forms include the free base form of a compound of structure (I), Form B, and Form D. The XRPD diffractogram of Forms B and D are shown in FIGS. 62 and 63, respectively.

It was discovered that Form A is a di-tartaric acid salt form and it was identified as having only one crystal form (Form A). For comparison, XPRD patterns showing an overlay of Form A (lower) and Form B (upper) illustrates a similar pattern, with some additional peaks.

(ii) Stability Profiles

Figure 65:
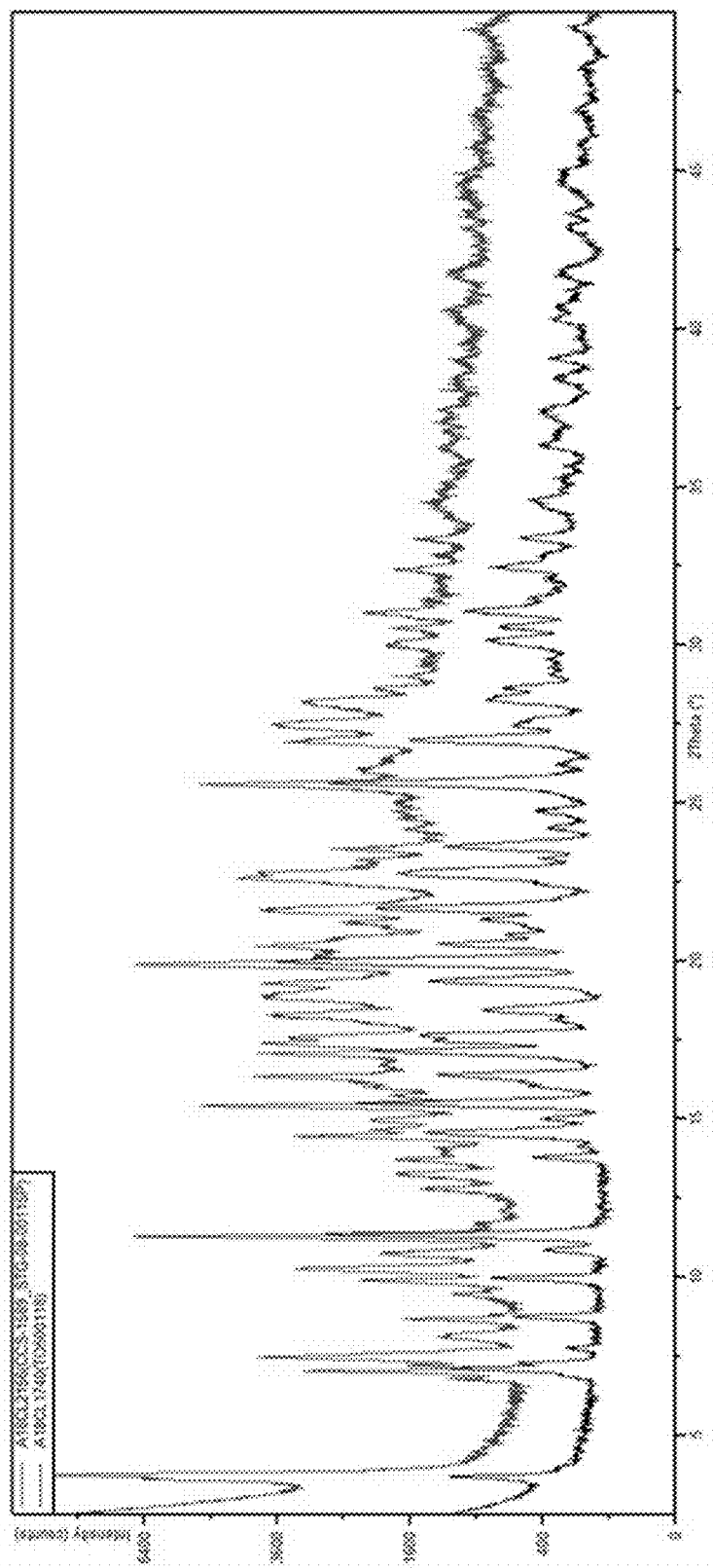
FIG. 65 shows a comparison between Form B (upper) and Form A (lower).

The different forms of the compound of structure (I) (i.e., FB, Form A, Form B, and Form D were each stored at 40° C. and a relative humidity of 75%. After 3 weeks, all samples showed good chemical stability with no significant HPLC purity decrease. Form change was observed only for Form B. Additionally, as shown in FIG. 65, which compares Form A and Form B, Form B appears to have weaker peak intensities. The weaker peak intensity can possibly be attributed to lower crystallinity.

(iii) Physical and Chemical Properties

The table below summarizes the characterization and solid state stability results observed for FB and Forms A, B, and D. Samples were prepared and data was obtained according to the procedures and processes listed above unless otherwise specified. More procedures, processes, and results are listed below in Table 14.

TABLE 14

Summary of physicochemical properties evaluation for Forms A, B, D, and free base

| Assay Description | | Form A | Form B | Form D | Free Base |
|---|---|---|---|---|---|
| XRPD | | Crystalline | Crystalline | Crystalline | Crystalline |
| Weight Loss (%) | | 1.8 (160° C.) | 2.3 (160° C.) | 2.0 (160° C.) | 0.22 (120° C.) |
| Endotherm (peak, ° C.) | | 107.8, 152.01, 189.1 | 101.9, 140.1 | 79.4, 140.7 | 221.1 |
| Initial HPLC Purity (area %) | | 99.6 | 98.1 | 98.8 | 98.3 |
| HPLC Purity at 3 weeks[#] (area %) | | 99.7 | 98.2 | 98.3 | 98.6 |
| Form Change at 3 weeks[#] | | No | Yes | No | No |
| Hygroscopicity/water uptake at 80% RH/FC | | 4.6%/No | 7.5%/No | 5.2%/Yes | Non-hygroscopic/ 0.07%/No |
| Morphology | | Fine particles with agglomeration | | | Diamond particles |
| Solubility* (mg/mL)/ FC | SGF | >17.4/NA | >6.4/NA | >11.0/NA | 5.7/No |
| | FaSSIF | >14.8/NA | >8.9/NA | 3.9/Yes | 0.021/No |
| | FeSSIF | 5.2/NA* | 4.7/NA* | 4.6/NA* | 1.7/No |
| | pH 2.0 | >6.7/NA | >6.6/NA | >6.8/NA | 2.6/Yes |
| | pH 4.0 | 0.45/Yes | 0.26/Yes | 0.23/Yes | 0.17/Yes |
| | pH 6.0 | 3.8/Yes | 2.5/Yes | 1.9/Yes | 0.014/No |
| | pH 8.0 | 0.020/Yes | 0.010/Yes | 0.0050/Yes | 0.038/No |
| | pH 10.0 | 0.0098/Yes | 0.018/Yes | 0.053/Yes | 0.076/No |

*The solubility was collected at 24 hours
[#]under 40° C./75% RH
FC: Form change
NA: solid-state results not available as clear solution formed
NA*: solid-state results not available as oil sample obtained.

(a) Dynamic Vapor Sorption (DVS)

DVS results showed up to 80% relative humidity at 25° C., the water uptake was in the range of 4.6~7.5% for Forms A, B, and D with form change observed for Form D. That is, Form D changed to a new form not consistent with all the four known crystal forms, and free base was non-hygroscopic (water uptake less than 0.2%) with no form change at the end of the test.

(b) Kinetic Solubility

Kinetic solubility was measured in bio-relevant buffers (FaSSIF, FeSSIF and SGF) at 37° C. Compared to free base sample, significant higher solubility (>5 mg/mL) was observed for Forms A, B, and D in all biorelevant buffers. Similar solubility observations were observed for all three forms in SGF and FeSSIF, but Form D showed lower solubility than other Forms A and B in FaSSIF.

(c) pH Solubility pH solubility was measured in pH 2, 4, 6, 8 and 10 buffers at 37° C. The results showed: i) higher solubility in pH 2 than that of in the other pH buffers for each sample and decreased solubility in higher pH buffer, especially in alkaline media, in which the solid form of residual solids also changed at the end of the test for Forms A, B, and D; ii) Form A showed higher solubility than other polymorphs in pH 2, 4 and 6 buffers.

Example 25: Toxicokinetic and Toxicology Profiles of Tartrate Salts of Compound of Structure (I)

Form A of the tartaric acid salt of structure (I) was developed to improve stability and reproducibility the drug formulation. Previous stability issues have been encountered with the polymorph Form B. To ensure the new drug formulation had an acceptable toxicokinetic and toxicology profile; studies were conducted in mice and rats comparing three formulations:

(1) polymorph Form A
(2) polymorph Form B
(3) polymorph Form D

In each study, comparisons were made to the free base (FB) form of the compound of structure (I). A single-dose study was conducted in rats and a 7-day repeat-dose study performed in mice.

Single Dose Toxicity Study

In this study, a comparison of the clinical effects and pharmacokinetics of the free base (FB) and tartaric acid salt polymorph forms (Forms A, B, and D) of the compound of structure (I) following a single oral dose were evaluated in male SD rats. The FB dose levels evaluated were 20, 50, and 150 mg/kg. The test articles were formulated with 1% Tween 80/5% TPGS/Sterile Water for Injection (v/v/v) and the study designed as indicated in Table 15 below:

TABLE 15

Study Design Single Dose Toxicity in Rats

| Group | Dose[1] (mg/kg) | Dose Volume (mL/kg) | Dosing Solution Concentration (mg/mL) | Number of Animals and Sex |
|---|---|---|---|---|
| 1. Vehicle | 0 | 10 | 0 | 3M |
| 2. Free Base Low Dose | 20 | 10 | 2 | 6M |
| 3. Free Base Mid Dose | 50 | 10 | 5 | 6M |
| 4. Free Base High Dose | 150 | 10 | 15 | 6M |
| 5. Form B Low Dose | 20 | 10 | 2 | 6M |
| 6. Form B Mid Dose | 50 | 10 | 5 | 6M |
| 7. Form B High Dose | 150 | 10 | 15 | 6M |
| 8. Form A Low Dose | 20 | 10 | 2 | 6M |
| 9. Form A Mid Dose | 50 | 10 | 5 | 6M |
| 10. Form A High Dose | 150 | 10 | 15 | 6M |

TABLE 15-continued

Study Design Single Dose Toxicity in Rats

| Group | Dose[1] (mg/kg) | Dose Volume (mL/kg) | Dosing Solution Concentration (mg/mL) | Number of Animals and Sex |
|---|---|---|---|---|
| 11. Form D Low Dose | 20 | 10 | 2 | 6M |
| 12. Form D Mid Dose | 50 | 10 | 5 | 6M |
| 13. Form D High Dose | 150 | 10 | 15 | 6M |

[1]Dose levels and dosing solution concentration were calculated as equivalents of FB based on correction for the tartaric acid content of Form A, Form B and Form D by dose multiplication factors of 1.58, 1.35 and 1.29, respectively.

Endpoints in the study consisted of mortality checks, clinical observations, body weight measurements and toxicokinetics. Following a 7-day post-dose observation period, animals were euthanized, necropsied and macroscopic observations recorded.

On the day of dosing, the vehicle and compound of structure (I) treatments ≤50 mg/kg were well tolerated with the exception of one mid-dose animal administered Form B that was found dead 7.5 hours post-dosing. In contrast, mortality was frequently observed on the day of dosing for the high-dose group. Mortality was observed beginning at 4.5 hours post-dosing, with 100% mortality observed by the end of the recovery period in the 150 mg/kg FB and Form A, B and D groups. During the 7-day post-administration observation period, mortality or moribundity was also noted in the mid-dose (50 mg/kg) groups but not in the low-dose or vehicle groups. The incidence of mortality was similar across different treatment groups.

Clinical signs were mostly present in rats at the mid- and high-dose levels, with only a few rats displaying clinical observations at the low-dose level. Clinical observations noted in the high-dose groups included passivity, soft feces and diarrhea, hunched back posture, piloerection, being "cool to the touch", weight loss, anorexia, and seizures. For mid-dose animals dosed with free base and Forms A, B and D, the primary clinical signs were anorexia, emaciation, and weight loss. Additional clinical signs included soft feces, diarrhea, hunched back posture, passivity, piloerection, being "cool to the touch," and scruffy fur. The only clinical signs noted in low-dose groups were soft feces and weight loss in some animals. No clinical signs were observed in vehicle dosed animals. The nature and incidence of clinical signs were similar across the different treatment groups.

A dose-related reduction in body weight/body weight gain was seen across all test article groups. Animals in the low-dose group gained weight over the 7-day post-dose observation period but at a rate less than the vehicle control whereas body weight loss was seen in the mid- and/or high-dose groups.

Frequent findings upon necropsy in all rats from the high-dose group were of gastrointestinal origin and included thick yellowish fluid in the small intestine, stomach full of undigested food, fluid filled cecum, and lack of formed feces; in one rat pallor of the spleen and liver and a reduction in the size of the thymus was noted. For rats in the mid-dose groups, abnormal findings were less frequently observed. The findings were similar to the gastrointestinal observations made in the high-dose groups. Non-gastrointestinal findings for several of the mid-dose group rats included pallor of the kidneys, pallor of the spleen and liver, enlarged adrenal glands, and a reduction of thymus size of several rats.

Following oral dosing with FB and Forms A, B and D, plasma concentrations of the compound increased in a dose-dependent manner. Comparatively, all three tartaric acid salt polymorph forms of the compound of structure (I) displayed similar plasma concentration profiles. Dose proportionality or close to dose proportionality for the plasma exposure to FB based on $C_{max}$ and $AUC_{0-4\ hrs}$ was observed for FB and Form B, while somewhat higher than dose proportional plasma exposure was observed for Form A and Form D.

In conclusion, oral administration of FB and Forms A, B and D at single free base equivalent dose levels of 50 and 150 mg/kg produced dose-dependent adverse effects in male rats, mortality at the high dose and similar and significant clinical findings at the mid and high dose levels characterized by anorexia, emaciation, weight loss, soft feces, diarrhea, hunched back posture, and scruffy fur. The dose level of 20 mg/kg was generally well tolerated by male rats with minor clinical observations and a reduction in body weight gain. Necropsy findings in rats dosed with FB and Forms A, B and D were similar but more frequent in the high dose group compared to the mid dose groups with abnormal gastrointestinal findings being the most common observation. Some higher dosed animals also displayed pallor of the liver and spleen, enlargement of the adrenal glands and a reduction in the size of the thymus. Oral administration of FB and free base equivalents of tartaric acid salt polymorph Forms A, B and D resulted in similar FB plasma profiles. Overall, similar exposures and dose-related adverse effects were observed in rats following oral dosing with Forms A, B, and D.

Repeat Dose Toxicity and Toxicokinetics

In this study, the clinical effects and the pharmacokinetics of the compound of structure (I) free base (FB) and three tartaric acid salt polymorph forms including Forms A, B, and D following single and 7-day repeated oral free base equivalent dose levels of 20, 50, and 80 mg/kg were evaluated in CD-1 mice. The test articles were formulated with 1% Tween 80/5% TPGS/Sterile Water for Injection (v/v/v) and the study designed as indicated in Table 16 below:

TABLE 16

Study Design Repeat Dose Toxicity in Mice

| Dose Group | Dose (mg/kg/day) | Dose Volume (mL/kg) | Dose Concentration (mg/mL) | Main Study | PK Satellite Groups Day 1* (Single Dose) | Day 7** (Repeated Dose) |
|---|---|---|---|---|---|---|
| Control Vehicle | | | | | | |
| Vehicle | 0 | 10 | 0 | 3 M[a] | — | — |
| Dosed With Different Forms of compound of structure (I) (i.e., Free Base, Form A, Form B and Form D) | | | | | | |
| Low Dose | 20 | 10 | 2 | — | 15 M | 15 M |
| Mid Dose | 50 | 10 | 5 | — | 15 M | 15 M |
| High Dose | 80 | 10 | 8 | — | 15 M | 15 M |

M = Male
[a]Control animals were dosed with a vehicle for 7 days
*PK on Day 1 (Terminal bleeding was by cardiac puncture on 3 M for each time point, 5 time points).
**PK on Day 7 following 7-day repeated dose (terminal bleeding was by cardiac puncture on 3 M for each time point, 5 time points).

Endpoints during the study consisted of clinical observations, body weight, and toxicokinetics. Animals euthanized due to excessive body weight loss in the toxicology-designated groups were euthanized, necropsied, and macroscopic observations recorded.

Administration of a single dose of vehicle and of compound of structure (I) (free base and polymorph forms) at the low-, mid- and high-dose levels and 7 daily doses of the low- and mid-dose levels for 7 days were well tolerated. At the high dose level only, one mouse died in the Form D group. The highest dose (80 mg/kg) resulted in a similar decline in mean body weight over the 7-day observation period across all groups. No effects upon body weight were seen at doses <50 mg/kg/day.

Clinical signs were present in mice in the high-dose groups beginning on Day 6 or 7 of treatment. The clinical signs noted included passivity, lethargy, piloerection, pallor, dyspnea, hunched back posture, ptosis, pallor, prostration, coolness to the touch and weight loss. Clinical signs were observed in 11/15 (73%) of mice dosed with FB, 10/15 (67%), 10/15 (67%), and 15/15 (100%) of mice dosed with Form A, Form B and Form D, respectively. By Day 7, severe weight loss (>25% of starting body weight) led to the euthanasia of 3/15 (20%) of the mice dosed with FB and 4/15 (27%), 3/15 (20%) and 4/15 (27%) of mice dosed with Form A, Form B and Form D, respectively.

Findings at early sacrifice necropsies performed for animals euthanized due to severe weight loss, were mostly of gastrointestinal origin. The primary finding was the presence of yellowish fluid in the small intestine and in some cases, hemorrhage of the small intestine. Distension of the cecum and the presence of fluid was observed in 7 animals subject to necropsy. Other organ findings included, distension of the stomach filled with food and a reduction in the size of the thymus. The findings were generally evenly distributed across the treatment groups.

Comparatively, all three of the polymorph forms displayed similar toxicokinetic profiles. Exposure increased with increasing dose levels with each polymorphic form.

In conclusion, single dose oral administration of FB and Forms A, B, and D at free base equivalent doses of 20, 50 and 80 mg/kg and 7 daily doses at 20 and 50 mg/kg/day were well tolerated. Daily administration of FB and Form A, Form B, and Form D for seven days produced clinical signs and severe body weight loss at the highest dose leading to the premature sacrifice of several animals on Day 6 or 7 of dosing. Necropsy findings in mice dosed that either died or were euthanized due to severe weight loss were predominantly confined to the gastrointestinal tract; a reduction in thymic size was also noted. The toxicokinetic profile of the various polymorph formulations was similar. Overall, the nature and incidence of effects observed at the high dose in mice were similar following seven days of oral dosing with FB and Forms A, B, and D.

Example 26 Ovarian Cancer Cell Lines are Susceptible to the Compound of Structure (I)

Ovarian cancer cell lines were treated with a range of doses of a tartrate salt of the compound of structure (I), and cell viability was assayed. Cell viability at each dose was plotted to create a dose response curve and determine $IC_{50}$ values for each cell line. The $IC_{50}$ values are shown in Table 17.

TABLE 17

| Cell Line | $IC_{50}$ values |
|---|---|
| | $IC_{50}$ Activity |
| Ovcar3 | ++ |
| Ovcar8 | ++ |
| Skov3 | + |
| OVTOKO | ++ |

TABLE 17-continued

| Cell Line | $IC_{50}$ values |
|---|---|
| | $IC_{50}$ Activity |
| OVMANA | ++ |
| Kuramochi | ++ |

$IC_{50}$ Activity: ++ = <1 µM; + = 1 to 10 µM

Example 27: Ovarian Cancer Cell Line ES-2 is Susceptible to the Compound of Structure (I)

Figure 66:
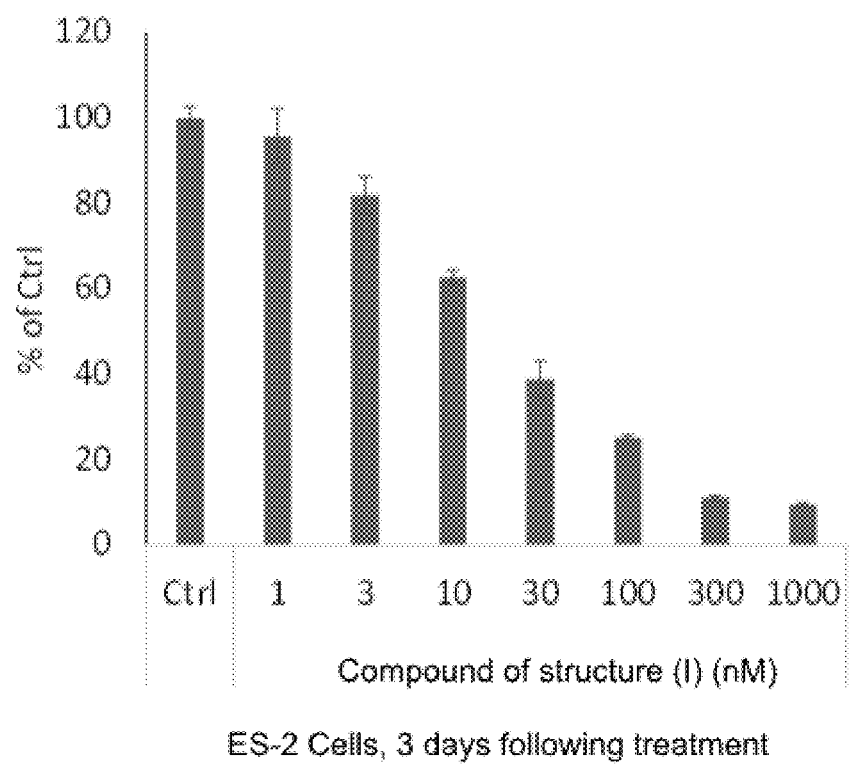
FIG. 66 shows the effects on cell viability of ES-2 cells treated with a compound of structure (I).

ES-2 cells, which is an ovarian cancer cell line of the clear cell histotype, were assayed for viability in the presence of a tartrate salt of the compound of structure (I). Cell viability was measured at a range of doses of a tartrate salt of the compound of structure (I) to create a dose response curve, which is shown in FIG. 66. As shown in FIG. 66, the $IC_{50}$ value for treating ES-2 cells with a tartrate salt of a compound of structure (I) is 20 nM.

Example 28: A Compound of Structure (I) Potently Inhibits the Growth of Chemotherapy Resistant Ovarian Tumor Cells and Clear Cell Ovarian Tumor Cells In Vitro To examine whether a tartrate salt of a compound of structure (I) has efficacy against chemotherapy resistant ovarian cell lines, cisplatin (CDDP) sensitivity was measured in various ovarian cell lines. PA-1, A2780, OVISE, and OVTOKO showed CDDP sensitivity ($IC_{50}$=<1 uM), while other cell lines showed CDDP resistant ($IC_{50}$>2.5 uM). The tartrate salt of the compound of structure (I) kills several chemotherapy-resistant ovarian cancer cell lines at low doses (FIG. 67, top left and right panels).

Figure 67:
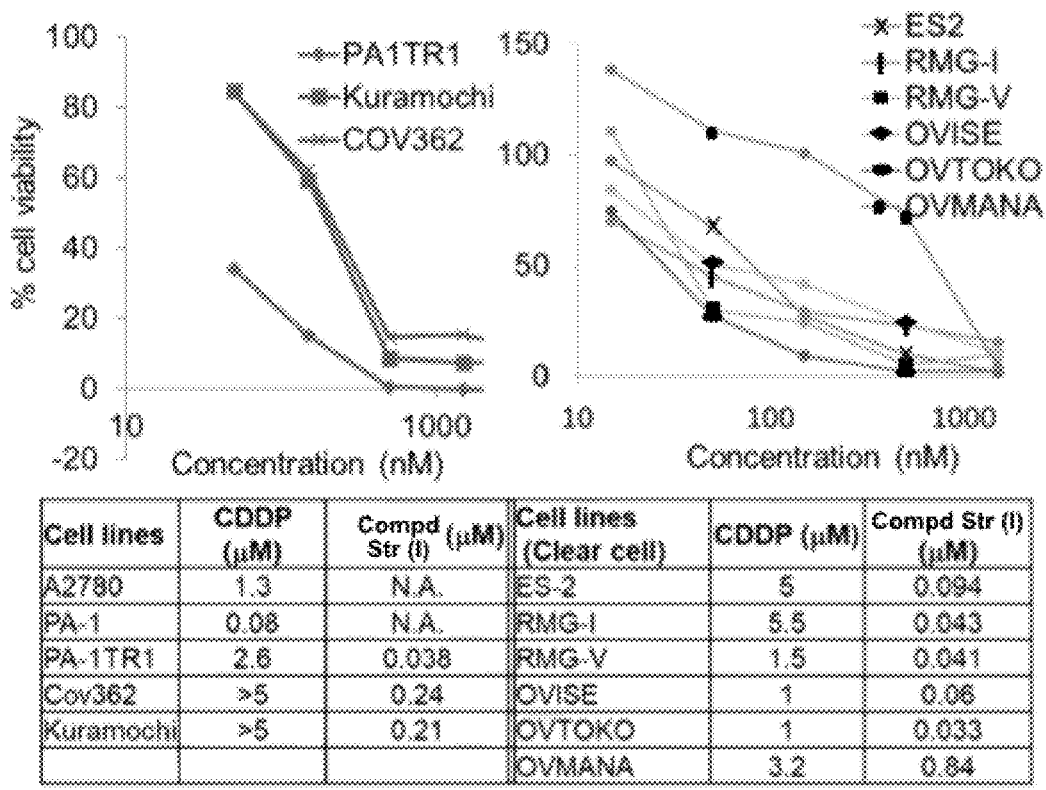
FIG. 67 shows the results of various concentrations of the compound of structure (I) on several chemotherapy-resistant ovarian cancer cell lines (top right and top left panels), and the results of comparative testing of the compound of structure (I), Cabozantinib, and Foretinib on cell viability of ovarian tumor cells in the platinum-resistant Kuramochi cell line (bottom panel).
Figure 67:
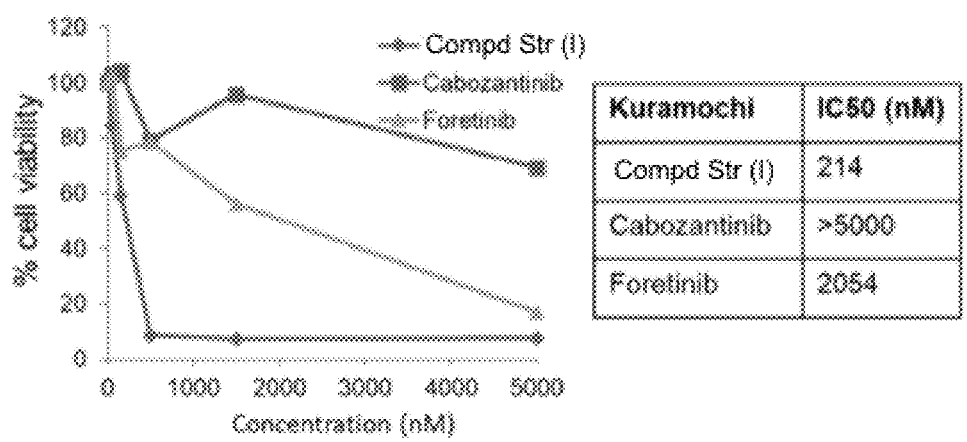
Figure 68:
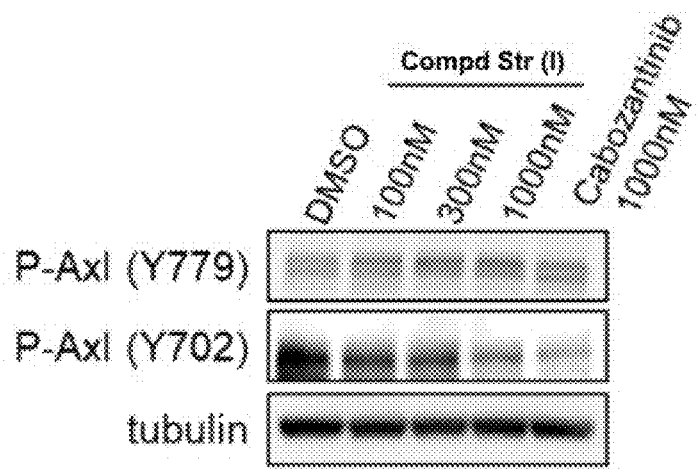
FIG. 68 compares the effects of the compound of structure (I) and Cabozantinib on phospho-AXL (Y702) levels in the platinum-resistant Kuramochi cell line.

Furthermore, a tartrate salt of the compound of structure (I) suppresses the growth of ovarian tumor cells more efficiently than other AXL-targeting compounds (Cabozantinib, Foretinib) in CDDP-resistant Kuramochi cell line (FIG. 67, bottom panel). Kuramochi cells were treated with varying doses of a tartrate salt of a compound of structure (I), Cabozantinib and Foretinib for 96 hrs. Subsequently, cell viability was determined by Alamar Blue assay from which $IC_{50}$ values for CDDP and a tartrate salt of compound of structure (I) were determined. Graphs represent the dose response of Kuramochi cells to each compound. Kuramochi cells were treated with the indicated concentration of a tartrate salt of the compound of structure (I) or Cabozantinib for 8 hrs, lysed and western blotted for tubulin and AXL phosphorylated at Y779 or Y702 site. Phospho-AXL (Y702) were reduced by a tartrate salt of the compound of structure (I) (100 nM) as well as Cabozantinib (1 µM), a c-Met, VEGFR2, and AXL inhibitor (FIG. 68). Note the dose-dependent loss of AXL phosphorylation at Y702 site, which best represents AXL kinase activity, by treatment with the compound of structure (I).

Example 29: EMT Markers are Suppressed in Ovarian Cancer Cells by Treatment with the Compound of Structure (I)

Figure 69:
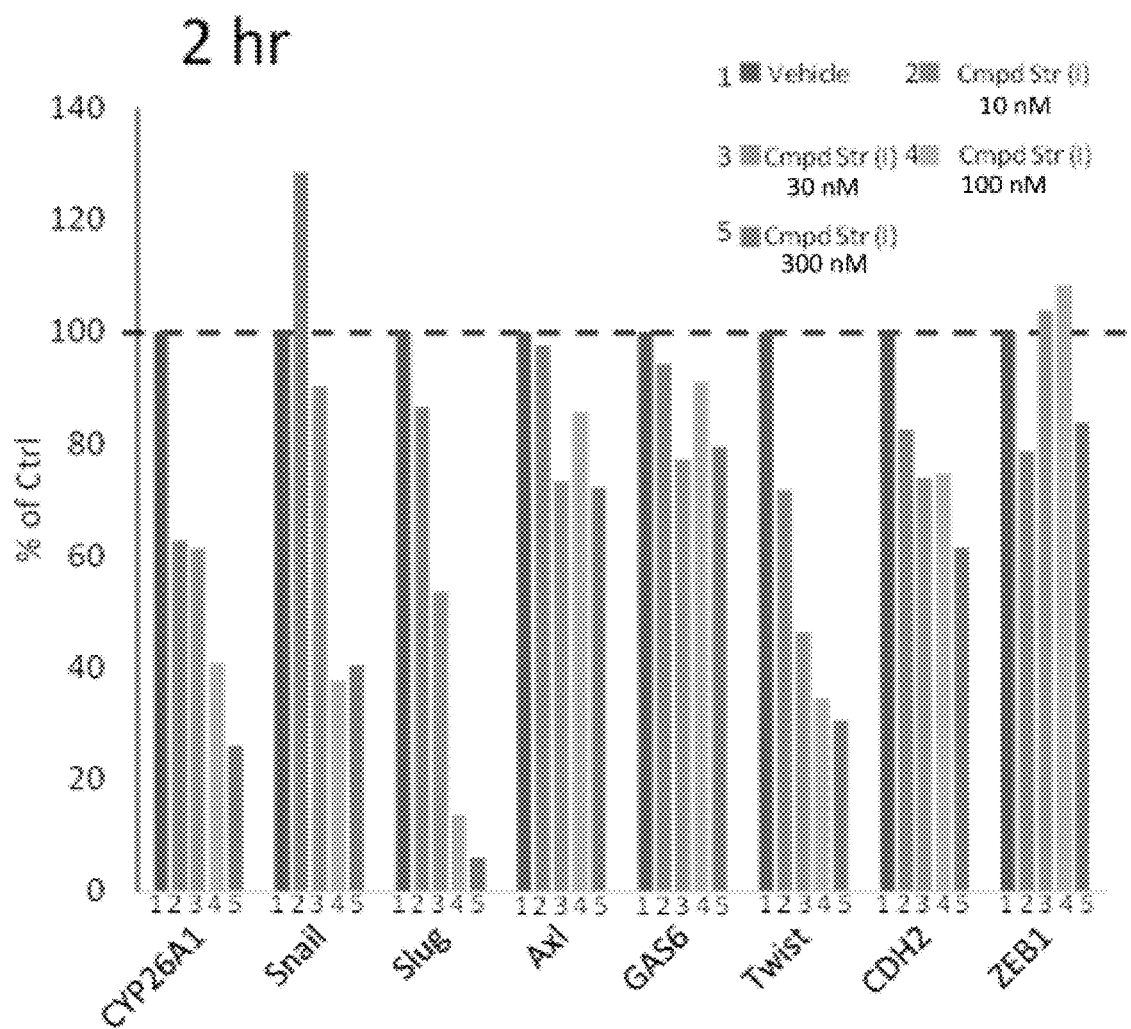
FIG. 69 shows the results of epithelial to mesenchymal (EMT) markers that were quantified by mRNA expression analysis two hours after treatment with the compound of structure (I) at various concentrations.

Epithelial to mesenchymal (EMT) markers were quantified by mRNA expression analysis (using RT-qPCR), following treatment with a tartrate salt of the compound of structure (I). As shown in FIG. 69, two hours after treatment with a tartrate salt of the compound of structure (I), EMT markers are suppressed by higher doses of the compound of structure (I).

Figure 70:
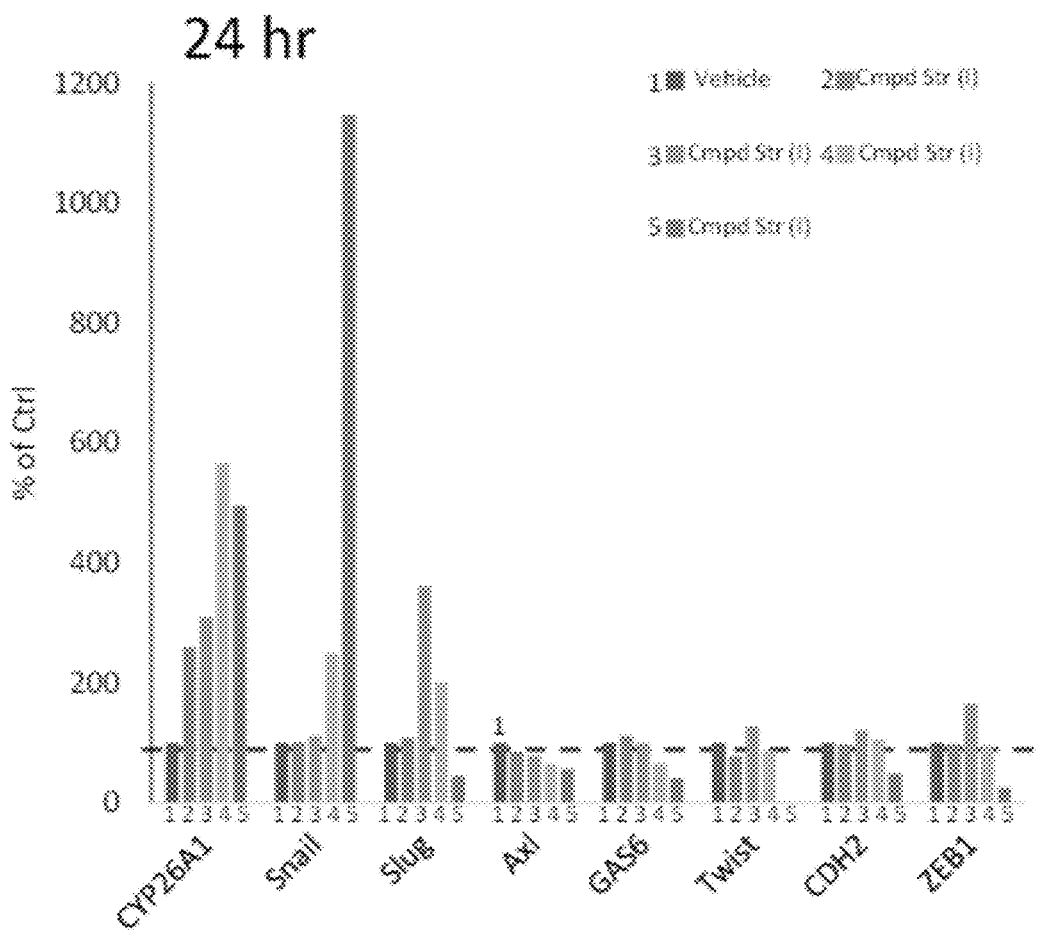
FIG. 70 shows the results of epithelial to mesenchymal (EMT) markers that were quantified by mRNA expression analysis twenty-four hours after treatment with the compound of structure (I) at various concentrations.
Figure 71:
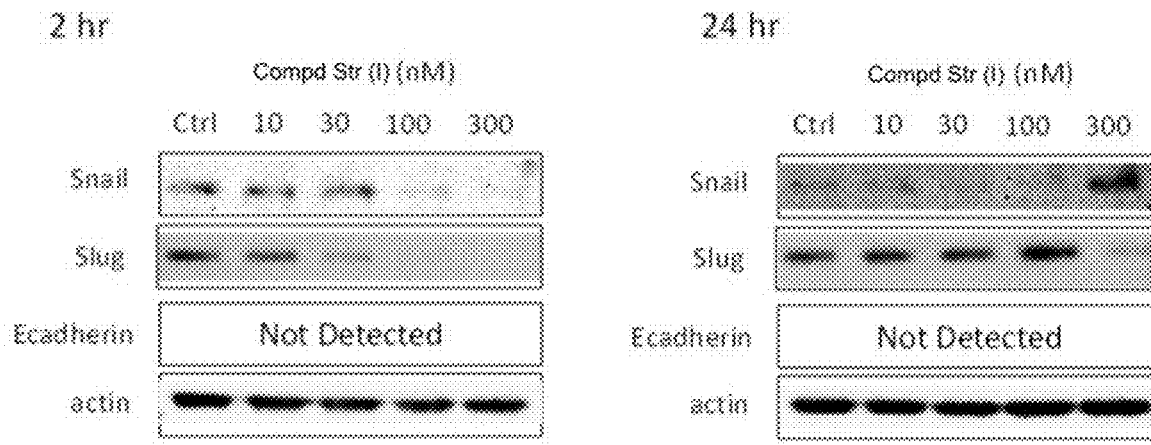
FIG. 71 shows the protein expression levels measured for the EMT markers Snail and Slug following treatment with the compound of structure (I) at various concentrations.

However, as shown in FIG. 70, EMT markers are no longer suppressed twenty-four hours after treatment with a tartrate salt of the compound of structure (I). As shown in FIG. 71, protein expression levels were measured for the EMT markers Snail and Slug following treatment with a tartrate salt of the compound of structure (I), and the protein expression levels were consistent with the mRNA expression levels.

Figure 72:
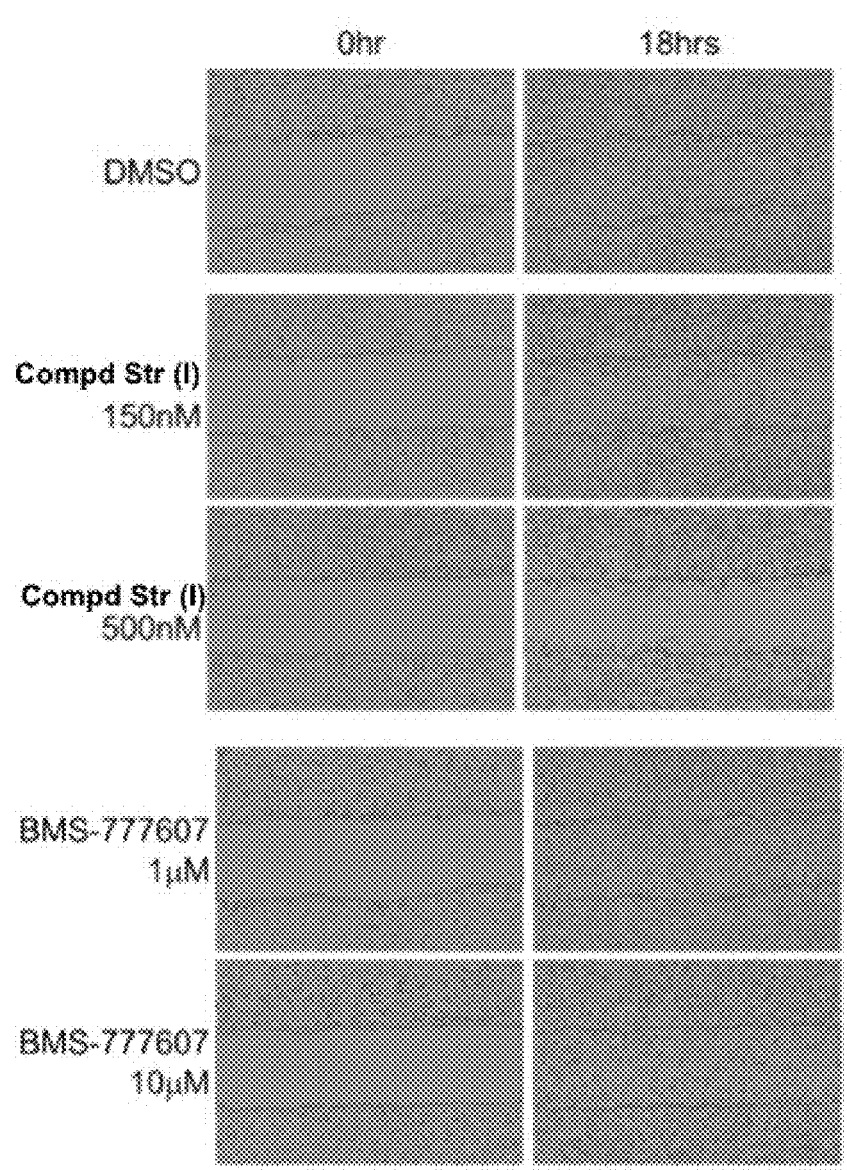
FIG. 72 shows the effects of a compound of structure (I) and BMS-777607 on the migration of ovarian tumor cells in a scratch assay.

Example 30: A Compound of Structure (I) Potently Inhibits the Migration of Ovarian Tumor Cells FIG. 72 shows the effects of AXL kinase inhibitors (a tartrate salt of a compound of structure (I) and BMS-777607) on the migration of ovarian tumor cells in a scratch assay. Ovarian tumor cells ES-2 were pre-treated with varying doses of a tartrate salt of the compound of structure (I) or another AXL inhibitor, BMS-777607, for 6 hours before scratching by the incucyte wound maker. The images were captured after 18 hours post-scratching. The tartrate salt of the compound of structure (I) showed strong inhibition of migration of ES-2 cells, an ovarian clear cell carcinoma cell line, whereas another AXL inhibitor, BMS-777607, did not inhibit migration, even at 10 µM.

Example 31: In Vivo Efficacy of the Compound of Structure (I) in a Mouse Ovarian Cancer Xenograft Model The efficacy of a tartrate salt of the compound of structure (I) was measured using a murine ES-2 intraperitoneal xenograft model. Mice were inoculated intraperitoneally with ES-2 cells, and then treated with either: a vehicle (n=6), 25 mg/kg of a tartrate salt of the compound of structure (I) (n=6), or 50 mg/kg of a tartrate salt of the compound of structure (I) (n=5).

Figure 73:
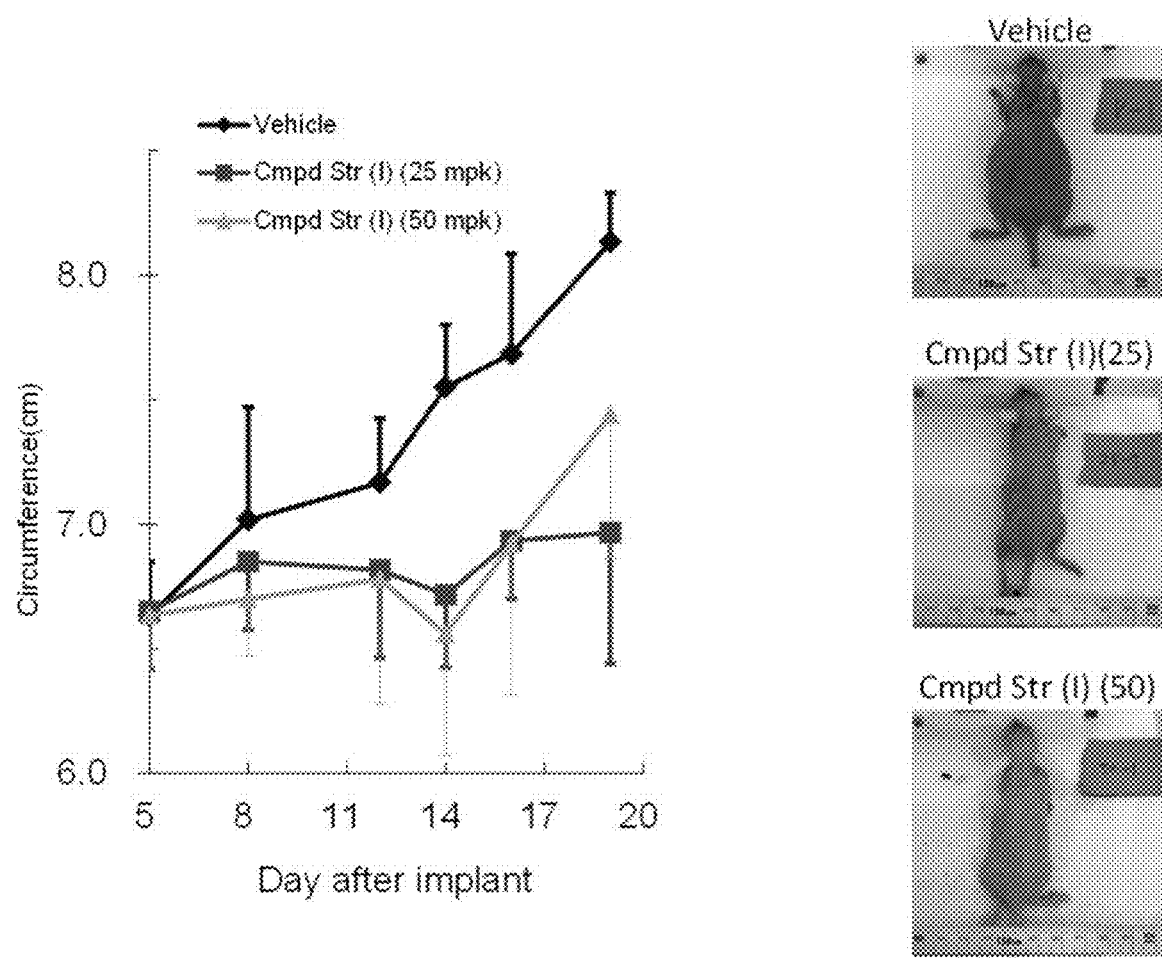
FIG. 73 shows the circumference of the mice following treatment and a representative photo of a mouse in each treatment group, as described in Example 33.
Figure 74:
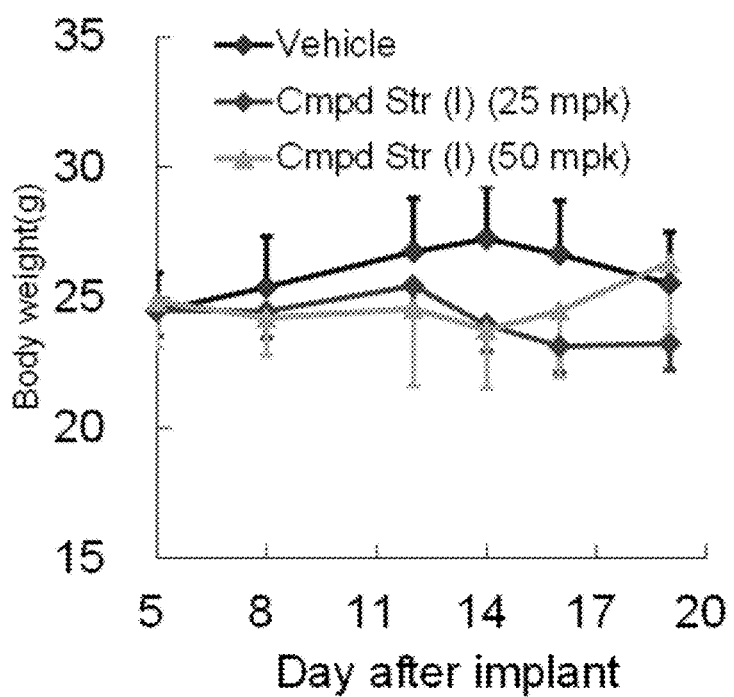
FIG. 74 shows a graph of the body weight of mice following treatment, as described in Example 33.

Treatment significantly suppressed ascites development (ascites volume, vehicle: 3.34 mL, a tartrate salt of a compound of structure (I): 0.28 mL; abdominal circumference, vehicle: 7.96 cm (day 15), a tartrate salt of a compound of structure (I): 6.82 cm (day 15), p<0.05). FIG. 73 shows the circumference of the mice following treatment (from day five to day nineteen after implant), and a representative photo of a mouse in each treatment group on day 20 after implant. FIG. 74 shows a graph of the body weight of mice following treatment, from day five to day nineteen following implant. As can be seen in FIG. 73 and FIG. 74, a tartrate salt of the compound of structure (I) showed efficacy at 25 mg/kg and 50 mg/kg in the ES-2 intraperitoneal dissemination model.

Example 32: Cytokines and Chemokines Profiles in Ascites Fluid Following In Vivo Treatment with a Compound of Structure (I)

Figure 75:
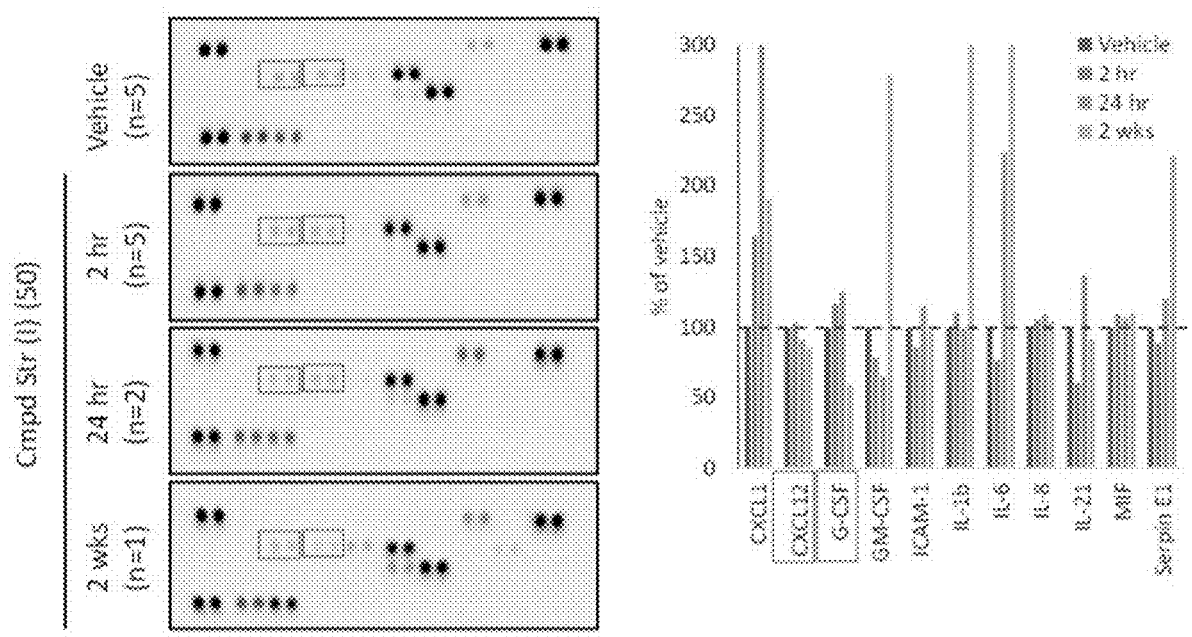
FIG. 75 shows the results of a panel of chemokines and cytokines measured following treatment of ES-2 xenograft mice with a compound of structure (I).

A panel of chemokines and cytokines were measured two hours, twenty-four hours, and two weeks following treatment of ES-2 xenograft mice with a tartrate salt of a compound of structure (I). FIG. 75 shows the imaging results of a Proteome Profiler Human Chemokine Array Kit (left panel) and the relative quantification of the cytokines/chemokines, as compared to a vehicle control. As can be seen in FIG. 75, CXCF12 and G-CSF were decreased following treatment with a tartrate salt of the compound of structure (I).

Example 33: EMT Markers in Ascites Fluid Following Treatment with a Compound of Structure (I)

Figure 76:
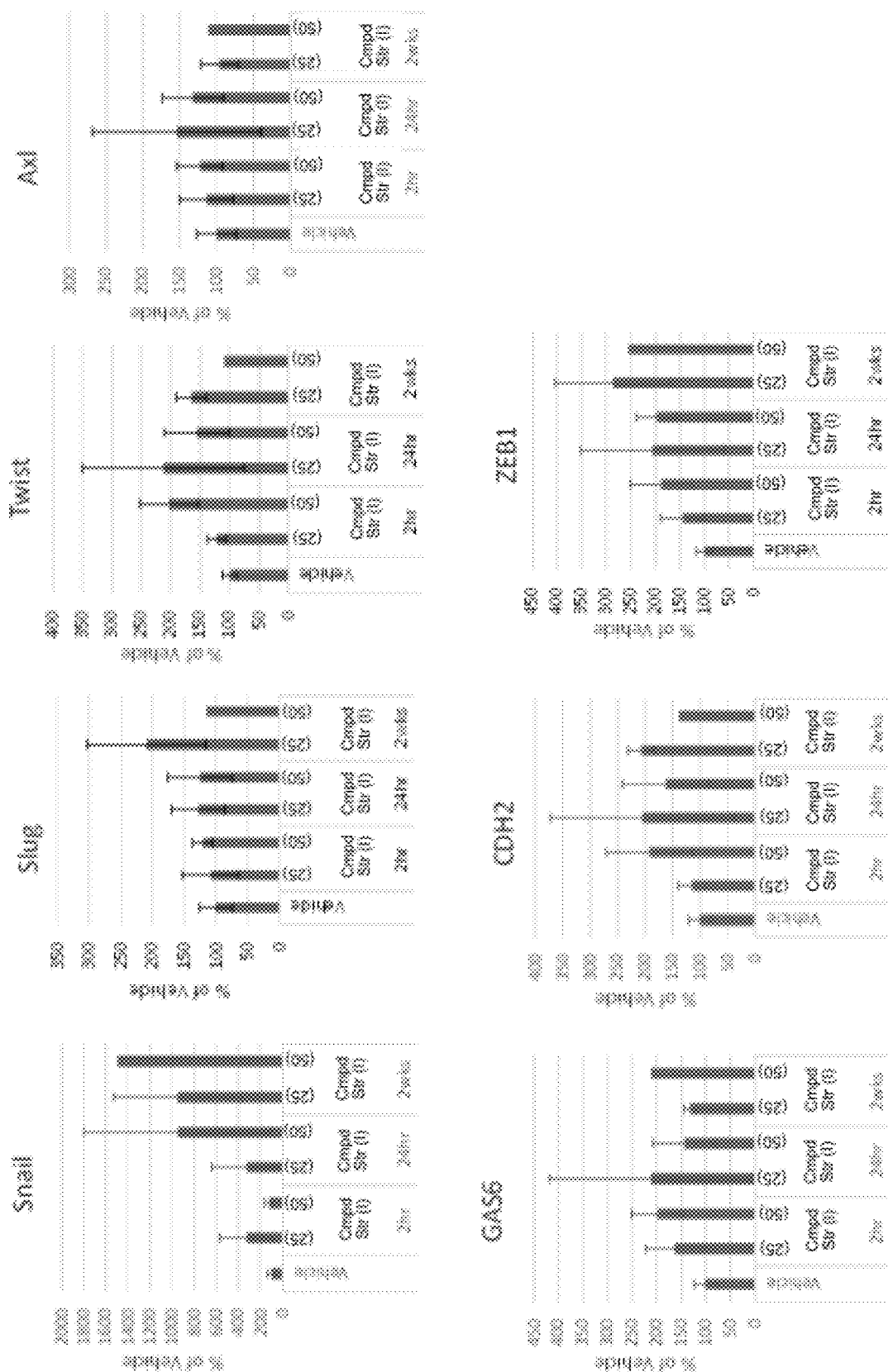
FIG. 76 shows the mRNA expression levels of EMT markers assayed from ascites fluid following treatment with the compound of structure (I).

FIG. 76 shows the mRNA expression levels of EMT markers assayed from ascites fluid following treatment with a tartrate salt of the compound of structure (I). As can be seen in FIG. 76, EMT markers were not suppressed in ascites fluid following treatment. In fact, GAS6, for example, was increased as soon as two hours following treatment with a tartrate salt of the compound of structure (I).

Example 34: Soluble Factors AXE, GAS6 and PD-F1 are Suppressed Following In Vivo Treatment with a Compound of Structure (I)

Figure 77:
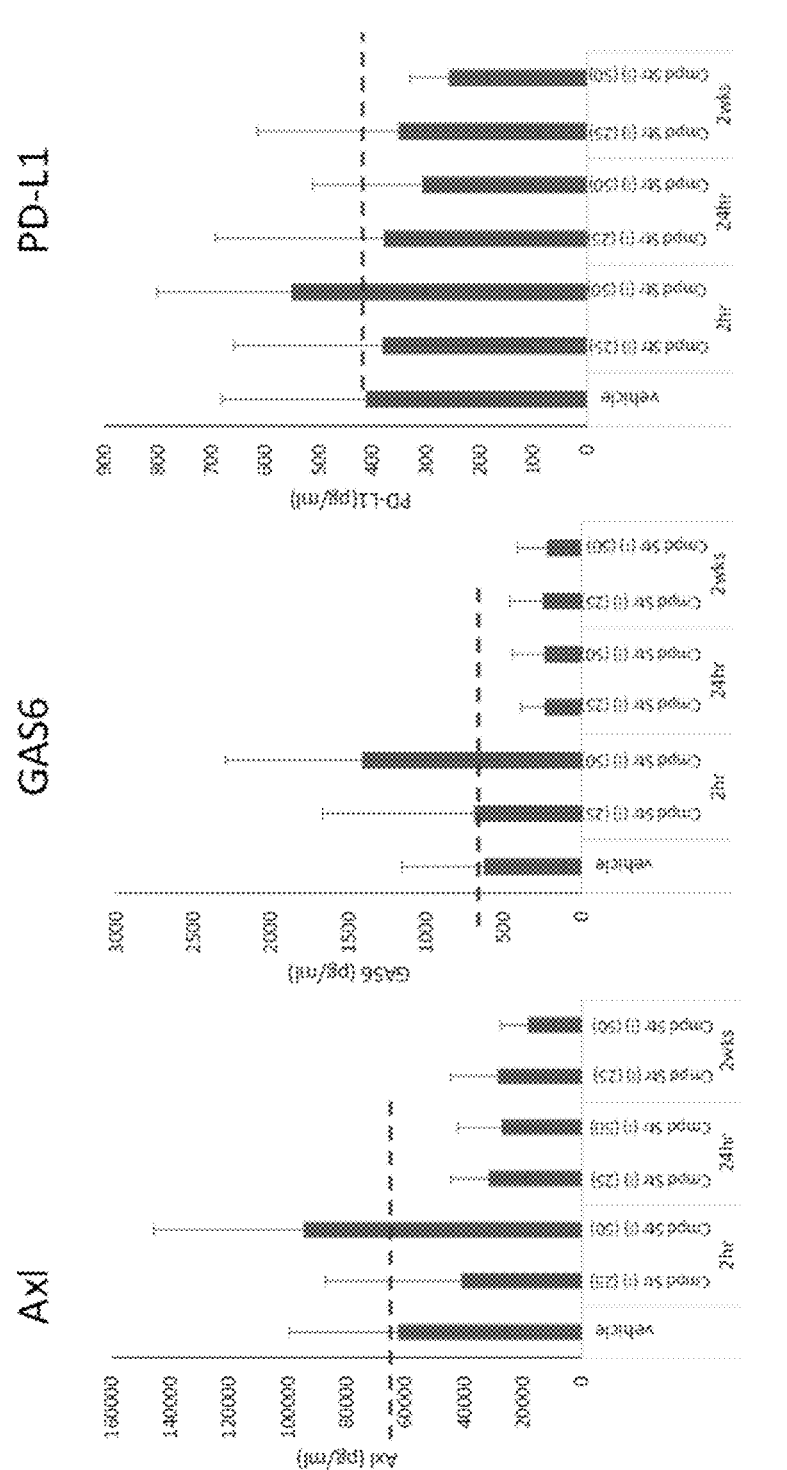
FIG. 77 shows soluble AXL, GAS6, and PD-L1 levels in blood following treatment with either 25 mg/kg or 50 mg/kg of the compound of structure (I), as described in Example 33.

FIG. 77 shows AXE, GAS6, and PD-F1 protein levels following treatment with either 25 mg/kg or 50 mg/kg of a tartrate salt of the compound of structure (I). Protein levels were measured by EFISA assay.

Figure 78:
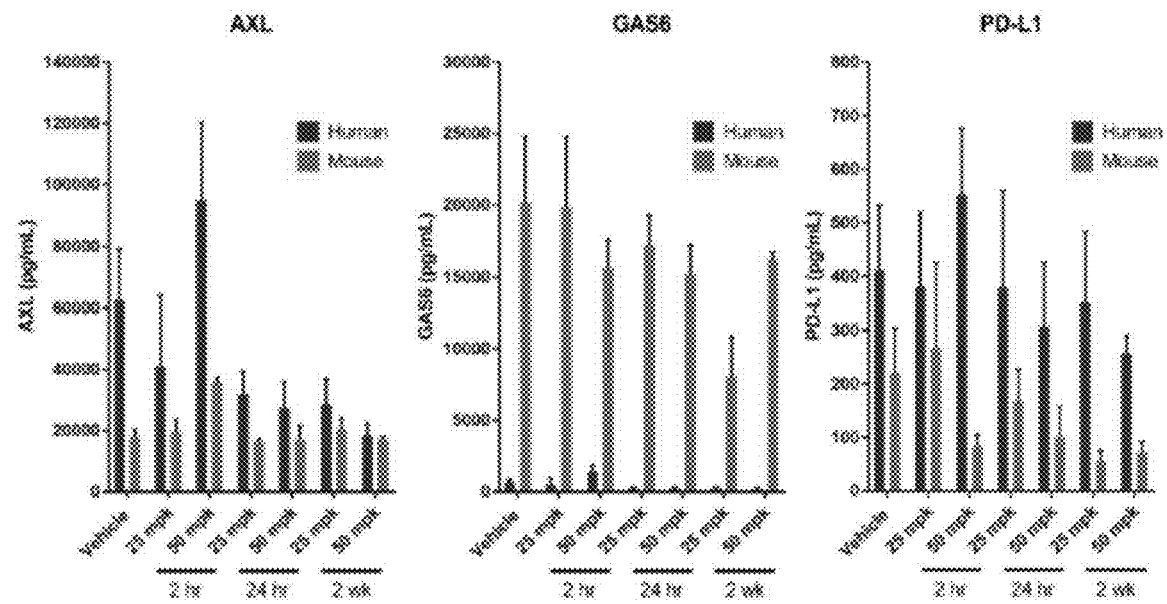
FIG. 78 shows the relative levels of mouse versus human AXL, GAS6, and PD-L1 in blood, following treatment as described in Example 33.

As can be seen in FIG. 77, AXE, GAS6, and PD-F1 were suppressed following treatment with a tartrate salt of the compound of structure (I). To determine if the suppressed levels of AXE, GAS6, and PD-F1 were due to suppression of these factors from the tumor cells, expression of mouse versus human level of each factor was measured. As can be seen in FIG. 78, AXE was mainly released from the ES-2 cells (human cells), whereas GAS6 was mainly released from non-cancer cells (murine cells). PD-F1 was equivalently released from ES-2 cells and non-cancer cells.

Example 35: In Vivo Efficacy of the Compound of Structure (I) at a Dose of 60 mg/kg in a Mouse Ovarian Cancer Xenograft Model In vivo efficacy was tested for 60 mg/kg of a tartrate salt of the compound of structure (I) in intraperitoneal transplantation model of ES-2 ovarian clear cell carcinoma cell line. Vascular permeability due to metastatic colonization of intraperitoneal membranes by tumor cells is a major cause of ascites development in ovarian cancer patients. This xenograft model allowed for evaluation of the development of ascites, and peritoneal and mesenterial spread of tumor cells.

Figure 79:
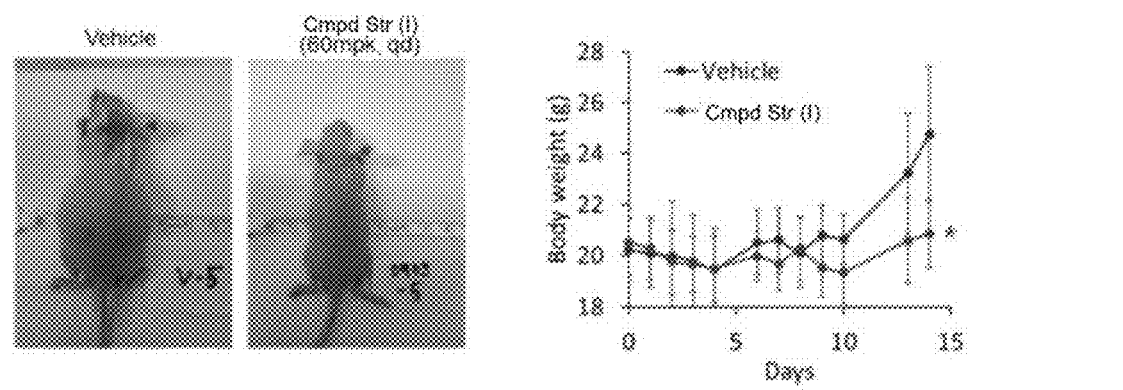
FIG. 79 shows a representative photo of a mouse treated with a compound of structure (I) versus a vehicle control (top left), body weight of the treated mice, abdominal circumference of the treated mice, volume of recovered ascites, and percent survival, for mice treated as described in Example 37.
Figure 79:
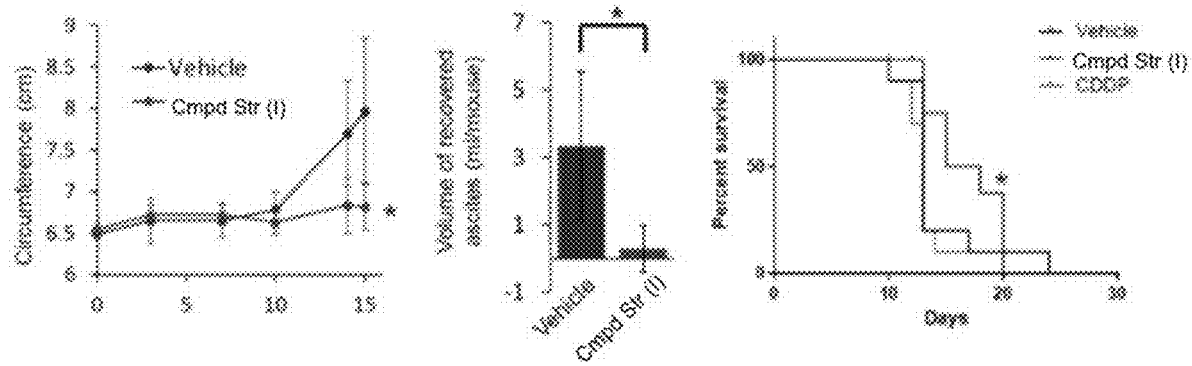

Ovarian clear cell carcinoma ES-2 cells were transfected with luciferase expression vector pGL4.1 ($1 \times 10^{\wedge}6$ cells) were injected intraperitoneally in to the BALB/cAnNCrj-nu/nu mice. After 5 days post-injection, luciferase expression was measured, which indicated cancer cells were growing intraperitoneally. Subsequently, 12 mice were randomized into two groups for vehicle and 60 mg/kg of a tartrate salt of the compound of structure (I). The compound of structure (I) was prepared in a vehicle of TPGS buffer and given by oral gavage. The drugs were provided a '5-day on, 2-day off' schedule for 2 cycles. Represent images of mice were taken at day 14 (FIG. 79, top left panel). For mice in both treatment groups (60 mg/kg of a tartrate salt of a compound of structure (I), versus a vehicle control), body weight is shown in FIG. 79, top right panel; abdominal circumference is shown in FIG. 79 bottom left panel; volume of recovered ascites is shown in FIG. 79, bottom middle panel; and percent survival is shown in FIG. 79, bottom right panel (which additionally includes mice treated with cisplatin, "CDDP", at 2.5 mg/kg, iv, 1/wk). Treatment with a tartrate salt of the compound of structure (I) (60 mg/kg, PO, qd) significantly suppressed ascites development (ascites volume, vehicle 3.34 mL, a tartrate salt of a compound of structure (I)-0.28 mL, abdominal circumference, vehicle-6.48 cm (day 0) to 7.96 cm (day 15), a tartrate salt of a compound of Structure (I) 6.55 cm (day 0) to 6.82 cm (day 15), p<0.05) without any body weight loss. The compound of structure (I) also prolonged overall survival significantly compared to vehicle or cisplatin, "CDDP."

Figure 80:
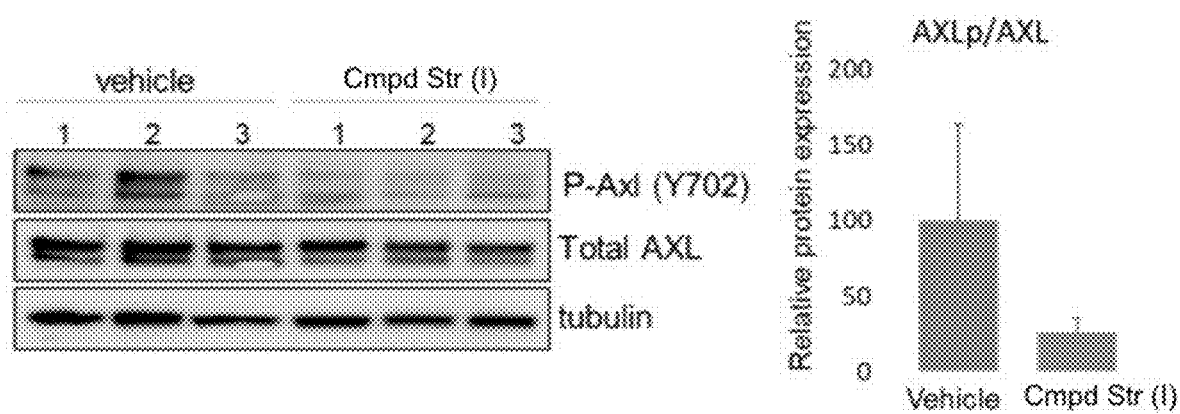
FIG. 80 shows the results of western blots for tubulin, AXL total and phosphorylated at Y702 site and relative AXL phosphorylation of ES-2 cell-injected mice compared to the control group, as described in Example 37.

Example 36: In Vivo Efficacy of the Compound of Structure (I) at a Dose of 60 mg/kg in a Mouse Ovarian Cancer Xenograft Model Twenty-four hours following injection with ES-2 cells as described in Example 10, tumor cells were collected from abdomen, then lysed and western blotted for tubulin, AXL total and phosphorylated at Y702 site (FIG. 80, left panel). The plot shows the relative AXL phosphorylation for the treatment group as compare to the vehicle-treated group (FIG. 80, right panel). As shown in FIG. 80, a tartrate salt of the compound of structure (I) at a dose of 60 mg/kg reduced at 24 hours the ratio of p-AXL (Y702)/AXL in the collected tumor cells from abdomen. These results indicated that a tartrate salt of the compound of structure (I) directly blocked the growth of metastasized ovarian cancer cells.

Example 37: OVCAR3 Tumor Ascites Model Development

Figure 81:
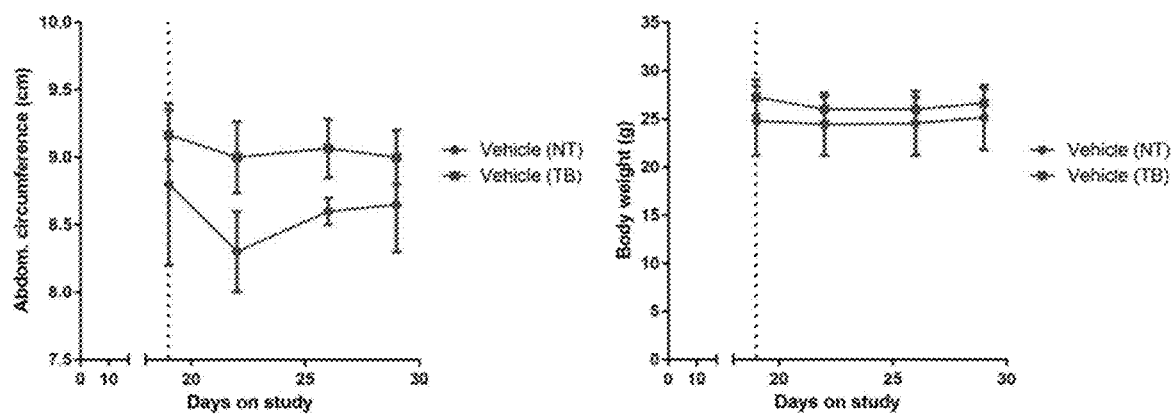
FIG. 81 shows the abdominal circumference and body weight of tumor-bearing versus non-tumor bearing mice, for mice treated as described in Example 39.
Figure 82:
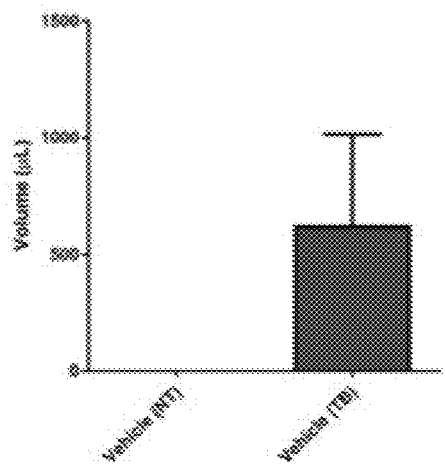
FIG. 82 shows the ascites volume and representative photographs of mice treated in the study described in Example 39, with non-tumor bearing mice shown on the left and tumor-bearing mice shown on the right.
Figure 82:
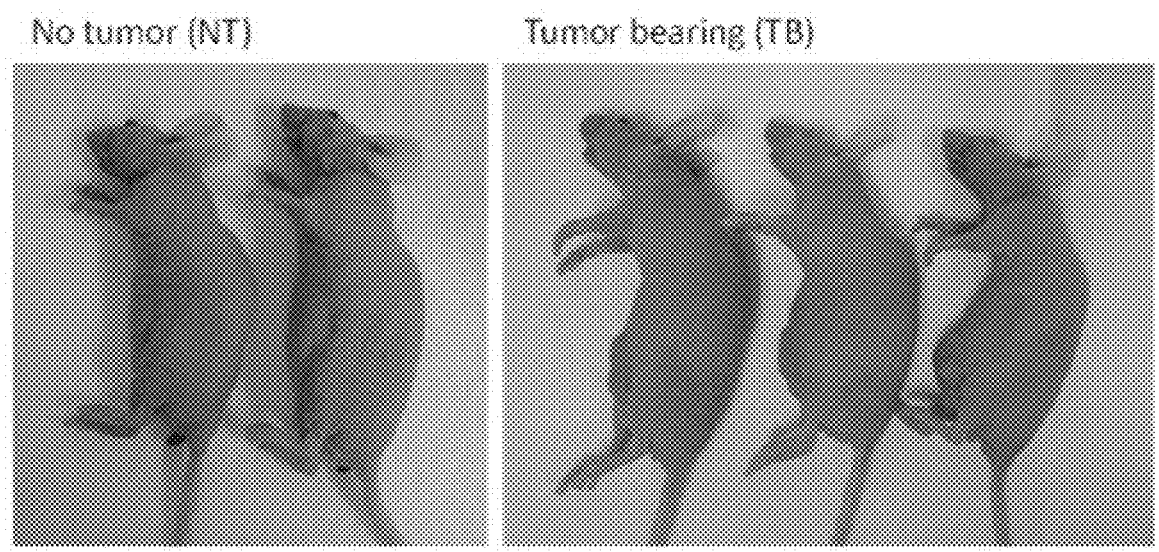

The OVCAR-3 model for ovarian cancer induced-ascites employed in this study was adapted from the following references: Hamilton et al. 1984. Can Res.; Hu et al. 2002. Am J Pathol. In brief, mice were injected with $1 \times 10^7$ OVCAR3 cells/mouse. Once subcutaneous tumors had begun to develop at the site of injection, the abdominal circumference was monitored regularly. FIG. 81 shows the abdominal circumference (left panel) and body weight (right panel) of tumor-bearing versus non-tumor bearing mice. FIG. 82 shows the ascetic volume and representative photographs of mice treated in the study, with non-tumor bearing mice shown on the left and tumor bearing mice shown on the right. With the intraperitoneal injection of the OVCAR3 cells, mice exhibited increased abdominal circumference and increased ascitic volume.

Figure 83:
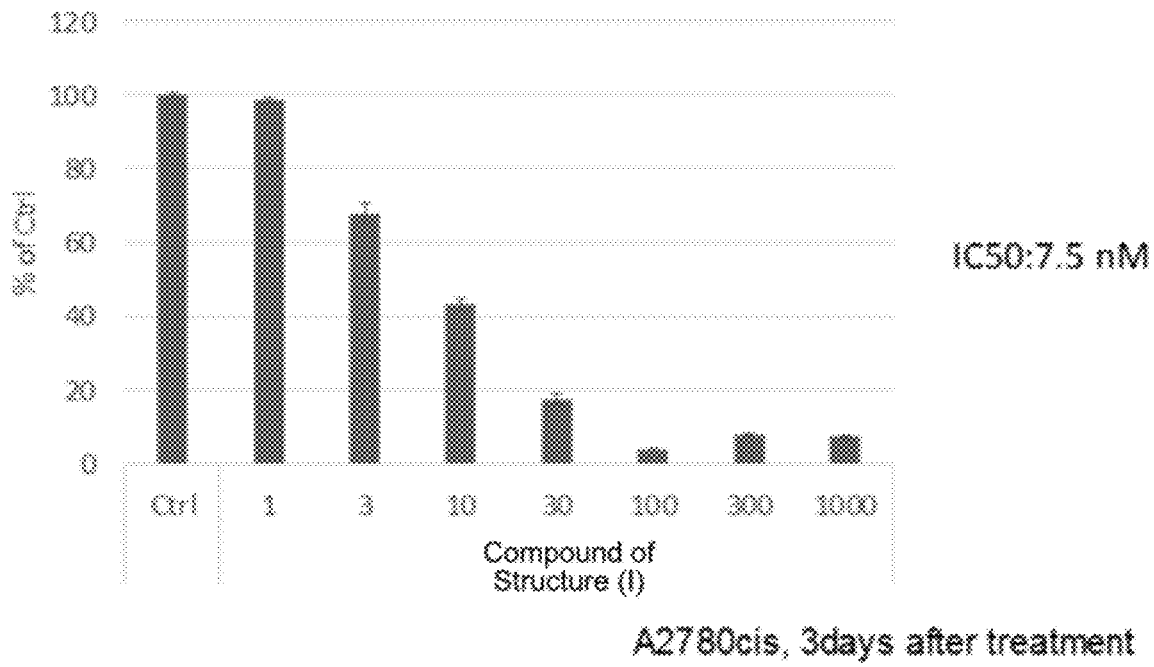
FIG. 83 shows the results of treating the cells with varying doses of the compound of structure (I) as described in Example 40.

Example 38: In Vitro Cytotoxicity and In Vivo Efficacy of the Compound of Structure (I) in an Intraperitoneal Xenograft Model In vitro cytotoxicity was tested in a proliferation assay of A2780cis cells. Cell viability was evaluated by CellTiter-Glo assay. The results of treating the cells with varying doses of a tartrate salt of the compound of structure (I) three days after treatment are shown in FIG. 83.

Figure 84:
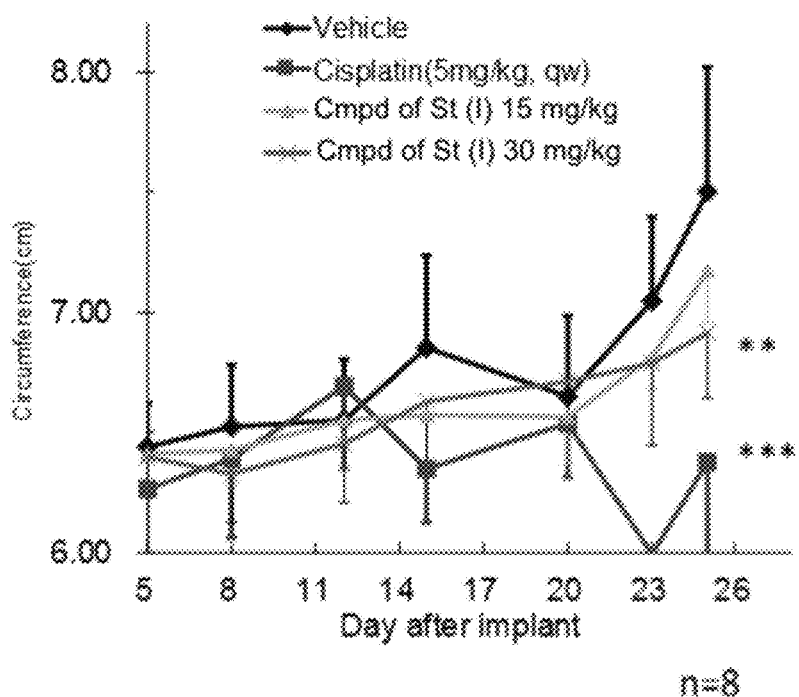
FIG. 84 shows the circumference of A2780cis xenograft mice 5-25 days after implant, as described in Example 40.
Figure 85:
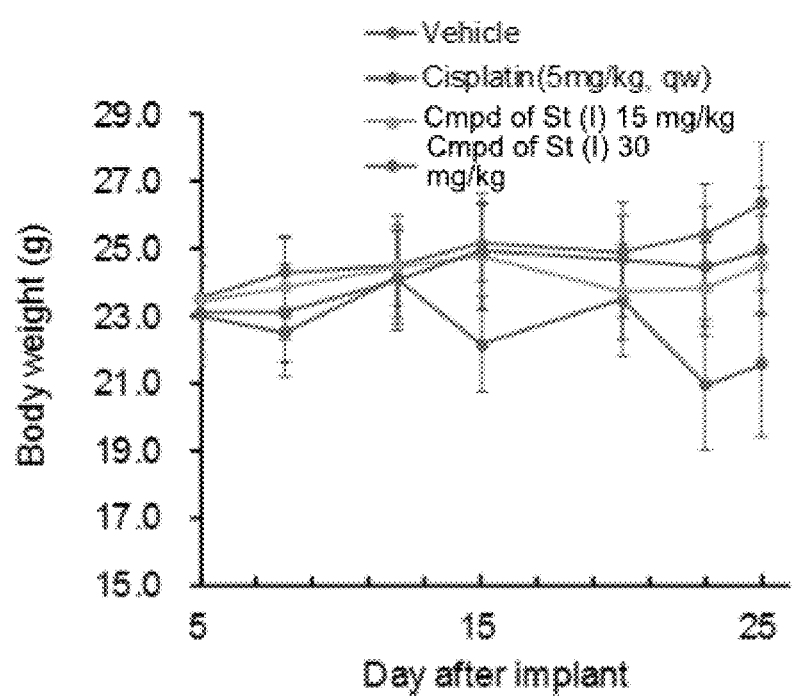
FIG. 85 shows the bodyweight of A2780cis xenograft mice 5-25 days after implant, as described in Example 40.
Figure 86:
FIG. 86 shows representative photographs of mice in the study at day 25 after treatment, as described in Example 40.
Figure 86:

In vivo efficacy was tested for vehicle (n=8), 15 mg/kg (n=8) and 30 mg/kg (n=8) of a tartrate salt of the compound of structure (I) and CDDP 5 mg/kg (n=8) in intraperitoneal transplantation model of A2780cis ovarian carcinoma cell line. Ovarian carcinoma A2780cis cells ($1 \times 10^{\wedge}7$/mouse) were injected intraperitoneally in to mice. Five days after implant, drugs except for CDDP were orally administered once a day and CDDP was administered intraperitoneally once a week. FIG. 84 shows the circumference and FIG. 85 shows the body weight of the mice 5-25 days after implant. FIG. 86 shows representative photographs of mice in the study at day 25 after treatment, a vehicle treated mouse is on the left and a mouse treated with 30 mg/kg of a tartrate salt of the compound of structure (I) is on the right.

Figure 87:
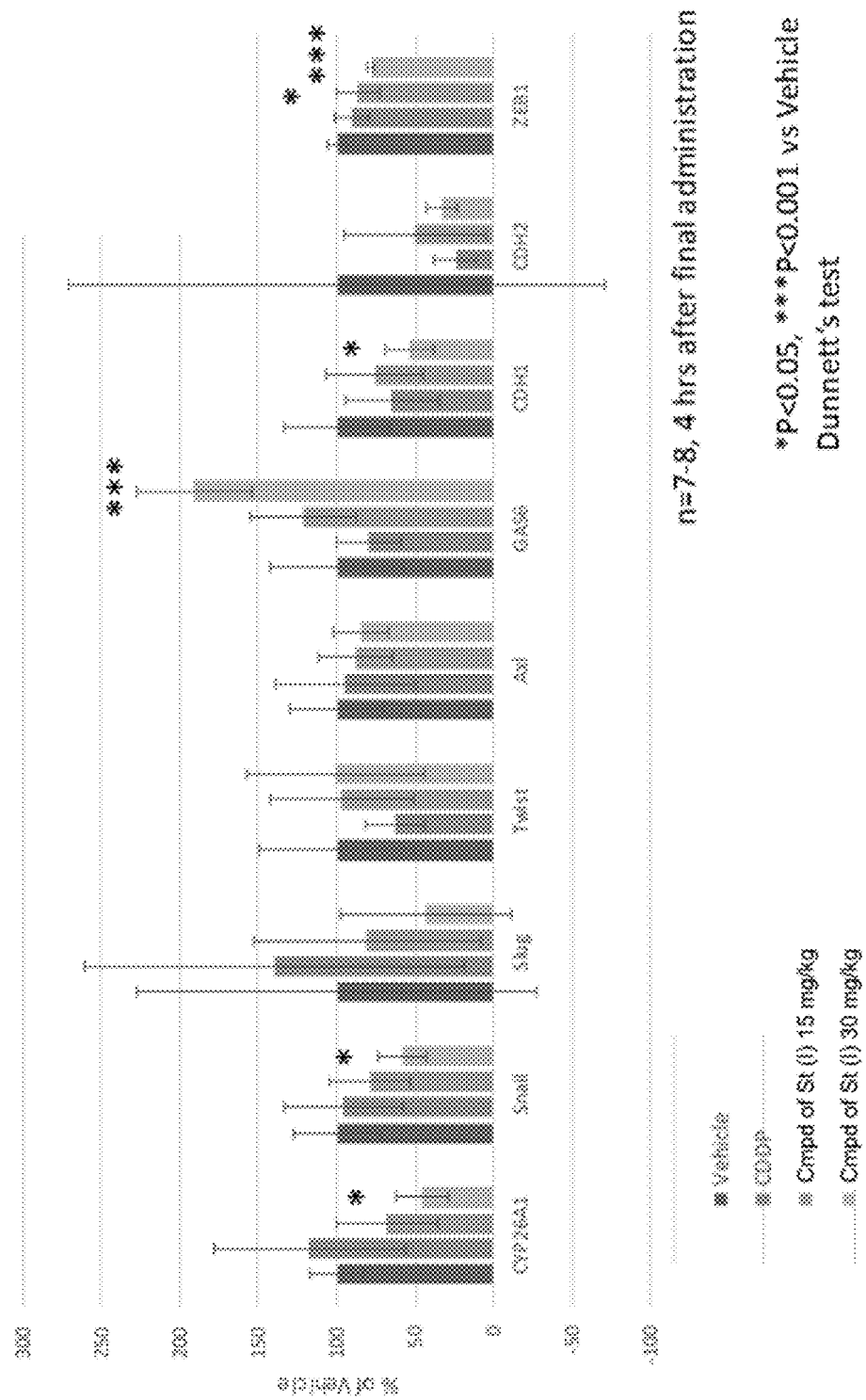
FIG. 87 shows gene expression levels in tumors of A2780cis xenograft mice, as described in Example 40.

Tumors were lysed and mRNA and protein were extracted four hours after the final administration of a tartrate salt of the compound of structure (I). Gene expression levels in the tumors were analyzed by RT-qPCR (n=7-8). The expression of CYP26A1, Snail, Slug, Twist, Axl, GAS6, CDH1, CDH2, and ZEB1, which are normalized by that of GAPDH, are shown in FIG. 87.

Figure 88:
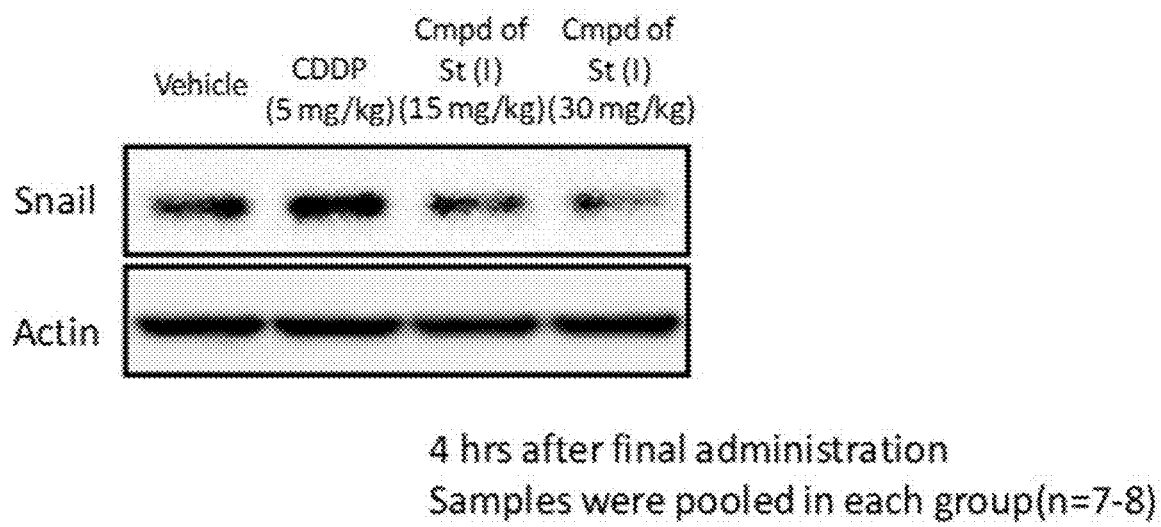
FIG. 88 shows protein expression levels were measured by western blot analysis for Snail and β-actin as a loading control following treatment with the compound of structure (I), as described in Example 40.

As shown in FIG. 88, protein expression levels were measured by western blot analysis for Snail and β-actin as a loading control following treatment with a tartrate salt of the compound of structure (I). Samples were pooled per each group (n=7-8).

Figure 89:
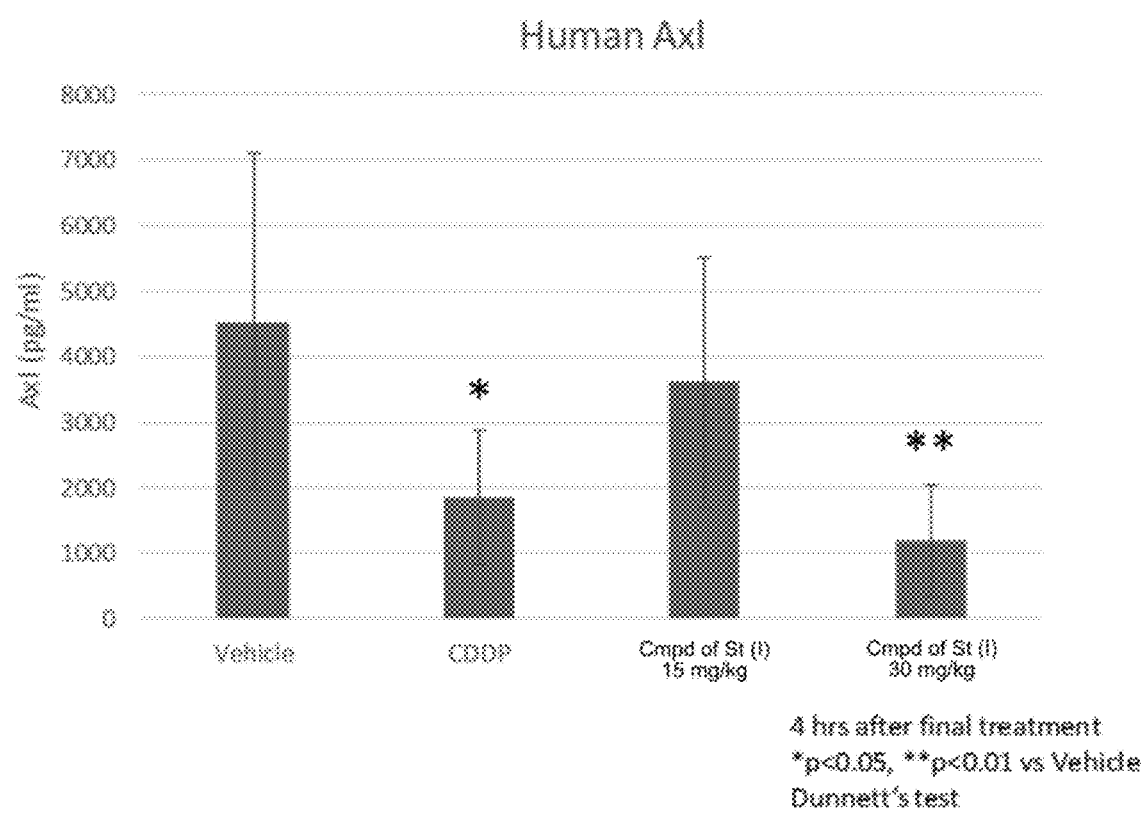
FIG. 89 shows human Axl expression in serum, as described in Example 40.

Serum were collected four hours after the final administration of a tartrate salt of the compound of structure (I). Human Axl expression in serum is measured by EFISA as shown in FIG. 89.

Example 39: Testing the Efficacy of a Compound of Structure (I) in an OVCAR3 Tumor Ascites Model Following intraperitoneal inoculation with the OVCAR3 cells, mice are treated with a tartrate salt of a compound of structure (I) (e.g., n=6) or a vehicle control (e.g., n=6), and the abdominal circumference and body weight of each mouse is measured to determine the efficacy of a tartrate salt of the compound of structure (I). Soluble AXE, GAS6, and PD-F1 levels are also measured from the mice in both treatment groups.

Example 40: Synthesis of Compound 1

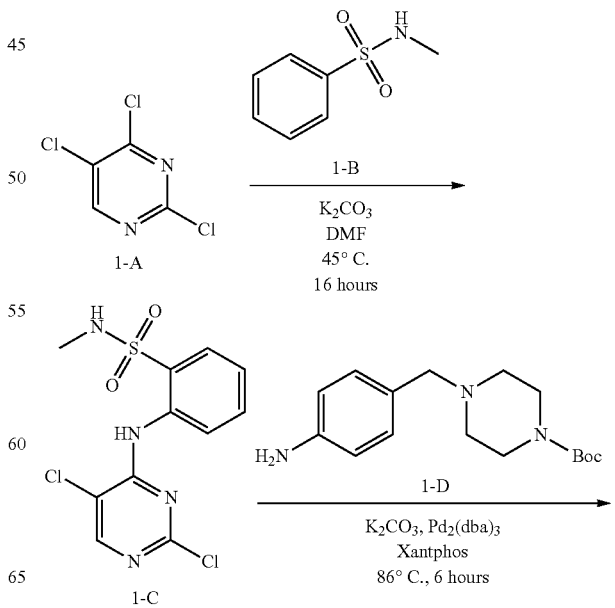

-continued

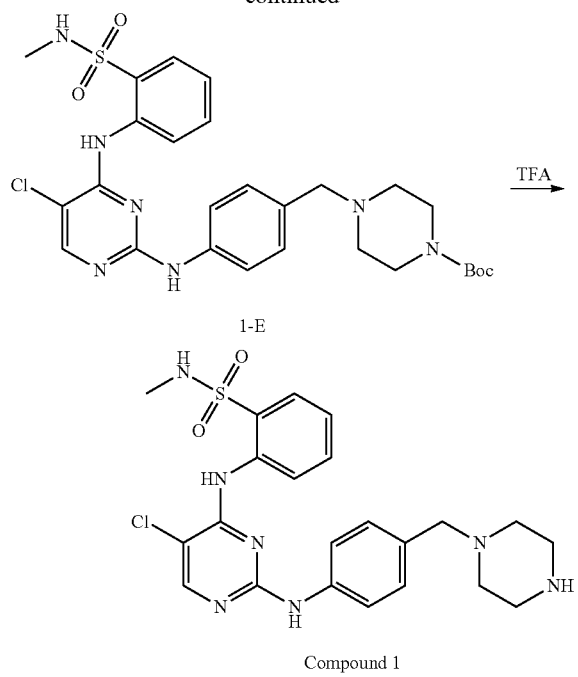

Compound 1 is synthesized by reacting compound 1-A with 1-B using the conditions indicated above. Compound 1-C is then reacted with compound 1-D using the reaction conditions shown to afford the product 1-E. The amine protecting group is then removed using suitable acidic conditions (e.g., TFA or HCl in dioxane). Purification using standard techniques (e.g., silica gel chromatography or prep-HPLC) as needed.

Example 41: Synthesis of Compound 2

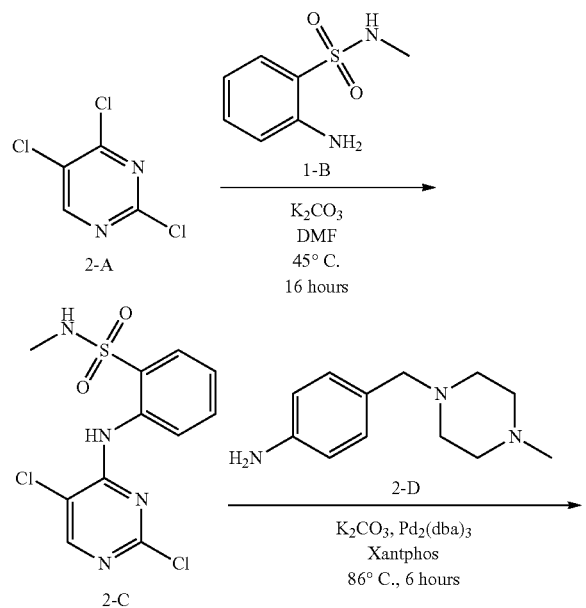

-continued

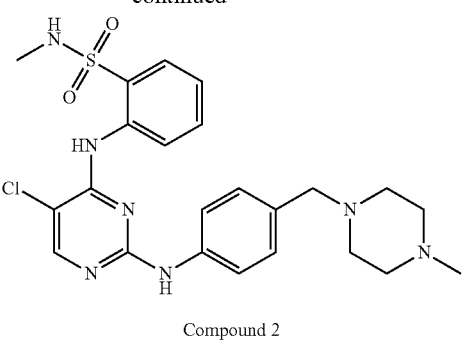

Compound 2 is synthesized by reacting compound 2-A with 2-B using the conditions indicated above. Compound 2-C is then reacted with compound 2-D using the reaction conditions shown to afford the desired product (Compound 2). Purification using standard techniques (e.g., silica gel chromatography or prep-HPLC) as needed.

Example 42: Synthesis of Compound 3

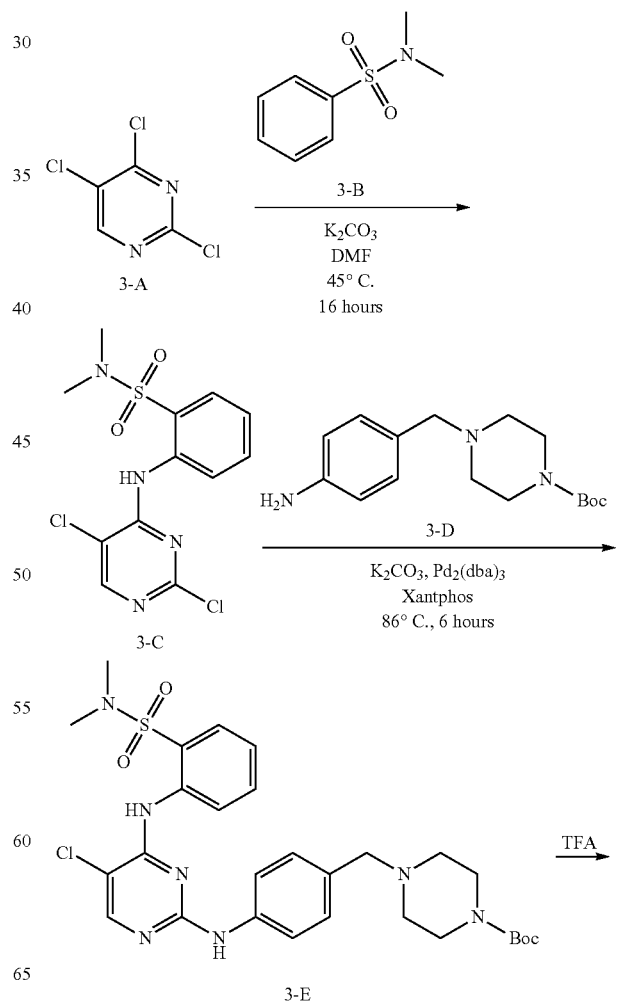

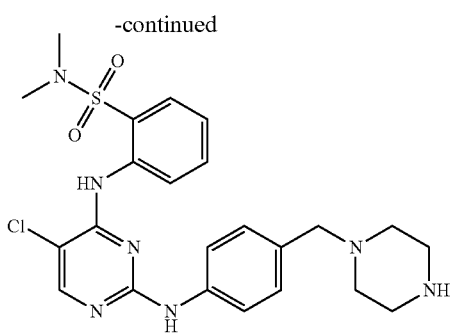

Compound 3

Compound 3 is synthesized by reacting compound 3-A with 3-B using the conditions indicated above. Compound 3-C is then reacted with compound 3-D using the reaction conditions shown to afford the product 3-E. The amine protecting group is then removed using suitable acidic conditions (e.g., TFA or HCl in dioxane) to afford Compound 3. Purification using standard techniques (e.g., silica gel chromatography or prep-HPLC) as needed.

Example 43: Synthesis of Compound 5

Compound 4-A is treated with Oxone® (i.e., potassium peroxymonosulfate) and deprotected using acidic conditions (e.g., TFA). The deprotected product 4-B is then coupled with aldehyde 4-C via a reductive amination to afford the desired product 4-D. The compound 4-D is then deprotected to afford compound 4-1 as indicated above.

In parallel, compound 4-F is reacted with 4-G using the conditions indicated above. Compound 4-H is then reacted with compound 4-1 prepared as described above to afford the desired product, Compound 5. Purification using standard techniques (e.g., silica gel chromatography or prep-HPLC) as needed.

Example 44: Compound IV Metabolite PK Data

Figure 90:
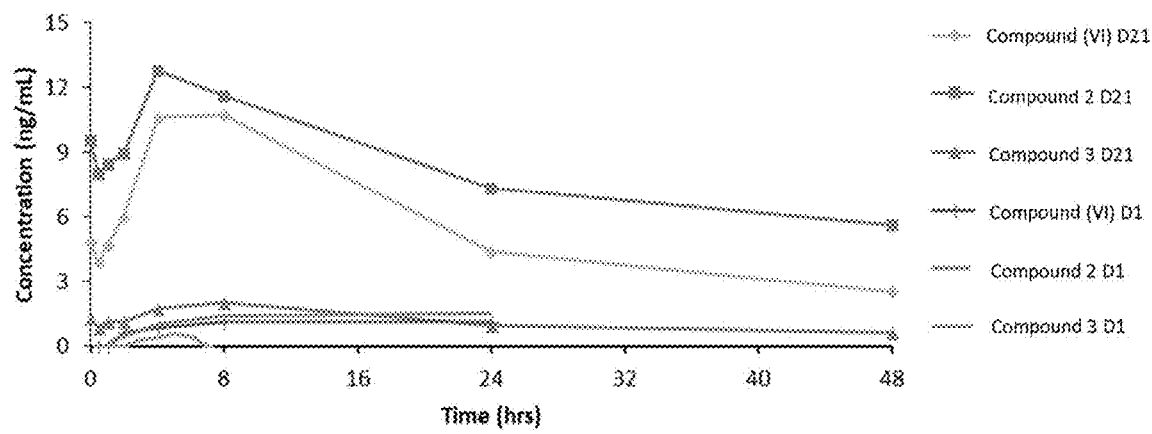
FIGS. 90-92 shows representative data for Compound IV plasma concentrations on day 1 and day 21 from subjects dosed for 21 consecutive days with Compound VI.
Figure 91:
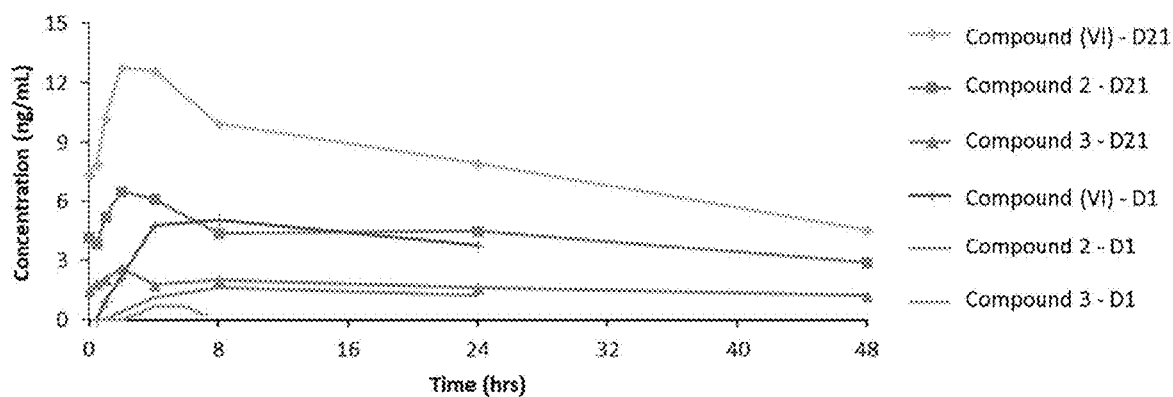
Figure 92:
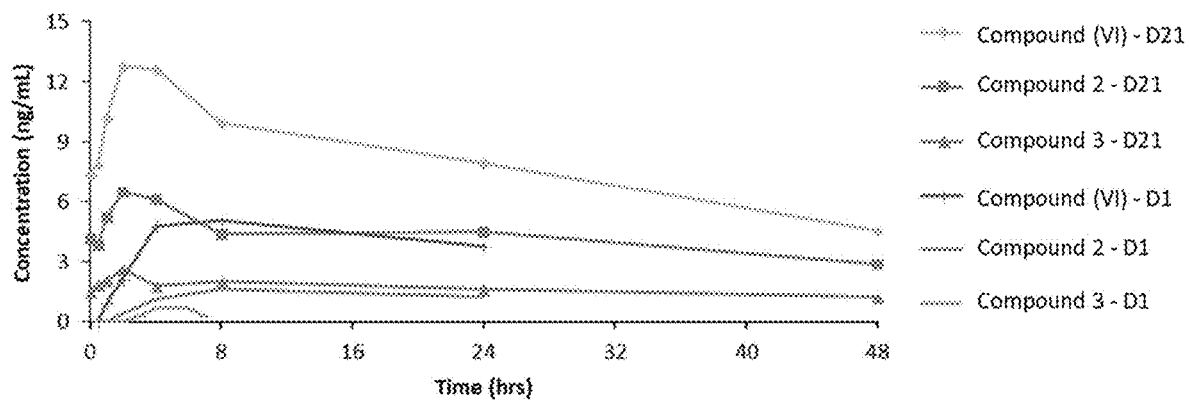

Representative exampled from subjects dosed with a compound of structure (IV) is presented in FIGS. 90-92 (16 mg/m$^2$). The data shows the concentration of the compound of structure (VI) and two metabolites compounds (i.e., Compounds 2 and 3). Data was collected on day one of the dosing (D1) and on day 21 (D21).

As shown in FIG. 90, Compound 2 and Compound 3 were observed at relative concentration levels of approximately 1:1 and 1:10 with the compound of structure (IV), respectively, in this subject. As shown in FIG. 91, Compound 2 and Compound 3 were observed at relative concentration levels

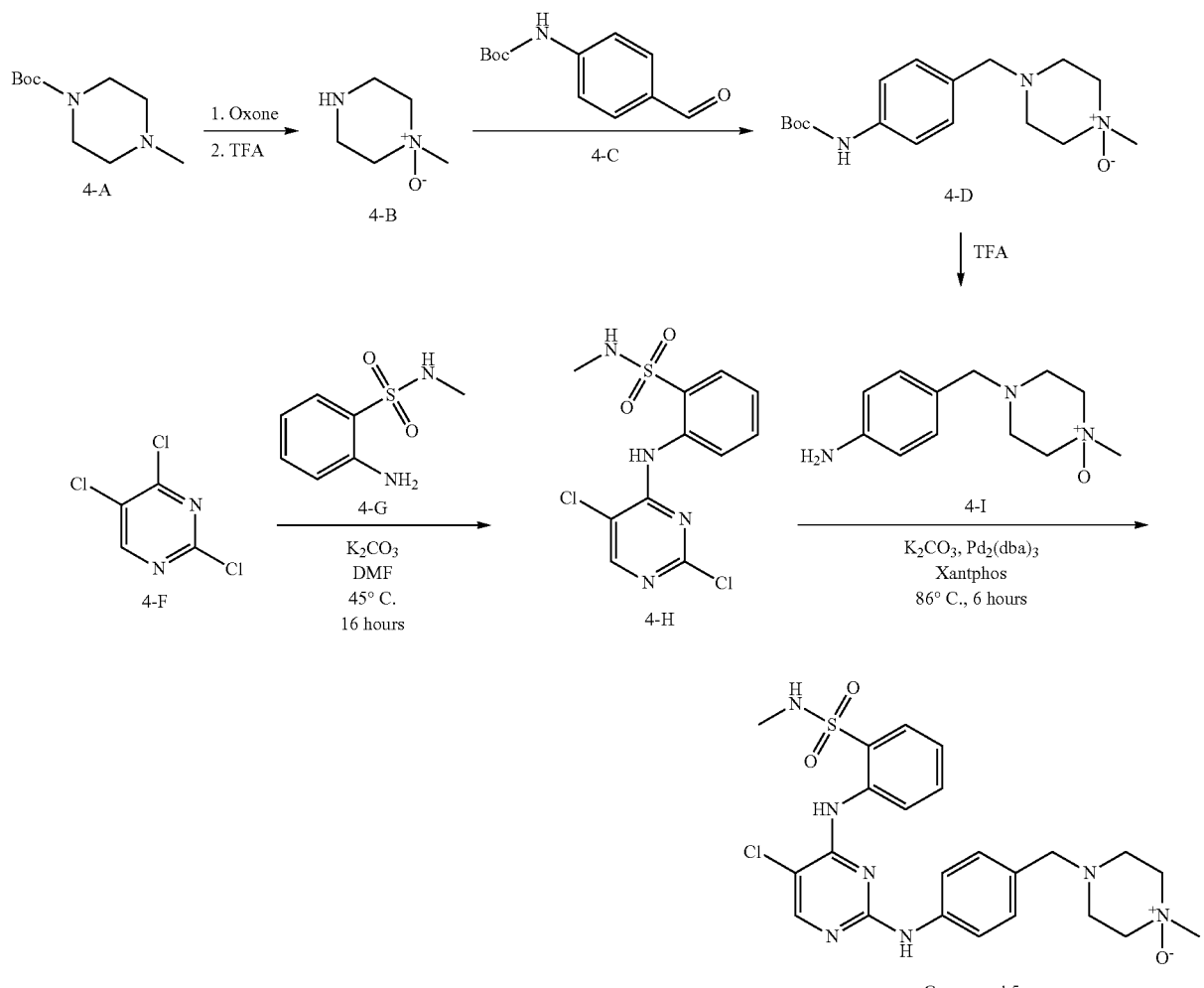

Compound 5 of approximately 1:2 and 1:4 with the compound of structure (IV), respectively, in this subject. As shown in FIG. 92, Compound 2 and Compound 3 were observed at relative concentration levels of approximately 1:1 and 1:3 with the compound of structure (IV), respectively, in this subject.

Figure 93:
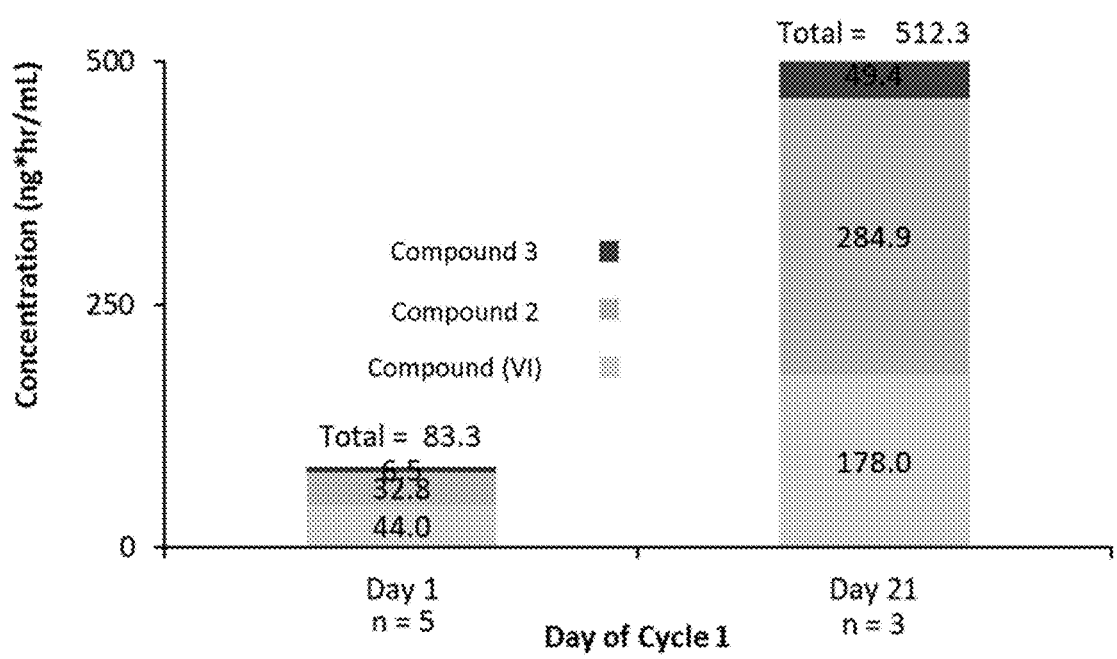
FIG. 93 provides Compound VI and active metabolite data collected and shown as area under the curve (AUC) values for day 1 and day 21 dosing with Compound VI for 21 consecutive days.

Additionally, the overall pharmacokinetic profile for Compound 2 and Compound 3 parallels the compound of structure (VI) in terms of the $T_{max}$ accumulation and clearance. The mean area under the curve (AUC) from the initial time point until the last time point is shown in FIG. 93. The AUC values with metabolites (Compounds 2 and 3) are 2-3× higher than Compound VI alone. By day 21, the AUC values are proportionally higher (approximately 4-fold higher).

Example 46: Cardiovascular Safety Assessment of Compound of Structure (I) in Dogs This example reports the study of the potential toxicity and toxicokinetics of a tartrate salt of the compound of structure (I) when administered orally to dogs for 28 consecutive days as well as the progression or regression of any effects following a 14-day treatment-free recovery period.

Electrocardiograms (6 limb leads) were obtained for all animals once during the pre-treatment period and on Day 27 of dosing at approximately 1.5 hours post dosing; close to the Tmax (2 hr±30 minutes). Tracings were assessed for gross changes indicative of cardiac electrical abnormalities. Heart rate (HR) (lead II), rhythm or conduction abnormalities were also evaluated. Each ECG was evaluated for HR, rhythm, P wave duration, QRS duration, PR interval, and QT duration. The morphology of the QRS complexes was evaluated in the frontal plane leads for gross abnormalities. Electrocardiograms were evaluated by a Board-certified Veterinary Cardiologist.

Blood pressure (BP) using a non-invasive technique was recorded at approximately the same time as ECGs, and included HR, and systolic/diastolic BP.

The heart rate, PR interval, P wave duration and QRS duration were within normal limits for all groups and there was no significant difference noted between groups at the different time points. The QT interval was within normal limits for all groups and all time points. Pre-study HR was significantly lower in the high dose group compared to all other groups and was considered an incidental finding. No arrhythmias were noted in the different groups at the different time points.

Example 47: Additional Pre-Clinical Studies; Safety Pharmacology and Animal Toxicity/Pharmacokinetics of Compound of Structure (I)

In Vivo Pharmacodynamic and Biomarker Studies

In order to determine bio marker movement in vivo, CYP26A1 levels were measured in tumors from mice treated with a tartrate salt of a compound of structure (I). Tumor tissues from athymic nude mice bearing subcutaneously xenografted MV4-11 tumors were removed at 6 or 24 hours following a single oral dose of the compound (180 mg/kg). CYP26A1 levels were measured by immunohistochemistry (IHC) as well as by RT-qPCR assessment. Results showed that a compound of structure (I) attenuates AXL-associated biomarkers in vivo.

Safety Pharmacology

A number of assays were performed to evaluate the potential effects of a tartrate salt of the compound of structure (I) on hERG activity.

(i) Effects on hERG Channel Function

Biochemical binding to the hERG channel was evaluated using the Predictor™ hERG Fluorescence Polarization Assay (Invitrogen). Results showed that a tartrate salt of a compound of structure (I) is a weak biochemical inhibitor of hERG activity, exhibiting an $IC_{50}$ greater than 1 µM. In addition, 3 separate hERG patch-clamp experiments were also conducted, 2 using HEK-293 cells and 1 using CHO cells. The data from cell-based Study No. 191081 suggests that a tartrate salt of the compound of structure (I) inhibits hERG activity by greater than 50% at 1 µM in transfected HEK-293 cells. However, data from the 2 other patch-clamp assays conducted in both HEK-293 and CHO cells are more consistent with the data from the cell-free biochemical screen, concluding that hERG inhibition is not significant (>50%) below 1 µM of a tartrate salt of the compound of structure (I).

(ii) Receptor Panel Screening

The tartrate salt of the compound of structure (I) was screened through the "Safety 44 panel" of safety-associated receptors and enzymes offered by Cerep. The compound of structure (I) inhibited only 15 of these assays when screened at the highest dose tested at 10 µM. Based on animal pharmacokinetic data, animal efficacy models and toxicology data, 10 µM concentrations have not been reached in animals and are not expected to be achieved in future human studies. Therefore, off-target receptor inhibition is not expected to lead to significant toxicity concerns in future testing of the compound of structure (I).

(iii) Cardiovascular Safety Assessment in Dogs

A study was carried out to examine the potential toxicity and toxicokinetics of a tartrate salt of the compound of structure (I) when administered orally to dogs for 28 consecutive days as well as the progression or regression of any effects following a 14-day treatment-free recovery period.

Electrocardiograms (ECGs) (6 limb leads) were obtained for all animals once during the pretreatment period and on Day 27 of dosing at approximately 1.5 hours postdose; close to the time to $C_{max}$ (peak time) ($T_{max}$) (2 hr±30 minutes). Tracings were assessed for gross changes indicative of cardiac electrical abnormalities. Heart rate (HR) (lead II), rhythm or conduction abnormalities were also evaluated. Each ECG was evaluated for HR, rhythm, P wave duration, QRS duration, PR interval, and QT duration. The morphology of the QRS complexes was evaluated in the frontal plane leads for gross abnormalities. ECGs were evaluated by a Board-certified Veterinary Cardiologist.

Blood pressure (BP) using a noninvasive technique was recorded at approximately the same time as ECGs, and included HR, and systolic/diastolic BP.

The HR, PR interval, P wave duration, and QRS duration were within normal limits for all groups and there was no significant difference noted between groups at the different time points. The QT interval was within normal limits for all groups and all time points. Prestudy HR was significantly lower in the high dose group compared to all other groups and was considered an incidental finding. No arrhythmias were noted in the different groups at the different time points.

Nonclinical Absorption, Distribution, Metabolism and Excretion Studies (i) Drug Transporter Effects The tartrate salt of the compound of structure (I) was tested in a bidirectional cell permeability assay using confluent monolayer of Caco-2 cells in a 96-well based format. Fenoterol, Propranolol, and Digoxin were used as controls. The efflux ratio (mean apparent permeability [Papp] A to B/mean Papp B to A) for a tartrate salt of the compound of structure (I) was determined to be 1.49. Although mass recovery was low, this data suggests that the compound of structure (I) is not a substrate for P-glycoprotein and is a compound of moderate permeability.

(ii) CYP450 Effects

A tartrate salt of the compound of structure (I) was evaluated for the inhibition of human cytochrome P450 (CYP) isozymes using human liver microsomes in the presence of NADPH. At 10 µM, a tartrate salt of the compound of structure (I) inhibited the activity of only isoform 2C19 by more than 50% out of the isozymes selected for testing. The $IC_{50}$ values were determined against all the CYP isozymes used in the panel and, consistent with the percent inhibition data, only 2C19 was inhibited at a concentration lower than 10 µM ($IC_{50}$ 4.4 µM).

(iii) Liver Microsome Stability Studies

The stability of a tartrate salt of the compound of structure (I) in the presence of isolated microsomes from 3 species (human, rat and dog) were determined. The concentration of a tartrate salt of the compound of structure (I) was measured by liquid chromatography-tandem mass spectrometry (LC-MS/MS) with reference to a standard curve. The $t_{1/2}$ of a tartrate salt of a compound of structure (I) ranged from 4.3 minutes in humans to 4.9 minutes in dogs.

(iv) Serum Albumin Binding

The serum albumin binding levels for the compound of a tartrate salt of compound of structure (I) were determined using human plasma in a dialysis plate-based assay. The free fraction of a tartrate salt of the compound of structure (I) was measured by LC-MS/MS, by reference to a standard curve, and warfarin was used as a control. Data showed that the compound of structure (I) has moderate human serum albumin binding (7% unbound). Recovery of protein bound drug (80.3%) indicated the binding was reversible.

(v) pKa of the Compound of Structure (I)

The pKa values for a tartrate salt of the compound of structure (I) were determined by titration using ultraviolet metric detection. The pKa was determined in aqueous buffer and separately in the presence of 2 cosolvents (80% methanol and 60% DMSO). The final pKa values were calculated as an average of the 3 values obtained under different solvent conditions with the exception of pKa 3, for which the pKa value determined in DMSO was excluded. The final pKa values for pKa1, pKa2, and pKa3 were 3.02, 3.96, and 7.81, respectively.

(vi) pH-Dependent Solubility of the Compound of Structure (I)

The equilibrium solubility of the compound of structure (I) tartrate was determined in the following media: pH 3.5, 4.5, 5.5, 6.5 USP buffers, 0.1N HCl, SGF, fasted state simulated intestinal fluid, and fed state simulated intestinal fluid. As expected, based on the pKa determination, a tartrate salt of the compound of structure (I) showed greatest solubility in acidic media.

Animal Toxicology and Pharmacokinetics (i) 7-day Repeated Oral Dose Range-finding Study of the compound of structure (I) with Single and Repeated Dose PK in Rats A 7-day repeated oral dose range-finding study of a tartrate salt of the compound of structure (I) with single and repeated dose pharmacokinetics (PK) was performed in rats. Groups of 4 male and 4 female rats received 2, 4, or 8 mg/kg of a tartrate salt of the compound of structure (I) dissolved in 1% Tween 80/5% D-α-tocopherol polyethylene glycol 1000 succinate (TPGS)/water (v/v/v) by oral gavage once daily for 7 consecutive days followed by a 7-day observation period.

Analysis of all generated data, clinical observations, body weight, body weight changes, food consumption, clinical pathology evaluations, gross necropsy, and organ weights revealed that dose levels of a tartrate salt of the compound of structure (I) at 2 and 4 mg/kg/day administered orally once a day for 7 days were well tolerated in both males and female rats. The plasma levels and exposure (based on area under the plasma concentration curve [AUC] from time 0 to 12 hours ($AUC_{0-12}$) displayed a linear increase with dose following a single, 3 and 7 days of dosing at 2 and 4 mg/kg/day with higher exposures in females compared to males and plasma levels that did not change during treatment.

At a dose of 8 mg/kg, male rats tolerated the 7 day repeated doses of a tartrate salt of the compound of structure (I) well and plasma concentrations of a tartrate salt of the compound of structure (I) did not change during treatment. In contrast, female rats treated orally with a tartrate salt of the compound of structure (I) at 8 mg/kg/day showed treatment-related toxicity including decreased food consumption, weight loss, pallor, diarrhea, and melena. The most prominent hematological finding at the end of treatment was a reduction of white blood cells associated with severe neutropenia. The main findings in gross necropsy for the female rats that were moribund sacrificed on Day 8 were spleen enlargement, renal pallor, and bone marrow as well as reduction of abdominal fat and muscle mass (cachexia). Plasma concentrations of a tartrate salt of the compound of structure (I) in female rats at a dose of 8 mg/kg were higher compared to male rats and much higher on Day 7 compared to Day 3 indicative of a dose accumulation effect.

Pharmacokinetic studies of a tartrate salt of the compound of structure (I) revealed a rapid absorption with Tmax values similar, between male and female rats, across all doses and days of dosing, ranging from 0.5-2.0 hrs. The magnitude of the plasma AUC from time 0 to the time of the last concentration (AUC0-Tlast) displayed a gender bias, being approximately 1.5-2-fold higher in females compared to males, with the only exception being high dose females following 7 days of dosing where the AUC0-Tlast was 5.8-fold higher. Maximum observed plasma concentration (Cmax) and AUC0-Tlast dropped slightly with increasing days of dosing, with the exception of high dose females where AUC0-Tlast did not change from Day 1 to Day 3 and increased from Day 3 to Day 7 by approximately 2-fold. Following a single dose and 3 days of dosing the AUC0-12 increased in a linear fashion between doses for both male and female rats. On the seventh day of dosing, the relationship between increasing dose and AUC0-12 deviated from linearity in female rats, due to a larger than expected increase of the high dose AUC0-12 suggesting that there was dose accumulation of the compound of structure (I).

(ii) 28-Day Repeated Oral Dose Toxicity and Toxicokinetic Study of the Compound of Structure (I) in Rats The potential toxicity and toxicokinetics of a tartrate salt of the compound of structure (I) when administered orally to rats daily for 28 days was evaluated. Groups of 10 male and female rats received 0.5, 2, or 4 mg/kg/day of a tartrate salt of a compound of structure (I) dissolved in 1% Tween 80/5% TPGS/water (v/v/v) by oral gavage once daily for 28 consecutive days. A control group (10 males/10 females) was dosed with the vehicle only. The progression or regression of any effects were evaluated during an additional 14-day treatment-free period in the control group and in rats dosed at 2 and 4 mg/kg/day.

There were no treatment-related observations recorded during the 28 days of dosing or 14-day treatment-free period in the control group. Mean body weights and mean body weight gains of the male rats in the high dose group were significantly lower at the end of treatment; however, this was not observed in the females of this group.

The main finding of toxicological relevance in the hematology evaluations was a slight reduction of reticulocyte counts in the high dose group which may reflect reduced erythropoiesis. This finding appeared to be transient since reticulocyte counts in the high dose recovery group were comparable to the control group. Coagulation, serum chemistry, and urinalysis evaluations did not reveal any test item treatment-related findings.

The compound of structure (I) was rapidly absorbed following oral administration, with the majority of the $T_{max}$ values between 1-2 hrs in both males and females. There was no evidence of dose accumulation observed on Days 1, 15, and 28 of dosing. Females had higher $C_{max}$ values than males at all doses and on all days of dosing but there were no differences in the $T_{max}$ values and the higher $C_{max}$ values in females were not associated with differences in clinical, clinical pathology and anatomo-histopathological findings. The elimination half-life ($t_{1/2(e)}$), determined from the available data of dose groups of 2 and 4 mg/kg ranged from 2.3-8.9 hours and was similar in both genders. The compound of structure (I) exhibited a high volume of distribution suggesting for a large tissue distribution.

There were no gross findings of toxicological relevance observed in gross necropsy examinations performed at the end of treatment and recovery periods. The only finding of possible toxicological relevance in the organ weight evaluation was a lower weight of thyroid with parathyroids in male rats dosed with the test item; however, there were no abnormal findings in the histopathology of thyroid and parathyroids.

The abnormalities found in histopathology of the high dose rats included small acute hemorrhages in mesenteric lymph nodes in 5 animals and focal inflammatory infiltrates and/or focal lobular atrophy in pancreas of 3 control and 7 high dose animals. These findings were equivocal and it could not be determined whether they were related to test item treatment. While exposure to the test item had a dose-related effect on the body weight of male rats in the high dose group and was associated with a transient mild reduction in erythropoiesis in males and females, no underlying mechanism of action was apparent from the histopathology evaluations. Hematopoiesis evaluated in the spleen and bone marrow tissues were similar in the high dose and control groups.

Based on all data generated, including clinical observations, body weights, food consumption, ophthalmoscopy, clinical pathology, toxicokinetics, gross pathology and histopathology, the No Observed Adverse Effect Level (NO-ALL) of a tartrate salt of the compound of structure (I) following 28 days of repeated oral dosing in rats was determined to be 2 mg/kg/day.

(iii) Single Oral Dose and 7-Day Repeated Oral Dose Toxicity and Pharmacokinetic Study of the Compound of Structure (I) in Dogs This study established a dose level by a single oral dose (Part A) and determined the toxicity and PK of a tartrate salt of the compound of structure (I) (Part B) dissolved in 1% Tween 80 and 5% vitamin-E TPGS in water following 7 days of repeated oral dosing in Beagle dogs. Doses were administered via a stomach tube at a dose volume of 2 mL/kg after overnight fasting. Food was offered approximately 1 hour after dosing.

Three groups of dogs, each consisting of 1 male and 1 female, received a single compound of structure (I) (tartrate) dose of 0.25, 0.5, or 1 mg/kg and observed for 14 days (Part A). Salivation was observed in the high dose (1 mg/kg) male dog approximately 30 minutes postdose. Emesis was observed in the high dose female dog approximately 60 minutes postdose. All dogs completed the treatment period and survived the scheduled observation period. There were no other observations of toxicological relevance seen in hematology and serum chemistry evaluations.

In Part B of the study, 3 groups of dogs, each consisting of 2 males and 2 females, received a tartrate salt of the compound of structure (I) for 7 consecutive days at doses of 0.25, 0.75, or 1.25 mg/kg/day followed by 7-day observation period. A control group comprised of 1 male and 1 female received vehicle only.

All dogs completed the treatment and observation periods and survived to scheduled necropsy. Analysis of all generated data, including clinical observations, body weights, food consumption, clinical pathology, gross necropsy, and organ weights revealed no test article treatment-related significant toxicity in dogs that were treated orally with a tartrate salt of the compound of structure (I) up to 1.25 mg/kg/day for 7 days. Clinically, a tartrate salt of a compound of structure (I) caused emesis at the initial dose level of 0.25 mg/kg/day and up to 1.25 mg/kg/day.

Pharmacokinetic studies of a tartrate salt of the compound of structure (I) revealed a rapid absorption with $T_{max}$ values similar between male and female dogs, across all doses and days of dosing, ranging from 0.5-6.0 hours. The magnitude of the plasma $AUC_{0-Tlast}$ did not display a gender bias. Oral $t_{(1/2)e}$ and mean residence time (MRT) values were slightly longer following 7 days of dosing. The $AUC_{0-Tlast}$ increased linearly with dose across genders and following a single and 7 days of dosing. At the doses employed, there was little evidence of dose accumulation for the compound of structure (I) in Beagle dogs following 7 days of repeated dosing.

(iv) Seven-Day, Three Times Per Day, Repeated Oral Dose Toxicity and Pharmacokinetic Study of the Compound of Structure (I) in Dogs This study evaluated the toxicity and pharmacokinetics of a tartrate salt of the compound of structure (I) following 7 days of 3 times a day, repeated oral dosing in dogs. This study was performed following the 7-day repeat dose, once a day repeat dose study to support the determination of the MTD of a tartrate salt of the compound of structure (I) in dogs.

To achieve sufficient systemic exposure at the high dose levels, 2 groups of 2 females were dosed with a tartrate salt of the compound of structure (I) incorporated in gelatin capsules at dose levels of 3 or 6 mg/kg/day (1 or 2 mg/kg/dose).

In the 3 mg/kg/day dose group, both dogs had emesis on most of the dosing days with the vomiting time ranging from approximately 15 minutes to 2 or 6 hours postdose. Soft feces or diarrhea was observed from Days 3 or 7 to 14. One of the dogs had a 1.1 kg body weight loss over the 7-day treatment period and started to regain body weight, gaining 400 g, during the 7-day recovery period. The other dog gained 300 and 600 grams body weight over the 7 and 14-day periods, respectively.

Both dogs in the 6 mg/kg/day (2 mg/kg/dose x 3 days) dose group, showed various signs of toxicity early in the treatment phase. The severity of the clinical signs increased, and the health condition of the dogs deteriorated after each subsequent dose. The clinical signs mostly consisted of vomiting, diarrhea, emaciation, anorexia, dehydration, apathy, and weight loss. Due to deteriorating health, the 2 dogs in this group were dosed only twice a day on Day 4 and dosing was skipped on Days 5 and 6, but the dogs were dosed for the PK evaluation on Day 7. After the end of treatment, the condition of animals continued to deteriorate, and their condition did not improve despite support with fluid therapy provided on Day 9. One dog was found dead the morning of Day 10 and the second dog was euthanized in moribund condition that same day.

Clinical pathology results in the dogs dosed at 6 mg/kg/day, on Day 8, showed slight increases in white blood cells (WBCs), red blood cells (RBCs) and neutrophils; increased hematocrit and hemoglobin values; and decreased reticulocyte counts in one of the dogs. In the other dog, there were increases in WBCs, RBCs, neutrophils, monocytes, and basophils; increased hematocrit and hemoglobin values; and decreased reticulocyte counts and platelets. In the dogs dosed at 3 mg/kg/day, on Day 8, all hematology parameters were within the normal ranges for of the dogs. In the second dog there was a slight increase in RBC count; increased hematocrit and hemoglobin values; and reticulocyte count, although within the normal range, was decreased compared to the pretreatment count.

On Day 14, hematology results were within the normal reference ranges with exception of a slight increase in reticulocyte counts in 1 of the dogs of this group. The only serum chemistry parameters that were affected in the dogs dosed at 3 mg/kg/day were elevated ALT (almost twice the normal upper limit) in 1 of the dogs and elevated triglycerides in both dogs.

Pharmacokinetic analysis revealed that the plasma exposure to a tartrate salt of the compound of structure (I) as measured by AUC from time 0 to infinity ($AUC_{0\text{-}inf}$) was not dose proportional and higher on Day 7 compared to Day 1 following the third dosing, and even more so for the 6 mg/kg/day dose compared to the 3 mg/kg/day dose. These observations were made despite the vomiting that occurred and a partial cessation of dosing at the 6 mg/kg/day dose, suggesting that there may be a tendency for dose-accumulation following consecutive days of dosing. $C_{max}$ values were minimally impacted while $T_{max}$ values were longer at the 6 mg/kg/day dose. Both the $t_{(1/2)e}$ and MRT values were slightly longer with increased days of dosing suggesting a change in the clearance mechanisms for the compound of structure (I) with consecutive days of dosing.

Necropsy was performed on the dogs that were unscheduled sacrificed and found dead on Day 10. At necropsy, cachexia and dark yellowish and watery lower intestinal contents were observed in 1 dog. In the other dog, cachexia, hyperemia of the glandular portion of the stomach; hemorrhagic lower intestines and rectum; dark reddish black color of lower intestinal contents; and hyperemia in the cortex and medulla of the kidneys were observed.

The MTD of a tartrate salt of the compound of structure (I) was reached following dosing of 1 mg/kg/dose 3 times per day (3 mg/kg/day) and the dogs recovered well within 1 week of cessation of treatment.

(v) 28-Day Repeated Oral Dose Toxicity Study of the Compound of Structure (I) in Beagle Dogs Followed by a 14-Day Recovery Period This study examined the potential toxicity and toxicokinetics of a tartrate salt of the compound of structure (I) when administered orally to dogs for 28 consecutive days. The progression or regression of any effects following a 14-day treatment-free recovery period was also assessed. Two groups of dogs (3 males/3 females) were dosed with a tartrate salt of the compound of structure (I) incorporated in gelatin capsules at the following dose levels: 0.1, 0.5 mg/kg/day for 28 days and another group was dosed at 1 mg/kg/day for the first 14 days, followed by 2 mg/kg/day for the remaining 14 days of the treatment period. A control group of dogs was included in the study and was dosed with empty gelatin capsules.

All dogs completed the 28-day treatment period and survived until scheduled termination for necropsy. Clinical signs noted in the high-dose group during the treatment period included vomition, salivation, diarrhea, and/or soft feces. Vomition affected all dogs in the high-dose group and was observed in some dogs in the mid-dose group. Reduced food consumption was observed in 1 male and 1 female; whereas weight loss was observed in 1 out of 5 males and 2 out of 5 females in the high-dose groups during Weeks 3 and/or 4 of treatment and following the dose increase from 1 mg/kg to 2 mg/kg. These signs were not observed at the end of the recovery period.

There were no ophthalmoscopy findings at the end of treatment in any of the animals. Evaluation of clinical pathology data (hematology, coagulation, serum chemistry, and urinalysis) did not reveal any findings clearly attributable to the test item. The compound of structure (I) resulted in a dose-dependent increase in plasma concentrations. The compound of structure (I) was quantified in some plasma samples following dosing at 0.1 mg/kg, however most plasma concentrations were below the lower limit of quantitation (0.2 ng/mL). The dose proportionality and linearity of plasma concentrations of the compound of structure (I) following oral dosing could not be well characterized given the low plasma levels at the lowest dose. However, a comparison of the mid and high doses suggests that plasma concentrations in male and female dogs increased approximately in a dose proportional manner. At both the mid and high doses, all predose levels of the compound of structure (I) were below the limit of quantification and for the high dose, the elimination half-lives were similar on all days of dosing, suggesting a lack of dose accumulation. The analysis of toxicokinetic data revealed a high clearance of the compound of structure (I) in plasma that was caused from a large volume of distribution suggesting that a tartrate salt of the compound of structure (I) was well distributed in tissues.

Gross pathology findings observed in a few animals in the high-dose group included hemorrhage in colon of 3 animals and cecum of 1 animal, as well as hyperemia in the pylorus in 1 dog and hyperemia in the rectum in another dog. The hemorrhages were likely agonal, but might indicate recent injury to the mucosa. No gross findings were observed in recovery animals in the high- and mid-dose groups.

There were no apparent differences in absolute and relative organ weights between the control group and test item groups (both genders) with the exception of a few incidental significant differences: higher mean weights of thyroids with parathyroids in the low-dose males and an increase in the mean weights for uterus sizes in Group 4 females, due to physiological luteal phase with endometrial hypertrophy.

Histopathological findings of possible toxicological significance included changes in the thymus and the lower gastrointestinal tract tissues:

Thymic atrophy was found at the end of the treatment period in 3 out of 6 high-dose animals, 3 out of 6 mid-dose animals, 1 out of 6 low-dose animals, and 1 out of 6 control animals. This finding was also noted in 2 of 4 dogs in both the high- and mid-dose groups at the end of the recovery period. Thymic atrophy is a physiological response to stress and an expected finding in young dogs around the onset of sexual maturity, so these findings are considered to be nonspecific and indirectly related to the treatment-associated gastrointestinal effects.

Minimal or mild degree of mucosal injury and inflammation in the small intestine were observed at the end of the treatment period in 1 mid-dose dog, 4 high-dose dogs, and 1 dog in the control group. At the end of the recovery period, 1 control dog, 1 mid-dose dog, and 2 high-dose dogs had similar mild residual changes. The small intestinal mucosal injury associated with the high-dose regimen was considered to have returned to background level at the end of the 14-day recovery period.

At the end of the treatment period, minimal or mild degree of mucosal injury and inflammation in the colonic mucosa was observed histologically in four animals in the high-dose group. These responses were characterized by increased amounts of cell debris in a few glands, associated with patchy neutrophil infiltrates, or focal areas of hemorrhage in the lamina propria. One control animal also had minimal injury to colonic glands without inflammation or hemorrhage. Similar findings were not observed in the large intestines in any of the animals of the mid-dose group. Minimal degeneration of the colon mucosal glands was observed at the end of the recovery period in one high-dose dog.

Evaluation of clinical observations, body weight assessment, food consumption, ophthalmology, ECGs, clinical pathology, gross necropsy, and organ weights did not reveal any findings of clinical or toxicological relevance in dogs dosed at 0.1 mg/kg/day. With the exception of vomiting, no other adverse findings of toxicological significance were found in dogs dosed with a tartrate salt of the compound of structure (I) at 0.5 mg/kg/day. Emetogenic effect is a common finding observed in dogs dosed with kinase inhibitor drugs and could be attributed in part to a higher susceptibility of this species toward this class of drugs.

Administration of a tartrate salt of a compound of structure (I) at a dose of 1 mg/kg/day for 14 days, followed by 2 mg/kg/day for 14 days was, for the most part, well tolerated by young male and female Beagle dogs used in this study. Emesis was the most obvious adverse effect occurring in this dose group and was more pronounced upon the dose increase to 2 mg/kg. Other clinical signs, including salivation, diarrhea or soft feces and reduction of body weight gains, were observed during the third and/or fourth weeks of treatment. Upon the ceasing of treatment, there were no clinical signs observed in the recovery animals. Histopathological findings indicated that the potential target organs of toxicity were the lower gastrointestinal tract and thymus. Upon completion of the treatment period, there were no clinical signs or histopathological findings observed in the recovery animals with the exception of thymic atrophy which was considered to be a stress-related nonspecific response and may have occurred during the treatment phase.

Example 48: A Phase 1a/1b Dose-Escalation, Safety, Pharmacodynamic Study in Patients with Advanced Solid Tumor This study enrolls a sufficient number of patients to establish the maximum tolerated dose (MTD) of a tartrate salt of a compound of structure (I) (approximately 40 patients) in the Phase 1a part of the study, and then up to 100 additional patients in the Phase 1b part (Expansion at the MTD and Biopsy Cohorts). Enrolled patients receive the study drug disclosed herein administered once daily for the first 21 out of 28 days. Patients who successfully complete a 4-week treatment cycle without evidence of significant treatment-related toxicity or progressive disease continue to receive treatment with the same dose and dosing schedule.

This study determines MTD and DLTs of oral, daily administration of the study drug for the first 21 days every 4 weeks, over a range of doses in patients with advanced solid tumors, establishing pharmacokinetics of the oral administration, and/or observing patients for antitumor activities of the study drug by objective radiographic assessment. For example, pharmacodynamics of the therapy include assessing biomarkers in tumor tissues, in peripheral blood mononuclear cells (PBMCs), plasma, and serum and determining in vivo markers of AXL deregulation (in patients treated at the MTD) by: evaluating tumor biopsies in patients with easily accessible, low-risk tumors (as defined by local interventional radiology), and/or assessing immune function and/or response using immunohistochemistry (IHC), flow cytometry, or other molecular methodologies.

Study Drug

The compound of structure (I) is a novel oral inhibitor that targets AXL kinase and reverses the mesenchymal phenotype associated with advanced cancers. Preclinical studies have shown promising antitumor activity of compound of structure (I) as a single agent against a variety of tumor types in both in vitro and in vivo studies. This first-in-human Phase 1a/1b study with the compound of structure (I) is conducted in patients with refractory solid tumors. The Phase 1a study is designed to identify the maximum tolerated dose (MTD) and to identify the safety profile and Recommended Phase 2 Dose (RP2D) of compound of structure (I). Once the MTD has been established, 5 additional cohorts of up to 20 patients each with specific tumor types (up to 100 additional patients total) are enrolled at the MTD in the Phase 1b study. Data collected from patients enrolled in each of these additional cohorts is used to confirm safety, explore potential biomarkers, and evaluate potential signals of activity when compound of structure (I) is administered to specific groups of heavily pretreated patients or given in combination with immunotherapy or a tyrosine kinase inhibitor (TKI). Compound of structure (I) is administered once a day, orally, for 21 days followed by a 7-day drug free period. In some instances, the 28-day cycle is repeated if the patient continues to show benefit and if compound of structure (I) is reasonably well tolerated.

Two drug substances are investigated in this clinical studies, a mono-tartrate salt of the compound of structure (I) and a di-tartrate salt of the compound of structure (I) (Form A; "study drug"). Results from additional development work on the compound of structure (I) drug substance including testing multiple tartrate salt polymorph forms for solubility, stability, reproducibility upon preparation and other physical attributes, as well as toxicology and pharmacokinetics (see Examples 23-27), the di-tartrate form of the drug substance, Form A, has been selected for further clinical use ("study drug"). The polymorph forms tested all exhibited similar solubility, toxicity, and pharmacokinetics characteristics compared to the drug substance used in the former clinical form of the compound of structure (I) (Form B). The di-tartrate salt form of the compound of structure (I) that was selected was based on reproducibility compared to the current clinical form.

A summary of important chemical characteristics of both drug substance forms is presented in Table 18.

TABLE 18

Nomenclature and Notable Chemical Characteristics of Clinical Drug Substance Forms (Form B and Form A)

| Chemical Characteristic | Clinical Drug Substance (Form B) | Clinical Drug Substance (Form A) ("study drug") (free base:tartaric acid ratio of 1:2) |
|---|---|---|
| Chemical Name (IUPAC) | {[5-chloro-2-({4-[{4-methylpiperazin-1-yl)methyl]phenyl} amino)pyrimidin-4-yl]aminol-N,N-dimethylbenzene-1-sulfonamide mono-tartrate salt | {[5-chloro-2-({4-[{4-methylpiperazin-1-yl)methyl]phenyl} amino)pyrimidin-4-yl]amino}-N,N-dimethylbenzene-1-sulfonamide di-(L)-tartrate salt |
| Description | White to off-white powder | Off-white to yellow- to brown-colored powder |
| Chemical Formula | $C_{28}H_{36}ClN_7O_8S$ | $C_{32}H_{42}ClN_7O_{14}S$ |
| Molecular Weight | 666.15 Daltons | 816.23 Daltons |
| Structural Formula | | |

The study drug is supplied in oral form as a powder in hard gelatin capsules (size #3 for the 1-, 4-, 16-, and 25-mg doses; size #0 for the 100-mg dose) and is manufactured under current Good Manufacturing Practices (cGMP) for investigational use.

Study drug capsules are formulated in 1-mg, 4-mg, 16-mg, 25-mg, and 100 mg strengths and are packaged into round high-density polyethylene bottles with polyester coils as headspace fillers. Bottles are then heat-sealed, fitted with child-resistant caps, and placed in low-density polyethylene bags as secondary packaging.

Clinical Results

Pharmacokinetic data from 9 patients treated at the first 3 dose levels using Form B of the compound of structure (I) demonstrated higher $C_{max}$ and AUC of compound of structure (I) on Day 21 versus Day 1 during Cycle 1, suggesting study drug accumulation. In addition, compound of structure (I) was detectable predose on Day 21 in 8 out of 9 patients. In order to further characterize the predose levels of compound of structure (I), additional PK samples are collected predose on Days 8 and 15 of Cycle 1; Days 1, 8, 15, and 21 of Cycle 2; and Day 1 of Cycle 3.

Data has been collected to support the target level of the compound of structure (I). Currently, dosing is based on a standard mg/m² approach. Alternatively, flat dosing can be used. There may be less interpatient variability in drug exposure when utilizing flat dosing versus BSA-dependent dosing. Flat dosing starts at the MTD. An average dose is calculated based on the dose administered in the MTD expansion safety cohort.

Preclinical studies suggest that bone marrow, gastrointestinal tract, and the thymus may be potential target organs of toxicity. In the rat, reticulocyte counts were reduced; however, these findings were not observed in the dog. In the dog, minimal to mild injury to the mucosal lining as well as inflammation was noted in the small intestines and colonic mucosa. Thymic atrophy was also noted in the dog. With the exception of vomiting, no other adverse effects of significance were observed in the dog. The preclinical GLP toxicology studies suggest that the observed toxicities were reversible following a recovery period of 14 days with the exception of thymic atrophy.

Patients over 7 different dose cohorts (See, e.g., Table 19 below) had been treated with a tartrate salt of compound of structure (I) in this study (Form B). No dose-limiting toxicities (DLTs) had been reported. National Cancer Institute Common Terminology Criteria for Adverse Events (CT-CAE) Grade 3 and 4 events that occurred in one patient each included anemia, hypocalcemia, hypokalemia, hyponatremia, pleural effusion, urinary tract infection, ascites, hyperkalemia, hypertension, bacterial peritonitis, sciatica, and syncope. None of these events was considered study drug-related. The most common Grade 1 and 2 AEs (ie, those that occurred in ≥3 patients each [13%]) included nausea, vomiting, fatigue, anemia, diarrhea, hypoalbuminemia, decreased appetite, hypomagnesemia, tachycardia, and thrombocytopenia. Grade 1 and 2 AEs that occurred in ≥3 patients each (13%) and judged as at least Possibly related to the compound of structure (I) included diarrhea, nausea, vomiting, dysgeusia, and thrombocytopenia. There were no serious AEs or deaths on study that were considered related to study drug.

TABLE 19

Patients on study with stable disease at least 4 cycles

| Cohort | Dose | Subject | Histology | # cycles | Best Response |
|---|---|---|---|---|---|
| 1 | 1.5 mg/m² | 102 | Breast Carcinoma (ER+/−HER2−) | 8 | SD |
| 2 | 3 mg/m² | 104 | Neuroendocrine carcinoma | 12 | SD |
| 3 | 6 mg/m² | 108 | Prostate adenocarcinoma | 8 | SD |

TABLE 19-continued

Patients on study with stable disease at least 4 cycles

| Cohort | Dose | Subject | Histology | # cycles | Best Response |
|---|---|---|---|---|---|
| 4 | 9 mg/m² | 109 | Colon adenocarcinoma (KRAS mutant) | 6 | SD |
| 4 | 9 mg/m² | 110 | Melanoma (BRAF wildtype) | 4 | PR |
| 4 | 9 mg/m² | 203 | Cholangiocarcinoma | 4 | SD |
| 5 | 12 mg/m² | 111 | Uterine carcinoma | 6 | SD |
| 5 | 12 mg/m² | 204 | Pancreatic | 8 | SD |
| 7 | 21 mg/m² | 115 | NSCLC | 7 (ongoing) | |

No dose-limiting toxicities (DLTs) had been reported. National Cancer Institute Common Terminology Criteria for Adverse Events (CTCAE) Grade 3 and 4 events that occurred in one patient each included anemia, hypocalcemia, hypokalemia, hyponatremia, pleural effusion, urinary tract infection, ascites, hyperkalemia, hypertension, bacterial peritonitis, sciatica, and syncope. None of these events was considered study drug-related. The most common Grade 1 and 2 AEs (i.e., those that occurred in ≥3 patients each [13%]) included nausea, vomiting, fatigue, anemia, diarrhea, hypoalbuminemia, decreased appetite, hypomagnesemia, tachycardia, and thrombocytopenia. Grade 1 and 2 AEs that occurred in ≥3 patients each (13%) and judged as at least possibly related to compound of structure (I) included diarrhea, nausea, vomiting, dysgeusia, and thrombocytopenia. There were no serious AEs or deaths on study that were considered related to study drug.

Study Design

This is a Phase 1a/1b, open-label, dose-escalation, safety, pharmacokinetics, and pharmacodynamic study.

(i) Phase 1a—Dose Escalation

The starting drug dose is 1.5 mg/m2 for 21 out of 28 days using a standard 3+3 design. Sequential cohorts of three (3) patients are treated with escalated doses until the MTD is established. In the absence of dose-limiting toxicities (DLTs), the dose is increased using a modified Fibonacci dose escalation scheme.

If a patient experiences a DLT, up to three additional patients is treated at that dose level. If no additional DLTs are observed in the expanded six-patient cohort, the dose is escalated in a new cohort of three patients. If two or more patients at a given dose level experience a DLT during the first cycle, then the MTD have been exceeded and up to a total of six patients will be treated at the previous lower dose level. If 0 or 1 of 6 patients experiences a DLT at this previous lower dose level, this dose is declared the MTD.

(ii) Phase 1b—Expansion at MTD and Biopsy Cohorts

Once the MTD has been established, 5 additional cohorts of up to 20 patients each with specific tumor types (up to 100 additional patients total) are enrolled at the MTD. Data collected from patients enrolled in each of these additional cohorts is used to confirm safety, explore potential biomarkers, and evaluate potential signals of activity when the drug is administered to specific groups of heavily pretreated patients or given in combination with immunotherapy or a tyrosine kinase inhibitor (TKI). Ten patients in each of these 5 Expansion Cohorts are required to consent to undergo pre- and post-dose tumor biopsies. All patients who undergo these biopsies comprise the 'Biopsy Cohorts'.

Patients may continue to receive study drug in 28-day cycles at the same dose given during Cycle 1 until they experience unacceptable toxicity or unequivocal disease progression. No intra-patient escalation of the study drug dose is permitted. Once the MTD has been established, dosing changes from BSA-dependent to a flat dose based on the average of the dose administered in the MTD expansion safety cohort.

Patient Populations (i) Phase 1a—Dose Escalation Patients with histologically confirmed solid tumors who have shown disease progression after receiving standard/approved chemotherapy or for whom there is no curative therapy.

(ii) Phase 1b—Expansion at MTD and Biopsy Cohorts

Given the fact that AXL is widely distributed in a variety of solid malignancies, the dose expansion phase of this study at the MTD includes five cohorts of specific patient tumor types to further assess the safety and uncover possible signals of efficacy when the study drug is administered as a single agent in groups of heavily pretreated patients or in combination regimens in patients with immunotherapy-resistant tumors or EGFR⁺ NSCLC.

a. Patients with tumors that have progressed after achieving a best documented response of at least stable disease (ie, SD, PR, or CR documented per iRECIST) following at least 2 cycles (8 weeks) of immunotherapy and are felt to be appropriate for this type of treatment.* b. Patients with EGFR+non-small cell lung cancer (NSCLC) who have demonstrated recent progression following a best documented response of at least stable disease (ie, SD, PR, or CR documented per RECIST v1.1) on ≤2 lines of oral TKIs and are felt to be appropriate for this type of treatment.* Prior chemotherapy±immunotherapy is allowed as long as the patient is clearly demonstrating current progression on an EGER TKI.

c. Patients with BRAF-, KRAS-, or NR AS-mutated colorectal carcinoma (CRC) for whom there is no standard therapy remaining.

d. Patients with persistent/recurrent ovarian cancer who would be platinum refractory/resistant and have had any number of lines of prior therapy, e. Patients with BRAF-mutated melanoma who have progressed on either immunotherapy or a combination BRAF/MEK inhibitor.

* Patients with immunotherapy-resistant tumors or EGFR+NSCLC who are enrolled in these expansion cohorts continue treatment with their previous immunotherapy or TKI regimens, respectively, and add study drug. The rationale is based on preclinical data that has shown that the combination is superior in patients who have progressed on prior immunotherapy or a TKI.

Inclusion Criteria:

To be eligible for participation in the study, patients must meet all of the following inclusion criteria:

1. Patients enrolled in the Phase 1a study must:

a. Have a histologically confirmed diagnosis of advanced metastatic or progressive solid tumor.

b. Be refractory to, or intolerant of, established therapy known to provide clinical benefit for their condition.

2. Patients enrolled in the Phase 1b study must meet criteria for one of the following tumor types:
   a. Have tumors that have progressed after achieving a best documented response of at least stable disease (ie, SD, PR, or CR documented per iRECIST) following at least 2 cycles (8 weeks) of immunotherapy and are felt to be appropriate for this type of treatment.
   b. Have EGFR+NSCLC and have demonstrated recent progression following a best documented response of at least stable disease (ie, SD, PR, or CR documented per RECIST v1.1) on ≤2 lines of oral TKIs and are felt to be appropriate for this type of treatment. Prior chemotherapy±immunotherapy is allowed as long as the patient is clearly demonstrating current progression on an EGER TKI.
   c. Have BRAF-, KRAS-, or NR AS-mutated CRC for whom there is no standard therapy remaining.
   d. Have persistent/recurrent ovarian cancer who would be platinum refractory/resistant and have had any number of lines of prior therapy.
   e. Have BRAF-mutated melanoma that has not responded to immunotherapy or a combination BRAF/MEK inhibitor
3. Have one or more tumors measurable or evaluable as outlined by modified RECIST v1.1 or iRECIST
4. Have an Eastern Cooperative Oncology Group (ECOG) (World Health Organization [WHO]) performance of ≤1
5. Have a life expectancy ≥3 months
6. Be ≥18 years of age
7. Have a negative pregnancy test (if female of childbearing potential)
8. Have acceptable liver function:
   a. Bilirubin ≤1.5× upper limit of normal (ULN). Patients receiving immunotherapy should have a bilirubin level ≤3.0×ULN.
   b. Aspartate aminotransferase (AST/SGOT), alanine aminotransferase (ALT/SGPT) and alkaline phosphatase ≤2.5× upper limit of normal (ULN). If liver metastases are present, then ≤5×ULN is allowed. Patients receiving immunotherapy should have AST and ALT levels ≤5.0×ULN.
9. Have acceptable renal function:
   a. Calculated creatinine clearance ≥30 mL/min
10. Have acceptable hematologic status:
   a. Granulocyte ≥1500 cells/mm3
   b. Platelet count ≥100,000 (plt/mm3)
   c. Hemoglobin ≥9 g/dL
11. Have no clinically significant abnormalities on urinalysis
12. Have acceptable coagulation status:
   a. Prothrombin time (PT) within 1.5× normal limits
   b. Activated partial thromboplastin time (aPTT) within 1.5× normal limits
13. Be nonfertile or agree to use an adequate method of contraception. Sexually active patients and their partners must use an effective method of contraception (hormonal or barrier method of birth control; or abstinence) prior to study entry and for the duration of study participation and for at least 30 days after the last study drug dose (see Section 4.6.3). Should a woman become pregnant or suspect she is pregnant while participating in this study, she should inform her treating physician immediately.
14. Have read and signed the IRB-approved informed consent form prior to any study related procedure. (In the event that the patient is re-screened for study participation or a protocol amendment alters the care of an ongoing patient, a new informed consent form must be signed.)
15. Patients enrolled in each of the five Expansion Cohorts must be willing to consider pre-study and on-study biopsies, if safe and medically feasible, as determined by local interventional radiology (3 to 5 core samples requested at each biopsy timepoint).

Exclusion Criteria:

Patients meeting any one of these exclusion criteria will be prohibited from participating in this study:
1. Have New York Heart Association (NYHA) Class III or IV, cardiac disease, myocardial infarction within the past 6 months prior to Day 1, unstable arrhythmia, or evidence of ischemia on electrocardiogram (ECG) or during Cardiac Stress Testing within 14 days prior to Day 1.
2. Have a corrected QT interval (QTcF, Fridericia's method) of >450 msec in men and >470 msec in women
3. Have a seizure disorders requiring anticonvulsant therapy
4. Presence of symptomatic central nervous system metastatic disease or disease that requires local therapy such as radiotherapy, surgery, or increasing dose of steroids within 2 weeks prior to Day 1
5. Have severe chronic obstructive pulmonary disease with hypoxemia (defined as resting O2 saturation of ≤88% breathing room air)
6. Have undergone major surgery, other than diagnostic surgery, within 2 weeks prior to Day 1
7. Have active, uncontrolled bacterial, viral, or fungal infections, requiring systemic therapy
8. Are pregnant or nursing
9. Received treatment with radiation therapy, surgery, chemotherapy, or investigational therapy within 28 days or 5 half lives, whichever occurs first, prior to study entry (6 weeks for nitrosoureas or Mitomycin C)
   a. This exclusion criterion is not applicable for patients with EGFR+NSCLC or immunotherapy-resistant tumors who are enrolled in expansion cohorts at the MTD.
10. Are unwilling or unable to comply with procedures required in this protocol
11. Have known infection with human immunodeficiency virus (HIV), hepatitis B, or hepatitis C. Patients with history of chronic hepatitis that is currently not active are eligible
12. Have a serious nonmalignant disease (eg, hydronephrosis, liver failure, or other conditions) that could compromise protocol objectives in the opinion of the investigator and/or the sponsor
13. Are currently receiving any other investigational agent
14. Have exhibited allergic reactions to a similar structural compound, biological agent, or formulation
15. Have undergone significant surgery to the gastrointestinal tract that could impair absorption or that could result in short bowel syndrome with diarrhea due to malabsorption
16. Have a history of severe adverse reaction (eg, hypersensitivity reaction, anaphylaxis) to sulfonamides
17. Patients scheduled to receive immunotherapy or TKI regimens plus the study drug must not be currently taking high-dose steroids (i.e., physiologic dose approximately equivalent to 15 mg/day of prednisone)

Study Assessments (Predose)

Screening/Baseline Period (within 14 Days Prior to First Dose)

The following activities and evaluations are performed within 14 days prior to administration of the first dose of study drug:
   Signed Informed Consent
   Collect and document a complete medical history including histologically confirmed diagnosis of advanced metastatic or progressive solid tumor and all other measures of disease and disease symptoms including extent of tumor burden, radiographic assessment, ie, computed tomography (CT) scan of the chest, abdomen, pelvis; appropriate tumor markers (e.g., PSA, CA19-9).

Perform a full physical examination including height (cm) and weight (kg)

Record vital signs (temperature, heart rate, systolic and diastolic blood pressures)

Assess Eastern Cooperative Oncology Group (ECOG) Performance Status (PS)

Perform a 12-lead electrocardiogram (ECG) including assessment of QTcF interval

Collect blood for evaluation of laboratory parameters:
  Hematology: complete blood count (CBC) with differential and platelet count
  Serum chemistries
  Coagulation status: prothrombin time (PT) and activated partial thromboplastin time (aPTT)

Collect urine sample for full urinalysis

Collect urine or serum sample for beta-human chorionic gonadotropin (β-hCG) pregnancy test for females of child-bearing potential Perform pre-dose tumor biopsies in those patients enrolled in the Biopsy Cohorts
  The "Biopsy Cohorts" include patients enrolled in the five expansion cohorts at the MTD who consent to undergo required pre- and post-dose tumor biopsies (3 to 5 core samples requested at each biopsy timepoint).

Record all concomitant medications including all prescription drugs, nonprescription drugs, and nutritional supplements within the past 14 days Within 72 Hours Prior to First Dose of Cycle 1

The following activities and evaluations are performed anytime within 72 hours prior to administration of the first dose (on Day 1) of study drug:

Perform a full physical examination including weight (kg) and calculation of BSA Collect blood for evaluation of laboratory parameters: Hematology and Serum chemistries Collect urine or serum sample for β-hCG pregnancy test for females of child-bearing potential Collect blood for PBMCs, plasma, and serum for biomarker assessments Obtain archived tumor tissue Record all concomitant medications including all prescription drugs, nonprescription drugs, and nutritional supplements Review all Inclusion/Exclusion criteria and determine if patient has met all eligibility criteria for inclusion into the study. Obtain Medical Monitor (or designee) approval to enroll patient.

Study Treatment

The dosage of study drug (tartrate salt) is recalculated at the beginning of each new treatment cycle to reflect changes in the body surface area (BSA) that may have occurred but will remain the same for all treatments within a treatment cycle. The dose is rounded down in the event the calculated number is <0.5 to the nearest achievable dose based on the amount of study drug in the capsules. The dose is rounded up to the next level if the calculated dose is ≥0.5 to the nearest achievable dose based on available capsule strength. Patient doses are only adjusted if there is a ≥10% increase or decrease in body weight compared to baseline.

Once the MTD has been determined in the expansion safety cohort, study drug (di tartrate salt) is administered as a flat dose instead of according to BSA.

Study drug is administered orally once daily for 21 days followed by 7 drug free days (each cycle=28 days). Dosing may be repeated every cycle in the absence of disease progression or unacceptable toxicity. Study drug should be taken in the morning after an overnight fast with up to 200 mL or 7 fluid ounces of water at least 1 hour before ingesting any food or other medications.

Since PK and PD sampling is to be conducted during the first two cycles of treatment, every effort is made to ensure timely transition from Cycle 1 to Cycle 2 (i.e., no extended delays between the cycles).

Evaluation of the safety and efficacy of study drug in this study occurs in two phases: Phase 1a: Dose Escalation and Phase 1b: Expansion at MTD and Biopsy Cohorts Phase 1a (Dose Escalation): Three-Patient Cohorts The starting dose is 1.5 mg/m² for 21 out of 28 days in 3-patient cohorts using a standard 3+3 design. Once the first patient in each cohort has completed 14 days of dosing with no DLTs, the second and third patients are be enrolled simultaneously at the same dose. Once the last patient enrolled has completed Day 28 without observation of a DLT and the next higher the compound of structure (I) dose level has not yet been studied, the dose is increased following a modified Fibonacci dose escalation scheme in a new 3-patient cohort according to the dose levels provided in Table 20.

TABLE 20

Dose Escalation

| Dose Level | Proposed Daily Dose | Increment from Previous Dose[a] | No. of Patients Per Cohort |
| --- | --- | --- | --- |
| -1[b] | 1 mg/m² | -33% | 3-6 |
| 1 | 1.5 mg/m² | Starting Dose | 3-6 |
| 2 | 3 mg/m² | 100% | 3-6 |
| 3 | 6 mg/m² | 100% | 3-6 |
| 4 | 9 mg/m² | 50% | 3-6 |
| 5 | 12 mg/m² | 33% | 3-6 |
| 6 | 16 mg/m² | 33% | 3-6 |
| 7 | 21 mg/m² | 33% | 3-6 |
| 8 | 28 mg/m² | 33% | 3-6 |
| 9 | 37 mg/m² | 33% | 3-6 |
| 10 | 49 mg/m² | 33% | 3-6 |
| 11[c] | 65 mg/m² | 33% | 3-6 |

[a]It is possible for additional and/or intermediate dose levels to be added during the course of the study.
[b]Dose level -1 represents treatment doses for patients requiring a dose reduction from the starting dose level. It will also serve as a lower dose level if the Starting Dose level is initially associated with unexpected or unacceptable toxicity.
[c]If clinically indicated, dose levels higher than 65 mg/m² may be investigated.

If a DLT is observed in 1 of 3 patients at a given dose level, up to 3 additional patients are enrolled and treated at that dose level. When up to 3 additional patients are added to a given dose level, if only 1 out of those 6 patients experiences a DLT, the dose is increased to the next dose level. If ≥2 out of 3-6 patients at a dose level experience DLTs, the dose is decreased to the previous (lower) dose level and 3 additional patients will be enrolled at that dose level.

If 0 or 1 patient in any of the 6 patients experience a DLT, but the next higher dose level has already been studied, then the current dose is declared the MTD and the study advances to Phase 1b. The MTD is defined as the dose at which ≤1 of 6 patients experience a DLT during Cycle 1 with the next higher dose having at least 2 of 3-6 patients experiencing a DLT during Cycle 1.

Phase 1 b: Expansion at MTD and Biopsy Cohorts

Once the MTD has been established, 5 additional cohorts of up to 20 patients each (100 additional patients total) with the various disease characteristics listed below are enrolled and treated in the Phase 1b study. Study drug is administered as a flat dose instead of according to BSA. Data collected from patients enrolled in each of these additional cohorts is used to confirm safety, explore potential biomarkers, and evaluate potential signals of activity when study drug is administered to specific groups of heavily pretreated patients or given in combination with immunotherapy or a TKI. Ten patients in each of these 5 expansion cohorts are required to consent to undergo pre- and post-dose tumor biopsies. All patients who undergo these biopsies comprise the 'Biopsy Cohorts'. The five separate expansion cohorts enrolled and treated at the MTD are described in the Patient Population section above.

Management of Toxicides and Dosage Modification

Management of Toxicities

Adverse events may be treated with concomitant medications, as deemed clinically indicated by the Principal Investigator. All concomitant medications are recorded in the source and on the appropriate CRF.

Adverse events that are moderate to severe in intensity and considered Possibly, Probably, or Definitely related to study drug treatments may result in the termination of study treatment in the affected study patient. Such termination is reviewed with the Sponsor's Medical Monitor at the earliest possible time. Following review with the Sponsor's Medical Monitor, the study patient may be permanently withdrawn from the study depending upon the nature and severity of the event.

Dose-limiting Toxicides (DLT)

A DLT is defined as any one of the following events observed within Cycle 1 regardless of attribution unless clearly and incontrovertibly related to the underlying disease or extraneous causes (such as progressive disease):

Grade 3 or greater febrile neutropenia

Grade 4 absolute neutrophil count (ANC) for ≥7 consecutive days

Grade 4 thrombocytopenia or Grade 3 thrombocytopenia with clinically significant bleeding or that requires a platelet transfusion Grade 3 or 4 non-hematologic AEs including nausea, vomiting, diarrhea, and electrolyte imbalances persisting for more than 48 hours despite optimal medical management Dosing delays ≥2 weeks due to treatment emergent adverse events or related severe laboratory test values Dose Modifications The dose of study drug is not reduced during Cycle 1. Doses of study drug may be adjusted for patients who receive multiple cycles of study drug. Dose reductions by one dose level is permitted based on the observed toxicity that occurred during the preceding cycle. No dose re-escalations are allowed for any patient who had a previous dose reduction due to toxicity or delayed recovery. All dose modifications need to be discussed and approved with the medical monitor.

If a patient experiences toxicity, the patient may continue to receive study drug as defined in Table 21.

TABLE 21

Guide to Dose Adjustments Based on Toxicities

| Drug-Related AE | Action |
| --- | --- |
| Grade 1 | Current dose level |
| Grade 2 | Investigator's option to reduce dose by 1 dose level with agreement of the Medical Monitor |
| Grade 3* | Withhold, then reduce dose by 1 dose level upon recovery to ≤ Grade 1 with agreement of the Medical Monitor. |
| Grade 4 | Investigator and Medical Monitor review to determine if patient may continue on study with appropriate dose reduction upon recovery to ≤ Grade 1. |

*Excluding brief (based on the investigator's judgment) Grade 3 vomiting or diarrhea with suboptimal management. Dose reduction to the next lower dose level tested is performed initially. If further toxicities occur during one or more cycles at the new reduce dose level, no further reductions are permitted, and the patient should be discontinued from the study.

Patients who experience a DLT are required to discontinue study participation, unless the Investigators and Medical Monitor determine that it is in the best interest of the patient to continue with the dose reduction and only upon recovery of the toxicity to Grade 2 or better.

Dose reduction is required for patients who have a delay in treatment greater than 2 weeks due to a lack of recovery of any hematologic or nonhematologic toxicity, even if DLT criteria are not met. Subsequent retreatment of patients who are not able to be treated after a 2-week delay and who eventually recover is to be determined taking into account the potential benefit/risk for the individual patient. In addition, dose reductions are permitted for patients who have toxicities that do not meet the criteria of a DLT.

For patients enrolled in the Phase 1b study receiving combination therapy (i.e., previous immunotherapy or TKI regimens plus study drug), modification of their immunotherapy or TKI regimen follow each approved drug's full prescribing information.

Concomitant Medications and Therapies

Previous Therapies

Patients subject to the instant treatment may have undergone one or more previous therapies.

Concomitant Therapies

Concomitant therapies are any new or existing medications or therapy taken by the patient including:

Drugs, including but not limited to, prescription, over-the-counter, birth control pills/patches/hormonal devices, and homeopathic preparations Nondrug therapies, including but not limited to, thermal/laser/radiation procedures, vitamins, herbal medicines/supplements.

During the Screening process (up to 14 days prior to anticipated first dose of study drug), information on all concomitant therapies, medications, and procedures are recorded in the source documents and appropriate CRF along with the diagnosis or reason for use.

Once the patient receives the first dose of study drug, recording of concomitant therapies are limited to any new medication or modification of an existing medication taken for treatment of an adverse event (AE). These therapies are recorded in the source documents and appropriate CRF along with the diagnosis or reason for use. Those therapies used for the treatment of an adverse event are to be linked to an AE and documentation of the AE must also be completed.

Permitted Therapies

Concomitant medications necessary for the health and well-being of the patient and that do not interfere with study assessments are permitted during the study at the Investigator's discretion. This includes the use of appropriate medications for the treatment of AEs and/or concurrent illnesses under the direction of the Principal Investigator. All such therapies must be recorded in the source and on the appropriate CRF.

Treatment with hematopoietic colony stimulating growth factors such as granulocyte colony stimulating factor or granulocyte-macrophage colony stimulating factor is not initiated during Cycle 1 unless the patient has experienced a DLT. Initiation of treatment with erythroid-stimulating agents may not occur during the first cycle of therapy. If a patient has been on a steady dose of an erythroid-stimulating agent, they may continue to use the agent at the same dose during Cycle 1 and later cycles.

Patients receiving immunotherapy plus study drug may receive concomitant steroids for the treatment of immune response AEs at the investigator's discretion.

Prohibited Therapies

The following medications are excluded from concomitant use by all patients:
  Anticancer therapies (chemotherapy, radiation therapy, immunotherapy) within the month prior to the first study drug administration and during the cycle of study treatment. Patients with EGFR+NSCLC or immunotherapy-resistant tumors who are enrolled in the Phase 1b study continue treatment with their previous immunotherapy or TKI regimens, respectively, and add study drug.
  CYP2C19 Metabolizers: Patients receiving CYP2C19 metabolizers prior to study treatment should be monitored closely. If possible, the investigator should cease patient's treatment with a CYP2C19 substrate prior to first dose, or at a minimum, switch to an alternative, but equivalent treatment that is not a CYP2C19 metabolizer. If a patient must remain on a CYP2C19 metabolizer, treatment with study drug should proceed cautiously and the patient observed closely throughout the duration of the study.
  Patients must not be taking H2-receptor antagonists such as cimetidine, ranitidine, and famotidine, or any proton pump inhibitors such as omeprazole, lansoprazole, esomeprazole and pantoprazole. Patients must stop these medications within 7 days prior to starting treatment.

Birth Control Requirements for Fertile Patients

Sexually active patients and their partners must use an effective method of contraception associated with a low failure rate prior to study entry and for the duration of study participation and for 30 days after the last dose of study drug. The following are considered effective contraceptives: (1) oral contraceptive pill; (2) condom plus spermicide; (3) diaphragm plus spermicide; (4) abstinence; (5) patient or partner surgically sterile; (6) patient or partner more than 2 years post-menopausal; or (7) injectable or implantable agent/device.

Treatment Assessments (i) Cycle 1

Day 1 (and as Otherwise Indicated):
  Record vital signs (temperature, heart rate, systolic and diastolic blood pressures) prior to first dose
  Obtain baseline signs and symptoms prior to first dose
  Perform 12-lead ECG including assessment of QTcF interval:
    For Phase 1a patients: ECG time points to include just prior to first dose, at 0.5, 1, 2 hours (±10-minute window for each time point), and at 4 hours (±20-minute window) post dosing
    For Phase 1b patients: ECG time points for the first 3 patients enrolled in the immunotherapy-resistant and EGFR+NSCFC cohorts to include just prior to first dose; at 0.5, 1, and 2 hours (±10-minute window for each time point); and 4 hours (±20-minute window) post dosing.
    All other Phase 1b patients: Perform 12-lead ECG including assessment of QTcF interval pre-dose only
  Collect blood for PBMCs, plasma, and serum for assessments according to the schedule in Section 7.4
  Collect blood for analysis of PK parameters Daily on Days 1-21
  Instruct patients to take study drug orally every day on Days 1-21
  Instruct patients to record the date and time they took their dose in their dosing diary Weekly (Days 8, 15, 22 [±3 Days])

The following activities and evaluations are performed weekly (or as otherwise indicated) during Cycle 1:
  On Day 8 and 22, collect blood for PBMCs, plasma, and serum for biomarker assessments according to the schedule in Section 7.4
  Perform an abbreviated physical examination
  Record vital signs (temperature, heart rate, systolic and diastolic blood pressures)
  Collect blood for evaluation of laboratory parameters: Hematology; Serum chemistries
  On Days 8, 15, and 21, collect blood for analysis of PK parameters
  Assess for adverse events (AEs)
  Record all concomitant medications including all prescription drugs, nonprescription drugs, and nutritional supplements (ii) Cycle 2

Daily on Days 1-21
  Instruct patients to take study drug orally every day on Days 1-21
  Instruct patients to record the date and time they took their dose in their dosing diary Day 1

The following activities and evaluations are performed on Day 1 of Cycle 2:
  Perform a full physical examination including weight (kg) and calculation of BSA
  Assess ECOG PS
  Collect urine or serum sample for β-hCG pregnancy test for females of child-bearing potential
  Perform 12-lead ECG just prior to dosing including assessment of QTcF interval
  Collect blood for PBMCs, plasma, and serum for biomarker assessments
  Collect blood for analysis of PK parameters Weekly (Days 1, 8, 15, 22 [±3 Days])

The following activities and evaluations are performed weekly during Cycle 2:
  Abbreviated physical examination (Days 8, 15, 22)
  Record vital signs (temperature, heart rate, systolic and diastolic blood pressures)
  Collect blood for evaluation of laboratory parameters: Hematology; Serum chemistries
  On Days 8, 15, and 21, collect blood for analysis of PK parameters according to the schedule in Section 7.3

Assess for adverse events (AEs)
Record all concomitant medications including all prescription drugs, nonprescription drugs, and nutritional supplements
Day 28 (−4 Days):
Assess for response and tumor burden using RECIST v1.1 and iRECIST including appropriate tumor markers using same methods used at baseline
Perform post-dose tumor biopsies in those patients enrolled in the Biopsy Cohorts. Ideally, the biopsy should be obtained from the same general location as the pre dose biopsy, if feasible and safe, and from a metastatic lesion and not the primary tumor. Three to five (3 to 5) core samples are requested at each biopsy timepoint.

(iii) Cycles ≥3

Patients may continue to receive study drug in 28-day cycles at the same dose given during Cycle 1 until they experience unacceptable toxicity or unequivocal disease progression. Before proceeding with the next odd numbered cycle, response and tumor burden must be assessed and confirmed for continued response/clinical benefit.

Daily on Days 1-21
Instruct patients to take study drug orally every day on Days 1-21
Instruct patients to record the date and time they took their dose in their dosing diary
Day 1
The following activities and evaluations are performed on Day 1 of Cycle 3 and all subsequent cycles of treatment:
Perform a full physical examination including weight (kg) and calculation of BSA
Assess ECOG PS
Collect urine or serum sample for β-hCG pregnancy test for females of child-bearing potential
Perform 12-lead ECG just prior to dosing including assessment of QTcF interval (Cycle 3 only)
Collect blood for PBMCs, plasma, and serum for biomarker assessments
Collect blood for analysis of PK parameters (Cycle 3 only)
Days 1 and 15 (±3 Days)
The following activities and evaluations are performed every two weeks during Cycle 3 and all subsequent cycles of treatment:
Abbreviated physical examination (Day 15)
Record vital signs (temperature, heart rate, systolic and diastolic blood pressures)
Collect blood for evaluation of laboratory parameters: Hematology; Serum chemistries
Assess for adverse events (AEs)
Record all concomitant medications including all prescription drugs, nonprescription drugs, and nutritional supplements
Day 28 (−4 Days)
The he following activities and evaluations are performed on Day 28 (−4 days) of every EVEN cycle (ie, Cycle 4, Cycle 6, etc): Assess for response and tumor burden using RECIST v1.1 and iRECIST including appropriate tumor markers using same methods used at baseline.

Criteria for Evaluation
Safety Endpoints

Tolerance and toxicity of oral study drug are assessed through evaluation of physical examinations, vital signs, laboratory studies, solicited and unsolicited adverse events including DLTs, and all causes of mortality.

Incidence rates of treatment-emergent adverse events are summarized within study drug dose level at the MedDRA preferred term and primary system organ class levels. Similar summaries are made for subsets of AEs such as (1) those judged by a physician to be related to study treatment, and (2) serious adverse events (SAEs).

Other routine safety assessments (e.g., clinical laboratory parameters and vital signs) are summarized by study drug dose level using mean, standard deviation, median, minimum and maximum changes from baseline values.

Efficacy Endpoints

Any objective response to treatment with study drug is noted using the RECIST v1.1 (see, e.g., Eisenhauer et at. "New response evaluation criteria in solid tumours: revised RECIST guideline (version 1.1)" *Fur J Cancer* 2009, 45, 228-247) definitions of response or the iRECIST guidelines (see, e.g., Seymour et at. "RECIST working group. iRECIST: guidelines for response criteria for use in trials testing immunotherapeutics." *Lancet Oncol* 2017, 18, e143-e152) for patients receiving concomitant immunotherapy during the Phase 1b study. A summary is provided below.

(i) Response Evaluation Criteria in Solid Tumors (RECIST), v1.1

Response Criteria—Evaluation of Target Lesions Include:
Complete Response (CR): Disappearance of all target lesions. Any pathological lymph nodes (whether target or nontarget) must have reduction in short axis to <10 mm.
Partial Response (PR): At least a 30% decrease in the sum of diameters of target lesions, taking as reference the baseline sum diameters.
Progressive Disease (PD): At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions in also considered progression).
Stable Disease (SD): Neither sufficient shrinkage to qualify for PR nor sufficient increase to qualify for PD taking as references the smallest sum diameters while on study.

Response Criteria—Evaluation of Nontarget Lesions Include:
Complete Response (CR): Disappearance of all nontarget lesions and normalization of tumor marker level. All lymph nodes must be nonpathological in size (<10 mm short axis).
Non-CR/Non-PD: Persistence of one or more nontarget lesion(s) and/or maintenance of tumor marker level above the normal limits.
Progressive Disease (PD): Unequivocal progression of existing nontarget lesions* (Note: the appearance of one or more new lesions is also considered progression)

Although a clear progression of "nontarget" lesions only is exceptional, in such circumstances, the opinion of the treating physician should prevail and the progression status should be confirmed later on by the review panel (or study chair).

(ii) Response Evaluation Criteria in Solid Tumors for Trials Using Immunotherapy (iRECIST)

A phenomenon known as 'pseudoprogression' can occur in patients with solid tumors receiving immunotherapy (i.e., checkpoint inhibitors and other immune-modulating agents). With pseudoprogression, tumor volume can temporarily increase as a result of immune-cell infiltration rather than true disease progression. Members of the RECIST Working Group, along with input from several pharmaceutical companies and regulatory agencies in the US and Europe, drafted the iRECIST guidelines for assessing changes in tumor burden in these patients. While similar to traditional RECIST guidelines, iRECIST requires additional imaging showing continued tumor growth 4-to-8 weeks after initial evidence of mounting tumor burden for the disease to be considered progressing (stable disease does not count as disease progression).

Pharmacokinetic Endpoints

Plasma concentrations of oral study drug are summarized by descriptive statistics, including mean, n, standard deviation, coefficient of variation, minimum, maximum, and median. Prior to analysis of study samples, the assay sensitivity, specificity, linearity, and reproducibility is documented.

Plasma PK analyses for oral study drug and known metabolites, if any, and dose proportionality will be determined on Days 1 and 21 of Cycle 1 in all patients enrolled into the Phase 1a study as well as those enrolled into selected cohorts in the Phase 1b study.

The PK schedule is followed for all patients enrolled in the Phase 1a study. In the Phase 1b study, this PK sampling schedule only applies to patients with EGFR+NSCLC or immunotherapy-resistant tumors who are enrolled in expansion cohorts at the MTD and who receive study drug in combination with their previous anticancer therapies.

Pharmacodynamic Endpoints

PBMCs, plasma, and serum is collected to assess activity of study drug on predictive biomarkers including, but not limited to, GAS6 and AXE.

A predose tumor biopsy (within 14 days prior to first dose) and a post-dose tumor biopsy (Cycle 2, Day 28 [−4] days) is performed in 10 patients enrolled in each of the 5 Phase 1b expansion cohorts (Biopsy Cohorts) to assess activity of study drug on predictive biomarkers. If a predose biopsy is not possible, adequate archival tissue (3 to 5 individual core samples collected within 4 weeks of screening) may be submitted instead with sponsor approval. Ideally, the post-dose biopsy should be obtained from the same general location as the predose biopsy if feasible and safe, and from a metastatic lesion and not the primary tumor. Three to five (3 to 5) individual core samples are requested at each biopsy timepoint. Tumor tissue is examined using a variety of techniques to assess changes in potential biomarkers after exposure to study drug. While these PD analyses are considered exploratory in nature, they are evaluated in conjunction with pharmacokinetic parameters, as well as any signals of efficacy and safety, to see if there is any correlation with changes in potential biomarkers.

Archived tumor tissue (primary and metastatic site[s], if available) is requested from all patients to assess potential predictive biomarkers.

Adverse Events

An adverse event (AE) is defined as any untoward medical occurrence associated with the use of a drug in humans, whether or not considered drug related. An AE can therefore be any unfavorable and unintended sign (including an abnormal laboratory finding), symptom, or disease temporally associated with the use of a drug, whether or not related to the drug product.)

Suspected adverse reaction means any adverse event for which there is a reasonable possibility that the drug caused the adverse event. For the purposes of Investigational New Drug (IND) safety reporting, 'reasonable possibility' means there is evidence to suggest a causal relationship between the drug and the adverse event.

Unexpected adverse event or unexpected suspected adverse reaction: An adverse event or suspected adverse reaction is considered unexpected if it is not listed in the current Investigator's Brochure or is not listed at the specificity or severity that has been observed; or, is not consistent with the risk information described in the general investigational plan (clinical study protocol).

Toxicities are assessed according to the NCI CTCAE, version 4.03. When the NCI CTCAE grade is not available, the investigator uses the following toxicity grading: mild, moderate, severe, life threatening or fatal.

TABLE 21A

Grades of Toxicities

| | |
|---|---|
| GRADE 1- Mild: | Transient or mild discomfort; no limitation in activity; no medical intervention/therapy required. |
| GRADE 2- Moderate: | Mild to moderate limitation in activity - some assistance may be needed; no or minimal medical intervention/therapy required. |
| GRADE 3- Severe: | Marked limitation in activity, some assistance usually required; medical intervention/therapy required, hospitalizations possible. |
| GRADE 4- Life Threatening: | Extreme limitation in activity, significant assistance required; life threatening (immediate risk of death); significant medical intervention/therapy required, hospitalization or hospice care probable. |
| GRADE 5- Fatal | Results in death. |

Relationship of the adverse event (AE) to the study drug should be defined as follows:

| | |
|---|---|
| Unrelated: | AE is clearly not related to the investigational agent(s) |
| Unlikely: | AE is doubtfully related to the investigational agent(s) |
| Possibly: | AE may be related to the investigational agent(s) |
| Probably: | AE is likely related to the investigational agent(s) |
| Definitely: | AE is clearly related to the investigational agent(s) |

A serious adverse event (SAE) is defined as any experience that suggests a significant hazard, contraindication, side effect, or precaution. An SAE includes:

Any death, or

Any life-threatening event (ie, the patient is at immediate risk of death from the event as it occurred), or Any event that is persistently, significantly, severely or permanently disabling, or requires intervention to prevent such disability, or Any event which requires inpatient hospitalization or prolongs hospitalization, or Any congenital abnormality/birth defect, or Any medically significant event that may jeopardize the patient or may require intervention to prevent one of the other outcomes listed above.

Example 49: Combined Phase 1/2 Study to Investigate the Safety, Pharmacokinetics, Pharmacodynamics, and Clinical Activity in Patients with Previously Treated Chronic Lymphocytic Leukemia (CLL)/Small Lymphocytic Lymphoma (SLL)

The compound of structure (I) (described in Example 48 above) is a novel oral inhibitor that targets AXL kinase and reverses the mesenchymal phenotype associated with advanced cancers. The compound has demonstrated profound single agent activity in CLL B cells taken directly from patients even if the patient has high risk factors (i.e., 17p/P53 deletions) or progressed on other agents (i.e., ibrutinib). This study is designed to identify the maximum tolerated dose (MTD), safety profile and recommended Phase 2 dose (RP2D) of study drug (described in Example 48 above) when administered orally once daily for 28 days on a 28 day cycle to patients with previously treated CLL. In some instances, treatment cycles are repeated if the patient continues to show benefit and if study drug is reasonably well tolerated.

The study drug, in oral form, is supplied as a powder in hard gelatin capsules (size #3 for the 1-, 4-, 16-, and 25-mg doses; size #0 for the 100-mg dose) and is manufactured under current Good Manufacturing Practices (cGMP) for investigational use.

Study drug capsules are formulated in 1-mg, 4-mg, 16-mg, 25-mg, and 100 mg strengths and are packaged into round high-density polyethylene bottles with polyester coils as headspace fillers. Bottles are then heat-sealed, fitted with child-resistant caps, and placed in low-density polyethylene bags as secondary packaging.

Ibrutinib, an approved pharmaceutical product, is provided by commercially available sources. Ibrutinib capsules for oral administration are supplied as white opaque capsules that contain 140 mg ibrutinib as the active ingredient. Each white opaque capsule is marked with "ibr 140 mg" in black ink.

The objectives for the Phase I trial include:
To characterize the safety and toxicity profile of study drug when administered orally once daily for 28 days (each cycle is 28 days; no drug-free period) in the following patient groups:
Group 1 (study drug monotherapy): those with CLL/SLL who are intolerant to, or have had progressive disease on B-cell receptor antagonists, BCL-2 antagonists or other investigational treatments for CLL/SLL
Group 2 (study drug and ibrutinib combination therapy): those with CLL/SLL who have progressed on ibrutinib, yet the treating provider considers continuation of ibrutinib therapy to be in the best interest of the patient
To determine the RP2D of study drug when administered orally on this schedule to the defined patient groups
To observe patients for any evidence of antileukemic activity of oral study drug by determining the Objective Response Rate ([ORR], ie, rate of complete response [CR] plus rate of partial response [PR] in the defined patient groups according to guidelines set forth by the 2018 International Workshop on CLL (IWCLL)
To evaluate the pharmacokinetics (PK) of oral study drug in the defined patient groups
To study potential biomarkers relevant to disease and pharmacodynamics (PD) of oral study drug in the defined patient groups through assessment of analytes including, but not limited to, soluble AXL, AXL expression and phosphorylation, growth arrest specific 6 (GAS6), and mesenchymal transcription factors in peripheral blood samples and bone marrow The Objectives for the Phase II trial include:
To determine the ORR in the two defined patient groups according to guidelines set forth by the 2018 IWCLL
To determine the Duration of Response (DoR, ie, the time from tumor response to disease progression)
To determine the Progression-free Survival (PFS, ie, the time from first dose to objective tumor progression or death)
To determine the rate of Overall Survival (OS, ie, the time from first dose to death from any cause)
To study potential biomarkers relevant to disease and pharmacodynamics (PD) of oral study drug in the defined patient groups through assessment of analytes including, but not limited to, soluble AXL, AXL expression and phosphorylation, growth arrest specific 6 (GAS6), and mesenchymal transcription factors in peripheral blood samples and bone marrow Justification for Treatment Plan The starting dose is based on a thorough review of both the rat and dog GLP toxicology studies, as well as preliminary results from the Phase 1 study in patients with advanced metastatic or progressive solid tumors (see Example 48). The compound of structure (I) was administered orally once each day for 28 days in the GLP toxicology studies. In the rat, all findings were reversible or felt not to be clinically significant and the NO ALL was determined as 2 mg/kg or 12 mg/m$^2$. Based on the animal toxicology and safety studies, the starting dose for the compound of structure (I) was 1.5 mg/m$^2$/day.

Given the clinical experience acquired in this solid tumor study and the lack of dose-limiting toxicities (DLTs) observed in any of the first 6 cohorts, the starting dose for the tartrate salt of compound of structure (I) in Group 1 (monotherapy) is a 25-mg flat dose. The starting dose is approximately one dose level below the current Phase 1a solid tumor study (Example 48 above). Group 2 patients (combination therapy) start at one dose level below Group 1, or a 20-mg flat dose, to ensure safety particularly with the combination of ibrutinib and the tartrate salt of compound of structure (I). The use of a flat, rather than body size-based dose, particularly for orally administered drugs, is preferable as it facilitates the use of the drug by patients and physicians and reduces the number of dosage strengths needed, improving compliance.

Because the tartrate salt of compound of structure (I) has been well tolerated to date in the solid tumor study, the starting dose of 25 mg in the monotherapy arm is equivalent to 700 mg (25 mg×28 days, or 80% of the current dose in the solid tumor study). The starting dose in the combination arm (i.e., the tartrate salt of compound of structure (I) plus ibrutinib) is 20 mg, which is a further 20% reduction from the 25 mg starting dose in the monotherapy arm. The safety information from the solid tumor study, together with the lower starting doses suggested in this study, support the proposed continuous, 28-day dosing schedule.

Patent Population

Adult patients with chronic lymphocytic leukemia (CLL) and/or small lymphocytic lymphoma (SLL) who:
1. are intolerant to, or have had progressive disease on B-cell receptor antagonists, BCL-2 antagonists or other investigational treatments for CLL/SLL (Group 1; monotherapy); or 2. have progression of disease on ibrutinib, yet the treating provider considers continuation of ibrutinib therapy to be in the best interest of the patient (Group 2; combination therapy with ibrutinib).

Additional Inclusion Criteria

To be eligible for participation, patients must meet all of the following inclusion criteria:
1. Be ≥18 years old
2. Have an established, pathologically confirmed diagnoses of CLL/SLL requiring therapy according to the 2018 IWCLL guidelines
3. Have received at least one prior therapy for CLL/SLL and can be classified in one of two patient groups:
   Group 1 (monotherapy): Patients with CLL/SLL who are intolerant to, or have progressed on B-cell receptor antagonists and/or BCL-2 antagonists or
   Group 2 (ibrutinib combination therapy): Patients with CLL/SLL who have progression of disease on ibrutinib and the treating provider considers continuation of ibrutinib therapy to be in the best interest of the patient
4. Have an Eastern Cooperative Oncology Group (ECOG) performance status ≤2
5. Have adequate hematologic function: (a) Absolute neutrophil count (ANC) ≥500/μL; (b) Platelet count ≥30,000/μL; (c) Hemoglobin ≥8 g/dL in the absence of transfusions within the previous 2 weeks
6. Have adequate organ function: (a) Creatinine clearance ≥30 mL/min; (b) Alanine aminotransferase (ALT)/aspartate aminotransferase (AST) level ≤2.5× upper limit of normal (ULN); (c) Have a total bilirubin level ≤1.5×ULN (unless secondary to Gilbert syndrome, hemolysis, or leukemia)
7. Have acceptable coagulation status: Activated partial thromboplastin (aPTT) and prothrombin time (PT) ≤1.5×ULN
8. Have a negative pregnancy test (if female of childbearing potential)
9. Be nonfertile or agree to use an adequate method of contraception. Sexually active patients and their partners must use an effective method of contraception (hormonal or barrier method of birth control, or abstinence) prior to study entry and for the duration of study participation and for at least 30 days after the last study drug dose. Should a woman become pregnant or suspect that she is pregnant while participating in this study, she should inform her treating physician immediately.
10. Have read and signed the Institutional Review Board (IRB)-approved informed consent form (ICF) prior to any study related procedure. (In the event that the patient is rescreened for study participation or a protocol amendment alters the care of an ongoing patient, a new ICF must be signed.)
11. Be able to comply with the requirements of the entire study Exclusion Criteria Patients meeting any 1 of these exclusion criteria will be prohibited from participating in the study.
1. Have undergone prior autologous or allogeneic stem cell transplant within ≤3 months, have not recovered from transplant associated toxicities, or requires graft versus host immunosuppressive therapy
2. Have known central nervous system (CNS) involvement
3. Have Richter's transformation of CLL
4. Have received any monoclonal antibody therapy directed at treatment of the patient's malignancy within 2 weeks prior to anticipated first dose
5. Have received any anticancer therapy including chemotherapy, radiotherapy, or an investigational anticancer drug within less than 5 half-lives of the last dose of that treatment. This exclusion criterion is not applicable to patients requiring continuation on ibrutinib. (Note: Certain patients with a rapidly rising white blood cell count while on ibrutinib may need to remain on this drug for medical reasons. These patients will need to be approved by the Medical Monitor and treated in accordance with the protocol.)
6. Have received >20 mg/day of prednisone and 0.1 mg/day of mineralocorticoids within 7 days prior to anticipated first dose
7. Have a corrected QT interval of >450 msec (males) and >470 msec (females) using Fridericia's correction formula
8. Have a significant history of renal, neurologic, psychiatric, endocrinologic, metabolic, immunologic, hepatic, or cardiovascular disease or any other medical condition that, in the opinion of the Investigator, would adversely affect his/her participation in the study
9. Are pregnant and/or nursing, or refuse to use appropriate contraceptives during the course of the study and for at least 30 days after the last dose of study drug
10. History of another malignancy in the last 5 years except for the following adequately treated: (a) Local basal cell or squamous cell carcinoma of the skin; (b) Carcinoma in situ of the cervix or breast; (c) Papillary, noninvasive bladder cancer; (d) Early stage prostate cancer for which observation is clinically indicated; (e) Other Stage 1 or 2 cancers currently in complete remission (f) Any other cancer that has been in complete remission for 2 years or surgically cured. Medical Monitor may be contacted for additional determination of acceptable prior cancer history
11. Have known gastrointestinal disorders (eg, malabsorption syndrome), complications (eg, dysphagia), or surgery that could make consumption or absorption of oral medications problematic
12. Have an uncontrolled systemic infection (viral, bacterial, or fungal) or fever and neutropenia within 7 days prior to anticipated first dose
13. Have active and uncontrolled autoimmune cytopenias for 2 or more weeks including autoimmune hemolytic anemia or idiopathic thrombocytopenic purpura (ITP)
14. Have received prior therapy with an AXL inhibitor
15. Have exhibited allergic reactions to a similar structural compound, biological agent, or formulation
16. Are unwilling or unable to comply with procedures required in this protocol
17. Have a history of severe adverse reaction (eg, hypersensitivity reaction, anaphylaxis) to sulfonamides Treatment Schedule and Dosing This is a combined Phase 1/2 study of oral study drug in patients with previously treated CLL/SLL. In both Phase 1 and Phase 2, study participants are assigned to 1 of 2 groups:
   Group 1 (study drug monotherapy): Patients who are intolerant to, or have had progressive disease on B-cell receptor antagonists and/or BCL-2 antagonists or other investigational treatments.
   Group 2 (study drug and ibrutinib combination therapy): Patients who have progression of disease on ibrutinib and the treating provider considers continuation of ibrutinib therapy to be in the best interest of the patient.

Both groups of patients are treated identically with study drug and undergo the same study assessments. The study may take up to 36 months to enroll up to 108 patients (up to 27 patients in each group (Group 1 and Group 2) in both Phase 1 (n=54) and Phase 2 (n=54).

Study drug is administered orally once daily for 28 days (each cycle is 28 days; no drug-free period). Dosing may be repeated every cycle in the absence of disease progression or unacceptable toxicity. Study drug should be taken in the morning after an overnight fast with up to 200 mL or 7 fluid ounces of water at least 1 hour before ingesting any food or other medications. Administer ibrutinib orally once daily at approximately the same time each day. Swallow the capsules whole with water. Do not open, break, or chew the capsules.

Phase 1

Patients are enrolled in Group 1 and Group 2 in cohorts of 3 to 6 patients simultaneously. Group 2 start at 1 dose level below the group 1 starting dose. In each group, escalation of the study drug dose follows a standard 3+3 design with sequential cohorts of 3 patients treated with incrementally higher doses of study drug until a DLT is observed and the MTD is established. Once the first patient at a dose level is enrolled, the second and third patients are enrolled after 3 weeks if the initial patient has not experienced a DLT or any unacceptable toxicity.

If 1 of 3 patients in a cohort experiences a DLT, up to 3 additional patients are treated at that dose level. If no additional DLTs are observed in the expanded 3- to 6 patient cohort within 28 days after the last patient was first dosed, the dose is escalated in a new cohort of 3 patients. If 2 or more of 3 to 6 patients at a given dose level experience a DLT during the first cycle, then the MTD is exceeded and up to a total of 6 patients will be treated at the previous lower dose level. If 0 or 1 of 6 patients experiences a DLT at this previous lower dose level, this dose is declared the MTD.

The MTD is defined as the dose at which ≤1 of 6 patients experience a DLT during Cycle 1 with the next higher dose having at least 2 of 3 to 6 patients experiencing a DLT during Cycle 1. Once the MTD or preliminary RP2D is identified, an expansion cohort of up to six patients is enrolled in each patient group to confirm safety/confirm the suitability of the preliminary RP2D, to collect additional biomarker data, and to further explore efficacy. Up to 27 patients may be enrolled in each patient group for a total of up to 54 patients in Phase 1.

Additional dose levels, schedules or disease indications of study drug may be explored, as appropriate, based on the modulation of key biomarkers, the safety profile and clinical signals of activity.

Group 1 (Study Drug Monotherapy):

The starting dose for study drug in Group 1 (monotherapy) is a 25-mg flat dose. The study drug is administered orally once daily for 28 days (each cycle is 28 days; no drug-free period). Patients may continue to receive study drug in 28-day cycles at the same dose given during Cycle 1 until they experience unacceptable toxicity or unequivocal disease progression. No intrapatient escalation of the study drug dose is permitted.

Group 2 (Study Drug in Combination with Ibrutinib):

The starting dose of study drug is a 20-mg flat dose. Study drug is administered orally once daily for 28 days (each cycle is 28 days; no drug-free period). Patients also receive ibrutinib at the same dose that they were receiving immediately prior to study enrollment. Patients continue with the combination of ibrutinib and study drug for at least 3 months after study start. After that time, patients either continue with combination therapy or discontinue ibrutinib and continue with study drug monotherapy at the discretion of the Investigator and in consultation with the Medical Monitor. Patients may continue to receive study drug in 28-day cycles at the same dose given during Cycle 1 until they experience unacceptable toxicity or unequivocal disease progression.

Ibrutinib may be stopped and reinitiated at the discretion of the Investigator and in consultation with the Medical Monitor; however, the total time patients may receive treatment with ibrutinib is 2 years.

The escalated doses of study drug in the Phase I trial are provided in Table 22 below:

TABLE 22

| Dose Level | Proposed Daily Dose | Increment from Previous Dose[a] | No. of Patients Per Cohort |
|---|---|---|---|
| Group 1 (Monotherapy) | | | |
| 1 | 25 mg | Starting Dose | 3-6 |
| 2 | 33 mg | 33% | 3-6 |
| 3 | 45 mg | 36% | 3-6 |
| 4 | 58 mg | 29% | 3-6 |
| 5 | 75 mg | 29% | 3-6 |
| 6[b] | 100 mg | 33% | 3-6 |
| Group 2 (Combination) | | | |
| 1 | 20 mg | Starting Dose | 3-6 |
| 2 | 25 mg | 25% | 3-6 |
| 3 | 33 mg | 33% | 3-6 |
| 4 | 45 mg | 36% | 3-6 |
| 5 | 58 mg | 29% | 3-6 |
| 6[b] | 75 mg | 29% | 3-6 |
| 7[b] | 100 mg | 33% | 3-6 |

[a]It is possible for additional and/or intermediate dose levels to be added during the course of the study.
[b]If clinically indicated, dose levels higher than 100 mg may be investigated.

Phase 2

In Phase 2, patients are enrolled in Group 1 and Group 2 based on the Simon 2 stage design. In Stage 1, up to 13 patients are enrolled into each patient group (total of 26 patients). If there are zero responses among these 13 patients in each group, the study is stopped. Otherwise, Stage 2 enrolls 14 additional patients in each group for a total of 27 patients per group. If 4 or more responses are observed among 27 patients, the conclusion is that the study treatment is worthy of further investigation. When the true response rate of 20% (alternative hypothesis) is tested against the null hypothesis response rate of 5%, this design yields a Type I error rate of 0.05 and power of 80%.

Group 1 (Study Drug Monotherapy):

The starting dose is the RP2D determined during Phase 1. Study drug is administered orally once daily for 28 days (each cycle is 28 days; no drug-free period). Dosing with study drug may continue until a patient experiences unacceptable toxicity or unequivocal disease progression Group 2 (Study Drug in Combination with Ibrutinib):

The starting dose is the RP2D determined during Phase 1. Study drug is administered orally once daily for 28 days (each cycle is 28 days; no drug-free period). Patients will also receive ibrutinib at the same dose that they were receiving immediately prior to study enrollment.

Patients should continue with the combination of ibrutinib and study drug for at least 3 months after study start. After that time, patients either continue with combination therapy or discontinue ibrutinib and continue with study drug monotherapy at the discretion of the Investigator and in consultation with the Medical Monitor. Patients may continue to receive study drug in 28-day cycles at the same dose given during Cycle 1 until they experience unacceptable toxicity or unequivocal disease progression.

Ibrutinib may be stopped and reinitiated at the discretion of the Investigator and in consultation with the Medical Monitor; however, the total time patients may receive treatment with ibrutinib is 2 years.

Management of Toxicides and Dosage Modification
Management of Toxicities

AEs may be treated with concomitant medications, as deemed clinically indicated by the Principal Investigator. All concomitant medications must be recorded in the source and on the appropriate electronic case report form (eCRF).

AEs that are moderate to severe in intensity for NCI CTCAE toxicity grading) and considered Possibly, Probably, or Definitely related to study drug treatments may result in the termination of study treatment in the affected study patient. A patient may be permanently withdrawn from the study depending upon the nature and severity of the event.

Dosing-Limiting Toxicides (DLLs)

A DLT is defined as any one of the following events observed within Cycle 1, regardless of attribution unless clearly and incontrovertibly related to the underlying disease or extraneous causes (such as progressive disease; other decreases in the white blood cell count, or in circulating granulocytes, are not to be considered, since a decrease in the white blood cell count is a desired therapeutic endpoint):

Any Grade ≥3 nonhematologic toxicity
Any Grade 3 AE that does not resolve to ≤Grade 1 within 72 hours with use of supportive care
Any AST and ALT elevation ≥5×ULN accompanied by serum bilirubin levels ≥2×ULN
Any Grade ≥3 electrolyte disturbances (eg, hyperkalemia, hypophosphatemia, hyperuricemia) that do not resolve within <72 hours
Any Grade ≥3 elevations in creatinine
Any Grade 5 toxicity
Any instance of febrile neutropenia Study Drug Dose Modification The dose of study drug is not reduced during Cycle 1. Doses of study drug may be adjusted for patients who receive multiple cycles of study drug. Dose reductions by one dose level is permitted based on the observed toxicity that occurred during the preceding cycle. No dose re-escalations are allowed for any patient who had a previous dose reduction due to toxicity or delayed recovery.

If a patient experiences toxicity, the patient may continue to receive study drug as defined in Table 23 in conjunction with the guidelines set forth by the 2018 IWCLL Grading Scale for Hematologic Toxicity.

TABLE 23

Guide to Dose Adjustments Based on Toxicities

| Drug-Related AE | Action |
|---|---|
| Grade 1 | Current dose level |
| Grade 2 | Investigator's option to reduce dose by 1 dose level with agreement of the Medical Monitor |
| Grade 3[a] | Withhold, then reduce dose by 1 dose level upon recovery to ≤ Grade 1 with agreement of the Medical Monitor. |
| Grade 4 | Investigator and Medical Monitor review to determine if patient may continue on study with appropriate dose reduction upon recovery to ≤ Grade 1. |

[a]Excluding brief (based on the Investigator's judgment) Grade 3 vomiting or diarrhea with suboptimal management.

Dose reduction to the next lower dose level tested are performed initially. If further toxicities occur during 1 or more cycles at the new reduced dose level, no further reductions are permitted, and the patient is discontinued from the study.

Patients who experience a DLT are required to discontinue study participation, unless the Investigators and Medical Monitor determine that it is in the best interest of the patient to continue with the dose reduction and only upon recovery of the toxicity to Grade 2 or better.

Dose reduction are required for patients who have a delay in treatment greater than 2 weeks due to a lack of recovery of any hematologic or nonhematologic toxicity, even if DLT criteria are not met. In addition, dose reductions are permitted for patients who have toxicities that do not meet the criteria of a DLT. These toxicities are discussed to determine if it would be in the best interest of the patient to continue to receive the compound of structure (I) at the next previous dose level.

Ibrutinib Dose Modifications

The package insert for ibrutinib therapy should be followed by the treating physician. As per the ibrutinib label: Interrupt ibrutinib therapy for any Grade 3 or greater non-hematological, Grade 3 or greater neutropenia with infection or fever, or Grade 4 hematological toxicities. Once the symptoms of the toxicity have resolved to Grade 1 or baseline (recovery), ibrutinib therapy may be reinitiated at the starting dose. If the toxicity reoccurs, reduce dose by one capsule (140 mg per day). A second reduction of dose by 140 mg may be considered as needed. If these toxicities persist or recur following two dose reductions, discontinue ibrutinib. Recommended dose modifications are described below in Table 24.

TABLE 24

Recommended Dose Modifications for Ibrutinib

| Toxicity Occurrence | CLL Dose Modification |
|---|---|
| First | Hold ibrutinib until recovery to Grade ≤ 1 or baseline; May restart at 420 mg daily |
| Second | Hold ibrutinib until recovery to Grade ≤ 1 or baseline; May restart at 280 mg daily |
| Third | Hold ibrutinib until recovery to Grade ≤ 1 or baseline; May restart at 140 mg daily |
| Fourth | Discontinue ibrutinib |

If ibrutinib is interrupted for a reason other than toxicity (eg, unrelated illness) the first instance of interruption must be restarted within 42 days. Subsequent study medication interruptions lasting more than 42 days, ibrutinib should be discontinued permanently.

Concomitant Medications and Therapies

Patients subject to the treatment disclosed in this Example may have previous therapies of the corresponding cancer.

Patients subject to the instant treatment may have one or more concomitant therapies, which are any new or existing medications or therapy taken by the patient. Examples include:

Drugs, including but not limited to, prescription, over-the-counter, birth control pills/patches/hormonal devices, and homeopathic preparations
Nondrug therapies, including but not limited to, thermal/laser/radiation procedures, vitamins, herbal medicines/supplements.

Once the patient receives the first dose of the Study Drug, recording of concomitant therapies is limited to any new medication or modification of an existing medication taken for treatment of an AE. These therapies are recorded in the source documents and appropriate eCRF along with the diagnosis or reason for use. Those therapies used for the treatment of an AE are to be linked to an AE and documentation of the AE must also be completed.

Concomitant medications necessary for the health and well-being of the patient and that do not interfere with study assessments are permitted during the study. This includes the use of appropriate medications for the treatment of AEs and/or concurrent illnesses.

Treatment with hematopoietic colony stimulating growth factors such as granulocyte colony stimulating factor or granulocyte-macrophage colony stimulating factor may not be initiated during Cycle 1 unless the patient has experienced a DLT. Initiation of treatment with erythroid stimulating agents may not occur during the first cycle of therapy. If a patient has been on a steady dose of an erythroid stimulating agent, they may continue to use the agent at the same dose during Cycle 1 and later cycles.

Supportive care includes:
Careful monitoring of patients at high risk for tumor lysis syndrome (TLS) (i.e., patients with any lymph node [LN]≥10 cm, or absolute lymphocyte count [ALC] ≥25×109/L and any LN ≥5 cm) by collection of blood and real-time (STAT) review of TLS laboratory parameters (i.e., uric acid, potassium, phosphate, calcium, and creatinine) on Day 1 of Cycle 1 at baseline (predose) and at 6 hours and 24 hours post dose.
Infection Prevention (ie, prophylactic antibiotic, antiviral, and/or antifungal therapy) to be initiated according to each institution's standardized protocols The following medications are excluded from concomitant use:
Anticancer therapies (chemotherapy, radiation therapy, immunotherapy) within less than 5 half-lives of the last dose of that treatment. Patients enrolled in Group 2 (study drug in combination with ibrutinib) continue treatment with the combination for at least 3 months. Ibrutinib may be stopped and reinitiated; however, the total time patients may receive treatment with ibrutinib is 2 years.
CYP2C19 Metabolizers: Patients who are known abnormal metabolizers of CYP2C19 (i.e., extensive or poor) prior to study treatment should be monitored closely. If possible, patient's treatment with a CYP2C19 substrate should be terminated prior to first dose, or at a minimum, switch to an alternative, but equivalent treatment that is not a CYP2C19 substrate (inhibitor or inducer). If a patient must remain on a CYP2C19 substrate, treatment with study drug should proceed cautiously and the patient observed closely throughout the duration of the study.
Group 2 patients (i.e., study drug in combination with ibrutinib) should avoid co-administration of strong or moderate CYP3A inhibitors (e.g., carbamazepine, rifampin, phenytoin, and St. John's Wort) as these substances may increase ibrutinib plasma concentrations.
Group 2 patients should avoid co-administration of strong CYP3A inducers as these substances may decrease ibrutinib concentrations.
Patients must not be taking H2-receptor antagonists such as cimetidine, ranitidine, and famotidine, or any proton pump inhibitors such as omeprazole, lansoprazole, esomeprazole and pantoprazole. Patients must stop these medications within 7 days prior to starting treatment.

Sexually active patients and their partners must use an effective method of contraception associated with a low failure rate prior to study entry and for the duration of study participation and for 30 days after the last dose of study drug. The following are considered effective contraceptives: (1) oral contraceptive pill; (2) condom plus spermicide; (3) diaphragm plus spermicide; (4) abstinence; (5) patient or partner surgically sterile; (6) patient or partner more than 2 years postmenopausal; or (7) injectable or implantable agent/device.

Safety and Efficacy Evaluations
Predose Assessments

The following procedures and evaluations are performed within 14 days prior to administration of the first dose of the Study Drug, after the IGF is signed unless otherwise noted:
Collect and document a complete medical history including histologically confirmed diagnosis of CLL/SLL. Examples include:
Perform a full physical examination, including height (cm) and weight (kg) and review the following constitutional symptoms suggestive of active disease
Unintentional weight loss ≥10% within previous 6 months
Marked fatigue
Fevers ≥100.5° F. or (38.0° C.) for ≥2 weeks without evidence of infection Night sweats for ≥1 month without evidence of infection
Record vital signs (body temperature, respirations, heart rate, blood pressure)
Assess ECOG Performance Status
Evaluate laboratory parameters, including full serum chemistry, hematology (complete blood count [CBC] with differential and platelet count), coagulation parameters (PT and aPTT), urinalysis, serum immunoglobulins, direct antiglobulin, and serum 132-microglobulin
Perform a 12-lead ECG including assessment of corrected QT interval (using Fridericia's correction formula) (QTcF)
Pregnancy test (urine or serum beta-human chorionic gonadotropin pregnancy test for females of childbearing potential)
Record all concomitant medications including all prescription drugs, nonprescription drugs, and nutritional supplements within the past 14 days
Assess baseline disease status per 2018 IWCLL guidelines (within 28 days of Cycle 1 Day 1):
Perform a computed tomography (CT) scan of neck, chest, abdomen, and pelvis for evaluation of lymphadenopathy, hepatomegaly, and splenomegaly;
Bone marrow biopsy and aspirate with matched peripheral blood sample
The following should be obtained (within 28 days of Cycle 1 Day 1): molecular cytogenetics (FISH) for del(13q), del(11q), del(17p), add(12) [peripheral blood]; karyotyping with CpG (or institutional standard) stimulation [bone marrow]; TP53 mutation analysis [peripheral blood]; and/or immunoglobulin heavy-chain variable (IGHV) mutational analysis [peripheral blood]
Positron emission tomography (PET) scan to assess for possible Richter's transformation (within 14 days of first dose)

The following baseline procedures and evaluations are performed any time within 3 days (72 hours) prior to administration of the first dose of study drug (not required to be repeated at Cycle 1 Day 1 if screening exams are within 3 days prior to first dose):
  Full physical examination, including weight (kg)
  Record vital signs (body temperature, respirations, heart rate, blood pressure)
  Evaluate laboratory parameters: full serum chemistry; hematology (CBC with differential and platelet count); pregnancy test (urine or serum beta-human chorionic gonadotropin pregnancy test for females of childbearing potential)
  Record all concomitant medications including all prescription drugs, nonprescription drugs, and nutritional supplements
  Review all inclusion/exclusion criteria and determine if patient has met all eligibility criteria for inclusion in the study. Obtain Medical Monitor (or designee) approval to enroll patient.
Treatment Assessments
  (i) Cycle 1
  Day 1
  Full physical examination, including weight (kg)
  Record vital signs (temperature, respirations, heart rate, blood pressure) prior to first dose
  Obtain baseline signs and symptoms prior to first dose
  Assess ECOG Performance Status
  Evaluate laboratory parameters: full serum chemistry; hematology (CBC with differential and platelet count); TLS labs to be assessed at baseline (predose) and at 6 hours and 24 hours post dose (real-time [SEAT] review) in patients at high risk for TLS (ie, patients with any LN ≥10 cm, or ALC ≥25×109/L and any LN ≥5 cm); and/or pregnancy test (urine or serum beta-human chorionic gonadotropin pregnancy test for females of childbearing potential)
  Perform 12-lead ECG just prior to first dose, including assessment of QTcF
  Collect blood for analysis of PK parameters in Phase 1 only
  Collect blood for exploratory biomarker assessments
  Assess for AEs
  Record all concomitant medications including all prescription drugs, nonprescription drugs, and nutritional supplements
  Daily on Days 1 Through 28
  Instruct patients to take study drug and ibrutinib (for Group 2 patients) orally every day on Days 1 through 28
  Instruct patients to record the date and time they took their dose(s) in their dosing diary
  Weekly (Days 8, 15, and 22 [±3 Days])
  The following activities and evaluations are performed weekly (or as otherwise indicated) during Cycle 1:
    Perform an abbreviated physical examination (AE- or symptom directed)
    Record vital signs (temperature, respirations, heart rate, blood pressure)
    Evaluate laboratory parameters: full serum chemistry; hematology (CBC with differential and platelet count)
    On Day 8, collect blood for exploratory biomarker
    Assess for AEs
    Record all concomitant medications including all prescription drugs, nonprescription drugs, and nutritional supplements
  Day 28
  On Day 28, collect blood for analysis of PK parameters according to the schedule in Section 7.3 in Phase 1 only
  (ii) Cycle 2
  Day 1
  Full physical examination, including weight (kg)
  Record vital signs (temperature, respirations, heart rate, blood pressure)
  Evaluate laboratory parameters: full serum chemistry; hematology (CBC with differential and platelet count); pregnancy test (urine or serum beta-human chorionic gonadotropin pregnancy test for females of childbearing potential)
  Assess ECOG Performance Status
  Perform 12-lead ECG just prior to dosing including assessment of QTcF
  Collect blood for exploratory biomarker assessments
  Assess for AEs
  Record all concomitant medications including all prescription drugs, nonprescription drugs, and nutritional supplements
  Daily on Days 1 Through 28
  Instruct patients to take study drug and ibrutinib (for Group 2 patients) orally every day on Days 1 through 28
  Instruct patients to record the date and time they took their dose(s) in their dosing diary
  Day 15 [±3 Days]
  Perform an abbreviated physical examination (AE- or symptom directed)
  Record vital signs (temperature, respirations, heart rate, blood pressure)
  Evaluate laboratory parameters: full serum chemistry; hematology (CBC with differential and platelet count)
  Assess for AEs
  Record all concomitant medications including all prescription drugs, nonprescription drugs, and nutritional supplements
  Day 28 (−4 Days)
  Disease assessment—Assess for response per 2018 IWCLL guidelines, including review of the following constitutional symptoms suggestive of active disease: unintentional weight loss ≥10% within previous 6 months, marked fatigue; fevers ≥100.5° F. or (38.0° C.) for ≥2 weeks without evidence of infection, and/or night sweats for ≥1 month without evidence of infection; and/or CT scan of neck, chest, abdomen, and pelvis evaluation of lymphadenopathy, hepatomegaly, and splenomegaly
  If clinical and laboratory results indicate possible CR: collect bone marrow and aspirate with matched peripheral blood for CBC and determination of MRD (central lab assessment)
  (iii) Cycles ≥3
  Patients may continue to receive study drug in 28-day cycles at the same dose given during Cycle 1 until they experience unacceptable toxicity or unequivocal disease progression.
  Day 1
  Perform the following activities and evaluations on Day 1 of Cycle 3 and all subsequent cycles of treatment:
    Full physical examination, including weight (kg)
    Record vital signs (temperature, respirations, heart rate, blood pressure)
    Evaluate laboratory parameters: full serum chemistry; hematology (CBC with differential and platelet count);

and/or pregnancy test (urine or serum beta-human chorionic gonadotropin pregnancy test for females of childbearing potential)

Assess ECOG Performance Status

Perform 12-lead ECG just prior to dosing including assessment of QTcF

Collect blood for analysis of PK parameters

Collect blood for exploratory biomarker

Assess for AEs

Record all concomitant medications including all prescription drugs, nonprescription drugs, and nutritional supplements Daily on Days 1 Through 28

Instruct patients to take study drug and ibrutinib (for Group 3 patients) orally every day on Days 1 through 28

Instruct patients to record the date and time they took their dose(s) in their dosing diary Day 15 (±3 Days)

The following activities and evaluations are performed during Cycle 3 and all subsequent cycles of treatment:

Perform an abbreviated physical examination (AE- or symptom directed)

Record vital signs (temperature, respirations, heart rate, blood pressure)

Evaluate laboratory parameters: full serum chemistry; and/or hematology (CBC with differential and platelet count)

Assess for AEs

Record all concomitant medications including all prescription drugs, nonprescription drugs, and nutritional supplements Day 28 (−4 Days)

The following evaluations are performed on Day 28 of every EVEN cycle (i.e., Cycle 4, Cycle 6, etc):

Disease assessment—Assess for response per 2018 IWCLL guidelines, including review of the following constitutional symptoms suggestive of active disease: unintentional weight loss ≥10% within previous 6 months, marked fatigue; fevers ≥100.5° F. or (38.0° C.) for ≥2 weeks without evidence of infection, and/or night sweats for ≥1 month without evidence of infection; and/or CT scan of neck, chest, abdomen, and pelvis evaluation of lymphadenopathy, hepatomegaly, and splenomegaly If clinical and laboratory results indicate possible CR: collect bone marrow and aspirate with matched peripheral blood for CBC and determination of MRD (central lab assessment)

End-of-Treatment Assessments

If, at any time, a patient discontinues study treatment, a visit is scheduled as soon as possible and within 14 days of the last dose of study drug or within 14 days of the decision to discontinue study treatment. If the decision to withdraw the patient occurs at a regularly scheduled visit, that visit may become the End-of-Study visit rather than having the patient return for an additional visit.

Perform a full physical examination including weight (kg)

Record vital signs (temperature, respirations, heart rate, blood pressure)

Evaluate laboratory parameters: full serum chemistry; hematology (CBC with differential and platelet count); and/or pregnancy test (urine or serum beta-human chorionic gonadotropin pregnancy test for females of childbearing potential)

Assess ECOG Performance Status

Perform a 12-lead ECG including assessment of QTcF

Disease assessment—Assess for response per 2018 IWCLL guidelines, including review of the following constitutional symptoms suggestive of active disease: unintentional weight loss ≥10% within previous 6 months, marked fatigue; fevers ≥100.5° F. or (38.0° C.) for ≥2 weeks without evidence of infection, and/or night sweats for ≥1 month without evidence of infection; and/or CT scan of neck, chest, abdomen, and pelvis evaluation of lymphadenopathy, hepatomegaly, and splenomegaly If clinical and laboratory results indicate possible CR: collect bone marrow and aspirate with matched peripheral blood for CBC and determination of MRD (central lab assessment)

Collect blood for exploratory biomarker assessments

Assess for AEs

Record all concomitant medications including all prescription drugs, nonprescription drugs, and nutritional supplements Criteria for Evaluation Safety Endpoints Phase 1

Safety is monitored from the time of the first dose until 30 days after the last dose of study drug. During Phase 1, the safety endpoints are evaluated after Cycle 1. The dose escalation committee, comprised of Investigators, sponsor and CRO representatives, has access to complete safety profiles of all patients receiving study drug to enable decision making.

The primary safety endpoint is to assess the tolerance and toxicity of continuous orally administered study drug through evaluation of physical examinations, vital signs, laboratory parameters, solicited and unsolicited AEs including DLTs, and all causes of mortality up to 30 days from the last dose in both phases of the study. In Phase 2, all causes of mortality are also evaluated at 60 days from the last administered dose.

Overall safety profile is characterized by type, frequency, severity, seriousness, timing, duration, and relationship of study drug to AEs and laboratory abnormalities. Treatment-emergent AEs (TEAEs), namely, AEs with initial onset or that worsen in severity after the first dose of study drug will be classified using the Medical Dictionary for Regulatory Activities (MedDRA) v20.0 or higher and graded according to NCI CTCAE v5.0. All DLTs will be reported and the MTD and RP2D identified.

Efficacy Endpoints

Phase 2

The primary efficacy endpoint of the Phase 2 portion of the study is to determine the ORR (rate of CR or PR) in patients with previously treated CLL/SLL according to IWCLL guidelines 2018 (see, e.g., Hallek el at. "Guidelines for Diagnosis, Indications for Treatment, Response Assessment and Supportive Management of Chronic Lymphocytic Leukemia" (an ppdate of the NCI-sponsored guidelines from the International Workshop on Chronic Lymphocytic Leukemia)).

The secondary efficacy endpoints include:

DoR, defined as the time from documentation of tumor response to disease progression.

PFS, defined as the time from study enrollment until objective tumor progression or death.

OS, defined as the time from study enrollment to death from any cause.

Efficacy assessments are performed at Cycle 2/Day 28 and then every even cycle (Cycle 4/Day 28, Cycle 6/Day 28, etc). Response rates are calculated in Stage 1 and Stage 2 as per the Simon 2 stage design.

A DSMB is monitor key outcomes from the study during the Phase 2 portion of the study.

Disease response is assessed at every 2 cycles per 2018 IWCLL guidelines

Pharmacokinetic Endpoints

Plasma PK analysis of oral study drug is performed in Cycle 1 on Days 1 and 28 in all patients enrolled in the Phase 1 portion of this study. Known metabolites of study drug, if any, may also be evaluated. Standard plasma PK parameters are calculated, including: Cmax, Tmax, AUC from time 0 to 24 hours (AUC0-24), AUC0 inf, AUC from time 0 to time t (AUCt), half-life (t1/2), and clearance using noncompartmental methods (CL). If data permit, dose proportionality and accumulation ratio are estimated in Phase 1 Cycle 1. PK samples should be drawn on the protocol-specified day.

Plasma concentrations of oral study drug are summarized by descriptive statistics, including mean, n, standard deviation, coefficient of variation, minimum, maximum, and median. A validated bioanalytical method for the detection of study drug in human plasma has been developed prior to this study to establish assay sensitivity, specificity, linearity, and reproducibility.

Pharmacodynamic Endpoints

The PD endpoints, including biomarker assessments, are evaluated during the study as follows:
  Blood for potential biomarkers including, but not limited to, soluble AXL, AXL expression and phosphorylation, GAS6, and mesenchymal transcription factors Analysis of the sample is limited to evaluations that are relative to the activity of the Study Drug or biomarkers of underlying disease.

Adverse Effects and Dose Modification

An adverse event (AE) is defined as any untoward medical occurrence associated with the use of a drug in humans, whether or not considered drug related. An AE can therefore be any unfavorable and unintended sign (including an abnormal laboratory finding), symptom, or disease temporally associated with the use of a drug, whether or not related to the drug product.

A suspected adverse reaction is any AE that had a reasonable possibility of being caused by the drug. Reasonable possibility means there is evidence to suggest a causal relationship between the drug and the AE.

An unexpected AE or unexpected suspected adverse reaction is an AE or suspected adverse reaction not known to those skilled in the art, not listed at the specificity or severity that has been observed, or not consistent with the risk information described in the protocol.

Toxicities are assessed according to the NCI CTCAE, v5.0. When the NCI CTCAE grade is not available, the following toxicity grading: mild, moderate, severe, life threatening, or fatal, may be used.

TABLE 25

| Grades of Toxicities | |
| --- | --- |
| GRADE 1-<br>Mild: | Asymptomatic or mild symptoms; clinical or diagnostic observations only; intervention not indicated |
| GRADE 2-<br>Moderate: | Minimal, local or noninvasive intervention indicated; limiting age-appropriate instrumental ADL[a] |

TABLE 25-continued

| Grades of Toxicities | |
| --- | --- |
| GRADE 3-<br>Severe: | Medically significant but not immediately life-threatening; hospitalization or prolongation of hospitalization indicated; disabling; limiting self-care ADL[b] |
| GRADE 4-<br>Life Threatening: | Life-threatening consequences; urgent intervention indicated |
| GRADE 5-<br>Fatal | Death related to AE |

[a]Instrumental activities of daily living (ADLs) refer to preparing meals, shopping for groceries or clothes, using the telephone, managing money, etc.
[b]Self-care ADLs refer to bathing, dressing and undressing, feeding self, using the toilet, taking medications, and not bedridden.

Relationship of the AE to the study drug should be defined as follows:

| Unrelated: | AE is clearly not related to the study drug (ie, there is no temporal association and no other possible cause [intercurrent illness, medication]) |
| --- | --- |
| Unlikely: | AE is doubtfully related to the study drug |
| Possibly: | AE may be related to the study drug |
| Probably: | AE is likely related to the study drug |
| Definitely: | AE is clearly related to the study drug |

A serious adverse event (SAE) is defined as any suspected adverse reaction at any dose that suggests a significant hazard, contraindication, side effect, or precaution, and results in the following outcomes:

Death;

A life-threatening event (ie, the patient is at immediate risk of death from the event as it occurred);

An event that is persistently, significantly, severely, or permanently disabling, or requires intervention to prevent such disability;

An event that requires inpatient hospitalization or prolongs hospitalization;

A congenital abnormality/birth defect; or

A medically significant event that may jeopardize the patient or may require intervention to prevent 1 of the other outcomes listed above.

Example 50: Route for the Synthesis of M3 (SULF-1) and M4 (SULF-2)

Metabolites M3 and M4 were prepared according to the following schemes.

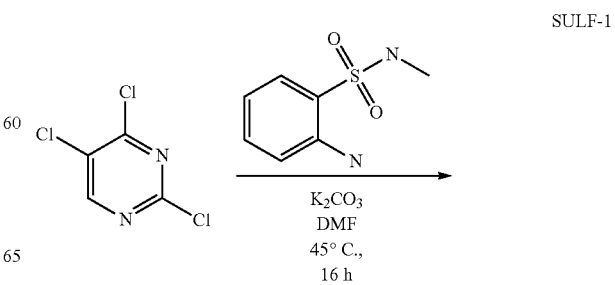

SULF-1

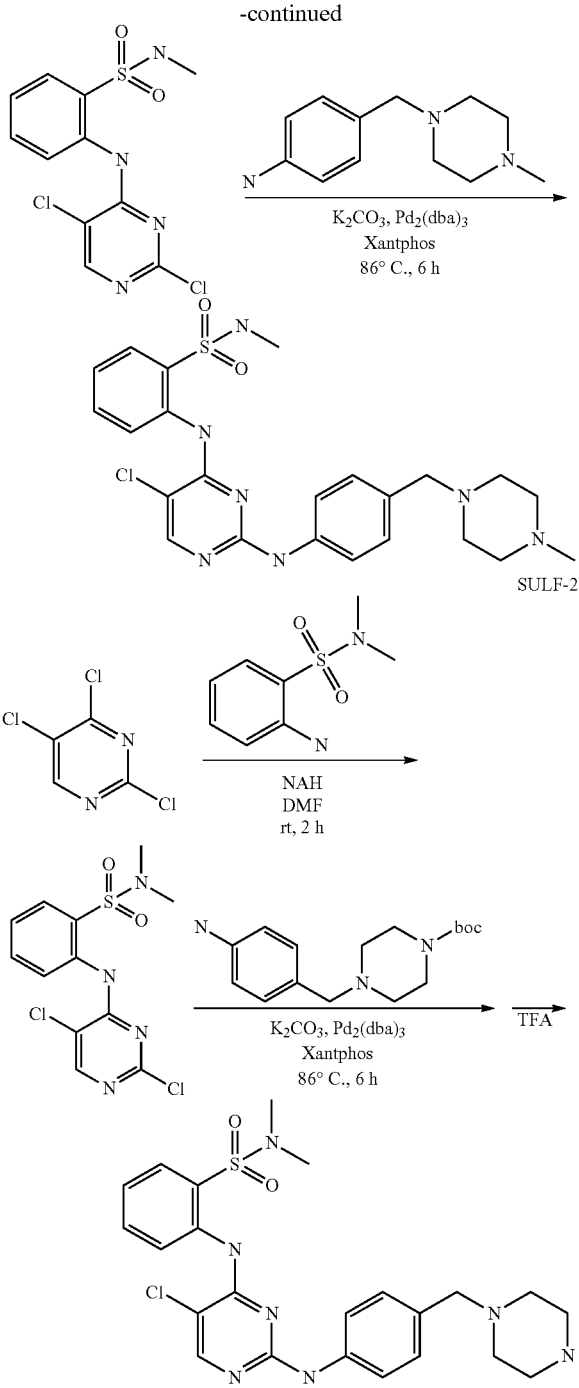

Example 51: Solvent and Slurry Screening of Crystalline Forms

The experimental conditions and the brief results acquired from the solvent screening and the slurry screening are listed in Tables 3-6. The variable organic solvents and those mixtures with water were used as solvent systems. From these screening studies, ten crystal forms, Form A', A, B, C, D, E, F, G, H and I, were assigned by XRPD patterns as shown in FIG. 98. The thermal behavior (DSC/TGA charts) for these crystals are also shown in FIGS. 99A-99I. The moisture sorption isotherms for Form A', A, B, C, and D are provided in FIG. 116.

Form A

The solvent screen was conducted as shown in Table 4. Form A was not transformed and was recrystallized in almost the organic solvent systems without H$_2$O. Two types of the stoichiometric crystals, which were indicated from initial studies, were respectively used in the slurry screen as shown in Tables 3 and 5. They were maintained in almost the solvent systems except for H2O during the screen. This indicated that Form A was basically stable and dominant form. Form A was transformed to Form B in H$_2$O, like as that observed in the solvent screen. The thermal analysis charts for the two types of Form A were shown in FIG. 99A. The significant weight-loss were observed for these batches with the higher melting point than that expected. The moisture sorption isotherm showed that these Form A were hygroscopic as shown in FIG. 116, and the additional XRPD analysis as shown in FIG. 117 found that Form A was maintained after the moisture absorption/desorption cycle. No significant changes were observed during the stability studies as shown in Table 26.

TABLE 26

Summary of Stability Results

| Form | Initial | 40° C. | 40° C./75% RH | 60° C. | 60° C./75% RH |
|---|---|---|---|---|---|
| A' | 97.9% | 98.1% | 98.0% | 97.8% | 98.1% |
| A | 99.3% | 99.3% | 99.3% | 99.3% | 99.3% |
| D | 98.4% | 98.2% | 98.4% | 98.2% | 98.2% |

The two types of the stoichiometric crystals of Form A were finally identified since the XRPD pattern of the 2 batches of compound of structure (I) tartrate salt were same but the quantitative analyses by ion chromatography were different. The ratios of free base and tartaric acid for these two types of stoichiometric crystal were 1:1.5 (Form A') and 1:2 (Form A). The Raman spectra of Form A were consistent as shown in FIG. 118.

Form B

In the solvent and slurry screen, Form A was transformed to Form B by being recrystallized/suspended in H$_2$O, as shown in Table 4 and Table 5. The XRPD pattern of Form B was similar to that of Form A but it seemed to be contaminated with another crystal form as shown in FIG. 98. About 4%-weight loss and a broad endotherm peak derived from adhered water/solvent was observed and the melting point was over 130° C. as shown in FIG. 99B. The moisture sorption isotherm showed that Form B was hygroscopic as shown in FIG. 116. The quantitative analysis by ion chromatography indicated that the stoichiometry of freebase and tartaric acid was 1:1.2. The representative Raman spectrum was shown in FIG. 118, but the Raman spectra varied depending on the measured area of the material. This result strongly suggested that Form B was mixture of Form A and another form.

Form C

In the solvent screen, as shown in Table 4, Form C was formed by the recrystallization of Form A with the mixture of H$_2$O and alcohol, such as methanol and 2-propanol. About 10%-weight loss and a broad endotherm peak was observed in the thermal analysis chart as shown in FIG. 99C. That suggested that Form C might be a solvate with alcohol and the alcohol was eliminated depending on the increase of temperature. The moisture sorption isotherm as shown in FIG. 116 indicated that Form C was hygroscopic.

Form D

Form D was not formed in the solvent screen from Form A. Form D used in the slurry screen was not transformed in ethanol and 2-propanol, but done to various forms, E, F, G, H and I, in the other solvents, as shown in Table 6. This data indicated that Form D would be difficult to control in the manufacturing process. About 3%-weight loss and a broad endotherm peak due to adhered water/solvent was observed in the thermal analysis chart as shown in FIG. 99D. The moisture sorption isotherm as shown in FIG. 116 indicated that Form D was hygroscopic. The additional XRPD analysis as shown in FIG. 117 found that Form D was transformed to the other forms after the moisture absorption/desorption cycle. No significant changes were observed during the stability studies as shown in Table 26. The stoichiometry of freebase and tartaric acid is 1:1.

Form E

Form E was formed in the slurry screen from Form D only in methanol at room temperature, as shown in Table 6. About 4%-weight loss was observed in the thermal analysis chart as shown in FIG. 99E.

Form. F

Form F was formed in the slurry screen from Form D in the mixture of alcohol and $H_2O$ at room temperature and 50° C. as shown in Table 6. About 6%-weight loss was observed in the thermal analysis chart as shown in FIG. 99F.

Form G

Form G was formed in the slurry screen from Form D in $H_2O$ at room temperature and 50° C. as shown in Table 6. The thermal analysis chart was provided in FIG. 99G. No further studies could be done because of the insufficient amount of sample.

Form H

Form H was formed in the slurry screen from Form D only in Methanol-$H_2O$ (5:1) at room temperature, as shown in Table 6. The thermal analysis chart is provided in FIG. 99H.

Form I

Form I was formed in the slurry screen from Form D only in acetnirnile-$H_2O$ (10:1) at 50° C., as shown in Table 6. Thermal analysis data is provided in FIG. 99I.

CONCLUSION

The polymorph screen revealed that the compound of structure (I) tartrate salt had the nine crystal forms involving solvates. Among them, Form A could be the most suitable form for the tartrate sale when its stoichiometry is well-controlled in the manufacturing process, in terms of the dominance in the screens and the acceptable solid-form properties.

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. A crystalline form of a tartrate salt of the compound of structure (I):

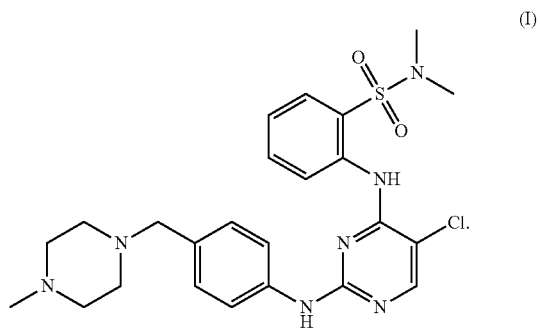

(I)

2. The crystalline form of claim 1, which is crystalline Form A, having a molar ratio of tartaric acid to the compound of structure (I) of about 2:1.

3. The crystalline form of claim 2, characterized by an x-ray powder diffraction (XRPD) pattern comprising peaks, in units 2-theta, at 11.2±0.2, 17.1±0.2, and 19.9±0.2.

4. The crystalline form of claim 2, characterized by an XRPD pattern comprising three or more peaks, in units of 2-theta, selected from 7.0±0.2, 11.2±0.2, 15.4±0.2, 16.3±0.2, 17.1±0.2, 19.9±0.2, 21.6±0.2, and 25.5±0.2.

5. A composition comprising the crystalline form of claim 1.

6. The composition of claim 5, comprising crystalline Form A in substantially pure form.

7. The composition of claim 5, wherein the composition is a pharmaceutical composition that is formulated for oral administration.

8. A unit dose comprising the composition of claim 5, wherein the composition is a pharmaceutical composition and the unit dose comprises about 1-100 mg of the tartrate salt.

9. The crystalline form of claim 1, wherein the tartrate salt is a salt of L-(+)-tartaric acid.

10. The crystalline form of claim 2, wherein Form A is in substantially pure form.

11. The crystalline form of claim 4, wherein the XRPD pattern is substantially identical to the XRPD pattern shown in FIG. 61A.

* * * * *